US009707195B2

(12) United States Patent
Tavazoie et al.

(10) Patent No.: US 9,707,195 B2
(45) **Date of Patent: *Jul. 18, 2017**

(54) TREATMENT AND DIAGNOSIS OF MELANOMA

(71) Applicant: The Rockefeller University, New York, NY (US)

(72) Inventors: Sohail F. Tavazoie, New York, NY (US); Nora Pencheva, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/228,643

(22) Filed: Aug. 4, 2016

(65) Prior Publication Data

US 2016/0331726 A1 Nov. 17, 2016

Related U.S. Application Data

(63) Continuation of application No. 14/486,477, filed on Sep. 15, 2014, which is a continuation of application No. PCT/US2013/054690, filed on Aug. 13, 2013.

(60) Provisional application No. 61/784,057, filed on Mar. 14, 2013, provisional application No. 61/682,339, filed on Aug. 13, 2012.

(51) Int. Cl.

| | |
|---|---|
| ***A61K 31/195*** | (2006.01) |
| ***A61K 38/17*** | (2006.01) |
| ***A61K 45/06*** | (2006.01) |
| ***A61K 31/18*** | (2006.01) |
| ***A61K 31/265*** | (2006.01) |
| ***A61K 31/415*** | (2006.01) |
| ***A61K 31/4164*** | (2006.01) |
| ***A61K 31/47*** | (2006.01) |
| ***A61K 31/5377*** | (2006.01) |
| ***G01N 33/574*** | (2006.01) |
| ***A61K 31/4174*** | (2006.01) |
| ***A61K 31/675*** | (2006.01) |
| ***C07C 217/54*** | (2006.01) |
| ***C07D 233/64*** | (2006.01) |
| ***C07F 9/6506*** | (2006.01) |
| ***A61K 31/136*** | (2006.01) |
| ***A61K 31/4155*** | (2006.01) |
| ***A61K 31/416*** | (2006.01) |
| ***C12Q 1/68*** | (2006.01) |

(52) U.S. Cl.

CPC .......... *A61K 31/195* (2013.01); *A61K 31/136* (2013.01); *A61K 31/18* (2013.01); *A61K 31/265* (2013.01); *A61K 31/415* (2013.01); *A61K 31/416* (2013.01); *A61K 31/4155* (2013.01); *A61K 31/4164* (2013.01); *A61K 31/4174* (2013.01); *A61K 31/47* (2013.01); *A61K 31/5377* (2013.01); *A61K 31/675* (2013.01); *A61K 38/177* (2013.01); *A61K 38/1709* (2013.01); *A61K 45/06* (2013.01); *C07C 217/54* (2013.01); *C07D 233/64* (2013.01); *C07F 9/65061* (2013.01); *C12Q 1/6886* (2013.01); *G01N 33/5743* (2013.01); *C12Q 2600/118* (2013.01); *C12Q 2600/136* (2013.01); *C12Q 2600/158* (2013.01); *C12Q 2600/178* (2013.01); *G01N 2500/10* (2013.01)

(58) Field of Classification Search

CPC .................................................... A61K 31/195

See application file for complete search history.

(56) References Cited

U.S. PATENT DOCUMENTS

| | | | |
|---|---|---|---|
| 5,324,731 A | 6/1994 | Kaddurah-Daouk et al. | |
| 5,676,978 A | 10/1997 | Teicher et al. | |
| 6,316,503 B1 | 11/2001 | Li et al. | |
| 7,247,748 B2 | 7/2007 | Thompson et al. | |
| 7,365,085 B2 | 4/2008 | Bhat et al. | |
| 7,560,586 B2 | 7/2009 | Thompson et al. | |
| 7,576,215 B2 | 8/2009 | Collini et al. | |
| 7,998,995 B2 | 8/2011 | Boren et al. | |
| 9,399,028 B2 * | 7/2016 | Tavazoie ............ | A61K 38/1709 |
| 2004/0072868 A1 | 4/2004 | Collins et al. | |
| 2005/0107444 A1 | 5/2005 | Thompsom et al. | |
| 2005/0113580 A1 | 5/2005 | Thompson et al. | |
| 2005/0131014 A1 | 6/2005 | Collini et al. | |
| 2005/0282908 A1 | 12/2005 | Collins et al. | |
| 2009/0286780 A1 | 11/2009 | Okuda et al. | |
| 2010/0048944 A1 | 2/2010 | Parhami | |
| 2010/0069367 A1 | 3/2010 | Boren et al. | |
| 2011/0028384 A1 | 2/2011 | Blacklow et al. | |
| 2011/0166079 A1 | 7/2011 | Vitek et al. | |

(Continued)

FOREIGN PATENT DOCUMENTS

| | | |
|---|---|---|
| WO | 03082802 A1 | 10/2003 |
| WO | 2007/002563 A1 | 1/2007 |
| WO | 2010138598 A2 | 12/2010 |

(Continued)

OTHER PUBLICATIONS

Chuu et al., "Modulation of Liver X Receptor Signaling As Novel Therapy for Prostate Cancer," Journal of Biomedical Science (Mar. 20, 2007): 14:543-553.

(Continued)

*Primary Examiner* — Rei-Tsang Shiao

(74) *Attorney, Agent, or Firm* — Fox Rothschild LLP

(57) ABSTRACT

The present invention discloses novel agents and methods for diagnosis and treatment of melanoma. Also disclosed are related arrays, kits, and screening methods.

28 Claims, 59 Drawing Sheets

(56) References Cited

U.S. PATENT DOCUMENTS

2013/0071403 A1 3/2013 Rolland et al.
2015/0023955 A1* 1/2015 Tavazoie ............ A61K 38/1709 424/133.1

FOREIGN PATENT DOCUMENTS

WO 2011130426 A2 10/2011
WO 2011158667 A1 12/2011
WO 2012135082 A1 10/2012

OTHER PUBLICATIONS

Li et al., "miR-495 and miR-551a inhibit the migration and invasion of human gastric cancer cells by directly interacting with PRL-3," Cancer Lett (Mar. 30, 2012); 323(1):41-47.
Pencheva et al., "Control of metastatic progression by microRNA regulatory networks," Nature Cell Biology (Jun. 3, 2013); 15(6):546-554.
Zhang et al., "Liver X receptor activation induces apoptosis of melanoma cell through caspase pathway," Cancer Cell International (Feb. 25, 2014); 14(1):16 (1-6).
Pencheva et al., "Broad-Spectrum Therapeutic Suppression of Metastatic melanoma thorugh Nuclear Hormone Receptor Activation," Cell (Feb. 27, 2014); 156(5):986-1001.
Zigler et al., "Tumor Immunotherapy in Melanoma—Strategies for Overcoming Mechanisms of Resistance and Escape," Am J Clin Dermatol (2008); 9(50):307-311.
Haas, M.J., "Melanoma: three ways around BRAF inhibition," SciBX 3(47); doi:10.1038/scibx.2010.1400 published inline Dec. 9, 2010.
Scoles et al., "LiverX receptor agonist inhibits proliferation of ovarian carcinoma cells stimulated by oxidized low tensity lipoprotein," Gynecology Oncology (2010): 116:109-116.
Talmadge et al., "History of myeloid derived suppressor cells (MDSCs) in the macro-and micro-environment of tumour-bearing hosts," Nat Rev Cancer (2013); 13(10):739-752.
Gros et al., "Myeloid Cells Obtained form the Blood but Not from the Tumor Can Suppress T-cell Proliferation in Patients with Melanoma," Clin Cancer Res. (Oct. 1, 2012); 18(19):5212-5223.
Weber et al., "Phase I/II Study of Metastatic Melanoma Patients Treated with Nivolumab Who Had Progressed after Ipilimumab," Cancer Immunol Res (Apr. 2016); 4(4):345-353.
Rudolph et al., "Increased frequencies of CD11b+CD33+CD14+HLA-DRlow myeloid-derived suppressor cells are an early eent in melanoma patients," Experimental Dermatology (2014); 23:199-218.
Zhang et al., A novel subset of B7-H3+CD14+HLA-DR-/low myeloid-derived suppressor cells are associated with progression of human NSCLC, OncoImmunology (Feb. 2015): 4(2): e977164-1-e977164-12.
Bergenfelz et al, "Systemic Monocytic-MDSCs Are Generated from Monocytes and Correlate with Disease Progressio in Breast Cancer Patients," PLoS One (2015); 10(5):e0127028 (pp. 1-15).
Gielen et al., "Increase in Both CD14-Positive and CD15-Positive Myeloid-Derived Suppressor Cell Subpopulations in the Blood of Patients with Glioma But Predominance of CD15-Positive Myeloid-Derived Suppressor Cells in Glioma Tissue," J Neuropathol Exp Neurol (May 2015); 74(5):390-400.
Obermajer et al., "PGE2-Induced CXCL12 Production and CXCR4 Expression Controls the Accumulation of Human MDSCs in Ovarian Cancer Environment," Cancer Res. (2011); 71(24):7463-7470.

* cited by examiner

Table S1 List of the 50 most upregulated genes in MeWo human melanoma cells in response to GW3965 treatment

| Gene ID | Fold-change* | q-value | Rank | Gene ID | Fold-change* | q-value | Rank |
|---|---|---|---|---|---|---|---|
| *ABCA1* | 19.34 | 1.98E-11 | 1 | *CEACAM1* | 1.83 | 5.58E-06 | 26 |
| *SREBF1* | 8.08 | 9.12E-15 | 2 | *LDLR* | 1.79 | 1.29E-05 | 27 |
| *FABP7* | 7.43 | 1.85E-11 | 3 | *IL1RAPL1* | 1.78 | 1.58E-09 | 28 |
| *LOC645313* | 4.34 | 2.25E-10 | 4 | *PPP1R3C* | 1.78 | 1.64E-07 | 29 |
| ***APOE*** | **4.11** | **1.04E-07** | 5 | *ABCD1* | 1.76 | 4.24E-07 | 30 |
| *KRT34* | 4.09 | 5.99E-18 | 6 | *C10ORF75* | 1.67 | 2.91E-06 | 31 |
| *FASN* | 3.72 | 2.48E-07 | 7 | *LSS* | 1.66 | 1.86E-05 | 32 |
| *IGFBP5* | 2.91 | 1.15E-13 | 8 | *DHCR7* | 1.64 | 2.58E-06 | 33 |
| *TF* | 2.88 | 2.37E-12 | 9 | *CAPS* | 1.63 | 8.35E-06 | 34 |
| *INSIG1* | 2.62 | 3.15E-16 | 10 | *PCYT2* | 1.63 | 3.08E-06 | 35 |
| *MYLIP* | 2.56 | 9.21E-07 | 11 | *C5ORF28* | 1.62 | 3.71E-02 | 36 |
| *LPCAT3* | 2.54 | 2.80E-15 | 12 | *TMEM119* | 1.60 | 1.15E-04 | 37 |
| *ACACA* | 2.43 | 1.56E-12 | 13 | *LPXN* | 1.60 | 1.15E-07 | 38 |
| *SCD* | 2.42 | 3.56E-08 | 14 | *SMPDL3A* | 1.59 | 2.39E-04 | 39 |
| *FCRLA* | 2.19 | 9.13E-09 | 15 | *SPOCD1* | 1.58 | 7.18E-07 | 40 |
| *FADS1* | 2.12 | 2.01E-09 | 16 | *ACLY* | 1.58 | 6.56E-11 | 41 |
| *ACSS2* | 2.02 | 1.88E-08 | 17 | *VGLL3* | 1.57 | 1.32E-04 | 42 |
| *SLC2A6* | 2.02 | 5.99E-18 | 18 | *MVD* | 1.57 | 1.13E-03 | 43 |
| *ACSL3* | 1.94 | 5.35E-10 | 19 | *NAV3* | 1.55 | 2.32E-04 | 44 |
| *TMEM135* | 1.91 | 9.06E-07 | 20 | *HS.538962* | 1.55 | 1.40E-07 | 45 |
| *ADM* | 1.88 | 3.78E-05 | 21 | *TUBB2B* | 1.53 | 3.46E-08 | 46 |
| *LPIN1* | 1.88 | 5.94E-08 | 22 | *LOC728285* | 1.53 | 2.19E-06 | 47 |
| *MID1IP1* | 1.85 | 7.48E-09 | 23 | *PHLDA2* | 1.52 | 2.77E-07 | 48 |
| *FDPS* | 1.84 | 5.49E-05 | 24 | *APOLD1* | 1.51 | 9.50E-05 | 49 |
| *CCL2* | 1.83 | 1.00E-08 | 25 | *BEX1* | 1.51 | 1.08E-09 | 50 |

* Fold-upregulation in array-based gene expression for GW3965 treatment (1 μM, 48 hrs) versus DMSO control treatment

FIG. 26

SEQUENCE LISTING

```
<160> NUMBER OF SEQ ID NOS: 141

<210> SEQ ID NO 1
<211> LENGTH: 1223
<212> TYPE: DNA
<213> ORGANISM: Homo sapiens

<400> SEQUENCE: 1

gggatccttg agtcctactc agccccagcg gaggtgaagg acgtccttcc ccaggagccg     60

actggccaat cacaggcagg aagatgaagg ttctgtgggc tgcgttgctg gtcacattcc    120

tggcaggatg ccaggccaag gtggagcaag cggtggagac agagccggag cccgagctgc    180

gccagcagac cgagtggcag agcggccagc gctgggaact ggcactgggt cgcttttggg    240

attacctgcg ctgggtgcag acactgtctg agcaggtgca ggaggagctg ctcagctccc    300

aggtcaccca ggaactgagg gcgctgatgg acgagaccat gaaggagttg aaggcctaca    360

aatcggaact ggaggaacaa ctgaccccgg tggcggagga gacgcgggca cggctgtcca    420

aggagctgca ggcggcgcag gcccggctgg gcgcggacat ggaggacgtg tgcggccgcc    480

tggtgcagta ccgcggcgag gtgcaggcca tgctcggcca gagcaccgag gagctgcggg    540

tgcgcctcgc ctcccacctg cgcaagctgc gtaagcggct cctccgcgat gccgatgacc    600

tgcagaagcg cctggcagtg taccaggccg gggcccgcga gggcgccgag cgcggcctca    660

gcgccatccg cgagcgcctg gggcccctgg tggaacaggg ccgcgtgcgg gccgccactg    720

tgggctccct ggccggccag ccgctacagg agcgggccca ggcctggggc gagcggctgc    780

gcgcgcggat ggaggagatg ggcagccgga cccgcgaccg cctggacgag gtgaaggagc    840

aggtggcgga ggtgcgcgcc aagctggagg agcaggccca gcagatacgc ctgcaggccg    900

aggccttcca ggcccgcctc aagagctggt tcgagcccct ggtggaagac atgcagcgcc    960

agtgggccgg gctggtggag aaggtgcagg ctgccgtggg caccagcgcc gcccctgtgc   1020

ccagcgacaa tcactgaacg ccgaagcctg cagccatgcg accccacgcc accccgtgcc   1080

tcctgcctcc gcgcagcctg cagcgggaga ccctgtcccc gccccagccg tcctcctggg   1140

gtggacccta gtttaataaa gattcaccaa gtttcacgca aaaaaaaaaa aaaaaaaaaa   1200

aaaaaaaaaa aaaaaaaaaa aaa                                           1223


<210> SEQ ID NO 2
<211> LENGTH: 317
<212> TYPE: PRT
<213> ORGANISM: Homo sapiens

<400> SEQUENCE: 2

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45
```

```
Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
            100                 105                 110

Lys Glu Leu Gln Ala Ala Gln Ala Arg Leu Gly Ala Asp Met Glu Asp
        115                 120                 125

Val Cys Gly Arg Leu Val Gln Tyr Arg Gly Glu Val Gln Ala Met Leu
    130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
        195                 200                 205

Arg Ala Ala Thr Val Gly Ser Leu Ala Gly Gln Pro Leu Gln Glu Arg
    210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
            260                 265                 270

Glu Ala Phe Gln Ala Arg Leu Lys Ser Trp Phe Glu Pro Leu Val Glu
        275                 280                 285

Asp Met Gln Arg Gln Trp Ala Gly Leu Val Glu Lys Val Gln Ala Ala
    290                 295                 300

Val Gly Thr Ser Ala Ala Pro Val Pro Ser Asp Asn His
305                 310                 315
```

<210> SEQ ID NO 3
<211> LENGTH: 3203
<212> TYPE: RNA
<213> ORGANISM: Homo sapiens

<400> SEQUENCE: 3

```
agucccaccc uucggcgcag ggcuccggcc aacacagccc uccaggccgc cuacucucca      60

gccagccggc uccacggacc cacggaaggg caagggggcg gccucggggc ggcgggacag     120

uugucggagg gcgcccucca ggcccaagcc gccuucuccg gcccccgcca uggcccgggg     180

cggcagucag agcuggagcu ccggggaauc agacgggcag ccaaaggagc agacgcccga     240

gaagcccaga cacaagaugg ugaaggagac ccaguacuau gacauccugg gcgugaagcc     300

cagcgcgucc ccggaggaga ucaagaaggc cuaucggaag cuggcgcuca aguaccaccc     360

ggacaagaac ccggaugagg gcgagaaguu uaaacucaua ucccaggcau augaagugcu     420

uucagaucca aagaaaaggg auguuuauga ccaaggcgga gagcaggcaa uuaaagaagg     480

aggcucaggc agccccagcu ucucuucacc cauggacauc uuugacaugu ucuuuggugg     540

ugguggacgg auggcuagag agagaagagg caagaauguu guacaccagu uaucuguaac     600
```

-continued

```
ucuugaagau cuauauaaug gagucacgaa gaaauuggcc cuccagaaaa auguaauuug    660
ugagaaaugu gaagguguug gugggaagaa gggaucggug gagaagugcc cgcugugcaa    720
ggggcggggg augcagaucc acauccagca gaucgggccg ggcaugguac agcagaucca    780
gaccgugugc aucgagugca agggccaggg ugagcgcauc aaccccaagg accgcugcga    840
gagcugcagc ggggccaagg ugauccguga gaagaagauu aucgagguac auguugaaaa    900
agguaugaaa gaugggcaaa agauacuauu ucauggagaa ggagaucagg agccugagcu    960
ggagccuggu gaugucauaa uugugcuuga ucagaaggau cauaguguu uucagagacg   1020
aggccaugac uugaucauga aaaugaaaau ucagcuuucu gaagcucuuu guggcuucaa   1080
gaagacgaua aaaacauugg acaaucgaau ucuuguuauu acauccaaag cagugaggu   1140
gauaaagcac ggggaccuga gaugcgugcg cgaugaagga augcccaucu acaaagcacc   1200
ccuggaaaaa gggauucuga ucauacaguu uuuaguaauc uuuccugaaa aacacuggcu   1260
uucucuggaa aagcuuccuc agcuggaagc uuuacucccu ccucgacaga aagugaggau   1320
uacagaugac auggaucagg uggagcugaa ggaguuuugu cccaaugagc agaacuggcg   1380
ucagcacagg gaggccuacg aggaggacga agacgggccc caggcuggag ugcagugcca   1440
gacggcauga cguggugcgg ggcagcgugg ccccaccgga cuagcacaug augaauguaa   1500
aguuggcaca augaaaauga caucgcuuua auggccuugu guuugggaug uccuguguau   1560
guguucagca uucuuaauug cugagugucu uuuuggcuuu ucuuuugguu guaacuuaag   1620
uuauagcuua auuuauauuu aaauguuuua aguauaaauc accucuaguc ugcauaugga   1680
aucuguucau uucuauuuuc aggauauacu uuugagaugu cagugauugc accaauacuu   1740
ugugcuucua guggcuuugc cauaaauucag ugucaccaau aaggcacagc ccaguuagca   1800
gcuuagcccc ccuagcaaac cccaaggcac aaagugggca uccugacuca ucucuagguc   1860
ugugguuucu ccccucuucc cuuggcagag uuauugaggg caugaucuca gggcugcuaa   1920
gauaacauuu cugaggauuc uagaugaucc ucuuaaagaa uaaaagcaca uccguggauc   1980
ggacauggcu gcaugugccu gcuuaacagg gccaacuuag uuccuacugu ucugugcccu   2040
ucaguggaug gaacgugagu gucugaucau cucucuugga aguuucuga accuuccaag   2100
cucugugug aggacaaacc aguguuugaa ucauaugcug auaacuguuu gccugugacc   2160
cucacaccuu guucuucagg guuuuaauga uuuucuguug acaacuuuug caaugcuuuc   2220
ccaccaaagu gcuuacuugu aaagaaaacu aaauccuucu gugucccegg cagccucagu   2280
gcagcaacag aagccaaggg agaaugcugc ugguuuggcc cauggcacag ccagcuucuc   2340
ugaccaguaa uccggggug cuugagggue ugcaaaggca uagaacuccc caguguuuuc   2400
caccucauuc ucccagauug agcucccuuc caaaggaucg uuccucucau ugcacagcca   2460
uauuacaaag gguuuccugc ucaagugaug uuuugguaag aacuucgcug aguuccacug   2520
uggauuacag uuuguaugga cuacuacugu aaauuauagc uuguuuggag ggauauuagu   2580
cauuauuuua uucaugacag guagacuaca auucgaacuu aggguuaccu cagucuuuag   2640
ccauuacugc uuauuucuuu uccccaaguc acaaaaaacu uguaagcugc uggguuaaag   2700
cagaggccac cugucagauc uacccuaccc uuauuugguu acauggcacc ugagaguuuc   2760
acucagacca gggaucuucc uuaggagggu caaagugcag aucagaccau gcagguaagg   2820
ugaaccagcu gcacggacca gguucccgca aaacauugcc agcuagugag gcauaauuug   2880
cucaaaguau agaaacagcc caccugugcc cacuuugacc auuggugagg auagauauaa   2940
```

aaucacuucu uccaacgaag ccuaggugaa aaucuauuua uaaauggacc acaacucugg 3000
ggugucguuu uugugcugug acuuccuaau uauugcuaaa gaacuacugu uuaguuggua 3060 auggguguaaa auuacauuca gcuccuucuu gucauauaaa aggaauuugg agggugucgc 3120
uuaaaauuuu auuccaccug uacauuuguc acuuuaaaau uaaaauugag cugguaugag 3180
agauaaaaaa aaaaaaaaaa aaa 3203

<210> SEQ ID NO 4
<211> LENGTH: 426
<212> TYPE: PRT
<213> ORGANISM: Homo sapiens

<400> SEQUENCE: 4

Met Ala Arg Gly Gly Ser Gln Ser Trp Ser Ser Gly Glu Ser Asp Gly
1 5 10 15

Gln Pro Lys Glu Gln Thr Pro Glu Lys Pro Arg His Lys Met Val Lys
20 25 30

Glu Thr Gln Tyr Tyr Asp Ile Leu Gly Val Lys Pro Ser Ala Ser Pro
35 40 45

Glu Glu Ile Lys Lys Ala Tyr Arg Lys Leu Ala Leu Lys Tyr His Pro
50 55 60

Asp Lys Asn Pro Asp Glu Gly Glu Lys Phe Lys Leu Ile Ser Gln Ala
65 70 75 80

Tyr Glu Val Leu Ser Asp Pro Lys Lys Arg Asp Val Tyr Asp Gln Gly
85 90 95

Gly Glu Gln Ala Ile Lys Glu Gly Gly Ser Gly Ser Pro Ser Phe Ser
100 105 110

Ser Pro Met Asp Ile Phe Asp Met Phe Phe Gly Gly Gly Gly Arg Met
115 120 125

Ala Arg Glu Arg Arg Gly Lys Asn Val Val His Gln Leu Ser Val Thr
130 135 140

Leu Glu Asp Leu Tyr Asn Gly Val Thr Lys Lys Leu Ala Leu Gln Lys
145 150 155 160

Asn Val Ile Cys Glu Lys Cys Glu Gly Val Gly Gly Lys Lys Gly Ser
165 170 175

Val Glu Lys Cys Pro Leu Cys Lys Gly Arg Gly Met Gln Ile His Ile
180 185 190

Gln Gln Ile Gly Pro Gly Met Val Gln Gln Ile Gln Thr Val Cys Ile
195 200 205

Glu Cys Lys Gly Gln Gly Glu Arg Ile Asn Pro Lys Asp Arg Cys Glu
210 215 220

Ser Cys Ser Gly Ala Lys Val Ile Arg Glu Lys Lys Ile Ile Glu Val
225 230 235 240

His Val Glu Lys Gly Met Lys Asp Gly Gln Lys Ile Leu Phe His Gly
245 250 255

Glu Gly Asp Gln Glu Pro Glu Leu Glu Pro Gly Asp Val Ile Ile Val
260 265 270

Leu Asp Gln Lys Asp His Ser Val Phe Gln Arg Arg Gly His Asp Leu
275 280 285

Ile Met Lys Met Lys Ile Gln Leu Ser Glu Ala Leu Cys Gly Phe Lys
290 295 300

Lys Thr Ile Lys Thr Leu Asp Asn Arg Ile Leu Val Ile Thr Ser Lys
305 310 315 320

Ala Gly Glu Val Ile Lys His Gly Asp Leu Arg Cys Val Arg Asp Glu

```
                325                 330                 335

Gly Met Pro Ile Tyr Lys Ala Pro Leu Glu Lys Gly Ile Leu Ile Ile
            340                 345                 350

Gln Phe Leu Val Ile Phe Pro Glu Lys His Trp Leu Ser Leu Glu Lys
        355                 360                 365

Leu Pro Gln Leu Glu Ala Leu Leu Pro Pro Arg Gln Lys Val Arg Ile
    370                 375                 380

Thr Asp Asp Met Asp Gln Val Glu Leu Lys Glu Phe Cys Pro Asn Glu
385                 390                 395                 400

Gln Asn Trp Arg Gln His Arg Glu Ala Tyr Glu Glu Asp Glu Asp Gly
                405                 410                 415

Pro Gln Ala Gly Val Gln Cys Gln Thr Ala
            420                 425


<210> SEQ ID NO 5
<211> LENGTH: 3064
<212> TYPE: RNA
<213> ORGANISM: Homo sapiens

<400> SEQUENCE: 5

gugaccguga cgcgcgagcg ggcggcgggg gcgcgggcca ggggcgcggg ccagggugcc      60

ggcaggggcg uccggggcgc ucugaccggc cucgcccgcc ccccccgcag acacaagaug     120

gugaaggaga cccaguacua ugacauccug ggcgugaagc ccagcgcguc cccggaggag     180

aucaagaagg ccuaucggaa gcuggcgcuc aaguaccacc cggacaagaa cccggaugag     240

ggcgagaagu uuaaacucau aucccaggca uaugaagugc uuucagaucc aaagaaaagg     300

gauguuuaug accaaggcgg agagcaggca auuaaagaag gaggcucagg cagccccagc     360

uucucuucac ccauggacau cuuugacaug uucuuuggug gugguggacg gauggcuaga     420

gagagaagag gcaagaaugu uguacaccag uuaucuguaa cucuugaaga ucuauauaau     480

ggagucacga agaaauuggc ccuccagaaa aauguaauuu gugagaaaug ugaagguguu     540

ggugggaaga agggaucggu ggagaagugc ccgcugugca aggggcgggg gaugcagauc     600

cacauccagc agaucgggcc gggcauggua cagcagaucc agaccgugug caucgagugc     660

aagggccagg gugagcgcau caaccccaag gaccgcugcg agagcugcag cggggccaag     720

gugauccgug agaagaagau uaucgaggua cauguugaaa aagguaugaa agaugggcaa     780

aagauacuau uucauggaga aggagaucag gagccugagc uggagccugg ugaugucaua     840

auugugcuug aucagaagga ucauaguguc uuucagagac gaggccauga cuugaucaug     900

aaaaugaaaa uucagcuuuc ugaagcucuu uguggcuuca agaagacgau aaaaacauug     960

gacaaucgaa uucuuguuau uacauccaaa gcaggugagg ugauaaagca cggggaccug    1020

agaugcgugc gcgaugaagg aaugcccauc uacaaagcac cccuggaaaa agggauucug    1080

aucauacagu uuuuaguaau cuuuccugaa aaacacuggc uuucucugga aaagcuuccu    1140

cagcuggaag cuuuacuccc uccucgacag aaagugagga uuacagauga cauggaucag    1200

guggagcuga aggaguuuug ucccaaugag cagaacuggc gucagcacag ggaggccuac    1260

gaggaggacg aagacgggcc ccaggcugga gugcagugcc agacggcaug acguggugcg    1320

gggcagcgug gccccaccgg acuagcacau gaugaaugua aaguuggcac aaugaaaaug    1380

acaucgcuuu aauggccuug uguuugggau guccugugua uguguucagc auucuuaauu    1440

gcugaguguc uuuuuggcuu uucuuuuggu uguaacuuaa guuauagcuu aauuuauauu    1500

uaaauguuuu aaguauaaau caccucuagu cugcauaugg aaucuguuca uuucuauuuu    1560
```

```
caggauauac uuuugagaug ucagugauug caccaauacu uugugcuucu aguggcuuug   1620
ccauaauuca gugucaccaa uaaggcacag cccaguuagc agcuuagccc cccuagcaaa   1680
ccccaaggca caaagugggc auccugacuc aucucuaggu cugugguuuc uccccucuuc   1740
ccuuggcaga guuauugagg gcaugaucuc agggcugcua agauaacauu ucugaggauu   1800
cuagaugauc cucuuaaaga auaaaagcac auccguggau cggacauggc ugcaugugcc   1860
ugcuuaacag ggccaacuua guuccuacug uucugugccc uucaguggau ggaacgugag   1920
ugucugauca ucucucuugg aaguuuucug aaccuuccaa gcucuguggu gaggacaaac   1980
caguguuuga aucauaugcu gauaacuguu ugccugugac ccucacaccu uguucuucag   2040
gguuuuaaug auuuucuguu gacaacuuuu gcaaugcuuu cccaccaaag ugcuuacuug   2100
uaaagaaaac uaaauccuuc ugugucccg gcagccucag ugcagcaaca gaagccaagg   2160
gagaaugcug cugguuuggc ccauggcaca gccagcuucu cugaccagua auccggggug   2220
acuugagggu cugcaaaggc auagaacucc ccaguguuuu ccaccucauu cucccagauu   2280
gagcucccuu ccaaaggauc guuccucuca uugcacagcc auauuacaaa ggguuuccug   2340
cucaagugau guuuugguaa gaacuucgcu gaguuccacu guggauuaca guuuguaugg   2400
acuacuacug uaaauuauag cuuguuugga gggauauuag ucauuauuuu auucaugaca   2460
gguagacuac aauucgaacu uaggguuacc ucagucuuua gccauuacug cuuauuucuu   2520
uuccccaagu cacaaaaaac uuguaagcug cuggguuaaa gcagaggcca ccugucagau   2580
cuacccuacc cuuauuuggu uacauggcac cugagaguuu cacucagacc agggaucuuc   2640
cuuaggaggg ucaaagugca gaucagacca ugcagguaag gugaaccagc ugcacggacc   2700
agguucccgc aaaacauugc cagcuaguga ggcauaauuu gcucaaagua uagaaacagc   2760
ccaccugugc ccacuuugac cauuggugag gauagauaua aaaucacuuc uuccaacgaa   2820
gccuagguga aaaucuauuu auaaauggac cacaacucug ggugucguu uuugugcugu   2880
gacuuccuaa uuauugcuaa agaacuacug uuuaguuggu aaugguguaa aauuacauuc   2940
agcuccuucu ugucauauaa aaggaauuug gagggugucg cuuaaaauuu uauuccaccu   3000
guacauuugu cacuuuaaaa uuaaaauuga gcugguauga gagauaaaaa aaaaaaaaaa   3060
aaaa                                                                3064
```

```
<210> SEQ ID NO 6
<211> LENGTH: 397
<212> TYPE: PRT
<213> ORGANISM: Homo sapiens

<400> SEQUENCE: 6

Met Val Lys Glu Thr Gln Tyr Tyr Asp Ile Leu Gly Val Lys Pro Ser
1               5                   10                  15

Ala Ser Pro Glu Glu Ile Lys Lys Ala Tyr Arg Lys Leu Ala Leu Lys
            20                  25                  30

Tyr His Pro Asp Lys Asn Pro Asp Glu Gly Glu Lys Phe Lys Leu Ile
        35                  40                  45

Ser Gln Ala Tyr Glu Val Leu Ser Asp Pro Lys Lys Arg Asp Val Tyr
    50                  55                  60

Asp Gln Gly Gly Glu Gln Ala Ile Lys Glu Gly Gly Ser Gly Ser Pro
65                  70                  75                  80

Ser Phe Ser Ser Pro Met Asp Ile Phe Asp Met Phe Phe Gly Gly Gly
                85                  90                  95
```

-continued

```
Gly Arg Met Ala Arg Glu Arg Arg Gly Lys Asn Val Val His Gln Leu
            100                 105                 110

Ser Val Thr Leu Glu Asp Leu Tyr Asn Gly Val Thr Lys Lys Leu Ala
        115                 120                 125

Leu Gln Lys Asn Val Ile Cys Glu Lys Cys Glu Gly Val Gly Gly Lys
    130                 135                 140

Lys Gly Ser Val Glu Lys Cys Pro Leu Cys Lys Gly Arg Gly Met Gln
145                 150                 155                 160

Ile His Ile Gln Gln Ile Gly Pro Gly Met Val Gln Gln Ile Gln Thr
                165                 170                 175

Val Cys Ile Glu Cys Lys Gly Gln Gly Glu Arg Ile Asn Pro Lys Asp
            180                 185                 190

Arg Cys Glu Ser Cys Ser Gly Ala Lys Val Ile Arg Glu Lys Lys Ile
        195                 200                 205

Ile Glu Val His Val Glu Lys Gly Met Lys Asp Gly Gln Lys Ile Leu
    210                 215                 220

Phe His Gly Glu Gly Asp Gln Glu Pro Glu Leu Glu Pro Gly Asp Val
225                 230                 235                 240

Ile Ile Val Leu Asp Gln Lys Asp His Ser Val Phe Gln Arg Arg Gly
                245                 250                 255

His Asp Leu Ile Met Lys Met Lys Ile Gln Leu Ser Glu Ala Leu Cys
            260                 265                 270

Gly Phe Lys Lys Thr Ile Lys Thr Leu Asp Asn Arg Ile Leu Val Ile
        275                 280                 285

Thr Ser Lys Ala Gly Glu Val Ile Lys His Gly Asp Leu Arg Cys Val
    290                 295                 300

Arg Asp Glu Gly Met Pro Ile Tyr Lys Ala Pro Leu Glu Lys Gly Ile
305                 310                 315                 320

Leu Ile Ile Gln Phe Leu Val Ile Phe Pro Glu Lys His Trp Leu Ser
                325                 330                 335

Leu Glu Lys Leu Pro Gln Leu Glu Ala Leu Leu Pro Pro Arg Gln Lys
            340                 345                 350

Val Arg Ile Thr Asp Asp Met Asp Gln Val Glu Leu Lys Glu Phe Cys
        355                 360                 365

Pro Asn Glu Gln Asn Trp Arg Gln His Arg Glu Ala Tyr Glu Glu Asp
    370                 375                 380

Glu Asp Gly Pro Gln Ala Gly Val Gln Cys Gln Thr Ala
385                 390                 395
```

<210> SEQ ID NO 7
<211> LENGTH: 2891
<212> TYPE: RNA
<213> ORGANISM: Homo sapiens

<400> SEQUENCE: 7

```
acauuucagc aagcuggcua aagacaugug ggaaagccug acccuggauu caggucaaau      60

cucagcacuc acaagauuua aacucauauc ccaggcauau gaagugcuuu cagauccaaa     120

gaaaagggau guuuaugacc aaggcggaga gcaggcaauu aaagaaggag gcucaggcag     180

ccccagcuuc ucuucaccca uggacaucuu ugacauguuc uuuggugggug guggacggau     240

ggcuagagag agaagaggca agaauguugu acaccaguua ucuguaacuc uugaagaucu     300

auauaaugga gucacgaaga aauuggcccu ccagaaaaau guaauuugug agaaauguga     360

agguguuggu gggaagaagg gaucggugga gaagugcccg cugugcaagg ggcgggggau     420
```

-continued

```
gcagauccac auccagcaga ucgggccggg caugguacag cagauccaga ccgugugcau    480
cgagugcaag ggccagggug agcgcaucaa ccccaaggac cgcugcgaga gcugcagcgg    540
ggccaaggug auccgugaga agaagauuau cgagguacau guugaaaaag guaugaaaga    600
ugggcaaaag auacuauuuc auggagaagg agaucaggag ccugagcugg agccuggug a    660
ugucauaauu gugcuugauc agaaggauca uagugucuuu cagagacgag gccaugacuu    720
gaucaugaaa augaaaauuc agcuuucuga agcucuuugu ggcuucaaga agacgauaaa    780
aacauuggac aaucgaauuc uuguuauuac auccaaagca ggugagguga uaaagcacgg    840
ggaccugaga ugcgugcgcg augaaggaau gcccaucuac aaagcacccc uggaaaaagg    900
gauucugauc auacaguuuu uaguaaucuu uccugaaaaa cacuggcuuu cucuggaaaa    960
gcuucccucag cuggaagcuu uacucccucc ucgacagaaa gugaggauua cagaugacau   1020
ggaucaggug gagcugaagg aguuuugucc caaugagcag aacuggcguc agcacaggga   1080
ggccuacgag gaggacgaag acgggcccca ggcuggagug cagugccaga cggcaugacg   1140
uggugcgggg cagcguggcc ccaccggacu agcacaugau gaauguaaag uuggcacaau   1200
gaaaaugaca ucgcuuuaau ggccuugugu uugggauguc cuguguaugu guucagcauu   1260
cuuaauugcu gagugucuuu uuggcuuuuc uuuugguugu aacuuaaguu auagcuuaau   1320
uuauauuuaa auguuuuaag uauaaaucac cucuagucug cauauggaau cuguucauuu   1380
cuauuuucag gauauacuuu ugagauguca gugauugcac caauacuuug ugcuucuagu   1440
ggcuuugcca uaauucagug ucaccaauaa ggcacagccc aguuagcagc uuagcccccc   1500
uagcaaaccc caaggcacaa agugggcauc cugacucauc ucuaggucug ugguuucucc   1560
ccucuucccu uggcagaguu auugagggca ugaucucagg gcugcuaaga uaacauuucu   1620
gaggauucua gaugauccuc uuaaagaaua aaagcacauc cguggaucgg acauggcugc   1680
augugccugc uuaacagggc caacuuaguu ccuacuguuc ugugcccuuc aguggaugga   1740
acgugagugu cugaucaucu cucuuggaag uuuucugaac cuuccaagcu cugugguga g   1800
gacaaaccag uguuugaauc auaugcugau aacuguuugc cugugacccu cacaccuugu   1860
ucuucagggu uuuaaugauu uucuguugac aacuuuugca augcuuuccc accaaagugc   1920
uuacuuguaa agaaaacuaa auccuucugu guccccggca gccucagugc agcaacagaa   1980
gccaagggag aaugcugcug guuuggccca uggcacagcc agcuucucug accaguaaauc  2040
cggggugacu ugagggucug caaaggcaua gaacucccca guguuuucca ccucauucuc   2100
ccagauugag cucccuucca aaggaucguu ccucucauug cacagccaua uuacaaaggg   2160
uuuccugcuc aagugauguu uugguaagaa cuucgcugag uuccacugug gauuacaguu   2220
uguauggacu acuacuguaa auuauagcuu guuuggaggg auauuaguca uuauuuuauu   2280
caugacaggu agacuacaau ucgaacuuag gguuaccuca gucuuuagcc auuacugcuu   2340
auuucuuuuc cccaagucac aaaaaacuug uaagcugcug gguuaaagca gaggccaccu   2400
gucagaucua cccuacccuu auuugguuac auggcaccug agaguuucac ucagaccagg   2460
gaucuucccu aggagggguca aagugcagau cagaccaugc agguaaggug aaccagcugc   2520
acggaccagg uucccgcaaa acauugccag cuagugaggc auaauuugcu caaaguauag   2580
aaacagccca ccugugccca cuuugaccau uggugaggau agauauaaaa ucacuucuuc   2640
caacgaagcc uaggugaaaa ucuauuuaua aauggaccac aacucugggg ugucguuuuu   2700
gugcugugac uuccuaauua uugcuaaaga acuacuguuu aguugguaau gguguaaaau   2760
uacauucagc uccuucuugu cauauaaaag gaauuuggag ggugucgcuu aaaauuuuau   2820
```

```
uccaccugua cauuugucac uuuaaaauua aaauugagcu gguaugagag auaaaaaaaa   2880

aaaaaaaaaa a                                                        2891


<210> SEQ ID NO 8
<211> LENGTH: 370
<212> TYPE: PRT
<213> ORGANISM: Homo sapiens

<400> SEQUENCE: 8

Met Trp Glu Ser Leu Thr Leu Asp Ser Gly Gln Ile Ser Ala Leu Thr
1               5                   10                  15

Arg Phe Lys Leu Ile Ser Gln Ala Tyr Glu Val Leu Ser Asp Pro Lys
            20                  25                  30

Lys Arg Asp Val Tyr Asp Gln Gly Gly Glu Gln Ala Ile Lys Glu Gly
        35                  40                  45

Gly Ser Gly Ser Pro Ser Phe Ser Ser Pro Met Asp Ile Phe Asp Met
    50                  55                  60

Phe Phe Gly Gly Gly Gly Arg Met Ala Arg Glu Arg Arg Gly Lys Asn
65                  70                  75                  80

Val Val His Gln Leu Ser Val Thr Leu Glu Asp Leu Tyr Asn Gly Val
                85                  90                  95

Thr Lys Lys Leu Ala Leu Gln Lys Asn Val Ile Cys Glu Lys Cys Glu
            100                 105                 110

Gly Val Gly Gly Lys Lys Gly Ser Val Glu Lys Cys Pro Leu Cys Lys
        115                 120                 125

Gly Arg Gly Met Gln Ile His Ile Gln Gln Ile Gly Pro Gly Met Val
    130                 135                 140

Gln Gln Ile Gln Thr Val Cys Ile Glu Cys Lys Gly Gln Gly Glu Arg
145                 150                 155                 160

Ile Asn Pro Lys Asp Arg Cys Glu Ser Cys Ser Gly Ala Lys Val Ile
                165                 170                 175

Arg Glu Lys Lys Ile Ile Glu Val His Val Glu Lys Gly Met Lys Asp
            180                 185                 190

Gly Gln Lys Ile Leu Phe His Gly Glu Gly Asp Gln Glu Pro Glu Leu
        195                 200                 205

Glu Pro Gly Asp Val Ile Ile Val Leu Asp Gln Lys Asp His Ser Val
    210                 215                 220

Phe Gln Arg Arg Gly His Asp Leu Ile Met Lys Met Lys Ile Gln Leu
225                 230                 235                 240

Ser Glu Ala Leu Cys Gly Phe Lys Lys Thr Ile Lys Thr Leu Asp Asn
                245                 250                 255

Arg Ile Leu Val Ile Thr Ser Lys Ala Gly Glu Val Ile Lys His Gly
            260                 265                 270

Asp Leu Arg Cys Val Arg Asp Glu Gly Met Pro Ile Tyr Lys Ala Pro
        275                 280                 285

Leu Glu Lys Gly Ile Leu Ile Ile Gln Phe Leu Val Ile Phe Pro Glu
    290                 295                 300

Lys His Trp Leu Ser Leu Glu Lys Leu Pro Gln Leu Glu Ala Leu Leu
305                 310                 315                 320

Pro Pro Arg Gln Lys Val Arg Ile Thr Asp Asp Met Asp Gln Val Glu
                325                 330                 335

Leu Lys Glu Phe Cys Pro Asn Glu Gln Asn Trp Arg Gln His Arg Glu
            340                 345                 350
```

-continued

Ala Tyr Glu Glu Asp Glu Asp Gly Pro Gln Ala Gly Val Gln Cys Gln
355 360 365

Thr Ala
370

<210> SEQ ID NO 9
<211> LENGTH: 14905
<212> TYPE: RNA
<213> ORGANISM: Homo sapiens

<400> SEQUENCE: 9
cagcggugcg agcuccaggc ccaugcacug aggaggcgga aacaagggga gcccccagag 60
cuccaucaag cccccuccaa aggcuccccu acccggucca cgccccccac ccccccuccc 120
cgccuccucc caauugugca uuuuugcagc cggaggcggc uccgagaugg ggcugugagc 180
uucgcccggg gagggggaaa gagcagcgag gagugaagcg gggggguggg gugaaggguu 240
uggauuucgg ggcagggggc gcacccccgu cagcaggccc uccccaaggg gcucggaacu 300
cuaccucuuc acccacgccc cuggugcgcu uugccgaagg aaagaauaag aacagagaag 360
gaggaggggg aaaggaggaa aagggggacc ccccaacugg gggggugaa ggagagaagu 420 agcaggacca gaggggaagg ggcugcugcu ugcaucagcc cacaccaugc ugaccccgcc 480
guugcuccug cugcugcccc ugcucucagc ucuggucgcg gcggcuaucg acgccccuaa 540
gacuugcagc cccaagcagu uugccugcag agaucaaaua accuguaucu caaagggcug 600
gcggugcgac ggugagaggg acugcccaga cggaucugac gaggccccug agauuugucc 660
acagaguaag gcccagcgau gccagccaaa cgagcauaac ugccugggua cugagcugug 720
uguucccaug ucccgccucu gcaauggggu ccaggacugc auggacggcu cagaugaggg 780
gccccacugc cgagagcucc aaggcaacug cucucgccug ggcugccagc accauugugu 840
ccccacacuc gaugggccca ccugcuacug caacagcagc uuucagcuuc aggcagaugg 900
caagaccugc aaagauuuug augagugcuc aguguacggc accugcagcc agcuaugcac 960
caacacagac ggcuccuuca uauguggcug uguugaagga uaccuccugc agccggauaa 1020
ccgcuccugc aaggccaaga acgagccagu agaccggccc ccugugcugu ugauagccaa 1080
cucccagaac aucuuggcca cguaccugag uggggcccag gugucuacca ucacaccuac 1140
gagcacgcgg cagaccacag ccauggacuu cagcuaugcc aacgagaccg uaugcugggu 1200
gcauguuggg gacagugcug cucagacgca gcucaagugu gcccgcaugc cuggccuaaa 1260
gggcuucgug gaugagcaca ccaucaacau cucccucagu cugcaccacg uggaacagau 1320
ggccaucgac uggcugacag gcaacuucua cuuuguggau gacaucgaug auaggaucuu 1380
ugucugcaac agaaaugggg acacaugugu cacauugcua gaccuggaac ucuacaaccc 1440
caagggcauu gcccuggacc cugccauggg gaagguguuu uucacugacu augggcagau 1500
cccaaaggug gaacgcugug acauggaugg gcagaaccgc accaagcucg ucgacagcaa 1560
gauuguguuu ccucauggca ucacgcugga ccuggucagc cgccuugucu acugggcaga 1620
ugccuaucug gacuauauug aagugggugga cuaugagggc aagggccgcc agaccaucau 1680
ccagggcauc cugauugagc accuguacgg ccugacugug uuugagaauu aucucuaugc 1740
caccaacucg gacaaugcca augcccagca gaagacgagu gugauccgug ugaaccgcuu 1800
uaacagcacc gaguaccagg uugucacccg gguggacaag gguggugccc uccacaucua 1860
ccaccagagg cgucagcccc gagugaggag ccaugccugu gaaaacgacc aguaugggaa 1920 gccgggguggc ugcucugaca ucugccugcu ggccaacagc cacaaggcgc ggaccugccg 1980

-continued

```
cugccguucc ggcuucagcc ugggcaguga cgggaaguca ugcaagaagc cggagcauga   2040
gcuguuccuc guguauggca agggccggcc aggcaucauc cggggcaugg auaugggggc   2100
caaggucccg gaugagcaca ugauccccau ugaaaaccuc augaaccccc gagcccugga   2160
cuuccacgcu gagaccggcu ucaucuacuu ugccgacacc accagcuacc ucauuggccg   2220
ccagaagauu gauggcacug agcgggagac cauccugaag gacggcaucc acaaugugga   2280
gggugugggcc guggacugga ugggagacaa ucuguacugg acggacgaug ggcccaaaaa   2340
gacaaucagc guggccaggc uggagaaagc ugcucagacc cgcaagacuu uaaucgaggg   2400
caaaaugaca caccccaggg cuauugugguu ggauccacuc aaugggugga uguacuggac   2460
agacugggag gaggacccca aggacagucg gcgugggcgg cuggagaggg cguggaugga   2520
uggcucacac cgagacaucu uugucaccuc caagacagug cuuuggccca augggcuaag   2580
ccuggacauc ccggcugggc gccucuacug gguggaugcc uucuacgacc gcaucgagac   2640
gauacugcuc aauggcacag accggaagau uguguaugaa gguccugagc ugaaccacgc   2700
cuuuggccug ugucaccaug gcaacuaccu cuucuggacu gaguaucgga guggcagugu   2760
cuaccgcuug gaacggggug uaggaggcgc accccccacu gugacccuuc ugcgcaguga   2820
gcggcccccc aucuuugaga uccgaaugua ugaugcccag cagcagcaag uuggcaccaa   2880
caaaugccgg gugaacaaug gcggcugcag cagccugugc uuggccaccc cugggagccg   2940
ccagugcgcc ugugcugagg accaggugu u ggacgcagac ggcgucacuu gcuuggcgaa   3000
cccauccuac gugccuccac cccagugcca gccaggcgag uuugccugug ccaacagccg   3060
cugcauccag gagcgcugga agugugacgg agacaacgau ugccuggaca acagugauga   3120
ggccccagcc cucugccauc agcacaccug ccccucggac cgauucaagu gcgagaacaa   3180
ccggugcauc cccaaccgcu ggcucugcga cggggacaau gacugugggga acagugaaga   3240
ugaguccaau gccacuuguu cagcccgcac cugccccccc aaccaguucu ccugugccag   3300
uggccgcugc auccccaucu ccuggacgug ugaucuggau gacgacugug gggaccgcuc   3360
ugaugagucu gcuucgugug ccuaucccac cugcuucccc cugacucagu uuaccugcaa   3420
caauggcaga uguaucaaca ucaacuggag augcgacaau gacaaugacu guggggacaa   3480
cagugacgaa gccggcugca gccacuccug uucuagcacc caguucaagu gcaacagcgg   3540
gcguugcauc cccgagcacu ggaccugcga uggggacaau gacugcggag acuacaguga   3600
ugagacacac gccaacugca ccaaccaggc cacgaggccc ccugguggcu gccacacuga   3660
ugaguuccag ugccggcugg auggacuaug caucccccug cgguggcgcu gcgaugggga   3720
cacugacugc auggacucca gcgaugagaa gagcugugag ggagugaccc acgucugcga   3780
ucccaguguc aaguuuggcu gcaaggacuc agcucggugc aucagcaaag cgugggugug   3840
ugauggcgac aaugacugug aggauaacuc ggacgaggag aacugcgagu cccuggccug   3900
caggccaccc ucgcacccuu gugccaacaa caccucaguc ugccugcccc cugacaagcu   3960
gugugauggc aacgacgacu guggcgacgg cucagaugag ggcgagcucu gcgaccagug   4020
cucucugaau aacgguggcu gcagccacaa cugcucagug gcaccuggcg aaggcauugu   4080
guguuccugc ccucugggca uggagcuggg gcccgacaac cacaccugcc agauccagag   4140
cuacugugcc aagcaucuca aaugcagcca aaagugcgac cagaacaagu ucagcgugaa   4200
gugcuccugc uacgagggcu ggguccugga accugacggc gagagcugcc gcagccugga   4260
ccccuucaag ccguucauca uuuucuccaa ccgccaugaa auccggcgca ucgaucuuca   4320
```

-continued

```
caaaggagac uacagcgucc uggugcccgg ccugcgcaac accaucgccc uggacuucca   4380
ccucagccag agcgcccucu acuggaccga cgugguggag gacaagaucu accgcgggaa   4440
gcugcuggac aacggagccc ugacuaguuu cgagguggug auucaguaug gccuggccac   4500
acccgagggc cuggcuguag acuggauugc aggcaacauc uacugggugg agaguaaccu   4560
ggaucagauc gagguggcca agcuggaugg gacccuccgg accacccugc uggccgguga   4620
cauugagcac ccaagggcaa ucgcacugga uccccgggau gggauccugu uuuggacaga   4680
cugggaugcc agccugcccc gcauugaggc agccuccaug aguggggcug ggcgccgcac   4740
cgugcaccgg gagaccggcu cugggggcug gcccaacggg cucaccgugg acuaccugga   4800
gaagcgcauc cuuuggauug acgccagguc agaugccauu uacucagccc guuacgacgg   4860
cucuggccac auggaggugc uucggggaca cgaguuccug ucgcacccgu uugcagugac   4920
gcuguacggg ggggaggucu acuggacuga cuggcgaaca aacacacugg cuaaggccaa   4980
caaguggacc ggccacaaug ucaccguggu acagaggacc aacacccagc ccuuugaccu   5040
gcagguguac caccccuccc gccagcccau ggcucccaau cccugugagg ccaauggggg   5100
ccagggcccc ugcucccacc ugugucucau caacuacaac cggaccgugu ccugcgccug   5160
cccccaccuc augaagcucc acaaggacaa caccaccugc uaugaguuua agaaguuccu   5220
gcuguacgca cgucagaugg agauccgagg uguggaccug gaugcucccu acuacaacua   5280
caucaucucc uucacggugc ccgacaucga caacgucaca gugcuagacu acgaugcccg   5340
cgagcagcgu guguacuggu cugacgugcg gacacaggcc aucaagcggg ccuucaucaa   5400
cggcacaggc guggagacag ucgucucugc agacuugcca aaugcccacg ggcuggcugu   5460
ggacuggguc ucccgaaacc uguucuggac aagcuaugac accaauaaga agcagaucaa   5520
uguggcccgg cuggauggcu ccuucaagaa cgcaguggug cagggccugg agcagcccca   5580
uggccuuguc guccacccuc ugcgugggaa gcucuacugg accgauggug acaacaucag   5640
cauggccaac auggauggca gcaaucgcac ccugcucuuc aguggccaga agggccccgu   5700
gggccuggcu auugacuucc cugaaagcaa acucuacugg aucagcuccg ggaaccauac   5760
caucaaccgc ugcaaccugg augggagugg gcuggagguc aucgaugcca ugcggagcca   5820
gcugggcaag gccaccgccc uggccaucau gggggacaag cuguggugggg cugaucaggu   5880
gucggaaaag augggcacau gcagcaaggc ugacggcucg ggcuccgugg uccuucggaa   5940
cagcaccacc cuggugaugc acaugaaggu cuaugacgag agcauccagc uggaccauaa   6000
gggcaccaac cccugcagug ucaacaacgg ugacugcucc cagcucugcc ugcccacguc   6060
agagacgacc cgcuccugca ugugcacagc cggcuauagc cuccggagug gccagcaggc   6120
cugcgagggc guagguuccu uucuccugua cucugugcau gagggaauca ggggaauucc   6180
ccuggauccc aaugacaagu cagaugcccu gguccccagug uccgggaccu cgcuggcugu   6240
cggcaucgac uuccacgcug aaaaugacac caucuacugg guggacaugg gccugagcac   6300
gaucagccgg gccaagcggg accagacgug gcgugaagac gugggugacca auggcauugg   6360
ccguguggag ggcauugcag uggacuggau cgcaggcaac aucuacugga cagaccaggg   6420
cuuugauguc aucgaggucg cccggcucaa uggcuccuuc cgcuacgugg ugaucuccca   6480
gggucuagac aagccccggg ccaucaccgu ccacccggag aaaggguacu uguucuggac   6540
ugagugggggu caguauccgc guauugagcg gucucggcua gauggcacgg agcguguggu   6600
gcuggucaac gucagcauca gcuggcccaa cggcaucuca guggacuacc aggaugggaa   6660
gcuguacugg ugcgaugcac ggacagacaa gauugaacgg aucgaccugg agacagguga   6720
```

-continued

```
gaaccgcgag gugguucugu ccagcaacaa cauggacaug uuuucagugu cuguguuuga   6780
ggauuucauc uacuggagug acaggacuca ugccaacggc ucuaucaagc gcgggagcaa   6840
agacaaugcc acagacuccg ugccccugcg aaccggcauc ggcguccagc uuaaagacau   6900
caaagucuuc aaccgggacc ggcagaaagg caccaacgug ugcgcggugg ccaauggcgg   6960
gugccagcag cugugccugu accggggccg ugggcagcgg gccugcgccu gugcccacgg   7020
gaugcuggcu gaagacggag caucgugccg cgaguaugcc ggcuaccugc ucuacucaga   7080
gcgcaccauu cucaagagua uccaccuguc ggaugagcgc aaccucaaug cgcccgugca   7140
gcccuucgag gacccugagc acaugaagaa cgucaucgcc cuggccuuug acuaccgggc   7200
aggcaccucu ccgggcaccc ccaaucgcau cuucuucagc gacauccacu uugggaacau   7260
ccaacagauc aacgacgaug gcuccaggag gaucaccauu guggaaaacg ugggcuccgu   7320
ggaaggccug gccuaucacc guggcuggga cacucucuau uggacaagcu acacgacauc   7380
caccaucacg cgccacacag uggaccagac ccgcccaggg gccuucgagc gugagaccgu   7440
caucacuaug ucuggagaug accacccacg ggccuucguu uuggacgagu gccagaaccu   7500
cauguucugg accaacugga augagcagca ucccagcauc augcgggcgg cgcucucggg   7560
agccaauguc cugacccuua ucgagaagga cauccguacc cccaauggcc uggccaucga   7620
ccaccgugcc gagaagcucu acuucucuga cgccacccug gacaagaucg agcggugcga   7680
guaugacggc ucccaccgcu augugauccu aaagucagag ccuguccacc ccuucgggcu   7740
ggccguguau ggggagcaca uuuucuggac ugacugggug cggcgggcag ugcagcgggc   7800
caacaagcac gugggcagca acaugaagcu gcugcgcgug gacauccccc agcagcccau   7860
gggcaucauc gccguggcca acgacaccaa cagcugugaa cucucuccau gccgaaucaa   7920
caacggugge ugccaggacc ugugucugcu cacucaccag ggccauguca acugcucaug   7980
ccgagggggc cgaauccucc aggaugaccu caccugccga gcggugaauu ccucuugccg   8040
agcacaagau gaguuugagu gugccaaugg cgagugcauc aacuucagcc ugaccugcga   8100
cggcgucccc cacugcaagg acaaguccga ugagaagcca ucccuacugca acucccgccg   8160
cugcaagaag acuuuccggc agugcagcaa ugggcgcugu guguccaaca ugcuguggug   8220
caacggggcc gacgacugug gggauggcuc ugacgagauc ccuugcaaca agacagccug   8280
uggugugggc gaguuccgcu gccgggacgg gaccugcauc gggaacucca gccgcugcaa   8340
ccaguuugug gauugugagg acgccucaga ugagaugaac ugcagugcca ccgacugcag   8400
cagcuacuuc cgccugggcg ugaagggcgu gcucuuccag cccugcgagc ggaccucacu   8460
cugcuacgca cccagcuggg ugugugaugg cgccaaugac ugugggggacu acagugauga   8520
gcgcgacugc ccagguguga aacgccccag augcccucug aauuacuucg ccugcccuag   8580
ugggcgcugc aucccccauga gcuggacgug ugacaaagag gaugacugug aacauggcga   8640
ggacgagacc cacugcaaca aguucugcuc agaggcccag uuugagugcc agaaccaucg   8700
cugcaucucc aagcaguggc ugugugacgg cagcgaugac ugugggggaug gcucagacga   8760
ggcugcucac ugugaaggca agacgugcgg ccccuccucc uucuccugcc cuggcaccca   8820
cgugugcguc cccgagcgcu ggcucuguga cggugacaaa gacugugcug auggugcaga   8880
cgagagcauc gcagcugguu gcuuguacaa cagcacuugu gacgaccgug aguucaugug   8940
ccagaaccgc cagugcaucc ccaagcacuu cgugugugac cacgaccgug acugugcaga   9000
uggcucugau gaguccccccg agugugagua cccgaccugc ggccccagug aguuccgcug   9060
```

-continued ugccaauggg cgcugucuga gcucccgcca gugggagugu gauggcgaga augacugcca 9120
cgaccagagu gacgaggcuc ccaagaaccc acacugcacc agccaagagc acaagugcaa 9180
ugccucguca caguuccugu gcagcagugg gcgcugugug gcugaggcac ugcucugcaa 9240
cggccaggau gacuguggcg acagcucgga cgagcguggc ugccacauca augagugucu 9300
cagccgcaag cucaguggcu gcagccagga cugugaggac cucaagaucg gcuucaagug 9360
ccgcugucgc ccuggcuucc ggcugaagga cgacggccgg acgugugcug auguggacga 9420
gugcagcacc accuuccccu gcagccagcg cugcaucaac acucauggca gcuauaagug 9480
ucugugugug gagggcuaug caccccgcgg cggcgacccc cacagcugca aggcugugac 9540
ugacgaggaa ccguuucuga ucuucgccaa ccgguacuac cugcgcaagc ucaaccugga 9600
cggguccaac uacacguuac uuaagcaggg ccugaacaac gccguugccu uggauuuuga 9660
cuaccgagag cagaugaucu acuggacaga ugugaccacc cagggcagca ugauccgaag 9720
gaugcaccuu aacgggagca augugcaggu ccuacaccgu acaggccuca gcaaccccga 9780
ugggcuggcu guggacuggg uggguggcaa ccuguacugg ugcgacaaag gccgggacac 9840
caucgaggug uccaagcuca augggggccua ucggacggug cuggucagcu cuggccuccg 9900
ugagcccagg gcucuggugg uggaugugca gaaugggguac cuguacugga cagacugggg 9960
ugaccauuca cugaucggcc gcaucggcau ggaugggucc agccgcagcg ucaucgugga 10020
caccaagauc acauggccca auggccugac gcuggacuau gucacugagc gcaucuacug 10080
ggccgacgcc cgcgaggacu acauugaauu ugccagccug gauggcucca aucgccacgu 10140
ugugcugagc caggacaucc cgcacaucuu ugcacugacc cuguuugagg acuacgucua 10200
cuggaccgac ugggaaacaa aguccauuaa ccgagcccac aagaccacgg gcaccaacaa 10260
aacgcuccuc aucagcacgc ugcaccggcc cauggaccug caugucuucc augcccugcg 10320
ccagccagac gugcccaauc accccugcaa ggucaacaau gguggcugca gcaaccugug 10380
ccugcugucc cccgggggag ggcacaaaug ugccugcccc accaacuucu accugggcag 10440
cgaugggcgc accugugugu ccaacugcac ggcuagccag uuuguaugca agaacgacaa 10500
gugcaucccc uucugguugga agugugacac cgaggacgac ugcggggacc acucagacga 10560
gcccccggac ugcccugagu ucaagugccg gcccggacag uuccagugcu ccacagguau 10620
cugcacaaac ccugccuuca ucugcgaugg cgacaaugac ugccaggaca acagugacga 10680
ggccaacugu gacauccacg ucugcuugcc cagucaguuc aaaugcacca acaccaaccg 10740
cuguauuccc ggcaucuucc gcugcaaugg gcaggacaac ugcggagaug gggaggauga 10800
gagggacugc cccgagguga ccugcgcccc caaccaguuc cagugcucca uuaccaaacg 10860
gugcaucccc cgggucuggg ucugcgaccg ggacaaugac ugugugggaug gcagugauga 10920 gcccgccaac ugcacccaga ugaccugugg uguggacgag uuccgcugca aggauucggg 10980
ccgcugcauc ccagcgcguu ggaaguguga cggagaggau gacugugggg auggcucgga 11040
ugagcccaag gaagagugug augaacgcac cugugagcca uaccaguucc gcugcaagaa 11100
caaccgcugc gugcccggcc gcuggcagug cgacuacgac aacgauugcg gugacaacuc 11160
cgaugaagag agcugcaccc cucggcccug cuccgagagu gaguucuccu gugccaacgg 11220
ccgcugcauc gcggggcgcu ggaaaugcga uggagaccac gacugcgcgg acggcucgga 11280
cgagaaagac ugcacccccc gcugugacau ggaccaguuc cagugcaaga gcggccacug 11340
caucccccug cgcuggcgcu gugacgcaga cgccgacugc auggacggca gcgacgagga 11400
ggccugcggc acuggcgugc ggaccugccc ccuggacgag uuccagugca acaacaccuu 11460
gugcaagccg cuggccugga agugcgaugg cgaggaugac uguggggaca acucagauga 11520
gaaccccgag gagugugccc gguucgugug cccucccaac cggcccuucc guugcaagaa 11580
ugaccgcguc ugucugugga ucgggcgcca augcgauggc acggacaacu guggggaugg 11640
gacugaugaa gaggacugug agcccccac agcccacacc acccacugca aagacaagaa 11700
ggaguuucug ugccggaacc agcgcugccu cuccuccucc cugcgcugca acauguucga 11760
ugacugcggg gacggcucug acgaggagga cugcagcauc gaccccaagc ugaccagcug 11820
cgccaccaau gccagcaucu guggggacga ggcacgcugc gugcgcaccg agaaagcggc 11880
cuacugugcc ugccgcucgg gcuuccacac cgugcccggc cagcccggau gccaagacau 11940
caacgagugc cugcgcuucg gcaccugcuc ccagcucugc aacaacacca agggcggcca 12000
ccucugcagc ugcgcucgga acuucaugaa gacgcacaac accugcaagg ccgaaggcuc 12060
ugaguaccag guccuguaca ucgcugauga caaugagauc cgcagccugu uccccggcca 12120
cccccauucg gcuuacgagc aggcauucca gggugacgag agugucgca uugaugcuau 12180
ggauguccau gucaaggcug gccgugucua uuggaccaac uggcacacgg gcaccaucuc 12240
cuaccgcagc cugccaccug cugcgccucc uaccacuucc aaccgccacc ggcgacagau 12300
ugaccggggu gucacccacc ucaacauuuc agggcugaag augcccagag gcaucgccau 12360
cgacugggug gccggaaacg uguacuggac cgacucgggc cgagauguga uugagguggc 12420
gcagaugaag ggcgagaacc gcaagacgcu caucucgggc augauugacg agccccacgc 12480
cauuguggug gacccacuga gggggaccau guacugguca gacuggggca accaccccaa 12540
gauugagacg gcagcgaugg augggacgcu ucgggagaca cuggugcagg acaacauuca 12600
guggcccaca ggccuggccg uggauuauca caaugagcgg cuguacuggg cagacgccaa 12660
gcuuucaguc aucggcagca uccggcucaa uggcacggac cccauugugg cugcugacag 12720
caaacgaggc cuaagucacc ccuucagcau cgacgucuuu gaggauuaca ucuauggugu 12780
caccuacauc aauaaaucgug ucuucaagau ccauaaguuu ggccacagcc ccuuggucaa 12840
ccugacaggg ggccugagcc acgccucuga cgugguccuu uaccaucagc acaagcagcc 12900
cgaagugacc aacccaugug accgcaagaa augcgagugg cucugccugc ugagccccag 12960
ugggccuguc ugcaccuguc ccaaugggaa gcggcuggac aacggcacau gcgugccugu 13020
gcccucucca acgccccccc cagaugcucc ccggccugga accuguaacc ugcagugcuu 13080
caacggugge agcuguuucc ucaaugcacg gaggcagccc aagugccgcu gccaaccccg 13140
cuacacgggu gacaagugug aacuggacca gugcugggag cacugucgca augggggcac 13200
cugugcugcc ucccccucug gcaugcccac gugccggugc ccccacgggcu ucacgggccc 13260
caaaugcacc cagcaggugu gugcgggcua cugugccaac aacagcaccu gcacugucaa 13320
ccagggcaac cagccccagu gccgaugccu acccggcuuc cugggcgacc gcugccagua 13380
ccggcagugc ucuggcuacu gugagaacuu uggcacaugc cagauggcug cugauggcuc 13440
ccgacaaugc cgcugcacug ccuacuuuga gggaucgagg ugugagguga acaagugcag 13500
ccgcugucuc gaaggggccu guguggucaa caagcagagu ggggauguca ccugcaacug 13560
cacggauggc cgggugggccc ccagcugucu gaccugcguc ggccacugca gcaauggcgg 13620
cuccuguacc augaacagca aaaugaugcc ugagugccag ugcccacccc acaugacagg 13680
gccccggugu gaggagcacg ucuucagcca gcagcagcca ggacauauag ccuccauccu 13740
aaucccucug cuguugcugc ugcugcuggu ucugguggcc ggaguggguau ucugguauaa 13800

```
gcggcgaguc caaggggcua agggcuucca gcaccaacgg augaccaacg gggccaugaa  13860

cguggagauu ggaaacccca ccuacaagau guacgaaggc ggagagccug augauguggg  13920

aggccuacug gacgcugacu uugcccugga cccugacaag cccaccaacu ucaccaaccc  13980

cguguaugcc acacucuaca ugggggggcca uggcagucgc cacucccugg ccagcacgga  14040

cgagaagcga gaacuccugg gccggggccc ugaggacgag auaggggacc ccuuggcaua  14100

gggcccugcc ccgucggacu gcccccagaa agccuccugc ccccugccgg ugaaguccuu  14160

cagugagccc cuccccagcc agcccuuccc uggccccgcc ggauguauaa auguaaaaau  14220

gaaggaauua cauuuuauau gugagcgagc aagccggcaa gcgagcacag uauuauuucu  14280

ccauccccuc ccugccugcu ccuuggcacc cccaugcugc cuucagggag acaggcaggg  14340

agggcuuggg gcugcaccuc cuacccuccc accagaacgc accccacugg gagagcuggu  14400

ggugcagccu uccccucccu guauaagaca cuuugccaag gcucuccccu cucgccccau  14460

cccugcuugc ccgcucccac agcuuccuga gggcuaauuc ugggaaggga gaguucuuug  14520

cugccccugu cuggaagacg uggcucuggg ugagguaggc gggaaaggau ggaguguuuu  14580

aguucuuggg ggaggccacc ccaaacccca gccccaacuc caggggcacc uaugagaugg  14640

ccaugcucaa ccccccuccc agacaggccc ucccugucuc cagggccccc accgagguuc  14700

ccagggcugg agacuuccuc ugguaaacau uccuccagcc uccccucccc uggggacgcc  14760

aaggaggugg gccacaccca ggaagggaaa gcgggcagcc ccguuuuggg gacgugaacg  14820

uuuuaauaau uuuugcugaa uuccuuuaca acuaaauaac acagauauug uuauaaauaa  14880

aauuguaaaa aaaaaaaaaa aaaaa                                        14905
```

<210> SEQ ID NO 10
<211> LENGTH: 4544
<212> TYPE: PRT
<213> ORGANISM: Homo sapiens

<400> SEQUENCE: 10

```
Met Leu Thr Pro Pro Leu Leu Leu Leu Leu Pro Leu Leu Ser Ala Leu
1               5                   10                  15

Val Ala Ala Ala Ile Asp Ala Pro Lys Thr Cys Ser Pro Lys Gln Phe
            20                  25                  30

Ala Cys Arg Asp Gln Ile Thr Cys Ile Ser Lys Gly Trp Arg Cys Asp
        35                  40                  45

Gly Glu Arg Asp Cys Pro Asp Gly Ser Asp Glu Ala Pro Glu Ile Cys
    50                  55                  60

Pro Gln Ser Lys Ala Gln Arg Cys Gln Pro Asn Glu His Asn Cys Leu
65                  70                  75                  80

Gly Thr Glu Leu Cys Val Pro Met Ser Arg Leu Cys Asn Gly Val Gln
                85                  90                  95

Asp Cys Met Asp Gly Ser Asp Glu Gly Pro His Cys Arg Glu Leu Gln
            100                 105                 110

Gly Asn Cys Ser Arg Leu Gly Cys Gln His His Cys Val Pro Thr Leu
        115                 120                 125

Asp Gly Pro Thr Cys Tyr Cys Asn Ser Ser Phe Gln Leu Gln Ala Asp
    130                 135                 140

Gly Lys Thr Cys Lys Asp Phe Asp Glu Cys Ser Val Tyr Gly Thr Cys
145                 150                 155                 160

Ser Gln Leu Cys Thr Asn Thr Asp Gly Ser Phe Ile Cys Gly Cys Val
                165                 170                 175
```

-continued

```
Glu Gly Tyr Leu Leu Gln Pro Asp Asn Arg Ser Cys Lys Ala Lys Asn
            180                 185                 190

Glu Pro Val Asp Arg Pro Pro Val Leu Leu Ile Ala Asn Ser Gln Asn
        195                 200                 205

Ile Leu Ala Thr Tyr Leu Ser Gly Ala Gln Val Ser Thr Ile Thr Pro
    210                 215                 220

Thr Ser Thr Arg Gln Thr Thr Ala Met Asp Phe Ser Tyr Ala Asn Glu
225                 230                 235                 240

Thr Val Cys Trp Val His Val Gly Asp Ser Ala Ala Gln Thr Gln Leu
                245                 250                 255

Lys Cys Ala Arg Met Pro Gly Leu Lys Gly Phe Val Asp Glu His Thr
            260                 265                 270

Ile Asn Ile Ser Leu Ser Leu His His Val Glu Gln Met Ala Ile Asp
        275                 280                 285

Trp Leu Thr Gly Asn Phe Tyr Phe Val Asp Asp Ile Asp Asp Arg Ile
    290                 295                 300

Phe Val Cys Asn Arg Asn Gly Asp Thr Cys Val Thr Leu Leu Asp Leu
305                 310                 315                 320

Glu Leu Tyr Asn Pro Lys Gly Ile Ala Leu Asp Pro Ala Met Gly Lys
                325                 330                 335

Val Phe Phe Thr Asp Tyr Gly Gln Ile Pro Lys Val Glu Arg Cys Asp
            340                 345                 350

Met Asp Gly Gln Asn Arg Thr Lys Leu Val Asp Ser Lys Ile Val Phe
        355                 360                 365

Pro His Gly Ile Thr Leu Asp Leu Val Ser Arg Leu Val Tyr Trp Ala
    370                 375                 380

Asp Ala Tyr Leu Asp Tyr Ile Glu Val Val Asp Tyr Glu Gly Lys Gly
385                 390                 395                 400

Arg Gln Thr Ile Ile Gln Gly Ile Leu Ile Glu His Leu Tyr Gly Leu
                405                 410                 415

Thr Val Phe Glu Asn Tyr Leu Tyr Ala Thr Asn Ser Asp Asn Ala Asn
            420                 425                 430

Ala Gln Gln Lys Thr Ser Val Ile Arg Val Asn Arg Phe Asn Ser Thr
        435                 440                 445

Glu Tyr Gln Val Val Thr Arg Val Asp Lys Gly Gly Ala Leu His Ile
    450                 455                 460

Tyr His Gln Arg Arg Gln Pro Arg Val Arg Ser His Ala Cys Glu Asn
465                 470                 475                 480

Asp Gln Tyr Gly Lys Pro Gly Gly Cys Ser Asp Ile Cys Leu Leu Ala
                485                 490                 495

Asn Ser His Lys Ala Arg Thr Cys Arg Cys Arg Ser Gly Phe Ser Leu
            500                 505                 510

Gly Ser Asp Gly Lys Ser Cys Lys Lys Pro Glu His Glu Leu Phe Leu
        515                 520                 525

Val Tyr Gly Lys Gly Arg Pro Gly Ile Ile Arg Gly Met Asp Met Gly
    530                 535                 540

Ala Lys Val Pro Asp Glu His Met Ile Pro Ile Glu Asn Leu Met Asn
545                 550                 555                 560

Pro Arg Ala Leu Asp Phe His Ala Glu Thr Gly Phe Ile Tyr Phe Ala
                565                 570                 575

Asp Thr Thr Ser Tyr Leu Ile Gly Arg Gln Lys Ile Asp Gly Thr Glu
            580                 585                 590

Arg Glu Thr Ile Leu Lys Asp Gly Ile His Asn Val Glu Gly Val Ala
```

-continued

```
        595                 600                 605

Val Asp Trp Met Gly Asp Asn Leu Tyr Trp Thr Asp Asp Gly Pro Lys
    610                 615                 620

Lys Thr Ile Ser Val Ala Arg Leu Glu Lys Ala Ala Gln Thr Arg Lys
625                 630                 635                 640

Thr Leu Ile Glu Gly Lys Met Thr His Pro Arg Ala Ile Val Val Asp
                645                 650                 655

Pro Leu Asn Gly Trp Met Tyr Trp Thr Asp Trp Glu Glu Asp Pro Lys
            660                 665                 670

Asp Ser Arg Arg Gly Arg Leu Glu Arg Ala Trp Met Asp Gly Ser His
        675                 680                 685

Arg Asp Ile Phe Val Thr Ser Lys Thr Val Leu Trp Pro Asn Gly Leu
    690                 695                 700

Ser Leu Asp Ile Pro Ala Gly Arg Leu Tyr Trp Val Asp Ala Phe Tyr
705                 710                 715                 720

Asp Arg Ile Glu Thr Ile Leu Leu Asn Gly Thr Asp Arg Lys Ile Val
                725                 730                 735

Tyr Glu Gly Pro Glu Leu Asn His Ala Phe Gly Leu Cys His His Gly
            740                 745                 750

Asn Tyr Leu Phe Trp Thr Glu Tyr Arg Ser Gly Ser Val Tyr Arg Leu
        755                 760                 765

Glu Arg Gly Val Gly Gly Ala Pro Pro Thr Val Thr Leu Leu Arg Ser
    770                 775                 780

Glu Arg Pro Pro Ile Phe Glu Ile Arg Met Tyr Asp Ala Gln Gln Gln
785                 790                 795                 800

Gln Val Gly Thr Asn Lys Cys Arg Val Asn Asn Gly Gly Cys Ser Ser
                805                 810                 815

Leu Cys Leu Ala Thr Pro Gly Ser Arg Gln Cys Ala Cys Ala Glu Asp
            820                 825                 830

Gln Val Leu Asp Ala Asp Gly Val Thr Cys Leu Ala Asn Pro Ser Tyr
        835                 840                 845

Val Pro Pro Pro Gln Cys Gln Pro Gly Glu Phe Ala Cys Ala Asn Ser
    850                 855                 860

Arg Cys Ile Gln Glu Arg Trp Lys Cys Asp Gly Asp Asn Asp Cys Leu
865                 870                 875                 880

Asp Asn Ser Asp Glu Ala Pro Ala Leu Cys His Gln His Thr Cys Pro
                885                 890                 895

Ser Asp Arg Phe Lys Cys Glu Asn Asn Arg Cys Ile Pro Asn Arg Trp
            900                 905                 910

Leu Cys Asp Gly Asp Asn Asp Cys Gly Asn Ser Glu Asp Glu Ser Asn
        915                 920                 925

Ala Thr Cys Ser Ala Arg Thr Cys Pro Pro Asn Gln Phe Ser Cys Ala
    930                 935                 940

Ser Gly Arg Cys Ile Pro Ile Ser Trp Thr Cys Asp Leu Asp Asp Asp
945                 950                 955                 960

Cys Gly Asp Arg Ser Asp Glu Ser Ala Ser Cys Ala Tyr Pro Thr Cys
                965                 970                 975

Phe Pro Leu Thr Gln Phe Thr Cys Asn Asn Gly Arg Cys Ile Asn Ile
            980                 985                 990

Asn Trp Arg Cys Asp Asn Asp Asn  Asp Cys Gly Asp Asn  Ser Asp Glu
        995                 1000                1005

Ala Gly  Cys Ser His Ser Cys  Ser Ser Thr Gln Phe  Lys Cys Asn
    1010                1015                1020
```

-continued

Ser Gly Arg Cys Ile Pro Glu His Trp Thr Cys Asp Gly Asp Asn
1025 1030 1035

Asp Cys Gly Asp Tyr Ser Asp Glu Thr His Ala Asn Cys Thr Asn
1040 1045 1050

Gln Ala Thr Arg Pro Pro Gly Gly Cys His Thr Asp Glu Phe Gln
1055 1060 1065

Cys Arg Leu Asp Gly Leu Cys Ile Pro Leu Arg Trp Arg Cys Asp
1070 1075 1080

Gly Asp Thr Asp Cys Met Asp Ser Ser Asp Glu Lys Ser Cys Glu
1085 1090 1095

Gly Val Thr His Val Cys Asp Pro Ser Val Lys Phe Gly Cys Lys
1100 1105 1110

Asp Ser Ala Arg Cys Ile Ser Lys Ala Trp Val Cys Asp Gly Asp
1115 1120 1125

Asn Asp Cys Glu Asp Asn Ser Asp Glu Glu Asn Cys Glu Ser Leu
1130 1135 1140

Ala Cys Arg Pro Pro Ser His Pro Cys Ala Asn Asn Thr Ser Val
1145 1150 1155

Cys Leu Pro Pro Asp Lys Leu Cys Asp Gly Asn Asp Asp Cys Gly
1160 1165 1170

Asp Gly Ser Asp Glu Gly Glu Leu Cys Asp Gln Cys Ser Leu Asn
1175 1180 1185

Asn Gly Gly Cys Ser His Asn Cys Ser Val Ala Pro Gly Glu Gly
1190 1195 1200

Ile Val Cys Ser Cys Pro Leu Gly Met Glu Leu Gly Pro Asp Asn
1205 1210 1215

His Thr Cys Gln Ile Gln Ser Tyr Cys Ala Lys His Leu Lys Cys
1220 1225 1230

Ser Gln Lys Cys Asp Gln Asn Lys Phe Ser Val Lys Cys Ser Cys
1235 1240 1245

Tyr Glu Gly Trp Val Leu Glu Pro Asp Gly Glu Ser Cys Arg Ser
1250 1255 1260

Leu Asp Pro Phe Lys Pro Phe Ile Ile Phe Ser Asn Arg His Glu
1265 1270 1275

Ile Arg Arg Ile Asp Leu His Lys Gly Asp Tyr Ser Val Leu Val
1280 1285 1290

Pro Gly Leu Arg Asn Thr Ile Ala Leu Asp Phe His Leu Ser Gln
1295 1300 1305

Ser Ala Leu Tyr Trp Thr Asp Val Val Glu Asp Lys Ile Tyr Arg
1310 1315 1320

Gly Lys Leu Leu Asp Asn Gly Ala Leu Thr Ser Phe Glu Val Val
1325 1330 1335

Ile Gln Tyr Gly Leu Ala Thr Pro Glu Gly Leu Ala Val Asp Trp
1340 1345 1350

Ile Ala Gly Asn Ile Tyr Trp Val Glu Ser Asn Leu Asp Gln Ile
1355 1360 1365

Glu Val Ala Lys Leu Asp Gly Thr Leu Arg Thr Thr Leu Leu Ala
1370 1375 1380

Gly Asp Ile Glu His Pro Arg Ala Ile Ala Leu Asp Pro Arg Asp
1385 1390 1395

Gly Ile Leu Phe Trp Thr Asp Trp Asp Ala Ser Leu Pro Arg Ile
1400 1405 1410

```
Glu Ala  Ala Ser Met Ser Gly  Ala Gly Arg Arg Thr  Val His Arg
    1415                 1420                 1425

Glu Thr  Gly Ser Gly Gly Trp  Pro Asn Gly Leu Thr  Val Asp Tyr
    1430                 1435                 1440

Leu Glu  Lys Arg Ile Leu Trp  Ile Asp Ala Arg Ser  Asp Ala Ile
    1445                 1450                 1455

Tyr Ser  Ala Arg Tyr Asp Gly  Ser Gly His Met Glu  Val Leu Arg
    1460                 1465                 1470

Gly His  Glu Phe Leu Ser His  Pro Phe Ala Val Thr  Leu Tyr Gly
    1475                 1480                 1485

Gly Glu  Val Tyr Trp Thr Asp  Trp Arg Thr Asn Thr  Leu Ala Lys
    1490                 1495                 1500

Ala Asn  Lys Trp Thr Gly His  Asn Val Thr Val Val  Gln Arg Thr
    1505                 1510                 1515

Asn Thr  Gln Pro Phe Asp Leu  Gln Val Tyr His Pro  Ser Arg Gln
    1520                 1525                 1530

Pro Met  Ala Pro Asn Pro Cys  Glu Ala Asn Gly Gly  Gln Gly Pro
    1535                 1540                 1545

Cys Ser  His Leu Cys Leu Ile  Asn Tyr Asn Arg Thr  Val Ser Cys
    1550                 1555                 1560

Ala Cys  Pro His Leu Met Lys  Leu His Lys Asp Asn  Thr Thr Cys
    1565                 1570                 1575

Tyr Glu  Phe Lys Lys Phe Leu  Leu Tyr Ala Arg Gln  Met Glu Ile
    1580                 1585                 1590

Arg Gly  Val Asp Leu Asp Ala  Pro Tyr Tyr Asn Tyr  Ile Ile Ser
    1595                 1600                 1605

Phe Thr  Val Pro Asp Ile Asp  Asn Val Thr Val Leu  Asp Tyr Asp
    1610                 1615                 1620

Ala Arg  Glu Gln Arg Val Tyr  Trp Ser Asp Val Arg  Thr Gln Ala
    1625                 1630                 1635

Ile Lys  Arg Ala Phe Ile Asn  Gly Thr Gly Val Glu  Thr Val Val
    1640                 1645                 1650

Ser Ala  Asp Leu Pro Asn Ala  His Gly Leu Ala Val  Asp Trp Val
    1655                 1660                 1665

Ser Arg  Asn Leu Phe Trp Thr  Ser Tyr Asp Thr Asn  Lys Lys Gln
    1670                 1675                 1680

Ile Asn  Val Ala Arg Leu Asp  Gly Ser Phe Lys Asn  Ala Val Val
    1685                 1690                 1695

Gln Gly  Leu Glu Gln Pro His  Gly Leu Val Val His  Pro Leu Arg
    1700                 1705                 1710

Gly Lys  Leu Tyr Trp Thr Asp  Gly Asp Asn Ile Ser  Met Ala Asn
    1715                 1720                 1725

Met Asp  Gly Ser Asn Arg Thr  Leu Leu Phe Ser Gly  Gln Lys Gly
    1730                 1735                 1740

Pro Val  Gly Leu Ala Ile Asp  Phe Pro Glu Ser Lys  Leu Tyr Trp
    1745                 1750                 1755

Ile Ser  Ser Gly Asn His Thr  Ile Asn Arg Cys Asn  Leu Asp Gly
    1760                 1765                 1770

Ser Gly  Leu Glu Val Ile Asp  Ala Met Arg Ser Gln  Leu Gly Lys
    1775                 1780                 1785

Ala Thr  Ala Leu Ala Ile Met  Gly Asp Lys Leu Trp  Trp Ala Asp
    1790                 1795                 1800

Gln Val  Ser Glu Lys Met Gly  Thr Cys Ser Lys Ala  Asp Gly Ser
```

```
    1805                1810                1815

Gly Ser  Val Val Leu Arg Asn  Ser Thr Thr Leu Val  Met His Met
    1820                1825                1830

Lys Val  Tyr Asp Glu Ser Ile  Gln Leu Asp His Lys  Gly Thr Asn
    1835                1840                1845

Pro Cys  Ser Val Asn Asn Gly  Asp Cys Ser Gln Leu  Cys Leu Pro
    1850                1855                1860

Thr Ser  Glu Thr Thr Arg Ser  Cys Met Cys Thr Ala  Gly Tyr Ser
    1865                1870                1875

Leu Arg  Ser Gly Gln Gln Ala  Cys Glu Gly Val Gly  Ser Phe Leu
    1880                1885                1890

Leu Tyr  Ser Val His Glu Gly  Ile Arg Gly Ile Pro  Leu Asp Pro
    1895                1900                1905

Asn Asp  Lys Ser Asp Ala Leu  Val Pro Val Ser Gly  Thr Ser Leu
    1910                1915                1920

Ala Val  Gly Ile Asp Phe His  Ala Glu Asn Asp Thr  Ile Tyr Trp
    1925                1930                1935

Val Asp  Met Gly Leu Ser Thr  Ile Ser Arg Ala Lys  Arg Asp Gln
    1940                1945                1950

Thr Trp  Arg Glu Asp Val Val  Thr Asn Gly Ile Gly  Arg Val Glu
    1955                1960                1965

Gly Ile  Ala Val Asp Trp Ile  Ala Gly Asn Ile Tyr  Trp Thr Asp
    1970                1975                1980

Gln Gly  Phe Asp Val Ile Glu  Val Ala Arg Leu Asn  Gly Ser Phe
    1985                1990                1995

Arg Tyr  Val Val Ile Ser Gln  Gly Leu Asp Lys Pro  Arg Ala Ile
    2000                2005                2010

Thr Val  His Pro Glu Lys Gly  Tyr Leu Phe Trp Thr  Glu Trp Gly
    2015                2020                2025

Gln Tyr  Pro Arg Ile Glu Arg  Ser Arg Leu Asp Gly  Thr Glu Arg
    2030                2035                2040

Val Val  Leu Val Asn Val Ser  Ile Ser Trp Pro Asn  Gly Ile Ser
    2045                2050                2055

Val Asp  Tyr Gln Asp Gly Lys  Leu Tyr Trp Cys Asp  Ala Arg Thr
    2060                2065                2070

Asp Lys  Ile Glu Arg Ile Asp  Leu Glu Thr Gly Glu  Asn Arg Glu
    2075                2080                2085

Val Val  Leu Ser Ser Asn Asn  Met Asp Met Phe Ser  Val Ser Val
    2090                2095                2100

Phe Glu  Asp Phe Ile Tyr Trp  Ser Asp Arg Thr His  Ala Asn Gly
    2105                2110                2115

Ser Ile  Lys Arg Gly Ser Lys  Asp Asn Ala Thr Asp  Ser Val Pro
    2120                2125                2130

Leu Arg  Thr Gly Ile Gly Val  Gln Leu Lys Asp Ile  Lys Val Phe
    2135                2140                2145

Asn Arg  Asp Arg Gln Lys Gly  Thr Asn Val Cys Ala  Val Ala Asn
    2150                2155                2160

Gly Gly  Cys Gln Gln Leu Cys  Leu Tyr Arg Gly Arg  Gly Gln Arg
    2165                2170                2175

Ala Cys  Ala Cys Ala His Gly  Met Leu Ala Glu Asp  Gly Ala Ser
    2180                2185                2190

Cys Arg  Glu Tyr Ala Gly Tyr  Leu Leu Tyr Ser Glu  Arg Thr Ile
    2195                2200                2205
```

```
Leu Lys Ser Ile His Leu Ser Asp Glu Arg Asn Leu Asn Ala Pro
    2210                2215                2220

Val Gln Pro Phe Glu Asp Pro Glu His Met Lys Asn Val Ile Ala
    2225                2230                2235

Leu Ala Phe Asp Tyr Arg Ala Gly Thr Ser Pro Gly Thr Pro Asn
    2240                2245                2250

Arg Ile Phe Phe Ser Asp Ile His Phe Gly Asn Ile Gln Gln Ile
    2255                2260                2265

Asn Asp Asp Gly Ser Arg Arg Ile Thr Ile Val Glu Asn Val Gly
    2270                2275                2280

Ser Val Glu Gly Leu Ala Tyr His Arg Gly Trp Asp Thr Leu Tyr
    2285                2290                2295

Trp Thr Ser Tyr Thr Thr Ser Thr Ile Thr Arg His Thr Val Asp
    2300                2305                2310

Gln Thr Arg Pro Gly Ala Phe Glu Arg Glu Thr Val Ile Thr Met
    2315                2320                2325

Ser Gly Asp Asp His Pro Arg Ala Phe Val Leu Asp Glu Cys Gln
    2330                2335                2340

Asn Leu Met Phe Trp Thr Asn Trp Asn Glu Gln His Pro Ser Ile
    2345                2350                2355

Met Arg Ala Ala Leu Ser Gly Ala Asn Val Leu Thr Leu Ile Glu
    2360                2365                2370

Lys Asp Ile Arg Thr Pro Asn Gly Leu Ala Ile Asp His Arg Ala
    2375                2380                2385

Glu Lys Leu Tyr Phe Ser Asp Ala Thr Leu Asp Lys Ile Glu Arg
    2390                2395                2400

Cys Glu Tyr Asp Gly Ser His Arg Tyr Val Ile Leu Lys Ser Glu
    2405                2410                2415

Pro Val His Pro Phe Gly Leu Ala Val Tyr Gly Glu His Ile Phe
    2420                2425                2430

Trp Thr Asp Trp Val Arg Arg Ala Val Gln Arg Ala Asn Lys His
    2435                2440                2445

Val Gly Ser Asn Met Lys Leu Leu Arg Val Asp Ile Pro Gln Gln
    2450                2455                2460

Pro Met Gly Ile Ile Ala Val Ala Asn Asp Thr Asn Ser Cys Glu
    2465                2470                2475

Leu Ser Pro Cys Arg Ile Asn Asn Gly Gly Cys Gln Asp Leu Cys
    2480                2485                2490

Leu Leu Thr His Gln Gly His Val Asn Cys Ser Cys Arg Gly Gly
    2495                2500                2505

Arg Ile Leu Gln Asp Asp Leu Thr Cys Arg Ala Val Asn Ser Ser
    2510                2515                2520

Cys Arg Ala Gln Asp Glu Phe Glu Cys Ala Asn Gly Glu Cys Ile
    2525                2530                2535

Asn Phe Ser Leu Thr Cys Asp Gly Val Pro His Cys Lys Asp Lys
    2540                2545                2550

Ser Asp Glu Lys Pro Ser Tyr Cys Asn Ser Arg Arg Cys Lys Lys
    2555                2560                2565

Thr Phe Arg Gln Cys Ser Asn Gly Arg Cys Val Ser Asn Met Leu
    2570                2575                2580

Trp Cys Asn Gly Ala Asp Asp Cys Gly Asp Gly Ser Asp Glu Ile
    2585                2590                2595
```

-continued

```
Pro Cys Asn Lys Thr Ala Cys Gly Val Gly Glu Phe Arg Cys Arg
    2600                2605                2610

Asp Gly Thr Cys Ile Gly Asn Ser Ser Arg Cys Asn Gln Phe Val
    2615                2620                2625

Asp Cys Glu Asp Ala Ser Asp Glu Met Asn Cys Ser Ala Thr Asp
    2630                2635                2640

Cys Ser Ser Tyr Phe Arg Leu Gly Val Lys Gly Val Leu Phe Gln
    2645                2650                2655

Pro Cys Glu Arg Thr Ser Leu Cys Tyr Ala Pro Ser Trp Val Cys
    2660                2665                2670

Asp Gly Ala Asn Asp Cys Gly Asp Tyr Ser Asp Glu Arg Asp Cys
    2675                2680                2685

Pro Gly Val Lys Arg Pro Arg Cys Pro Leu Asn Tyr Phe Ala Cys
    2690                2695                2700

Pro Ser Gly Arg Cys Ile Pro Met Ser Trp Thr Cys Asp Lys Glu
    2705                2710                2715

Asp Asp Cys Glu His Gly Glu Asp Glu Thr His Cys Asn Lys Phe
    2720                2725                2730

Cys Ser Glu Ala Gln Phe Glu Cys Gln Asn His Arg Cys Ile Ser
    2735                2740                2745

Lys Gln Trp Leu Cys Asp Gly Ser Asp Asp Cys Gly Asp Gly Ser
    2750                2755                2760

Asp Glu Ala Ala His Cys Glu Gly Lys Thr Cys Gly Pro Ser Ser
    2765                2770                2775

Phe Ser Cys Pro Gly Thr His Val Cys Val Pro Glu Arg Trp Leu
    2780                2785                2790

Cys Asp Gly Asp Lys Asp Cys Ala Asp Gly Ala Asp Glu Ser Ile
    2795                2800                2805

Ala Ala Gly Cys Leu Tyr Asn Ser Thr Cys Asp Asp Arg Glu Phe
    2810                2815                2820

Met Cys Gln Asn Arg Gln Cys Ile Pro Lys His Phe Val Cys Asp
    2825                2830                2835

His Asp Arg Asp Cys Ala Asp Gly Ser Asp Glu Ser Pro Glu Cys
    2840                2845                2850

Glu Tyr Pro Thr Cys Gly Pro Ser Glu Phe Arg Cys Ala Asn Gly
    2855                2860                2865

Arg Cys Leu Ser Ser Arg Gln Trp Glu Cys Asp Gly Glu Asn Asp
    2870                2875                2880

Cys His Asp Gln Ser Asp Glu Ala Pro Lys Asn Pro His Cys Thr
    2885                2890                2895

Ser Gln Glu His Lys Cys Asn Ala Ser Ser Gln Phe Leu Cys Ser
    2900                2905                2910

Ser Gly Arg Cys Val Ala Glu Ala Leu Leu Cys Asn Gly Gln Asp
    2915                2920                2925

Asp Cys Gly Asp Ser Ser Asp Glu Arg Gly Cys His Ile Asn Glu
    2930                2935                2940

Cys Leu Ser Arg Lys Leu Ser Gly Cys Ser Gln Asp Cys Glu Asp
    2945                2950                2955

Leu Lys Ile Gly Phe Lys Cys Arg Cys Arg Pro Gly Phe Arg Leu
    2960                2965                2970

Lys Asp Asp Gly Arg Thr Cys Ala Asp Val Asp Glu Cys Ser Thr
    2975                2980                2985

Thr Phe Pro Cys Ser Gln Arg Cys Ile Asn Thr His Gly Ser Tyr
```

-continued

```
    2990                2995                3000

Lys Cys  Leu Cys Val Glu Gly  Tyr Ala Pro Arg Gly  Gly Asp Pro
    3005                3010                3015

His Ser  Cys Lys Ala Val Thr  Asp Glu Glu Pro Phe  Leu Ile Phe
    3020                3025                3030

Ala Asn  Arg Tyr Tyr Leu Arg  Lys Leu Asn Leu Asp  Gly Ser Asn
    3035                3040                3045

Tyr Thr  Leu Leu Lys Gln Gly  Leu Asn Asn Ala Val  Ala Leu Asp
    3050                3055                3060

Phe Asp  Tyr Arg Glu Gln Met  Ile Tyr Trp Thr Asp  Val Thr Thr
    3065                3070                3075

Gln Gly  Ser Met Ile Arg Arg  Met His Leu Asn Gly  Ser Asn Val
    3080                3085                3090

Gln Val  Leu His Arg Thr Gly  Leu Ser Asn Pro Asp  Gly Leu Ala
    3095                3100                3105

Val Asp  Trp Val Gly Gly Asn  Leu Tyr Trp Cys Asp  Lys Gly Arg
    3110                3115                3120

Asp Thr  Ile Glu Val Ser Lys  Leu Asn Gly Ala Tyr  Arg Thr Val
    3125                3130                3135

Leu Val  Ser Ser Gly Leu Arg  Glu Pro Arg Ala Leu  Val Val Asp
    3140                3145                3150

Val Gln  Asn Gly Tyr Leu Tyr  Trp Thr Asp Trp Gly  Asp His Ser
    3155                3160                3165

Leu Ile  Gly Arg Ile Gly Met  Asp Gly Ser Ser Arg  Ser Val Ile
    3170                3175                3180

Val Asp  Thr Lys Ile Thr Trp  Pro Asn Gly Leu Thr  Leu Asp Tyr
    3185                3190                3195

Val Thr  Glu Arg Ile Tyr Trp  Ala Asp Ala Arg Glu  Asp Tyr Ile
    3200                3205                3210

Glu Phe  Ala Ser Leu Asp Gly  Ser Asn Arg His Val  Val Leu Ser
    3215                3220                3225

Gln Asp  Ile Pro His Ile Phe  Ala Leu Thr Leu Phe  Glu Asp Tyr
    3230                3235                3240

Val Tyr  Trp Thr Asp Trp Glu  Thr Lys Ser Ile Asn  Arg Ala His
    3245                3250                3255

Lys Thr  Thr Gly Thr Asn Lys  Thr Leu Leu Ile Ser  Thr Leu His
    3260                3265                3270

Arg Pro  Met Asp Leu His Val  Phe His Ala Leu Arg  Gln Pro Asp
    3275                3280                3285

Val Pro  Asn His Pro Cys Lys  Val Asn Asn Gly Gly  Cys Ser Asn
    3290                3295                3300

Leu Cys  Leu Leu Ser Pro Gly  Gly Gly His Lys Cys  Ala Cys Pro
    3305                3310                3315

Thr Asn  Phe Tyr Leu Gly Ser  Asp Gly Arg Thr Cys  Val Ser Asn
    3320                3325                3330

Cys Thr  Ala Ser Gln Phe Val  Cys Lys Asn Asp Lys  Cys Ile Pro
    3335                3340                3345

Phe Trp  Trp Lys Cys Asp Thr  Glu Asp Asp Cys Gly  Asp His Ser
    3350                3355                3360

Asp Glu  Pro Pro Asp Cys Pro  Glu Phe Lys Cys Arg  Pro Gly Gln
    3365                3370                3375

Phe Gln  Cys Ser Thr Gly Ile  Cys Thr Asn Pro Ala  Phe Ile Cys
    3380                3385                3390
```

-continued

```
Asp Gly Asp Asn Asp Cys Gln Asp Asn Ser Asp Glu Ala Asn Cys
    3395                3400                3405

Asp Ile His Val Cys Leu Pro Ser Gln Phe Lys Cys Thr Asn Thr
    3410                3415                3420

Asn Arg Cys Ile Pro Gly Ile Phe Arg Cys Asn Gly Gln Asp Asn
    3425                3430                3435

Cys Gly Asp Gly Glu Asp Glu Arg Asp Cys Pro Glu Val Thr Cys
    3440                3445                3450

Ala Pro Asn Gln Phe Gln Cys Ser Ile Thr Lys Arg Cys Ile Pro
    3455                3460                3465

Arg Val Trp Val Cys Asp Arg Asp Asn Asp Cys Val Asp Gly Ser
    3470                3475                3480

Asp Glu Pro Ala Asn Cys Thr Gln Met Thr Cys Gly Val Asp Glu
    3485                3490                3495

Phe Arg Cys Lys Asp Ser Gly Arg Cys Ile Pro Ala Arg Trp Lys
    3500                3505                3510

Cys Asp Gly Glu Asp Asp Cys Gly Asp Gly Ser Asp Glu Pro Lys
    3515                3520                3525

Glu Glu Cys Asp Glu Arg Thr Cys Glu Pro Tyr Gln Phe Arg Cys
    3530                3535                3540

Lys Asn Asn Arg Cys Val Pro Gly Arg Trp Gln Cys Asp Tyr Asp
    3545                3550                3555

Asn Asp Cys Gly Asp Asn Ser Asp Glu Glu Ser Cys Thr Pro Arg
    3560                3565                3570

Pro Cys Ser Glu Ser Glu Phe Ser Cys Ala Asn Gly Arg Cys Ile
    3575                3580                3585

Ala Gly Arg Trp Lys Cys Asp Gly Asp His Asp Cys Ala Asp Gly
    3590                3595                3600

Ser Asp Glu Lys Asp Cys Thr Pro Arg Cys Asp Met Asp Gln Phe
    3605                3610                3615

Gln Cys Lys Ser Gly His Cys Ile Pro Leu Arg Trp Arg Cys Asp
    3620                3625                3630

Ala Asp Ala Asp Cys Met Asp Gly Ser Asp Glu Glu Ala Cys Gly
    3635                3640                3645

Thr Gly Val Arg Thr Cys Pro Leu Asp Glu Phe Gln Cys Asn Asn
    3650                3655                3660

Thr Leu Cys Lys Pro Leu Ala Trp Lys Cys Asp Gly Glu Asp Asp
    3665                3670                3675

Cys Gly Asp Asn Ser Asp Glu Asn Pro Glu Glu Cys Ala Arg Phe
    3680                3685                3690

Val Cys Pro Pro Asn Arg Pro Phe Arg Cys Lys Asn Asp Arg Val
    3695                3700                3705

Cys Leu Trp Ile Gly Arg Gln Cys Asp Gly Thr Asp Asn Cys Gly
    3710                3715                3720

Asp Gly Thr Asp Glu Glu Asp Cys Glu Pro Pro Thr Ala His Thr
    3725                3730                3735

Thr His Cys Lys Asp Lys Lys Glu Phe Leu Cys Arg Asn Gln Arg
    3740                3745                3750

Cys Leu Ser Ser Ser Leu Arg Cys Asn Met Phe Asp Asp Cys Gly
    3755                3760                3765

Asp Gly Ser Asp Glu Glu Asp Cys Ser Ile Asp Pro Lys Leu Thr
    3770                3775                3780
```

Ser Cys Ala Thr Asn Ala Ser Ile Cys Gly Asp Glu Ala Arg Cys
3785 3790 3795

Val Arg Thr Glu Lys Ala Ala Tyr Cys Ala Cys Arg Ser Gly Phe
3800 3805 3810

His Thr Val Pro Gly Gln Pro Gly Cys Gln Asp Ile Asn Glu Cys
3815 3820 3825

Leu Arg Phe Gly Thr Cys Ser Gln Leu Cys Asn Asn Thr Lys Gly
3830 3835 3840

Gly His Leu Cys Ser Cys Ala Arg Asn Phe Met Lys Thr His Asn
3845 3850 3855

Thr Cys Lys Ala Glu Gly Ser Glu Tyr Gln Val Leu Tyr Ile Ala
3860 3865 3870

Asp Asp Asn Glu Ile Arg Ser Leu Phe Pro Gly His Pro His Ser
3875 3880 3885

Ala Tyr Glu Gln Ala Phe Gln Gly Asp Glu Ser Val Arg Ile Asp
3890 3895 3900

Ala Met Asp Val His Val Lys Ala Gly Arg Val Tyr Trp Thr Asn
3905 3910 3915

Trp His Thr Gly Thr Ile Ser Tyr Arg Ser Leu Pro Pro Ala Ala
3920 3925 3930

Pro Pro Thr Thr Ser Asn Arg His Arg Arg Gln Ile Asp Arg Gly
3935 3940 3945

Val Thr His Leu Asn Ile Ser Gly Leu Lys Met Pro Arg Gly Ile
3950 3955 3960

Ala Ile Asp Trp Val Ala Gly Asn Val Tyr Trp Thr Asp Ser Gly
3965 3970 3975

Arg Asp Val Ile Glu Val Ala Gln Met Lys Gly Glu Asn Arg Lys
3980 3985 3990

Thr Leu Ile Ser Gly Met Ile Asp Glu Pro His Ala Ile Val Val
3995 4000 4005

Asp Pro Leu Arg Gly Thr Met Tyr Trp Ser Asp Trp Gly Asn His
4010 4015 4020

Pro Lys Ile Glu Thr Ala Ala Met Asp Gly Thr Leu Arg Glu Thr
4025 4030 4035

Leu Val Gln Asp Asn Ile Gln Trp Pro Thr Gly Leu Ala Val Asp
4040 4045 4050

Tyr His Asn Glu Arg Leu Tyr Trp Ala Asp Ala Lys Leu Ser Val
4055 4060 4065

Ile Gly Ser Ile Arg Leu Asn Gly Thr Asp Pro Ile Val Ala Ala
4070 4075 4080

Asp Ser Lys Arg Gly Leu Ser His Pro Phe Ser Ile Asp Val Phe
4085 4090 4095

Glu Asp Tyr Ile Tyr Gly Val Thr Tyr Ile Asn Asn Arg Val Phe
4100 4105 4110

Lys Ile His Lys Phe Gly His Ser Pro Leu Val Asn Leu Thr Gly
4115 4120 4125

Gly Leu Ser His Ala Ser Asp Val Val Leu Tyr His Gln His Lys
4130 4135 4140

Gln Pro Glu Val Thr Asn Pro Cys Asp Arg Lys Lys Cys Glu Trp
4145 4150 4155

Leu Cys Leu Leu Ser Pro Ser Gly Pro Val Cys Thr Cys Pro Asn
4160 4165 4170

Gly Lys Arg Leu Asp Asn Gly Thr Cys Val Pro Val Pro Ser Pro 4175 4180 4185

Thr Pro Pro Pro Asp Ala Pro Arg Pro Gly Thr Cys Asn Leu Gln
4190 4195 4200

Cys Phe Asn Gly Gly Ser Cys Phe Leu Asn Ala Arg Arg Gln Pro
4205 4210 4215

Lys Cys Arg Cys Gln Pro Arg Tyr Thr Gly Asp Lys Cys Glu Leu
4220 4225 4230

Asp Gln Cys Trp Glu His Cys Arg Asn Gly Gly Thr Cys Ala Ala
4235 4240 4245

Ser Pro Ser Gly Met Pro Thr Cys Arg Cys Pro Thr Gly Phe Thr
4250 4255 4260

Gly Pro Lys Cys Thr Gln Gln Val Cys Ala Gly Tyr Cys Ala Asn
4265 4270 4275

Asn Ser Thr Cys Thr Val Asn Gln Gly Asn Gln Pro Gln Cys Arg
4280 4285 4290

Cys Leu Pro Gly Phe Leu Gly Asp Arg Cys Gln Tyr Arg Gln Cys
4295 4300 4305

Ser Gly Tyr Cys Glu Asn Phe Gly Thr Cys Gln Met Ala Ala Asp
4310 4315 4320

Gly Ser Arg Gln Cys Arg Cys Thr Ala Tyr Phe Glu Gly Ser Arg
4325 4330 4335

Cys Glu Val Asn Lys Cys Ser Arg Cys Leu Glu Gly Ala Cys Val
4340 4345 4350

Val Asn Lys Gln Ser Gly Asp Val Thr Cys Asn Cys Thr Asp Gly
4355 4360 4365

Arg Val Ala Pro Ser Cys Leu Thr Cys Val Gly His Cys Ser Asn
4370 4375 4380

Gly Gly Ser Cys Thr Met Asn Ser Lys Met Met Pro Glu Cys Gln
4385 4390 4395

Cys Pro Pro His Met Thr Gly Pro Arg Cys Glu Glu His Val Phe
4400 4405 4410

Ser Gln Gln Gln Pro Gly His Ile Ala Ser Ile Leu Ile Pro Leu
4415 4420 4425

Leu Leu Leu Leu Leu Leu Val Leu Val Ala Gly Val Val Phe Trp
4430 4435 4440

Tyr Lys Arg Arg Val Gln Gly Ala Lys Gly Phe Gln His Gln Arg
4445 4450 4455

Met Thr Asn Gly Ala Met Asn Val Glu Ile Gly Asn Pro Thr Tyr
4460 4465 4470

Lys Met Tyr Glu Gly Gly Glu Pro Asp Asp Val Gly Gly Leu Leu
4475 4480 4485

Asp Ala Asp Phe Ala Leu Asp Pro Asp Lys Pro Thr Asn Phe Thr
4490 4495 4500

Asn Pro Val Tyr Ala Thr Leu Tyr Met Gly Gly His Gly Ser Arg
4505 4510 4515

His Ser Leu Ala Ser Thr Asp Glu Lys Arg Glu Leu Leu Gly Arg
4520 4525 4530

Gly Pro Glu Asp Glu Ile Gly Asp Pro Leu Ala
4535 4540

<210> SEQ ID NO 11
<211> LENGTH: 7783
<212> TYPE: RNA
<213> ORGANISM: Homo sapiens

<400> SEQUENCE: 11
gcuggcggcg gccgcccagg gccggggccg cgcgcccagc cugagcccgc cccgccgccg 60
agcgucaccg aaccugcuug aaaugcagcc gaggagccgg ggcgggcggc agcggcggcg 120
gcggcggcgg cgggggcagc ggcaaccccg gcgccgcggc aaggacucgg agggcugaga 180
cgcggcggcg gcggcgcggg gagcgcgggg cgcggcggcc ggagccccgg gcccgccaug 240
ggccuccccg agccgggccc ucuccggcuu cuggcgcugc ugcugcugcu gcugcugcug 300
cugcugcugc agcuccagca ucuugcggcg gcagcggcug auccgcugcu cggcggccaa 360
gggccggcca aggauugcga aaaggaccaa uuccagugcc ggaacgagcg cugcaucccc 420
ucugugugga gaugcgacga ggacgaugac ugcuuagacc acagcgacga ggacgacugc 480
cccaagaaga ccugugcaga cagugacuuc accugugaca acggccacug cauccacgaa 540
cgguggaagu gugacggcga ggaggagugu ccugauggcu ccgaugaguc cgaggccacu 600
ugcaccaagc aggugugucc ugcagagaag cugagcugug gacccaccag ccacaagugu 660
guaccugccu cguggcgcug cgacggggag aaggacugcg aggguggagc ggaugaggcc 720
ggcugugcua ccuugugcgc cccgcacgag uuccagugcg gcaaccgcuc gugccuggcc 780
gccguguucg ugugcgacgg cgacgacgac uguggugacg gcagcgauga gcgcggcugu 840
gcagacccgg ccugcgggcc ccgcgaguuc cgcugcggcg gcgauggcgg cggcgccugc 900
aucccggagc gcugggucug cgaccgccag uuugacugcg aggaccgcuc ggacgaggca 960
gccgagcucu gcggccgucc gggccccggg gccacguccg cgcccgccgc cugcgccacc 1020
gccucccagu ucgccugccg cagcggcgag ugcgugcacc ugggcuggcg cugcgacggc 1080
gaccgcgacu gcaaagacaa aucggacgag gccgacugcc cacugggcac cugccguggg 1140
gacgaguucc agugugggga ugggacaugu guccuugcaa ucaagcacug caaccaggag 1200
caggacuguc cagaugggag ugaugaagcu ggcugccuac aggggcugaa cgagugucug 1260
cacaacaaug gcggcugcuc acacaucugc acugaccuca agauuggcuu ugaaugcacg 1320
ugcccagcag gcuuccagcu ccuggaccag aagaccugug gcgacauuga ugagugcaag 1380
gacccagaug ccugcagcca gaucugugcc aauuacaagg gcuauuuuaa gugugagugc 1440
uacccuggcu acgagaugga ccuacugacc aagaacugca aggcugcugc uggcaagagc 1500
ccaucccuaa ucuucaccaa ccggcacgag gugcggagga ucgaccuggu gaagcggaac 1560
uauucacgcc ucauccccau gcucaagaau gucguggcac uagaugugga aguugccacc 1620
aaucgcaucu acuggugugu ccucuccuac cguaagaucu auagcgccua cauggacaag 1680
gccagugacc cgaaagagca ggaggucuc auugacgagc aguugcacuc uccagagggc 1740
cuggcagugg acugggucca caagcacauc uacuggacug acucgggcaa uaagaccauc 1800
ucaguggcca caguugaugg uggccgccga cgcacucucu ucagccguaa ccucagugaa 1860
ccccgggcca ucgcuguuga cccccugcga ggguucaugu auuggucuga cugggggggac 1920
caggccaaga uugagaaauc ugggcucaac ggugugggacc ggcaaacacu ggugucagac 1980
aauauugaau ggcccaacgg aaucacccug gaucugcuga gccagcgcuu guacuggua 2040
gacuccaagc uacaccaacu guccagcauu gacuucagug gaggcaacag aaagacgcug 2100
aucuccucca cugacuuccu gagccacccu uuugggauag cuguguuuga ggacaaggug 2160
uucuggacag accuggagaa cgaggccauu uucagugcaa aucggcucaa uggccuggaa 2220
aucuccaucc uggcugagaa ccucaacaac ccacaugaca uugucaucuu ccaugagcug 2280

-continued

```
aagcagccaa gagcuccaga ugccugugag cugagugucc agccuaaugg aggcugugaa   2340
uaccugugcc uuccugcucc ucagaucucc agccacucuc ccaaguacac augugccugu   2400
ccugacacaa uguggcuggg uccagacaug aagaggugcu accgagcacc ucaaucuacc   2460
ucaacuacga cguuagcuuc uaccaugacg aggacaguac cugccaccac aagagccccc   2520
gggaccaccg uccacagauc caccuaccag aaccacagca cagagacacc aagccugaca   2580
gcugcagucc caagcucagu uagugucccc agggcuccca gcaucagccc gucuacccua   2640
agcccugcaa ccagcaacca cucccagcac uaugcaaaug aagacaguaa gaugggcuca   2700
acagucacug ccgcuguuau cgggaucauc gugcccauag uggugauagc ccuccugugc   2760
augaguggau accugaucug gagaaacugg aagcggaaga acaccaaaag caugaauuuu   2820
gacaacccag ucuacaggaa aacaacagaa gaagaagacg aagaugagcu ccauauaggg   2880
agaacugcuc agauuggcca ugucuauccu gcagcaauca gcagcuuuga ucgcccacug   2940
ugggcagagc ccugucuugg ggagaccaga gaaccggaag acccagcccc ugcccucaag   3000
gagcuuuuug ucuugccggg ggaaccaagg ucacagcugc accaacuccc gaagaacccu   3060
cuuuccgagc ugccugucgu caaauccaag cgaguggcau uaagccuuga agaugaugga   3120
cuacccugag gaugggauca cccccuucgu gccucaugga auucaguccc augcacuaca   3180
cucuggaugg uguaugacug gaugaauggg uuucuauaua ugggucugug ugaguguaug   3240
ugugugugug auuuuuuuuu uaaauuuaug uugcggaaag guaaccacaa aguuaugaug   3300
aacugcaaac auccaaagga ugugagaguu uuucuaugua uaauguuuua uacacuuuuu   3360
aacugguugc acuacccaug aggaauucgu ggaauggcua cugcugacua acaugaugca   3420
cauaaccaaa uggggggccaa uggcacagua ccuuacucau cauuuaaaaa cuauauuuac   3480
agaagauguu ugguugcugg gggggcuuuu uuagguuuug gggcauuugu uuuuuguaaa   3540
uaagaugauu augcuuugug gcuauccauc aacauaagua aaaaaaaaaa aaaaacacuu   3600
caacucccuc ccccauuuag auuauuuauu aacauauuuu aaaaaucaga ugaguucuau   3660
aaauaauuua gagaagugag aguauuuauu uuuggcaugu uuggcccacc acacagacuc   3720
ugugugugua ugugugugu uauaugugua ugugugugac agaaaaaucu guagagaaga   3780
ggcacaucua uggcuacugu ucaaauacau aaagauaaau uuauuuucac acaguccaca   3840
agggguauau cuuguaguuu ucagaaaagc cuuuggaaau cuggaucaga aaauagauac   3900
caugguuugu gcaauuaugu aguaaaaaag gcaaaucuuu ucaccucugg cuauuccuga   3960
gaccccagga agucaggaaa agccuuucag cucacccaug gcugcuguga cuccuaccag   4020
ggcuuucuug gcuuuggcga aggucagugu acagacauuc caugguacca gagugcucag   4080
aaacucaaga uaggauaugc cucacccuca gcuacuccuu guuuuaaagu ucagcucuuu   4140
gaguaacuuc uucaauuucu uucaggacac uuggguugaa uucaguaagu uuccucugaa   4200
gcacccugaa gggugccauc cuuacagagc uaaguggaga cguuuccaga ucagcccaag   4260
uuuacuauag agacuggccc aggcacugaa ugucuaggac augcugugga ugaagauaaa   4320
gaugguggaa uagguuuuau cacaucucuu auuucucuuu uccccuuacu cucuaccauu   4380
uccuuuaugu ggggaaacau uuuaagguaa uaaauagguu acuuaccauc auauguucau   4440
auagaugaaa cuaauuuuug gcuuaaguca gaacaacugg ccaaaauuga agucauauuu   4500
gagggggggaa auggcauacg caauauuaua uuauauugga uauuuauguu cacacaggaa   4560
uugguuuac ugcuuuguaa auaaaaggaa aaacuccggg uauauguaua gauguucuuc   4620
auuauagaca ucuucuuugc uuuucuuggc cuugggggag gaagggagaa gugcucuuuu   4680
```

-continued

```
cuacuugugg ggucucccau uggaaacaua auccuauagu cccagaagga uucagucccc   4740
aguggcuuuc ccauccaaag agaaagaguu ugaguuucuu aacucugcug uucugccacu   4800
uacucccacu agacaaccag ggacaaggug caacauggaa guguuugacu uaaguaggag   4860
cagaggagcu gcaucuaauc ucaucauacc uggaacuuga cacacuuaag caaaugccuu   4920
cccaucccua ccugccagau gcccccaacu caaugaaguu ggaugucuca ccagcuugau   4980
acccuuugaa uuuucaguca gacauucugg aguucuagca uccuguaccu aggaccuucc   5040
ucugugucac ucuuggccuc cuaaacucua agaaaauaac uauauucugg agcuugggca   5100
guguguuuug cauaauccag caaucuccuc augacaugca uguguugaua guccugaaac   5160
auucauugag aggguaaaug caguugaccu agaaugacca auaccaaaca gaauuuuaag   5220
aacagguggc caacuccuau ggagcuuacu cacauauuac uauucuuuua agaacggaaa   5280
guaaaauuau uuuugacuga agaaaaauga ugacagugaa aaacauggaa auguacucaa   5340
aacaagugac uuuuucugua accuuccaaa gaaacugaau uuuccaagga auuaaaugau   5400
aacaguggcu aaggcauagu uucuaaacuu ucaguaagau ccuggcauuc acagaaaaaa   5460
augaugaaug ggucuggac auacagccug agaucucaaa augacaauga aauucacaac   5520
uuuuucucag agacauucau guuuccugca uaugcuacaa cugcaguuug aaagaggcag   5580
caaugggagc aacccuuuac aagaaacaaa uugugauaua uucauguguu ggacggcagu   5640
aaauaagaug aaaccugagg agucagaucc accuuccccc auucauagag gcuuuucagc   5700
cucauuuuga gguacaguua cauaucuuuu gccuuuugcc cccgugcaua gcuaucuaca   5760
gccaaucaca gaucacagag ucacuggacu auagagcugg aaggaagcuc agagacaaug   5820
ccaagggggc agaaaauuua ucagaagcca gucccagugc guuuccucca uuuccuucug   5880
caggaagacu auuuugggcu gccugaacau uguaucaaac cugcuaccua uacuauggguc  5940
uaccuuuccu ccaguggaau uacaaaggca cuaacugaaa ugccuucuag aaacagagaa   6000
aacgaaacug uacuuauuua cucuugauac acagauuauu uauaaaacag auugaaguaa   6060
ccuguuaacu ggcaaaaaga gaaugagauc ggauuuaaau guauggcagu aaguccuauu   6120
gaucccucca guuaucucag uaugacugca guauauucau ucacuaaaac cacucacuag   6180
auaccaacua cacaccuggc acugcagaug uaaaggucag ucacacaugu ucugacuuua   6240
cagaguucac aguagcagug gaggaugaua uauguggaaa caaaaaaggc auugauucua   6300
uucagagcac uguuagggcu caaaggagag aggggucuuu ccaccuaaga aaugaggaau   6360
agggucauca uagaagugac cuuaagucuu aaaaauuaag aaggggauuc caagcugcuu   6420
cagacagaga cacaucgagc uaaaacacag agguaugaaa gagcacaggg acuuuaggaa   6480
uugcacaguu cauucuaaca ggaacaaaag gcucaagggg ggcaagaaau gaggcuguau   6540
ggaaagagau ucaauguaag cacuuuauaa aauagauuaa uuucugauuc aaugaagcau   6600
uucuugauca uuguguacaa ggcacuacau gcaucaugga aaauucauua ggaugcauug   6660
ccagcacuuu gcagaacuga uauuauucag ccucaagcuu uccaguggcc aaagggaaau   6720
gcugacugcu uuucauauau uugagucaaa gauuuuuuau auggucaaug aagacuaaua   6780
uaagggcagu gggauuuuca cagaugcaug ccauguuguc gagagccucu uagauuuucu   6840
caacugugag aaagaaaaac gaaaauguug aagacguuga gucuggagag gggauacuaa   6900
ucacugucca guugggcacu gguggggaaug gggaaauggc acaggaaugc aagccucucc  6960
acccuacccc ccgaacucca gccauacacu caucguuuca caaaauauaa augaguuagc   7020
```

```
auuaaauguu ucagaguaaa uaauuccuuu ucccgaaaug caugaagaua gaguaacaga   7080

cuucucacac uguauuuuua ggguauggag aauuuagaag guuaaagaau uacugcuuca   7140

auuuuucagu uaaaaaaaaa ucaggaagcu cuguucauuc aggcuaugca ccaugugcac   7200

agucaagaau uagcagaaac ccucugcauu uacaaacacu uugugcuaua aaaaaguaau   7260

uuuuaaaaag ccacgugugu guguguguau auauauauau auauauauau uuaaagccaa   7320

gguuuugaua cuuuuuuaca aaaacuacaa gagaaaacaa auauaccugu ccaaaccaua   7380

uacuuuuaaa agagcauuuu uuuuuccaua caagcuguug uuaauuuggg gguaaagugc   7440

ugauuugcaa acuucaucaa auuguuccca aguggauucu ccuuguuugu cuccccccuac   7500

caaccccaaa guuaccauau uugauguaag aaucaggcau guuagaaugu ugugucacac   7560

uaacugauuc ugcucuuuuu gucuugucau ucaaguuccg uuagcuucug uacgcggugc   7620

ccuuugcagu cuggugucuc uuccagaggc gagggggcug aggaugggu gcugcaucuc   7680

acuagcuaua cuggcaucau cuugguaaac ugaaaaccaa auguggacau uuguaaaauc   7740

agugcacugu uucuagagag agauuaaauu cauuuaaaaa aaa                     7783
```

```
<210> SEQ ID NO 12
<211> LENGTH: 963
<212> TYPE: PRT
<213> ORGANISM: Homo sapiens

<400> SEQUENCE: 12

Met Gly Leu Pro Glu Pro Gly Pro Leu Arg Leu Leu Ala Leu Leu Leu
1               5                   10                  15

Leu Leu Leu Leu Leu Leu Leu Leu Gln Leu Gln His Leu Ala Ala Ala
            20                  25                  30

Ala Ala Asp Pro Leu Leu Gly Gly Gln Gly Pro Ala Lys Asp Cys Glu
        35                  40                  45

Lys Asp Gln Phe Gln Cys Arg Asn Glu Arg Cys Ile Pro Ser Val Trp
    50                  55                  60

Arg Cys Asp Glu Asp Asp Asp Cys Leu Asp His Ser Asp Glu Asp Asp
65                  70                  75                  80

Cys Pro Lys Lys Thr Cys Ala Asp Ser Asp Phe Thr Cys Asp Asn Gly
                85                  90                  95

His Cys Ile His Glu Arg Trp Lys Cys Asp Gly Glu Glu Glu Cys Pro
            100                 105                 110

Asp Gly Ser Asp Glu Ser Glu Ala Thr Cys Thr Lys Gln Val Cys Pro
        115                 120                 125

Ala Glu Lys Leu Ser Cys Gly Pro Thr Ser His Lys Cys Val Pro Ala
    130                 135                 140

Ser Trp Arg Cys Asp Gly Glu Lys Asp Cys Glu Gly Gly Ala Asp Glu
145                 150                 155                 160

Ala Gly Cys Ala Thr Leu Cys Ala Pro His Glu Phe Gln Cys Gly Asn
                165                 170                 175

Arg Ser Cys Leu Ala Ala Val Phe Val Cys Asp Gly Asp Asp Asp Cys
            180                 185                 190

Gly Asp Gly Ser Asp Glu Arg Gly Cys Ala Asp Pro Ala Cys Gly Pro
        195                 200                 205

Arg Glu Phe Arg Cys Gly Gly Asp Gly Gly Gly Ala Cys Ile Pro Glu
    210                 215                 220

Arg Trp Val Cys Asp Arg Gln Phe Asp Cys Glu Asp Arg Ser Asp Glu
225                 230                 235                 240
```

-continued

```
Ala Ala Glu Leu Cys Gly Arg Pro Gly Pro Gly Ala Thr Ser Ala Pro
                245                 250                 255

Ala Ala Cys Ala Thr Ala Ser Gln Phe Ala Cys Arg Ser Gly Glu Cys
            260                 265                 270

Val His Leu Gly Trp Arg Cys Asp Gly Asp Arg Asp Cys Lys Asp Lys
        275                 280                 285

Ser Asp Glu Ala Asp Cys Pro Leu Gly Thr Cys Arg Gly Asp Glu Phe
    290                 295                 300

Gln Cys Gly Asp Gly Thr Cys Val Leu Ala Ile Lys His Cys Asn Gln
305                 310                 315                 320

Glu Gln Asp Cys Pro Asp Gly Ser Asp Glu Ala Gly Cys Leu Gln Gly
                325                 330                 335

Leu Asn Glu Cys Leu His Asn Asn Gly Gly Cys Ser His Ile Cys Thr
            340                 345                 350

Asp Leu Lys Ile Gly Phe Glu Cys Thr Cys Pro Ala Gly Phe Gln Leu
        355                 360                 365

Leu Asp Gln Lys Thr Cys Gly Asp Ile Asp Glu Cys Lys Asp Pro Asp
    370                 375                 380

Ala Cys Ser Gln Ile Cys Val Asn Tyr Lys Gly Tyr Phe Lys Cys Glu
385                 390                 395                 400

Cys Tyr Pro Gly Tyr Glu Met Asp Leu Leu Thr Lys Asn Cys Lys Ala
                405                 410                 415

Ala Ala Gly Lys Ser Pro Ser Leu Ile Phe Thr Asn Arg His Glu Val
            420                 425                 430

Arg Arg Ile Asp Leu Val Lys Arg Asn Tyr Ser Arg Leu Ile Pro Met
        435                 440                 445

Leu Lys Asn Val Val Ala Leu Asp Val Glu Val Ala Thr Asn Arg Ile
    450                 455                 460

Tyr Trp Cys Asp Leu Ser Tyr Arg Lys Ile Tyr Ser Ala Tyr Met Asp
465                 470                 475                 480

Lys Ala Ser Asp Pro Lys Glu Gln Glu Val Leu Ile Asp Glu Gln Leu
                485                 490                 495

His Ser Pro Glu Gly Leu Ala Val Asp Trp Val His Lys His Ile Tyr
            500                 505                 510

Trp Thr Asp Ser Gly Asn Lys Thr Ile Ser Val Ala Thr Val Asp Gly
        515                 520                 525

Gly Arg Arg Arg Thr Leu Phe Ser Arg Asn Leu Ser Glu Pro Arg Ala
    530                 535                 540

Ile Ala Val Asp Pro Leu Arg Gly Phe Met Tyr Trp Ser Asp Trp Gly
545                 550                 555                 560

Asp Gln Ala Lys Ile Glu Lys Ser Gly Leu Asn Gly Val Asp Arg Gln
                565                 570                 575

Thr Leu Val Ser Asp Asn Ile Glu Trp Pro Asn Gly Ile Thr Leu Asp
            580                 585                 590

Leu Leu Ser Gln Arg Leu Tyr Trp Val Asp Ser Lys Leu His Gln Leu
        595                 600                 605

Ser Ser Ile Asp Phe Ser Gly Gly Asn Arg Lys Thr Leu Ile Ser Ser
    610                 615                 620

Thr Asp Phe Leu Ser His Pro Phe Gly Ile Ala Val Phe Glu Asp Lys
625                 630                 635                 640

Val Phe Trp Thr Asp Leu Glu Asn Glu Ala Ile Phe Ser Ala Asn Arg
                645                 650                 655

Leu Asn Gly Leu Glu Ile Ser Ile Leu Ala Glu Asn Leu Asn Asn Pro
```

```
            660                 665                 670

His Asp Ile Val Ile Phe His Glu Leu Lys Gln Pro Arg Ala Pro Asp
        675                 680                 685

Ala Cys Glu Leu Ser Val Gln Pro Asn Gly Gly Cys Glu Tyr Leu Cys
    690                 695                 700

Leu Pro Ala Pro Gln Ile Ser Ser His Ser Pro Lys Tyr Thr Cys Ala
705                 710                 715                 720

Cys Pro Asp Thr Met Trp Leu Gly Pro Asp Met Lys Arg Cys Tyr Arg
                725                 730                 735

Ala Pro Gln Ser Thr Ser Thr Thr Thr Leu Ala Ser Thr Met Thr Arg
            740                 745                 750

Thr Val Pro Ala Thr Thr Arg Ala Pro Gly Thr Thr Val His Arg Ser
        755                 760                 765

Thr Tyr Gln Asn His Ser Thr Glu Thr Pro Ser Leu Thr Ala Ala Val
    770                 775                 780

Pro Ser Ser Val Ser Val Pro Arg Ala Pro Ser Ile Ser Pro Ser Thr
785                 790                 795                 800

Leu Ser Pro Ala Thr Ser Asn His Ser Gln His Tyr Ala Asn Glu Asp
                805                 810                 815

Ser Lys Met Gly Ser Thr Val Thr Ala Ala Val Ile Gly Ile Ile Val
            820                 825                 830

Pro Ile Val Val Ile Ala Leu Leu Cys Met Ser Gly Tyr Leu Ile Trp
        835                 840                 845

Arg Asn Trp Lys Arg Lys Asn Thr Lys Ser Met Asn Phe Asp Asn Pro
    850                 855                 860

Val Tyr Arg Lys Thr Thr Glu Glu Glu Asp Glu Asp Glu Leu His Ile
865                 870                 875                 880

Gly Arg Thr Ala Gln Ile Gly His Val Tyr Pro Ala Ala Ile Ser Ser
                885                 890                 895

Phe Asp Arg Pro Leu Trp Ala Glu Pro Cys Leu Gly Glu Thr Arg Glu
            900                 905                 910

Pro Glu Asp Pro Ala Pro Ala Leu Lys Glu Leu Phe Val Leu Pro Gly
        915                 920                 925

Glu Pro Arg Ser Gln Leu His Gln Leu Pro Lys Asn Pro Leu Ser Glu
    930                 935                 940

Leu Pro Val Val Lys Ser Lys Arg Val Ala Leu Ser Leu Glu Asp Asp
945                 950                 955                 960

Gly Leu Pro


<210> SEQ ID NO 13
<211> LENGTH: 7273
<212> TYPE: RNA
<213> ORGANISM: Homo sapiens

<400> SEQUENCE: 13

gcuggcggcg gccgcccagg gccggggccg cgcgcccagc cugagcccgc cccgccgccg      60

agcgucaccg aaccugcuug aaaugcagcc gaggagccgg ggcgggcggc agcggcggcg     120

gcggcggcgg cgggggcagc ggcaaccccg gcgccgcggc aaggacucgg agggcugaga     180

cgcggcggcg gcggcgcggg gagcgcgggg cgcggcggcc ggagccccgg gcccgccaug     240

ggccuccccg agccgggccc ucuccggcuu cuggcgcugc ugcugcugcu gcugcugcug     300

cugcugcugc agcuccagca ucuugcggcg gcagcggcug auccgcugcu cggcggccaa     360

gggccggcca aggauugcga aaaggaccaa uuccagugcc ggaacgagcg cugcaucccc     420
```

ucugugugga gaugcgacga ggacgaugac ugcuuagacc acagcgacga ggacgacugc 480
cccaagaaga ccugugcaga cagugacuuc accugugaca acggccacug cauccacgaa 540
cgguggaagu gugacggcga ggaggagugu ccugauggcu ccgaugaguc cgaggccacu 600
ugcaccaagc aggugugucc ugcagagaag cugagcugug gacccaccag ccacaagugu 660
guaccugccu cguggcgcug cgacggggag aaggacugcg aggguggagc ggaugaggcc 720
ggcugugcua ccuggcugaa cgagugucug cacaacaaug gcggcugcuc acacaucugc 780
acugaccuca agauuggcuu ugaaugcacg ugcccagcag gcuuccagcu ccuggaccag 840
aagaccugug gcgacauuga ugagugcaag gacccagaug ccugcagcca gaucuguguc 900
aauuacaagg gcuauuuuaa gugugagugc uacccuggcu acgagaugga ccuacugacc 960
aagaacugca aggcugcugc uggcaagagc ccaucccuaa ucuucaccaa ccggcacgag 1020
gugcggagga ucgaccuggu gaagcggaac uauucacgcc ucauccccau gcucaagaau 1080
gucguggcac uagaugugga aguugccacc aaucgcaucu acuggugugua ccucuccuac 1140 cguaagaucu auagcgccua cauggacaag gccagugacc cgaaagagca ggagguccuc 1200
auugacgagc aguugcacuc uccagagggc cuggcagugg acugggucca caagcacauc 1260
uacuggacug acucgggcaa uaagaccauc ucaguggcca caguugaugg uggccgccga 1320
cgcacucucu ucagccguaa ccucagugaa ccccgggcca ucgcuguuga cccccugcga 1380
ggguucaugu auuggucuga cuggggggac caggccaaga uugagaaauc ugggcucaac 1440
gguguggacc ggcaaacacu ggugucagac aauauugaau ggcccaacgg aaucacccug 1500
gaucugcuga gccagcgcuu guacugggua gacuccaagc uacaccaacu guccagcauu 1560
gacuucagug gaggcaacag aaagacgcug aucuccucca cugacuuccu gagccacccu 1620
uuugggauag cuguguuuga ggacaaggug uucuggacag accuggagaa cgaggccauu 1680
uucagugcaa aucggcucaa uggccuggaa aucuccaucc uggcugagaa ccucaacaac 1740
ccacaugaca uugucaucuu ccaugagcug aagcagccaa gagcuccaga ugccugugag 1800
cugagugucc agccuaaugg aggcugugaa uaccugugcc uuccugcucc ucagaucucc 1860
agccacucuc ccaaguacac augugccugu ccugacacaa uguggcuggg uccagacaug 1920
aagaggugcu accgagcacc ucaaucuacc ucaacuacga cguuagcuuc uaccaugacg 1980
aggacaguac cugccaccac aagagccccc gggaccaccg uccacagauc caccuaccag 2040
aaccacagca cagagacacc aagccugaca gcugcagucc caagcucagu uagugucccc 2100
agggcuccca gcaucagccc gucuacccua agcccugcaa ccagcaacca cucccagcac 2160
uaugcaaaug aagacaguaa gaugggcuca acagucacug ccgcuguuau cgggaucauc 2220
gugcccauag uggugauagc ccuccugugc augaguggau accugaucug gagaaacugg 2280
aagcggaaga acaccaaaag caugaauuuu gacaacccag ucuacaggaa aacaacagaa 2340
gaagaagacg aagaugagcu ccauauaggg agaacugcuc agauuggcca ugucuauccu 2400
gcagcaauca gcagcuuuga ucgcccacug ugggcagagc ccugucuugg ggagaccaga 2460
gaaccggaag acccagcccc ugcccucaag gagcuuuuug ucuugccggg ggaaccaagg 2520
ucacagcugc accaacuccc gaagaacccu cuuuccgagc ugccugucgu caaauccaag 2580
cgaguggcau uaagccuuga agaugaugga cuacccugag gaugggauca cccccuucgu 2640
gccucaugga auucaguccc augcacuaca cucuggaugg uguaugacug gaugaauggg 2700
uuucuauaua ugggucugug ugaguguaug ugugugugug auuuuuuuuu uaaauuuaug 2760

-continued

```
uugcggaaag guaaccacaa aguuaugaug aacugcaaac auccaaagga ugugagaguu   2820
uuucuaugua uaauguuuua uacacuuuuu aacugguugc acuacccaug aggaauucgu   2880
ggaauggcua cugcugacua acaugaugca cauaaccaaa ugggggccaa uggcacagua   2940
ccuuacucau cauuuaaaaa cuauauuuac agaagauguu ugguugcugg gggggcuuuu   3000
uuagguuuug gggcauuugu uuuuuguaaa uaagaugauu augcuuugug gcuauccauc   3060
aacauaagua aaaaaaaaaa aaaaacacuu caacuccccuc ccccauuuag auuauuuauu   3120
aacauauuuu aaaaaucaga ugaguucuau aaauaauuua gagaagugag aguauuuauu   3180
uuuggcaugu uuggcccacc acacagacuc ugugugugua ugugugugu uauaugugua   3240
ugugugugac agaaaaaucu guagagaaga ggcacaucua uggcuacugu ucaaauacau   3300
aaagauaaau uuauuuucac acaguccaca aggguauau cuuguaguuu ucagaaaagc   3360
cuuuggaaau cuggaucaga aaauagauac caugguuugu gcaauuaugu aguaaaaaag   3420
gcaaaucuuu ucaccucugg cuauuccuga gaccccagga agucaggaaa agccuuucag   3480
cucacccaug gcugcuguga cuccuaccag ggcuuucuug gcuuuggcga aggucagugu   3540
acagacauuc caugguacca gagugcucag aaacucaaga uaggauaugc cucacccuca   3600
gcuacuccuu guuuuaaagu ucagcucuuu gaguaacuuc uucaauuucu uucaggacac   3660
uuggguugaa uucaguaagu uuccucugaa gcacccugaa gggugccauc cuuacagagc   3720
uaaguggaga cguuuccaga ucagcccaag uuuacuauag agacuggccc aggcacugaa   3780
ugucuaggac augcugugga ugaagauaaa gauggugggaa uagguuuuau cacaucucuu   3840
auuucucuuu uccccuuacu cucuaccauu uccuuuaugu ggggaaacau uuuaagguaa   3900
uaaauagguu acuuaccauc auauguucau auagaugaaa cuaauuuuug gcuuaaguca   3960
gaacaacugg ccaaaauuga agucauauuu gagggggggaa auggcauacg caauauuaua   4020
uuauauugga uauuuauguu cacacaggaa uuugguuuac ugcuuuguaa auaaaaggaa   4080
aaacuccggg uauauguaua gauguucuuc auuauagaca ucuucuuugc uuuucuuggc   4140
cuuggggggag gaagggagaa gugcucuuuu cuacuugugg ggucucccau uggaaacaua   4200
auccuauagu cccagaagga uucagucccc aguggcuuuc ccauccaaag agaaagaguu   4260
ugaguuucuu aacucugcug uucugccacu uacuccccacu agacaaccag ggacaaggug   4320
caacauggaa guguuugacu uaaguaggag cagaggagcu gcaucuaauc ucaucauacc   4380
uggaacuuga cacacuuaag caaaugccuu cccaucccua ccugccagau gcccccaacu   4440
caaugaaguu ggaugucuca ccagcuugau acccuuugaa uuuucaguca gacauucugg   4500
aguucuagca uccuguaccu aggaccuucc ucugugucac ucuuggccuc cuaaacucua   4560
agaaaauaac uauauucugg agcuugggca guguguuuug cauaauccag caaucuccuc   4620
augacaugca uguguugaua guccugaaac auucauugag aggguaaaug caguugaccu   4680
agaaugacca auaccaaaca gaauuuuaag aacagguggc caacuccuau ggagcuuacu   4740
cacauauuac uauucuuuua agaacggaaa guaaaauuau uuuugacuga agaaaaauga   4800
ugacagugaa aaacauggaa auguacucaa aacaagugac uuuuucugua accuuccaaa   4860
gaaacugaau uuuccaagga auuaaaugau aacaguggcu aaggcauagu uucuaaacuu   4920
ucaguaagau ccuggcauuc acagaaaaaa augaugaaug gggucuggac auacagccug   4980
agaucucaaa augacaauga aauucacaac uuuuucucag agacauucau guuuccugca   5040
uaugcuacaa cugcaguuug aaagaggcag caaugggagc aacccuuuac aagaaacaaa   5100
uugugauaua uucauguguu ggacggcagu aaauaaagaug aaaccugagg agucagaucc   5160
```

accuucccccc auucauagag gcuuuucagc cucauuuuga gguacaguua cauaucuuuu 5220
gccuuuugcc cccgugcaua gcuaucuaca gccaaucaca gaucacagag ucacuggacu 5280
auagagcugg aaggaagcuc agagacaaug ccaagggggc agaaaauuua ucagaagcca 5340
gucccagugc guuuccucca uuuccuucug caggaagacu auuuugggcu gccugaacau 5400
uguaucaaac cugcuaccua uacuauggUc uaccuuuccu ccaguggaau uacaaaggca 5460
cuaacugaaa ugccuucuag aaacagagaa aacgaaacug uacuuauuua cucuugauac 5520
acagauuauu uauaaaaacag auugaaguaa ccuguuaacu ggcaaaaaga gaaugagauc 5580
ggauuuaaau guauggcagu aaguccuauu gaucccucca guuaucucag uaugacugca 5640
guauauucau ucacuaaaac cacucacuag auaccaacua cacaccuggc acugcagaug 5700
uaaaggucag ucacacaugu ucugacuuua cagaguucac aguagcagug gaggaugaua 5760
uauguggaaa caaaaaaggc auugauucua uucagagcac uguuagggcu caaaggagag 5820
aggggucuuu ccaccuaaga aaugaggaau agggucauca uagaagugac cuuaagucuu 5880
aaaaauuaag aaggggauuc caagcugcuu cagacagaga cacaucgagc uaaaacacag 5940
agguaugaaa gagcacaggg acuuuaggaa uugcacaguu cauucuaaca ggaacaaaag 6000
gcucaagggg ggcaagaaau gaggcuguau ggaaagagau ucaauguaag cacuuuauaa 6060
aauagauuaa uuucugauuc aaugaagcau uucuugauca uuguguacaa ggcacuacau 6120
gcaucaugga aaauucauua ggaugcauug ccagcacuuu gcagaacuga uauuauucag 6180
ccucaagcuu uccaguggcc aaagggaaau gcugacugcu uuucauauau uugagucaaa 6240
gauuuuuuau auggucaaug aagacuaaua uaagggcagu gggauuuuca cagaugcaug 6300
ccauguuguc gagagccucu uagauuuucu caacugugag aaagaaaaac gaaaauguug 6360
aagacguuga gucuggagag gggauacuaa ucacugucca guugggcacu ggugggaaug 6420
gggaaauggc acaggaaugc aagccucucc acccuacccc ccgaacucca gccauacacu 6480
caucguuuca caaaauauaa augaguuagc auuaaaaguu ucagaguaaa uaauuccuuu 6540
ucccgaaaug caugaagaua gaguaacaga cuucucacac uguauuuuua ggguauggag 6600
aauuuagaag guuaaagaau uacugcuuca auuuuucagu uaaaaaaaaa ucaggaagcu 6660
cuguucauuc aggcuaugca ccaugugcac agucaagaau uagcagaaac ccucugcauu 6720
uacaaacacu uugugcuaua aaaaaguaau uuuuaaaaag ccacgugugu guguguguau 6780
auauauauau auauauauau uuaaagccaa gguuuugaua cuuuuuuaca aaaacuacaa 6840
gagaaaacaa auauaccugu ccaaaccaua uacuuuuaaa agagcauuuu uuuuuccaua 6900
caagcuguug uuaauuuggg gguaaagugc ugauuugcaa acuucaucaa auuguuccca 6960
aguggauucu ccuuguuugu cuccccccuac caaccccaaa guuaccauau uugauguaag 7020
aaucaggcau guuagaaugu ugugucacac uaacugauuc ugcucuuuuu gucuugucau 7080
ucaaguuccg uuagcuucug uacgcggugc ccuuugcagu cuggugucuc uuccagaggc 7140
gagggggcug aggauggggu gcugcaucuc acuagcuaua cuggcaucau cuugguaaac 7200
ugaaaaccaa auguggacau uuguaaaauc agugcacugu uucuagagag agauuaaauu 7260
cauuuaaaaa aaa 7273

<210> SEQ ID NO 14
<211> LENGTH: 793
<212> TYPE: PRT
<213> ORGANISM: Homo sapiens -continued

<400> SEQUENCE: 14

```
Met Gly Leu Pro Glu Pro Gly Pro Leu Arg Leu Leu Ala Leu Leu Leu
1               5                   10                  15

Leu Leu Leu Leu Leu Leu Leu Leu Gln Leu Gln His Leu Ala Ala Ala
            20                  25                  30

Ala Ala Asp Pro Leu Leu Gly Gly Gln Gly Pro Ala Lys Asp Cys Glu
        35                  40                  45

Lys Asp Gln Phe Gln Cys Arg Asn Glu Arg Cys Ile Pro Ser Val Trp
    50                  55                  60

Arg Cys Asp Glu Asp Asp Asp Cys Leu Asp His Ser Asp Glu Asp Asp
65                  70                  75                  80

Cys Pro Lys Lys Thr Cys Ala Asp Ser Asp Phe Thr Cys Asp Asn Gly
                85                  90                  95

His Cys Ile His Glu Arg Trp Lys Cys Asp Gly Glu Glu Glu Cys Pro
            100                 105                 110

Asp Gly Ser Asp Glu Ser Glu Ala Thr Cys Thr Lys Gln Val Cys Pro
        115                 120                 125

Ala Glu Lys Leu Ser Cys Gly Pro Thr Ser His Lys Cys Val Pro Ala
    130                 135                 140

Ser Trp Arg Cys Asp Gly Glu Lys Asp Cys Glu Gly Gly Ala Asp Glu
145                 150                 155                 160

Ala Gly Cys Ala Thr Trp Leu Asn Glu Cys Leu His Asn Asn Gly Gly
                165                 170                 175

Cys Ser His Ile Cys Thr Asp Leu Lys Ile Gly Phe Glu Cys Thr Cys
            180                 185                 190

Pro Ala Gly Phe Gln Leu Leu Asp Gln Lys Thr Cys Gly Asp Ile Asp
        195                 200                 205

Glu Cys Lys Asp Pro Asp Ala Cys Ser Gln Ile Cys Val Asn Tyr Lys
    210                 215                 220

Gly Tyr Phe Lys Cys Glu Cys Tyr Pro Gly Tyr Glu Met Asp Leu Leu
225                 230                 235                 240

Thr Lys Asn Cys Lys Ala Ala Ala Gly Lys Ser Pro Ser Leu Ile Phe
                245                 250                 255

Thr Asn Arg His Glu Val Arg Arg Ile Asp Leu Val Lys Arg Asn Tyr
            260                 265                 270

Ser Arg Leu Ile Pro Met Leu Lys Asn Val Val Ala Leu Asp Val Glu
        275                 280                 285

Val Ala Thr Asn Arg Ile Tyr Trp Cys Asp Leu Ser Tyr Arg Lys Ile
    290                 295                 300

Tyr Ser Ala Tyr Met Asp Lys Ala Ser Asp Pro Lys Glu Gln Glu Val
305                 310                 315                 320

Leu Ile Asp Glu Gln Leu His Ser Pro Glu Gly Leu Ala Val Asp Trp
                325                 330                 335

Val His Lys His Ile Tyr Trp Thr Asp Ser Gly Asn Lys Thr Ile Ser
            340                 345                 350

Val Ala Thr Val Asp Gly Gly Arg Arg Arg Thr Leu Phe Ser Arg Asn
        355                 360                 365

Leu Ser Glu Pro Arg Ala Ile Ala Val Asp Pro Leu Arg Gly Phe Met
    370                 375                 380

Tyr Trp Ser Asp Trp Gly Asp Gln Ala Lys Ile Glu Lys Ser Gly Leu
385                 390                 395                 400

Asn Gly Val Asp Arg Gln Thr Leu Val Ser Asp Asn Ile Glu Trp Pro
                405                 410                 415
```

```
Asn Gly Ile Thr Leu Asp Leu Leu Ser Gln Arg Leu Tyr Trp Val Asp
            420                 425                 430

Ser Lys Leu His Gln Leu Ser Ser Ile Asp Phe Ser Gly Gly Asn Arg
        435                 440                 445

Lys Thr Leu Ile Ser Ser Thr Asp Phe Leu Ser His Pro Phe Gly Ile
    450                 455                 460

Ala Val Phe Glu Asp Lys Val Phe Trp Thr Asp Leu Glu Asn Glu Ala
465                 470                 475                 480

Ile Phe Ser Ala Asn Arg Leu Asn Gly Leu Glu Ile Ser Ile Leu Ala
                485                 490                 495

Glu Asn Leu Asn Asn Pro His Asp Ile Val Ile Phe His Glu Leu Lys
            500                 505                 510

Gln Pro Arg Ala Pro Asp Ala Cys Glu Leu Ser Val Gln Pro Asn Gly
        515                 520                 525

Gly Cys Glu Tyr Leu Cys Leu Pro Ala Pro Gln Ile Ser Ser His Ser
    530                 535                 540

Pro Lys Tyr Thr Cys Ala Cys Pro Asp Thr Met Trp Leu Gly Pro Asp
545                 550                 555                 560

Met Lys Arg Cys Tyr Arg Ala Pro Gln Ser Thr Ser Thr Thr Thr Leu
                565                 570                 575

Ala Ser Thr Met Thr Arg Thr Val Pro Ala Thr Thr Arg Ala Pro Gly
            580                 585                 590

Thr Thr Val His Arg Ser Thr Tyr Gln Asn His Ser Thr Glu Thr Pro
        595                 600                 605

Ser Leu Thr Ala Ala Val Pro Ser Ser Val Ser Val Pro Arg Ala Pro
    610                 615                 620

Ser Ile Ser Pro Ser Thr Leu Ser Pro Ala Thr Ser Asn His Ser Gln
625                 630                 635                 640

His Tyr Ala Asn Glu Asp Ser Lys Met Gly Ser Thr Val Thr Ala Ala
                645                 650                 655

Val Ile Gly Ile Ile Val Pro Ile Val Val Ile Ala Leu Leu Cys Met
            660                 665                 670

Ser Gly Tyr Leu Ile Trp Arg Asn Trp Lys Arg Lys Asn Thr Lys Ser
        675                 680                 685

Met Asn Phe Asp Asn Pro Val Tyr Arg Lys Thr Thr Glu Glu Glu Asp
    690                 695                 700

Glu Asp Glu Leu His Ile Gly Arg Thr Ala Gln Ile Gly His Val Tyr
705                 710                 715                 720

Pro Ala Ala Ile Ser Ser Phe Asp Arg Pro Leu Trp Ala Glu Pro Cys
                725                 730                 735

Leu Gly Glu Thr Arg Glu Pro Glu Asp Pro Ala Pro Ala Leu Lys Glu
            740                 745                 750

Leu Phe Val Leu Pro Gly Glu Pro Arg Ser Gln Leu His Gln Leu Pro
        755                 760                 765

Lys Asn Pro Leu Ser Glu Leu Pro Val Val Lys Ser Lys Arg Val Ala
    770                 775                 780

Leu Ser Leu Glu Asp Asp Gly Leu Pro
785                 790
```

<210> SEQ ID NO 15
<211> LENGTH: 6994
<212> TYPE: RNA
<213> ORGANISM: Homo sapiens -continued

<400> SEQUENCE: 15

```
gcuggcggcg gccgcccagg gccggggccg cgcgcccagc cugagcccgc cccgccgccg     60
agcgucaccg aaccugcuug aaaugcagcc gaggagccgg ggcgggcggc agcggcggcg    120
gcggcggcgg cgggggcagc ggcaaccccg gcgccgcggc aaggacucgg agggcugaga    180
cgcggcggcg gcggcgcggg gagcgcgggg cgcggcggcc ggagccccgg gcccgccaug    240
ggccuccccg agccgggccc ucuccggcuu cuggcgcugc ugcugcugcu gcugcugcug    300
cugcugcugc agcuccagca ucuugcggcg gcagcggcug auccgcugcu cggcggccaa    360
gggccggcca aggauugcga aaaggaccaa uuccagugcc ggaacgagcg cugcaucccc    420
ucugugugga gaugcgacga ggacgaugac ugcuuagacc acagcgacga ggacgacugc    480
cccaagaaga ccugugcaga cagugacuuc accugugaca acggccacug cauccacgaa    540
cgguggaagu gugacggcga ggaggagugu ccugauggcu ccgaugaguc cgaggccacu    600
ugcaccaagc aggugugucc ugcagagaag cugagcugug gacccaccag ccacaagugu    660
guaccugccu cguggcgcug cgacggggag aaggacugcg aggguggagc ggaugaggcc    720
ggcugugcua ccucacuggg caccugccgu ggggacgagu uccagugugg ggaugggaca    780
ugugucccuug caaucaagca cugcaaccag gagcaggacu guccagaugg gagugaugaa    840
gcuggcugcc uacaggggcu gaacgagugu cugcacaaca auggcggcug cucacacauc    900
ugcacugacc ucaagauugg cuuugaaugc acgugcccag caggcuucca gcuccuggac    960
cagaagaccu guggcgacau ugaugagugc aaggacccag augccugcag ccagaucugu   1020
gucaauuaca agggcuauuu uaagugugag ugcuacccug gcuacgagau ggaccuacug   1080
accaagaacu gcaaggcugc ugcuggcaag agcccauccc uaaucuucac caaccggcac   1140
gaggugcgga ggaucgaccu ggugaagcgg aacuauucac gccucauccc caugcucaag   1200
aaugucgugg cacuagaugu ggaaguugcc accaaucgca ucuacuggug ugaccucucc   1260
uaccguaaga ucuauagcgc cuacauggac aaggccagug acccgaaaga gcaggagguc   1320
cucauugacg agcaguugca cucuccagag ggccuggcag uggacugggu ccacaagcac   1380
aucuacugga cugacucggg caauaagacc aucucagugg ccacaguuga ugguggccgc   1440
cgacgcacuc ucuucagccg uaaccucagu gaaccccggg ccaucgcugu ugacccccug   1500
cgaggguuca uguauugguc ugacuggggg gaccaggcca agauugagaa aucugggcuc   1560
aacggugugg accggcaaac acuggugucu gacaauauug aauggcccaa cggaaucacc   1620
cuggaucugc ugagccagcg cuuguacugg guagacucca agcuacacca acuguccagc   1680
auugacuuca guggaggcaa cagaaagacg cugaucuccu ccacugacuu ccugagccac   1740
ccuuuuggga uagcuguguu ugaggacaag guguucugga cagaccugga gaacgaggcc   1800
auuuucagug caaaucggcu caauggccug gaaaucucca uccuggcuga gaaccucaac   1860
aacccacaug acauugucau cuuccaugag cugaagcagc caagagcucc agaugccugu   1920
gagcugagug uccagccuaa uggaggcugu gaauaccugu gccuuccugc uccucagauc   1980
uccagccacu cucccaagua cacaugugcc uguccugaca caauguggcu ggguccagac   2040
augaagaggu gcuaccgaga ugcaaaugaa gacaguaaga ugggcucaac agucacugcc   2100
gcuguuaucg ggaucaucgu gcccauagug gugauagccc uccugugcau gaguggauac   2160
cugaucugga gaaacuggaa gcggaagaac accaaaagca ugaauuuuga caacccaguc   2220
uacaggaaaa caacagaaga agaagacgaa gaugagcucc auauagggag aacugcucag   2280
auuggccaug ucuauccugc acgaguggca uuaagccuug aagaugaugg acuacccuga   2340
```

-continued

```
ggauggggauc accccccuucg ugccucaugg aauucagucc caugcacuac acucuggaug   2400
guguaugacu ggaugaaugg guuucuauau augggucugu gugaguguau gugugugugu   2460
gauuuuuuuu uuaaauuuau guugcggaaa gguaaccaca aaguuaugau gaacugcaaa   2520
cauccaaagg augugagagu uuuucuaugu auaauguuuu auacacuuuu uaacugguug   2580
cacuacccau gaggaauucg uggaauggcu acugcugacu aacaugaugc acauaaccaa   2640
augggggcca auggcacagu accuuacuca ucauuuaaaa acuauauuua cagaagaugu   2700
uugguugcug ggggggcuuu uuuagguuuu ggggcauuug uuuuuuguaa auaagaugau   2760
uaugcuuugu ggcuauccau caacauaagu aaaaaaaaaa aaaaaacacu ucaacucccu   2820
cccccauuua gauuauuuau uaacauauuu uaaaaaucag augaguucua uaaauaauuu   2880
agagaaguga gaguauuuau uuuuggcaug uuuggcccac cacacagacu cugugugugu   2940
augugugugu uuauaugugu auguguguga cagaaaaauc uguagagaag aggcacaucu   3000
auggcuacug uucaaauaca uaaagauaaa uuuauuuuca cacaguccac aaggggguaua   3060
ucuuguaguu uucagaaaag ccuuuggaaa ucuggaucag aaaauagaua ccaugguuug   3120
ugcaauuaug uaguaaaaaa ggcaaaucuu uucaccucug gcuauuccug agaccccagg   3180
aagucaggaa aagccuuuca gcucacccau ggcugcugug acuccuacca gggcuuucuu   3240
ggcuuuggcg aaggucagug uacagacauu ccaugguacc agagugcuca gaaacucaag   3300
auaggauaug ccucacccuc agcuacuccu uguuuuaaag uucagcucuu ugaguaacuu   3360
cuucaauuuc uuucaggaca cuuggguuga auucaguaag uuuccucuga agcacccuga   3420
agggugccau ccuuacagag cuaagugag acguuuccag aucagcccaa guuuacuaua   3480
gagacuggcc caggcacuga augucuagga caugcugugg augaagauaa agauggugga   3540
auagguuuua ucacaucucu uauuucucuu uuccccuuac ucucuaccau uuccuuuaug   3600
uggggaaaca uuuuaaggua auaaauaggu uacuuaccau cauauguuca uauagaugaa   3660
acuaauuuuu ggcuuaaguc agaacaacug gccaaaauug aagucauauu ugaggggga   3720
aauggcauac gcaauauuau auuauauugg auauuuaugu ucacacagga auuugguuua   3780
cugcuuugua aauaaaagga aaaacuccgg guauauguau agauguucuu cauuauagac   3840
aucuucuuug cuuuucuugg ccuuggggga ggaagggaga agugcucuuu ucuacuugug   3900
gggucuccca uuggaaacau aauccuauag ucccagaagg auucaguccc caguggcuuu   3960
cccauccaaa gagaaagagu uugaguuucu uaacucugcu guucugccac uuacucccac   4020
uagacaacca gggacaaggu gcaacaugga aguguuugac uuaaguagga gcagaggagc   4080
ugcaucuaau cucaucauac cuggaacuug acacacuuaa gcaaaugccu ucccaucccu   4140
accugccaga ugcccccaac ucaaugaagu uggaugucuc accagcuuga uacccuuuga   4200
auuuucaguc agacauucug gaguucuagc auccuguacc uaggaccuuc cucuguguca   4260
cucuuggccu ccuaaacucu aagaaaauaa cuauauucug gagcuugggc aguguguuuu   4320
gcauaaucca gcaaucuccu caugacaugc auguguugau aguccugaaa cauucauuga   4380
gaggguaaau gcaguugacc uagaaugacc aauaccaaac agaauuuuaa gaacaggugg   4440
ccaacuccua uggagcuuac ucacauauua cuauucuuuu aagaacggaa aguaaaauua   4500
uuuuugacug aagaaaaaug augacaguga aaaacaugga aauguacuca aaacaaguga   4560
cuuuuucugu aaccuuccaa agaaacugaa uuuuccaagg aauuaaauga uaacaguggc   4620
uaaggcauag uuucuaaacu uucaguaaga uccuggcauu cacagaaaaa aaugaugaau   4680
```

| | |
|---|---|
| ggggucugga cauacagccu gagaucucaa augacaaug aaauucacaa cuuuuucuca | 4740 |
| gagacauuca uguuccugc auaugcuaca acugcaguuu gaaagaggca gcaaugggag | 4800 |
| caacccuuua caagaaacaa auugugauau auucaugugu uggacggcag uaaauaagau | 4860 |
| gaaaccugag gagucagauc caccuucccc cauucauaga ggcuuuucag ccucauuuug | 4920 |
| agguacaguu acauaucuuu ugccuuuugc ccccgugcau agcuaucuac agccaaucac | 4980 |
| agaucacaga gucacuggac uauagagcug gaaggaagcu cagagacaau gccaggggg | 5040 |
| cagaaaauuu aucagaagcc aguccagug cguuccucc auuccuucu gcaggaagac | 5100 |
| uauuuugggc ugccugaaca uuguaucaaa ccugcuaccu auacuauggu cuaccuuucc | 5160 |
| uccaguggaa uuacaaaggc acaacugaa augccuucua gaaacagaga aaacgaaacu | 5220 |
| guacuuauuu acucuugaua cacagauuau uuauaaaaca gauugaagua accguuaac | 5280 |
| uggcaaaaag agaaugagau cggauuuaaa uguauggcag uaaguccuau ugaucccucc | 5340 |
| aguuaucuca guaugacugc aguauauuca uucacuaaaa ccacucacua gauaccaacu | 5400 |
| acacaccugg cacugcagau guaaagguca gucacacaug uucugacuuu acagaguuca | 5460 |
| caguagcagu ggaggaugau auaugugaa acaaaaaagg cauugauucu auucagagca | 5520 |
| cuguuagggc ucaaaggaga gaggggucuu uccaccuaag aaaugaggaa uagggucauc | 5580 |
| auagaaguga ccuuaagucu uaaaaauuaa gaagggauu ccaagcugcu ucagacagag | 5640 |
| acacaucgag cuaaaacaca gagguaugaa agagcacagg gacuuuagga auugcacagu | 5700 |
| ucauucuaac aggaacaaaa ggcucaaggg gggcaagaaa ugaggcugua uggaaagaga | 5760 |
| uucaauguaa gcacuuuaua aaauagauua auuucugauu caaugaagca uuucuugauc | 5820 |
| auugugaca aggcacuaca ugcaucaugg aaaauucauu aggaugcauu gccagcacuu | 5880 |
| ugcagaacug auauuauuca gcccuaagcu uccagguggc caaagggaaa ugcugacugc | 5940 |
| uuuucauaua uuugagucaa agauuuuuua uauggucaau gaagacuaau auaagggcag | 6000 |
| ugggauuuuc acagaugcau gccauguugu cgagagccuc uuagauuuuc ucaacuguga | 6060 |
| gaaagaaaaa cgaaaauguu gaagacguug agucuggaga ggggauacua aucacugucc | 6120 |
| aguugggcac uggugggaau ggggaaaugg cacaggaaug caagcccucuc cacccuaccc | 6180 |
| cccgaacucc agccauacac ucaucguuuc acaaaauaua aaugaguuag cauuaaaugu | 6240 |
| uucagaguaa auaauccuu uuccccgaaau gcaugaagau agaguaacag acuucucaca | 6300 |
| cuguauuuuu agggauagga gaauuuagaa gguuaaagaa uuacugcuuc aauuuuucag | 6360 |
| uuaaaaaaaa aucaggaagc ucuguucauu caggcuaugc accaugugca cagucaagaa | 6420 |
| uuagcagaaa cccucugcau uuacaaacac uuugugcuau aaaaaguaa uuuuaaaaa | 6480 |
| gccacgugug ugugugugua uauauauaua uauauauaua uuuaaagcca agguuuugau | 6540 |
| acuuuuuuac aaaaacuaca agagaaaaca aauauaccug uccaaaccau auacuuuuaa | 6600 |
| aagagcauuu uuuuuccau acaagcuguu guuaauuugg ggguaaagug cugauuugca | 6660 |
| aacuucauca aauuguuccc aaguggauuc uccuuguuug ucuccccua ccaaccccaa | 6720 |
| aguuaccaua uuugauguaa gaaucaggca uguuagaaug uguguacaca cuaacugauu | 6780 |
| cugcucuuuu ugucuguca uucaagucc guuagcuucu uacgcggug cccuuugcag | 6840 |
| ucuggugucu cuuccagagg cgaggggcu gaggaugggg ugcugcaucu cacuagcuau | 6900 |
| acuggcauca ucuugguaaa cugaaaacca aaugugagaca uuuguaaaau cagugcacug | 6960 |
| uuucuagaga gagauuaaau ucauuuaaaa aaaa | 6994 |

<210> SEQ ID NO 16
<211> LENGTH: 700
<212> TYPE: PRT
<213> ORGANISM: Homo sapiens

<400> SEQUENCE: 16

```
Met Gly Leu Pro Glu Pro Gly Pro Leu Arg Leu Leu Ala Leu Leu Leu
1               5                   10                  15

Leu Leu Leu Leu Leu Leu Leu Leu Gln Leu Gln His Leu Ala Ala Ala
            20                  25                  30

Ala Ala Asp Pro Leu Leu Gly Gly Gln Gly Pro Ala Lys Asp Cys Glu
        35                  40                  45

Lys Asp Gln Phe Gln Cys Arg Asn Glu Arg Cys Ile Pro Ser Val Trp
    50                  55                  60

Arg Cys Asp Glu Asp Asp Asp Cys Leu Asp His Ser Asp Glu Asp Asp
65                  70                  75                  80

Cys Pro Lys Lys Thr Cys Ala Asp Ser Asp Phe Thr Cys Asp Asn Gly
                85                  90                  95

His Cys Ile His Glu Arg Trp Lys Cys Asp Gly Glu Glu Glu Cys Pro
            100                 105                 110

Asp Gly Ser Asp Glu Ser Glu Ala Thr Cys Thr Lys Gln Val Cys Pro
        115                 120                 125

Ala Glu Lys Leu Ser Cys Gly Pro Thr Ser His Lys Cys Val Pro Ala
    130                 135                 140

Ser Trp Arg Cys Asp Gly Glu Lys Asp Cys Glu Gly Gly Ala Asp Glu
145                 150                 155                 160

Ala Gly Cys Ala Thr Ser Leu Gly Thr Cys Arg Gly Asp Glu Phe Gln
                165                 170                 175

Cys Gly Asp Gly Thr Cys Val Leu Ala Ile Lys His Cys Asn Gln Glu
            180                 185                 190

Gln Asp Cys Pro Asp Gly Ser Asp Glu Ala Gly Cys Leu Gln Gly Leu
        195                 200                 205

Asn Glu Cys Leu His Asn Asn Gly Gly Cys Ser His Ile Cys Thr Asp
    210                 215                 220

Leu Lys Ile Gly Phe Glu Cys Thr Cys Pro Ala Gly Phe Gln Leu Leu
225                 230                 235                 240

Asp Gln Lys Thr Cys Gly Asp Ile Asp Glu Cys Lys Asp Pro Asp Ala
                245                 250                 255

Cys Ser Gln Ile Cys Val Asn Tyr Lys Gly Tyr Phe Lys Cys Glu Cys
            260                 265                 270

Tyr Pro Gly Tyr Glu Met Asp Leu Leu Thr Lys Asn Cys Lys Ala Ala
        275                 280                 285

Ala Gly Lys Ser Pro Ser Leu Ile Phe Thr Asn Arg His Glu Val Arg
    290                 295                 300

Arg Ile Asp Leu Val Lys Arg Asn Tyr Ser Arg Leu Ile Pro Met Leu
305                 310                 315                 320

Lys Asn Val Val Ala Leu Asp Val Glu Val Ala Thr Asn Arg Ile Tyr
                325                 330                 335

Trp Cys Asp Leu Ser Tyr Arg Lys Ile Tyr Ser Ala Tyr Met Asp Lys
            340                 345                 350

Ala Ser Asp Pro Lys Glu Gln Glu Val Leu Ile Asp Glu Gln Leu His
        355                 360                 365

Ser Pro Glu Gly Leu Ala Val Asp Trp Val His Lys His Ile Tyr Trp
    370                 375                 380
```

-continued

```
Thr Asp Ser Gly Asn Lys Thr Ile Ser Val Ala Thr Val Asp Gly Gly
385                 390                 395                 400

Arg Arg Arg Thr Leu Phe Ser Arg Asn Leu Ser Glu Pro Arg Ala Ile
                405                 410                 415

Ala Val Asp Pro Leu Arg Gly Phe Met Tyr Trp Ser Asp Trp Gly Asp
            420                 425                 430

Gln Ala Lys Ile Glu Lys Ser Gly Leu Asn Gly Val Asp Arg Gln Thr
        435                 440                 445

Leu Val Ser Asp Asn Ile Glu Trp Pro Asn Gly Ile Thr Leu Asp Leu
    450                 455                 460

Leu Ser Gln Arg Leu Tyr Trp Val Asp Ser Lys Leu His Gln Leu Ser
465                 470                 475                 480

Ser Ile Asp Phe Ser Gly Gly Asn Arg Lys Thr Leu Ile Ser Ser Thr
                485                 490                 495

Asp Phe Leu Ser His Pro Phe Gly Ile Ala Val Phe Glu Asp Lys Val
            500                 505                 510

Phe Trp Thr Asp Leu Glu Asn Glu Ala Ile Phe Ser Ala Asn Arg Leu
        515                 520                 525

Asn Gly Leu Glu Ile Ser Ile Leu Ala Glu Asn Leu Asn Asn Pro His
    530                 535                 540

Asp Ile Val Ile Phe His Glu Leu Lys Gln Pro Arg Ala Pro Asp Ala
545                 550                 555                 560

Cys Glu Leu Ser Val Gln Pro Asn Gly Gly Cys Glu Tyr Leu Cys Leu
                565                 570                 575

Pro Ala Pro Gln Ile Ser Ser His Ser Pro Lys Tyr Thr Cys Ala Cys
            580                 585                 590

Pro Asp Thr Met Trp Leu Gly Pro Asp Met Lys Arg Cys Tyr Arg Asp
        595                 600                 605

Ala Asn Glu Asp Ser Lys Met Gly Ser Thr Val Thr Ala Ala Val Ile
    610                 615                 620

Gly Ile Ile Val Pro Ile Val Val Ile Ala Leu Leu Cys Met Ser Gly
625                 630                 635                 640

Tyr Leu Ile Trp Arg Asn Trp Lys Arg Lys Asn Thr Lys Ser Met Asn
                645                 650                 655

Phe Asp Asn Pro Val Tyr Arg Lys Thr Thr Glu Glu Glu Asp Glu Asp
            660                 665                 670

Glu Leu His Ile Gly Arg Thr Ala Gln Ile Gly His Val Tyr Pro Ala
        675                 680                 685

Arg Val Ala Leu Ser Leu Glu Asp Asp Gly Leu Pro
    690                 695                 700
```

<210> SEQ ID NO 17
<211> LENGTH: 7606
<212> TYPE: RNA
<213> ORGANISM: Homo sapiens

<400> SEQUENCE: 17

```
gcuggcggcg gccgcccagg gccggggccg cgcgcccagc cugagcccgc cccgccgccg      60

agcgucaccg aaccugcuug aaaugcagcc gaggagccgg ggcgggcggc agcggcggcg     120

gcggcggcgg cgggggcagc ggcaaccccg gcgccgcggc aaggacucgg agggcugaga     180

cgcggcggcg gcggcgcggg gagcgcgggg cgcggcggcc ggagccccgg gcccgccaug     240

ggccuccccg agccgggccc ucuccggcuu cuggcgcugc ugcugcugcu gcugcugcug     300

cugcugcugc agcuccagca ucuugcggcg gcagcggcug auccgcugcu cggcggccaa     360
```

```
gggccggcca aggauugcga aaaggaccaa uuccagugcc ggaacgagcg cugcaucccc    420
ucugugugga gaugcgacga ggacgaugac ugcuuagacc acagcgacga ggacgacugc    480
cccaagaaga ccugugcaga cagugacuuc accugugaca acggccacug cauccacgaa    540
cgguggaagu gugacggcga ggaggagugu ccugauggcu ccgaugaguc cgaggccacu    600
ugcaccaagc aggugugucc ugcagagaag cugagcugug gacccaccag ccacaagugu    660
guaccugccu cguggcgcug cgacggggag aaggacugcg agggguggagc ggaugaggcc    720
ggcugugcua ccuugugcgc cccgcacgag uuccagugcg gcaaccgcuc gugccuggcc    780
gccguguucg ugugcgacgg cgacgacgac uguggugacg gcagcgauga gcgcggcugu    840
gcagacccgg ccugcgggcc ccgcgaguuc cgcugcggcg gcgauggcgg cggcgccugc    900
aucccggagc gcugggucug cgaccgccag uuugacugcg aggaccgcuc ggacgaggca    960
gccgagcucu gcggccgucc gggccccggg gccacguccg cgcccgccgc cugcgccacc   1020
gccucccagu ucgccugccg cagcggcgag ugcgugcacc ugggcuggcg cugcgacggc   1080
gaccgcgacu gcaaagacaa aucggacgag gccgacugcc cacugggcac cugccguggg   1140
gacgaguucc aguguggga ugggacaugu guccuugcaa ucaagcacug caaccaggag   1200
caggacuguc cagaugggag ugaugaagcu ggcugccuac aggggcugaa cgagugucug   1260
cacaacaaug gcggcugcuc acacaucugc acugaccuca agauuggcuu ugaaugcacg   1320
ugcccagcag gcuuccagcu ccuggaccag aagaccugug gcgacauuga ugagugcaag   1380
gacccagaug ccugcagcca gaucugugucaauuacaagg gcuauuuuaa gugugagugc   1440
uacccuggcu acgagaugga ccuacugacc aagaacugca aggcugcugc uggcaagagc   1500
ccaucccuaa ucuucaccaa ccggcacgag gugcggagga ucgaccuggu gaagcggaac   1560
uauucacgcc ucauccccau gcucaagaau gucguggcac uagaugugga aguugccacc   1620
aaucgcaucu acuggugugaccucuccuac cguaagaucu auagcgccua cauggacaag   1680
gccagugacc cgaaagagca ggagguccuc auugacgagc aguugcacuc uccagagggc   1740
cuggcagugg acugggucca caagcacauc uacuggacug acucgggcaa uaagaccauc   1800
ucaguggcca caguugaugg uggccgccga cgcacucucu ucagccguaa ccucagugaa   1860
ccccgggcca ucgcuguuga cccccugcga ggguucaugu auuggucuga cugggggggac   1920
caggccaaga uugagaaauc ugggcucaac ggugugggacc ggcaaacacu ggugucagac   1980
aauauugaau ggcccaacgg aaucacccug gaucugcuga gccagcgcuu guacugggua   2040
gacuccaagc uacaccaacu guccagcauu gacuucagug gaggcaacag aaagacgcug   2100
aucuccucca cugacuuccu gagccacccu uuugggauag cuguguuuga ggacaaggug   2160
uucuggacag accuggagaa cgaggccauu uucagugcaa aucggcucaa uggccuggaa   2220
aucuccaucc uggcugagaa ccucaacaac ccacaugaca uugucaucuu ccaugagcug   2280
aagcagccaa gagcuccaga ugccugugag cugagugucc agccuaaugg aggcugugaa   2340
uaccugugcc uuccugcucc ucagaucucc agccacucuc ccaaguacac augugccugu   2400
ccugacacaa uguggcuggg uccagacaug aagaggugcu accgagcacc ucaaucuacc   2460
ucaacuacga cguuagcuuc uaccaugacg aggacaguac cugccaccac aagagccccc   2520
gggaccaccg uccacagauc caccuaccag aaccacagca cagagacacc aagccugaca   2580
gcugcagucc caagcucagu uagugucccc agggcuccca gcaucagccc gucuacccua   2640
agcccugcaa ccagcaacca cucccagcac uaugcaaaug aagacaguaa gaugggcuca   2700
```

-continued

```
acagucacug ccgcuguuau cgggaucauc gugcccauag uggugauagc ccuccugugc   2760
augaguggau accugaucug gagaaacugg aagcggaaga acaccaaaag caugaauuuu   2820
gacaacccag ucuacaggaa aacaacagaa gaagaagacg aagaugagcu ccauauaggg   2880
agaacugcuc agauuggcca ugucuauccu gcacgagugg cauuaagccu ugaagaugau   2940
ggacuacccu gaggauggga ucacccccuu cgugccucau ggaauucagu cccaugcacu   3000
acacucugga ugguguauga cuggaugaau ggguuucuau auaugggucu gugugagugu   3060
augugugugu gugauuuuuu uuuuaaauuu auguugcgga aagguaacca caaaguuaug   3120
augaacugca aacauccaaa ggaugugaga guuuuucuau guauaaauguu uuauacacuu   3180
uuuaacuggu ugcacuaccc augaggaauu cguggaaugg cuacugcuga cuaacaugau   3240
gcacauaacc aaaugggggc caauggcaca guaccuuacu caucauuuaa aaacuauauu   3300
uacagaagau guuugguugc ugggggggcu uuuuuagguu uuggggcauu uguuuuuugu   3360
aaauaagaug auuaugcuuu guggcuaucc aucaacauaa guaaaaaaaa aaaaaaaaca   3420
cuucaacucc cucccccauu uagauuauuu auuaacauau uuuaaaaauc agaugaguuc   3480
uauaaauaau uuagagaagu gagaguauuu auuuuuggca uguuuggccc accacacaga   3540
cucugugugu guaugugugu guuuauaugu guaugugugu gacagaaaaa ucuguagaga   3600
agaggcacau cuauggcuac uguucaaaua cauaaagaua aauuuauuuu cacacagucc   3660
acaaggggua uaucuuguag uuuucagaaa agccuuugga aaucuggauc agaaaauaga   3720
uaccaugguu ugugcaauua uguaguaaaa aaggcaaauc uuuucaccuc uggcuauucc   3780
ugagacccca ggaagucagg aaaagccuuu cagcucaccc auggcugcug ugacuccuac   3840
cagggcuuuc uuggcuuugg cgaaggucag uguacagaca uuccauggua ccagagugcu   3900
cagaaacuca agauaggaua ugccucaccc ucagcuacuc cuuguuuuaa aguucagcuc   3960
uuugaguaac uucuucaauu ucuuucagga cacuuggguu gaauucagua aguuuccucu   4020
gaagcacccu gaagggugcc auccuuacag agcuaagugg agacguuucc agaucagccc   4080
aaguuuacua uagagacugg cccaggcacu gaaugucuag gacaugcugu ggaugaagau   4140
aaagauggug gaauagguuu uaucacaucu cuuauuucuc uuuuccccuu acucucuacc   4200
auuuccuuua ugugggaaa cauuuuaagg uaauaaaauag guuacuuacc aucauauguu   4260
cauauagaug aaacuaauuu uuggcuuaag ucagaacaac uggccaaaau ugaagucaua   4320
uuugaggggg gaaauggcau acgcaauauu auauuauauu ggauauuuau guucacacag   4380
gaauuugguu uacugcuuug uaaauaaaag gaaaaacucc ggguauaugu auagauguuc   4440
uucauuauag acaucuucuu ugcuuuucuu ggccuugggg gaggaaggga gaagugcucu   4500
uuucuacuug ugggguccc cauuggaaac auaauccuau agucccagaa ggauucaguc   4560
cccaguggcu uucccaucca aagagaaaga guuugaguuu cuuaacucug cuguucugcc   4620
acuuacuccc acuagacaac cagggacaag gugcaacaug gaaguguuug acuuaaguag   4680
gagcagagga gcugcaucua aucucaucau accuggaacu ugacacacuu aagcaaaugc   4740
cuucccaucc cuaccugcca gaugccccca acucaaugaa guuggauguc ucaccagcuu   4800
gauacccuuu gaauuuucag ucagacauuc uggaguucua gcauccugua ccuaggaccu   4860
uccucugugu cacucuuggc cuccuaaacu cuaagaaaau aacuauauuc uggagcuugg   4920
gcagugugu uugcauaauc cagcaaucuc cucaugacau gcauguguug auaguccuga   4980
aacauucauu gagaggguaa augcaguuga ccuagaauga ccaauaccaa acagaauuuu   5040
aagaacaggu ggccaacucc uauggagcuu acucacauau uacuauucuu uuaagaacgg   5100
```

-continued aaaguaaaau uauuuuugac ugaagaaaaa ugaugacagu gaaaaacaug gaaauguacu 5160
caaaacaagu gacuuuuucu guaaccuucc aaagaaacug aauuuuccaa ggaauuaaau 5220
gauaacagug gcuaaggcau aguuucuaaa cuuucaguaa gauccuggca uucacagaaa 5280
aaaaugauga auggggucug gacauacagc cugagaucuc aaaaugacaa ugaaauucac 5340
aacuuuuucu cagagacauu cauguuuccu gcauaugcua caacugcagu uugaaagagg 5400
cagcaauggg agcaacccuu uacaagaaac aaauugugau auauucaugu guuggacggc 5460
aguaaauaag augaaaccug aggagucaga uccaccuucc cccauucaua gaggcuuuuc 5520
agccucauuu ugagguacag uuacauaucu uuugccuuuu gcccccgugc auagcuaucu 5580
acagccaauc acagaucaca gagucacugg acuauagagc uggaaggaag cucagagaca 5640
augccaaggg ggcagaaaau uuaucagaag ccagucccag ugcguuuccu ccauuuccuu 5700
cugcaggaag acuauuuugg gcugccugaa cauuguauca aaccugcuac cuauacuaug 5760
gucuaccuuu ccuccagugg aauuacaaag gcacuaacug aaaugccuuc uagaaacaga 5820
gaaaacgaaa cuguacuuau uuacucuuga uacacagauu auuuauaaaa cagauugaag 5880
uaaccuguua acuggcaaaa agagaaugag aucggauuua aauguauggc aguaaguccu 5940
auugaucccu ccaguuaucu caguaugacu gcaguauauu cauucacuaa aaccacucac 6000
uagauaccaa cuacacaccu ggcacugcag auguaaaggu cagucacaca uguucugacu 6060
uuacagaguu cacaguagca guggaggaug auauaugugg aaacaaaaaa ggcauugauu 6120
cuauucagag cacuguuagg gcucaaagga gagaggggguc uuuccaccua agaaaugagg 6180
aauaggguca ucauagaagu gaccuuaagu cuuaaaaauu aagaagggga uuccaagcug 6240
cuucagacag agacacaucg agcuaaaaca cagagguaug aaagagcaca gggacuuuag 6300
gaauugcaca guucauucua acaggaacaa aaggcucaag gggggcaaga aaugaggcug 6360
uauggaaaga gauucaaugu aagcacuuua uaaaauagau uaauuucuga uucaaugaag 6420
cauuucuuga ucauugugua caaggcacua caugcaucau ggaaaauuca uuaggaugca 6480
uugccagcac uuugcagaac ugauauuauu cagccucaag cuuuccagug gccaaaggga 6540
aaugcugacu gcuuuucaua uauuugaguc aaagauuuuu uauaugguca augaagacua 6600
auauaagggc agugggauuu ucacagaugc augccauguu gucgagagcc ucuuagauuu 6660
ucucaacugu gagaaagaaa aacgaaaaug uugaagacgu ugagucugga gaggggauac 6720
uaaucacugu ccaguugggc acugguggga augggggaaau ggcacaggaa ugcaagccuc 6780
uccacccuac cccccgaacu ccagccauac acucaucguu ucacaaaaua uaaaugaguu 6840
agcauuaaau guuucagagu aaauaauucc uuuucccgaa augcaugaag auagaguaac 6900
agacuucuca cacuguauuu uuagggguaug gagaauuuag aagguuaaag aauuacugcu 6960
ucaauuuuuc aguuaaaaaa aaaucaggaa gcucuguuca uucaggcuau gcaccaugug 7020
cacagucaag aauuagcaga aacccucugc auuuacaaac acuuugugcu auaaaaaagu 7080
aauuuuuaaa aagccacgug ugugugugug uauauauaua uauauauaua uauuuaaagc 7140
caagguuuug auacuuuuuu acaaaaacua caagagaaaa caaauauacc uguccaaacc 7200
auauacuuuu aaaagagcau uuuuuuuucc auacaagcug uuguuaauuu gggguaaag 7260
ugcugauuug caaacuucau caaauuguuc ccaaguggau ucuccuuguu ugucuccccc 7320
uaccaacccc aaaguuacca uauuugaugu aagaaucagg cauguuagaa uguuguguca 7380
cacuaacuga uucugcucuu uuugucuugu cauucaaguu ccguuagcuu cuguacgcgg 7440

-continued

```
ugcccuuugc agucuggugu cucuuccaga ggcgaggggg cugaggaugg ggugcugcau   7500

cucacuagcu auacuggcau caucuuggua aacugaaaac caaaugugga cauuuguaaa   7560

aucagugcac uguuucuaga gagagauuaa auucauuuaa aaaaaa                  7606


<210> SEQ ID NO 18
<211> LENGTH: 904
<212> TYPE: PRT
<213> ORGANISM: Homo sapiens

<400> SEQUENCE: 18

Met Gly Leu Pro Glu Pro Gly Pro Leu Arg Leu Leu Ala Leu Leu Leu
1               5                   10                  15

Leu Leu Leu Leu Leu Leu Leu Leu Gln Leu Gln His Leu Ala Ala Ala
            20                  25                  30

Ala Ala Asp Pro Leu Leu Gly Gly Gln Gly Pro Ala Lys Asp Cys Glu
        35                  40                  45

Lys Asp Gln Phe Gln Cys Arg Asn Glu Arg Cys Ile Pro Ser Val Trp
    50                  55                  60

Arg Cys Asp Glu Asp Asp Asp Cys Leu Asp His Ser Asp Glu Asp Asp
65                  70                  75                  80

Cys Pro Lys Lys Thr Cys Ala Asp Ser Asp Phe Thr Cys Asp Asn Gly
                85                  90                  95

His Cys Ile His Glu Arg Trp Lys Cys Asp Gly Glu Glu Glu Cys Pro
            100                 105                 110

Asp Gly Ser Asp Glu Ser Glu Ala Thr Cys Thr Lys Gln Val Cys Pro
        115                 120                 125

Ala Glu Lys Leu Ser Cys Gly Pro Thr Ser His Lys Cys Val Pro Ala
    130                 135                 140

Ser Trp Arg Cys Asp Gly Glu Lys Asp Cys Glu Gly Gly Ala Asp Glu
145                 150                 155                 160

Ala Gly Cys Ala Thr Leu Cys Ala Pro His Glu Phe Gln Cys Gly Asn
                165                 170                 175

Arg Ser Cys Leu Ala Ala Val Phe Val Cys Asp Gly Asp Asp Asp Cys
            180                 185                 190

Gly Asp Gly Ser Asp Glu Arg Gly Cys Ala Asp Pro Ala Cys Gly Pro
        195                 200                 205

Arg Glu Phe Arg Cys Gly Gly Asp Gly Gly Gly Ala Cys Ile Pro Glu
    210                 215                 220

Arg Trp Val Cys Asp Arg Gln Phe Asp Cys Glu Asp Arg Ser Asp Glu
225                 230                 235                 240

Ala Ala Glu Leu Cys Gly Arg Pro Gly Pro Gly Ala Thr Ser Ala Pro
                245                 250                 255

Ala Ala Cys Ala Thr Ala Ser Gln Phe Ala Cys Arg Ser Gly Glu Cys
            260                 265                 270

Val His Leu Gly Trp Arg Cys Asp Gly Asp Arg Asp Cys Lys Asp Lys
        275                 280                 285

Ser Asp Glu Ala Asp Cys Pro Leu Gly Thr Cys Arg Gly Asp Glu Phe
    290                 295                 300

Gln Cys Gly Asp Gly Thr Cys Val Leu Ala Ile Lys His Cys Asn Gln
305                 310                 315                 320

Glu Gln Asp Cys Pro Asp Gly Ser Asp Glu Ala Gly Cys Leu Gln Gly
                325                 330                 335

Leu Asn Glu Cys Leu His Asn Asn Gly Gly Cys Ser His Ile Cys Thr
            340                 345                 350
```

```
Asp Leu Lys Ile Gly Phe Glu Cys Thr Cys Pro Ala Gly Phe Gln Leu
        355                 360                 365

Leu Asp Gln Lys Thr Cys Gly Asp Ile Asp Glu Cys Lys Asp Pro Asp
    370                 375                 380

Ala Cys Ser Gln Ile Cys Val Asn Tyr Lys Gly Tyr Phe Lys Cys Glu
385                 390                 395                 400

Cys Tyr Pro Gly Tyr Glu Met Asp Leu Leu Thr Lys Asn Cys Lys Ala
                405                 410                 415

Ala Ala Gly Lys Ser Pro Ser Leu Ile Phe Thr Asn Arg His Glu Val
            420                 425                 430

Arg Arg Ile Asp Leu Val Lys Arg Asn Tyr Ser Arg Leu Ile Pro Met
        435                 440                 445

Leu Lys Asn Val Val Ala Leu Asp Val Glu Val Ala Thr Asn Arg Ile
    450                 455                 460

Tyr Trp Cys Asp Leu Ser Tyr Arg Lys Ile Tyr Ser Ala Tyr Met Asp
465                 470                 475                 480

Lys Ala Ser Asp Pro Lys Glu Gln Glu Val Leu Ile Asp Glu Gln Leu
                485                 490                 495

His Ser Pro Glu Gly Leu Ala Val Asp Trp Val His Lys His Ile Tyr
            500                 505                 510

Trp Thr Asp Ser Gly Asn Lys Thr Ile Ser Val Ala Thr Val Asp Gly
        515                 520                 525

Gly Arg Arg Arg Thr Leu Phe Ser Arg Asn Leu Ser Glu Pro Arg Ala
    530                 535                 540

Ile Ala Val Asp Pro Leu Arg Gly Phe Met Tyr Trp Ser Asp Trp Gly
545                 550                 555                 560

Asp Gln Ala Lys Ile Glu Lys Ser Gly Leu Asn Gly Val Asp Arg Gln
                565                 570                 575

Thr Leu Val Ser Asp Asn Ile Glu Trp Pro Asn Gly Ile Thr Leu Asp
            580                 585                 590

Leu Leu Ser Gln Arg Leu Tyr Trp Val Asp Ser Lys Leu His Gln Leu
        595                 600                 605

Ser Ser Ile Asp Phe Ser Gly Gly Asn Arg Lys Thr Leu Ile Ser Ser
    610                 615                 620

Thr Asp Phe Leu Ser His Pro Phe Gly Ile Ala Val Phe Glu Asp Lys
625                 630                 635                 640

Val Phe Trp Thr Asp Leu Glu Asn Glu Ala Ile Phe Ser Ala Asn Arg
                645                 650                 655

Leu Asn Gly Leu Glu Ile Ser Ile Leu Ala Glu Asn Leu Asn Asn Pro
            660                 665                 670

His Asp Ile Val Ile Phe His Glu Leu Lys Gln Pro Arg Ala Pro Asp
        675                 680                 685

Ala Cys Glu Leu Ser Val Gln Pro Asn Gly Gly Cys Glu Tyr Leu Cys
    690                 695                 700

Leu Pro Ala Pro Gln Ile Ser Ser His Ser Pro Lys Tyr Thr Cys Ala
705                 710                 715                 720

Cys Pro Asp Thr Met Trp Leu Gly Pro Asp Met Lys Arg Cys Tyr Arg
                725                 730                 735

Ala Pro Gln Ser Thr Ser Thr Thr Thr Leu Ala Ser Thr Met Thr Arg
            740                 745                 750

Thr Val Pro Ala Thr Thr Arg Ala Pro Gly Thr Thr Val His Arg Ser
        755                 760                 765
```

```
Thr Tyr Gln Asn His Ser Thr Glu Thr Pro Ser Leu Thr Ala Ala Val
    770                 775                 780

Pro Ser Ser Val Ser Val Pro Arg Ala Pro Ser Ile Ser Pro Ser Thr
785                 790                 795                 800

Leu Ser Pro Ala Thr Ser Asn His Ser Gln His Tyr Ala Asn Glu Asp
                805                 810                 815

Ser Lys Met Gly Ser Thr Val Thr Ala Ala Val Ile Gly Ile Ile Val
            820                 825                 830

Pro Ile Val Val Ile Ala Leu Leu Cys Met Ser Gly Tyr Leu Ile Trp
        835                 840                 845

Arg Asn Trp Lys Arg Lys Asn Thr Lys Ser Met Asn Phe Asp Asn Pro
    850                 855                 860

Val Tyr Arg Lys Thr Thr Glu Glu Glu Asp Glu Asp Glu Leu His Ile
865                 870                 875                 880

Gly Arg Thr Ala Gln Ile Gly His Val Tyr Pro Ala Arg Val Ala Leu
                885                 890                 895

Ser Leu Glu Asp Asp Gly Leu Pro
            900
```

<210> SEQ ID NO 19
<211> LENGTH: 2358
<212> TYPE: RNA
<213> ORGANISM: Homo sapiens

<400> SEQUENCE: 19

```
aaacucacac aacaacucuu ccccgcugag aggagacagc cagugcgacu ccacccucca     60

gcucgacggc agccgccccg gccgacagcc ccgagacgac agcccggcgc gucccggucc    120

ccaccuccga ccaccgccag cgcuccaggc cccgccgcuc cccgcucgcc gccaccgcgc    180

ccuccgcucc gcccgcagug ccaaccauga ccgccgccag uaugggcccc guccgcgucg    240

ccuucguggu ccuccucgcc cucugcagcc ggccggccgu cggccagaac ugcagcgggc    300

cgugccggug cccggacgag ccggcgccgc gcugcccggc gggcgugagc cucgugcugg    360

acggcugcgg cugcugccgc gucugcgcca agcagcuggg cgagcugugc accgagcgcg    420

accccugcga cccgcacaag ggccucuucu gugacuucgg cuccccggcc aaccgcaaga    480

ucggcgugug caccgccaaa gauggugcuc ccugcaucuu cgguggguacg guguaccgca    540

gcggagaguc cuuccagagc agcugcaagu accagugcac gugccuggac ggggcggugg    600

gcugcaugcc ccugugcagc auggacguuc gucugcccag cccugacugc cccuucccga    660

ggagggucaa gcugcccggg aaaugcugcg aggagugggu gugugacgag cccaaggacc    720

aaaccguggu ugggccugcc cucgcggcuu accgacugga agacacguuu ggcccagacc    780

caacuaugau uagagccaac ugccuggucc agaccacaga guggagcgcc uguuccaaga    840

ccugugggau gggcaucucc acccgguua ccaaugacaa cgccuccugc aggcuagaga    900

agcagagccg ccugugcaug gucaggccuu gcgaagcuga ccuggaagag aacauuaaga    960

agggcaaaaa gugcauccgu acucccaaaa ucuccaagcc uaucaaguuu gagcuuucug   1020

gcugcaccag caugaagaca uaccgagcua aauucugugg aguauguacc gacggccgau   1080

gcugcacccc ccacagaacc accacccugc cgguggaguu caagugcccu gacggcgagg   1140

ucaugaagaa gaacaugaug uucaucaaga ccugugccug ccauuacaac ugucccggag   1200

acaaugacau cuuugaaucg cuguacuaca ggaagaugua cggagacaug gcaugaagcc   1260

agagagugag agacauuaac ucauuagacu ggaacuugaa cugauucaca ucucauuuuu   1320
```

-continued

```
ccguaaaaau gauuucagua gcacaaguua uuuaaaucug uuuuucuaac ugggggaaaa   1380

gauucccacc caauucaaaa cauugugcca ugucaaacaa auagucuauc aaccccagac   1440

acugguuuga agaauguuaa gacuugacag uggaacuaca uuaguacaca gcaccagaau   1500

guauauuaag guguggcuuu aggagcagug ggaggguacc agcagaaagg uuaguaucau   1560

cagauagcau cuuauacgag uaauaugccu gcuauuugaa guguaauuga gaaggaaaau   1620

uuuagcgugc ucacugaccu gccuguagcc ccagugacag cuaggaugug cauucuccag   1680

ccaucaagag acugagucaa guuguuccuu aagucagaac agcagacuca gcucugacau   1740

ucugauucga augacacugu ucaggaaucg gaauccuguc gauuagacug gacagcuugu   1800

ggcaagugaa uuugccugua acaagccaga uuuuuuaaaa uuuauauugu aaauauugug   1860

ugugugugug uguguguaua uauauauaua uguacaguua ucuaaguuaa uuuaaaguug   1920

uuugugccuu uuuauuuuug uuuuuaaugc uuugauauuu caauguuagc cucaauuucu   1980

gaacaccaua gguagaaugu aaagcuuguc ugaucguuca aagcaugaaa uggauacuua   2040

uauggaaauu cugcucagau agaaugacag uccgucaaaa cagauuguuu gcaaagggga   2100

ggcaucagug uccuuggcag gcugauuucu agguaggaaa ugugguagcc ucacuuuuaa   2160

ugaacaaaug gccuuuauua aaaacugagu gacucuauau agcugaucag uuuuuucacc   2220

uggaagcauu uguuucuacu uugauaugac uguuuuucgg acaguuuauu uguugagagu   2280

gugaccaaaa guuacauguu ugcaccuuuc uaguugaaaa uaaaguguau auuuuuucua   2340

uaaaaaaaaa aaaaaaaa                                                 2358


<210> SEQ ID NO 20
<211> LENGTH: 349
<212> TYPE: PRT
<213> ORGANISM: Homo sapiens

<400> SEQUENCE: 20

Met Thr Ala Ala Ser Met Gly Pro Val Arg Val Ala Phe Val Val Leu
1               5                   10                  15

Leu Ala Leu Cys Ser Arg Pro Ala Val Gly Gln Asn Cys Ser Gly Pro
            20                  25                  30

Cys Arg Cys Pro Asp Glu Pro Ala Pro Arg Cys Pro Ala Gly Val Ser
        35                  40                  45

Leu Val Leu Asp Gly Cys Gly Cys Cys Arg Val Cys Ala Lys Gln Leu
    50                  55                  60

Gly Glu Leu Cys Thr Glu Arg Asp Pro Cys Asp Pro His Lys Gly Leu
65                  70                  75                  80

Phe Cys Asp Phe Gly Ser Pro Ala Asn Arg Lys Ile Gly Val Cys Thr
                85                  90                  95

Ala Lys Asp Gly Ala Pro Cys Ile Phe Gly Gly Thr Val Tyr Arg Ser
            100                 105                 110

Gly Glu Ser Phe Gln Ser Ser Cys Lys Tyr Gln Cys Thr Cys Leu Asp
        115                 120                 125

Gly Ala Val Gly Cys Met Pro Leu Cys Ser Met Asp Val Arg Leu Pro
    130                 135                 140

Ser Pro Asp Cys Pro Phe Pro Arg Arg Val Lys Leu Pro Gly Lys Cys
145                 150                 155                 160

Cys Glu Glu Trp Val Cys Asp Glu Pro Lys Asp Gln Thr Val Val Gly
                165                 170                 175

Pro Ala Leu Ala Ala Tyr Arg Leu Glu Asp Thr Phe Gly Pro Asp Pro
            180                 185                 190
```

```
Thr Met Ile Arg Ala Asn Cys Leu Val Gln Thr Thr Glu Trp Ser Ala
        195                 200                 205

Cys Ser Lys Thr Cys Gly Met Gly Ile Ser Thr Arg Val Thr Asn Asp
    210                 215                 220

Asn Ala Ser Cys Arg Leu Glu Lys Gln Ser Arg Leu Cys Met Val Arg
225                 230                 235                 240

Pro Cys Glu Ala Asp Leu Glu Glu Asn Ile Lys Lys Gly Lys Lys Cys
                245                 250                 255

Ile Arg Thr Pro Lys Ile Ser Lys Pro Ile Lys Phe Glu Leu Ser Gly
            260                 265                 270

Cys Thr Ser Met Lys Thr Tyr Arg Ala Lys Phe Cys Gly Val Cys Thr
        275                 280                 285

Asp Gly Arg Cys Cys Thr Pro His Arg Thr Thr Thr Leu Pro Val Glu
    290                 295                 300

Phe Lys Cys Pro Asp Gly Glu Val Met Lys Lys Asn Met Met Phe Ile
305                 310                 315                 320

Lys Thr Cys Ala Cys His Tyr Asn Cys Pro Gly Asp Asn Asp Ile Phe
                325                 330                 335

Glu Ser Leu Tyr Tyr Arg Lys Met Tyr Gly Asp Met Ala
            340                 345
```

```
<210> SEQ ID NO 21
<211> LENGTH: 1939
<212> TYPE: RNA
<213> ORGANISM: Homo sapiens

<400> SEQUENCE: 21

aggaaggagg gguggccuga ccccucggca gucccucccc ucagccuuuc cccaaauugc      60
uacuucucug gggcuccagg uccugcuugu gcucagcucc agcucacugg cuggccaccg     120
agacuucugg acaggaaacu gcaccauccu cuucucccag caaggggggcu ccagagacug     180
cccacccagg aagucuggug gccuggggau uuggacagug ccuugguaau gaccagggcu     240
ccaggaagag auguccuugu ggcugggggc cccugugccu gacauuccuc cugacucugc     300
gguggagcug uggaagccag gcgcacagga ugcaagcagc caggcccagg gaggcagcag     360
cugcauccuc agagaggaag ccaggaugcc ccacucugcu gggggguacug caggggguggg   420
gcuggaggcu gcagagccca cagcccugcu caccagggca gagccccccuu cagaacccac    480
agagauccgu ccacaaaagc ggaaaaaggg gccagccccc aaaaugcugg ggaacgagcu     540
augcagcgug ugugggggaca aggccucggg cuuccacuac aauguucuga gcugcgaggg    600
cugcaaggga uucuuccgcc gcagcgucau caagggagcg cacuacaucu gccacagugg     660
cggccacugc cccauggaca ccuacaugcg ucgcaagugc caggaguguc ggcuucgcaa     720
augccgucag gcuggcaugc gggaggagug uguccuguca gaagaacaga uccgccugaa     780
gaaacugaag cggcaagagg aggaacaggc ucaugccaca uccuugcccc ccagggcuuc     840
cucacccccc caaauccugc cccagcucag cccggaacaa cugggcauga ucgagaagcu     900
cgucgcugcc cagcaacagu guaaccggcg cuccuuuucu gaccggcuuc gagucacgcc     960
uuggcccaug gcaccagauc cccauagccg ggaggcccgu cagcagcgcu uugcccacuu    1020
cacugagcug gccaucgucu cugugcagga gauaguugac uuugcuaaac agcuacccgg    1080
cuuccugcag cucagccggg aggaccagau ugcccugcug aagaccucug cgaucgaggu    1140
gaugcuucug gagacaucuc ggagguacaa cccugggagu gagaguauca ccuuccucaa    1200
```

-continued

```
ggauuucagu uauaaccggg aagacuuugc caaagcaggg cugcaagugg aauucaucaa   1260

ccccaucuuc gaguucucca gggccaugaa ugagcugcaa cucaaugaug ccgaguuugc   1320

cuugcucauu gcuaucagca ucuucucugc agaccggccc aacgugcagg accagcucca   1380

gguagagagg cugcagcaca cauaugugga agcccugcau gccuacgucu ccauccacca   1440

uccccaugac cgacugaugu ucccacggau gcuaaugaaa cuggugagcc uccggacccu   1500

gagcagcguc cacucagagc aaguguuugc acugcgucug caggacaaaa agcucccacc   1560

gcugcucucu gagaucuggg augugcacga augacuguuc uguccccaua uuuucuguuu   1620

ucuuggccgg auggcugagg ccugguggcu gccuccuaga aguggaacag acugagaagg   1680

gcaaacauuc cugggagcug ggcaaggaga uccucccgug gcauuaaaag agagucaaag   1740

gguugcgagu uuuguggcua cugagcagug gagcccucgc uaacacugug cugugucuga   1800

agaucaugcu gaccccacaa acggaugggc cugggggcca cuuugcacag gguucuccag   1860

agcccugccc auccugccuc caccacuucc uguuuuuccc acagggcccc aagaaaaauu   1920

cuccacuguc aaaaaaaaa                                                 1939
```

<210> SEQ ID NO 22
<211> LENGTH: 447
<212> TYPE: PRT
<213> ORGANISM: Homo sapiens

<400> SEQUENCE: 22

```
Met Ser Leu Trp Leu Gly Ala Pro Val Pro Asp Ile Pro Pro Asp Ser
1               5                   10                  15

Ala Val Glu Leu Trp Lys Pro Gly Ala Gln Asp Ala Ser Ser Gln Ala
            20                  25                  30

Gln Gly Gly Ser Ser Cys Ile Leu Arg Glu Glu Ala Arg Met Pro His
        35                  40                  45

Ser Ala Gly Gly Thr Ala Gly Val Gly Leu Glu Ala Ala Glu Pro Thr
    50                  55                  60

Ala Leu Leu Thr Arg Ala Glu Pro Pro Ser Glu Pro Thr Glu Ile Arg
65                  70                  75                  80

Pro Gln Lys Arg Lys Lys Gly Pro Ala Pro Lys Met Leu Gly Asn Glu
                85                  90                  95

Leu Cys Ser Val Cys Gly Asp Lys Ala Ser Gly Phe His Tyr Asn Val
            100                 105                 110

Leu Ser Cys Glu Gly Cys Lys Gly Phe Phe Arg Arg Ser Val Ile Lys
        115                 120                 125

Gly Ala His Tyr Ile Cys His Ser Gly Gly His Cys Pro Met Asp Thr
    130                 135                 140

Tyr Met Arg Arg Lys Cys Gln Glu Cys Arg Leu Arg Lys Cys Arg Gln
145                 150                 155                 160

Ala Gly Met Arg Glu Glu Cys Val Leu Ser Glu Glu Gln Ile Arg Leu
                165                 170                 175

Lys Lys Leu Lys Arg Gln Glu Glu Glu Gln Ala His Ala Thr Ser Leu
            180                 185                 190

Pro Pro Arg Ala Ser Ser Pro Pro Gln Ile Leu Pro Gln Leu Ser Pro
        195                 200                 205

Glu Gln Leu Gly Met Ile Glu Lys Leu Val Ala Ala Gln Gln Gln Cys
    210                 215                 220

Asn Arg Arg Ser Phe Ser Asp Arg Leu Arg Val Thr Pro Trp Pro Met
225                 230                 235                 240
```

```
Ala Pro Asp Pro His Ser Arg Glu Ala Arg Gln Gln Arg Phe Ala His
                245                 250                 255

Phe Thr Glu Leu Ala Ile Val Ser Val Gln Glu Ile Val Asp Phe Ala
            260                 265                 270

Lys Gln Leu Pro Gly Phe Leu Gln Leu Ser Arg Glu Asp Gln Ile Ala
        275                 280                 285

Leu Leu Lys Thr Ser Ala Ile Glu Val Met Leu Leu Glu Thr Ser Arg
    290                 295                 300

Arg Tyr Asn Pro Gly Ser Glu Ser Ile Thr Phe Leu Lys Asp Phe Ser
305                 310                 315                 320

Tyr Asn Arg Glu Asp Phe Ala Lys Ala Gly Leu Gln Val Glu Phe Ile
                325                 330                 335

Asn Pro Ile Phe Glu Phe Ser Arg Ala Met Asn Glu Leu Gln Leu Asn
            340                 345                 350

Asp Ala Glu Phe Ala Leu Leu Ile Ala Ile Ser Ile Phe Ser Ala Asp
        355                 360                 365

Arg Pro Asn Val Gln Asp Gln Leu Gln Val Glu Arg Leu Gln His Thr
    370                 375                 380

Tyr Val Glu Ala Leu His Ala Tyr Val Ser Ile His His Pro His Asp
385                 390                 395                 400

Arg Leu Met Phe Pro Arg Met Leu Met Lys Leu Val Ser Leu Arg Thr
                405                 410                 415

Leu Ser Ser Val His Ser Glu Gln Val Phe Ala Leu Arg Leu Gln Asp
            420                 425                 430

Lys Lys Leu Pro Pro Leu Leu Ser Glu Ile Trp Asp Val His Glu
        435                 440                 445


<210> SEQ ID NO 23
<211> LENGTH: 1759
<212> TYPE: RNA
<213> ORGANISM: Homo sapiens

<400> SEQUENCE: 23

aggaaggagg gguggccuga ccccucggca gucccucccc ucagccuuuc cccaaauugc      60

uacuucucug gggcuccagg uccugcuugu gcucagcucc agcucacugg cuggccaccg     120

agacuucugg acaggaaacu gcaccauccu cuucucccag caagggggcu ccagagacug     180

cccacccagg aagucuggug gccuggggau uuggacagug ccuugguaau gaccagggcu     240

ccaggaagag auguccuugu ggcugggggc ccugugccu gacauucccuc cugacucugc     300

gguggagcug uggaagccag gcgcacagga ugcaagcagc caggcccagg gaggcagcag     360

cugcauccuc agagaggaag ccaggaugcc ccacucugcu gggggacug cagggguggg     420

gcuggaggcu gcagagccca cagcccugcu caccagggca gagcccccuu cagaacccac     480

agagauccgu ccacaaaagc ggaaaaaggg gccagccccc aaaaugcugg ggaacgagcu     540

augcagcgug uguggggaca aggccucggg cuuccacuac aauguucuga gcugcgaggg     600

cugcaaggga uucuuccgcc gcagcgucau caagggagcg cacuacaucu gccacagugg     660

cggccacugc cccauggaca ccuacaugcg ucgcaagugc caggaguguc ggcuucgcaa     720

augccgucag gcuggcaugc gggaggagug uguccuguca gaagaacaga uccgccugaa     780

gaaacugaag cggcaagagg aggaacaggc ucaugccaca uccuugcccc ccagggcuuc     840

cucaccccccc caaauccugc cccagcucag cccggaacaa cugggcauga ucgagaagcu     900

cgucgcugcc cagcaacagu guaaccggcg cuccuuuucu gaccggcuuc gagucacggu     960
```

gaugcuucug gagacaucuc ggagguacaa cccugggagu gagaguauca ccuucccucaa 1020 ggauuucagu uauaaccggg aagacuuugc caaagcaggg cugcaagugg aauucaucaa 1080
ccccaucuuc gaguucucca gggccaugaa ugagcugcaa cucaaugaug ccgaguuugc 1140
cuugcucauu gcuaucagca ucuucucugc agaccggccc aacgugcagg accagcucca 1200
gguagagagg cugcagcaca cauaugugga agcccugcau gccuacgucu ccauccacca 1260
uccccaugac cgacugaugu ucccacggau gcuaaugaaa cuggugagcc uccggacccu 1320
gagcagcguc cacucagagc aaguguuugc acugcgucug caggacaaaa agcucccacc 1380
gcugcucucu gagaucuggg augugcacga augacuguuc uguccccaua uuuucuguuu 1440
ucuuggccgg auggcugagg ccugguggcu gccuccuaga aguggaacag acugagaagg 1500
gcaaacauuc cugggagcug ggcaaggaga uccucccgug gcauuaaaag agagucaaag 1560
gguugcgagu uuuguggcua cugagcagug gagcccucgc uaacacugug cugugucuga 1620
agaucaugcu gaccccacaa acggaugggc cugggggcca cuuugcacag gguucuccag 1680
agcccugccc auccugccuc caccacuucc uguuuuuccc acagggcccc aagaaaaauu 1740
cuccacuguc aaaaaaaaa 1759

<210> SEQ ID NO 24
<211> LENGTH: 387
<212> TYPE: PRT
<213> ORGANISM: Homo sapiens

<400> SEQUENCE: 24

Met Ser Leu Trp Leu Gly Ala Pro Val Pro Asp Ile Pro Pro Asp Ser
1               5                   10                  15

Ala Val Glu Leu Trp Lys Pro Gly Ala Gln Asp Ala Ser Ser Gln Ala
            20                  25                  30

Gln Gly Gly Ser Ser Cys Ile Leu Arg Glu Glu Ala Arg Met Pro His
        35                  40                  45

Ser Ala Gly Gly Thr Ala Gly Val Gly Leu Glu Ala Ala Glu Pro Thr
    50                  55                  60

Ala Leu Leu Thr Arg Ala Glu Pro Pro Ser Glu Pro Thr Glu Ile Arg
65                  70                  75                  80

Pro Gln Lys Arg Lys Lys Gly Pro Ala Pro Lys Met Leu Gly Asn Glu
                85                  90                  95

Leu Cys Ser Val Cys Gly Asp Lys Ala Ser Gly Phe His Tyr Asn Val
            100                 105                 110

Leu Ser Cys Glu Gly Cys Lys Gly Phe Phe Arg Arg Ser Val Ile Lys
        115                 120                 125

Gly Ala His Tyr Ile Cys His Ser Gly Gly His Cys Pro Met Asp Thr
    130                 135                 140

Tyr Met Arg Arg Lys Cys Gln Glu Cys Arg Leu Arg Lys Cys Arg Gln
145                 150                 155                 160

Ala Gly Met Arg Glu Glu Cys Val Leu Ser Glu Glu Gln Ile Arg Leu
                165                 170                 175

Lys Lys Leu Lys Arg Gln Glu Glu Glu Gln Ala His Ala Thr Ser Leu
            180                 185                 190

Pro Pro Arg Ala Ser Ser Pro Pro Gln Ile Leu Pro Gln Leu Ser Pro
        195                 200                 205

Glu Gln Leu Gly Met Ile Glu Lys Leu Val Ala Ala Gln Gln Gln Cys
    210                 215                 220

Asn Arg Arg Ser Phe Ser Asp Arg Leu Arg Val Thr Val Met Leu Leu

-continued

```
225                 230                 235                 240

Glu Thr Ser Arg Arg Tyr Asn Pro Gly Ser Glu Ser Ile Thr Phe Leu
                245                 250                 255

Lys Asp Phe Ser Tyr Asn Arg Glu Asp Phe Ala Lys Ala Gly Leu Gln
            260                 265                 270

Val Glu Phe Ile Asn Pro Ile Phe Glu Phe Ser Arg Ala Met Asn Glu
        275                 280                 285

Leu Gln Leu Asn Asp Ala Glu Phe Ala Leu Leu Ile Ala Ile Ser Ile
    290                 295                 300

Phe Ser Ala Asp Arg Pro Asn Val Gln Asp Gln Leu Gln Val Glu Arg
305                 310                 315                 320

Leu Gln His Thr Tyr Val Glu Ala Leu His Ala Tyr Val Ser Ile His
                325                 330                 335

His Pro His Asp Arg Leu Met Phe Pro Arg Met Leu Met Lys Leu Val
            340                 345                 350

Ser Leu Arg Thr Leu Ser Ser Val His Ser Glu Gln Val Phe Ala Leu
        355                 360                 365

Arg Leu Gln Asp Lys Lys Leu Pro Pro Leu Leu Ser Glu Ile Trp Asp
    370                 375                 380

Val His Glu
385
```

<210> SEQ ID NO 25
<211> LENGTH: 1748
<212> TYPE: RNA
<213> ORGANISM: Homo sapiens

<400> SEQUENCE: 25

```
aucuuacuua gggaccugcu ggggugcggg gaaaaggcgc agucucggug ggauugcgug      60

caggagggug gugguguggc uguggcggag gagcauaaga agacucugcg guggagcugu     120

ggaagccagg cgcacaggau gcaagcagcc aggcccaggg aggcagcagc ugcauccuca     180

gagaggaagc caggaugccc cacucugcug gggguacugc aggggugggg cuggaggcug     240

cagagcccac agcccugcuc accagggcag agccccccuuc agaacccaca gagauccguc     300

cacaaaagcg gaaaaagggg ccagccccca aaaugcuggg gaacgagcua ugcagcgugu     360

guggggacaa ggccucgggc uuccacuaca auguucugag cugcgagggc ugcaagggau     420

ucuuccgccg cagcgucauc aagggagcgc acuacaucug ccacaguggc ggccacugcc     480

ccauggacac cuacaugcgu cgcaagugcc aggagugucg gcuucgcaaa ugccgucagg     540

cuggcaugcg ggaggagugu guccugucag aagaacagau ccgccugaag aaacugaagc     600

ggcaagagga ggaacaggcu caugccacau ccuugccccc cagggcuucc ucaccccccc     660

aaauccugcc ccagcucagc ccggaacaac ugggcaugau cgagaagcuc gucgcugccc     720

agcaacagug uaaccggcgc uccuuuucug accggcuucg agucacgccu uggcccaugg     780

caccagaucc ccauagccgg gaggcccguc agcagcgcuu ugcccacuuc acugagcugg     840

ccaucgucuc ugugcaggag auaguugacu uugcuaaaca gcuacccggc uuccugcagc     900

ucagccggga ggaccagauu gcccugcuga agaccucugc gaucgaggug augcuucugg     960

agacaucucg gagguacaac ccugggagug agaguaucac cuuccucaag gauuucaguu    1020

auaaccggga agacuuugcc aaagcagggc ugcaagugga auucaucaac cccaucuucg    1080

aguucuccag ggccaugaau gagcugcaac ucaaugaugc cgaguuugcc uugcucauug    1140

cuaucagcau cuucucugca gaccggccca acgugcagga ccagcuccag guagagaggc    1200
```

```
ugcagcacac auauguggaa gcccugcaug ccuacgucuc cauccaccau ccccaugacc   1260

gacugauguu cccacggaug cuaaugaaac uggugagccu ccggacccug agcagcgucc   1320

acucagagca aguguuugca cugcgucugc aggacaaaaa gcucccaccg cugcucucug   1380

agaucuggga ugugcacgaa ugacuguucu guccccauau uuucuguuuu cuuggccgga   1440

uggcugaggc cugguggcug ccuccuagaa guggaacaga cugagaaggg caaacauucc   1500

ugggagcugg gcaaggagau ccucccgugg cauuaaaaga gagucaaagg guugcgaguu   1560

uuguggcuac ugagcagugg agcccucgcu aacacugugc ugugucugaa gaucaugcug   1620

accccacaaa cggaugggcc ugggggccac uuugcacagg guucuccaga gcccugccca   1680

uccugccucc accacuuccu guuuucccca cagggcccca agaaaaauuc uccacuguca   1740

aaaaaaaa                                                             1748


<210> SEQ ID NO 26
<211> LENGTH: 402
<212> TYPE: PRT
<213> ORGANISM: Homo sapiens

<400> SEQUENCE: 26

Met Pro His Ser Ala Gly Gly Thr Ala Gly Val Gly Leu Glu Ala Ala
1               5                   10                  15

Glu Pro Thr Ala Leu Leu Thr Arg Ala Glu Pro Pro Ser Glu Pro Thr
            20                  25                  30

Glu Ile Arg Pro Gln Lys Arg Lys Lys Gly Pro Ala Pro Lys Met Leu
        35                  40                  45

Gly Asn Glu Leu Cys Ser Val Cys Gly Asp Lys Ala Ser Gly Phe His
    50                  55                  60

Tyr Asn Val Leu Ser Cys Glu Gly Cys Lys Gly Phe Phe Arg Arg Ser
65                  70                  75                  80

Val Ile Lys Gly Ala His Tyr Ile Cys His Ser Gly Gly His Cys Pro
                85                  90                  95

Met Asp Thr Tyr Met Arg Arg Lys Cys Gln Glu Cys Arg Leu Arg Lys
            100                 105                 110

Cys Arg Gln Ala Gly Met Arg Glu Glu Cys Val Leu Ser Glu Glu Gln
        115                 120                 125

Ile Arg Leu Lys Lys Leu Lys Arg Gln Glu Glu Glu Gln Ala His Ala
    130                 135                 140

Thr Ser Leu Pro Pro Arg Ala Ser Ser Pro Pro Gln Ile Leu Pro Gln
145                 150                 155                 160

Leu Ser Pro Glu Gln Leu Gly Met Ile Glu Lys Leu Val Ala Ala Gln
                165                 170                 175

Gln Gln Cys Asn Arg Arg Ser Phe Ser Asp Arg Leu Arg Val Thr Pro
            180                 185                 190

Trp Pro Met Ala Pro Asp Pro His Ser Arg Glu Ala Arg Gln Gln Arg
        195                 200                 205

Phe Ala His Phe Thr Glu Leu Ala Ile Val Ser Val Gln Glu Ile Val
    210                 215                 220

Asp Phe Ala Lys Gln Leu Pro Gly Phe Leu Gln Leu Ser Arg Glu Asp
225                 230                 235                 240

Gln Ile Ala Leu Leu Lys Thr Ser Ala Ile Glu Val Met Leu Leu Glu
                245                 250                 255

Thr Ser Arg Arg Tyr Asn Pro Gly Ser Glu Ser Ile Thr Phe Leu Lys
            260                 265                 270
```

```
Asp Phe Ser Tyr Asn Arg Glu Asp Phe Ala Lys Ala Gly Leu Gln Val
        275                 280                 285

Glu Phe Ile Asn Pro Ile Phe Glu Phe Ser Arg Ala Met Asn Glu Leu
    290                 295                 300

Gln Leu Asn Asp Ala Glu Phe Ala Leu Leu Ile Ala Ile Ser Ile Phe
305                 310                 315                 320

Ser Ala Asp Arg Pro Asn Val Gln Asp Gln Leu Gln Val Glu Arg Leu
                325                 330                 335

Gln His Thr Tyr Val Glu Ala Leu His Ala Tyr Val Ser Ile His His
            340                 345                 350

Pro His Asp Arg Leu Met Phe Pro Arg Met Leu Met Lys Leu Val Ser
        355                 360                 365

Leu Arg Thr Leu Ser Ser Val His Ser Glu Gln Val Phe Ala Leu Arg
    370                 375                 380

Leu Gln Asp Lys Lys Leu Pro Pro Leu Leu Ser Glu Ile Trp Asp Val
385                 390                 395                 400

His Glu


<210> SEQ ID NO 27
<211> LENGTH: 1928
<212> TYPE: RNA
<213> ORGANISM: Homo sapiens

<400> SEQUENCE: 27

gauucuaacu uagcuaagca augcuacugg agaccauagg caaagccaag guacagcuuc     60

agggaagucu uuggugagcc caucucucau uaccaaggua acgaagcgca gacuccgggc    120

ccgggugggc ggcaucacca ccagguucac gccgagaagg agcuggagga gagccgcccg    180

gcuccagccg gaccgcuugc ccgccaucac cguuguaauc uaugcagcaa acaagcugga    240

acccgcuggg uggcaccugc aagcagccgc ccggacgcac ccacucugcg guggagcugu    300

ggaagccagg cgcacaggau gcaagcagcc aggcccaggg aggcagcagc ugcauccuca    360

gagaggaagc caggaugccc cacucugcug gggguacugc aggggugggg cuggaggcug    420

cagagcccac agcccugcuc accagggcag agcccccuuc agaacccaca gagauccguc    480

cacaaaagcg gaaaaagggg ccagcccccca aaaugcuggg gaacgagcua ugcagcgugu    540

guggggacaa ggccucgggc uuccacuaca auguucugag cugcgagggc ugcaagggau    600

ucuuccgccg cagcgucauc aagggagcgc acuacaucug ccacaguggc ggccacugcc    660

ccauggacac cuacaugcgu cgcaagugcc aggagugucg gcuucgcaaa ugccgucagg    720

cuggcaugcg ggaggagugu guccugucag aagaacagau ccgccugaag aaacugaagc    780

ggcaagagga ggaacaggcu caugccacau ccuugccccc cagggcuucc ucacccccccc    840

aaauccugcc ccagcucagc ccggaacaac ugggcaugau cgagaagcuc gucgcugccc    900

agcaacagug uaaccggcgc uccuuuucug accggcuucg agucacgccu uggcccaugg    960

caccagaucc ccauagccgg gaggcccguc agcagcgcuu ugcccacuuc acugagcugg   1020

ccaucgucuc ugugcaggag auaguugacu uugcuaaaca gcuacccggc uuccugcagc   1080

ucagccggga ggaccagauu gcccugcuga agaccucugc gaucgaggug augcuucugg   1140

agacaucucg gagguacaac ccugggagug agaguaucac cuuccucaag gauuucaguu   1200

auaaccggga agacuuugcc aaagcagggc ugcaagugga auucaucaac cccaucuucg   1260

aguucuccag ggccaugaau gagcugcaac ucaaugaugc cgaguuugcc uugcucauug   1320
```

cuaucagcau cuucucugca gaccggccca acgugcagga ccagcuccag guagagaggc 1380
ugcagcacac auauguggaa gcccugcaug ccuacgucuc cauccaccau ccccaugacc 1440
gacugauguu cccacggaug cuaaugaaac uggugagccu ccggacccug agcagcgucc 1500
acucagagca aguguuugca cugcgucugc aggacaaaaa gcucccaccg cugcucucug 1560
agaucuggga ugugcacgaa ugacuguucu guccccauau uuucuguuuu cuuggccgga 1620
uggcugaggc cugguggcug ccuccuagaa guggaacaga cugagaaggg caaacauucc 1680
ugggagcugg gcaaggagau ccucccgugg cauuaaaaga gagucaaagg guugcgaguu 1740
uuguggcuac ugagcagugg agcccucgcu aacacugugc ugugucugaa gaucaugcug 1800
accccacaaa cggaugggcc ugggggccac uuugcacagg guucuccaga gcccugccca 1860
uccugccucc accacuuccu guuuuuccca cagggcccca agaaaaauuc uccacuguca 1920
aaaaaaaa 1928

<210> SEQ ID NO 28
<211> LENGTH: 453
<212> TYPE: PRT
<213> ORGANISM: Homo sapiens

<400> SEQUENCE: 28

Met Gln Gln Thr Ser Trp Asn Pro Leu Gly Gly Thr Cys Lys Gln Pro
1 5 10 15

Pro Gly Arg Thr His Ser Ala Val Glu Leu Trp Lys Pro Gly Ala Gln
20 25 30

Asp Ala Ser Ser Gln Ala Gln Gly Gly Ser Ser Cys Ile Leu Arg Glu
35 40 45

Glu Ala Arg Met Pro His Ser Ala Gly Gly Thr Ala Gly Val Gly Leu
50 55 60

Glu Ala Ala Glu Pro Thr Ala Leu Leu Thr Arg Ala Glu Pro Pro Ser
65 70 75 80

Glu Pro Thr Glu Ile Arg Pro Gln Lys Arg Lys Lys Gly Pro Ala Pro
85 90 95

Lys Met Leu Gly Asn Glu Leu Cys Ser Val Cys Gly Asp Lys Ala Ser
100 105 110

Gly Phe His Tyr Asn Val Leu Ser Cys Glu Gly Cys Lys Gly Phe Phe
115 120 125

Arg Arg Ser Val Ile Lys Gly Ala His Tyr Ile Cys His Ser Gly Gly
130 135 140

His Cys Pro Met Asp Thr Tyr Met Arg Arg Lys Cys Gln Glu Cys Arg
145 150 155 160

Leu Arg Lys Cys Arg Gln Ala Gly Met Arg Glu Glu Cys Val Leu Ser
165 170 175

Glu Glu Gln Ile Arg Leu Lys Lys Leu Lys Arg Gln Glu Glu Glu Gln
180 185 190

Ala His Ala Thr Ser Leu Pro Pro Arg Ala Ser Ser Pro Pro Gln Ile
195 200 205

Leu Pro Gln Leu Ser Pro Glu Gln Leu Gly Met Ile Glu Lys Leu Val
210 215 220

Ala Ala Gln Gln Gln Cys Asn Arg Arg Ser Phe Ser Asp Arg Leu Arg
225 230 235 240

Val Thr Pro Trp Pro Met Ala Pro Asp Pro His Ser Arg Glu Ala Arg
245 250 255

Gln Gln Arg Phe Ala His Phe Thr Glu Leu Ala Ile Val Ser Val Gln

```
            260                 265                 270

Glu Ile Val Asp Phe Ala Lys Gln Leu Pro Gly Phe Leu Gln Leu Ser
        275                 280                 285

Arg Glu Asp Gln Ile Ala Leu Leu Lys Thr Ser Ala Ile Glu Val Met
    290                 295                 300

Leu Leu Glu Thr Ser Arg Arg Tyr Asn Pro Gly Ser Glu Ser Ile Thr
305                 310                 315                 320

Phe Leu Lys Asp Phe Ser Tyr Asn Arg Glu Asp Phe Ala Lys Ala Gly
                325                 330                 335

Leu Gln Val Glu Phe Ile Asn Pro Ile Phe Glu Phe Ser Arg Ala Met
            340                 345                 350

Asn Glu Leu Gln Leu Asn Asp Ala Glu Phe Ala Leu Leu Ile Ala Ile
        355                 360                 365

Ser Ile Phe Ser Ala Asp Arg Pro Asn Val Gln Asp Gln Leu Gln Val
    370                 375                 380

Glu Arg Leu Gln His Thr Tyr Val Glu Ala Leu His Ala Tyr Val Ser
385                 390                 395                 400

Ile His His Pro His Asp Arg Leu Met Phe Pro Arg Met Leu Met Lys
                405                 410                 415

Leu Val Ser Leu Arg Thr Leu Ser Ser Val His Ser Glu Gln Val Phe
            420                 425                 430

Ala Leu Arg Leu Gln Asp Lys Lys Leu Pro Pro Leu Leu Ser Glu Ile
        435                 440                 445

Trp Asp Val His Glu
    450
```

<210> SEQ ID NO 29
<211> LENGTH: 2093
<212> TYPE: RNA
<213> ORGANISM: Homo sapiens

<400> SEQUENCE: 29

```
ucgucaaguu ucacgcuccg ccccucuucc ggacgugacg caagggcggg guugccggaa     60

gaaguggcga aguuacuuuu gaggguauuu gaguagcggc ggugugucag ggcuaaaga    120

ggaggacgaa gaaaagcaga gcaagggaac ccagggcaac aggaguaguu cacuccgcga    180

gaggccgucc acgagacccc cgcgcgcagc caugagcccc gcccccgcu guugcuugga    240

gaggggcggg accuggagag aggcugcucc gugaccccac cauguccucu ccuaccacga    300

guucccugga uacccccug ccuggaaaug gcccccuca gccuggcgcc ccuucuucuu    360

cacccacugu aaaggaggag gguccggagc cguggcccgg ggguccggac ccugaugucc    420

caggcacuga ugaggccagc ucagccugca gcacagacug ggucauccca gaucccgaag    480

aggaaccaga gcgcaagcga aagaagggcc cagccccgaa gaugcugggc cacgagcuuu    540

gccgugucug uggggacaag gccuccggcu uccacuacaa cgugcucagc ugcgaaggcu    600

gcaagggcuu cuuccggcgc aguguggucc gugguggggc caggcgcuau gccugccggg    660

guggcggaac cugccagaug gacgcuuuca ugcggcgcaa gugccagcag ugccggcugc    720

gcaagugcaa ggaggcaggg augagggagc agugcguccu uucugaagaa cagauccgga    780

agaagaagau ucggaaacaa cagcagcagg agucacaguc acagucgcag ucaccugugg    840

ggccgcaggg cagcagcagc ucagccucug ggccuggggc uuccccuggu ggaucugagg    900

caggcagcca gggcuccggg gaaggcgagg guguccagcu aacagcggcu caagaacuaa    960

ugauccagca guugguggcg gcccaacugc agugcaacaa acgcuccuuc uccgaccagc   1020
```

```
ccaaagucac gcccuggccc cugggcgcag acccccaguc ccgagaugcc cgccagcaac   1080

gcuuugccca cuucacggag cuggccauca ucucagucca ggagaucgug gacuucgcua   1140

agcaagugcc ugguuuccug cagcugggcc gggaggacca gaucgcccuc cugaaggcau   1200

ccacuaucga gaucaugcug cuagagacag ccaggcgcua caaccacgag acagagugua   1260

ucaccuucuu gaaggacuuc accuacagca aggacgacuu ccaccgugca ggccugcagg   1320

uggaguucau caaccccauc uucgaguucu cgcgggccau gcggcggcug ggccuggacg   1380

acgcugagua cgcccugcuc aucgccauca acaucuucuc ggccgaccgg cccaacgugc   1440

aggagccggg ccgcguggag gcguugcagc agcccuacgu ggaggcgcug cuguccuaca   1500

cgcgcaucaa gaggccgcag gaccagcugc gcuucccgcg caugcucaug aagcugguga   1560

gccugcgcac gcugagcucu gugcacucgg agcaggucuu cgccuugcgg cuccaggaca   1620

agaagcugcc gccucugcug ucggagaucu gggacgucca cgagugaggg gcuggccacc   1680

cagccccaca gccuugccug accacccucc agcagauaga cgccggcacc ccuuccucuu   1740

ccuagggugg aaggggcccu gggccgagcc uguagaccua ucggcucuca ucccuuggga   1800

uaagccccag uccaggucca ggaggcuccc ucccugccca gcgagucuuc cagaaggggu   1860

gaaaggguug cagguccega ccacugaccc uucccggcug cccucccucc ccagcuuaca   1920

ccucaagccc agcacgcagu gcaccuugaa cagagggagg ggaggaccca uggcucuccc   1980

cccuagcccg ggagaccagg gccuuccucu uccucugcuu uuauuuaaua aaaacuaaaa   2040

acagaaacag gaaaauaaaa uaugaauaca auccagcccg gagcuggagu gca          2093
```

<210> SEQ ID NO 30
<211> LENGTH: 461
<212> TYPE: PRT
<213> ORGANISM: Homo sapiens

<400> SEQUENCE: 30

```
Met Ser Ser Pro Thr Thr Ser Ser Leu Asp Thr Pro Leu Pro Gly Asn
1               5                   10                  15

Gly Pro Pro Gln Pro Gly Ala Pro Ser Ser Ser Pro Thr Val Lys Glu
            20                  25                  30

Glu Gly Pro Glu Pro Trp Pro Gly Gly Pro Asp Pro Asp Val Pro Gly
        35                  40                  45

Thr Asp Glu Ala Ser Ser Ala Cys Ser Thr Asp Trp Val Ile Pro Asp
    50                  55                  60

Pro Glu Glu Glu Pro Glu Arg Lys Arg Lys Lys Gly Pro Ala Pro Lys
65                  70                  75                  80

Met Leu Gly His Glu Leu Cys Arg Val Cys Gly Asp Lys Ala Ser Gly
                85                  90                  95

Phe His Tyr Asn Val Leu Ser Cys Glu Gly Cys Lys Gly Phe Phe Arg
            100                 105                 110

Arg Ser Val Val Arg Gly Gly Ala Arg Arg Tyr Ala Cys Arg Gly Gly
        115                 120                 125

Gly Thr Cys Gln Met Asp Ala Phe Met Arg Arg Lys Cys Gln Gln Cys
    130                 135                 140

Arg Leu Arg Lys Cys Lys Glu Ala Gly Met Arg Glu Gln Cys Val Leu
145                 150                 155                 160

Ser Glu Glu Gln Ile Arg Lys Lys Lys Ile Arg Lys Gln Gln Gln Gln
                165                 170                 175

Glu Ser Gln Ser Gln Ser Gln Ser Pro Val Gly Pro Gln Gly Ser Ser
```

-continued

```
            180                 185                 190

Ser Ser Ala Ser Gly Pro Gly Ala Ser Pro Gly Gly Ser Glu Ala Gly
        195                 200                 205

Ser Gln Gly Ser Gly Glu Gly Glu Gly Val Gln Leu Thr Ala Ala Gln
    210                 215                 220

Glu Leu Met Ile Gln Gln Leu Val Ala Ala Gln Leu Gln Cys Asn Lys
225                 230                 235                 240

Arg Ser Phe Ser Asp Gln Pro Lys Val Thr Pro Trp Pro Leu Gly Ala
                245                 250                 255

Asp Pro Gln Ser Arg Asp Ala Arg Gln Gln Arg Phe Ala His Phe Thr
            260                 265                 270

Glu Leu Ala Ile Ile Ser Val Gln Glu Ile Val Asp Phe Ala Lys Gln
        275                 280                 285

Val Pro Gly Phe Leu Gln Leu Gly Arg Glu Asp Gln Ile Ala Leu Leu
    290                 295                 300

Lys Ala Ser Thr Ile Glu Ile Met Leu Leu Glu Thr Ala Arg Arg Tyr
305                 310                 315                 320

Asn His Glu Thr Glu Cys Ile Thr Phe Leu Lys Asp Phe Thr Tyr Ser
                325                 330                 335

Lys Asp Asp Phe His Arg Ala Gly Leu Gln Val Glu Phe Ile Asn Pro
            340                 345                 350

Ile Phe Glu Phe Ser Arg Ala Met Arg Arg Leu Gly Leu Asp Asp Ala
        355                 360                 365

Glu Tyr Ala Leu Leu Ile Ala Ile Asn Ile Phe Ser Ala Asp Arg Pro
    370                 375                 380

Asn Val Gln Glu Pro Gly Arg Val Glu Ala Leu Gln Gln Pro Tyr Val
385                 390                 395                 400

Glu Ala Leu Leu Ser Tyr Thr Arg Ile Lys Arg Pro Gln Asp Gln Leu
                405                 410                 415

Arg Phe Pro Arg Met Leu Met Lys Leu Val Ser Leu Arg Thr Leu Ser
            420                 425                 430

Ser Val His Ser Glu Gln Val Phe Ala Leu Arg Leu Gln Asp Lys Lys
        435                 440                 445

Leu Pro Pro Leu Leu Ser Glu Ile Trp Asp Val His Glu
    450                 455                 460


<210> SEQ ID NO 31
<211> LENGTH: 1802
<212> TYPE: RNA
<213> ORGANISM: Homo sapiens

<400> SEQUENCE: 31

ucgucaaguu ucacgcuccg ccccucuucc ggacgugacg caagggcggg guugccggaa      60

gaaguggcga aguuacuuuu gaggguauuu gaguagcggc ggugugucag gggcuaaaga     120

ggaggacgaa gaaaagcaga gcaagggaac ccagggcaac aggaguaguu cacuccgcga     180

gaggccgucc acgagacccc cgcgcgcagc caugagcccc gcccccgcu guugcuugga     240

gaggggcggg accuggagag aggcugcucc gugaccccac cauguccucu ccuaccacga     300

guucccugga uacccccug ccuggaaaug gcccccuca gccuggcgcc ccuucuucuu     360

cacccacugu aaaggaggag gguccggagc cguggcccgg ggguccggac ccugaugucc     420

caggcacuga ugaggccagc ucagccugca gcacagacug gggcguccuu ucugaagaac     480

agauccggaa gaagaagauu cggaaacaac agcagcagga gucacaguca cagucgcagu     540
```

caccuguggg gccgcagggc agcagcagcu cagccucugg gccuggggcu uccccuggug 600
gaucugaggc aggcagccag ggcuccgggg aaggcgaggg uguccagcua acagcggcuc 660
aagaacuaau gauccagcag uugguggcgg cccaacugca gugcaacaaa cgcuccuucu 720
ccgaccagcc caaagucacg cccuggcccc ugggcgcaga cccccagucc cgagaugccc 780
gccagcaacg cuuugcccac uucacggagc uggccaucau cucaguccag gagaucgugg 840
acuucgcuaa gcaagugccu gguuuccugc agcugggccg ggaggaccag aucgcccucc 900
ugaaggcauc cacuaucgag aucaugcugc uagagacagc caggcgcuac aaccacgaga 960
cagaguguau caccuucuug aaggacuuca ccuacagcaa ggacgacuuc caccgugcag 1020
gccugcaggu ggaguucauc aaccccaucu ucgaguucuc gcgggccaug cggcggcugg 1080
gccuggacga cgcugaguac gcccugcuca ucgccaucaa caucuucucg gccgaccggc 1140
ccaacgugca ggagccgggc cgcguggagg cguugcagca gcccuacgug gaggcgcugc 1200
uguccuacac gcgcaucaag aggccgcagg accagcugcg cuucccgcgc augcucauga 1260
agcuggugag ccugcgcacg cugagcucug ugcacucgga gcaggucuuc gccuugcggc 1320
uccaggacaa gaagcugccg ccucugcugu cggagaucug ggacguccac gagugagggg 1380
cuggccaccc agccccacag ccuugccuga ccacccucca gcagauagac gccggcaccc 1440
cuuccucuuc cuagggugga aggggcccug ggccgagccu guagaccuau cggcucucau 1500
cccuugggau aagccccagu ccagguccag gaggcucccu cccugcccag cgagucuucc 1560
agaaggggug aaaggguugc agguccgac cacugacccu ucccggcugc ccucccuccc 1620
cagcuuacac cucaagccca gcacgcagug caccuugaac agagggaggg gaggacccau 1680
ggcucucccc ccuagcccgg gagaccaggg ccuuccucuu ccucugcuuu uauuuaauaa 1740
aaacuaaaaa cagaaacagg aaaauaaaau augaauacaa uccagcccgg agcuggagug 1800
ca 1802

<210> SEQ ID NO 32
<211> LENGTH: 364
<212> TYPE: PRT
<213> ORGANISM: Homo sapiens

<400> SEQUENCE: 32

Met Ser Ser Pro Thr Thr Ser Ser Leu Asp Thr Pro Leu Pro Gly Asn
1 5 10 15

Gly Pro Pro Gln Pro Gly Ala Pro Ser Ser Ser Pro Thr Val Lys Glu
20 25 30

Glu Gly Pro Glu Pro Trp Pro Gly Gly Pro Asp Pro Asp Val Pro Gly
35 40 45

Thr Asp Glu Ala Ser Ser Ala Cys Ser Thr Asp Trp Gly Val Leu Ser
50 55 60

Glu Glu Gln Ile Arg Lys Lys Lys Ile Arg Lys Gln Gln Gln Gln Glu
65 70 75 80

Ser Gln Ser Gln Ser Gln Ser Pro Val Gly Pro Gln Gly Ser Ser Ser
85 90 95

Ser Ala Ser Gly Pro Gly Ala Ser Pro Gly Gly Ser Glu Ala Gly Ser
100 105 110

Gln Gly Ser Gly Glu Gly Glu Gly Val Gln Leu Thr Ala Ala Gln Glu
115 120 125

Leu Met Ile Gln Gln Leu Val Ala Ala Gln Leu Gln Cys Asn Lys Arg
130 135 140

-continued

```
Ser Phe Ser Asp Gln Pro Lys Val Thr Pro Trp Pro Leu Gly Ala Asp
145                 150                 155                 160

Pro Gln Ser Arg Asp Ala Arg Gln Gln Arg Phe Ala His Phe Thr Glu
                165                 170                 175

Leu Ala Ile Ile Ser Val Gln Glu Ile Val Asp Phe Ala Lys Gln Val
            180                 185                 190

Pro Gly Phe Leu Gln Leu Gly Arg Glu Asp Gln Ile Ala Leu Leu Lys
        195                 200                 205

Ala Ser Thr Ile Glu Ile Met Leu Leu Glu Thr Ala Arg Arg Tyr Asn
    210                 215                 220

His Glu Thr Glu Cys Ile Thr Phe Leu Lys Asp Phe Thr Tyr Ser Lys
225                 230                 235                 240

Asp Asp Phe His Arg Ala Gly Leu Gln Val Glu Phe Ile Asn Pro Ile
                245                 250                 255

Phe Glu Phe Ser Arg Ala Met Arg Arg Leu Gly Leu Asp Asp Ala Glu
            260                 265                 270

Tyr Ala Leu Leu Ile Ala Ile Asn Ile Phe Ser Ala Asp Arg Pro Asn
        275                 280                 285

Val Gln Glu Pro Gly Arg Val Glu Ala Leu Gln Gln Pro Tyr Val Glu
    290                 295                 300

Ala Leu Leu Ser Tyr Thr Arg Ile Lys Arg Pro Gln Asp Gln Leu Arg
305                 310                 315                 320

Phe Pro Arg Met Leu Met Lys Leu Val Ser Leu Arg Thr Leu Ser Ser
                325                 330                 335

Val His Ser Glu Gln Val Phe Ala Leu Arg Leu Gln Asp Lys Lys Leu
            340                 345                 350

Pro Pro Leu Leu Ser Glu Ile Trp Asp Val His Glu
        355                 360
```

<210> SEQ ID NO 33
<211> LENGTH: 71
<212> TYPE: RNA
<213> ORGANISM: Homo sapiens

<400> SEQUENCE: 33

```
gccaacccag uguucagacu accuguucag gaggcucuca auguguacag uagucugcac      60

auugguuagg c                                                          71
```

<210> SEQ ID NO 34
<211> LENGTH: 110
<212> TYPE: RNA
<213> ORGANISM: Homo sapiens

<400> SEQUENCE: 34

```
aggaagcuuc uggagauccu gcuccgucgc cccaguguuc agacuaccug uucaggacaa      60

ugccguugua caguagucug cacauugguu agacugggca agggagagca               110
```

<210> SEQ ID NO 35
<211> LENGTH: 80
<212> TYPE: RNA
<213> ORGANISM: Homo sapiens

<400> SEQUENCE: 35

```
cgggaaugcc gcggcgggga cggcgauugg uccguaugug uggugccacc ggccgccggc      60

uccgccccgg cccccgcccc                                                 80
```

<210> SEQ ID NO 36
<211> LENGTH: 110
<212> TYPE: RNA
<213> ORGANISM: Homo sapiens

<400> SEQUENCE: 36
uuggauguug gccuaguucu guguggaaga cuagugauuu uguuguuuuu agauaacuaa 60
aucgacaaca aaucacaguc ugccauaugg cacaggccau gccucuacag 110

<210> SEQ ID NO 37
<211> LENGTH: 110
<212> TYPE: RNA
<213> ORGANISM: Homo sapiens

<400> SEQUENCE: 37
cuggauacag aguggaccgg cuggccccau cuggaagacu agugauuuug uuguugucuu 60
acugcgcuca acaacaaauc ccagucuacc uaauggugcc agccaucgca 110

<210> SEQ ID NO 38
<211> LENGTH: 110
<212> TYPE: RNA
<213> ORGANISM: Homo sapiens

<400> SEQUENCE: 38
agauuagagu ggcugugguc uagugcugug uggaagacua gugauuuugu uguucugaug 60
uacuacgaca acaagucaca gccggccuca uagcgcagac ucccuucgac 110

<210> SEQ ID NO 39
<211> LENGTH: 71
<212> TYPE: DNA
<213> ORGANISM: Homo sapiens

<400> SEQUENCE: 39
gatccgacag tagcctgcac attagtcact tcctgtcagt aaccaatgtg cagactactg 60 tttttgaat t 71

<210> SEQ ID NO 40
<211> LENGTH: 73
<212> TYPE: DNA
<213> ORGANISM: Homo sapiens

<400> SEQUENCE: 40
gatccgccca gtgctcagac tacccgtgcc ttcctgtcag gaacaggtag tctgaacact 60
gggtttttga att 73

<210> SEQ ID NO 41
<211> LENGTH: 69
<212> TYPE: DNA
<213> ORGANISM: Homo sapiens

<400> SEQUENCE: 41
gatccgcggc gggaacggcg atcggccctt cctgtcagga ccaatcgccg tccccgccgt 60
ttttgaatt 69

<210> SEQ ID NO 42
<211> LENGTH: 73
<212> TYPE: DNA
<213> ORGANISM: Homo sapiens

<400> SEQUENCE: 42

```
gatccgtgga agattagtga gtttattatc ttcctgtcag acaacaaaat cactagtctt     60

ccatttttga att                                                        73


<210> SEQ ID NO 43
<211> LENGTH: 14
<212> TYPE: PRT
<213> ORGANISM: Mus musculus

<400> SEQUENCE: 43

Thr Gln Gln Ile Arg Leu Gln Ala Glu Ile Phe Gln Ala Arg
1               5                   10


<210> SEQ ID NO 44
<211> LENGTH: 14
<212> TYPE: PRT
<213> ORGANISM: Homo sapiens

<400> SEQUENCE: 44

Ala Gln Gln Ile Arg Leu Gln Ala Glu Ala Phe Gln Ala Arg
1               5                   10


<210> SEQ ID NO 45
<211> LENGTH: 14
<212> TYPE: PRT
<213> ORGANISM: Artificial
<220> FEATURE:
<223> OTHER INFORMATION: Synthetic

<400> SEQUENCE: 45

Thr Ala Gln Ile Arg Leu Gln Ala Glu Ile Phe Gln Ala Arg
1               5                   10


<210> SEQ ID NO 46
<211> LENGTH: 14
<212> TYPE: PRT
<213> ORGANISM: Artificial
<220> FEATURE:
<223> OTHER INFORMATION: Synthetic

<400> SEQUENCE: 46

Thr Gln Ala Ile Arg Leu Gln Ala Glu Ile Phe Gln Ala Arg
1               5                   10


<210> SEQ ID NO 47
<211> LENGTH: 14
<212> TYPE: PRT
<213> ORGANISM: Artificial
<220> FEATURE:
<223> OTHER INFORMATION: Synthetic

<400> SEQUENCE: 47

Thr Gln Gln Ala Arg Leu Gln Ala Glu Ile Phe Gln Ala Arg
1               5                   10


<210> SEQ ID NO 48
<211> LENGTH: 14
<212> TYPE: PRT
<213> ORGANISM: Artificial
<220> FEATURE:
<223> OTHER INFORMATION: Synthetic

<400> SEQUENCE: 48

Thr Gln Gln Ile Ala Leu Gln Ala Glu Ile Phe Gln Ala Arg
1               5                   10
```

<210> SEQ ID NO 49
<211> LENGTH: 15
<212> TYPE: PRT
<213> ORGANISM: Artificial
<220> FEATURE:
<223> OTHER INFORMATION: Synthetic

<400> SEQUENCE: 49

Gln Thr Gln Gln Ile Arg Leu Gln Ala Glu Ile Phe Gln Ala Arg
1 5 10 15

<210> SEQ ID NO 50
<211> LENGTH: 13
<212> TYPE: PRT
<213> ORGANISM: Artificial
<220> FEATURE:
<223> OTHER INFORMATION: Synthetic

<400> SEQUENCE: 50

Gln Gln Ile Arg Leu Gln Ala Glu Ile Phe Gln Ala Arg
1 5 10

<210> SEQ ID NO 51
<211> LENGTH: 57
<212> TYPE: DNA
<213> ORGANISM: Artificial
<220> FEATURE:
<223> OTHER INFORMATION: Synthetic shAPOE

<400> SEQUENCE: 51
ccgggaagga gttgaaggcc tacaactcga gttgtaggcc ttcaactcct tcttttt 57

<210> SEQ ID NO 52
<211> LENGTH: 57
<212> TYPE: DNA
<213> ORGANISM: Artificial
<220> FEATURE:
<223> OTHER INFORMATION: Synthetic shAPOE

<400> SEQUENCE: 52
ccgggcagac actgtctgag caggtctcga gacctgctca gacagtgtct gcttttt 57

<210> SEQ ID NO 53
<211> LENGTH: 57
<212> TYPE: DNA
<213> ORGANISM: Artificial
<220> FEATURE:
<223> OTHER INFORMATION: Synthetic shDNAJA

<400> SEQUENCE: 53
ccgggcgaga agtttaaact catatctcga gatatgagtt taaacttctc gcttttt 57

<210> SEQ ID NO 54
<211> LENGTH: 57
<212> TYPE: DNA
<213> ORGANISM: Artificial
<220> FEATURE:
<223> OTHER INFORMATION: Synthetic shDNAJA4

<400> SEQUENCE: 54
ccggcctcga cagaaagtga ggattctcga gaatcctcac tttctgtcga ggttttt 57

<210> SEQ ID NO 55
<211> LENGTH: 30
<212> TYPE: DNA
<213> ORGANISM: Artificial
<220> FEATURE:

<223> OTHER INFORMATION: Synthetic ApoE Forward Primer

<400> SEQUENCE: 55
tcatgaggat ccatgaaggt tctgtgggct 30

<210> SEQ ID NO 56
<211> LENGTH: 29
<212> TYPE: DNA
<213> ORGANISM: Artificial
<220> FEATURE:
<223> OTHER INFORMATION: Synthetic ApoE Reverse Primer

<400> SEQUENCE: 56
tagcagaatt ctcagtgatt gtcgctggg 29

<210> SEQ ID NO 57
<211> LENGTH: 31
<212> TYPE: DNA
<213> ORGANISM: Artificial
<220> FEATURE:
<223> OTHER INFORMATION: Synthetic DNAJA4 Forward Primer

<400> SEQUENCE: 57
atccctggat ccatgtggga aagcctgacc c 31

<210> SEQ ID NO 58
<211> LENGTH: 31
<212> TYPE: DNA
<213> ORGANISM: Artificial
<220> FEATURE:
<223> OTHER INFORMATION: Synthetic DNAJA4 Reverse Primer

<400> SEQUENCE: 58
taccatgtcg actcatgccg tctggcactg c 31

<210> SEQ ID NO 59
<211> LENGTH: 19
<212> TYPE: RNA
<213> ORGANISM: Artificial
<220> FEATURE:
<223> OTHER INFORMATION: Synthetic LRP1 target sequence

<400> SEQUENCE: 59
cgaggacgau gacugcuua 19

<210> SEQ ID NO 60
<211> LENGTH: 19
<212> TYPE: RNA
<213> ORGANISM: Artificial
<220> FEATURE:
<223> OTHER INFORMATION: Synthetic LRP1 target sequence

<400> SEQUENCE: 60
gcuaugaguu uaagaaguu 19

<210> SEQ ID NO 61
<211> LENGTH: 19
<212> TYPE: RNA
<213> ORGANISM: Artificial
<220> FEATURE:
<223> OTHER INFORMATION: Synthetic LRP8 target sequence

<400> SEQUENCE: 61
cgaggacgau gacugcuua 19

<210> SEQ ID NO 62
<211> LENGTH: 19
<212> TYPE: RNA
<213> ORGANISM: Artificial
<220> FEATURE:
<223> OTHER INFORMATION: Synthetic LRP8 target sequence

<400> SEQUENCE: 62
gaacuauuca cgccucauc 19

<210> SEQ ID NO 63
<211> LENGTH: 20
<212> TYPE: DNA
<213> ORGANISM: Artificial
<220> FEATURE:
<223> OTHER INFORMATION: Synthetic ApoE Forward Primer

<400> SEQUENCE: 63
tgggtcgctt ttgggattac 20

<210> SEQ ID NO 64
<211> LENGTH: 21
<212> TYPE: DNA
<213> ORGANISM: Artificial
<220> FEATURE:
<223> OTHER INFORMATION: Synthetic ApoE Reverse Primer

<400> SEQUENCE: 64
ttcaactcct tcatggtctc g 21

<210> SEQ ID NO 65
<211> LENGTH: 20
<212> TYPE: DNA
<213> ORGANISM: Artificial
<220> FEATURE:
<223> OTHER INFORMATION: Synthetic DNAJA4 Forward Primer

<400> SEQUENCE: 65
ccagcttctc ttcacccatg 20

<210> SEQ ID NO 66
<211> LENGTH: 20
<212> TYPE: DNA
<213> ORGANISM: Artificial
<220> FEATURE:
<223> OTHER INFORMATION: Synthetic DNAJA4 Reverse Primer

<400> SEQUENCE: 66
gccaatttct tcgtgactcc 20

<210> SEQ ID NO 67
<211> LENGTH: 19
<212> TYPE: DNA
<213> ORGANISM: Artificial
<220> FEATURE:
<223> OTHER INFORMATION: Synthetic GAPDH Forward Primer

<400> SEQUENCE: 67
agccacatcg ctcagacac 19

<210> SEQ ID NO 68
<211> LENGTH: 19
<212> TYPE: DNA
<213> ORGANISM: Artificial
<220> FEATURE:
<223> OTHER INFORMATION: Synthetic GAPDH Synthetic Primer

<400> SEQUENCE: 68
gcccaatacg accaaatcc 19

<210> SEQ ID NO 69
<211> LENGTH: 21
<212> TYPE: DNA
<213> ORGANISM: Artificial
<220> FEATURE:
<223> OTHER INFORMATION: Synthetic LRP1 Forward Primer

<400> SEQUENCE: 69
tttaacagca ccgagtacca g 21

<210> SEQ ID NO 70
<211> LENGTH: 19
<212> TYPE: DNA
<213> ORGANISM: Artificial
<220> FEATURE:
<223> OTHER INFORMATION: Synthetic LRP1 Reverse Primer

<400> SEQUENCE: 70
caggcagatg tcagagcag 19

<210> SEQ ID NO 71
<211> LENGTH: 20
<212> TYPE: DNA
<213> ORGANISM: Artificial
<220> FEATURE:
<223> OTHER INFORMATION: Synthetic LRP8 Forward Primer

<400> SEQUENCE: 71
gctaccctgg ctacgagatg 20

<210> SEQ ID NO 72
<211> LENGTH: 20
<212> TYPE: DNA
<213> ORGANISM: Artificial
<220> FEATURE:
<223> OTHER INFORMATION: Synthetic LRP8 Reverse Primer

<400> SEQUENCE: 72
gattagggat gggctcttgc 20

<210> SEQ ID NO 73
<211> LENGTH: 8
<212> TYPE: DNA
<213> ORGANISM: Artificial
<220> FEATURE:
<223> OTHER INFORMATION: Synthetic miRNA seed sequence

<400> SEQUENCE: 73 caguaguc 8

<210> SEQ ID NO 74
<211> LENGTH: 8
<212> TYPE: DNA
<213> ORGANISM: Artificial
<220> FEATURE:
<223> OTHER INFORMATION: Synthetic miRNA seed sequence

<400> SEQUENCE: 74 ccaguguu 8

<210> SEQ ID NO 75
<211> LENGTH: 8

<212> TYPE: DNA
<213> ORGANISM: Artificial
<220> FEATURE:
<223> OTHER INFORMATION: Synthetic miRNA seed sequence

<400> SEQUENCE: 75 ggcgggga 8

<210> SEQ ID NO 76
<211> LENGTH: 31
<212> TYPE: DNA
<213> ORGANISM: Artificial
<220> FEATURE:
<223> OTHER INFORMATION: Synthetic Primer

<400> SEQUENCE: 76
agtacctcga ggggatcctt gagtcctact c 31

<210> SEQ ID NO 77
<211> LENGTH: 34
<212> TYPE: DNA
<213> ORGANISM: Artificial
<220> FEATURE:
<223> OTHER INFORMATION: Synthetic Primer

<400> SEQUENCE: 77
taattgcggc cgctcagaca gtgtctgcac ccag 34

<210> SEQ ID NO 78
<211> LENGTH: 31
<212> TYPE: DNA
<213> ORGANISM: Artificial
<220> FEATURE:
<223> OTHER INFORMATION: Synthetic Primer

<400> SEQUENCE: 78
taatatctcg agatgtggga aagcctgacc c 31

<210> SEQ ID NO 79
<211> LENGTH: 32
<212> TYPE: DNA
<213> ORGANISM: Artificial
<220> FEATURE:
<223> OTHER INFORMATION: Synthetic Primer

<400> SEQUENCE: 79
caattgcggc cgctcatgcc gtctggcact gc 32

<210> SEQ ID NO 80
<211> LENGTH: 30
<212> TYPE: DNA
<213> ORGANISM: Artificial
<220> FEATURE:
<223> OTHER INFORMATION: Synthetic Primer

<400> SEQUENCE: 80
ttagcctcga gacgccgaag cctgcagcca 30

<210> SEQ ID NO 81
<211> LENGTH: 35
<212> TYPE: DNA
<213> ORGANISM: Artificial
<220> FEATURE:
<223> OTHER INFORMATION: Synthetic Primer

<400> SEQUENCE: 81
ttactgcggc cgctgcgtga aacttggtga atctt 35

<210> SEQ ID NO 82
<211> LENGTH: 30
<212> TYPE: DNA
<213> ORGANISM: Artificial
<220> FEATURE:
<223> OTHER INFORMATION: Synthetic Primer

<400> SEQUENCE: 82
taatatctcg agcgtggtgc ggggcagcgt 30

<210> SEQ ID NO 83
<211> LENGTH: 35
<212> TYPE: DNA
<213> ORGANISM: Artificial
<220> FEATURE:
<223> OTHER INFORMATION: Synthetic Primer

<400> SEQUENCE: 83
caattgcggc cgcttatctc tcataccagc tcaat 35

<210> SEQ ID NO 84
<211> LENGTH: 43
<212> TYPE: DNA
<213> ORGANISM: Artificial
<220> FEATURE:
<223> OTHER INFORMATION: Synthetic Primer

<400> SEQUENCE: 84
gccagcgctg ggaactggca actggtcgct tttgggatta cct 43

<210> SEQ ID NO 85
<211> LENGTH: 43
<212> TYPE: DNA
<213> ORGANISM: Artificial
<220> FEATURE:
<223> OTHER INFORMATION: Synthetic Primer

<400> SEQUENCE: 85
cagcgggaga ccctgtcccc ataccagccg tcctcctggg gtg 43

<210> SEQ ID NO 86
<211> LENGTH: 43
<212> TYPE: DNA
<213> ORGANISM: Artificial
<220> FEATURE:
<223> OTHER INFORMATION: Synthetic Primer

<400> SEQUENCE: 86
tccccgcccc agccgtcctc acagggtgga ccctagttta ata 43

<210> SEQ ID NO 87
<211> LENGTH: 43
<212> TYPE: DNA
<213> ORGANISM: Artificial
<220> FEATURE:
<223> OTHER INFORMATION: Synthetic Primer

<400> SEQUENCE: 87
gggatcggtg gagaagtgcc tattgtgcaa ggggcggggg atg 43

<210> SEQ ID NO 88
<211> LENGTH: 43
<212> TYPE: DNA
<213> ORGANISM: Artificial

<220> FEATURE:
<223> OTHER INFORMATION: Synthetic Primer

<400> SEQUENCE: 88
gtagggggcg gggaacgtgt tatccgtgaa gaggtggcta ggg 43

<210> SEQ ID NO 89
<211> LENGTH: 43
<212> TYPE: DNA
<213> ORGANISM: Artificial
<220> FEATURE:
<223> OTHER INFORMATION: Synthetic Primer

<400> SEQUENCE: 89
cagggccaac ttagttccta acattctgtg cccttcagtg gat 43

<210> SEQ ID NO 90
<211> LENGTH: 43
<212> TYPE: DNA
<213> ORGANISM: Artificial
<220> FEATURE:
<223> OTHER INFORMATION: Synthetic Primer

<400> SEQUENCE: 90
acagtttgta tggactacta tcttaaatta tagcttgttt gga 43

<210> SEQ ID NO 91
<211> LENGTH: 43
<212> TYPE: DNA
<213> ORGANISM: Artificial
<220> FEATURE:
<223> OTHER INFORMATION: Synthetic Primer

<400> SEQUENCE: 91
taattattgc taaagaacta tgttttagtt ggtaatggtg taa 43

<210> SEQ ID NO 92
<211> LENGTH: 45
<212> TYPE: DNA
<213> ORGANISM: Artificial
<220> FEATURE:
<223> OTHER INFORMATION: Synthetic Primer

<400> SEQUENCE: 92
cagctgcacg gaccaggttc cataaaaaca ttgccagcta gtgag 45

<210> SEQ ID NO 93
<211> LENGTH: 22
<212> TYPE: DNA
<213> ORGANISM: Artificial
<220> FEATURE:
<223> OTHER INFORMATION: Synthetic primer

<400> SEQUENCE: 93
tgagtatttt tgtggcaact gc 22

<210> SEQ ID NO 94
<211> LENGTH: 18
<212> TYPE: DNA
<213> ORGANISM: Artificial
<220> FEATURE:
<223> OTHER INFORMATION: Synthetic primer

<400> SEQUENCE: 94
ctctgctggg aaagcggc 18

<210> SEQ ID NO 95
<211> LENGTH: 20
<212> TYPE: DNA
<213> ORGANISM: Artificial
<220> FEATURE:
<223> OTHER INFORMATION: Synthetic primer

<400> SEQUENCE: 95
caagcactct gcgaactgag 20

<210> SEQ ID NO 96
<211> LENGTH: 21
<212> TYPE: DNA
<213> ORGANISM: Artificial
<220> FEATURE:
<223> OTHER INFORMATION: Synthetic primer

<400> SEQUENCE: 96
aagtttttga aggcaagatg c 21

<210> SEQ ID NO 97
<211> LENGTH: 23
<212> TYPE: DNA
<213> ORGANISM: Artificial
<220> FEATURE:
<223> OTHER INFORMATION: Synthetic primer

<400> SEQUENCE: 97
gcggtctggc agtaaaaact atc 23

<210> SEQ ID NO 98
<211> LENGTH: 23
<212> TYPE: DNA
<213> ORGANISM: Artificial
<220> FEATURE:
<223> OTHER INFORMATION: Synthetic primer

<400> SEQUENCE: 98
gtgaaacagc attgctgtca ctt 23

<210> SEQ ID NO 99
<211> LENGTH: 24
<212> TYPE: DNA
<213> ORGANISM: Artificial
<220> FEATURE:
<223> OTHER INFORMATION: Synthetic primer

<400> SEQUENCE: 99
ctaggccaca gaattgaaag atct 24

<210> SEQ ID NO 100
<211> LENGTH: 25
<212> TYPE: DNA
<213> ORGANISM: Artificial
<220> FEATURE:
<223> OTHER INFORMATION: Synthetic primer

<400> SEQUENCE: 100
gtaggtggaa attctagcat catcc 25

<210> SEQ ID NO 101
<211> LENGTH: 20
<212> TYPE: DNA
<213> ORGANISM: Artificial
<220> FEATURE:
<223> OTHER INFORMATION: Synthetic primer

<400> SEQUENCE: 101
gcctagccga gggagagccg 20

<210> SEQ ID NO 102
<211> LENGTH: 22
<212> TYPE: DNA
<213> ORGANISM: Artificial
<220> FEATURE:
<223> OTHER INFORMATION: Synthetic primer

<400> SEQUENCE: 102
tgtgacttgg gagctctgca gc 22

<210> SEQ ID NO 103
<211> LENGTH: 18
<212> TYPE: DNA
<213> ORGANISM: Artificial
<220> FEATURE:
<223> OTHER INFORMATION: Synthetic primer

<400> SEQUENCE: 103
gccgccccga ctgcatct 18

<210> SEQ ID NO 104
<211> LENGTH: 20
<212> TYPE: DNA
<213> ORGANISM: Artificial
<220> FEATURE:
<223> OTHER INFORMATION: Synthetic primer

<400> SEQUENCE: 104
tcagtggagg gaaggaaatg 20

<210> SEQ ID NO 105
<211> LENGTH: 20
<212> TYPE: DNA
<213> ORGANISM: Artificial
<220> FEATURE:
<223> OTHER INFORMATION: Synthetic primer

<400> SEQUENCE: 105
ttcctgccct ggacacttac 20

<210> SEQ ID NO 106
<211> LENGTH: 22
<212> TYPE: DNA
<213> ORGANISM: Artificial
<220> FEATURE:
<223> OTHER INFORMATION: Synthetic primer

<400> SEQUENCE: 106
ttgtgcccag tcatagccga at 22

<210> SEQ ID NO 107
<211> LENGTH: 19
<212> TYPE: DNA
<213> ORGANISM: Artificial
<220> FEATURE:
<223> OTHER INFORMATION: Synthetic primer

<400> SEQUENCE: 107
ccttttctcc ctgacaccg 19

<210> SEQ ID NO 108

<211> LENGTH: 19
<212> TYPE: DNA
<213> ORGANISM: Artificial
<220> FEATURE:
<223> OTHER INFORMATION: Synthetic primer

<400> SEQUENCE: 108
gcatccatct ggcaggttc 19

<210> SEQ ID NO 109
<211> LENGTH: 20
<212> TYPE: DNA
<213> ORGANISM: Artificial
<220> FEATURE:
<223> OTHER INFORMATION: Synthetic primer

<400> SEQUENCE: 109
aggtgagatg acaggagatc 20

<210> SEQ ID NO 110
<211> LENGTH: 57
<212> TYPE: DNA
<213> ORGANISM: Artificial
<220> FEATURE:
<223> OTHER INFORMATION: Synthetic

<400> SEQUENCE: 110
ccggccgact gatgttccca cggatctcga gatccgtggg aacatcagtc ggttttt 57

<210> SEQ ID NO 111
<211> LENGTH: 57
<212> TYPE: DNA
<213> ORGANISM: Artificial
<220> FEATURE:
<223> OTHER INFORMATION: Synthetic

<400> SEQUENCE: 111
ccgggcaact caatgatgcc gagttctcga gaactcggca tcattgagtt gcttttt 57

<210> SEQ ID NO 112
<211> LENGTH: 57
<212> TYPE: DNA
<213> ORGANISM: Artificial
<220> FEATURE:
<223> OTHER INFORMATION: Synthetic

<400> SEQUENCE: 112
ccggagagtg tatcaccttc ttgaactcga gttcaagaag gtgatacact ctttttt 57

<210> SEQ ID NO 113
<211> LENGTH: 57
<212> TYPE: DNA
<213> ORGANISM: Artificial
<220> FEATURE:
<223> OTHER INFORMATION: Synthetic

<400> SEQUENCE: 113
ccgggaaggc atccactatc gagatctcga gatctcgata gtggatgcct tcttttt 57

<210> SEQ ID NO 114
<211> LENGTH: 57
<212> TYPE: DNA
<213> ORGANISM: Artificial
<220> FEATURE:
<223> OTHER INFORMATION: Synthetic

<400> SEQUENCE: 114
ccgggcagac actgtctgag caggtctcga gacctgctca gacagtgtct gcttttt 57

<210> SEQ ID NO 115
<211> LENGTH: 57
<212> TYPE: DNA
<213> ORGANISM: Artificial
<220> FEATURE:
<223> OTHER INFORMATION: Synthetic

<400> SEQUENCE: 115
ccgggcaact caatgatgct gagttctcga gaactcagca tcattgagtt gcttttt 57

<210> SEQ ID NO 116
<211> LENGTH: 58
<212> TYPE: DNA
<213> ORGANISM: Artificial
<220> FEATURE:
<223> OTHER INFORMATION: Synthetic

<400> SEQUENCE: 116
ccggtgagat catgttgcta gaaacctcga ggtttctagc aacatgatct catttttg 58

<210> SEQ ID NO 117
<211> LENGTH: 57
<212> TYPE: DNA
<213> ORGANISM: Artificial
<220> FEATURE:
<223> OTHER INFORMATION: Synthetic

<400> SEQUENCE: 117
ccgggaggac actatgacgg aagtactcga gtacttccgt catagtgtcc tcttttt 57

<210> SEQ ID NO 118
<211> LENGTH: 20
<212> TYPE: DNA
<213> ORGANISM: Artificial
<220> FEATURE:
<223> OTHER INFORMATION: Synthetic primer

<400> SEQUENCE: 118
tgggtcgctt ttgggattac 20

<210> SEQ ID NO 119
<211> LENGTH: 21
<212> TYPE: DNA
<213> ORGANISM: Artificial
<220> FEATURE:
<223> OTHER INFORMATION: Synthetic primer

<400> SEQUENCE: 119
ttcaactcct tcatggtctc g 21

<210> SEQ ID NO 120
<211> LENGTH: 19
<212> TYPE: DNA
<213> ORGANISM: Artificial
<220> FEATURE:
<223> OTHER INFORMATION: Synthetic primer

<400> SEQUENCE: 120
agccacatcg ctcagacac 19

<210> SEQ ID NO 121
<211> LENGTH: 19
<212> TYPE: DNA

<213> ORGANISM: Artificial
<220> FEATURE:
<223> OTHER INFORMATION: Synthetic primer

<400> SEQUENCE: 121
gcccaatacg accaaatcc 19

<210> SEQ ID NO 122
<211> LENGTH: 22
<212> TYPE: DNA
<213> ORGANISM: Artificial
<220> FEATURE:
<223> OTHER INFORMATION: Synthetic primer

<400> SEQUENCE: 122
gttataaccg ggaagacttt gc 22

<210> SEQ ID NO 123
<211> LENGTH: 21
<212> TYPE: DNA
<213> ORGANISM: Artificial
<220> FEATURE:
<223> OTHER INFORMATION: Synthetic primer

<400> SEQUENCE: 123
aaactcggca tcattgagtt g 21

<210> SEQ ID NO 124
<211> LENGTH: 22
<212> TYPE: DNA
<213> ORGANISM: Artificial
<220> FEATURE:
<223> OTHER INFORMATION: Synthetic primer

<400> SEQUENCE: 124
tttgagggta tttgagtagc gg 22

<210> SEQ ID NO 125
<211> LENGTH: 19
<212> TYPE: DNA
<213> ORGANISM: Artificial
<220> FEATURE:
<223> OTHER INFORMATION: Synthetic primer

<400> SEQUENCE: 125
ctctcgcgga gtgaactac 19

<210> SEQ ID NO 126
<211> LENGTH: 20
<212> TYPE: DNA
<213> ORGANISM: Artificial
<220> FEATURE:
<223> OTHER INFORMATION: Synthetic primer

<400> SEQUENCE: 126
gaccctggag gctaaggact 20

<210> SEQ ID NO 127
<211> LENGTH: 20
<212> TYPE: DNA
<213> ORGANISM: Artificial
<220> FEATURE:
<223> OTHER INFORMATION: Synthetic primer

<400> SEQUENCE: 127
agagccttca tcttcgcaat 20

<210> SEQ ID NO 128
<211> LENGTH: 20
<212> TYPE: DNA
<213> ORGANISM: Artificial
<220> FEATURE:
<223> OTHER INFORMATION: Synthetic primer

<400> SEQUENCE: 128
gcacagtcaa ggccgagaat 20

<210> SEQ ID NO 129
<211> LENGTH: 20
<212> TYPE: DNA
<213> ORGANISM: Artificial
<220> FEATURE:
<223> OTHER INFORMATION: Synthetic primer

<400> SEQUENCE: 129
gccttctcca tggtggtgaa 20

<210> SEQ ID NO 130
<211> LENGTH: 19
<212> TYPE: DNA
<213> ORGANISM: Artificial
<220> FEATURE:
<223> OTHER INFORMATION: Synthetic primer

<400> SEQUENCE: 130
gcgctcagct cttgtcact 19

<210> SEQ ID NO 131
<211> LENGTH: 20
<212> TYPE: DNA
<213> ORGANISM: Artificial
<220> FEATURE:
<223> OTHER INFORMATION: Synthetic primer

<400> SEQUENCE: 131
ctccagccac aaggacatct 20

<210> SEQ ID NO 132
<211> LENGTH: 20
<212> TYPE: DNA
<213> ORGANISM: Artificial
<220> FEATURE:
<223> OTHER INFORMATION: Synthetic primer

<400> SEQUENCE: 132
gctctgccta catcgtggtc 20

<210> SEQ ID NO 133
<211> LENGTH: 18
<212> TYPE: DNA
<213> ORGANISM: Artificial
<220> FEATURE:
<223> OTHER INFORMATION: Synthetic primer

<400> SEQUENCE: 133
ctcatggccc agcatctt 18

<210> SEQ ID NO 134
<211> LENGTH: 19
<212> TYPE: DNA
<213> ORGANISM: Artificial
<220> FEATURE:

<223> OTHER INFORMATION: Synthetic primer

<400> SEQUENCE: 134
atggagcagg gaagaccac 19

<210> SEQ ID NO 135
<211> LENGTH: 19
<212> TYPE: DNA
<213> ORGANISM: Artificial
<220> FEATURE:
<223> OTHER INFORMATION: Synthetic primer

<400> SEQUENCE: 135
gtaggccgtg ccagaagtt 19

<210> SEQ ID NO 136
<211> LENGTH: 34
<212> TYPE: DNA
<213> ORGANISM: Artificial
<220> FEATURE:
<223> OTHER INFORMATION: Synthetic primer

<400> SEQUENCE: 136
tcatagctag cgcagagcca ggattcacgc cctg 34

<210> SEQ ID NO 137
<211> LENGTH: 35
<212> TYPE: DNA
<213> ORGANISM: Artificial
<220> FEATURE:
<223> OTHER INFORMATION: Synthetic primer

<400> SEQUENCE: 137
tggtcctcga ggaaccttca tcttcctgcc tgtga 35

<210> SEQ ID NO 138
<211> LENGTH: 30
<212> TYPE: DNA
<213> ORGANISM: Artificial
<220> FEATURE:
<223> OTHER INFORMATION: Synthetic primer

<400> SEQUENCE: 138
tagttacgcg tagtagcccc catctttgcc 30

<210> SEQ ID NO 139
<211> LENGTH: 29
<212> TYPE: DNA
<213> ORGANISM: Artificial
<220> FEATURE:
<223> OTHER INFORMATION: Synthetic primer

<400> SEQUENCE: 139
aatcagctag cccctcagct gcaaagctc 29

<210> SEQ ID NO 140
<211> LENGTH: 29
<212> TYPE: DNA
<213> ORGANISM: Artificial
<220> FEATURE:
<223> OTHER INFORMATION: Synthetic primer

<400> SEQUENCE: 140
tagttacgcg tagtagcccc ctctttgcc 29

-continued

```
<210> SEQ ID NO 141
<211> LENGTH: 31
<212> TYPE: DNA
<213> ORGANISM: Artificial
<220> FEATURE:
<223> OTHER INFORMATION: Synthetic primer

<400> SEQUENCE: 141

aatcagctag cccttcagct gcaaagctct g                                31
```

TREATMENT AND DIAGNOSIS OF MELANOMA

CROSS REFERENCE TO RELATED APPLICATIONS

This application is a Continuation of U.S. patent application Ser. No. 14/486,477, filed Sep. 15, 2014, which is a Continuation of International Application No. PCT/US2013/54690 filed Aug. 13, 2013, which claims priority to U.S. Provisional Application No. 61/682,339 filed Aug. 13, 2012 and U.S. Provisional Application No. 61/784,057 filed Mar. 14, 2013. The contents of the applications are incorporated herein by reference in their entirety.

STATEMENT OF GOVERNMENT FUNDING

This invention was made with government support under NIH OD0006506 awarded by the NIG. The government has certain rights in the invention.

FIELD OF THE INVENTION

This invention relates to diagnosis and treatment of migrating cancers and melanoma.

BACKGROUND OF THE INVENTION

Melanoma, a malignant tumor, develops from abnormal melanocytes in the lower epidermis and can metastasize to distant sites in the body via the blood and lymph systems. Although it accounts for less than 5% of skin cancer cases, melanoma is much more dangerous and responsible for a large majority of the deaths associated with skin cancer. Across the world the incidence of melanoma has been increasing at an alarming rate, with a lifetime risk of developing melanoma as high as 1/58 for males in the U.S. (Jemal et al., 2008, CA: Cancer J. Clin. 58:71-96). The mortality rate of malignant melanoma also continues to rise dramatically throughout the world. According to a 2006 WHO report, about 48,000 melanoma related deaths occur worldwide per year (Lucas et al. (2006) Environmental Burden of Disease Series. 13. World Health Organization. ISBN 92-4-159440-3). In the United States, it was estimated that almost 70,000 people were diagnosed with melanoma during 2010 and approximately 9,000 people would be expected to die from the disease (American Cancer Society; www.cancer.org).

Although some conventional cancer therapies have been used in treating metastatic melanoma, they are not effective. Metastatic melanoma therefore remains one of the most difficult cancers to treat and one of the most feared neoplasms. Accordingly, there is a need for new agents and methods for diagnosis and treatment of melanoma.

SUMMARY OF INVENTION

This invention addresses the above-mentioned need by providing agents and methods for diagnosis and treatment of melanoma. The invention is based, at least in part, on an unexpected discovery of a cooperative miRNA-protein network deregulated in metastatic melanoma. This network includes a number of metastasis suppressor factors and metastasis promoter factors.

In one aspect, the invention features a method for treating cancer, including administering to a subject in need thereof, a LXR agonist, wherein the LXR agonist is administered in an amount sufficient to increase the expression level or activity level of ApoE to a level sufficient to slow the spread of metastasis of the cancer.

In another aspect, the invention features a method for treating cancer, including administering to a subject in need thereof, an ApoE polypeptide in an amount sufficient to treat the cancer.

In another aspect, the invention features a method of slowing the spread of a migrating cancer, comprising administering to a subject in need thereof, a LXR agonist or an ApoE polypeptide.

In some embodiments of any of the aforementioned methods, the LXR agonist is a LXRβ agonist. In certain embodiments, the LXR agonist increases the expression level of ApoE at least 2.5-fold in vitro. In certain embodiments, the LXRβ agonist is selective for LXRβ over LXRα. In other embodiments, the LXRβ agonist has activity for LXRβ that is at least 2.5-fold greater than the activity of said agonist for LXRα. In some embodiments, the LXRβ agonist has activity for LXRβ that is at least 10-fold greater than the activity of said agonist for LXRα. In further embodiments, the LXRβ agonist has activity for LXRβ that is at least 100-fold greater than the activity of said agonist for LXRα. In certain embodiments, the LXR agonist has activity for LXRβ that is at least within 2.5-fold of the activity of said agonist for LXRα.

In some embodiments the migrating cancer is metastatic cancer. The metastatic cancer can include cells exhibiting migration and/or invasion of migrating cells and/or include cells exhibiting endothelial recruitment and/or angiogenesis. In other embodiments, the migrating cancer is a cell migration cancer. In still other embodiments, the cell migration cancer is a non-metastatic cell migration cancer.

The migrating cancer can be a cancer spread via seeding the surface of the peritoneal, pleural, pericardial, or subarachnoid spaces. Alternatively, the migrating cancer can be a cancer spread via the lymphatic system, or a cancer spread hematogenously.

In particular embodiments, the migrating cancer is a cell migration cancer that is a non-metastatic cell migration cancer, such as ovarian cancer, mesothelioma, or primary lung cancer.

In a related aspect, the invention provides a method for inhibiting or reducing metastasis of cancer comprising administering a LXR agonist or an ApoE polypeptide.

In another aspect, the invention provides a method for inhibiting proliferation or growth of cancer stem cells or cancer initiating cells, including contacting the cell with a LXR agonist or an ApoE polypeptide in an amount sufficient to inhibit proliferation or growth of said cell.

In yet another aspect, the invention provides a method of reducing the rate of tumor seeding of a cancer including administering to a subject in need thereof a LXR agonist or an ApoE polypeptide in an amount sufficient to reduce tumor seeding.

In still a further aspect, the invention provides a method of reducing or treating metastatic nodule-forming of cancer including administering to a subject in need thereof a LXR agonist or an ApoE polypeptide in an amount sufficient to treat said metastatic nodule-forming of cancer.

In other embodiments, the cancer is breast cancer, colon cancer, renal cell cancer, non-small cell lung cancer, hepatocellular carcinoma, gastric cancer, ovarian cancer, pancreatic cancer, esophageal cancer, prostate cancer, sarcoma, or melanoma. In some embodiments, the cancer is melanoma. In other embodiments, the cancer is breast cancer. In certain embodiments, the cancer is renal cell cancer. In further embodiments, the cancer is pancreatic cancer. In other embodiments, the cancer is non-small cell lung cancer. In some embodiments the cancer is colon cancer. In further embodiments, the cancer is ovarian cancer.

In other embodiments, the cancer is a drug resistant cancer. In further embodiments, the cancer is resistant to vemurafenib, dacarbazine, a CTLA4 inhibitor, a PD1 inhibitor, or a PDL1 inhibitor.

In some embodiments, the method comprises administering an LXR agonist selected from the list consisting of a compound of any one of Formula I-IV or any of compound numbers 1-39, or pharmaceutically acceptable salts thereof. In some embodiments, the LXR agonist is compound 1 or a pharmaceutically acceptable salt thereof. In other embodiments, the LXR agonist is compound 2 or a pharmaceutically acceptable salt thereof. In certain embodiments, the LXR agonist is compound 3 or a pharmaceutically acceptable salt thereof. In further embodiments, the LXR agonist is compound 12 or a pharmaceutically acceptable salt thereof. In some embodiments, the LXR agonist is compound 25 or a pharmaceutically acceptable salt thereof. In other embodiments, the LXR agonist is compound 38 or a pharmaceutically acceptable salt thereof. In further embodiments, the LXR agonist is compound 39 or a pharmaceutically acceptable salt thereof.

The method can further include administering an antiproliferative, wherein said LXR agonist and said antiproliferative are administered in an amount that together, is sufficient to slow the progression of migrating cancer. For example, the antiproliferative and LXR agonist can be administered within 28 days of each (e.g., within 21, 14, 10, 7, 5, 4, 3, 2, or 1 days) or within 24 hours (e.g., 12, 6, 3, 2, or 1 hours; or concomitantly) other in amounts that together are effective to treat the subject.

In some embodiments, the method comprises administering an ApoE polypeptide. The ApoE polypeptide fragment can increase the activity level or expression level of LRP1 or LRP8, and/or the ApoE polypeptide can bind to LRP1 or LRP8, the ApoE polypeptide can be the receptor binding region (RBR) of ApoE. The method can further include administering an antiproliferative, wherein said ApoE polypeptide and said antiproliferative are administered in an amount that together, is sufficient to slow the progression of migrating cancer. For example, the antiproliferative and ApoE polypeptide can be administered within 28 days of each (e.g., within 21, 14, 10, 7, 5, 4, 3, 2, or 1 days) or within 24 hours (e.g., 12, 6, 3, 2, or 1 hours; or concomitantly) other in amounts that together are effective to treat the subject.

In some embodiments, the pharmaceutical composition may further comprise an additional compound having anti-proliferative activity. The additional compound having anti-proliferative activity can be selected from the group of compounds such as chemotherapeutic and cytotoxic agents, differentiation-inducing agents (e.g. retinoic acid, vitamin D, cytokines), hormonal agents, immunological agents and anti-angiogenic agents. Chemotherapeutic and cytotoxic agents include, but are not limited to, alkylating agents, cytotoxic antibiotics, antimetabolites, vinca alkaloids, etoposides, and others (e.g., paclitaxel, taxol, docetaxel, taxotere, cis-platinum). A list of additional compounds having antiproliferative activity can be found in L. Brunton, B. Chabner and B. Knollman (eds). Goodman and Gilman's The Pharmacological Basis of Therapeutics, Twelfth Edition, 2011, McGraw Hill Companies, New York, N.Y.

The method may further include administering a antiproliferative compound selected from the group consisting of alkylating agents, platinum agents, antimetabolites, topoisomerase inhibitors, antitumor antibiotics, antimitotic agents, aromatase inhibitors, thymidylate synthase inhibitors, DNA antagonists, farnesyltransferase inhibitors, pump inhibitors, histone acetyltransferase inhibitors, metalloproteinase inhibitors, ribonucleoside reductase inhibitors, TNF alpha agonists/antagonists, endothelin A receptor antagonist, retinoic acid receptor agonists, immuno-modulators, hormonal and antihormonal agents, photodynamic agents, tyrosine kinase inhibitors, antisense compounds, corticosteroids, HSP90 inhibitors, proteosome inhibitors (for example, NPI-0052), CD40 inhibitors, anti-CSI antibodies, FGFR3 inhibitors, VEGF inhibitors, MEK inhibitors, cyclin D1 inhibitors, NF-kB inhibitors, anthracyclines, histone deacetylases, kinesin inhibitors, phosphatase inhibitors, COX2 inhibitors, mTOR inhibitors, calcineurin antagonists, IMiDs, or other agents used to treat proliferative diseases. Examples of such compounds are provided in Tables 1.

In another aspect, the invention features a method for treating melanoma (e.g., metastatic melanoma) in a subject in need thereof. The method includes (a) increasing in the subject the expression level or activity level of a metastasis suppressor factor selected from the group consisting of DNAJA4, Apolipoprotein E (ApoE), LRP1, LRP8, Liver X Receptor (LXR, e.g., both LXR-alpha and LXR-beta), and miR-7 or (b) decreasing in the subject the expression level or activity level of a metastasis promoter factor selected from the group consisting of miR-199a-3p, miR-199a-5p, miR-1908, and CTGF.

In the method, the increasing step can be carried out by administering to the subject one or more of the followings: (i) a polypeptide having a sequence of DNAJA4, ApoE or an ApoE fragment, LRP1, LRP8, or LXR; (ii) a nucleic acid having a sequence encoding DNAJA4, ApoE, LRP1, LRP8, or LXR; (iii) a ligand for LRP1, LRP8, or LXR; and (iv) an RNAi agent encoding miR-7. Examples of the LRP1 or LRP8 ligand include the receptor binding portion of ApoE, anti-LRP1 or anti-LRP8 antibodies, and small molecule ligands. In one example, increasing the ApoE expression level can be carried out by increasing the activity level or expression level of LXR. Increasing the DNAJA4 expression level can also be carried out by increasing the activity level or expression level of LXR. The LXR activity level can be increased by administering to the subject a ligand of LXR, such as compounds of Formula I-IV as disclosed below. The increasing step can also be carried out by decreasing the expression level or activity level of a microRNA selected from the group consisting of miR-199a-3p, miR-199a-5p, and miR-1908. To this end, one can use a number of techniques known in the art, including, but not limited to, the miR-Zip technology, Locked Nucleic Acid (LNA), and antagomir technology as described in the examples below.

In a another aspect, the invention provides a method for determining whether a subject has, or is at risk of having, metastatic melanoma. The method includes obtaining from the subject a sample; measuring in the sample (i) a first expression level of a metastasis promoter factor selected from the group consisting of miR-199a-3p, miR-199a-5p, miR-1908, and CTGF, or (ii) a second expression level of a metastasis suppressor factor selected from the group consisting of DNAJA4, ApoE, LRP1, LRP8, LXR, and miR-7; and comparing the first expression level with a first predetermined reference value, or the second expression level with a second predetermined reference value. The subject is determined to have, or to be at risk of having, metastatic melanoma if (a) the first expression level is above a first predetermined reference value or (b) the second expression level is below a second predetermined reference value. The first and second predetermined reference values can be obtained from a control subject that does not have metastatic melanoma. In one embodiment, the measuring step includes measuring both the first expression level and the second expression level. The sample can be a body fluid sample, a tumor sample, a nevus sample, or a human skin sample.

In a another aspect, the invention provides an array having a support having a plurality of unique locations, and any combination of (i) at least one nucleic acid having a sequence that is complementary to a nucleic acid encoding a metastasis promoter factor selected from the group consisting of miR-199a-3p, miR-199a-5p, miR-1908, and CTGF or a complement thereof, or (ii) at least one nucleic acid having a sequence that is complementary to a nucleic acid encoding a metastasis suppressor factor selected from the group consisting of DNAJA4, ApoE, LRP1, LRP8, LXR, and miR-7 or a complement thereof. Preferably, each nucleic acid is immobilized to a unique location of the support. This array can be used for metastatic melanoma diagnosis and prognosis.

Accordingly, the invention also provides a kit for diagnosing a metastatic potential of melanoma in a subject. The kit includes a first reagent that specifically binds to an expression product of a metastasis suppressor gene selected from the group consisting of DNAJA4, ApoE, LRP1, LRP8, LXR, and miR-7; or a second reagent that specifically binds to an expression product of a metastasis promoter gene selected from the group consisting of miR-199a-3p, miR-199a-5p, miR-1908, and CTGF. The second agent can be a probe having a sequence complementary to the suppressor or promoter gene or a complement thereof. The kit can further contain reagents for performing an immunoassay, a hybridization assay, or a PCR assay. In one embodiment, the kit contained the above-mentioned array.

In a another aspect, the invention provides a method of identifying a compound useful for treating melanoma or for inhibiting endothelial recruitment, cell invasion, or metastatic angiogenesis. The method includes (i) obtaining a test cell expressing a reporter gene encoded by a nucleic acid operatively liked to a promoter of a marker gene selected from the group consisting of miR-199a-3p, miR-199a-5p, miR-1908, and CTGF; (ii) exposing the test cell to a test compound; (iii) measuring the expression level of the reporter gene in the test cell; (iv) comparing the expression level with a control level; and (v) selecting the test compound as a candidate useful for treating melanoma or for inhibiting endothelial recruitment, cancer cell invasion, or metastatic angiogenesis, if the comparison indicates that the expression level is lower than the control level.

The invention provides another method of identifying a compound useful for treating melanoma or for inhibiting endothelial recruitment, cell invasion, or metastatic angiogenesis. The method includes (i) obtaining a test cell expressing a reporter gene encoded by a nucleic acid operatively liked to a promoter of a marker gene selected from the group consisting of DNAJA4, ApoE, LRP1, LRP8, LXR, and miR-7; (ii) exposing the test cell to a test compound; (iii) measuring the expression level of the reporter gene in the test cell; (iv) comparing the expression level with a control level; and (v) selecting the test compound as a candidate useful for treating melanoma or for inhibiting endothelial recruitment, cancer cell invasion, or metastatic angiogenesis, if the comparison indicates that the expression level is higher than the control level.

In the above-mentioned identification methods, the reporter gene can be a standard reporter gene (such as LaxZ, GFP, or luciferase gene, or the like), known in the art, or one of the aforementioned metastasis suppressor genes or metastasis promoter genes. In the methods, the control level can be obtained from a control cell that is the same as the test cell except that the control cell has not be exposed to the test compound.

In a another aspect, the invention provides a method for inhibiting endothelial recruitment, inhibiting tumor cell invasion, or treating metastatic cancer in a subject in need thereof, by administering to the subject an agent that inhibits expression or activity of CTGF. The subject can be one having a disorder characterized by pathological angiogenesis, including but not limited to cancer (e.g., metastatic melanoma), an eye disorder, and an inflammatory disorder. An example of the tumor cell is a metastatic melanoma cell. Examples of the agent include an antibody, a nucleic acid, a polypeptide, and a small molecule compound. In a preferred embodiment, the antibody is a monoclonal antibody.

In a another aspect, the invention provides a method for inhibiting endothelial recruitment, inhibiting tumor cell invasion, or treating metastatic cancer in a subject in need thereof, by administering to the subject an agent that increases expression or activity of miR-7. An example of the tumor cell is a metastatic melanoma cell. Examples of the agent include an antibody, a nucleic acid, a polypeptide, and a small molecule compound. In one example, the agent has miR-7 activity. The nucleic acid can be an oligonucleotide. And, the oligonucleotide can include a sequence selected from the group consisting of SEQ ID Nos. 36-38.

As used herein, "migrating cancer" refers to a cancer in which the cancer cells forming the tumor migrate and subsequently grow as malignant implants at a site other than the site of the original tumor. The cancer cells migrate via seeding the surface of the peritoneal, pleural, pericardial, or subarachnoid spaces to spread into the body cavities; via invasion of the lymphatic system through invasion of lymphatic cells and transport to regional and distant lymph nodes and then to other parts of the body; via haematogenous spread through invasion of blood cells; or via invasion of the surrounding tissue. Migrating cancers include metastatic tumors and cell migration cancers, such as ovarian cancer, mesothelioma, and primary lung cancer, each of which is characterized by cellular migration.

As used herein, "slowing the spread of migrating cancer" refers to reducing or stopping the formation of new loci; or reducing, stopping, or reversing the tumor load.

As used herein, "metastatic tumor" refers to a tumor or cancer in which the cancer cells forming the tumor have a high potential to or have begun to, metastasize, or spread from one location to another location or locations within a subject, via the lymphatic system or via haematogenous spread, for example, creating secondary tumors within the subject. Such metastatic behavior may be indicative of malignant tumors. In some cases, metastatic behavior may be associated with an increase in cell migration and/or invasion behavior of the tumor cells.

As used herein, "slowing the spread of metastasis" refers to reducing or stopping the formation of new loci; or reducing, stopping, or reversing the tumor load.

The term "cancer" refers to any cancer caused by the proliferation of malignant neoplastic cells, such as tumors, neoplasms, carcinomas, sarcomas, leukimias, lymphomas, and the like.

As used herein, "drug resistant cancer" refers to any cancer that is resistant to an antiproliferative in Table 2.

Examples of cancers that can be defined as metastatic include but are not limited to non-small cell lung cancer, breast cancer, ovarian cancer, colorectal cancer, biliary tract cancer, bladder cancer, brain cancer including glioblastomas and medullablastomas, cervical cancer, choriocarcinoma, endometrial cancer, esophageal cancer, gastric cancer, hematological neoplasms, multiple myeloma, leukemia, intraepithelial neoplasms, livercancer, lymphomas, neuroblastomas, oral cancer, pancreatic cancer, prostate cancer, sarcoma, skin cancer including melanoma, basocellular cancer, squamous cell cancer, testicular cancer, stromal tumors, germ cell tumors, thyroid cancer, and renal cancer.

"Proliferation" as used in this application involves reproduction or multiplication of similar forms (cells) due to constituting (cellular) elements.

"Cell migration" as used in this application involves the invasion by the cancer cells into the surrounding tissue and the crossing of the vessel wall to exit the vasculature in distal organs of the cancer cell.

By "cell migration cancers" is meant cancers that migrate by invasion by the cancer cells into the surrounding tissue and the crossing of the vessel wall to exit the vasculature in distal organs of the cancer cell.

"Non-metastatic cell migration cancer" as used herein refers to cancers that do not migrate via the lymphatic system or via haematogenous spread.

As used herein, "cell to cell adhesion" refers to adhesion between at least two cells through an interaction between a selectin molecule and a selectin specific ligand. Cell to cell adhesion includes cell migration.

A "cell adhesion related disorder" is defined herein as any disease or disorder which results from or is related to cell to cell adhesion or migration. A cell adhesion disorder also includes any disease or disorder resulting from inappropriate, aberrant, or abnormal activation of the immune system or the inflammatory system. Such diseases include but are not limited to, myocardial infarction, bacterial or viral infection, metastatic conditions, e.g. cancer. The invention further features methods for treating a cell adhesion disorder by administering a LXR agonist or ApoE polypeptide.

As used herein, "cancer stem cells" or "cancer initiating cells" refers to cancer cells that possess characteristics associated with normal stem cells, specifically the ability to give rise to all cell types found in a particular cancer sample. Cancer stem cells are therefore tumorgenic or tumor forming, perhaps in contrast to other non-tumorgenic cancer cells. Cancer stem cells may persist in tumors as a distinct population and cause cancer recurrence and metastasis by giving rise to new tumors.

As used herein, "tumor seeding" refers to the spillage of tumor cell clusters and their subsequent growth as malignant implants at a site other than the site of the original tumor.

As used herein, "metastatic nodule" refers to an aggregation of tumor cells in the body at a site other than the site of the original tumor.

The details of one or more embodiments of the invention are set forth in the description below. Other features, objects, and advantages of the invention will be apparent from the description and from the claims.

Figures 1A, 1B:
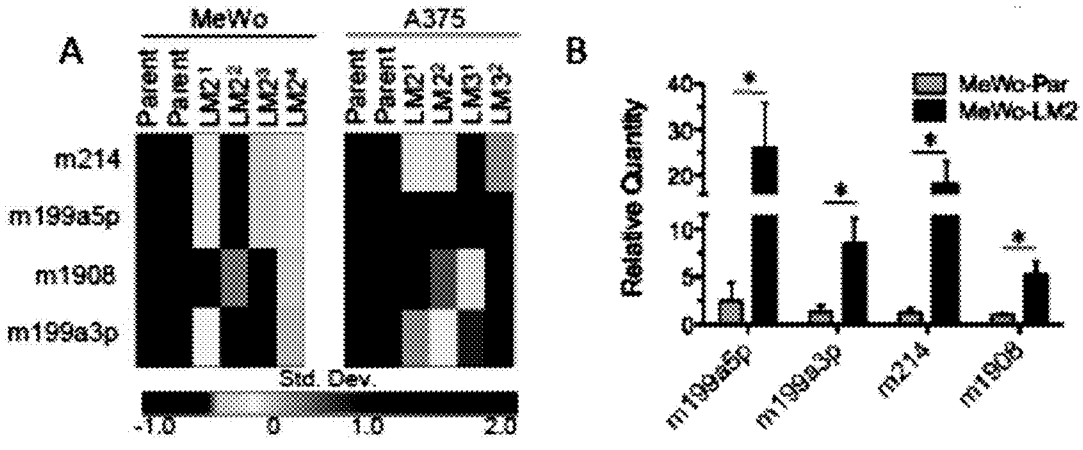
FIGS. 1A, 1B, 1C, 1D, 1E and 1F. Systematic Identification of miR-1908, miR-199a-3p, and miR-199a-5p as Endogenous Promoters of Human Melanoma Metastasis (1A) Heat map illustrating variance-normalized microarray expression values of miRNAs up-regulated in independent MeWo and A375 metastatic derivatives relative to their respective parental cells. Standard deviation changes from the mean of each heat map row are indicated by color map. (1B) miRNAs found to be up-regulated by microarray hybridization were validated by qRT-PCR in MeWo-LM2 metastatic derivatives. n=3. (1C) Bioluminescence imaging plot of lung metastatic colonization following intravenous injection of 4×104 parental MeWo cells over-expressing the precursors for miR-199a, miR-1908, miR-214, or a control hairpin. Lungs were extracted 63 days post-injection and H&E-stained. n=5. (1D) Bioluminescence imaging plot and H&E-stained lungs corresponding to lung metastasis following intravenous injection of 4×104 LM2 cells expressing a short hairpin (miR-Zip) inhibiting miR-1908 (m1908 KD), miR-199a-3p (m199a3p KD), miR-199a-5p (m199a5p KD), or a control sequence (shCTRL). Lungs were extracted and H&E-stained 49 days post-injection n=5-8. (1E) Lung colonization by 2×105 A375-LM3 metastatic derivatives with miR-Zip-induced silencing of miR-1908, miR-199a-3p, miR-199a-5p, or a control sequence was quantified at day 42 by bioluminescence imaging. n=5-8 (1F) The expression levels of miR-199a-3p, miR-199a-5p, and miR-1908 were determined in a blinded fashion by qRT-PCR in a cohort of non-metastatic (n=38) and metastatic (n=33) primary melanoma skin lesions from MSKCC patients. n=71. All data are represented as mean±SEM. *p<0.05, p<0.01, *p<0.001. See also FIG. 12.

n=6-7. (6H) 1×105 endothelial cells were transduced with siRNAs targeting LRP8 or a control sequence, and trans-well chemotactic migration was assessed along an ApoE gradient. n=6-8. (6I) Endothelial recruitment into matrigel plugs, implanted subcutaneously above the ventral flank of mice, containing BSA (10 μg/mL), VEGF (400 ng/mL)+BSA (10 μg/mL), or VEGF (400 ng/mL)+recombinant ApoE3 (10 μg/mL). n=3-6.(6J) Blood vessel density within lung metastatic nodules formed following intravenous injection of 5×104 B16F10 mouse melanoma cells into wild-type or ApoE genetically null mice. Lung sections from FIG. 5M were immunohistochemically stained for MECA-32, and the percentage MECA-32 positive area within each metastatic nodule, outlined based on cell pigmentation, was quantified. n=17-20. All data are represented as mean±SEM. Scale bar, 100 μm.

FIGS. 7A, 7B, 7C, 7D, 7E, 7F, 7G, 7H, 7I AND 7K. Clinical and Therapeutic Cooperativity among miR-199a-3p, miR-199a-5p, and miR-1908 in Melanoma Metastasis (7A-7D). Kaplan-Meier curves for the MSKCC cohort (N=71) representing metastasis-free survival of patients as a function of their primary melanoma lesion's miR-199a-3p (7A), miR-199a-5p (7B), miR-1908 (7C), or aggregate three miRNA expression levels (7D). Patients whose primary tumors' miRNA expression or aggregate miRNA expression levels (sum of the expression values of miR-199a-3p, miR-199a-5p, and miR-1908) were greater than the median for the population were classified as miRNA expression positive (red), while those whose primary tumors expressed the given miRNAs at a level below the median were classified as miRNA expression negative (blue). (7E) Lung metastasis by highly metastatic LM2 cells transfected with LNAs individually targeting each miR-1908, miR-199a-3p, or miR-199a-5p, a combination of LNAs targeting all three miRNAs, or a control LNA. 48 hours post-transfection, 1×105 cells were intravenously injected into immuno-deficient mice. n=5-6. (7F) Systemic metastasis by 1×105 MeWo-LM2 cells transfected with a control LNA (LNA-CTRL) or a cocktail of LNAs targeting miR-1908, miR-199a-3p, miR-199a-5p (LNA-3 miRNAs) 48 hours prior to intracardiac injection into athymic nude mice. n=5. (7G) Number of systemic metastatic foci arising from LNA-CTRL and LNA-3 miRNAs LM2 cells at day 28 post-intracardiac injection. n=5. (7H-7I) Bioluminescence signal quantification of bone metastasis (7H) and brain metastasis (7I) at day 28 post-intracardiac injection of LNA-CTRL and LNA-3 miRNAs LM2 cells. n=5. (7J) 4×104 highly metastatic MeWo-LM2 cells were tail-vein injected into immuno-compromised mice, and the mice were intravenously treated with a cocktail of in vivo-optimized LNAs targeting miR-1908, miR-199a-3p, and miR-199a-5p at a total dose of 12.5 mg/kg or a mock PBS control on a bi-weekly basis for four weeks. Lung colonization was assessed by bioluminescence imaging, and representative H&E-stained lungs extracted at day 56 are shown. n=5-6. (7K) Model of miRNA-dependent regulation of metastatic invasion, endothelial recruitment, and colonization in melanoma through targeting of ApoE-mediated melanoma cell LRP1 and endothelial cell LRP8 receptor signaling.

FIGS. 8A, 8B, 8C, 8D and 8E. MiRNA-dependent targeting of ApoE/LRP1 signaling promotes cancer cell invasion and endothelial recruitment through CTGF induction. (8A) A heat-map of variance-normalized CTGF expression levels, determined by qRT-PCR analysis, in (1) MeWo parental and MeWo-LM2 cells, (2) MeWo parental cells over-expressing miR-199a, miR-1908, or a control hairpin, and (3) MeWo parental cells transduced with short hairpins targeting ApoE or a control sequence. Color-map indicates the standard deviations change from the mean. (8B) CTGF levels in conditioned media from MeWo parental cells with ApoE knock-down determined by ELISA. n=6; p-values based on a one-sided student's t-test. (8C) CTGF levels, quantified by ELISA, in conditioned media from highly metastatic MeWo-LM2 cells treated with recombinant ApoE in the setting of LRP1 knock-down or a control knock-down. n=3-4; p-values based on a one-sided student's t-test. (8D-8E) Parental MeWo cells with shRNA-induced ApoE knock-down were (1) transfected with independent siRNAs targeting CTGF or a control sequence or (2) incubated in the presence of a CTGF neutralizing antibody (20 μg/mL) or an IgG control antibody (20 μg/mL), and the cells were subjected to cell invasion (8D) and endothelial recruitment (8E) assays. n=6-8; p-values based on a one-sided student's t-test; scale bar indicates 100 All data are represented as mean±SEM.

Figures 9A, 9B, 9C:
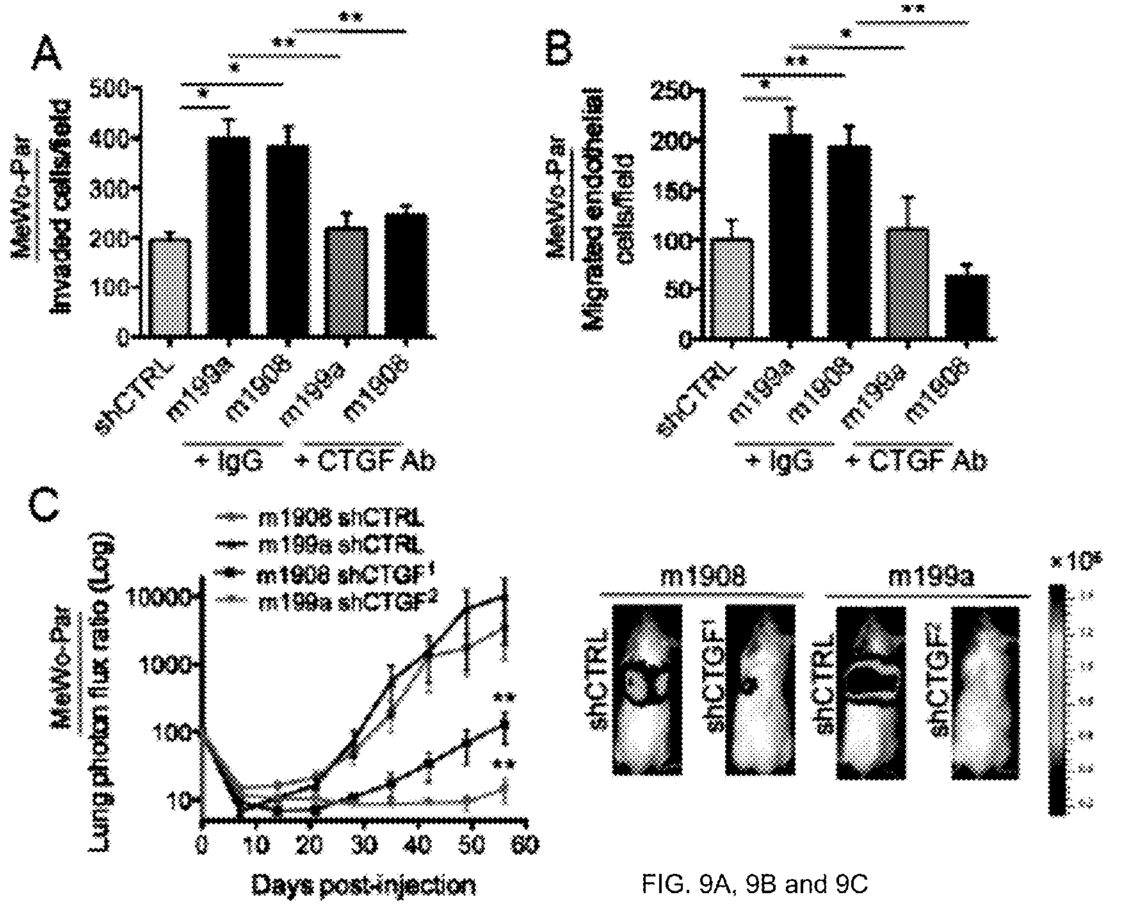

FIGS. 9A, 9B and 9C. CTGF mediates miRNA-dependent metastatic invasion, endothelial recruitment, and colonization. (9A) 1×105 parental MeWo cells expressing a control hairpin or over-expressing miR-199a or miR-1908 were subjected to a trans-well cell invasion assay in the presence of a blocking antibody targeting CTGF (20 μg/mL) or a control IgG antibody (20 μg/mL) as indicated in the figure. n=4-10; p-values based on a one-sided student's t-test. All data are represented as mean±SEM. (9B) Endothelial recruitment by parental MeWo cells expressing a control hairpin or over-expressing miR-199a or miR-1908. At the beginning of the assay, a neutralizing antibody targeting CTGF (20 μg/mL) or a control IgG antibody (20 μg/mL) were added to endothelial cells as indicated, and 1×105 endothelial cells were allowed to migrate towards 5×104 cancer cells in a trans-well migration assay. n=3-8; p-values based on a one-sided student's t-test. (9C) Bioluminescence imaging of lung metastasis by 5×104 parental MeWo cells knocked down for CTGF in the setting of miR-199a or miR-1908 over-expression. n=5-6; p-values obtained using a one-way Mann-Whitney t-test. All data are represented as mean±SEM.

FIGS. 10A, 10B, 10C, 10D and 10E. Treatment with the LXR agonist GW3965 elevates melanoma cell ApoE levels and suppresses cancer cell invasion, endothelial recruitment, and metastatic colonization. (10A-10B) Parental MeWo cells were incubated in the presence of DMSO or GW3965 at the indicated concentrations. After 48 hours, total RNA was extracted, and the levels of ApoE (10A) and DNAJA4 (10B) were determined by qRT-PCR. n=3. (10C) Cell invasion by 1×105 parental MeWo cells pre-treated with GW3965 or DMSO for 48 hours. n=6-7. p-values based on a one-sided student's t-test. All data are represented as mean±SEM. (10D) Endothelial recruitment by 5×104 parental MeWo cells pre-treated with GW3965 or DMSO for 48 hours. n=6-7. p-values based on a one-sided student's t-test. (10E) Mice were fed with grain-based chow diet containing GW3965 (20 mg/kg) or a control diet. After 10 days, 4×104 parental MeWo cells were tail-vein injected into mice, and the mice were continuously fed with GW3965-containing chow or a control diet throughout the experiment. Lung colonization was assessed by bioluminescence imaging. n=5-6; p-values obtained using a one-way Mann-Whitney t-test All data are represented as mean±SEM.

Figures 11A, 11B:
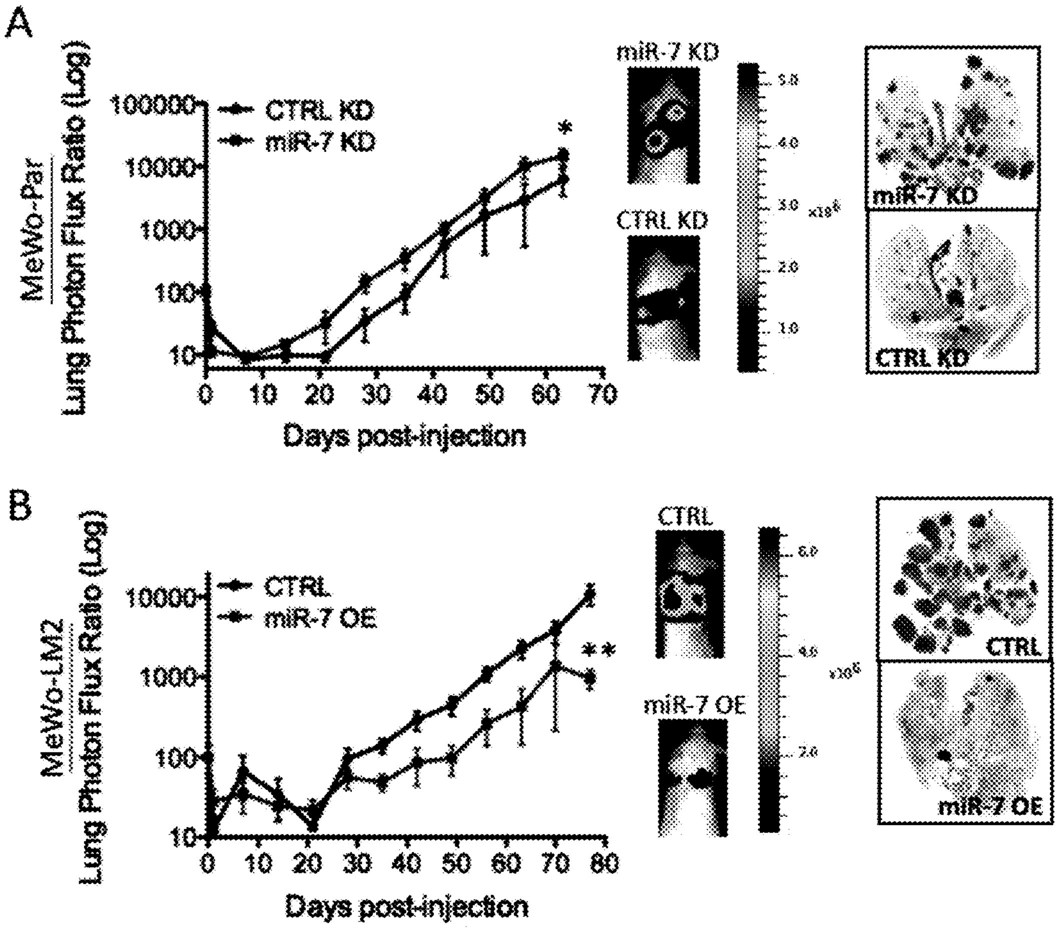

FIGS. 11A and 11B. Identification of miR-7 as an endogenous suppressor of melanoma metastasis. (11A) Bioluminescence imaging plot of lung metastatic colonization following intravenous injection of 4×104 parental MeWo cells expressing a short hairpin (miR-Zip) inhibiting miR-7

(miR-7 KD). Lungs were extracted 63 days post-injection and H&E-stained. n=5. (11B). Lung metastasis by 4×104 LM2 cells over-expressing the precursor for miR-7 or a control hairpin. Lung colonization was monitored weekly by bioluminescence imaging, and lungs were extracted at day 77 post-injection. n=5. All data are represented as mean±SEM; p-values were determined using a one-way Mann-Whitney t-test. *p<0.05, **p<0.01.

FIGS. 12A, 12B, 12C, 12D, 12E and 12F. In Vivo Selection For Highly Metastatic Human Melanoma Cell Line Derivatives and Identification of miR-199a-3p, miR-199a-5p, and miR-1908 as Metastasis-Promoter miRNAs (12A-12B) Bioluminescence imaging of lung metastasis and representative images of H&E-stained lungs corresponding to MeWo-LM2 (12A) and A375-LM3 metastatic derivatives (12B) and their respective parental cell lines. 4×104 MeWo-Par/MeWo-LM2 cells and 1×105 A375-Par/A375-LM3 cells were intravenously injected into NOD-SCID mice, and lungs were extracted and H&E stained on day 72 and day 49, respectively. n=4-5. (12C) Expression levels of miR-199a-5p, miR-199a-3p, miR-1908, and miR-214 were determined by qRT-PCR in A375-LM3 metastatic derivatives and their parental cells. n=3. (12D) Parental MeWo cells were transduced with retrovirus expressing a control hairpin or a pre-miRNA hairpin construct giving rise to miR-199a (both miR-199a-3p and miR-199a-5p), miR-1908, or miR-214. The expression levels of the target miRNAs were determined by qRT-PCR.12 n=3. (12E) H&E-stained lung sections from FIG. 1C were analyzed for the number of metastatic nodules resulting from parental MeWo cells over-expressing miR-199a, miR-1908, or a control hairpin. n=3. (12F) The number of metastatic nodules formed by LM2 cells with silenced expression of miR-199a-3p, miR-199a-5p, miR-1908, or a control sequence was analyzed in H&E-stained lung sections from FIG. 1D. n=3. All data are represented as mean±SEM.

FIGS. 13A, 13B, 13C, 13D, 13E, 13F, 13G and 13H. MiR-199a and miR-1908 Inhibit Proliferation in vitro and Selectively Promote Cell Invasion and Endothelial Recruitment (13A) 2.5×104 MeWo cells over-expressing miR-199a, miR-1908, or a control hairpin were seeded in triplicate, and viable cells were counted after 5 days. n=3. (13B) 1×105 poorly metastatic parental MeWo and highly metastatic LM2 cells were compared for their ability to invade though matrigel in a trans-well assay. n=3-4. (13C) 1×105 endothelial cells were seeded in a 6-well plate and allowed to form a monolayer. 2×105 parental MeWo cells over-expressing miR-199a, miR-1908, or a control hairpin were seeded on top of the endothelial monolayer and incubated for 30 minutes. Each monolayer was subsequently imaged, and the number of cancer cells adhering to endothelial cells was quantified. n=3. (13D) 1×106 parental MeWo cells over-expressing miR-199a, miR-1908, or a control hairpin were seeded in low adherent plates containing cell media supplemented with 0.2% methylcellulose. Following 48 hours in suspension, the numbers of dead and viable cells were quantified. n=3. (13E) 5×105 parental MeWo cells over-expressing miR-199a, miR-1908, or a control hairpin were seeded in a 6-well plate and incubated in low-serum media for 48 hours, after which the number of viable cells was quantified. n=4. (13F) Colony formation by parental MeWo cells over-expressing miR-199a, miR-1908, or a control hairpin. 50 cells were seeded in a 6-cm plate, and the number of colonies formed was quantified 2 weeks later. n=4. (13G) 5×104 parental MeWo and LM2 cells were seeded on the bottom of a well and assessed for their ability to recruit endothelial cells. n=6-8. (13H) Percentage blood vessel density, shown as a cumulative fraction plot, for metastatic nodules formed by parental MeWo cells over-expressing miR-199a, miR-1908, or a control hairpin. Lung sections from FIG. 1C were immunohistochemically double-stained for human vimentin and MECA-32, and the MECA-32 positive area relative to the total nodule area, given by human vimentin staining, was quantified using ImageJ. n=43 nodules (control); n=117 nodules (miR-199a OE); n=55 nodules (miR-1908 OE). All data are represented as mean±SEM. Scale bar, 100 μm.

FIGS. 14A, 14B, 14C, 14D, 14E, 14F, 14G. MiR-199a and miR-1908 Convergently and Cooperatively Target ApoE and DNAJA4 (14A) Venn diagram showing the integrative experimental approach that lead to the identification of putative target genes common to miR-199a-3p, miR-199a-5p, and miR-1908. Transcriptomic profiling of genes down-regulated by greater than 1.5-fold upon each miRNA over-expression were overlapped with genes up-regulated by more than 1.5-fold upon each miRNA silencing and with genes down-regulated by more than 1.5-fold in metastatic LM2 cells relative to their parental cell line. (14B, 14C, 14D) Expression levels of ApoE and DNAJA4 measured by qRT-PCR in parental MeWo cells over-expressing miR-199a, miR-1908, or a control hairpin (14B), in parental MeWo cells and their highly metastatic LM2 derivative cell line (14C), and in MeWo-LM2 cells with miR-Zip-based silencing of miR-199a-3p, miR-199a-5p, miR-1908, or a control sequence (14D). n=3. (14E) Heterologous luciferase reporter assays measuring the stability of miR-199a-3p, miR-199a-5p, or miR-1908 target site mutant ApoE and DNAJA4 3'UTR/CDS luciferase fusions in highly metastatic LM2 cells with inhibition of miR-199a-3p, miR-199a-5p, miR-1908, or a control sequence. n=3-4. (14F) MeWo-LM2 cells were transduced with retrovirus expressing a control vector or an over-expression vector giving rise to ApoE or DNAJA4. The expression levels of the target genes were determined by qRT-PCR. (14G) Expression levels of ApoE and DNAJA4, determined by qRT-PCR, in parental MeWo cells were transduced with lentiviral shRNAs targeting ApoE, DNAJA4, or a control sequence. All data are represented as mean±SEM.

FIGS. 15A, 15B, 15C, 15D, 15E, 15F, 15G, 15H, 15I and 15K. Epistatic Interactions between miR-199a/miR-1908 and ApoE/DNAJA4 (15A, 15B, 15C and 15D). MeWo-LM2 cells were transduced with lentiviral shRNAs targeting ApoE (15A, 15C), DNAJA4 (15B, 15D), or a control shRNA in the setting of miR-Zip-induced silencing of miR-1908 (15A, 15B), miR-199a-5p (15C, 15D), or a control sequence. The levels of the target genes were analyzed by qRT-PCR. (15E) Bioluminescence imaging of lung metastasis by 1×105 LM2 cells expressing a control hairpin or shRNAs (independent from the shRNAs used in FIG. 4E) targeting ApoE, DNAJA4, or a control sequence in the setting of miR-1908 inhibition. Representative bioluminescence images and H&E-stained lungs correspond to day 42 post-injection. n=5. (15F-15G) The expression levels of ApoE and DNAJA4 were analyzed by qRT-PCR in parental MeWo cells transduced with retrovirus expressing a control vector or an over-expression vector for ApoE or DNAJA4 in the setting of miR-1908 (15F) or miR-199a (15G) over-expression. (15H-15I). Parental MeWo cells over-expressing ApoE or DNAJA4 or expressing a control vector in the setting of miR-199a over-expression were examined for the invasion (15H) and endothelial recruitment (15I) phenotypes. n=7-8. (15J) Bioluminescence imaging of lung metastasis by 4×104 parental MeWo cells over-expressing ApoE or DNAJA4 or expressing a control vector in the setting of miR-1908 over-expression. Representative bioluminescence images and H&E-stained lungs correspond to day 56 post-injection n=4-8. (15K). Expression levels of ApoE and DNAJA4, determined by qRT-PCR, in highly metastatic A375-LM3 derivatives transduced with lentivirus expressing shRNA constructs targeting ApoE and DNAJA4 or a control sequence. All data are represented as mean±SEM. Scale bar, 100 μm.

FIGS. 16A, 16B, 16C, 16C, 16D, 16E, 16F, 16G, 16H and 16I. Extracellular ApoE Inhibits Melanoma Invasion and Endothelial Recruitment Phenotypes Independent of Any Effects on Cancer or Endothelial Cell Proliferation and Survival (16A) Extracellular ApoE levels were measured by ELISA in conditioned media from MeWo cells over-expressing miR-199a, miR-1908, or a control hairpin. n=3. (16B-16C) 3×104 MeWo-LM2 cells (16B) or endothelial cells (16C) were cultured in the presence of BSA (100 μM) or APOE (100 μM), and cell proliferation was monitored over time by counting the number of viable cells at each indicated time-point. n=3. (16D-16E) Survival of MeWo-LM2 cells (16D) or endothelial cells (16E) in the context of serum starvation in the presence of BSA (100 μM) or APOE (100 μM). n=3. (16F-16G) The mRNA expression levels of ApoE were assessed in parental MeWo cells transduced with lentivirus expressing a control hairpin or short hairpin constructs targeting DNAJA4 (16F) and in LM2 cells transduced with retrovirus expressing a control vector or an over-expression vector for DNAJA4 (16G). n=3. (H-I) LM2 cells transduced with retrovirus expressing a control vector or an over-expression vector for DNAJA4 were assessed for their ability to invade through matrigel (16H; n=6-8) and recruit endothelial cells in a trans-well assay (16I; n=4) in the presence of IgG (40 μg/mL) or 1D7 (40 μg/mL) ApoE neutralization antibodies. All data are represented as mean±SEM.

FIGS. 17A, 17B, 17C, 17D and 17E. ApoE Inhibits Cell Invasion and Endothelial Recruitment by Targeting Melanoma Cell LRP1 and Endothelial Cell LRP8 Receptors (17A) 1×105 LM2 cells transduced with siRNAs against LRP1 or a control sequence were analyzed for the ability to invade through matrigel. n=9-12. (17B) 1×105 MeWo-LM2 cells inhibited for miR-199a-5p or a control sequence were transfected with siRNAs targeting LRP1 or a control siRNA and examined for their matrigel invasion capacity. n=4. (17C) Representative H&E-stained lungs extracted at day 56 from NOD-SCID mice injected with MeWo-LM2 miR-1908 KD cells transduced with a control siRNA or siRNAs targeting LRP1 (See FIG. 6C). (17D-17E) 1×105 endothelial cells were transfected with siRNAs targeting LRP8 or a control sequence and allowed to trans-well migrate towards 5×104 MeWo-LM2 cells expressing a short control hairpin (17D; n=8) or 5×104 MeWo-LM2 cells inhibited for miR-199a-5p or a control sequence (17E; n=4). All data are represented as mean±SEM. Scale bar, 100 μm.

Figures 18A, 18B, 18C:
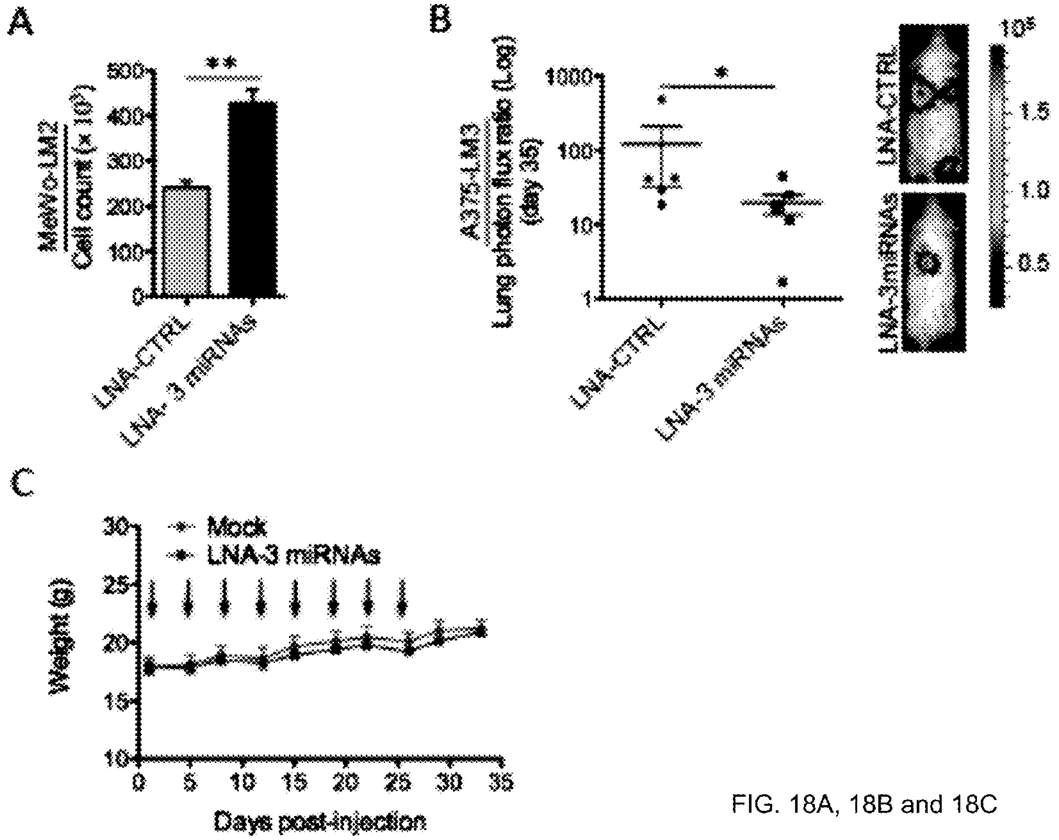

FIGS. 18A, 18B, and 18C. LNA-Based Inhibition of miR-199a and miR-1908 Suppresses Melanoma Metastasis (18A) In vitro cell proliferation by 2.5×104 MeWo-LM2 cells transduced with a control LNA or a cocktail of LNAs targeting miR-199a-3p, miR199a-5p and miR-1908. The number of viable cells was quantified after five days. n=3. (18B) Lung colonization by highly metastatic A375-LM3 derivatives transfected with a control LNA or a cocktail of LNAs targeting miR-199a-3p, miR199a-5p, and miR-1908. 48 hours post-transfection, 5×105 cells were injected intravenously into NOD-SCID mice, and lung colonization was determined by measuring bioluminescence 35 days later. n=5-6. (18C) The weight of mice treated with a cocktail of LNAs targeting the three miRNAs or a mock PBS control treatment (FIG. 7J) was monitored bi-weekly. n=5-6. All data are represented as mean±SEM.

FIGS. 19A, 19B, 19C, 19D, 19E, 19F and 19G. Activation of LXRβ Signaling Suppresses Melanoma Cell Invasion and Endothelial Recruitment. (19A) Heat-map depicting microarray-based expression levels of LXR and RXR isoforms in the NCI-60 melanoma cell line collection. The heat map for these genes is extracted from the larger nuclear hormone receptor family heat map (FIG. 20). Color-map key indicates the change in standard deviations for the expression value of each receptor relative to the average expression value of all microarray-profiled genes (>39,000 transcript variants) in each cell line. (19B) Cell invasion by 1×105 MeWo, 5×104 HT-144, 5×105 SK-Mel-2, and 5×104 SK-Mel-334.2 human melanoma cells. Cells were treated with DMSO, GW3965, T0901317, or Bexarotene at 1 μM for 72 hours and subjected to a trans-well matrigel invasion assay. n=4-8. (19C) 5×104 MeWo, HT-144, SK-Mel-2, and SK-Mel-334.2 human melanoma cells were tested for their ability to recruit 1×105 endothelial cells in a trans-well migration assay, following treatment of the melanoma cells with DMSO, GW3965, T0901317, or Bexarotene at 1 μM for 72 hours. n=4-8. (19D-19E) 1×105 MeWo (19D) and 1×105 HT-144 (19E) melanoma cells expressing a control shRNA or shRNAs targeting LXRα or LXRβ were subjected to the cell invasion assay following treatment of the cells with DMSO, GW3965, or T0901317 at 1 μM for 72 hours. n=4-12. (19F-19G) 5×104 MeWo (19F) and 5×104 HT-144 (19G) cells, transduced with lentiviral shRNAs targeting LXRα or LXRβ or a control shRNA, were treated with DMSO, GW3965, or T0901317 at 1 μM for 72 hours and tested for their ability to recruit 1×105 endothelial cells in a trans-well migration assay. n=7-8. All data are represented as mean±SEM. Scale bar, 50 μm. *p<0.05, p<0.01, *p<0.001, ****p<0.0001.

FIGS. 20A, 20B, 20C, 20D, 20E, 20F and 20G. Analysis of Nuclear Hormone Receptor Expression in Melanoma and Effects of LXR and RXR Agonists on In Vitro Cell Growth, Related to FIG. 19(A-G). (20A) Heat-map showing microarray-based expression levels of all nuclear hormone receptor family members across the NCI-60 collection of melanoma lines. The expression levels of each receptor is presented as the number of standard deviations below or above the average expression levels of all genes (>39,000 transcript variants) detected by the microarray in each respective cell line. (20B) 2.5×104 MeWo, HT-144, or SK-Mel-334.2 human melanoma cells were seeded in 6-well plates and cultured in the presence of DMSO, GW3965, T0901317, or Bexarotene at 1 μM. Viable cells were counted on day 5 post-seeding. n=3-6. (20C) 2.5×104 MeWo, HT-144, or SK-Mel-334.2 cells were plated in triplicates and incubated in media containing DMSO, GW3965, T0901317, or Bexarotene at 1 μM for 5 days, after which the number of dead cells was quantified using trypan blue dead cell stain. n=3. (20D-20G) Relative expression of LXRα and LXRβ, determined by qRT-PCR, in MeWo (20D, 20E) and HT-144 (20F, 20G) human melanoma cells expressing a control shRNA or shRNAs targeting LXRα or LXRβ. All data are represented as mean±SEM.

FIGS. 21A, 21B, 21C, 21D, 21E, 21F, 21G, 21H, 21J, 21K and 21L. Therapeutic LXR Activation Inhibits Melanoma Tumor Growth. (21A-21B) Primary tumor growth by 5×104 B16F10 mouse melanoma cells subcutaneously injected into C57BL/6-WT mice. Following tumor growth to 5-10 mm3 in volume, mice were continuously fed a control chow or a chow supplemented with GW3965 (20 mg/kg/day or 100 mg/kg/day) (21A) or T0901317 (20 mg/kg/day) (21B). Representative tumor images shown correspond to tumors extracted at the final day (d12). n=10-18 (21A), 8-10 (21B). (21C-21E) Primary tumor growth by 1×106 MeWo (21C), 7.5×105 SK-Mel-334.2 (21D), and 2×106 SK-Mel-2 (21E) human melanoma cells subcutaneously injected into immunocompromised mice. Following tumor growth to 5-10 mm3 in volume, mice were randomly assigned to a control diet or a diet supplemented with GW3965 (20 mg/kg or 100 mg/kg, as indicated). Tumor images shown correspond to last day of measurements. n=6-34 (21C), 8 (21D), 5 (21E). (21F) 5×104 B16F10 cells were injected subcutaneously into C57BL/6-WT mice. Upon tumor growth to 150 mm3, mice were fed continuously with a control chow or a chow containing GW3965 (150 mg/kg), and tumor growth was measured daily. n=6-13. (21G-21I) Mouse overall survival following subcutaneous grafting of 5×104 B16F10 (21G), 1×106 MeWo (21H), and 7.5×105 SK-Mel-334.2 cells (21I) into mice that were administered a normal chow or a chow supplemented with GW3965 (100 mg/kg) upon formation of tumors measuring 5-10 mm3 in volume. n=6-9 (21F), 4-7(21H), 3-6 (21I). (21J, 21K, 21L) Tumor endothelial cell density, determined by immunohistochemical staining for the mouse endothelial cell antigen MECA-32 (21J), tumor cell proliferation, determined by staining for the proliferative marker Ki-67 (21K), and tumor cell apoptosis, determined by staining for cleaved caspase-3 (21L), in subcutaneous melanoma tumors formed by 1×106 MeWo human melanoma cells in response to mouse treatment with a control diet or a GW3965-supplemented diet (20 mg/kg) for 35 days. n=5. Tumor volume was calculated as (small diameter)2×(large diameter)/2. All data are represented as mean±SEM. Scale bars, 5 mm (21A, 21B, 21C, 21D), 50 μm (21J, 21K), 25 μm (21L).

Figures 21A, 21B, 21C, 21D, 21E, 21F, 21G, 21H, 21I:
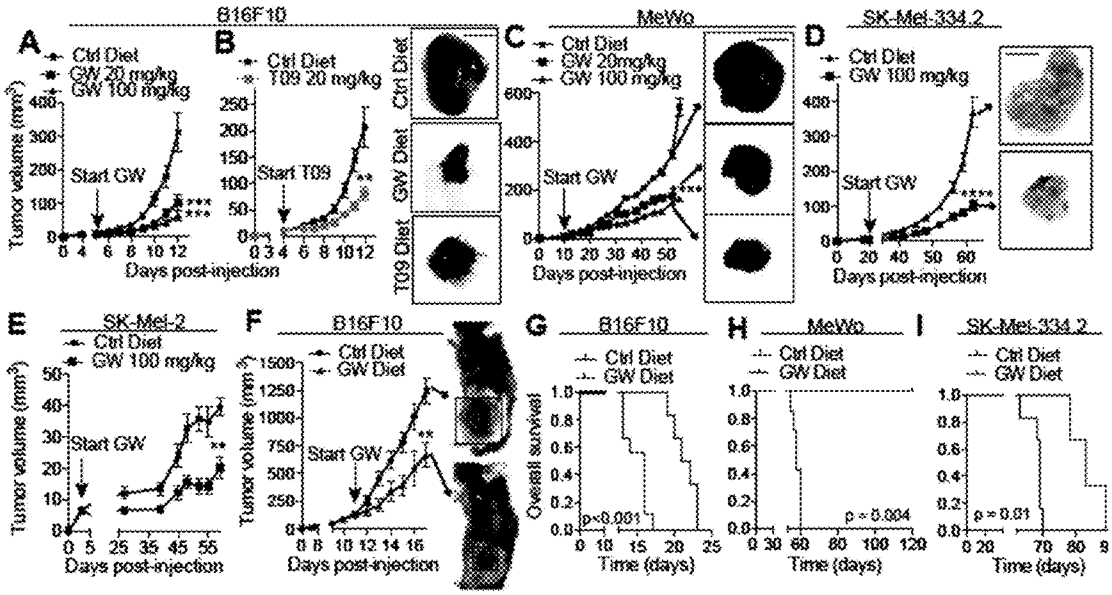
Figures 21J, 21K, 21L:
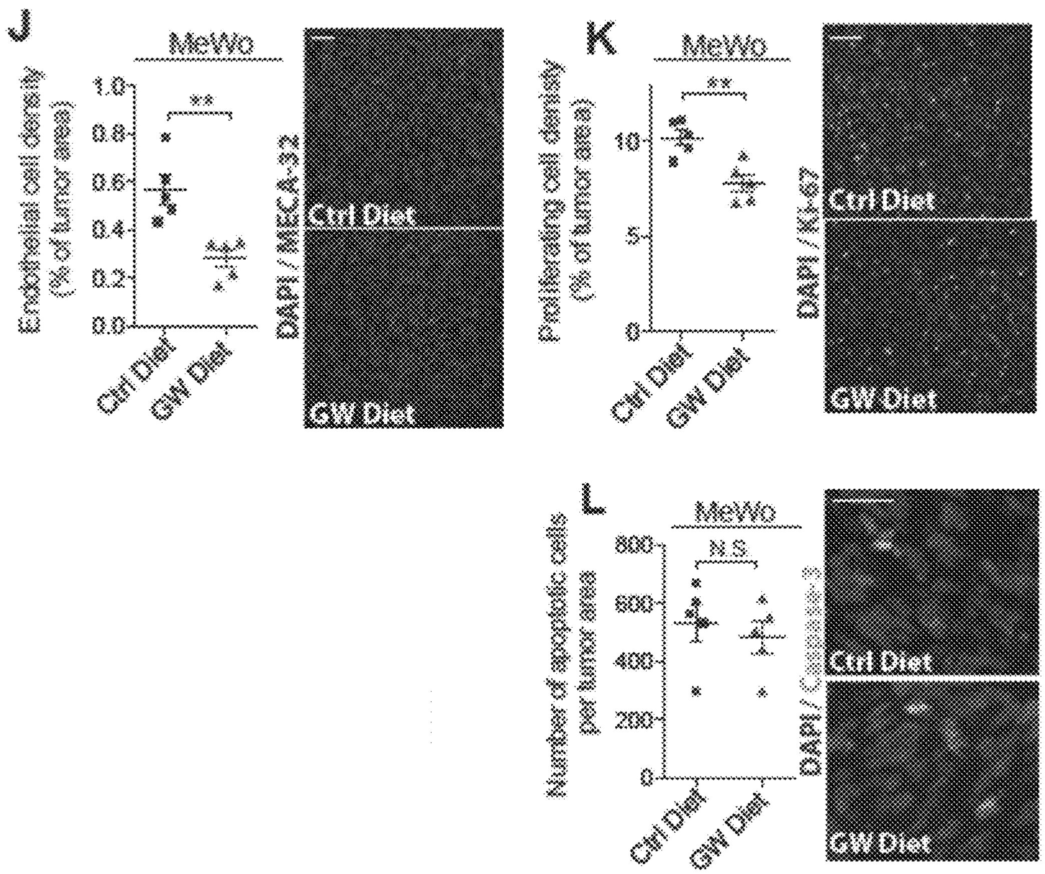
Figure 22:
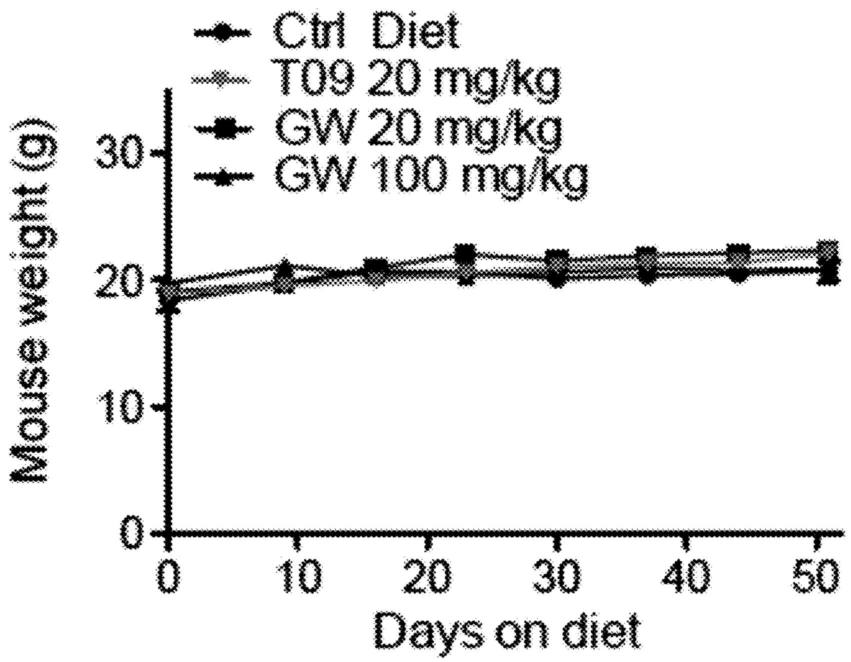

FIG. 22. LXRβ Agonism Suppresses Melanoma Tumor Growth, Related to FIG. 21(A-E). Weight measurements of mice fed a control diet or a diet supplemented with GW3965 (20 mg/kg/day or 100 mg/kg/day) or T0901317 (20 mg/kg) for 65 days. n=5-6.

FIGS. 23A, 23B, 23C, 23D, 23E, 23F, 23G, 23H, 23I, 23J and 23K. LXR Agonism Suppresses Melanoma Metastasis to the Lung and Brain. (23A) MeWo cells were pre-treated with DMSO or GW3965 (1 μM) for 48 hours and 4×104 cells were intravenously injected via the tail-vein into NOD Scid mice. Lung colonization was monitored by weekly bioluminescence imaging. Representative H&E-stained lungs correspond to the final day (d70) are shown. n=4-5. (23B-23C) Bioluminescence imaging of lung metastasis by 4×104 MeWo cells intravenously injected into NOD Scid mice that were fed a control chow or a chow containing GW3965 (20 mg/kg) or T0901317 (20 mg/kg) starting 10 days prior to cancer cell injection. Representative H&E-stained lungs correspond to final imaging day n=5-6. (23B-23C) Bioluminescence imaging of lung metastasis by 4×104 MeWo cells intravenously injected into NOD Scid mice that were fed a control chow or a chow containing GW3965 (20 mg/kg) or T0901317 (20 mg/kg) starting 10 days prior to cancer cell injection. Representative H&E-stained lungs correspond to final imaging day n=5-6. (23F) Systemic and brain photon flux following intracardiac injection of 1×105 MeWo brain metastatic derivative cells into athymic nude mice that were fed a control diet or a GW3965-supplemented diet (100 mg/kg) starting on day 0 post-injection. n=7. (23G) Schematic of experimental orthotopic metastasis model used to assess the ability of GW3965 treatment to suppress lung metastasis post-tumor excision. (23H) Ex-vivo lung photon flux, determined by bioluminescence imaging, in NOD Scid mice that were administered a control chow or a chow containing GW3965 (100 mg/kg) for 1 month following the excision of size-matched (~300-mm3 in volume) subcutaneous melanoma tumors formed by 1×106 MeWo melanoma cells. Representative lungs stained for human vimentin are also shown. n=7-9. (23I) 4×104 MeWo cells were intravenously injected into NOD Scid mice. Following initiation of metastases, detected by bioluminescence imaging on d42, mice were administered a control diet or a GW3965 diet (100 mg/kg) as indicated, and lung colonization progression was measured weekly. n=6. (23J) Number of macroscopic metastatic nodules in H&E-stained lungs extracted at the final day (d77) from NOD Scid mice administered a control diet or a diet supplemented with GW3965 (100 mg/kg), as indicated in (23I). n=4-5. (23K) Overall mouse survival following intravenous injection of 4×104 MeWo cells into NOD-Scid mice that were continuously fed a control chow or a GW3965-supplemented chow (20 mg/kg) starting 10 days prior to cancer cell injection. n=5-6. All data are represented as mean±SEM.

FIGS. 24A, 24B, 24C, 24D, 24E and 24F. Suppression of Genetically-Driven Melanoma Progression by LXR Activation Therapy. (24A) Overall survival of Tyr::CreER; BrafV600E/+; Ptenlox/+C57BL/6 mice following general melanoma induction by intraperitoneal administration of 4-HT (25 mg/kg) on three consecutive days. After the first 4-HT injection, mice were randomly assigned to a control diet or a diet supplemented with GW3965 (100 mg/kg). n=10-11. (24B) Melanoma tumor burden, expressed as the percentage of dorsal skin area, measured on day 35 in Tyr::CreER; BrafV600E/+; Ptenlox/lox mice administered a control chow or a chow supplemented with GW3965 (100 mg/kg) upon melanoma induction as described in (24A). n=4-5. (24C) Number of macroscopic metastatic nodules to the salivary gland lymph nodes detected post-mortem in Tyr::CreER; BrafV600E/+; Ptenlox/lox mice that were fed a control chow or a chow containing GW3965 (100 mg/kg) following global induction of melanoma progression as described in (24A). n=7-8. (24D) Tumor growth following subcutaneous injection of 1×105 BrafV600E/+; Pten−/−; CDKN2A−/− primary melanoma cells into syngeneic C57BL/6-WT mice. Upon tumor growth to 5-10 mm3 in volume, mice were fed with a control chow or a chow supplemented with GW3965 (100 mg/kg). n=16-18. (24E) Overall survival of C57BL/6-WT mice subcutaneously injected with 1×105 BrafV600E/+; Pten−/−; CDKN2A−/− melanoma cells and treated with a GW3965 diet (100 mg/kg) or a control diet following tumor growth to 5-10 mm3 in volume. n=7-8. (24F) Lung colonization by 1×105 BrafV600E/+; Pten−/−; CDKN2A−/− primary melanoma cells intravenously injected into C57BL/6-WT mice. Immediately following cancer cell injection, mice were randomly assigned to a control diet or a GW3965-supplemented diet (100 mg/kg) for the remainder of the experiment. n=14-15. All data are represented as mean±SEM. Scale bar, 2 mm (24B), 5 mm (24D).

Figures 24A, 24B, 24C, 24D, 24E, 24F:
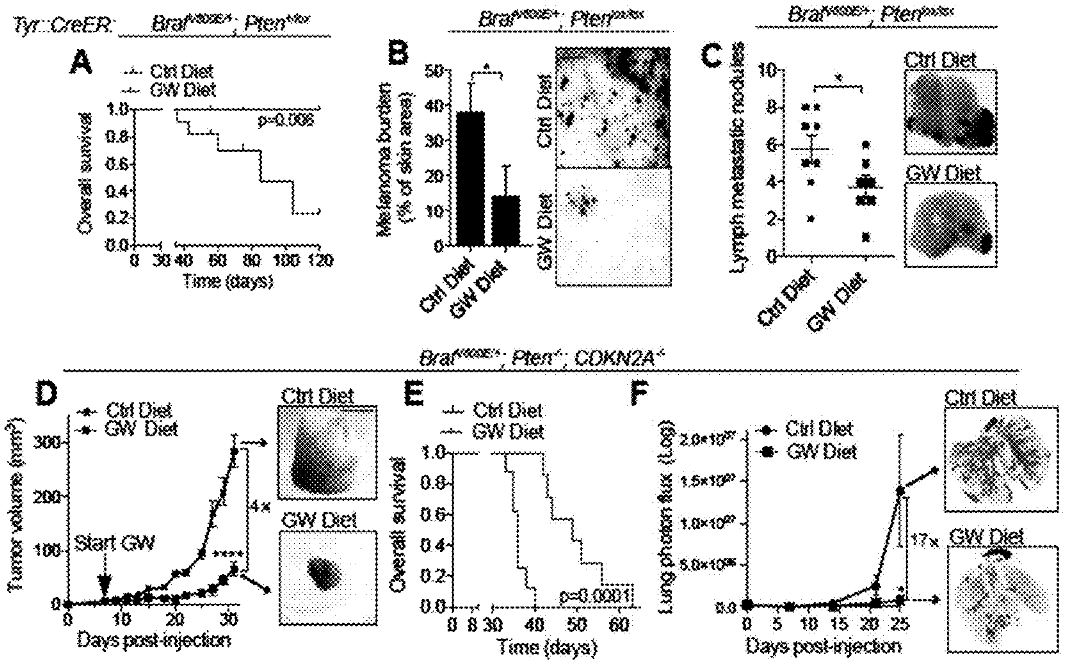
Figures 25A, 25B:
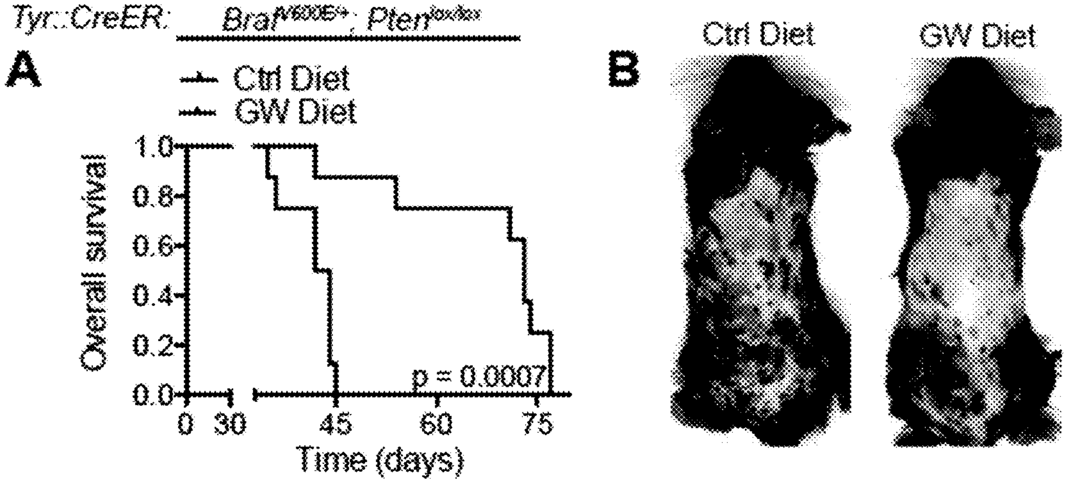

FIGS. 25A and 25B. LXR-Mediated Suppression of Melanoma Progression in a Genetically-Driven Melanoma Mouse Model, Related to FIG. 24(A-C). (25A) Overall survival of Tyr::CreER; BrafV600E/+; Ptenlox/lox C57BL/6 mice following general melanoma induction by intraperitoneal administration of 4-HT (25 mg/kg) on three consecutive days. After the first 4-HT injection, mice were randomly assigned to a control diet or a diet supplemented with GW3965 (100 mg/kg). n=7. (25B) Representative images of Tyr::CreER; BrafV600E/+; Ptenlox/lox C57BL/6 mice fed a control diet of GW3965-supplemented diet (100 mg/kg) taken 43 days following melanoma induction by intraperitoneal 4-HT administration.

FIG. 26. A List of the 50 most upregulated genes in MeWo human melanoma cells in response to GW3965 treatment.

FIGS. 27A, 27B, 27C, 27D, 27E, 27F, 27G, 27H, 27I, 27J and 27K. LXRβ Activation Induces ApoE Expression in Melanoma Cells; ApoE mediates LXRβ-Dependent Suppression of In Vitro Melanoma Progression Phenotypes. (27A, 27B, 27C) MeWo (27A), HT-144 (27B), and WM-266-4 (27C) human melanoma cells were treated with GW3965 or T0901317 at the indicated concentrations for 48 hours, and the expression levels of ApoE were analysed by qRT-PCR. n=3. (27D) Extracellular ApoE protein levels, quantified by ELISA, in serum-free conditioned media collected from HT-144 human melanoma cells treated with DMSO, GW3965, or T0901317 at 1 μM for 72 hours. n=3-4. (27E-27F) 5×104 HT-144 cells, treated with DMSO, GW3965, or T0901317 at 1 μM for 72 hours, were tested for the cell invasion (27E) and endothelial recruitment phenotypes (27F) in the presence of an ApoE neutralization antibody (1D7) or an IgG control antibody added at 40 μg/mL to each trans-well at the start of the assay. n=4. (27G-27H) Cell invasion (27G) and endothelial recruitment (27F) by 1×105 and 5×104 MeWo cells, respectively, expressing a control shRNA or an shRNA targeting ApoE and treated with DMSO or GW3965 at 1 μM for 72 hours prior to each assay. n=7-8. (27I-27J) Relative ApoE expression, quantified by qRT-PCR, in MeWo (I) and HT-144 (27J) cells transduced with a control shRNA or shRNAs targeting LXRα or LXRβ and subsequently treated with DMSO, GW3965, or T0901317 at 1 μM for 48 hours. n=3-9. (27K) Extracellular ApoE protein levels, measured by ELISA, in serum-free conditioned media harvested from HT-144 cells transduced with a control shRNA or an shRNA targeting LXRα or LXRβ and treated with DMSO or GW3965 at 1 μM for 72 hours. n=3. All data are represented as mean±SEM. Scale bar, 50 μm.

FIGS. 28A, 28B, 28C, 28D, 28E, 28F, 28G, 28H and 281. LXRβ Activation Suppresses Melanoma Invasion and Endothelial Recruitment by Transcriptionally Enhancing Melanoma-Cell ApoE Expression. (28A) Luciferase activity driven off the ApoE promoter fused downstream of multi-enhancer element 1 (ME.1) or multi-enhancer element 2 (ME.2) sequences and transfected into MeWo cells treated with DMSO, GW3965, or T0901317 at 1 μM for 24 hours. n=4-8. (28B) Extracellular ApoE protein levels were quantified by ELISA in serum-free conditioned media harvested from MeWo cells treated with DMSO, GW3965, or T0901317 at 1 μM for 72 hours. n=3-4. (28C) Cell invasion by 1×105 MeWo cells pre-treated with DMSO, GW3965, or T0901317 at 1 μM for 72 hours. At the start of the assay, an ApoE neutralization antibody (1D7) or an IgG control antibody was added at 40 μg/mL to each trans-well, as indicated. n=7-8. (28D) 5×104 MeWo cells, pre-treated with DMSO, GW3965, or T0901317 at 1 μM for 72 hours, were tested for their ability to recruit 1×105 endothelial cells in the presence of 1D7 or IgG antibodies at 40 μg/mL. n=6-8. (28E) Extracellular ApoE protein levels, quantified by ELISA, in serum-free conditioned media from SK-Mel-334.2 primary human melanoma cells treated with DMSO or GW3965 at 1 μM for 72 hours. n=4. (28F-28G) 5×104 SK-Mel-334.2 cells, pre-treated with GW3965 at 1 μM for 72 hours, were subjected to the cell invasion (28F) and endothelial recruitment (28G) assays in the presence of 1D7 or IgG antibodies at 40 μg/mL. n=7-8. (28H) Activity of the ApoE promoter fused to ME.1 or ME.2 enhancer elements was determined through measuring luciferase reporter activity in MeWo cells expressing a control shRNA or shRNAs targeting LXRα or LXRβ in the presence of DMSO or GW3965 (1 μM) for 24 hours. n=3-8. (28I) Extracellular ApoE protein levels, quantified by ELISA, were assessed in serum-free conditioned media collected from human MeWo melanoma cells expressing a control shRNA or shRNAs targeting LXRα or LXRβ in response to treatment with GW3965 or T0901317 (1 μM) for 72 hours. n=3-8. All data are represented as mean±SEM. Scale bar, 50 μm.

FIGS. 29A, 29B, 29C, 29D, 29E, 29F, 29G, 29H, 29I, 29J and 29K. Therapeutic Delivery of LXR Agonists Upregulates Melanoma-Derived and Systemic ApoE Expression. (29A-29B) ApoE expression levels, quantified by qRT-PCR, in subcutaneous tumors formed by B16F10 mouse melanoma cells injected into C57BL/6 mice. After 5-mm3 tumor formation, mice were fed a control diet or diet containing GW3965 (20 mg/kg) (29A) or T0901317 (20 mg/kg) (29B) for 7 days. n=3-4. (29C, 29D, 29E) ApoE transcript expression in primary tumors (29C), lung metastases (29D), and brain metastases (29E) formed by MeWo human melanoma cells grafted onto NOD Scid mice that were administered control chow or chow supplemented with GW3965 (20 mg/kg). ApoE levels were assessed on day 35 (29C), day 153 (29D), and day 34 (29E) post-injection of the cancer cells. n=3-5. (29F) Relative expression levels of LXRα, LXRβ, and ApoE were determined by qRT-PCR in B16F10 mouse melanoma cells expressing a control hairpin or an shRNA targeting mouse LXRα (sh_mLXRα), mouse LXRβ (sh_mLXRβ), or mouse ApoE (sh_mApoE). (29G-29H) ApoE (29G) and ABCA1 (29H) mRNA levels, measured by qRT-PCR, in B16F10 cells expressing a control shRNA or shRNAs targeting mouse LXRβ or mouse ApoE. The cells were treated with DMSO or GW3965 at 5 μM for 48 hours. n=3. (29I) ABCA1 mRNA levels, measured by qRT-PCR, in systemic white blood cells extracted from LXRα −/− or LXRβ −/− mice fed a control diet or a GW3965-supplemented diet (20 mg/kg) for 10 days. n=3-4. (29J) Relative expression of ApoE mRNA, expressed as the frequency of SAGE tags, in mouse skin and lung tissues was determined using the public mSAGE Expression Matrix database available through the NCI-funded Cancer Genome Anatomy Project (CGAP). (29K) Relative expression of ApoE mRNA, determined by qRT-PCR, in MeWo melanoma cells dissociated from lung metastatic nodules (LM2) or primary tumors relative to control unselected MeWo parental cells. n=3.

FIGS. 30A, 30B, 30C, 30D, 30E, 30F, 30G, 30H and 30I. LXRβ Agonism Suppresses Melanoma Tumor Growth and Metastasis by Inducing Melanoma-Derived and Systemic ApoE Expression. (30A) Western blot measurements of ApoE protein levels in adipose, lung, and brain tissue lysates extracted from wild-type mice fed with a control chow or a chow supplemented with GW3965 (20 mg/kg) or T0901317 (20 mg/kg) for 10 days. (30B) Quantification of ApoE protein expression based on western blots shown in (30A). Total tubulin was used as an endogenous control for normalization. n=3-5. (30C) Expression levels of ApoE, determined by qRT-PCR, in systemic white blood cells from mice fed a control diet or a diet supplemented with GW3965 or T0901317 at 20 mg/kg for 10 days. n=3-6. (30D) B16F10 control cells or B16F10 cells expressing shRNAs targeting mouse LXRα (sh_mLXRα) or mouse LXRβ (sh_mLXRβ) were subcutaneously injected into C57BL/6-WT, LXRα −/−, or LXRβ −/− mice. Once the tumors reached 5-10 mm3 in volume, mice were fed a control diet or a diet supplemented with GW3965 (20 mg/kg) for 7 days, after which final tumor volume was measured. Representative tumor images extracted at the end point are shown in the right panel. n=6-18. (30E) ApoE transcript levels, quantified by qRT-PCR, in systemic white blood cells extracted from LXRα −/− or LXRβ −/− mice fed a control diet or a GW3965-supplemented diet (20 mg/kg) for 10 days. n=3-5. (30F) Subcutaneous tumor growth by 5×104 B16F10 control cells or B16F10 cells expressing an shRNA targeting mouse ApoE (sh_mApoE) in C57BL/6-WT or ApoE−/− mice. Following the formation of tumors measuring 5-10 mm3 in volume, mice were fed a control diet or a diet supplemented with GW3965 (20 mg/kg) for 7 days, and final tumor volume was quantified. Representative images of tumors extracted at the final day of measurement (d12) are shown on the right. n=8-18. (30G) Lung colonization by 5×104 B16F10 cells transduced with a control shRNA or sh_mApoE and intravenously injected into C57BL/6-WT or ApoE−/− mice. Starting 10 days prior to cancer cell injection, mice were assigned to a control diet or a GW3965-supplemented diet (20 mg/kg) treatment. Lung metastasis was quantified on d22 by bioluminescence imaging. Representative lungs extracted at the end point (d22) are shown in the right panel. n=5-10. (30H) ApoE protein expression, determined by blinded immunohistochemical analysis, in non-metastatic (n=39) and metastatic (n=34) primary melanoma skin lesion samples obtained from patients at MSKCC. The fraction of ApoE-positively staining cell area was quantified as a percentage of total tumor area. (30I) Kaplan-Meier curves for the MSKCC cohort (n=71) depicting the metastasis-free survival of patients as a function of ApoE protein expression in patients' primary melanoma lesions. Melanomas that had ApoE levels above the median of the population were classified as ApoE-positive (pos), whereas tumors with ApoE expression below the median were classified as ApoE-negative (neg). All data are represented as mean±SEM. Scale bar, 5 mm (30D and 30F), 100 μm (30H).

FIGS. 31A, 31B, 31C, 31D, 31E, 31F, 31G, 31H and 31I. Activation of LXRβ Suppresses the In Vivo Growth of Melanoma Lines Resistant to Dacarbazine and Vemurafenib. (31A) In vitro cell growth by 2.5×104 B16F10 parental cells and in vitro-derived B16F10 DTIC-resistant cells in response to varying doses of dacarbazine (DTIC) added to the cell media for 4 days. n=3. (31B-31D) Tumor growth by 5×104 DTIC-sensitive B16F10 parental cells (31B) or 5×104 DTIC-resistant B16F10 cells (31C) subcutaneously injected into C57BL/6-WT mice. Following tumor growth to 5-10 mm3 in volume, mice were treated with dacarbazine (50 mg/kg, i.p., daily) or a control vehicle and randomly assigned to regular chow or a chow supplemented with GW3965 (100 mg/kg). Final day tumor volume measurements are shown in (31D). n=8-16 (31B), 7-8 (31C). (31E-31F) Tumor growth by DTIC-sensitive MeWo parental cells and in vivo-derived DTIC-resistant MeWo human melanoma cells in response to DTIC or GW3965 treatments. 5×105 cells were subcutaneously injected into NOD Scid gamma mice. After formation of tumors measuring 5-10 mm3 in volume, mice were blindedly assigned to a control treatment, a DTIC treatment (50 mg/kg, i.p., administered daily in 5-day cycles with 2-day off-treatment intervals), or a GW3965-supplemented diet treatment (100 mg/kg). Final day tumor measurements are show in (31F). n=6-8. (31G) Tumor growth by 2×106 SK-Mel-239 vemurafenib-resistant clone cells subcutaneously injected into NOD Scid gamma mice that were assigned to a control diet or a diet supplemented with GW3965 (100 mg/kg) subsequent to growth of tumors to 5-10 mm3 in volume. n=7-8. (31H) Overall mouse survival post-grafting of 2×106 SK-Mel-239 vemurafenib-resistant cells. Upon the growth of tumors to 5-10 mm3 in volume, mice were continuously fed a control diet or a diet supplemented with GW3965 (100 mg/kg). n=7. (31I) Experimentally derived model depicting the engagement of systemic and melanoma-autonomous ApoE by LXRβ activation therapy in mediating the suppression of melanoma progression phenotypes. Extracellular ApoE suppresses melanoma metastasis by coordinately inhibiting melanoma cell invasion and non-cell-autonomous endothelial recruitment through targeting melanoma-cell LRP1 and endothelial-cell LRP8 receptors, respectively. All data are represented as mean±SEM. Scale bar, 5 mm.

Figure 32:
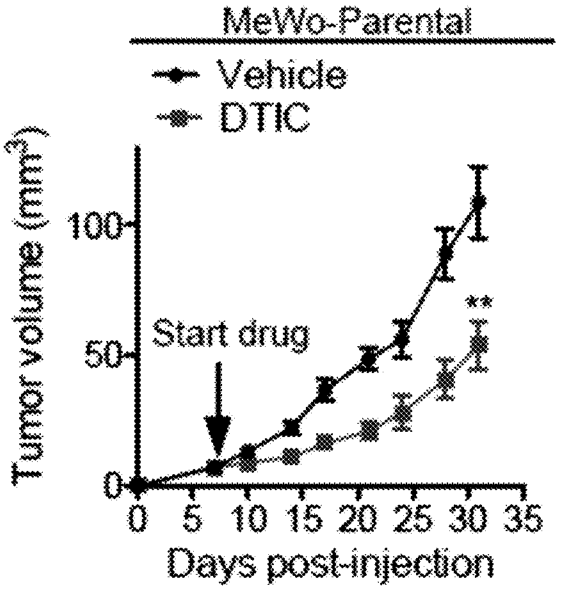
Figures 33A, 33B, 33C, 33D, 33E, 33F, 33G, 33H, 33I:
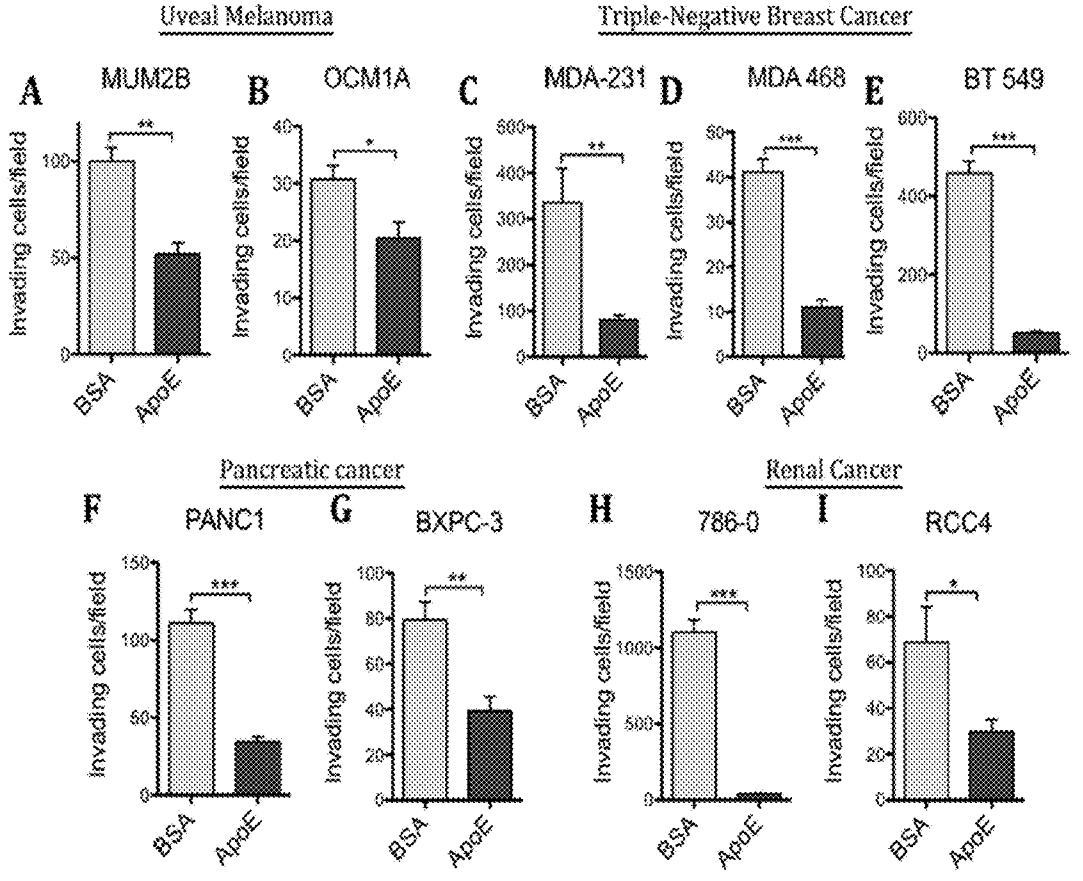

FIG. 32. Dacarbazine-Induced Suppression of Tumor Growth by Human Melanoma Cells. Tumor growth by 5×105 DTIC-sensitive MeWo parental cells subcutaneously injected into Nod SCID gamma mice. When tumors reached 5-10 mm3 volume, mice were treated with a control vehicle or DTIC (50 mg/kg, i.p., administered daily in 5-day cycles with 2-day off-treatment intervals), and tumor volume was measured twice a week. n=6.

FIGS. 33A, 33B, 33C, 33D, 33E, 33F, 33G, 33H and I. ApoE-mediated suppression of cell invasion across multiple cancer types. (33A-33B) 5×104 MUM2B and OCM1 human uveal melanoma cells, (33C-33E) 5×104 MDA-231, MDA-468, and BT 549 human triple-negative breast cancer cells, (33F-33G) 5×104 PANC1 and BXPC-3 human pancreatic cancer cells, and (33H-33I) 5×104 786-00 and RCC4 human renal cancer cells were tested for their ability to invade through matrigel-coated trans-well inserts in vitro. BSA or recombinant ApoE were added to the cell media at 100 μg/mL at the start of the assay. n=4. All data are represented as mean±SEM; *p<0.05, p<0.01, *p<0.001.

FIGS. 34A, 34B, 34C and 34D. Effects of LXR agonists LXR-623, WO-2007-002563 Ex. 19, WO-2010-0138598 Ex. 9, and SB742881 on ApoE expression in human melanoma cells. (34A-34D) MeWo human melanoma cells were treated with DMSO or the LXR agonists LXR-623 (34A), WO-2007-002563 (34B), WO-2010-0138598 (34C), or SB742881 (34D) at 500 nM, 1 μM, or 2 μM for 48 hours. The expression levels of ApoE were subsequently quantified by qRT-PCR. n=3. All data are represented as mean±SEM. *p<0.05, **p<0.01.

Figures 35A, 35B, 35C:
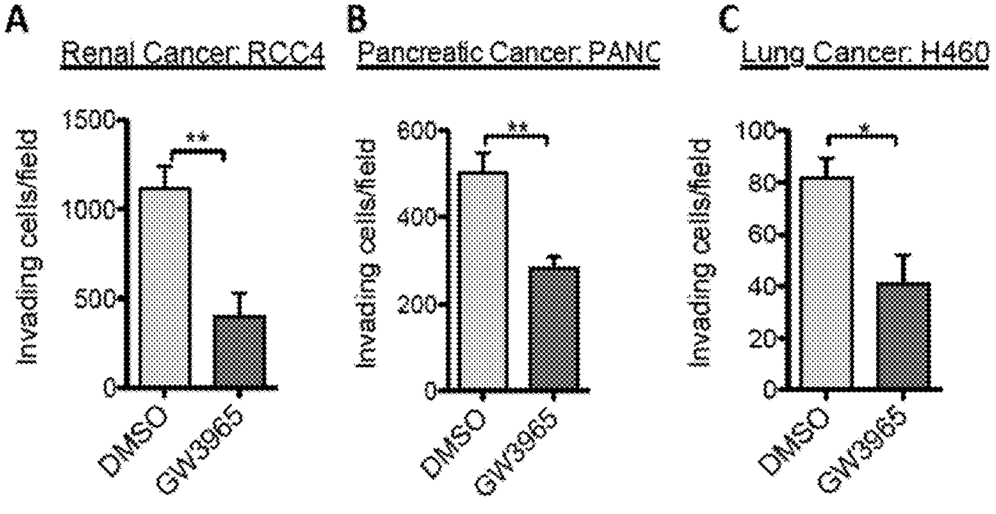

FIGS. 35A, 35B and 35C. Treatment with the LXR agonist GW3965 inhibits In Vitro tumor cell invasion of renal cancer, pancreatic cancer, and lung cancer. (35A, 35B, 35C) Trans-well matrigel invasion by 5×104 RCC human renal cancer cells (35A), 5×104 PANC1 human pancreatic cancer cells (35B), and 5×104 H460 human lung cancer cells (35C) that were treated with DMSO or GW3965 at 1 μM for 72 hours prior to the assay. n=4. All data are represented as mean±SEM. *p<0.05, **p<0.01.

Figure 36:
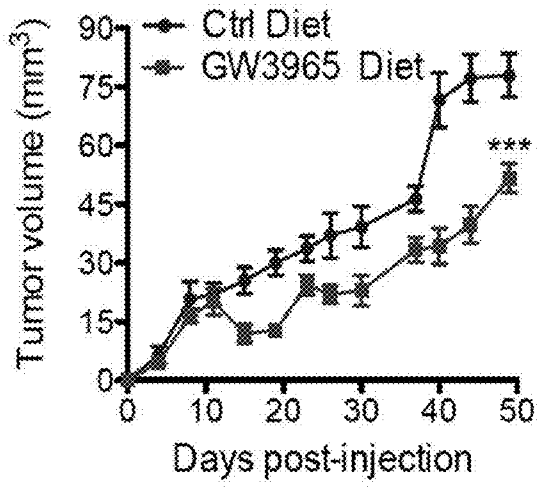

FIG. 36. Treatment with the LXR agonist GW3965 inhibits breast cancer tumor growth In Vivo. Primary tumor growth by 2×106 MDA-468 human breast cancer cells injected into the mammary fat pads of NOD Scid gamma mice. Two days prior to cancer cell injection, the mice were assigned to a control diet treatment or a diet supplemented with GW3965 (75 mg/kg) and maintained on the corresponding diet throughout the experiment. n=8. All data are represented as mean±SEM. ***p<0.001.

Figures 37A, 37B:
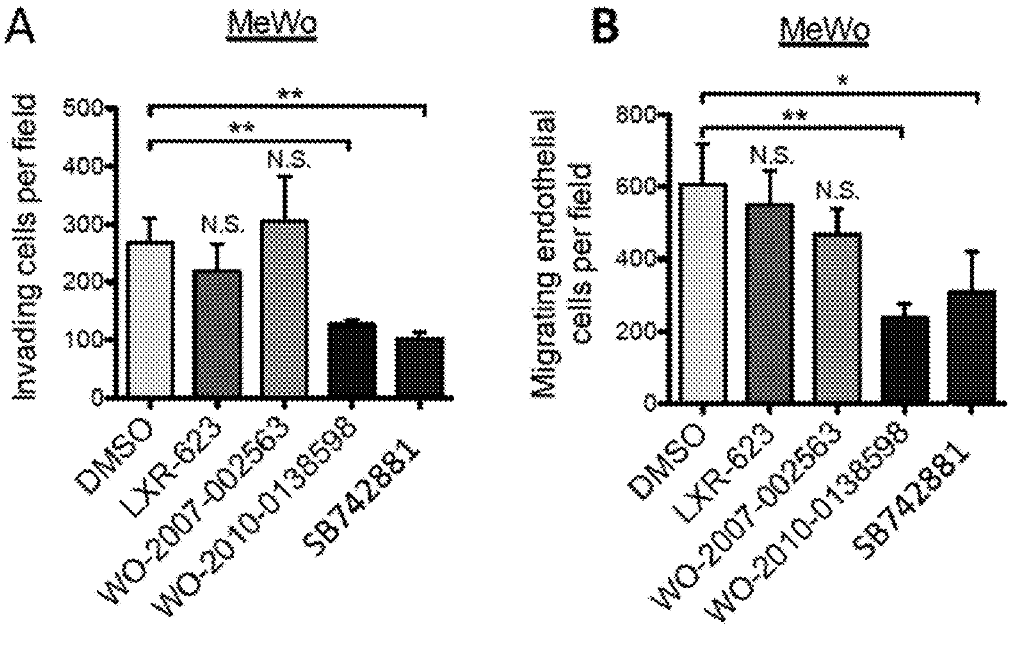
Figures 38A, 38B, 38C, 38D:
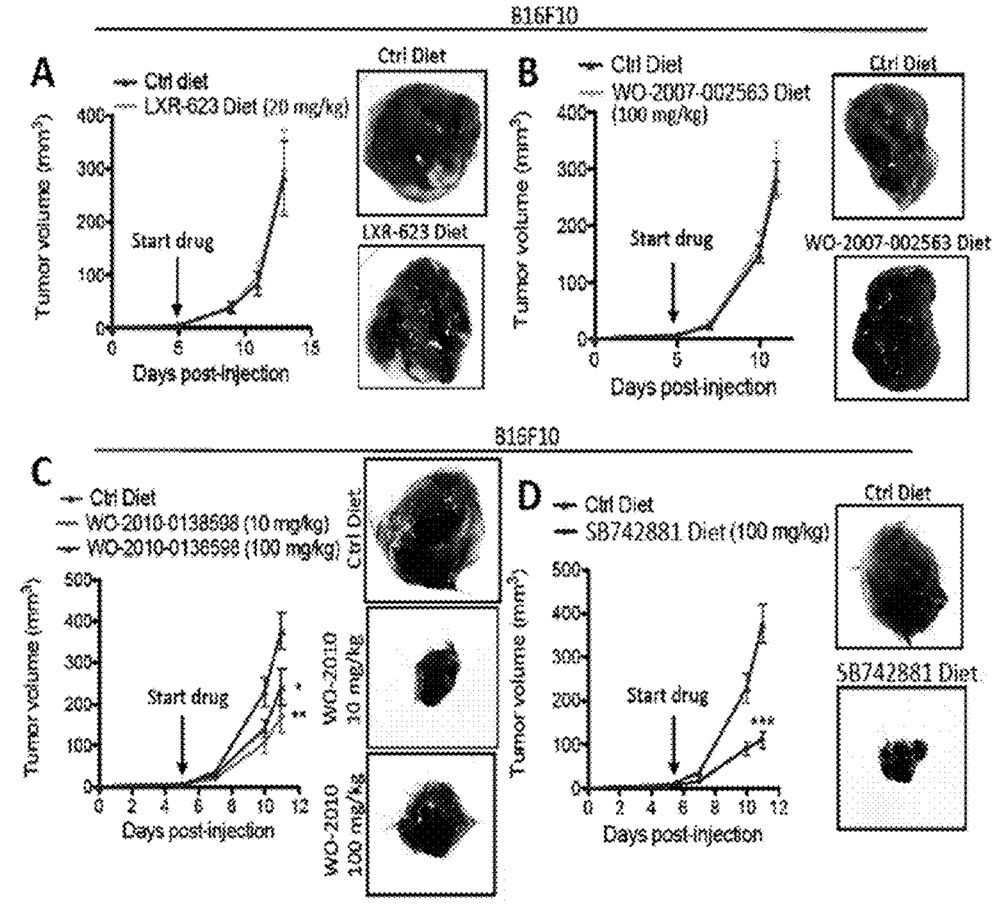

FIGS. 37A and 37B. Effects of LXR agonists LXR-623, WO-2007-002563 Ex. 19, WO-2010-0138598 Ex. 9, and SB742881 on in vitro melanoma progression phenotypes. (37A) Cell invasion by 1×105 MeWo human melanoma cells pre-treated with DMSO, LXR-623, WO-2007-002563 Ex. 19, WO-2010-0138598 Ex. 9, or SB742881 at 1 μM each for 72 hours. The number of cells invading into the basal side of matrigel-coated trans-well inserts was quantified. n=5. (37B) Endothelial recruitment by 5×104 MeWo cells pre-treated with DMSO, LXR-623, WO-2007-002563 Ex. 19, WO-2010-0138598 Ex.9, or SB742881 at 1 μM each for 72 hours. Cancer cells were seeded at the bottom of a 24-well plate. Endothelial cells were seeded in a trans-well insert fitted into each well and allowed to migrate towards the cancer cells. The number of endothelial cells migrating to the basal side of each trans-well insert was quantified. n=4-5. All data are represented as mean±SEM. *p<0.05, **p<0.01.

FIGS. 38A, 38B, 38C and 38D. Effects of LXR agonists LXR-623, WO-2007-002563 Ex. 19, WO-2010-0138598 Ex. 9, and SB742881 on in vivo tumor growth. (38A, 38B, 38C, 38D) Tumor growth by 5×104 B16F10 mouse melanoma cells subcutaneously injected into 7-week-old C57BL/6 mice. After tumors reached 5-10 mm3 in volume, the mice were randomly assigned to a control diet treatment, an LXR-623-supplemented diet treatment at 20 mg/kg/day (38A) a WO-2007-002563 Ex. 19-supplemented diet treatment at 100 mg/kg/day (38B), a WO-2010-0138598 Ex. 19-supplemented diet treatment at 10 mg/kg/day or 100 mg/kg/day (38C), or an SB742881-supplemented diet treatment at 100 mg/kg/day (38D). n=8-10. All data are represented as mean±SEM.

DETAILED DESCRIPTION OF THE INVENTION

The present invention features methods for preventing or reducing aberrant proliferation, differentiation, or survival of cells. For example, compounds of the invention may be useful in reducing the risk of, or preventing, tumors from increasing in size or from reaching a metastatic state. The subject compounds may be administered to halt the progression or advancement of cancer. In addition, the instant invention includes use of the subject compounds to reduce the risk of, or prevent, a recurrence of cancer.

Metastatic progression requires that sets of effector proteins involved in common cellular phenotypes be coherently expressed (Gupta and Massagué, 2006 Cell 127, 679-695; Hanahan and Weinberg, 2011 Cell 144, 646-674; Talmadge and Fidler, 2010 Cancer Res. 70, 5649-5669; Hynes, 2003 Cell 113, 821-823). Such concerted expression states are apparent in gene expression profiles of primary breast cancers that metastasize (Wang et al., 2005 Lancet 365, 671-679), as well as profiles of human cancer cell clones that display enhanced metastatic activity (Kang et al., 2003 Cancer Cell 3, 537-549; Minn et al., 2005 Nature 436, 518-524). In recent years, post-transcriptional regulation has emerged as a pervasive and robust mode of concerted expression-state and phenotype-level control. The most studied class of post-transcriptional regulators with metastatic regulatory activity are small non-coding RNAs (miRNAs) (Bartel, 2009 Cell 136, 215-233; Fabian et al., 2010 Annu. Rev. Biochem, 79, 351-379; Filipowicz et al., 2008 Nat. Rev. Genet. 9, 102-114). Metastasis promoter miRNAs (Ma et al., 2007 Nature 449, 682-688; Huang et al., 2008 Nat. Cell Biol. 10, 202-210) and suppressor miRNAs (Tavazoie et al., 2008 Nature 451, 147-152) were originally discovered in breast cancer. Subsequent studies revealed many more miRNAs with regulatory roles in the tumorigenesis and metastasis of other cancer types (Hatziapostolou et al., 2011 Cell 147, 1233-1247; Hurst et al., 2009 Cancer Res. 69, 7495-7498; Olson et al., 2009 Genes Dev. 23, 2152-2165; Zhang et al., 2010 Oncogene 29, 937-948) In many cases, the expression levels of these miRNAs in human cancer samples have supported their experimental roles in metastasis. Thus, deregulated miRNA expression (Garzon et al., 2010 Nat. Rev. Drug Discov. 9, 775-789; Lujambio and Lowe, 2012 Nature 482, 347-355) and, more recently, deregulated expression of long non-coding RNAs (Calin et al., 2007 Nat. Rev. Cancer 6, 857-866; Gupta et al., 2010 Nature 464, 1071-1076; Guttman et al., 2009 Nature 458, 223-227; Huarte et al., 2010.Cell 142, 409-419; Loewer et al., 2010 Nat. Genet. 42, 1113-1117) as well as non-coding pseudogenes competing for endogenous miRNA binding (Poliseno et al., 2010 Nature 465, 1033-1038) appear to be pervasive features of human cancer. Clues regarding the robust control exerted by specific miRNAs on metastatic progression came from early work showing that concerted targeting of multiple metastasis genes by a single metastasis suppressor miRNA was responsible for the dramatic metastasis suppression effects (Tavazoie et al., 2008 Nature 451, 147-152). Such divergent gene targeting by miRNAs has appeared to be a defining feature of these regulators.

At a conceptual level, the need for divergent regulation of gene expression in cancer is readily understood. A miRNA could exert robust metastatic suppression by virtue of its ability to target multiple genes required for metastasis. The miRNA's silencing through genetic or epigenetic mechanisms would readily promote cancer progression by derepressing multiple promoters of metastasis (Png et al., 2011 Nature 481, 190-194). A role for convergent regulation of a single gene by multiple metastasis regulatory miRNAs is more nuanced. This scenario would emerge if there existed a key gene that acted as a robust suppressor of metastatic progression. Convergent and cooperative targeting of this gene by multiple miRNAs could achieve maximal silencing of such a key metastasis suppressor gene. This scenario, as opposed to genetic deletion, may be seen in cases where complete loss of a target gene could not be tolerated by the cell, and the gene would be required at low levels to mediate metabolic actions, for example. Given this possibility, a search for cooperative metastasis promoter miRNAs may uncover novel genes that are pivotal for metastasis suppression and may provide therapeutic insights into more effective treatments for metastasis prevention.

As disclosed herein, via a systematic, in vivo selection-based approach, a set of miRNAs were identified to be deregulated in multiple independent metastatic lines derived from multiple patients with melanoma—a highly prevalent cancer with increasing incidence (Garbe and Leiter, 2009 Clin. Dermatol. 27, 3-9). As disclosed herein, miR-1908, miR-199a-3p, and miR-199a-5p act as robust endogenous promoters of melanoma metastasis through convergent targeting of the metabolic gene ApoE and the heat-shock protein DNAJA4. Through loss-of-function, gain-of-function, and epistatic analyses, a cooperative miRNA network that maximally silences ApoE signaling is delineated. Cancer cell-secreted ApoE inhibits metastatic invasion and endothelial recruitment, which is mediated through its actions on distinct receptors on melanoma and endothelial cells. These miRNAs display significant prognostic capacity in identifying patients that develop melanoma metastatic relapse, while therapeutic delivery of LNAs targeting these miRNAs significantly inhibits melanoma metastasis. The current lack of effective therapies for the prevention of melanoma metastasis after surgical resection (Garbe et al., 2011 Oncologist 16, 5-24) requires an improved molecular and mechanistic understanding of melanoma metastatic progression. To this end, the findings disclosed herein reveal a number of key novel non-coding and coding genes involved in melanoma progression and offer a novel avenue for both identifying patients at high-risk for melanoma metastasis and treating them.

Listed below are the nucleic acid and amino acid sequences of the members of the above-mentioned network and a number of other sequences.

APOE - RNA sequence (SEQ ID NO: 1)

gggatccttgagtcctactcagccccagcggaggtgaaggacgtccttccccaggagccgactggccaatcacaggcaggaagatgaag gttctgtgggctgcgttgctggtcacattcctggcaggatgccaggccaaggtggagcaagcggtggagacagagccggagcccgagct gcgccagcagaccgagtggcagagcggccagcgctgggaactggcactgggtcgcttttgggattacctgcgctgggtgcagacactgt ctgagcaggtgcaggaggagctgctcagctcccaggtcacccaggaactgagggcgctgatggacgagaccatgaaggagttgaaggc ctacaaatcggaactggaggaacaactgaccccggtggcggaggagacgcgggcacggctgtccaaggagctgcaggcggcgcagg cccggctgggcgcggacatggaggacgtgtgeggccgcctggtgcagtaccgcggcgaggtgcaggccatgctcggccagagcacc gaggagctgcgggtgcgcctcgcctcccacctgcgcaagctgcgtaagcggctcctccgcgatgccgatgacctgcagaagcgcctgg cagtgtaccaggccggggcccgcgagggcgccgagcgcggcctcagcgccatccgcgagcgcctggggcccctggtggaacaggg ccgcgtgcgggccgccactgtgggctccctggccggccagccgctacaggagcgggcccaggcctggggcgagcggctgcgcgcgc ggatggaggagatgggcagccggacccgcgaccgcctggacgaggtgaaggagcaggtggcggaggtgcgcgccaagctggagga gcaggcccagcagatacgcctgcaggccgaggccttccaggcccgcctcaagagctggttcgagcccctggtggaagacatgcagcgc cagtgggccgggctggtggagaaggtgcaggctgccgtgggcaccagcgccgcccctgtgcccagcgacaatcactgaacgccgaag cctgcagccatgcgaccccacgccaccccgtgcctcctgcctccgcgcagcctgcagcgggagaccctgtccccgccccagccgtcctc ctggggtggaccctagtttaataaagattcaccaagtttcacgcaaaaaaaaaaaaaaaaaaaaaaaaaaaaaaaaaaaaaaaaa APOE - Amino acid sequence (SEQ ID NO: 2)

mkvlwaallv tflagcqakv eqavetepep elrqqtewqs gqrwelalgr fwdylrwvqt lseqvqeell ssqvtqelra lmdetmkelk aykseleeql tpvaeetrar lskelqaaqa rlgadmedvc grlvqyrgev qamlgqstee lrvrlashlr klrkrllrda ddlqkrlavy qagaregaer glsairerlg plveqgrvra atvgslagqp lqeraqawge rlrarmeemg srtrdrldev keqvaevrak leeqaqqirl qaeafqarlk swfeplvedm qrqwaglvek vqaavgtsaa pvpsdnh
(Underlined residues 136-150 represent the LRP-binding domain of Apo E)

DNAJA4 isoform 1 - RNA sequence (SEQ ID NO: 3)

agucccacccuucggcgcagggcuccggccaacacagcccuccaggccgccuacucuccagccagccggcuccacggacccacg gaagggcaagggggcggccucggggcggcgggacaguugucggagggcgcccuccaggcccaagccgccuucuccggccccc gccauggcccggggcggcagucagagcuggagcuccggggaaucagacgggcagccaaaggagcagacgcccgagaagcccag acacaagaugguguaaggagacccaguacuaugacauccugggcgugaagcccagcgcguccccggaggagaucaagaaggccu aucggaagcuggcgcucaaguaccacccggacaagaacccggaugagggcgagaaguuuaaacucauaucccaggcauaugaa gugcuuucagauccaaagaaaagggauguuuaugaccaaggcggagagcaggcaauuaaagaaggaggcucaggcagcccca gcuucucuucacccauggacaucuuugacauguucuuuggugguggggacggauggcuagagagagaagaggcaagaaug uuguacaccaguuaucuguaacucuugaagaucuauauaauggagucacgaagaaauuggcccuccagaaaaauguaauuug ugagaaaugugaagguguuggugggaagaagggaucgguggagaagugcccgcugugcaaggggcgggggaugcagaucca cauccagcagaucgggccgggcaugguacagcagauccagaccgugugcaucgagugcaagggccagggugagcgcaucaac cccaaggaccgcugcgagagcugcagcggggccaaggugauccgugagaagaagauuaucgagguacauguugaaaaaggua ugaaagaugggcaaaagauacuauuucauggagaaggagaucaggagccugagcuggagccuggugaugucauaauugugcu ugaucagaaggaucauagugucuuucagagacgaggccaugacuugaucaugaaaaugaaaauucagcuuucugaagcucuu uguggcuucaagaagacgauaaaaacauuggacaaucgaauucuuguuauuacauccaaagcaggugaggugauaaagcacg gggaccugagaugcgugcgcgaugaaggaaugcccaucuacaaagcaccccuggaaaaagggauucugaucauacaguuuuu aguaaucuuuccugaaaaacacuggcuuucucuggaaaagcuucccucagcuggaagcuuuacucccuccucgacagaaaguga ggauuacagaugacauggaucagguggagcugaaggaguuugucccaaugagcagaacuggcgucagcacagggaggccua -continued cgaggaggacgaagacgggccccaggcuggagugcagugccagacggcaugacguggugcggggcagcguggccccaccgga
cuagcacaugaugaauguaaaguuggcacaaugaaaaugacaucgcuuuaaauggccuuguguuugggauguccuguguaug
uguucagcauucuuaauugcugagugucuuuuuggcuuuucuuuugguuguaacuuaaguuauagcuuaaauuuauauuua
aauguuuuaaguauaaaucaccucuagucugcauauggaaucuguucauuucuauuuucaggauauacuuuugagauguca
gugauugcaccaauacuuugugcuucuaguggcuuugccauaaauucagugucaccaauaaggcacagcccaguuagcagcuu
agccccccuagcaaaccccaaggcacaaagugggcauccugacucaucucuaggucugugguuucuccccucuucccuuggca
gaguuauugagggcaugaucucagggcugcuaagauaacauuucugaggauucuagaugauccucuuaaagaauaaaagcac
auccguggaucggacauggcugcaugugccugcuuaacagggccaacuuaguuccuacuguucugugcccuucaguggaug
gaacgugagugucugaucaucucucuuggaaguuuucugaaccuuccaagcucugugguga ggacaaaccaguguuugaauc
auaugcugauaacuguuugccugugacccucacaccuuguucuucaggguuuuaaugauuuucuguugacaacuuuugcaa
ugcuuucccaccaaagugcuuacuuguaaagaaaacuaaauccuucugugucccggcagccucagugcagcaacagaagcca
agggagaaugcugcugguuuggcccauggcacagccagcuucucugaccaguaauccggggugacuugagggucugcaaagg
cauagaacuccccaguguuuccaccucauucucccagauugagcucccuuccaaaggaucguucccucucauugcacagccau
auuacaaaggguuuccugcucaagugauguuuugguaagaacuucgcugaguuccacuguggauuacaguuuguauggacu
acuacuguaaaauuauagcuuguuuggagggauauuagucauuauuuuauucaugacagguagacuacaauucgaacuuagg
guuaccucagucuuuagccauuacugcuuauuucuuuuccccaagucacaaaaaacuuguaagcugcuggguuaaagcagag
gccaccugucagaucuacccuacccuuauuugguuacauggcaccugagaguuucacucagaccagggaucuuccuuaggag
ggucaaagugcagaucagaccaugcagguaaggugaaccagcugcacggaccagguucccgcaaaacauugccagcuagugag
gcauaauuugcucaaaguauagaaacagcccaccugugcccacuuugaccauuggugaggauagauauaaaaucacuucuucc
aacgaagccuaggugaaaaucuauuuauaaauggaccacaacucuggggugucguuuuugugcugugacuuccuaauuauug
cuaaagaacuacuguuuaguugguaaugguguaaaauuacauucagcucccuucuugucauauaaaaggaauuuggagggug
ucgcuuaaaaauuuuauuccaccuguacauuugucacuuuaaaauuaaaauugagcugguaugagagauaaaaaaaaaaaaaa
aaaa DNAJA4 isoform 1 - Amino acid sequence (SEQ ID NO: 4)

marggsqsws sgesdgqpke qtpekprhkm vketqyydil gvkpsaspee ikkayrklal kyhpdknpde gekfldisqa
yevlsdpkkr dvydqggeqa ikeggsgsps fsspmdifdm ffggggrmar errgknvvhq lsvtledlyn gvtkklalqk
nvicekcegv ggkkgsvekc plckgrgmqi hiqqigpgmv qqiqtvciec kgqgerinpk drcescsgak virekkiiev
hvekgmkdgq kilfhgegdq epelepgdvi ivldqkdhsv fqrrghdlim kmkiqlseal cgfkktiktl dnrilvitsk
agevikhgdl revrdegmpi ykaplekgil iiqflvifpe khwlsleklp qleallpprq kvritddmdq velkefcpne
qnwrqhreay eededgpqag vqcqta DNAJA4 isoform 2 - RNA sequence (SEQ ID NO: 5)

gugaccgugacgcgcgagcgggcggcgggggcgcgggccaggggcgcgggccagggugccggcaggggcguccggggcgcu
cugaccggccucgcccgcccccccgcagacacaagaugguga aggagacccaguacuaugacauccugggcgugaagcccag
cgcguccccggaggagaucaagaaggccuaucggaagcuggcgcucaaguaccacccggacaagaacccggaugagggcgaga
aguuuaaacucauaucccaggcauaugaagugcuuucagauccaaagaaaaagggauguuuaugaccaaggcggagagcaggc
aauuaaagaaggaggcucaggcagccccagcuucucuucacccauggacaucuuugacauguucuuugguggugguggacgg
auggcuagagagagaagaggcaagaauguuguacaccaguuaucuguaacucuugaagaucuauauaaauggagucacgaaga
aauuggcccuccagaaaaauguaauuugugagaaaugugaagguguugguggga agaagggaucgguggagaagugcccgc
ugugcaaggggcgggggaugcagauccacauccagcagaucgggccgggcaugguacagcagauccagaccgugugcaucga -continued gugcaagggccagggugagcgcaucaaccccaaggaccgcugcgagagcugcagcggggccaagguga uccgugagaagaag auuaucgagguacauguugaaaaagguaugaaagaugggcaaaagauacuauuucauggagaaggagaucaggagccugagc uggagccuggugaugucauaauugugcuugaucagaaggaucauagugucuuucagagacgaggccaugacuugaucauga aaaugaaaauucagcuuucugaagcucuuuguggcuucaagaagacgauaaaaaacauuggacaaucgaauucuuguuauuac auccaaagcaggugaggugauaaagcacggggaccugagaugcgugcgcgaugaaggaaugcccaucuacaaagcaccccugg aaaaagggauucugaucauacaguuuuuaguaaucuuuccugaaaaacacuggcuuucucuggaaaagcuucccucagcugga agcuuuacucccuccucgacagaaagugaggauuacagaugacauggaucagguggagcugaaggaguuuugucccaaugag cagaacuggcgucagcacagggaggccuacgaggaggacgaagacgggccccaggcuggagugcagugccagacggcaugac guggugcggggcagcguggccccaccggacuagcacaugaugaauguaaaguuggcacaaugaaaaugacaucgcuuuaaug gccuuguguuugggauguccuguguauguguucagcauucuuaauugcugagugucuuuuuggcuuuucuuuugguugua acuuaaguuauagcuuaauuuauauuuaaauguuuuaaguauaaaucaccucuagucugcauauggaaucuguucauuucua uuuucaggauauacuuuugagaugucagugauugcaccaauacuuugugcuucuaguggcuuugccauaauucagugucac caauaaggcacagcccaguuagcagcuuagcccccuagcaaaccccaaggcacaaagugggcauccugacucaucucuaggu cugugguuucuccccucuucccuuggcagaguuauugagggcaugaucucagggcugcuaagauaacauuucugaggauuc uagaugauccucuuaaagaauaaaagcacauccguggaucggacauggcugcaugugccugcuuaacagggccaacuuaguu ccuacuguucugugcccuucaguggauggaacgugagugucugaucaucucucuuggaaguuuucugaaccuuccaagcuc ugguggugaggacaaaccaguguuugaaucauaugcugauaacuguuugccugugacccucacaccuuguucuucaggguuu uaaugauuuucuguugacaacuuuugcaaugcuuucccaccaaagugcuuacuuguaaagaaaacuaaauccuucugugucc ccggcagccucagugcagcaacagaagccaagggagaaugcugcugguuuggcccauggcacagccagcuucucugaccagua auccggggugacuugagggucugcaaaggcauagaacuccccaguguuuccaccucauucucccagauugagcuccccuucc aaaggaucguucccucucauugcacagccauauuacaaaggguuuccugcucaagugauguuuugguaagaacuucgcugagu uccacuguggauuacaguuuguauggacuacuacuguaaauuauagcuuguuuggagggauauuagucauuauuuuauuca ugacagguagacuacaauucgaacuuaggguuaccucagucuuuagccauuacugcuuauuucuuuuccccaagucacaaaa aacuuguaagcugcuggguuaaagcagaggccaccugucagaucuacccuacccuuauuugguuacauggcaccugagaguu ucacucagaccagggaucuucccuuaggagggucaaagugcagaucagaccaugcagguaaggugaaccagcugcacggaccag guucccgcaaaacauugccagcuagugaggcauaauuugcucaaaguauagaaacagcccaccugugcccacuuugaccauug gugaggauagauauaaaaucacuucuuccaacgaagccuaggugaaaaucuauuuauaaaggaccacaacucugggguguc guuuuugugcugugacuuccuaauuauugcuaaagaacuacuguuuaguugguaauggugu aaaaauuacauucagcuccuu cuugucauauaaaaggaauuuggagggugucgcuuaaaaauuuuauuccaccuguacauuugucacuuuaaaauuaaaauuga gcugguaugagagauaaaaaaaaaaaaaaaaaa DNAJA4 isoform 2 - Amino acid sequence (SEQ ID NO: 6)

mvketqyydi lgvkpsaspe eikkayrkla lkyhpdknpd egekfklisq ayevlsdpkk rdvydqggeq aikeggsgsp sfsspmdifd mffggggrma rerrgknvvh qlsvtledly ngvtkkklalq knvicekceg vggkkgsvek cplckgrgmq ihiqqigpgm vqqiqtvcie ckgqgerinp kdrcescsga kvirekkiie vhvekgmkdg qkilfhgegd qepelepgdv iivldqkdhs vfqrrghdli mkmkiqlsea lcgfkktikt ldnrilvits kagevikhgd lrcvrdegmp iykaplekgi liiqflvifp ekhwlslekl pqleallppr qkvritddmd qvelkefcpn eqnwrqhrea yeededgpqa gvqcqta DNAJA4 isoform 3 - RNA sequence (SEQ ID NO: 7)

acauuucagcaagcuggcuaaagacaugugggaaagccugacccuggauucaggucaaaucucagcacucacaagauuuaaac ucauaucccaggcauaugaagugcuuucagauccaaagaaaagggauguuuaugaccaaggcggagagcaggcaauuaaagaa ggaggcucaggcagccccagcuucucuucacccauggacaucuuugacauguucuuugguggugguggacggauggcuaga gagagaagaggcaagaauguuguacaccaguuaucuguaacucuugaagaucuauauaauggagucacgaagaaauuggccc -continued uccagaaaaauguaauuugugagaaaugugaagguguuggugggaagaagggaucgguggagaagugcccgcugugcaagg ggcgggggaugcagauccacauccagcagaucgggccgggcaugguacagcagauccagaccgugugcaucgagugcaaggg ccagggugagcgcaucaaccccaaggaccgcugcgagagcugcagcggggccaaggugauccgugagaagaagauuaucgag guacauguugaaaaagguaugaaagaugggcaaaagauacuauuucauggagaaggagaucaggagccugagcuggagccug gugaugucauaauugugcuugaucagaaggaucauagugucuuucagagacgaggccaugacuugaucaugaaaaugaaaau ucagcuuucugaagcucuuuguggcuucaagaagacgauaaaaacauuggacaaucgaauucuuguuauuacauccaaagca ggugaggugauaaagcacggggaccugagaugcgugcgcgaugaaggaaugcccaucuacaaagcaccccuggaaaaaggga uucugaucauacaguuuuuaguaaucuuuccugaaaaacacuggcuuucucuggaaaagcuuccucagcuggaagcuuuacu cccuccucgacagaaagugaggauuacagaugacauggaucagguggagcugaaggaguuuugucccaaugagcagaacugg cgucagcacagggaggccuacgaggaggacgaagacgggccccaggcuggagugcagugccagacggcaugacgugggugcgg ggcagcguggccccaccggacuagcacaugaugaauguaaaguuggcacaaugaaaaugacaucgcuuuaauggccuugugu uugggauguccuguguauguguucagcauucuuaauugcugagugucuuuuuggcuuuucuuuugguuguaacuuaaguu auagcuuaauuuauauuuaaauguuuuaaguauaaaucaccucuagucugcauauggaaucuguucauuucuauuuucagga uauacuuuugagaugucagugauugcaccaauacuuugugcuucuaguggcuuugccauaauucagugucaccaauaaggca cagcccaguuagcagcuuagccccccuagcaaaccccaaggcacaaagugggcauccugacucaucucuaggucugugguuuc uccccucuucccuuggcagaguuauugagggcaugaucucagggcugcuaagauaacauuucugaggauucuagaugauccu cuuaaagaauaaaaagcacauccguggaucggacauggcugcaugugccugcuuaacagggccaacuuaguuccuacuguucu gugcccuucaguggauggaacgugagugucugaucaucucucuuggaaguuuucugaaccuuccaagcucugugggugagga caaaccaguguuugaaucauaugcugauaacuguuugccugugacccucacaccuuguucuucaggguuuuaaugauuuucu guugacaacuuuugcaaugcuuucccaccaaagugcuuacuuguaaagaaaacuaaauccuucugugucccccggcagccucag ugcagcaacagaagccaagggagaaugcugcugguuuggcccauggcacagccagcuucucugaccaguaauccggggugac uugagggucugcaaaggcauagaacuccccaguguuuuccaccucauucucccagauugagcucccuuccaaaggaucguuc cucucauugcacagccauauuacaaaggguuuccugcucaagugauguuuugguaagaacuucgcugaguucccacuguggau uacaguuuguauggacuacuacuguaaauuauagcuuguuuggagggauauuagucauuauuuuauucaugacagguagac uacaauucgaacuuaggguuaccucagucuuuagccauuacugcuuauuucuuuccccaagucacaaaaaacuuguaagcu gcuggguuaaagcagaggccaccugucagaucuacccuacccuuauuugguuacauggcaccugagaguuucacucagacca gggaucuucccuuaggagggucaaagugcagaucagaccaugcagguaaggugaaccagcugcacggaccagguucccgcaaa acauugccagcuagugaggcauaauuugcucaaaguauagaaacagcccaccugugcccacuuugaccauuggugaggauag auauaaaaucacuucuuccaacgaagccuaggugaaaaucuauuuauaaauggaccacaacucuggggugucguuuuugugc ugugacuuccuaauuauugcuaaagaacuacuguuuaguugguaaugguguaaaauuacauucagcuccuucuugucauaua aaaggaauuuggagggugucgcuuaaaaauuuuauuccaccuguacauuugucacuuuaaaauuaaaauugagcugguaugag agauaaaaaaaaaaaaaaaaaaa DNAJA4 isoform 3 - Amino acid sequence (SEQ ID NO: 8)

mwesltldsg qisaltrfkl isqayevlsd pkkrdvydqg geqaikeggs gspsfsspmd ifdmffgggg rmarerrgkn vvhqlsvtle dlyngvtkkl alqknvicek cegvggkkgs vekcplckgr gmqihiqqig pgmvqqiqtv cieckgqger inpkdrcesc sgakvirekk iievhvekgm kdgqkilfhg egdqepelep gdviivldqk dhsvfqrrgh dlimkmkiql sealcgfkkt iktldnrilv itskagevik hgdlrcvrde gmpiykaple kgiliiqflv ifpekhwlsl eklpqleall pprqkvritd dmdqvelkef cpneqnwrqh reayeededg pqagvqcqta -continued LRP1 - RNA sequence (SEQ ID NO: 9)

cagcggugcgagcuccaggcccaugcacugaggaggcggaaacaaggggagcccccagagcuccaucaagccccccuccaaagg cucccccuacccgguccacgcccccccacccccccucccccgccuccucccaauugugcauuuuugcagccggaggcggcuccgag auggggcugugagcuucgcccggggagggggaaagagcagcgaggagugaagcgggggggugggggugaaggguuuggauu ucggggcagggggcgcacccccgucagcaggcccuccccaaggggcucggaacucuaccucuucacccacgccccuggugcgc uuugccgaaggaaagaauaagaacagagaaggaggagggggaaaggaggaaaagggggacccccaacugggggggugaag gagagaaguagcaggaccagaggggaaggggcugcugcuugcaucagcccacaccaugcugaccccgccguugcuccugcug cugccccugcucucagcucuggucgcggcggcuaucgacgccccuaagacuugcagccccaagcaguuugccugcagagauca aauaaccuguaucucaaagggcuggcggugcgacggugagagggacugcccagacggaucugacgaggccccugagauuugu ccacagaguaaggcccagcgaugccagccaaacgagcauaacugccugggguacugagcuguguguucccaugucccgccucug caauggggguccaggacugcauggacggcucagaugaggggccccacugccgagagcuccaaggcaacugcucucgccugggc ugccagcaccauuguguccccacacucgaugggcccaccugcuacugcaacagcagcuuucagcuucaggcagauggcaagac cugcaaagauuuugaugagugcucaguguacggcaccugcagccagcuaugcaccaacacagacggcuccuucauauguggc uguguugaaggauaccuccugcagccggauaaccgcuccugcaaggccaagaacgagccaguagaccggccccccugugcugu ugauagccaacucccagaacaucuuggccacguaccugaguggggcccaggugucuaccaucacaccuacgagcacgcggcag accacagccauggacuucagcuaugccaacgagaccguaugcuggggugcauguuggggacagugcugcucagacgcagcuca agugugcccgcaugccuggccuaaagggcuucguggaugagcacaccaucaacaucucccucagucugcaccacguggaacag auggccaucgacuggcugacaggcaacuucuacuuuguggaugacaucgaugauaggaucuuugucugcaacagaaauggggg acacaugugucacauugcuagaccuggaacucuacaaccccaagggcauugcccuggacccugccauggggaagguguuuuu cacugacuaugggcagaucccaaagguggaacgcugugacauggaugggcagaaccgcaccaagcucgucgacagcaagauug uguuuccucauggcaucacgcuggaccuggucagccgccuugucuacugggcagaugccuaucuggacuauauugaagugg uggacuaugagggcaagggccgccagaccaucauccagggcauccugauugagcaccuguacggccugacuguguuugagaa uuaucucuaugccaccaacucggacaaugccaaugcccagcagaagacgagugugauccgugugaaccgcuuuaacagcaccg aguaccagguugucacccggguggacaaggguggugcccuccacaucuaccaccagaggcgucagccccgagugaggagcca ugccugugaaaacgaccaguaugggaagccggguggcugcucugacaucugccugcuggccaacagccacaaggcgcggacc ugccgcugccguuccggcuucagccugggcagugacgggaagucaugcaagaagccggagcaugagcuguuccucguguaug gcaagggccggccaggcaucauccggggcauggauaugggggccaaggucccggaugagcacaugauccccauugaaaaccu caugaacccccgagcccuggacuuccacgcugagaccggcuucaucuacuuugccgacaccaccagcuaccucauuggccgcc agaagauugauggcacugagcgggagaccauccugaaggacggcauccacaauguggaggguguggccguggacuggaugg gagacaaucuguacuggacggacgaugggcccaaaaagacaaucagcguggccaggcuggagaaagcugcucagacccgcaag acuuuaaucgagggcaaaaugacacaccccagggcuauugugguggauccacucaaugggugguguacuggacagacuggg aggaggaccccaaggacagucggcgugggcggcuggagagggcguggauggauggcucacaccgagacaucuuugucaccuc caagacagugcuuuggcccaaugggcuaagccuggacaucccggcugggcgccucuacuggguggaugccuucuacgaccgc aucgagacgauacugcucaauggcacagaccggaagauuguguaugaagguccugagcugaaccacgccuuuggccuguguc accauggcaacuaccucuucuggacugaguaucggaguggcagugucuaccgcuuggaacgggguguaggaggcgcaccccc cacugugacccuucugcgcagugagcggcccccccaucuuugagauccgaauguaugaugcccagcagcagcaaguuggcacca acaaaugccgggugaacaauggcggcugcagcagccugugcuuggccaccccugggagccgccagugcgccugugcugagga ccagguguuggacgcagacggcgucacuugcuuggcgaacccauccuacgugccuccaccccagugccagccaggcgaguuu gccugugccaacagccgcugcauccaggagcgcuggaagugugacggagacaacgauugccuggacaacagugaugaggccc cagcccucugccaucagcacaccugccccucggaccgauucaagugcgagaacaaccggugcauccccaaccgcuggcucugc gacggggacaaugacugugggaacagugaagaugaguccaaugccacuuguucagcccgcaccugcccccccaaccaguucuc -continued cugugccaguggccgcugcauccccaucuccuggacgugugaucuggaugacgacuguggggaccgcucugaugagucugc uucgugugccuaucccaccugcuucccccugacucaguuuaccugcaacaauggcagauguaucaacaucaacuggagaugcg acaaugacaaugacuguggggacaacagugacgaagccggcugcagccacuccuguucuagcacccaguucaagugcaacagc gggcguugcauccccgagcacuggaccugcgauggggacaaugacugcggagacuacagugaugagacacacgccaacugcac caaccaggccacgaggcccccugguggcugccacacugaugaguuccagugccggcuggauggacuaugcaucccccugcgg uggcgcugcgauggggacacugacugcauggacuccagcgaugagaagagcugugagggagugacccacgucugcgauccca gugucaaguuuggcugcaaggacucagcucggugcaucagcaaagcguggguguguggauggcgacaaugacugugaggaua acucggacgaggagaacugcgagucccuggccugcaggccacccucgcacccuugugccaacaacaccucagucugccugccc ccugacaagcugugugauggcaacgacgacuguggcgacggcucagaugagggcgagcucugcgaccagugcucucugaaua acgguggcugcagccacaacugcucaguggcaccuggcgaaggcauuguguguuccugcccucugggcauggagcuggggcc cgacaaccacaccugccagauccagagcuacugugccaagcaucucaaaugcagccaaaagugcgaccagaacaaguucagcgu gaagugcuccugcuacgagggcuggguccuggaaccugacggcgagagcugccgcagccuggaccccuucaagccguucauc auuuucuccaaccgccaugaaauccggcgcaucgaucuucacaaaggagacuacagcguccuggugcccggccugcgcaacac caucgcccuggacuuccaccucagccagagcgcccucuacuggaccgacgugguggaggacaagaucuaccgcgggaagcugc uggacaacggagcccugacuaguuucgagguggugauucaguauggccuggccacacccgagggccuggcuguagacuggau ugcaggcaacaucuacuggguggagaguaaccuggaucagaucgagguggccaagcuggaugggacccuccggaccacccug cuggccggugacauugagcacccaagggcaaucgcacuggauccccgggaugggauccuguuuuggacagacugggaugcca gccugccccgcauugaggcagccuccaugaguggggcugggcgccgcaccgugcaccgggagaccggcucugggggcuggcc caacgggcucaccguggacuaccuggagaagcgcauccuuuggauugacgccaggucagaugccauuuacucagcccguuac gacggcucuggccacauggaggugcuucggggacacgaguuccugucgcacccguuugcagugacgcuguacggggggggag gucuacuggacugacuggcgaacaaacacacuggcuaaggccaacaaguggaccggccacaaugucaccgugguacagaggac caacacccagcccuuugaccugcagguguaccaccccucccgccagcccauggcucccaaucccugugaggccaauggggggcc agggccccugcucccaccugugucucaucaacuacaaccggaccguguccugcgccugcccccaccucaugaagcuccacaag gacaacaccaccugcuaugaguuuaagaaguuccugcuguacgcacgucagauggagauccgaggugugggaccuggaugcuc ccuacuacaacuacaucaucuccuucacggugcccgacaucgacaacgucacagugcuagacuacgaugcccgcgagcagcgu guguacuggucugacgugcggacacaggccaucaagcgggccuucaucaacggcacaggcguggagacagucgucucugcag acuugccaaaugcccacgggcuggcuguggacugggucucccgaaaccuguucuggacaagcuaugacaccaauaagaagcag aucaauguggcccggcuggauggcuccuucaagaacgcaguggugcagggccuggagcagccccauggccuugucguccacc cucugcgugggaagcucuacuggaccgauggugacaacaucagcauggccaacauggauggcagcaaucgcacccugcucuu caguggccagaagggccccgugggccuggcuauugacuucccugaaagcaaacucuacuggaucagcuccgggaaccauacca ucaaccgcugcaaccuggaugggagugggcuggaggucaucgaugccaugcggagccagcugggcaaggccaccgcccuggc caucauggggggacaagcuguggugggcugaucaggugucggaaaagaugggcacaugcagcaaggcugacggcucgggcucc gugguccuucggaacagcaccacccuggugaugcacaugaaggucuaugacgagagcauccagcuggaccauaagggcaccaa ccccugcagugucaacaacggugacugcucccagcucugccugcccacgucagagacgacccgcuccugcaugugcacagccg gcuauagccuccggaguggccagcaggccugcgagggcguagguuccuuucuccuguacucugugcaugagggaaucaggg gaauuccccuggaucccaaugacaagucagaugcccuggucccaguguccgggaccucgcuggcugucggcaucgacuucca cgcugaaaaugacaccaucuacuggguggacaugggccugagcacgaucagccgggccaagcgggaccagacguggcgugaa gacguggugaccaauggcauuggccguguggagggcauugcaguggacuggaucgcaggcaacaucuacuggacagaccagg gcuuugaugucaucgaggucgcccggcucaauggcuccuuccgcuacguggugaucucccagggucuagacaagccccgggc caucaccguccacccggagaaagguacuuguucuggacugaguggggucaguauccgcguauugagcggucucggcuagau -continued ggcacggagcguguggugcuggucaacgucagcaucagcuggcccaacggcaucucaguggacuaccaggaugggaagcugu acuggugcgaugcacggacagacaagauugaacggaucgaccuggagacaggugagaaccgcgagguggguucuguccagcaa caacauggacauguuuucagugucuguguuugaggauuucaucuacuggagugacaggacucaugccaacggcucuaucaag cgcgggagcaaagacaaugccacagacuccgugccccugcgaaccggcaucggcguccagcuuaaagacaucaaagucuucaa ccgggaccggcagaaaggcaccaacgugugcgcgguggccaauggcgggugccagcagcugugccuguaccggggccguggg cagcgggccugcgccugugcccacgggaugcuggcugaagacggagcaucgugccgcgaguaugccggcuaccugcucuacu cagagcgcaccauucucaagaguauccaccugucggaugagcgcaaccucaaugcgcccgugcagcccuucgaggacccugag cacaugaagaacgucaucgcccuggccuuugacuaccgggcaggcaccucuccgggcacccccaaucgcaucuucuucagcga cauccacuuugggaacauccaacagaucaacgacgauggcuccaggaggaucaccauuguggaaaacgugggcuccguggaag gccuggccuaucaccguggcugggacacucucuauuggacaagcuacacgacauccaccaucacgcgccacacaguggaccag acccgcccaggggccuucgagcgugagaccgucaucacuaugucuggagaugaccacccacgggccuucguuuuggacgagu gccagaaccucauguucuggaccaacuggaaugagcagcaucccagcaucaugcgggcggcgcucucgggagccaauguccu gacccuuaucgagaaggacauccguaccccaauggccuggccaucgaccaccgugccgagaagcucuacuucucugacgcca cccuggacaagaucgagcggugcgaguaugacggcucccaccgcuaugugauccuaaagucagagccuguccaccccuucgg gcuggccguguauggggagcacauuuucuggacugacugggugcggcgggcagugcagcgggccaacaagcacgugggcag caacaugaagcugcugcgcguggacaucccccagcagcccaugggcaucaucgccguggccaacgacaccaacagcugugaac ucucuccaugccgaaucaacaacgguggcugccaggaccugugucugcucacucaccagggccaugucaacugcucaugccga gggggccgaauccuccaggaugaccucaccugccgagcggugaauuccucuugccgagcacaagaugaguuugagugugcca auggcgagugcaucaacuucagccugaccugcgacggcguccccccacugcaaggacaaguccgaugagaagccauccuacugc aacucccgccgcugcaagaagacuuuccggcagugcagcaaugggcgcuguguguccaacaugcugugguggcaacggggccg acgacugugggggauggcucugacgagaucccuugcaacaagacagccugugguguggggcgaguuccgcugccgggacgggac cugcaucgggaacuccagccgcugcaaccaguuuguggauugugaggacgccucagaugagaugaacugcagugccaccgac ugcagcagcuacuuccgccugggcgugaagggcgugcucuuccagcccugcgagcggaccucacucugcuacgcacccagcu gggugugugauggcgccaaugacuguggggacuacagugaugagcgcgacugcccaggugugaaacgccccagaugcccucu gaauuacuucgccugcccuagugggcgcugcauccccaugagcuggacgugugacaaagaggaugacugugaacauggcgag gacgagacccacugcaacaaguucugcucagaggcccaguuugagugccagaaccaucgcugcaucuccaagcaguggcugug ugacggcagcgaugacugugggggauggcucagacgaggcugcucacugugaaggcaagacgugcggccccuccuccuucucc ugcccuggcacccacgugugcgucccgagcgcuggcucugugacggugacaaagacugugcugauggugcagacgagagca ucgcagcugguugcuuguacaacagcacuugugacgaccgugaguucaugugccagaaccgccagugcauccccaagcacuu cgugugugaccacgaccgugacugugcagauggcucugaugaguccccgagugugaguacccgaccugcggccccagugag uuccgcugugccaaugggcgcugucugagcucccgccagugggagugugauggcgagaaugacugccacgaccagagugacg aggcucccaagaacccacacugcaccagccaagagcacaagugcaaugccucgucacaguuccugugcagcagugggcgcugu guggcugaggcacugcucugcaacggccaggaugacuguggcgacagcucggacgagcguggcugccacaucaaugagugcuc ucagccgcaagcucaguggcugcagccaggacugugaggaccucaagaucggcuucaagugccgcugucgcccuggcuuccg gcugaaggacgacggccggacgugugcugauguggacgagugcagcaccaccuuccccugcagccagcgcugcaucaacacuc auggcagcuauaagugucugugugugggagggcuaugcaccccgcggcggcgacccccacagcugcaaggcugugacugacga ggaaccguuucugaucuucgccaaccgguacuaccugcgcaagcucaaccuggacggguccaacuacacguuacuuaagcagg gccugaacaacgccguugccuuggauuuugacuaccgagagcagaugaucuacuggacagaugugaccacccagggcagcau gauccgaaggaugcaccuuaacgggagcaaugugcagguccuacaccguacaggccucagcaaccccgaugggcuggcugug gacuggguggguggcaaccuguacuggugcgacaaaggccgggacaccaucgagguguccaagcucaauggggccuaucgga cggugcuggucagcucuggccuccgugagcccagggcucuggugguggaugugcagaaugguaccuguacuggacagacu -continued ggggugaccauucacugaucggccgcaucggcauggaugggguccagccgcagcgucaucguggacaccaagaucacauggcc caauggccugacgcuggacuaugucacugagcgcaucuacugggccgacgcccgcgaggacuacauugaauuugccagccug gauggcuccaaucgccacguugugcugagccaggacaucccgcacaucuuugcacugacccuguuugaggacuacgucuacu ggaccgacugggaaacaaaguccauuaaccgagcccacaagaccacgggcaccaacaaaacgcuccucaucagcacgcugcacc ggcccauggaccugcaugucuuccaugcccugcgccagccagacgugcccaaucaccccugcaaggucaacaaugguggcugc agcaaccugugccugcuguccccgggggagggcacaaaugugccugccccaccaacuucuaccugggcagcgaugggcgcac cuguguguccaacugcacggcuagccaguuuguaugcaagaacgacaagugcauccccuucugguggaagugugacaccgag gacgacugcggggaccacucagacgagcccccggacugcccugaguucaagugccggcccggacaguuccagugcuccacagg uaucugcacaaacccugccuucaucugcgauggcgacaaugacugccaggacaacagugacgaggccaacugugacauccacg ucugcuugcccagucaguucaaaugcaccaacaccaaccgcuguauucccggcaucuuccgcugcaaugggcaggacaacugc ggagauggggaggaugagagggacugccccgaggugaccugcgcccccaaccaguuccagugcuccauuaccaaacggugca ucccccgggucugggucugcgaccgggacaaugacuguguggauggcagugaugagcccgccaacugcacccagaugaccug uggugugga cgaguuccgcugcaaggauucgggccgcugcaucccagcgcguuggaagugugacggagaggaugacugugg ggauggcucggaugagcccaaggaagagugugaugaacgcaccugugagccauaccaguuccgcugcaagaacaaccgcugc gugcccggccgcuggcagugcgacuacgacaacgauugcggugacaacuccgaugaagagagcugcaccccucggcccugcuc cgagagugaguucuccugugccaacggccgcugcaucgcggggcgcuggaaaugcgauggagaccacgacugcgcggacggc ucggacgagaaagacugcacccccgcugugacauggaccaguuccagugcaagagcggccacugcauccccugcgcuggcg cugugacgcagacgccgacugcauggacggcagcgacgaggaggccugcggcacuggcgugcggaccugcccccuggacgag uuccagugcaacaacaccuugugcaagccgcuggccuggaagugcgauggcgaggaugacuguggggacaacucagaugaga accccgaggagugugcccgguucgugugcccucccaaccggcccuuccguugcaagaaugaccgcgucugucuguggaucgg gcgccaaugcgauggcacggacaacuguggggaugggacugaugaagaggacugugagcccccacagcccacaccacccacu gcaaagacaagaaggaguuucugugccggaaccagcgcugccucuccuccucccugcgcugcaacauguucgaugacugcgg ggacggcucugacgaggaggacugcagcaucgaccccaagcugaccagcugcgccaccaaugccagcaucuguggggacgagg cacgcugcgugcgcaccgagaaagcggccuacugugccugccgcucgggcuuccacaccgugcccggccagcccggaugccaa gacaucaacgagugccugcgcuucggcaccugcucccagcucugcaacaacaccaagggcggccaccucugcagcugcgcucg gaacuucaugaagacgcacaacaccugcaaggccgaaggcucugaguaccagguccuguacaucgcugaugacaaugagaucc gcagccuguuccccggccacccccauucggcuuacgagcaggcauuccagggugacgagaguguccgcauugaugcuaugga uguccaugucaaggcuggccgugucuauuggaccaacuggcacacgggcaccaucuccuaccgcagccugccaccugcugcgc cuccuaccacuuccaaccgccaccggcgacagauugaccgggguguucacccaccucaacauuucagggcugaagaugcccaga ggcaucgccaucgacuggguggccggaaacguguacuggaccgacucgggccgagaugugauugagguggcgcagaugaag ggcgagaaccgcaagacgcucaucucgggcaugauugacgagccccacgccauugugguggacccacugagggggaccaugu acuggucagacuggggcaaccaccccaagauugagacggcagcgauggaugggacgcuucgggagacacuggugcaggacaa cauucaguggcccacaggccuggccguggauuaucacaaugageggcuguacugggcagacgccaagcuuucagucaucggc agcauccggcucaauggcacggaccccauuguggcugcugacagcaaacgaggccuaagucaccccuucagcaucgacgucuu ugaggauuacaucuaugguguucaccuacaucaauaaucgugucuucaagauccauaaguuuggccacagccccuuggucaac cugacagggggccugagccacgccucugacgugguccuuuaccaucagcacaagcagcccgaagugaccaacccaugugaccg caagaaaugcgaguggcucugccugcugagccccagugggccugucugcaccugucccaaugggaageggcuggacaacggc acaugcgugccugugcccucuccaacgcccccccagaugcuccccggccuggaaccuguaaccugcagugcuucaacggugg cagcuguuuccucaaugcacggaggcagcccaagugccgcugccaaccccgcuacacgggugacaagugugaacuggaccagu gcugggagcacugucgcaauggggcaccugugcugccucccccucuggcaugcccacgugccggugccccacgggcuucac -continued gggccccaaaugcacccagcaggugugugegggcuacugugccaacaacagcaccugcacugucaaccagggcaaccagcccc agugccgaugccuacccggcuuccugggcgaccgcugccaguaccggcagugcucuggcuacugugagaacuuuggcacaug ccagauggcugcugauggcucccgacaaugccgcugcacugccuacuuugagggaucgaggugugaggugaacaagugcagc cgcugucucgaaggggccugugugguacaacaagcagaguggggaugucaccugcaacugcacggauggccgggugguggccccca gcugucugaccugcgucggccacugcagcaauggeggcuccuguaccaugaacagcaaaaugaugccugagugccagugccc accccacaugacagggccccggugugaggagcacgucuucagccagcagcagccaggacauauagccuccauccuaaucccuc ugcuguugcugcugcugcugguucugguggccggagugguauucugguauaageggcgaguccaaggggcuaagggcuucc agcaccaacggaugaccaacggggccaugaacguggagauuggaaaccccaccuacaagauguacgaaggeggagagccugau gaugugggaggccuacuggacgcugacuuugcccuggacccugacaagcccaccaacuucaccaaccccguguaugccacacu cuacaugggggccauggcagucgccacucccuggccagcacggacgagaagcgagaacuccugggccggggcccugaggac gagauaggggaccccuuggcauagggcccugccccgucggacugcccccagaaagccuccugcccccugccggugaaguccuu cagugagccccuccccagccagcccuucccuggccccgccggauguauaaauguaaaaaugaaggaauuacauuuuauaugug agcgagcaagccggcaagcgagcacaguauuauuucuccauccccucccugccugcuccuuggcacccccaugcugccuucag ggagacaggcagggagggcuuggggcugcaccuccuacccucccaccagaacgcaccccacugggagagcugguggugcagc cuuccccucccuguauaagacacuuugccaaggcucuccccucucgccccaucccugcuugcccgcucccacagcuuccugag ggcuaauucugggaagggagaguucuuugcugccccugucuggaagacguggcucugggugagguaggegggaaaggaugg aguguuuaguucuuggggggaggccaccccaaaccccagccccaacuccaggggcaccuaugagauggccaugcucaaccccc cucccagacaggcccucccugucuccagggcccccaccgagguucccagggcuggagacuucccucugguaaacauuccuccag ccuccccuccccuggggacgccaaggaggugggccacacccaggaagggaaagegggcagccccguuuuggggacgugaacg uuuuaauaauuuuugcugaauuccuuuacaacuaaauaacacagauauuguuauaaauaaaauuguaaaaaaaaaaaaaaaa aa LRP1 - Amino acid sequence (SEQ ID NO: 10)

mltppllll pllsalvaaa idapktcspk qfacrdqitc iskgwrcdge rdcpdgsdea peicpqskaq rcqpnehncl gtelcvpmsr lcngvqdcmd gsdegphcre lqgncsrlgc qhhcvptldg ptcycnssfq lqadgktckd fdecsvygtc sqlctntdgs ficgcvegyl lqpdnrscka knepvdrppv lliansqnil atylsgaqvs titptstrqt tamdfsyane tvcwvhvgds aaqtqlkcar mpglkgfvde htinislslh hveqmaidwl tgnfyfvddi ddrifvcnrn gdtcvtlldl elynpkgial dpamgkvfft dygqipkver cdmdgqnrtk lvdskivfph gitldlvsrl vywadayldy ievvdyegkg rqtiiqgili ehlygltvfe nylyatnsdn anaqqktsvi rvnrfnstey qvvtrvdkgg alhiyhqrrq prvrshacen dqygkpggcs dicllanshk artcrcrsgf slgsdgksck kpehelflvy gkgrpgiirg mdmgakvpde hmipienlmn praldfhaet gfiyfadtts yligrqkidg teretilkdg ihnvegvavd wmgdnlywtd dgpkktisva rlekaaqtrk tliegkmthp raivvdplng wmywtdweed pkdsrrgrle rawmdgshrd ifvtsktvlw pnglsldipa grlywvdafy drietillng tdrkivyegp elnhafglch hgnylfwtey rsgsvyrler gvggapptvt llrserppif eirmydaqqq qvgtnkcrvn nggcsslcla tpgsrqcaca edqvldadgv tclanpsyvp ppqcqpgefa cansrciqer wkcdgdndcl dnsdeapalc hqhtcpsdrf kcennrcipn rwlcdgdndc gnsedesnat csartcppnq fscasgrcip iswtcdlddd cgdrsdesas cayptcfplt qftcnngrci ninwrcdndn dcgdnsdeag cshscsstqf kcnsgrcipe hwtcdgdndc gdysdethan ctnqatrppg gchtdefqcr ldglciplrw rcdgdtdcmd ssdekscegv thvcdpsvkf gckdsarcis kawvcdgdnd cednsdeenc eslacrppsh pcanntsycl ppdklcdgnd dcgdgsdege lcdqcslnng gcshncsvap gegivcscpl gmelgpdnht cqiqsycakh lkcsqkcdqn kfsvkcscye gwvlepdges crsldpfkpf iifsnrheir ridlhkgdys vlvpglrnti aldfhlsqsa lywtdvvedk iyrgklldng altsfevviq yglatpegla vdwiagniyw vesnldqiev akldgtlrtt llagdiehpr aialdprdgi lfwtdwdasl prieaasmsg agrrtvhret gsggwpnglt vdylekrilw idarsdaiys arydgsghme vlrgheflsh pfavtlygge vywtdwrtnt lakankwtgh nvtvvqrtnt -continued qpfdlqvyhp srqpmapnpc eanggqgpcs hlclinynrt vscacphlmk lhkdnttcye fkfkllyarq meirgvdlda pyynyiisft vpdidnvtvl dydareqrvy wsdvrtqaik rafingtgve tvvsadlpna hglavdwvsr nlfwtsydtn kkqinvarld gsfknavvqg leqphglvvh plrgklywtd gdnismanmd gsnrtllfsg qkgpvglaid fpesklywis sgnhtinrcn ldgsglevid amrsqlgkat alaimgdklw wadqvsekmg tcskadgsgs vvlrnsttlv mhmkvydesi qldhkgtnpc synngdcsql clptsettrs cmctagyslr sgqqacegvg sfllysvheg irgipldpnd ksdalvpvsg tslavgidfh aendtiywvd mglstisrak rdqtwredvv tngigrvegi avdwiagniy wtdqgfdvie varlngsfry vvisqgldkp raitvhpekg ylfwtewgqy priersrldg tervvlvnvs iswpngisvd yqdgklywcd artdkierid letgenrevv lssnnmdmfs vsvfedfiyw sdrthangsi krgskdnatd svplrtgigv qlkdikvfnr drqkgtnvca vanggcqqlc lyrgrgqrac acahgmlaed gascreyagy llysertilk sihlsdernl napvqpfedp ehmknviala fdyragtspg tpnriffsdi hfgniqqind dgsrritive nvgsveglay hrgwdtlywt syttstitrh tvdqtrpgaf eretvitmsg ddhprafvld ecqnlmfwtn wneqhpsimr aalsganylt liekdirtpn glaidhraek lyfsdatldk ierceydgsh ryvilksepv hpfglavyge hifwtdwvrr avqrankhvg snmkllrvdi pqqpmgiiav andtnscels pcrinnggcq dlcllthqgh vncscrggri lqddltcrav nsscraqdef ecangecinf sltcdgvphc kdksdekpsy cnsrrckktf rqcsngrcvs nmlwcngadd cgdgsdeipc nktacgvgef rcrdgtcign ssrcnqfvdc edasdemncs atdcssyfrl gykgylfqpc ertslcyaps wvcdgandcg dysderdcpg vkrprcplny facpsgrcip mswtcdkedd cehgedethc nkfcseaqfe cqnhrciskq wlcdgsddcg dgsdeaahce gktcgpssfs cpgthvcype rwlcdgdkdc adgadesiaa gclynstcdd refmcqnrqc ipkhfvcdhd rdcadgsdes peceyptcgp sefrcangrc lssrqwecdg endchdqsde apknphctsq ehkcnassqf lcssgrcvae allcngqddc gdssdergch ineclsrkls gcsqdcedlk igfkcrcrpg frlkddgrtc advdecsttf pcsqrcinth gsykclcveg yaprggdphs ckavtdeepf lifanryylr klnldgsnyt llkqglnnav aldfdyreqm iywtdvttqg smirrmhlng snvqvlhrtg lsnpdglavd wvggnlywcd kgrdtievsk ingayrtvlv ssglrepral vvdvqngyly wtdwgdhsli grigmdgssr svivdtkitw pngltldyvt eriywadare dyiefasldg snrhvvlsqd iphifaltlf edyvywtdwe tksinrahkt tgtnktllis tlhrpmdlhv fhalrqpdvp nhpckvnngg csnlcllspg gghkcacptn fylgsdgrtc vsnctasqfv ckndkcipfw wkcdteddcg dhsdeppdcp efkcrpgqfq cstgictnpa ficdgdndcq dnsdeancdi hyclpsqfkc tntnrcipgi frcngqdncg dgederdcpe vtcapnqfqc sitkrciprv wvcdrdndcv dgsdepanct qmtcgvdefr ckdsgrcipa rwkcdgeddc gdgsdepkee cdertcepyq frcknnrcvp grwqcdydnd cgdnsdeesc tprpcsesef scangrciag rwkcdgdhdc adgsdekdct prcdmdqfqc ksghciplrw rcdadadcmd gsdeeacgtg vrtcpldefq cnntlckpla wkcdgeddcg dnsdenpeec arfvcppnrp frckndrycl wigrqcdgtd ncgdgtdeed cepptahtth ckdkkeflcr nqrclssslr cnmfddcgdg sdeedcsidp kltscatnas icgdearcvr tekaaycacr sgfhtvpgqp gcqdineclr fgtcsqlcnn tkgghlcsca rnfmkthntc kaegseyqvl yiaddneirs lfpghphsay eqafqgdesv ridamdvhvk agrvywtnwh tgtisyrslp paappttsnr hrrqidrgvt hlnisglkmp rgiaidwvag nvywtdsgrd vievaqmkge nrktlisgmi dephaivvdp lrgtmywsdw gnhpkietaa mdgtlretlv qdniqwptgl avdyhnerly wadaklsvig sirlngtdpi vaadskrgls hpfsidvfed yiygvtyinn rvfkihkfgh splvnltggl shasdvvlyh qhkqpevtnp cdrkkcewlc llspsgpvct cpngkrldng tcvpvpsptp ppdaprpgtc nlqcfnggsc flnarrqpkc rcqprytgdk celdqcwehc rnggtcaasp sgmptcrcpt gftgpkctqq vcagycanns tctvnqgnqp qcrclpgflg drcqyrqcsg ycenfgtcqm aadgsrqcrc tayfegsrce vnkcsrcleg acvvnkqsgd vtcnctdgrv apscltcvgh csnggsctmn skmmpecqcp phmtgprcee hvfsqqqpgh iasiliplll llllvlvagv vfwykrrvqg akgfqhqrmt ngamnveign ptykmyegge pddvgglllda dfaldpdkpt nftnpvyatl ymgghgsrhs lastdekrel lgrgpedeig dpla -continued LRP8 isoform 1 - RNA sequence (SEQ ID NO: 11)

gcuggcggcggccgcccagggccggggccgcgcgcccagccugagcccgccccgccgccgagcgucaccgaaccugcuugaaa ugcagccgaggagccggggcgggcggcagcggcggcggcggcggcggcgggggcagcggcaaccccggcgccgcggcaagga cucggagggcugagacgcggcggcggcggcgcggggagcgcggggcgcggcggccggagccccgggcccgccaugggccucc ccgagccgggcccucuccggcuucuggcgcugcugcugcugcugcugcugcugcugcugcugcagcuccagcaucuugcggc ggcagcggcugauccgcugcucggcggccaagggccggccaaggauugcgaaaaggaccaauuccagugccggaacgagcgc ugcauccccucuguguggagaugcgacgaggacgaugacugcuuagaccacagcgacgaggacgacugccccaagaagaccug ugcagacagugacuucaccugugacaacggccacugcauccacgaacgguggaagugugacggcgaggaggaguguccugau ggcuccgaugaguccgaggccacuugcaccaagcaggugugucccugcagagaagcugagcuguggacccaccagccacaagu guguaccugccucguggcgcugcgacggggagaaggacugcgaggguggagcggaugaggccggcugugcuaccuugugcg ccccgcacgaguuccagugcggcaaccgcucgugccuggccgcccguguucgugugcgacggcgacgacgacuguggugacgg cagcgaugagcgcggcugugcagacccggccugcgggccccgcgaguuccgcugcggcggcgauggcggcggcgccugcauc ccggagcgcugggucugcgaccgccaguuugacugcgaggaccgcucggacgaggcagccgagcucugcggccguccgggcc ccggggccacguccgcgcccgccgccugcgccaccgccucccaguucgccugccgcagcggcgagugcgugcaccugggcug gcgcugcgacggcgaccgcgacugcaaagacaaaucggacgaggccgacugcccacugggcaccugccguggggacgaguucc agugugggggaugggacauguguccuugcaaucaagcacugcaaccaggagcaggacuguccagaugggagugaugaagcugg cugccuacaggggcugaacgagugucugcacaacaauggcggcugcucacacaucugcacugaccucaagauuggcuuugaa ugcacgugcccagcaggcuuccagcuccuggaccagaagaccuguggcgacauugaugagugcaaggacccagaugccugca gccagaucugugucaauuacaagggcuauuuuaagugugagugcuacccuggcuacgagauggaccuacugaccaagaacug caaggcugcugcuggcaagagcccaucccuaaucuucaccaaccggcacgaggugcggaggaucgaccuggugaagcggaacu auucacgccucaucccca ugcucaagaaugucguggcacuagauguggaaguugccaccaaucgcaucuacuggugugaccu cuccuaccguaagaucuauagcgccuacauggacaaggccagugacccgaaagagcaggagguccucauugacgagcaguugc acucuccagagggccuggcaguggacugggucc acaagcacaucuacuggacugacucgggcaauaagaccaucucaguggcc acaguugaugguggccgccgacgcacucucuucagccguaaccucagugaaccccgggccaucgcuguugaccccugcgag gguucauguauuggucugacugggggggaccaggccaagauugagaaaucugggcucaacgguguggaccggcaaacacugg ugucagacaauauugaauggcccaacggaaucacccuggaucugcugagccagcgcuuguacugguagacuccaagcuacac caacuguccagcauugacuucaguggaggcaacagaaagacgcugaucucccuccacugacuuccugagccacccuuuugggau agcuguguuugaggacaagguguucuggacagaccuggagaacgaggccauuuucagugcaaaucggcucaauggccuggaa aucuccauccuggcugagaaccucaacaacccacaugacauugucaucuuccaugagcugaagcagccaagagcuccagaugc cugugagcugaguguccagccuaauggaggcugugaauaccugugccuuccugcucccucagaucuccagccacucucccaag uacacaugugccuguccugacacaauguggcuggguccagacaugaagaggugcuaccgagcaccucaaucuaccucaacuac gacguuagcuucuaccaugacgaggacaguaccugccaccacaagagccccccgggaccaccguccacagauccaccuaccagaa ccacagcacagagacaccaagccugacagcugcagucccaagcucaguuagugucccccagggcucccagcaucagcccgucuac ccuaagcccugcaaccagcaaccacucccagcacuaugcaaaugaagacaguaagaugggcucaacagucacugccgcuguua ucgggaucaucgugcccauagugguguagcccuccugugcaugaguggauaccugaucuggagaaacuggaagcggaagaa caccaaaagcaugaauuuugacaacccagucuacaggaaaacaacagaagaagaagacgaagaugagcuccauauagggagaac ugcucagauuggccaugucuauccugcagcaaucagcagcuuugaucgcccacugugggcagagcccugucuuggggagacc agagaaccggaagacccagccccugcccucaaggagcuuuuugucuugccgggggaaccaaggucacagcugcaccaacuccc gaagaacccucuuuccgagcugccugucgucaaauccaagcgaguggcauuaagccuugaagaugauggacuacccugagga ugggaucacccccuucgugccucauggaauucagucccaugcacuacacucuggaugguguaugacuggaugaaugggguuuc uauauaugggucugugugaguguaugugugugugugauuuuuuuuuuaaauuuauguugcggaaagguaaccacaaaguu -continued augaugaacugcaaacauccaaaggaugugagaguuuuucuauguauaauguuuuauacacuuuuuaacugguugcacuacc caugaggaauucguggaauggcuacugcugacuaacaugaugcacauaaccaaaugggggccaauggcacaguaccuuacuca ucauuuaaaaacuauauuuacagaagauguuugguugcugggggggcuuuuuuagguuuuggggcauuuguuuuuuguaa auaagaugauuaugcuuuguggcuauccaucaacauaaguaaaaaaaaaaaaaaaacacuucaacucccucccccauuuagau uauuuauuaacauauuuuaaaaaucagaugaguucuauaaauaauuuagagaagugagaguauuuauuuuuggcauguuug gcccaccacacagacucuguguguguaugugugugguuuauauguguaugugugugacagaaaaaucuguagagaagaggca caucuauggcuacuguucaaauacauaaagauaaauuuauuuucacacaguccacaagggguauaucuuguaguuucagaa aagccuuuggaaaucuggaucagaaaauagauaccaugguuugugcaauuauguaguaaaaaaggcaaaucuuuucaccucu ggcuauuccugagaccccaggaagucaggaaaagccuuucagcucacccauggcugcugugacuccuaccagggcuuucuug gcuuuggcgaaggucaguguacagacauuccaugguaccagagugcucagaaacucaagauaggauaugccucacccucagc uacuccuuguuuuaaaguucagcucuuugaguaacuucuucaauuucuuucaggacacuugggguugaauucaguaaguuuc cucugaagcacccugaagggugccauccuuacagagcuaaguggagacguuuccagaucagcccaaguuuacuauagagacu ggcccaggcacugaaugucuaggacaugcuguggaugaagauaaagaugguggaauagguuuuaucacaucucuuauuucuc uuuuccccuuacucucuaccauuuccuuuauguggggaaacauuuuaagguaauaaauagguuacuuaccaucauauguuca uauagaugaaacuaauuuuuggcuuaagucagaacaacuggccaaaauugaagucauauuugagggggggaaauggcauacgc aauauuauauuauauuggauauuuauguucacacaggaauuugguuuacugcuuuguaaauaaaaggaaaaacuccggguau auguauagauguucuucauuauagacaucuucuuugcuuuucuuggccuuggggggaggaagggagaagugcucuuuucuac uuguggggucucccauuggaaacauaauccuauagucccagaaggauucaguccccaguggcuuucccauccaaagagaaaga guuugaguuucuuaacucugcuguucugccacuuacucccacuagacaaccagggacaaggugcaacauggaaguguuugac uuaaguaggagcagaggagcugcaucuaaucucaucauaccuggaacuugacacacuuaagcaaaugccuucccaucccuacc ugccagaugcccccaacucaaugaaguuggaugucucaccagcuugauacccuuugaauuucagucagacauucuggaguu cuagcauccuguaccuaggaccuuccucugugucacucuuggccuccuaaacucuaagaaaauaacuauauucuggagcuug ggcaguguguuuugcauaauccagcaaucuccucaugacaugcauguguugauaguccugaaacauucauugagagguaaa ugcaguugaccuagaaugaccaauaccaaacagaauuuuaagaacagguggccaacuccuauggagcuuacucacauauuacu auucuuuuaagaacggaaaguaaaauuauuuuugacugaagaaaaaugaugacagugaaaaacauggaaauguacucaaaaca agugacuuuuucuguaaccuuccaaagaaacugaauuuuccaaggaauuaaaugauaacaguggcuaaggcauaguuucuaa acuuucaguaagauccuggcauucacagaaaaaaaugaugaauggggucuggacauacagccugagaucucaaaaugacaaug aaauucacaacuuuuucucagagacauucauguuuccugcauaugcuacaacugcaguuugaaagaggcagcaaugggagca acccuuuacaagaaacaaauugugauauauucauguguuggacggcaguaaauaagaugaaaccugaggagucagauccaccu ucccccauucauagaggcuuuucagccucauuuugagguacaguuacauaucuuuugccuuuugcccccgugcauagcuauc uacagccaaucacagaucacagagucacuggacuauagagcuggaaggaagcucagagacaaugccaaggggcagaaaauuu aucagaagccagucccagugcguuuccuccauuuccuucugcaggaagacuauuuugggcugccugaacauuguaucaaacc ugcuaccuauacuauggucuaccuuuccuccaguggaauuacaaaggcacuaacugaaaugccuucuagaaacagagaaaacg aaacuguacuuauuuacucuugauacacagauuauuuauaaaacagauugaaguaaccuguuaacuggcaaaaagagaaugag aucggauuuaaauguauggcaguaaguccuauugaucccuccaguuaucucaguaugacugcaguauauucauucacuaaaa ccacucacuagauaccaacuacacaccuggcacugcagauguaaaggucagucacacauguucugacuuuacagaguucacag uagcaguggaggaugauauauguggaaacaaaaaaggcauugauucuauucagagcacuguuagggcucaaaggagagaggg gucuuuccaccuaagaaaugaggaauagggucaucauagaagugaccuuaagucuuaaaaauuaagaaggggauuccaagcu gcuucagacagagacacaucgagcuaaaacacagagguaugaaagagcacagggacuuuaggaauugcacaguucauucuaac aggaacaaaaggcucaagggggggcaagaaaugaggcuguauggaaagagauucaauguaagcacuuuauaaaauagauuaau -continued uucugauucaaugaagcauuucuugaucauuguguacaaggcacuacaugcaucauggaaaauucauuaggaugcauugcca gcacuuugcagaacugauauuauucagccucaagcuuuccaguggccaaagggaaaugcugacugcuuuucauauauuugag ucaaagauuuuuuauauggucaaugaagacuaaauauaagggcagugggauuuucacagaugcaugccauguugucgagagcc ucuuagauuuucucaacugugagaaagaaaaacgaaaauguugaagacguugagucuggagaggggauacuaaucacugucc aguugggcacugguggggaauggggaaauggcacaggaaugcaagccucuccacccuacccccccgaacuccagccauacacuca ucguuucacaaaauauaaaugaguuagcauuaaauguuucagaguaaauaauuccuuuucccgaaaugcaugaagauagagu aacagacuucucacacuguauuuuuaggguauggagaauuuagaagguuaaagaauuacugcuucaauuuuucaguuaaaaa aaaaucaggaagcucuguucauucaggcuaugcaccaugugcacagucaagaauuagcagaaacccucugcauuuacaaacac uuugugcuauaaaaaaguaauuuuuaaaaagccacgugugugugugugguauauauauauauauauauauauuuaaagccaag guuuugauacuuuuuuacaaaaacuacaagagaaaacaaauauaccuguccaaaccauauacuuuuaaaagagcauuuuuuuu uccauacaagcuguuguuaauuuggggguaaagugcugauuugcaaacuucaucaaauuguucccaaguggauucuccuug uuugucucccccuaccaaccccaaaguuaccauauuugauguaagaaucaggcauguuagaauguugugucacacuaacuga uucugcucuuuuugucuugucauucaaguuccguuagcuucuguacgcggugcccuuugcagucuggugucucuuccagag gcgagggggcugaggauggggugcugcaucucacuagcuauacuggcaucaucuugguaaacugaaaaccaaauguggacau uuguaaaaucagugcacuguuucuagagagagauuaaaauucauuuaaaaaaaa LRP8 isoform 1 - Amino acid sequence (SEQ ID NO: 12)

mglpepgplr llalllllll llllqlqhla aaaadpllgg qgpakdcekd qfqcrnerci psvwrcdedd dcldhsdedd cpkktcadsd ftcdnghcih erwkcdgeee cpdgsdesea tctkqvcpae klscgptshk cvpaswrcdg ekdceggade agcaticaph efqcgnrscl aavfvcdgdd dcgdgsderg cadpacgpre frcggdggga ciperwvcdr qfdcedrsde aaelcgrpgp gatsapaaca tasqfacrsg ecvhlgwrcd gdrdckdksd eadcplgtcr gdefqcgdgt cvlaikhcnq eqdcpdgsde agclqqglnec lhnnggcshi ctdlkigfec tcpagfqlld qktcgdidec kdpdacsqic vnykgyfkce cypgyemdll tknckaaagk spslifltnrh evrridlvkr nysrlipmlk nvvaldveva tnriywcdls yrkiysaymd kasdpkeqev lideqlhspe glavdwvhkh iywtdsgnkt isvatvdggr rrtlfsrnls epraiavdpl rgfmywsdwg dqakieksgl ngvdrqtlvs dniewpngit ldllsqrlyw vdsklhqlss idfsggnrkt lisstdflsh pfgiavfedk vfwtdlenea ifsanrlngl eisilaenln nphdivifhe lkqprapdac elsvqpnggc eylclpapqi sshspkytca cpdtmwlgpd mkrcyrapqs tstttlastm trtvpattra pgttvhrsty qnhstetpsl taavpssysv prapsispst lspatsnhsq hyanedskmg stvtaavigi ivpivviall cmsgyliwrn wkrkntksmn fdnpvyrktt eeededelhi grtaqighvy paaissfdrp lwaepclget repedpapal kelfvlpgep rsqlhqlpkn plselpvvks krvalsledd glp LRP8 isoform 2 - RNA sequence (SEQ ID NO: 13)

gcuggcggcggccgcccagggccggggccgcgcgcccagccugagcccgccccgccgccgagcgucaccgaaccugcuugaaa ugcagccgaggagccggggcgggcggcagcggcggcggcggcggcggcgggggcagcggcaaccccggcgccgcggcaagga cucggagggcugagacgcggcggcggcggcgcggggagcgcggggcgcggcggccggagccccgggcccgccaugggccucc ccgagccgggcccucuccggcuucuggcgcugcugcugcugcugcugcugcugcugcugcugcagcuccagcaucuugcggc ggcagcggcugauccgcugcucggcggccaagggccggccaaggauugcgaaaaggaccaauuccagugccggaacgagcgc ugcauccccucuguguggagaugcgacgaggacgaugacugcuuagaccacagcgacgaggacgacugccccaagaagaccug ugcagacagugacuucaccugugacaacggccacugcauccacgaacgguggaagugugacggcgaggaggaguguccugau ggcuccgaugaguccgaggccacuugcaccaagcaggugugucccugcagagaagcugagcuguggacccaccagccacaagu guguaccugccucguggcgcugcgacggggagaaggacugcgaggguggagcggaugaggccggcugugcuaccuggcuga acgagugucugcacaacaauggcggcugcucacacaucugcacugaccucaagauuggcuuugaaugcacgugcccagcaggc uuccagcuccuggaccagaagaccuguggcgacauugaugagugcaaggacccagaugccugcagccagaucugugucaauu -continued acaagggcuauuuuaagugugagugcuacccuggcuacgagauggaccuacugaccaagaacugcaaggcugcugcuggcaa gagcccaucccuaaucuucaccaaccggcacgaggugcggaggaucgaccuggugaagcggaacuauucacgccucaucccca ugcucaagaaugucguggcacuagauguggaaguugccaccaaucgcaucuacuggugugaccucuccuaccguaagaucua uagcgccuacauggacaaggccagugacccgaaagagcaggagguccucauugacgagcaguugcacucuccagagggccug gcaguggacugggguccacaagcacaucuacuggacugacucgggcaauaagaccaucucaguggccacaguugauggugcc gccgacgcacucucuucagccguaaccucagugaaccccgggccaucgcuguugaccccccugcgaggguucauguauugguc ugacugggggaccaggccaagauugagaaaucugggcucaacgguguggaccggcaaacacuggugucagacaauauugaa uggcccaacggaaucacccuggaucugcugagccagcgcuuguacuggguagacuccaagcuacaccaacuguccagcauuga cuucaguggaggcaacagaaagacgcugaucuccuccacugacuuccugagccacccuuuugggauagcuguguuugaggac aagguguucuggacagaccuggagaacgaggccauuuucagugcaaaucggcucaauggccuggaaaucuccauccuggcug agaaccucaacaacccacaugacauugucaucuuccaugagcugaagcagccaagagcuccagaugccugugagcugaguguc cagccuaauggaggcugugaauaccugugccuuccugcuccucagaucuccagccacucucccaaguacacaugugccugucc ugacacaauguggcuggguccagacaugaagaggugcuaccgagcaccucaaucuaccucaacuacgacguuagcuucuacca ugacgaggacaguaccugccaccacaagagcccccgggaccaccguccacagauccaccuaccagaaccacagcacagagacac caagccugacagcugcagucccaagcucaguuagugucccagggcucccagcaucagcccgucuacccuaagcccugcaacc agcaaccacucccagcacuaugcaaaugaagacaguaagaugggcucaacagucacugccgcuguuaucgggaucaucgugcc cauaguggugauagcccuccugugcaugaguggauaccugaucuggagaaacuggaagcggaagaacaccaaaagcaugaau uuugacaacccagucuacaggaaaacaacagaagaagaagacgaagaugagcuccauauagggagaacugcucagauuggcca ugucuauccugcagcaaucagcagcuuugaucgcccacugugggcagagcccugucuuggggagaccagagaaccggaagac ccagccccugcccucaaggagcuuuuugucuugccgggggaaccaaggucacagcugcaccaacucccgaagaacccucuuuc cgagcugccugucgucaaauccaagcgaguggcauuaagccuugaagaugauggacuacccugaggaugggaucaccccccuu cgugccucauggaauucagucccaugcacuacacucuggaugguguaugacuggaugaauggguuucuauauaugggucug ugugaguguaugugugugugugauuuuuuuuuuaaauuuauguugcggaaagguaaccacaaaguuaugaugaacugcaaa cauccaaaggaugugagaguuuuucuauguauaauguuuuauacacuuuuuaacugguugcacuacccaugaggaauucgu ggaauggcuacugcugacuaacaugaugcacauaaccaaaugggggccaauggcacaguaccuuacucaucauuuaaaaacua uauuuacagaagauguuugguugcugggggggcuuuuuuagguuuuggggcauuuguuuuuuguaaauaagaugauuaug cuuuguggcuauccaucaacauaaguaaaaaaaaaaaaaaaacacuucaacucccucccccauuuagauuauuuauuaacauau uuuaaaaaucagaugaguucuauaaauaauuuagagaagugagaguauuuauuuuuggcauguuuggcccaccacacagacu cugugugugguaugugugugguuuauauguguaugugugugacagaaaaaucuguagagaagaggcacaucuauggcuacugu ucaaauacauaaagauaaauuuauuuucacacaguccacaagggguauaucuuguaguuuucagaaaagccuuuggaaaucu ggaucagaaaauagauaccaugguuugugcaauuauguaguaaaaaaggcaaaucuuuucaccucuggcuauuccugagacc ccaggaagucaggaaaagccuuucagcucacccauggcugcugugacuccuaccagggcuuucuuggcuuuggcgaagguca guguacagacauuccaugguaccagagugcucagaaacucaagauaggauaugccucacccucagcuacuccuuguuuuaaag uucagcucuuugaguaacuucuucaauuucuuucaggacacuuggguugaauucaguaaguuuccucugaagcacccugaag ggugccauccuuacagagcuaaguggagacguuuccagaucagcccaaguuuacuauagagacuggcccaggcacugaaugu cuaggacaugcuguggaugaagauaaagaugguggaauagguuuuaucacaucucuuauuucucuuuuccccuuacucucua ccauuuccuuuauguggggaaacauuuuaagguaauaaauagguuacuuaccaucauauguucauauagaugaaacuaauuu uuggcuuaagucagaacaacuggccaaaauugaagucauauuugagggggaaauggcauacgcaauauuauauuauauugg auauuuauguucacacaggaauuugguuuacugcuuuguaaauaaaaggaaaaacuccggguauauguauagauguucuuca uuauagacaucuucuuugcuuuucuuggccuugggggaggaagggagaagugcucuuuucuacuugugggucucccauug -continued gaaacauaauccuauagucccagaaggauucaguccccaguggcuuucccauccaaagagaaagaguuugaguuucuuaacuc ugcuguucugccacuuacucccacuagacaaccagggacaaggugcaacauggaaguguuugacuuaaguaggagcagagga gcugcaucuaaucucaucauaccuggaacuugacacacuuaagcaaaugccuucccaucccuaccugccagaugcccccaacuc aaugaaguuggaugucucaccagcuugauacccuuugaauuuucagucagacauucuggaguucuagcauccuguaccuagg accuuccucugugucacucuuggccuccuaaacucuaagaaaauaacuauauucuggagcuugggcaguguguuuugcauaa uccagcaaucuccucaugacaugcauguguugauaguccugaaacauucauugagaggguaaaugcaguugaccuagaauga ccaauaccaaacagaauuuuaagaacagguggccaacuccuauggagcuuacucacauauuacuauucuuuuaagaacggaaa guaaaauuauuuuugacugaagaaaaaugaugacagugaaaaacauggaaauguacucaaaacaagugacuuuuucuguaacc uuccaaagaaacugaauuuuccaaggaauuaaaugauaacaguggcuaaggcauaguuucuaaacuuucaguaagauccugg cauucacagaaaaaaaugaugaauggggucuggacauacagccugagaucucaaaaugacaaugaaauucacaacuuuuucuc agagacauucauguuuccugcauaugcuacaacugcaguuugaaagaggcagcaaugggagcaacccuuuacaagaaacaaau ugugauauauucauguguuggacggcaguaaauaagaugaaaccugaggagucagauccaccuucccccauucauagaggcu uuucagccucauuuugagguacaguuacauaucuuuugccuuuugcccccgugcauagcuaucuacagccaaucacagauca cagagucacuggacuauagagcuggaaggaagcucagagacaaugccaagggggcagaaaauuuaucagaagccagucccagu gcguuuccuccauuuccuucugcaggaagacuauuuugggcugccugaacauuguaucaaaccugcuaccuauacuauggucu accuuuccuccaguggaauuacaaaggcacuaacugaaaugccuucuagaaacagagaaaacgaaacuguacuuauuuacuc uugauacacagauuauuuauaaaacagauugaaguaaccuguuaacuggcaaaaagagaaugagaucggauuuaaauguaug gcaguaaguccuauugaucccuccaguuaucucaguaugacugcaguauauucauucacuaaaaccacucacuagauaccaac uacacaccuggcacugcagauguaaaggucagucacacauguucugacuuuacagaguucacaguagcaguggaggaugaua uauguggaaacaaaaaaggcauugauucuauucagagcacuguuagggcucaaaggagagaggggucuuuccaccuaagaaa ugaggaauagggucaucauagaagugaccuuaagucuuaaaaauuaagaaggggauuccaagcugcuucagacagagacaca ucgagcuaaaacacagagguaugaaagagcacagggacuuuaggaauugcacaguucauucuaacaggaacaaaggcucaag gggggcaagaaaugaggcuguauggaaagagauucaauguaagcacuuuauaaaauagauuaauuucugauucaaugaagca uuucuugaucauuguguacaaggcacuacaugcaucauggaaaauucauuaggaugcauugccagcacuuugcagaacugau auuauucagccucaagcuuuccaguggccaaagggaaaugcugacugcuuuucauauauuugagucaaagauuuuuuauaug gucaaugaagacuaauauaagggcaguggauuuucacagaugcaugccauguugucgagagccucuuagauuuucucaacu gugagaaagaaaaacgaaaauguugaagacguugagucuggagaggggauacuaaucacuguccaguugggcacuggugga auggggaaauggcacaggaaugcaagccucuccacccuacccccgaacuccagccauacacucaucguuucacaaaauauaaa ugaguuagcauuaaauguuucagaguaaauaauuccuuuucccgaaaugcaugaagauagaguaacagacuucucacacugu auuuuuaggguauggagaauuuagaagguuaaagaauuacugcuucaauuuuucaguuaaaaaaaaaucaggaagcucuguu cauucaggcuaugcaccaugugcacagucaagaauuagcagaaacccucugcauuuacaaacacuuugugcuauaaaaaagua auuuuuaaaaagccacguguguguguguauauauauauauauauauauuuaaagccaagguuuugauacuuuuuuac aaaaacuacaagagaaaacaaauauaccuguccaaaccauauacuuuuaaaagagcauuuuuuuuuccauacaagcuguuguu aauuuggggguaaagugcugauuugcaaacuucaucaaauuguucccaaguggauucuccuuguuugucucccccuaccaac cccaaaguuaccauauuugauguaagaaucaggcauguuagaauguugugucacacuaacugauucugcucuuuuugucuug ucauucaaguuccguuagcuucuguacgcggugcccuuugcagucuggugucucuuccagaggcgagggggcugaggaugg ggugcugcaucucacuagcuauacuggcaucaucuugguaaacugaaaaccaaauguggacauuuguaaaaucagugcacug uuucuagagagagauuaaauucauuuaaaaaaaa LRP8 isoform 2 - Amino acid sequence (SEQ ID NO: 14)

mglpepgplr llalllllll llllqlqhla aaaadpllgg qgpakdcekd qfqcrnerci psvwrcdedd dcldhsdedd cpkktcadsd ftcdnghcih erwkcdgeee cpdgsdesea tctkqvcpae klscgptshk cvpaswrcdg ekdceggade -continued agcatwlnec lhnnggcshi ctdlkigfec tcpagfqlld qktcgdidec kdpdacsqic vnykgyfkce cypgyemdll tknckaaagk spsliftnrh evrridlvkr nysrlipmlk nvvaldveva tnriywcdls yrkiysaymd kasdpkeqev lideqlhspe glavdwvhkh iywtdsgnkt isvatvdggr rrtlfsrnls epraiavdpl rgfmywsdwg dqakieksgl ngvdrqtlvs dniewpngit ldllsqrlyw vdsklhqlss idfsggnrkt lisstdflsh pfgiavfedk vfwtdlenea ifsanrlngl eisilaenln nphdivifhe lkqprapdac elsvqpnggc eylclpapqi sshspkytca cpdtmwlgpd mkrcyrapqs tstttlastm trtvpattra pgttvhrsty qnhstetpsl taavpssvsv prapsispst lspatsnhsq hyanedskmg stvtaavigi ivpivviall cmsgyliwrn wkrkntksmn fdnpvyrktt eeededelhi grtaqighvy paaissfdrp lwaepclget repedpapal kelfvlpgep rsqlhqlpkn plselpvvks krvalsledd glp LRP8 isoform 3 - RNA sequence (SEQ ID NO: 15)

gcuggcggcggccgcccagggccggggccgcgcgcccagccugagcccgccccgccgccgagcgucaccgaaccugcuugaaa ugcagccgaggagccggggcgggcggcagcggcggcggcggcggcgggggcagcggcaaccccggcgccgcggcaagga cucggagggcugagacgcggcggcggcggcgcggggagcgcggggcgcggcggccggagccccgggcccgccaugggccucc ccgagccgggcccucuccggcuucuggcgcugcugcugcugcugcugcugcugcugcugcagcuccagcaucuugcggc ggcagcggcugauccgcugcucggcggccaagggccggccaaggauugcgaaaaggaccaauuccagugccggaacgagcgc ugcauccccucuguguggagaugcgacgaggacgaugacugcuuagaccacagcgacgaggacgacugccccaagaagaccug ugcagacagugacuucaccugugacaacggccacugcauccacgaacgguggaagugugacggcgaggaggaguguccugau ggcuccgaugaguccgaggccacuugcaccaagcaggugugucc ugcagagaagcugagcuguggacccaccagccacaagu guguaccugccucguggcgcugcgacggggagaaggacugcgaggguggagcggaugaggccggcugugcuaccucacugg gcaccugccguggggacgaguuccaguguggggaugggacauguguccuugcaaucaagcacugcaaccaggagcaggacug uccagaugggagugaugaagcuggcugccuacaggggcugaacgagugucugcacaacaauggcggcugcucacacaucugc acugaccucaagauuggcuuugaaugcacgugcccagcaggcuuccagcuccuggaccagaagaccuguggcgacauugaug agugcaaggacccagaugccugcagccagaucugugucaauuacaagggcuauuuuaagugugagugcuacccuggcuacga gauggaccuacugaccaagaacugcaaggcugcugcuggcaagagcccaucccuaaucuucaccaaccggcacgaggugcgga ggaucgaccuggugaagcggaacuauucacgccucauccccaugcucaagaaugucguggcacuagauguggaaguugccac caaucgcaucuacuggugugaccucuccuaccguaagaucuauagcgccuacauggacaaggccagugacccgaaagagcagg agguccucauugacgagcaguugcacucuccagagggccuggcaguggacugggguccacaagcacaucuacuggacugacuc gggcaauaagaccaucucaguggccacaguugaugguggccgccgacgcacucucuucagccguaaccucagugaaccccggg ccaucgcuguugaccccugcgaggguucauguauuggucugacugggggggaccaggccaagauugagaaaucugggcucaa cgguguggaccggcaaacacuggugucagacaauauugaauggcccaacggaaucacccuggaucugcugagccagcgcuug uacugggguagacuccaagcuacaccaacuguccagcauugacuucaguggaggcaacagaaagacgcugaucuccuccacuga cuuccugagccacccuuuugggauagcuguguuugaggacaagguguucuggacagaccuggagaacgaggccauuuucag ugcaaaucggcucaauggccuggaaaucuccauccuggcugagaaccucaacaacccacaugacauugucaucuuccaugagc ugaagcagccaagagcuccagaugccugugagcugaguguccagccuaauggaggcugugaauaccugugccuuccugcucc ucagaucuccagccacucucccaaguacacaugugccuguccugacacaauguggcuggguccagacaugaagaggugcuacc gagaugcaaaugaagacaguaagaugggcucaacagucacugccgcuguuaucgggaucaucgugcccauaguggugauagc ccuccugugcaugaguggauaccugaucuggagaaacuggaagcggaagaacaccaaaagcaugaauuuugacaacccagucu acaggaaaacaacagaagaagaagacgaagaugagcuccauauagggagaacugcucagauuggccaugucuauccugcacga guggcauuaagccuugaagaugauggacuacccugaggaugggaucacccccuucgugccucauggaauucagucccaugca cuacacucuggaugguguaugacuggaugaauggguuucuauauaugggucugugugaguguaugugugugugugauuuu uuuuuuaaauuuauguugcggaaagguaaccacaaaguuaugaugaacugcaaacauccaaaggaugugagaguuuuucuau -continued guauaauguuuuauacacuuuuuaacugguugcacuacccaugaggaauucguggaauggcuacugcugacuaacaugaugc acauaaccaaaugggggccaauggcacaguaccuuacucaucauuuaaaaacuauauuuacagaagauguugguugcuggg ggggcuuuuuuagguuuuggggcauuuguuuuuuguaaauaagaugauuaugcuuuguggcuauccaucaacauaaguaaa aaaaaaaaaaaaacacuucaacucccucccccauuuagauuauuuauuaacauauuuaaaaaucagaugaguucuauaaauaa uuuagagaagugagaguauuuauuuuuggcauguuuggcccaccacacagacucuguguguguauguguguguuuauaugu guauguguguguacagaaaaaucuguagagaagaggcacaucuauggcuacuguucaaauacauaaagauaaauuuauuuuca cacaguccacaagggguauaucuuguaguuucagaaaagccuuuggaaaucuggaucagaaaauagauaccaugguuugug caauuauguaguaaaaaaggcaaaucuuuucaccucuggcuauuccugagaccccaggaagucaggaaaagccuuucagcuca cccauggcugcugugacuccuaccagggcuuucuuggcuuuggcgaaggucaguguacagacauuccaugguaccagagugc ucagaaacucaagauaggauaugccucacccucagcuacuccuuguuuuaaaguucagcucuuugaguaacuucuucaauuu cuuucaggacacuuggguugaauucaguaaguuuccucugaagcacccugaagggugccauccuuacagagcuaaguggaga cguuuccagaucagcccaaguuuacuauagagacuggcccaggcacugaaugucuaggacaugcuguggaugaagauaaaga ugguggaauagguuuuaucacaucucuuauuucucuuuuccccuuacucucuaccauuuccuuuaugugggaaacauuuu aagguaauaaauagguuacuuaccaucauauguucauauagaugaaacuaauuuuuggcuuaagucagaacaacuggccaaaa uugaagucauauuugaggggggaaauggcauacgcaauauuauauuauauuggauauuuauguucacacaggaauuugguu uacugcuuuguaaauaaaaggaaaaacuccggguauauguauagauguucuucauuauagacaucuucuuugcuuuucuug gccuuggggggaggaagggagaagugcucuuuucuacuuguggggucucccauuggaaacauaauccuauagucccagaagga uucaguccccaguggcuuucccauccaaagagaaagaguuugaguuucuuaacucugcuguucugccacuuacucccacuag acaaccagggacaaggugcaacauggaaguguuugacuuaaguaggagcagaggagcugcaucuaaucucaucauaccugga acuugacacacuuaagcaaaugccuucccaucccuaccugccagaugcccccaacucaaugaaguuggaugucucaccagcuu gauacccuuugaauuuucagucagacauucuggaguucuagcauccuguaccuaggaccuuccucugugucacucuuggccu ccuaaacucuaagaaaauaacuauauucuggagcuugggcagugugguuuugcauaauccagcaaucuccucaugacaugcau guguugauaguccugaaacauucauugagaggguaaaugcaguugaccuagaaugaccaauaccaaacagaauuuuaagaaca gguggccaacuccuauggagcuuacucacauauuacuauucuuuuaagaacggaaaguaaaauuauuuuugacugaagaaaa augaugacagugaaaaacauggaaauguacucaaaacaagugacuuuuucuguaaccuuccaaagaaacugaauuuuccaagg aauuaaaugauaacaguggcuaaggcauaguuucuaaacuuucaguaagauccuggcauucacagaaaaaaaugaugaaugg ggucuggacauacagccugagaucucaaaaugacaaugaaauucacaacuuuuucucagagacauucauguuuccugcauau gcuacaacugcaguuugaaagaggcagcaaugggagcaacccuuuacaagaaacaaauugugauauauucauguguuggacg gcaguaaauaagaugaaaccugaggagucagauccaccuucccccauucauagaggcuuuucagccucauuuugagguacag uuacauaucuuuugccuuuugcccccgugcauagcuaucuacagccaaucacagaucacagagucacuggacuauagagcug gaaggaagcucagagacaaugccaaggggggcagaaaauuuaucagaagccagucccagugcguuuccuccauuuccuucugca ggaagacuauuuugggcugccugaacauuguaucaaaccugcuaccuauacuauggucuaccuuuccuccaguggaauuaca aaggcacuaacugaaaugccuucuagaaacagagaaaacgaaacuguacuuauuuacucuugauacacagauuauuuauaaaa cagauugaaguaaccuguuaacuggcaaaaagagaaugagaucggauuuaaauguauggcaguaaguccuauugaucccucc aguuaucucaguaugacugcaguauauucauucacuaaaaccacucacuagauaccaacuacacaccuggcacugcagaugua aaggucagucacacauguucugacuuuacagaguucacaguagcaguggaggaugauauauguggaaacaaaaaaggcauug auucuauucagagcacuguuagggcucaaaggagagaggggucuuuccaccuaagaaaugaggaauagggucaucauagaag ugaccuuaagucuuaaaaauuaagaaggggauuccaagcugcuucagacagagacacaucgagcuaaaacacagagguaugaa agagcacagggacuuuaggaauugcacaguucauucuaacaggaacaaaaggcucaagggggggcaagaaaugaggcuguaug gaaagagauucaauguaagcacuuuauaaaauagauuaauuucugauucaaugaagcauuucuugaucauuguguacaaggc acuacaugcaucauggaaaauucauuaggaugcauugccagcacuuugcagaacugauauuauucagccucaagcuuuccag -continued uggccaaagggaaaugcugacugcuuuucauauauuugagucaaagauuuuuuauauggucaaugaagacuaauauaagggc agugggauuuucacagaugcaugccauguugucgagagccucuuagauuuucucaacugugagaaagaaaaacgaaaauguu gaagacguugagucuggagaggggauacuaaucacuguccaguugggcacugguggaauggggaaauggcacaggaaugc aagccucuccacccuacccccccgaacuccagccauacacucaucguuucacaaaauauaaaugaguuagcauuaaaauguuucag aguaaauaauuccuuuucccgaaaugcaugaagauagaguaacagacuucucacacuguauuuuuaggguauggagaauuua gaagguuaaagaauuacugcuucaauuuuucaguuaaaaaaaaaucaggaagcucuguucauucaggcuaugcaccaugugc acagucaagaauuagcagaaacccucugcauuuacaaacacuuugugcuauaaaaaaguaauuuuuaaaaagccacgugugug ugugugauauauauauauauauauauauauauuuaaagccaagguuuugauacuuuuuuacaaaaacuacaagagaaaacaaaua uaccuguccaaaccauauacuuuuaaaagagcauuuuuuuuuccauacaagcuguuguuaauuuggggguaaagugcugauu ugcaaacuucaucaaauuguucccaaguggauucuccuuguuugucucccccuaccaaccccaaaguuaccauauuugaugua agaaucaggcauguuagaauguugugucacacuaacugauucugcucuuuuugucuugucauucaaguuccguuagcuucu guacgcggugcccuuugcagucuggugucucuuccagaggcgagggggcugaggauggggugcugcaucucacuagcuaua cuggcaucaucuugguaaacugaaaaccaaauguggacauuuguaaaaucagugcacuguuucuagagagagauuaaauuca uuuaaaaaaaa LRP8 isoform 3 - Amino acid sequence (SEQ ID NO: 16)

mglpepgplr llallllllll llllqlqhla aaaadpllgg qgpakdcekd qfqcrnerci psvwrcdedd dcldhsdedd cpkktcadsd ftcdnghcih erwkcdgeee cpdgsdesea tctkqvcpae klscgptshk cvpaswrcdg ekdceggade agcatslgtc rgdefqcgdg tcvlaikhcn qeqdcpdgsd eagclqglne clhnnggcsh ictdlkigfe ctcpagfqll dqktcgdide ckdpdacsqi cvnykgyfkc ecypgyemdl ltknckaaag kspsliftnr hevrridlvk rnysrlipml knvvaldvev atnriywcdl syrkiysaym dkasdpkeqe vlideqlhsp eglavdwvhk hiywtdsgnk tisvatvdgg rrrtlfsrnl sepraiavdp lrgfmywsdw gdqakieksg lngvdrqtlv sdniewpngi tldllsqrly wvdsklhqls sidfsggnrk tlisstdfls hpfgiavfed kvfwtdlene aifsanrlng leisilaenl nnphdivifh elkqprapda celsvqpngg ceylclpapq isshspkytc acpdtmwlgp dmkrcyrdan edskmgstvt aavigiivpi vviallcmsg yliwrnwkrk ntksmnfdnp vyrktteeed edelhigrta qighvyparv alsleddglp LRP8 isoform 4 - RNA sequence (SEQ ID NO: 17)

gcuggcggcggccgcccagggccggggccgcgcgcccagccugagcccgccccgccgccgagcgucaccgaaccugcuugaaa ugcagccgaggagccggggcgggcggcagcggcggcggcggcggcggcgggggcagcggcaaccccggcgccgcggcaagga cucggagggcugagacgcggcggcggcggcgcggggagcgcggggcgcggcggccggagccccgggcccgccaugggccucc ccgagccgggcccucuccggcuucuggcgcugcugcugcugcugcugcugcugcugcugcugcagcuccagcaucuugcggc ggcagcggcugauccgcugcucggcggccaagggccggccaaggauugcgaaaaggaccaauuccagugccggaacgagcgc ugcauccccucuguguggagaugcgacgaggacgaugacugcuuagaccacagcgacgaggacgacugccccaagaagaccug ugcagacagugacuucaccugugacaacggccacugcauccacgaacgguggaagugugacggcgaggaggagguguccugau ggcuccgaugaguccgaggccacuugcaccaagcaggugugucccugcagagaagcugagcuguggacccaccagccacaagu guguaccugccucguggcgcugcgacggggagaaggacugcgaggguggagcggaugaggccggcugugcuaccuugugcg ccccgcacgaguuccagugcggcaaccgcucgugccuggccgcccguguucgugugcgacggcgacgacgacuguggugacgg cagcgaugagcgcggcugugcagacccggccugcgggcccccgcgaguuccgcugcggcggcgauggcggcggcgccugcauc ccggagcgcugggucugcgaccgccaguuugacugcgaggaccgcucggacgaggcagccgagcucugcggccguccgggcc ccggggccacguccgcgcccgccgccugcgccaccgccucccaguucgccugccgcagcggcgagugcgugcaccugggcug gcgcugcgacggcgaccgcgacugcaaagacaaaucggacgaggccgacugcccacugggcaccugccgugggggacgaguucc agugugggggaugggacauguguccuugcaaucaagcacugcaaccaggagcaggacuguccagaugggagugaugaagcugg -continued cugccuacaggggcugaacgagugucugcacaacaauggcggcugcucacacaucugcacugaccucaagauuggcuuugaa ugcacgugcccagcaggcuuccagcucccuggaccagaagaccuguggcgacauugaugagugcaaggacccagaugccugca gccagaucuguguguagucaauuacaagggcuauuuuaagugugagugcuacccuggcuacgagauggaccuacugaccaagaacug caaggcugcugcuggcaagagcccaucccuaaucuucaccaaccggcacgaggugcggaggaucgaccuggugaagcggaacu auucacgccucaucccccaugcucaagaaugucguggcacuagauguggaaguugccaccaaucgcaucuacuggugugaccu cuccuaccguaagaucuauagcgccuacauggacaaggccagugacccgaaagagcaggagguccucauugacgagcaguugc acucuccagagggccuggcaguggacugggucccacaagcacaucuacuggacugacucgggcaauaagaccaucucaguggcc acaguugauggugggccgccgacgcacucucuucagccguaaccucagugaaccccgggccaucgcuguugacccccugcgag gguucauguauuggucugacugggggggaccaggccaagauugagaaaucugggcucaacgguguggaccggcaaacacugg ugucagacaauauugaauggcccaacggaaucacccuggaucugcugagccagcgcuuguacuggguagacuccaagcuacac caacuguccagcauugacuucaguggaggcaacagaaagacgcugaucuccuccacugacuuccugagccacccuuuugggau agcuguguuugaggacaagguguucuggacagaccuggagaacgaggccauuuucagugcaaaucggcucaauggccuggaa aucuccauccuggcugagaaccucaacaacccacaugacauugucaucuuccaugagcugaagcagccaagagcuccagaugc cugugagcugaguguccagccuaauggaggcugugaauaccugugccuuccugcucccucagaucuccagccacucucccaag uacacaugugccuguccugacacaaugugcugggucccagacaugaagaggugcuaccgagcaccucaaucuaccucaacuac gacguuagcuucuaccaugacgaggacaguaccugccaccacaagagcccccgggaccaccguccacagauccaccuaccagaa ccacagcacagagacaccaagccugacagcugcagucccaagcucaguuagugucccccagggcucccagcaucagcccgucuac ccuaagcccugcaaccagcaaccacucccagcacuaugcaaaugaagacaguaagaugggcucaacagucacugccgcuguua ucgggaucaucgugcccauaguggugauagcccuccugugcaugaguggauaccugaucuggagaaacuggaagcggaagaa caccaaaagcaugaauuuugacaacccagucuacaggaaaacaacagaagaagaagacgaagaugagcuccauauagggagaac ugcucagauuggccaugucuauccugcacgaguggcauuaagccuugaagaugauggacuacccugaggaugggaucacccc cuucgugccucauggaauucagucccaugcacuacacucuggaugguguaugacuggaugaaugguuucuauauaugggu cugugugaguguaugugugugugugauuuuuuuuuuaaauuuauguugcggaaagguaaccacaaaguuaugaugaacugc aaacauccaaaggaugugagaguuuuucuauguauaaauguuuuauacacuuuuuaacugguugcacuacccaugaggaauuc guggaauggcuacugcugacuaacaugaugcacauaaccaaaugggggccaauggcacaguaccuuacucaucauuuaaaaac uauauuuacagaagauguuugguugcugggggggcuuuuuuagguuuuggggcauuuguuuuuuguaaauaagaugauua ugcuuuguggcuauccaucaacauaaguaaaaaaaaaaaaaaaacacuucaacucccucccccauuuagauuauuuauuaaca uauuuuaaaaaucagaugaguucuauaaauaauuuagagaagugagaguauuuauuuuuggcauguuuggcccaccacacag acucugugugugauguguguguuuauauguguaugugugugacagaaaaaucuguagagaagaggcacaucuauggcuac uguucaaauacauaaagauaaauuuauuuucacacaguccacaagggguauaucuuguaguuuucagaaaagccuuuggaaa ucuggaucagaaaauagauaccaugguuugugcaauuauguaguaaaaaaggcaaaucuuuucaccucuggcuauuccugag accccaggaagucaggaaaagccuuucagcucacccauggcugcugugacuccuaccagggcuuucuuggcuuuggcgaagg ucaguguacagacauuccaugguaccagagugcucagaaacucaagauaggauaugccucacccucagcuacuccuuguuuua aaguucagcucuuugaguaacuucuucaauuucuuucaggacacuuggguugaauucaguaaguuuccucugaagcacccug aagggugccauccuuacagagcuaaguggagacguuuccagaucagcccaaguuuacuauagagacuggcccaggcacugaa ugucuaggacaugcuguggaugaagauaaagaugguggaauagguuuuaucacaucucuuauuucucuuuccccuuacuc ucuaccauuuccuuuauguggggaaacauuuuaagguaauaaaauagguuacuuaccaucauauguucauauagaugaaacua auuuuuggcuuaagucagaacaacuggccaaaauugaagucauauuugagggggaaauggcauacgcaauauuauauuaua uuggauauuuauguucacacaggaauuugguuuacugcuuuguaaauaaaaggaaaaacuccggguauauguauagauguu cuucauuauagacaucuucuuugcuuuucuuggccuugggggaggaagggagaagugcucuuuucuacuugugggggucucc cauuggaaacauaauccuauaguccagaaggauucaguccccaguggcuuucccauccaaagagaaagaguuugaguuucu -continued uaacucugcuguucugccacuuacucccacuagacaaccagggacaaggugcaacauggaaguguuugacuuaaguaggagc agaggagcugcaucuaaucucaucauaccuggaacuugacacacuuaagcaaaugccuucccaucccuaccugccagaugccc ccaacucaaugaaguuggaugucucaccagcuugauacccuuugaauuuucagucagacauucuggaguucuagcauccugu accuaggaccuuccucugugucacucuuggccuccuaaacucuaagaaaauaacuauauucuggagcuugggcagugugu uu ugcauaauccagcaaucuccucaugacaugcauguguugauaguccugaaacauucauugagagguaaaugcaguugaccu agaaugaccaauaccaaacagaauuuuaagaacagguggccaacuccuauggagcuuacucacauauuacuauucuuuuaaga acggaaaguaaaauuauuuuugacugaagaaaaaugaugacagugaaaaacauggaaauguacucaaaacaagugacuuuuuc uguaaccuuccaaagaaacugaauuuuccaaggaauuaaaugauaacaguggcuaaggcauaguuucuaaacuuucaguaaga uccuggcauucacagaaaaaaaugaugaauggggucuggacauacagccugagaucucaaaaugacaaugaaauucacaacuu uuucucagagacauucauguuuccugcauaugcuacaacugcaguuugaaagaggcagcaaugggagcaacccuuuacaaga aacaaauugugauauauucauguguuggacggcaguaaauaagaugaaaccugaggagucagauccaccuucccccauucaua gaggcuuuucagccucauuuugagguacaguuacauaucuuuugccuuuugcccccgugcauagcuaucuacagccaaucac agaucacagagucacuggacuauagagcuggaaggaagcucagagacaaugccaagggggcagaaaauuuaucagaagccagu cccagugcguuuccuccauuuccuucugcaggaagacuauuuugggcugccugaacauuguaucaaaccugcuaccuauacu auggucuaccuuuccuccaguggaauuacaaaggcacuaacugaaaugccuucuagaaacagagaaaacgaaacuguacuuau uuacucuugauacacagauuauuuauaaaacagauugaaguaaccuguuaacuggcaaaaagagaaugagaucggauuuaaa uguauggcaguaaguccuauugaucccuccaguuaucucaguaugacugcaguauauucauucacuaaaaccacucacuaga uaccaacuacacaccuggcacugcagauguaaaggucagucacacauguucugacuuuacagaguucacaguagcaguggagg augauauauguggaaacaaaaaaggcauugauucuauucagagcacuguuagggcucaaaggagagaggggucuuuccaccu aagaaaugaggaauagggucaucauagaagugaccuuaagucuuaaaaauuaagaaggggauuccaagcugcuucagacaga gacacaucgagcuaaaacacagagguaugaaagagcacagggacuuuaggaauugcacaguucauucuaacaggaacaaaagg cucaagggggcaagaaaugaggcuguauggaaagagauucaauguaagcacuuuauaaaauagauuaauuucugauucaau gaagcauuucuugaucauuguguacaaggcacuacaugcaucauggaaaauucauuaggaugcauugccagcacuuugcaga acugauauuauucagccucaagcuuuccaguggccaaagggaaaugcugacugcuuuucauauauuugagucaaagauuuuu uauauggucaaugaagacuaauauaagggcagugggauuuucacagaugcaugccauguugucgagagccucuuagauuuuc ucaacugugagaaagaaaaacgaaaauguugaagacguugagucuggagaggggauacuaaucacuguccaguugggcacug gugggaauggggaaauggcacaggaaugcaagccucuccacccuacccccccgaacuccagccauacacucaucguuucacaaa auauaaaugaguuagcauuaaauguuucagaguaaauaauuccuuuucccgaaaugcaugaagauagaguaacagacuucuc acacuguauuuuuaggguauggagaauuuagaagguuaaagaauuacugcuucaauuuuucaguuaaaaaaaaaucaggaag cucuguucauucaggcuaugcaccaugugcacagucaagaauuagcagaaacccucugcauuuacaaacacuuugugcuauaa aaaaguaauuuuuaaaaagccacgugugugugugugu auauauauauauauauauauauuuaaagccaagguuuugauacuu uuuuacaaaaacuacaagagaaaacaaauauaccuguccaaaccauauacuuuuaaaagagcauuuuuuuuuccauacaagcu guuguuaauuugggguaaagugcugauuugcaaacuucaucaaauuguucccaaguggauucuccuuguuugucuccccc uaccaaccccaaaguuaccauauuugauguaagaaucaggcauguuagaauguugugucacacuaacugauucugcucuuuu ugucuugucauucaaguuccguuagcuucuguacgcggugcccuuugcagucuggugucucuuccagaggcgagggggcug aggaugggggugcugcaucucacuagcuauacuggcaucaucuugguaaacugaaaaccaaauguggacauuuguaaaaucag ugcacuguuucuagagagagauuaaauucauuuaaaaaaaa LRP8 isoform 4 - Amino acid sequence (SEQ ID NO: 18)

mglpepgplr llalllllll llllqlqhla aaaadpllgg qgpakdcekd qfqcrnerci psvwrcdedd dcldhsdedd cpkktcadsd ftcdnghcih erwkcdgeee cpdgsdesea tctkqvcpae klscgptshk cvpaswrcdg ekdceggade -continued agcatlcaph efqcgnrscl aavfvcdgdd dcgdgsderg cadpacgpre frcggdggga ciperwvcdr qfdcedrsde aaelcgrpgp gatsapaaca tasqfacrsg ecvhlgwrcd gdrdckdksd eadcplgtcr gdefqcgdgt cvlaikhcnq eqdcpdgsde agclqglnec lhnnggcshi ctdlkigfec tcpagfqlld qktcgdidec kdpdacsqic vnykgyfkce cypgyemdll tknckaaagk spsliftnrh evrridlvkr nysrlipmlk nvvaldveva tnriywcdls yrkiysaymd kasdpkeqev lideqlhspe glavdwvhkh iywtdsgnkt isvatvdggr rrtlfsrnls epraiavdpl rgfmywsdwg dqakieksgl ngvdrqtlvs dniewpngit ldllsqrlyw vdsklhqlss idfsggnrkt lisstdflsh pfgiavfedk vfwtdlenea ifsanrlngl eisilaenln nphdivifhe lkqprapdac elsvqpnggc eylclpapqi sshspkytca cpdtmwlgpd mkrcyrapqs tstttlastm trtvpattra pgttvhrsty qnhstetpsl taavpssvsv prapsispst lspatsnhsq hyanedskmg stvtaavigi ivpivviall cmsgyliwrn wkrkntksmn fdnpvyrktt eeededelhi grtaqighvy parvalsled dglp CTGF - RNA sequence (SEQ ID NO: 19)

aaacucacacaacaacucuuccccgcugagaggagacagccagugcgacuccacccuccagcucgacggcagccgccccggccg acagccccgagacgacagcccggcgcgucccggucccaccuccgaccaccgccagcgcuccaggccccgccgcuccccgcucg ccgccaccgcgcccuccgcuccgcccgcagugccaaccaugaccgccgccaguaugggccccguccgcgucgccuucgugguc cuccucgcccucugcagccggccggccgucggccagaacugcagcgggccgugccggugcccggacgagccggcgccgcgcu gcccggcgggcgugagccucgugcuggacggcugcggcugcugccgcgucugcgccaagcagcugggcgagcugugcaccga gcgcgaccccugcgacccgcacaagggccucuucugugacuucggcuccccggccaaccgcaagaucggcgugugcaccgcca aagaugguguucccugcaucuucgguggua cgguguaccgcagcggagaguccuuccagagcagcugcaaguaccagugcac gugccuggacggggcggugggcugcaugccccugugcagcauggacguucgucugcccagcccugacugccccuucccgagg agggucaagcugcccgggaaaugcugcgaggagugggugugugacgagcccaaggaccaaaccgugguugggccugcccucg cggcuuaccgacuggaagacacguuuggcccagacccaacuaugauuagagccaacugccugguccagaccacagaguggagc gccuguuccaagaccugugggaugggcaucuccacccggguuaccaaugacaacgccuccugcaggcuagagaagcagagccg ccugugcauggucaggccuugcgaagcugaccuggaagagaacauuaagaagggcaaaaagugcauccguacucccaaaaucu ccaagccuaucaaguuugagcuuucuggcugcaccagcaugaagacauaccgagcuaaauucuguggaguauguaccgacgg ccgaugcugcacccccacagaaccaccacccugccgguggaguucaagugcccugacggcgaggucaugaagaagaacauga uguucaucaagaccugugccugccauuacaacugucccggagacaaugacaucuuugaaucgcuguacuacaggaagaugua cggagacauggcaugaagccagagagugagagacauuaacucauuagacuggaacuugaacugauucacaucucauuuuucc guaaaaaugauuucaguagcacaaguuauuuaaaucuguuuuucuaacuggggga aaagauucccacccaauucaaaacauu gugccaugucaaacaaauagucuaucaaccccagacacugguuugaagaauguuaagacuugacaguggaacuacauuaguac acagcaccagaauguauauuaagguguggcuuuaggagcagugggaggguaccagcagaaagguuaguaucaucagauagca ucuuauacgaguaauaugccugcuauuugaaguguaauugagaaggaaaauuuuagcgugcucacugaccugccuguagccc cagugacagcuaggaugugcauucuccagccaucaagagacugagucaaguuguuccuuaagucagaacagcagacucagcuc ugacauucugauucgaaugacacuguucaggaaucggaauccugucgauuagacuggacagcuuguggcaagugaauuugcc uguaacaagccagauuuuuuaaaauuuauauuguaaauauugugugugugugugugugugugguauauauauauauauguacag uuaucuaaguuaauuuaaaguuguuugugccuuuuuauuuuuguuuuuaaugcuuugauauuucaauguuagccucaauu ucugaacaccauagguagaauguaaagcuugucugaucguucaaagcaugaaauggauacuuauauggaaauucugcucaga uagaaugacaguccgucaaaacagauuguuugcaaaggggaggcaucaguguccuuggcaggcugauuucuagguaggaaau gugguagccucacuuuuaaugaacaaauggccuuuauuaaaaacugagugacucuauauagcugaucaguuuuuucaccugg aagcauuuguuucuacuuugauaugacuguuuuucggacaguuuauuuguugagagugugaccaaaguuacauguuugca ccuuucuaguugaaaauaaaguguauauuuuuucuauaaaaaaaaaaaaaaaaa -continued CTGF - Amino Acid sequence (SEQ ID NO: 20)

mtaasmgpvr vafvvllalc srpavgqncs gpcrcpdepa prcpagvslv ldgcgccrvc akqlgelcte rdpcdphkgl fcdfgspanr kigvctakdg apcifggtvy rsgesfqssc kyqctcldga vgcmplcsmd vrlpspdcpf prrvklpgkc ceewvcdepk dqtvvgpala ayrledtfgp dptmirancl vqttewsacs ktcgmgistr vtndnascrl ekqsrlcmvr pceadleeni kkgkkcirtp kiskpikfel sgctsmktyr akfcgvctdg rcctphrttt lpvefkcpdg evmkknmmfi ktcachyncp gdndifesly yrkmygdma LXR-a isoform 1: RNA sequence (SEQ ID NO: 21)

aggaaggaggggguggccugaccccucggcagucccucccccucagccuuuccccaaauugcuacuucucuggggcuccagguc cugcuugugcucagcuccagcucacuggcuggccaccgagacuucuggacaggaaacugcaccauccucuucucccagcaagg gggcuccagagacugcccacccaggaagucugguggccuggggauuuggacagugccuugguaaugaccagggcuccaggaa gagauguccuuguggcugggggccccugugccugacauuccuccugacucugcgguggagcuguggaagccaggcgcacag gaugcaagcagccaggcccagggaggcagcagcugcauccucagagaggaagccaggaugccccacucugcugggggguacug caggggugggggcuggaggcugcagagcccacagcccugcucaccagggcagagcccccuucagaacccacagagauccgucca caaaagcggaaaaaggggccagcccccaaaaugcuggggaacgagcuaugcagcgugugugggggacaaggccucgggcuucc acuacaauguucugagcugcgagggcugcaagggauucuuccgccgcagcgucaucaagggagcgcacuacaucugccacag uggcggccacugccccauggacaccuacaugcgucgcaagugccaggagugucggcuucgcaaaugccgucaggcuggcaug cgggaggagugugucugucagaagaacagauccgccugaagaaacugaagcggcaagaggaggaacaggcucaugccacauc cuugcccccccagggcuuccucaccccccccaaauccugccccagcucagcccggaacaacugggcaugaucgagaagcucgucg cugcccagcaacaguguaaccggcgcuccuuuucugaccggcuucgagucacgccuuggcccauggcaccagaucccccauagc cgggaggcccgucagcagcgcuuugcccacuucacugagcuggccaucgucucugugcaggagauaguugacuuugcuaaac agcuacccggcuuccugcagcucagccgggaggaccagauugcccugcugaagaccucugcgaucgaggugaugcuucugga gacaucucggagguacaacccugggagugagaguaucaccuuccucaaggauuucaguuauaaccgggaagacuuugccaaa gcagggcugcaaguggaauucaucaaccccaucuucgaguucuccagggccaugaaugagcugcaacucaaugaugccgagu uugccuugcucauugcuaucagcaucuucucugcagaccggcccaacgugcaggaccagcuccagguagagaggcugcagca cacauauguggaagcccugcaugccuacgucuccauccaccauccccaugaccgacugauguucccacggaugcuaaugaaac uggugagccuccggacccugagcagcguccacucagagcaaguguuugcacugcgucugcaggacaaaaagcucccaccgcug cucucugagaucugggaugugcacgaaugacuguucuguccccauauuuucuguuuucuuggccggauggcugaggccugg uggcugccuccuagaaguggaacagacugagaagggcaaacauuccugggagcugggcaaggagauccuccccguggcauuaa aagagagucaaaggguugcgaguuuuguggcuacugagcaguggagcccucgcuaacacugugcugugucugaagaucaug cugaccccacaaacggaugggccugggggccacuuugcacaggguucuccagagcccugcccauccugccuccaccacuuccu guuuucccacagggccccaagaaaaauucuccacugucaaaaaaaaa LXR-a (NR1H3) isoform 1: Amino acid sequence (SEQ ID NO: 22)

mslwlgapvp dippdsavel wkpgaqdass qaqggsscil reearmphsa ggtagvglea aeptalltra eppsepteir pqkrkkgpap kmlgnelcsv cgdkasgfhy nvlscegckg ffrrsvikga hyichsgghc pmdtymrrkc qecrlrkcrq agmreecvls eeqirlkklk rqeeeqahat slpprasspp qilpqlspeq lgmieklvaa qqqcnrrsfs drlrvtpwpm apdphsrear qqrfahftel aivsvqeivd fakqlpgflq lsredqiall ktsaievmll etsrrynpgs esitflkdfs ynredfakag lqvefinpif efsramnelq lndaefalli aisifsadrp nvqdqlqver lqhtyvealh ayvsihhphd rlmfprmlmk lvslrtlssv hseqvfalrl qdkklpplls eiwdvhe LXR-a (NR1H3) isoform 2: RNA sequence (SEQ ID NO: 23)

aggaaggaggggguggccugaccccucggcagucccucccccucagccuuuccccaaauugcuacuucucuggggcuccagguc cugcuugugcucagcuccagcucacuggcuggccaccgagacuucuggacaggaaacugcaccauccucuucucccagcaagg -continued gggcuccagagacugcccacccaggaagucugguggccuggggauuuggacagugccuugguaaugaccagggcuccaggaa gagauguccuuguggcugggggccccugugccugacauucccucugacucugcgguggagcuguggaagccaggcgcacag gaugcaagcagccaggcccagggaggcagcagcugcauccucagagaggaagccaggaugccccacucugcugggggguacug caggggugggggcuggaggcugcagagcccacagcccugcucaccagggcagagccccccuucagaacccacagagauccgucca caaaagcggaaaaaggggccagcccccaaaaugcuggggaacgagcuaugcagcgugugugggggacaaggccucgggcuucc acuacaauguucugagcugcgagggcugcaagggauucuuccgccgcagcgucaucaagggagcgcacuacaucugccacag uggcggccacugccccauggacaccuacaugcgucgcaagugccaggagugucggcuucgcaaaugccgucaggcuggcaug cgggaggagugugucccugucagaagaacagauccgccugaagaaacugaagcggcaagaggaggaacaggcucaugccacauc cuugcccccccagggcuuccucacccccccaaauccugccccagcucagcccggaacaacugggcaugaucgagaagcucgucg cugcccagcaacaguguaaccggcgcuccuuuucugaccggcuucgagucacggugaugcuucuggagacaucucggaggua caacccugggagugagaguaucaccuuccucaaggauuucaguuauaaccgggaagacuuugccaaagcagggcugcaagug gaauucaucaaccccaucuucgaguucuccagggccaugaaugagcugcaacucaaugaugccgaguuugccuugcucauug cuaucagcaucuucucugcagaccggcccaacgugcaggaccagcuccagguagagaggcugcagcacacauauguggaagcc cugcaugccuacgucuccauccaccauccccaugaccgacugauguucccacggaugcuaaugaaacuggugagccuccggac ccugagcagcguccacucagagcaaguguuugcacugcgucugcaggacaaaaagcucccaccgcugcucucugagaucugg gaugugcacgaaugacuguucuguccccauauuuucuguuuucuuggccggauggcugaggccugguggcugccuccuaga aguggaacagacugagaagggcaaacauuccugggagcugggcaaggagauccucccguggcauuaaaagagagucaaaggg uugcgaguuuuguggcuacugagcaguggagcccucgcuaacacugugcugugucugaagaucaugcugaccccacaaacgg augggccugggggccacuuugcacaggguucuccagagcccugcccauccugccuccaccacuuccuguuuuucccacaggg ccccaagaaaaauucuccacugucaaaaaaaaa LXR-a (NR1H3) isoform 2: Amino acid sequence (SEQ ID NO: 24)

mslwlgapvp dippdsavel wkpgaqdass qaqggsscil reearmphsa ggtagvglea aeptalltra eppsepteir pqkrkkgpap kmlgnelcsv cgdkasgfhy nvlscegckg ffrrsvikga hyichsgghc pmdtymrrkc qecrlrkcrq agmreecvls eeqirlkklk rqeeeqahat slpprasspp qilpqlspeq lgmieklvaa qqqcnrrsfs drlrvtvmll etsrrynpgs esitflkdfs ynredfakag lqvefinpif efsramnelq lndaefalli aisifsadrp nvqdqlqver lqhtyvealh ayvsihhphd rlmfprmlmk lvslrtlssv hseqvfalrl qdkklpplls eiwdvhe LXR-a (NR1H3) isoform 3: RNA sequence (SEQ ID NO: 25)

aucuuacuuagggaccugcuggggugcggggaaaaggcgcagucucggugggauugcgugcaggagggucgugguucuggcu guggcggaggagcauaagaagacucugcgguggagcuguggaagccaggcgcacaggaugcaagcagccaggcccagggagg cagcagcugcauccucagagaggaagccaggaugccccacucugcugggggguacugcaggggugggggcuggaggcugcagag cccacagcccugcucaccagggcagagccccccuucagaacccacagagauccguccacaaaagcggaaaaaggggccagcccccc aaaaugcuggggaacgagcuaugcagcgugugugggggacaaggccucgggcuuccacuacaauguucugagcugcgagggcu gcaagggauucuuccgccgcagcgucaucaagggagcgcacuacaucugccacaguggcggccacugccccauggacaccuac augcgucgcaagugccaggagugucggcuucgcaaaugccgucaggcuggcaugcgggaggagugugucccugucagaagaac agauccgccugaagaaacugaagcggcaagaggaggaacaggcucaugccacauccuugcccccccagggcuuccucaccccccc caaauccugccccagcucagcccggaacaacugggcaugaucgagaagcucgucgcugcccagcaacaguguaaccggcgcuc cuuuucugaccggcuucgagucacgccuuggcccauggcaccagauccccauagccgggaggcccgucagcagcgcuuugcc cacuucacugagcuggccaucgucucugugcaggagauaguugacuuugcuaaacagcuacccggcuuccugcagcucagcc gggaggaccagauugcccugcugaagaccucugcgaucgaggugaugcuucuggagacaucucggagguacaacccugggag ugagaguaucaccuuccucaaggauuucaguuauaaccgggaagacuuugccaaagcagggcugcaaguggaauucaucaac -continued cccaucuucgaguucuccagggccaugaaugagcugcaacucaaugaugccgaguuugccuugcucauugcuaucagcaucu ucucugcagaccggcccaacgugcaggaccagcuccagguagagaggcugcagcacacauauguggaagcccugcaugccuac gucuccauccaccauccccaugaccgacugauguucccacggaugcuaaugaaacuggugagccuccggacccugagcagcgu ccacucagagcaaguguuugcacugcgucugcaggacaaaaagcucccaccgcugcucucugagaucugggaugugcacgaa ugacuguucuguccccauauuuucuguuuucuuggccggauggcugaggccugguggcugccuccuagaaguggaacagac ugagaagggcaaacauuccugggagcugggcaaggagaucuccccguggcauuaaaagagagucaaaggguugcgaguuuug uggcuacugagcaguggagcccucgcuaacacugugcugugucugaagaucaugcugaccccacaaacggaugggccugggg gccacuuugcacaggguucuccagagcccugcccauccugccuccaccacuuccuguuuucccacagggccccaagaaaaau ucuccacugucaaaaaaaaa LXR-a (NR1H3) isoform 3: Amino acid sequence (SEQ ID NO: 26)

mphsaggtag vgleaaepta lltraeppse pteirpqkrk kgpapkmlgn elcsvcgdka sgfhynvlsc egckgffrrs vikgahyich sgghcpmdty mrrkcqecrl rkcrqagmre ecvlseeqir lkklkrqeee qahatslppr assppqilpq lspeqlgmie klvaaqqqcn rrsfsdrlrv tpwpmapdph srearqqrfa hftelaivsv qeivdfakql pgflqlsred qiallktsai evmlletsrr ynpgsesitf lkdfsynred fakaglqvef inpifefsra mnelqlndae falliaisif sadrpnvqdq lqverlqhty vealhayvsi hhphdrlmfp rmlmklvslr tlssvhseqv falrlqdkkl ppllseiwdv he LXR-a (NR1H3) isoform 4: RNA sequence (SEQ ID NO: 27)

gauucuaacuuagcuaagcaaugcuacuggagaccauaggcaaagccaagguacagcuucagggaagucuuuggugagccca ucucucauuaccaagguaacgaagcgcagacuccgggcccggguggggcggcaucaccaccagguucacgccgagaaggagcug gaggagagccgcccggcuccagccggaccgcuugcccgccaucaccguuguaaucuaugcagcaaacaagcuggaacccgcug gguggcaccugcaagcagccgcccggacgcacccacucugcgguggagcuguggaagccaggcgcacaggaugcaagcagcca ggcccagggaggcagcagcugcauccucagagaggaagccaggaugccccacucugcuggggguacugcaggggugggggcug gaggcugcagagcccacagcccugcucaccagggcagagccccccuucagaacccacagagauccguccacaaaagcggaaaaag gggccagccccaaaaugcuggggaacgagcuaugcagcgugugugggacaaggccucgggcuuccacuacaauguucuga gcugcgagggcugcaagggauucuuccgccgcagcgucaucaagggagcgcacuacaucugccacaguggcggccacugccc cauggacaccuacaugcgucgcaagugccaggagugucggcuucgcaaaugccgucaggcuggcaugcgggaggagugugu cugucagaagaacagauccgccugaagaaacugaagcggcaagaggaggaacaggcucaugccacauccuugcccccagggc uucccucacccccccaaauccugccccagcucagcccggaacaacugggcaugaucgagaagcucgucgcugcccagcaacagu guaaccggcgcuccuuuucugaccggcuucgagucacgccuuggcccauggcaccagauccccauagccgggaggcccguca gcagcgcuuugcccacuucacugagcuggccaucgucucugugcaggagauaguugacuuugcuaaacagcuacccggcuuc cugcagcucagccgggaggaccagauugcccugcugaagaccucugcgaucgaggugaugcuucuggagacaucucggaggu acaacccugggagugagaguaucaccuuccucaaggauuucaguuauaaccgggaagacuuugccaaagcagggcugcaagu ggaauucaucaaccccaucuucgaguucuccagggccaugaaugagcugcaacucaaugaugccgaguuugccuugcucauu gcuaucagcaucuucucugcagaccggcccaacgugcaggaccagcuccagguagagaggcugcagcacacauauguggaagc ccugcaugccuacgucuccauccaccauccccaugaccgacugauguucccacggaugcuaaugaaacuggugagccuccgga cccugagcagcguccacucagagcaaguguuugcacugcgucugcaggacaaaaagcucccaccgcugcucucugagaucugg gaugugcacgaaugacuguucuguccccauauuuucuguuuucuuggccggauggcugaggccugguggcugccuccuaga aguggaacagacugagaagggcaaacauuccugggagcugggcaaggagaucuccccguggcauuaaaagagagucaaaggg uugcgaguuuuguggcuacugagcaguggagcccucgcuaacacugugcugugucugaagaucaugcugaccccacaaacgg augggccugggggccacuuugcacaggguucuccagagcccugcccauccugccuccaccacuuccuguuuucccacaggg ccccaagaaaaauucuccacugucaaaaaaaaa -continued LXR-a (NR1H3) isoform 4: Amino acid sequence (SEQ ID NO: 28)

mqqtswnplg gtckqppgrt hsavelwkpg aqdassqaqg gsscilreea rmphsaggta gvgleaaept alltraepps epteirpqkr kkgpapkmlg nelcsvcgdk asgfhynvls cegckgffrr svikgahyic hsgghcpmdt ymrrkcqecr lrkcrqagmr eecvlseeqi rlkklkrqee eqahatslpp rassppqilp qlspeqlgmi eklvaaqqqc nrrsfsdrlr vtpwpmapdp hsrearqqrf ahftelaivs vqeivdfakq lpgflqlsre dqiallktsa ievmlletsr rynpgsesit flkdfsynre dfakaglqve finpifefsr amnelqlnda efalliaisi fsadrpnvqd qlqverlqht yvealhayvs ihhphdrlmf prmlmklvsl rtlssvhseq vfalrlqdkk lppllseiwd vhe LXR-b (NR1H2) isoform 1: RNA sequence (SEQ ID NO: 29)

ucgucaaguuucacgcuccgccccucuucccggacgugacgcaagggcggggguugccggaagaaguggcgaaguuacuuuuga ggguauuugaguagcggcggugugucaggggcuaaagaggaggacgaagaaaagcagagcaagggaacccagggcaacagga guaguucacuccgcgagaggccguccacgagaccccgcgcgcagccaugagccccgcccccgcuguugcuuggagaggggc gggaccuggagagaggcugcuccgugaccccaccauguccucuccuaccacgaguucccuggauaccccccugccuggaaaug gcccccucagccuggcgcccuucuucuucacccacuguaaaggaggagggucccggagccguggcccggggguccggaccc ugaugucccaggcacugaugaggccagcucagccugcagcacagacugggucaucccagaucccgaagaggaaccagagcgca agcgaaagaagggcccagccccgaagaugcugggccacgagcuuugccgugucuguggggacaaggccuccggcuuccacua caacgugcucagcugcgaaggcugcaagggcuucuuccggcgcaguguggucgugguggggccaggcgcuaugccugccg gggugggcggaaccugccagauggacgcuuucaugcggcgcaagugccagcagugccggcugcgcaagugcaaggaggcaggg augagggagcagugcguccuuucugaagaacagauccggaagaagaagauucggaaacaacagcagcaggagucacagucaca gucgcagucaccugugggggccgcagggcagcagcagcucagccucugggccuggggcuuccccugguggaucugaggcaggc agccagggcuccggggaaggcgaggguguccagcuaacagcggcucaagaacuaaugauccagcaguuggugguggcggcccaac ugcagugcaacaaacgcuccuucuccgaccagcccaaagucacgcccuggccccugggcgcagaccccccagucccgagaugccc gccagcaacgcuuugcccacuucacggagcuggccaucaucucaguccaggagaucguggacuucgcuaagcaagugccugg uuuccugcagcugggccgggaggaccagaucgcccuccugaaggcauccacuaucgagaucaugcugcuagagacagccagg cgcuacaaccacgagacagaguguaucaccuucuugaaggacuucaccuacagcaaggacgacuuccaccgugcaggccugca gguggaguucaucaaccccaucuucgaguucucgcgggccaugcggcggcugggccuggacgacgcugaguacgcccugcuc aucgccaucaacaucuucucggccgaccggcccaacgugcaggagccgggccgcguggaggcguugcagcagcccuacgugg aggcgcugcuguccuacacgcgcaucaagaggccgcaggaccagcugcgcuucccgcgcaugcucaugaagcugguggagccu gcgcacgcugagcucugugcacucggagcaggucuucgccuugcggcuccaggacaagaagcugccgccucugcugucggag aucugggacguccacgagugaggggcuggccacccagccccacagccuugccugaccacccuccagcagauagacgccggcac cccuuccucuuccuaggguggaaggggcccugggccgagccuguagaccuaucggcucucaucccuugggauaagccccagu ccagguccaggaggcucccucccugcccagcgagucuuccagaaggggugaaaggguugcaggucccgaccacugacccuucc cggcugcccucccuccccagcuuacaccucaagcccagcacgcagugcaccuugaacagagggaggggaggacccauggcucu cccccuagcccgggagaccagggccuuccucuucccucugcuuuuauuuaauaaaaacuaaaaacagaaacaggaaaauaaaa uaugaauacaauccagcccggagcuggagugca LXR-b (NR1H2) isoform 1: Amino acid sequence (SEQ ID NO: 30)

msspttssld tplpgngppq pgapssssptv keegpepwpg gpdpdvpgtd eassacstdw vipdpeeepe rkrkkgpapk mlghelcrvc gdkasgfhyn vlscegckgf frrsvvrgga rryacrgggt cqmdafmrrk cqqcrlrkck eagmreqcvl seeqirkkki rkqqqqesqs qsqspvgpqg ssssasgpga spggseagsq gsgegegvql taaqelmiqq lvaaqlqcnk rsfsdqpkvt pwplgadpqs rdarqqrfah ftelaiisvq eivdfakqvp gflqlgredq iallkastie imlletarry nhetecitfl kdftyskddf hraglqvefi npifefsram rrlglddaey alliainifs adrpnvqepg rvealqqpyv -continued eallsytrik rpqdqlrfpr mlmklvslrt lssvhseqvf alrlqdkklp pllseiwdvh e LXR-b (NR1H2) isoform 2: RNA sequence (SEQ ID NO: 31)

ucgucaaguuucacgcuccgccccucuuccggacgugacgcaagggcggggugccggaagaaguggcgaaguuacuuuuga ggguauuugaguagcggcggugugucaggggcuaaagaggaggacgaagaaaagcagagcaagggaacccagggcaacagga guaguucacuccgcgagaggccguccacgagacccccgcgcgcagccaugagccccgcccccgcuguugcuuggagaggggc gggaccuggagagaggcugcuccgugaccccaccauguccucuccuaccacgaguucccuggauaccccccugccuggaaaug gcccccucagccuggcgccccuucuucuucacccacuguaaaggaggaggguccggagccguggcccgggggguccggaccc ugaugucccaggcacugaugaggccagcucagccugcagcacagacuggggcguccuuucugaagaacagauccggaagaag aagauucggaaacaacagcagcaggagucacagucacagucgcagucaccugugggggccgcagggcagcagcagcucagccuc ugggccuggggcuuccccugguggaucugaggcaggcagccagggcuccggggaaggcgagggguguccagcuaacagcggc ucaagaacuaaugauccagcaguuggugggcggcccaacugcagugcaacaaacgcuccuucuccgaccagcccaaagucacgc ccuggccccugggcgcagacccccagucccgagaugcccgccagcaacgcuuugcccacuucacggagcuggccaucaucuca guccaggagaucguggacuucgcuaagcaagugccugguuuccugcagcugggccgggaggaccagaucgcccuccugaagg cauccacuaucgagaucaugcugcuagagacagccaggcgcuacaaccacgagacagagguguaucaccuucuugaaggacuuc accuacagcaaggacgacuuccaccgugcaggccugcagguggaguucaucaaccccaucuucgaguucucgcgggccaugcg gcggcugggccuggacgacgcugaguacgcccugcucaucgccaucaacaucuucucggccgaccggcccaacgugcaggagc cgggccgcguggaggcguugcagcagcccuacguggaggcgcugcuguccuacacgcgcaucaagaggccgcaggaccagcu gcgcuucccgcgcaugcucaugaagcuggugagccugcgcacgcugagcucugugcacucggagcaggucuucgccuugcgg cuccaggacaagaagcugccgccucugcugucggagaucugggacguccacgagugaggggcuggccacccagccccacagcc uugccugaccacccuccagcagauagacgccggcaccccuuccucuucccuagggugggaaggggcccugggccgagccuguag accuaucggcucucaucccuugggauaagccccaguccagguccaggaggcucccucccugcccagcgagucuuccagaaggg gugaaaggguugcaggucccgaccacugacccuucccggcugcccucccucccccagcuuacaccucaagcccagcacgcagug caccuugaacagagggaggggaggacccauggcucuccccccuagcccgggagaccagggccuuccucuuccucugcuuuua uuuaauaaaaacuaaaaacagaaacaggaaaauaaaauaugaauacaauccagcccggagcuggagugca LXR-b (NR1H2) isoform 2: Amino acid sequence (SEQ ID NO: 32)

msspttssld tplpgngppq pgapssssptv keegpepwpg gpdpdvpgtd eassacstdw gvlseeqirk kkirkqqqqe sqsqsqspvg pqgssssasg pgaspggsea gsqgsgegeg vqltaaqelm iqqlvaaqlq cnkrsfsdqp kvtpwplgad pqsrdarqqr fahftelaii svqeivdfak qvpgflqlgr edqiallkas tieimlleta rrynheteci tflkdftysk ddfhraglqv efinpifefs ramrrlgldd aeyalliain ifsadrpnvq epgrvealqq pyveallsyt rikrpqdqlr fprmlmklvs lrtlssvhse qvfalrlqdk klppllseiw dvhe has-miR-199a-1 sequence (SEQ ID NO: 33)

GCCAACCCAGUGUUCAGACUACCUGUUCAGGAGGCUCUCAAUGUGUACAGUAGUC

UGCACAUUGGUUAGGC has-miR-199a-2 sequence (SEQ ID NO: 34)

AGGAAGCUUCUGGAGAUCCUGCUCCGUCGCCCCAGUGUUCAGACUACCUGUUCAG

GACAAUGCCGUUGUACAGUAGUCUGCACAUUGGUUAGACUGGGCAAGGGAGAGC

A has-miR-1908 sequence (SEQ ID NO: 35)

CGGGAAUGCCGCGGCGGGGACGGCGAUUGGUCCGUAUGUGUGGUGCCACCGGCCG

CCGGCUCCGCCCCGGCCCCCGCCCC

-continued has-miR-7-1 sequence (SEQ ID NO: 36)

UUGGAUGUUGGCCUAGUUCUGUGUGGAAGACUAGUGAUUUUGUUGUUUUUAGAU

AACUAAAUCGACAACAAAUCACAGUCUGCCAUAUGGCACAGGCCAUGCCUCUACA

G has-miR-7-2 sequence (SEQ ID NO: 37)

CUGGAUACAGAGUGGACCGGCUGGCCCCAUCUGGAAGACUAGUGAUUUUGUUGU

UGUCUUACUGCGCUCAACAACAAAUCCCAGUCUACCUAAUGGUGCCAGCCAUCGC

A has-miR-7-3 sequence (SEQ ID NO: 38)

AGAUUAGAGUGGCUGUGGUCUAGUGCUGUGUGGAAGACUAGUGAUUUUGUUGUU

CUGAUGUACUACGACAACAAGUCACAGCCGGCCUCAUAGCGCAGACUCCCUUCGA

C miR-Zip 199a-3p sequence (SEQ ID NO: 39)

GATCCGACAGTAGCCTGCACATTAGTCACTTCCTGTCAGTAACCAATGTGCAGACTA

CTGTTTTTTGAATT miR-Zip 199a-5p sequence (SEQ ID NO: 40)

GATCCGCCCAGTGCTCAGACTACCCGTGCCTTCCTGTCAGGAACAGGTAGTCTGA

ACACTGGGTTTTTGAATT miR-Zip 1908 sequence (SEQ ID NO: 41)

GATCCGCGGCGGGAACGGCGATCGGCCCTTCCTGTCAGGACCAATCGCCGTCCCCG

CCGTTTTTGAATT miR-Zip 7 sequence (SEQ ID NO: 42)

GATCCGTGGAAGATTAGTGAGTTTATTATCTTCCTGTCAGACAACAAAATCACTAGT

CTTCCATTTTTGAATT

The members of this network can be used as targets for treating metastatic melanoma. In addition, the members can be used a biomarkers for determining whether a subject has, or is at risk of having, a metastatic melanoma or for determining a prognosis or surveillance of patient having the disorder. Accordingly, the present invention encompasses methods of treating metastatic melanoma by targeting one or more of the members, methods of determining the efficacy of therapeutic regimens for inhibiting the cancer, and methods of identifying anti-cancer agent. Also provided are methods of diagnosing whether a subject has, or is at risk for having, metastatic melanoma, and methods of screening subjects who are thought to be at risk for developing the disorder. The invention also encompasses various kits suitable for carrying out the above mentioned methods.

ApoE Polypeptides

The term "polypeptide or peptide" as used herein includes recombinantly or synthetically produced fusion or chimeric versions of any of the aforementioned metastasis suppressors, having the particular domains or portions that are involved in the network. The term also encompasses an analog, fragment, elongation or derivative of the peptide (e.g. that have an added amino-terminal methionine, useful for expression in prokaryotic cells).

"Apolipoprotein polypeptide or ApoE polypeptide" as used herein means a peptide, drug, or compound that mimics a function of the native apolipoprotein either in vivo or in vitro including apolipoprotein analogs, fragments, elongations or derivatives that are a peptide of between 10 and 200 amino acid residues in length, such peptides can contain either natural, or non-natural amino acids containing amide bonds. Apolipoprotein peptide fragments may be modified to improve their stability or bioavailability in vivo as known in the art and may contain organic compounds bound to the amino acid side chains through a variety of bonds.

In one aspect, our invention is a method for using an isolated apoEp1.B peptide having the amino acid sequence TQQIRLQAEIFQAR (murine)(SEQ. ID. No.43) or AQQIRLQAEAFQAR (human)(SEQ. ID. No.44) or an analog, fragment, elongation or derivative of the peptide. The invention also includes a nucleic acid molecule encoding the apoEpI.B peptide, or an analog, fragment, elongation or derivative thereof.

The term "analog" includes any peptide having an amino acid residue sequence substantially identical to the native peptide in which one or more residues have been conservatively substituted with a functionally similar residue and which displays the ability to mimic the native peptide. Examples of conservative substitutions include the substitution of one non-polar (hydrophobic) residue such as alanine, isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such polypeptide displays the requisite activity. Analogs of the peptides include peptides having the following sequences: TAQIRLQAEIFQAR (SEQ.ID.NO.:45); TQAIRLQAEIFQAR (SEQ.ID.NO.:46); TQQARLQAEIFQAR (SEQ.ID.NO.:47) and TQQIALQAEIFQAR (SEQ.ID.NO.:48).

"Derivative" refers to a peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

The term "fragment" refers to any subject peptide having an amino acid residue sequence shorter than that of a peptide whose amino acid residue sequence is shown herein.

The term "elongation" refers to any subject peptide having an amino acid sequence longer by one or two amino acids (either at the carboxy or amino terminal end) than that of a peptide of the present invention. Preferably, the elongation occurs at the amino terminal end. Fragments and elongations of the peptides include peptides that have the following sequences: QTQQIRLQAEIFQAR (SEQ.ID.NO.:49) and QQIRLQAEIFQAR (SEQ.ID.NO.:50).

ApoE polypeptides and methods for their preparation are described in U.S. Pat. No. 6,652,860, incorporated herein by reference.

LXR Agonists

The methods of the invention can include administering a LXR agonist for the prevention and treatment of metastasis. The LXR agonist can be a compound according to the Formula I, II, III, or IV shown below.

Formula I is provided below:

Formula I

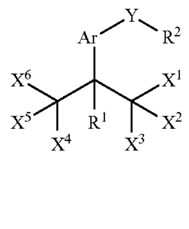

or a pharmaceutically acceptable salt thereof, wherein

Ar is an aryl group;

$R^1$ is a member selected from the group consisting of —OH, —$CO_2H$, —O—($C_1$-$C_7$)alkyl, —OC(O)—, —($C_1$-$C_7$)alkyl, —O—($C_1$-$C_7$)heteroalkyl, —OC(O)—($C_1$-$C_7$)heteroalkyl, —$NH_2$, —NH($C_1$-$C_7$) alkyl, —N(($C_1$-$C_7$) alkyl)$_2$ and —NH—$S(O)_2$($C_1$-$C_5$)alkyl;

$R^2$ is a member selected from the group consisting of ($C_1$-$C_7$)alkyl, ($C_1$-$C_7$)heteroalkyl, aryl and aryl ($C_1$-$C_7$) alkyl;

$X^1$, $X^2$, $X^3$, $X^4$, $X^5$ and $X^6$ are each independently a member selected from the group consisting of:

H, ($C^1$-$C^5$)alkyl, ($C^1$-$C^5$)heteroalkyl, F and CI, with the proviso that no more than three of $X^1$ through $X^6$ are H, ($C^1$-$C^5$)alkyl, ($C^1$-$C^5$)heteroalkyl; and Y is a divalent linking group selected from the group consisting of:

—N($R^{12}$)$S(O)_m$—, —N($R^{12}$)$S(O)_m$N($R^{13}$)—, —N($R^{12}$)C(O)—, —N($R^{12}$)C(O)N($R^{13}$)—, —N($R^{12}$)C(S)— and —N($R^{12}$)C(O)O—;

wherein $R^{12}$ and $R^{13}$ are each independently selected from the group consisting of:

H, ($C_1$-$C_7$)alkyl, ($C_1$-$C_7$)heteroalkyl, aryl and aryl($C_1$-$C_7$) alkyl, and optionally when Y is —N($R^{12}$)$S(O)_m$— or —N($R^{12}$)$S(O)_m$N($R^{13}$)—, $R^{12}$ forms a five- or six-membered ring fused to Ar or to $R^2$ through covalent attachment to Ar or to $R^2$, respectively; and the subscript m is an integer of from 1 to 2;

with the proviso that when $R^1$ is OH, and —Y—$R^2$ is —N($R^{12}$)$S(O)_m$—$R^2$ or —N($R^{12}$)C(O)N($R^{13}$)—$R^2$ and is attached to a position para to the quaternary carbon attached to Ar, and when $R^2$ is phenyl, benzyl, or benzoyl, then i) at least one of $R^{12}$ or $R^{13}$ is other than hydrogen and contains an electron-withdrawing substituent, or ii) $R^2$ is substituted with a moiety other than amino, acetamido, di($C_1$-$C_7$)alkylamino, ($C_1$-$C_7$)alkylamino, halogen, hydroxy, nitro, or ($C_1$-$C_7$)alkyl, or iii) the benzene ring portion of $R^2$ is substituted with at least three independently selected groups in addition to the Y group or point of attachment to Y.

In some embodiments, Y is —N(R12)S(O)2- and R1 is OH.

Accordingly, the compounds of Formula I include but are not limited the compound with the structure shown below:

1

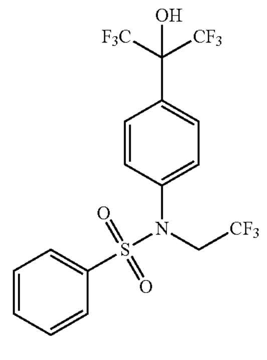

Compounds of Formula I can be synthesized as described by U.S. Pat. No. 6,316,503, incorporated herein by reference.

Formula II is provided below:

Formula II

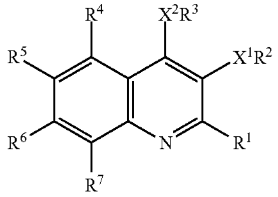

wherein:

$R^1$ is —H;

$X^1$ is a bond, $C_1$ to $C_5$ alkyl, —C(O)—, —C(=$CR^8R^9$)—, —O—, —$S(O)_t$, $NR^8$—, —$CR^8R^9$—, —$CHR^{23}$, —$CR^8(CR^9)$—, —$C(CR^8)_2$—, —$CR_8(OC(O)R^9)$—, —C=$NOR^9$—, —$C(O)NR^8$—, —$CH_2O$—, —$CH_2S$—, —$CH_2NR^8$—, —$OCH_2$—, —$SCH_2$—, —$NR^8CH_2$—, or

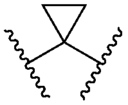
;

$R^2$ is H, $C_1$ to $C_6$alkyl, $C_2$ to $C_6$alkenyl, $C_2$ to $C_6$alkynyl, $C_3$ to $C_6$ cycloalkyl, —$CH_2OH$, C7 to $C_{11}$ arylalkyl, phenyl, naphthyl, $C_1$ to $C_3$ perfluoroalkyl, CN, $C(O)NH_2$, $CO_2R^{12}$ or phenyl substituted independently by one or more of the groups independently selected from $C_1$ to $C_3$ alkyl, $C_2$ to $C_4$ alkenyl, $C_2$ to $C_4$ alkynyl, $C_1$ to $C_3$ alkoxy, $C_1$ to $C_3$ perfluoroalkyl, halogen, —$NO_2$, —$NR^8R^9$, —CN, —OH, and $C_1$ to $C_3$alkyl substituted with 1 to 5 fluorines, or $R^2$ is a heterocycle selected from the group consisting of pyridine, thiophene, benzisoxazole, benzothiophene, oxadiazole, pyrrole, pyrazole, imidazole, and furan, each of which may be optionally substituted with one to three groups independently selected from $C_1$ to $C_3$alkyl, $C_1$ to $C_3$ alkoxy, $C_1$ to $C_3$ perfluoroalkyl, halogen, —$NO_2$, —$NR^8R^9$, —CN, and $C_1$ to $C_3$alkyl substituted with 1 to 5 fluorines;

$X^2$ is a bond or —$CH_2$—;

$R^3$ is phenyl, naphthyl, or phenyl or naphthyl substituted independently by one to four groups independently selected from $C_1$ to $C_3$ alkyl, hydroxy, phenyl, acyl, halogen, —$NH_2$, —CN, —$NO_2$, $C_1$ to $C_3$ alkoxy, $C_1$ to $C_3$perfluoroalkyl, $C_1$ to $C_3$ alkyl substituted with 1 to 5 fluorines, $NR^{14}R^{15}$, —$C(O)R^{10}$, —$C(O)NR^{10}R^{11}$, —$C(O)NR^{11}A$, —C≡$CR^8$, —CH=$CHR^8$, —WA, —C≡CA, —CH=CHA, —WYA, —$WYNR^{11}$-A, —$WYR^{10}$, —WY$(CH2)_j$A, —$WCHR^{11}(CH2)_jA$, —$W(CH2)_jA$, —$W(CH2)_jR^{10}$, —$CHR^{11}W(CH_2)_jR^{10}$, —$CHR^{11}W(CH_2)_jA$, —$CHR^{11}NR^{12}YA$, —$CHR^{11}NR^{12}YR^{10}$, pyrrole, —$W(CH_2)_jA(CH_2)_kD(CH_2)_pZ$, —$W(CR^{18}R^{19})A(CH_2)_kD(CH_2)_pZ$, —$(CH_2)_jWA(CH_2)_kD(CH_2)_pZ$, —CH=$CHA(CH2)_kD(CH2)pZ$, —C≡$CA(CH_2)_kD(CH_2)_pZ$, —$W(CH_2)_j$C≡$CA(CH_2)_kD(CH2)_pZ$, and —$W(CH_2)_jZ$, or $R^3$ is a heterocycle selected from pyrimidine, thiophene, furan, benzothiophene, indole, benzofuran, benzimidazole, benzothiazole, benzoxazole, and quinoline, each of which may be optionally substituted with one to three groups independently selected from $C_1$ to $C_3$alkyl, $C_1$ to $C_3$ alkoxy, hydroxy, phenyl, acyl, halogen, —$NH_2$, —CN, —$NO_2$, $C_1$ to $C_3$ perfluoroalkyl, $C_1$ to $C_3$ alkyl substituted with 1 to 5 fluorines, —$C(O)R^{10}$, —C(O) $NR^{10}R^{11}$, —$C(O)NR^{11}A$, —CH=$CHR^8$, —WA, —C≡CA, —CH=CHA, —WYA, —$WYR^{10}$, —$WY(CH_2)_jA$, —$W(CH_2)_jA$, —$W(CH_2)_jR^{10}$, —$CHR^{11}W(CH_2)_jR^{10}$, —$CHR^{11}W(CH_2)_jA$, —$CHR^{11}NR^{12}YA$, —$CHR^{11}NR^{12}YR^{10}$, —$WCHR^{11}(CH_2)_jA$, —$W(CH_2)_jA(CH_2)_kD(CH_2)_pZ$, —$W(CR^{18}R^{19})A(CH_2)_kD(CH_2)_pZ$, —$(CH_2)_jWA(CH_2)_kD(CH_2)_pZ$, —CH=$CHA(CH_2)_kD(CH_2)_pZ$, —C≡$CA(CH_2)_kD(CH_2)_pZ$, —$W(CH_2)_j$C≡$CA(CH_2)_kD(CH_2)_pZ$, and —$W(CH_2)_jZ$;

W is a bond, —O–, —S—, —S(O)—, —$S(O)_2$—, —$NR^{11}$—, or —$N(COR^{12})$—;

Y is —CO—, —$S(O)^2$—, —$CONR^{13}$, —$CONR^{13}CO$—, —$CONR^{13}SO_2$—, —C(NCN)—, —$CSNR^{13}$, —C(NH)$NR^{13}$, or —C(O)O—;

j is 0 to 3;

k is 0 to 3;

t is 0 to 2;

D is a bond, —CH=CH—, —C≡C—, —C=, —C(O)—, phenyl, —O—, —NH—, —S—, —$CHR^{14}$—, —$CR^{14}R^{15}$—, —$OCHR^{14}$, —$OCR^{14}R^{15}$—, or —CH(OH)CH(OH)—;

p is 0 to 3;

Z is —$CO_2R^{11}$, —$CONR^{10}R^{11}$, —$C(NR^{10})NR^{11}R^{12}$, —$CONH_2NH_2$, —CN, —$CH_2OH$, —$NR^{16}R^{17}$, phenyl, $CONHCH(R^{20})COR^{12}$, phthalimide, pyrrolidine-2,5dione, thiazolidine-2,4-dione, tetrazolyl, pyrrole, indole, oxazole, 2-thioxo-1,3-thiazolinin-4-one, $C_1$ to $C_7$ amines, $C_3$ to $C_7$ cyclic amines, or $C_1$ to $C_3$ alkyl substituted with one to two OH groups; wherein said pyrrole is optionally substituted with one or two substituents independently selected from the group consisting of —$CO_2CH_3$, —$CO_2H$, —$COCH_3$, —$CONH_2$, and —CN;

wherein said $C_1$ to $C_7$amines are optionally substituted with one to two substituents independently selected from the group consisting of —OH, halogen, —$OCH_3$, and —C≡CH;

wherein said phenyl is optionally substituted with $CO_2R^{11}$, and wherein said $C_3$ to $C_7$ cyclic amines are optionally substituted with one or two substituents independently selected from the group consisting of —OH —$CH_2OH$, $C_1$ to $C_3$ alkyl, —$CH_2OCH_3$, —$CO_2CH_3$, and —$CONH_2$, and wherein said oxazole is optionally substituted with $CH_2CO_2R^{11}$;

A is phenyl, naphthyl, tetrahydronaphthyl, indan or biphenyl, each of which may be optionally substituted by one to four groups independently selected from halogen, $C_1$ to $C_3$ alkyl, $C_2$ to $C_4$ alkenyl, $C_2$ to $C_4$ alkynyl, acyl, hydroxy, halogen, —CN, —$NO_2$, —$CO_2R^{11}$, —$CH_2CO_2R^{11}$, phenyl, $C_1$ to $C_3$perfluoroalkoxy, $C_1$ to $C_3$ perfluoroalkyl, —$NR^{10}R^{11}$, —$CH_2NR^{10}R^{11}$, —$SR^{11}$, $C_1$ to $C_6$ alkyl substituted with 1 to 5 fluorines, $C_1$ to $C_3$alkyl substituted with 1 to 2-OH groups, $C_1$ to $C_6$ alkoxy optionally substituted with 1 to 5 fluorines, or phenoxy optionally substituted with 1 to 2 $CF_3$ groups; or A is a heterocycle selected from pyrrole, pyridine, pyridine-N-oxide, pyrimidine, pyrazole, thiophene, furan, quinoline, oxazole, thiazole, imidazole, isoxazole, indole, benzo[1,3]-dioxole,benzo[1,2,5]-oxadiazole, isochromen-1-one, benzothiophene, benzofuran,2,3-di-5 hydrobenzo[1,4]-dioxine, bitheinyl, quinazolin-2,4-9[3H]dione, and 3-H-isobenzofuran-1-one, each of which may be optionally substituted by one to three groups independently selected from halogen, $C_1$ to $C_3$ alkyl, acyl, hydroxy, —CN, —$NO_2$, $C_1$ to $C_3$perfluoroalkyl, —$NR^{10}R^{11}$, —$CH_2NR^{10}R^{11}$, —$SR^{11}$, $C_1$ to $C_3$ alkyl substituted with 1 to 5 fluorines, and $C_1$ to $C_3$ alkoxy optionally substituted with 1 to 5 fluorines;

$R^4$, $R^5$, and $R^6$ are each, independently, —H or —F;

$R^7$ is $C_1$ to $C_4$ alkyl, $C_1$ to $C_4$ perfluoroalkyl, halogen, —$NO_2$, —CN, phenyl or phenyl substituted with one or two groups independently selected from halogen, $C_1$ to $C_2$alkyl and OH;

provided that if $X_1R^2$ forms hydrogen, then $R^3$ is selected from:

(a) phenyl substituted by —$W(CH_2)_jA(CH_2)_kD(CH_2)_pZ$, —$W(CR^{18}R^{19})A(CH_2)_kD(CH_2)_pZ$, —$(CH_2)_jWA(CH_2)_kD(CH_2)_pZ$, —$CH{=}CHA(CH_2)_kD(CH_2)_pZ$, —$C{\equiv}CA(CH_2)_kD(CH_2)_pZ$, or —$W(CH_2)_jC{\equiv}CA(CH_2)_kD(CH_2)_pZ$, wherein the phenyl moiety is further optionally substituted with one or two groups independently selected from $C_1$ to $C_2$ alkyl, $C_1$ to $C_2$perfluoroalkyl, halogen, and CN; and (b) a heterocycle selected from pyrimidine, thiophene, and furan, each of which is substituted by one of —$W(CH_2)_jA(CH_2)_kD(CH_2)_pZ$, —$W(CR^{18}R^{19})A(CH_2)_kD(CH_2)_pZ$, —$(CH2)_jWA(CH_2)_kD(CH_2)_pZ$, —$CH{=}CHA(CH_2)_kD(CH_2)_pZ$, —$C{\equiv}CA(CH_2)_kD(CH_2)_pZ$, or —$W(CH_2)_jC{\equiv}CA(CH_2)_kD(CH_2)_pZ$;

each $R^8$ is independently-H, or $C_1$ to $C_3$alkyl;

each $R^9$ is independently-H, or $C_1$ to $C_3$alkyl;

each $R^{10}$ is independently-H, —CH, $C_1$ to $C_3$alkoxy, $C_1$ to $C_7$ alkyl, $C_3$ to $C_7$ alkenyl, $C_3$ to $C_7$ alkynyl, $C_3$ to $C_7$ cycloalkyl, —$CH_2CH_2OCH_3$, 2-methyl-tetrahydro-furan, 2-methyl-tetrahydro-pyran, 4-methyl-piperidine, morpholine, pyrrolidine, or phenyl optionally substituted with one or two $C_1$ to $C_3$alkoxy groups, wherein said $C_1$ to $C_7$ alkyl is optionally substituted with 1, 2 or 3 groups independently selected from $C_1$ to $C_3$ alkoxy, $C_1$ to $C_3$thioalkoxy, and CN;

each $R^{11}$ is independently-H, $C_1$ to $C_3$alkyl or $R^{22}$; or $R^{10}$ and $R^{11}$, when attached to the same atom, together with said atom form:

a 5 to 7 membered saturated ring, optionally substituted by 1 to 2 groups independently selected from $C_1$ to $C_3$ alkyl, OH and $C_1$-$C_3$alkoxy; or a 5 to 7 membered ring containing 1 or 2 heteroatoms, optionally substituted by 1 to 2 groups independently selected from $C_1$ to $C_3$alkyl, OH and $C_1$-$C_3$ alkoxy;

each $R^{12}$ is independently-H, or $C_1$ to $C_3$alkyl;

each $R^{13}$ is independently-H, or $C_1$ to $C_3$alkyl;

each $R^{14}$ and $R^{15}$ is, independently, $C_1$ to $C_7$ alkyl, $C_3$ to $C_8$ cycloalkyl, $C_2$ to $C_7$ alkenyl, $C_2$ to $C_7$ alkynyl, —CH, —F, $C_7$ to $C_{14}$arylalkyl, where said arylalkyl is optionally substituted with 1 to 3 groups independently selected from $NO_2$, $C_1$ to $C_6$ alkyl, $C_1$ to $C_3$perhaloalkyl, halogen, $CH_2CO_2R^{11}$, phenyl and $C_1$ to $C_3$ alkoxy, or $R^{12}$ and $R^{15}$ together with the atom to which they are attached can form a 3 to 7 membered saturated ring;

each $R^{16}$ and $R^{17}$ is, independently, hydrogen, $C_1$ to $C_3$ alkyl, $C_1$ to $C_3$alkenyl, $C_1$ to $C_3$ alkynyl, phenyl, benzyl or $C_3$ to $C_8$ cycloalkyl, wherein said $C_1$ to $C_3$ alkyl is optionally substituted with one OH group, and wherein said benzyl is optionally substituted with 1 to 3 groups selected from $C_1$ to $C_3$alkyl and $C_1$ to $C_3$alkoxy; or $R^{16}$ and $R^{17}$, together with the atom to which they are attached, can form a 3 to 8 membered heterocycle which is optionally substituted with one or two substituents independently selected from the group consisting of $C_1$ to $C_3$alkyl, —OH, $CH_2OH$, —$CH_2OCH_3$, —$CO_2CH_3$, and —$CONH_2$;

each $R^{18}$ and $R^{19}$ is, independently, $C_1$ to $C_3$alkyl;

each $R^{20}$ is independently H, phenyl, or the side chain of a naturally occurring alpha amino acid;

each $R^{22}$ is independently arylalkyl optionally substituted with $CH_2COOH$; and each $R_{23}$ is phenyl;

or a pharmaceutically acceptable salt thereof.

Compounds of Formula II can be synthesized as described in U.S. Pat. No. 7,576,215, incorporated herein by reference. The compound of formula II can be any of compounds 26-32, or a pharmaceutically acceptable salt thereof.

26

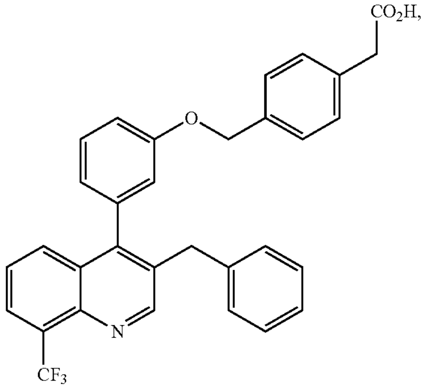

27

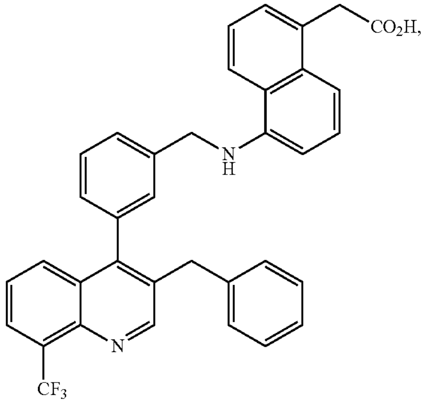

28

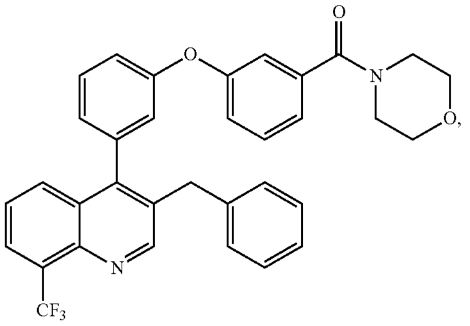

-continued

29

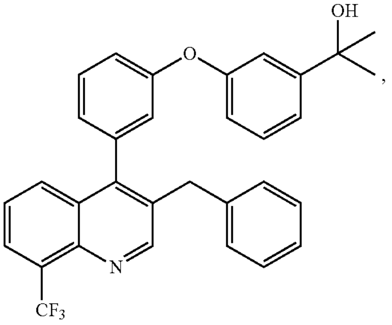

30

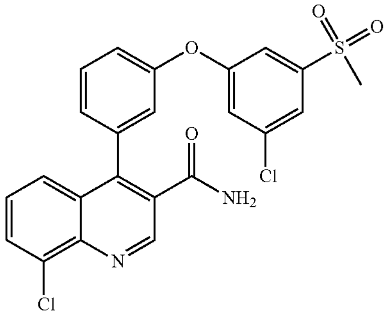

31

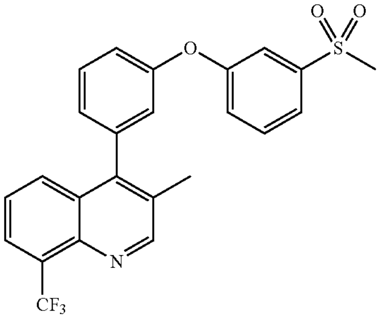

32

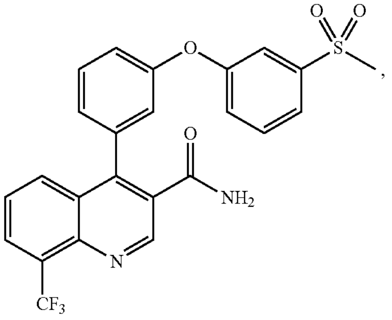

Formula III is provided below:

Formula III

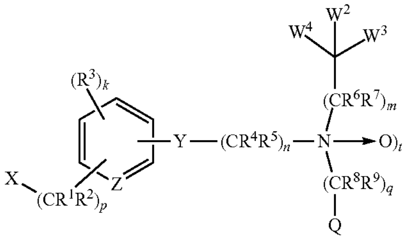

wherein:

X is selected from hydrogen, $C_1$-$C_8$ alkyl, halo, —$OR^{10}$, —$NR^{10}R^{11}$, nitro, cyano, —$COOR^{10}$, or —$COR^{10}$.

Z is CH, $CR^3$ or N, wherein when Z is CH or $CR^3$, k is 0-4 and t is 0 or 1, and when Z is N, k is 0-3 and t is 0;

Y is selected from —O—, —S—, —$N(R^{12})$—, and —$C(R^4)(R^5)$—;

$W^1$ is selected from $C_1$-$C_6$ alkyl, $C_0$-$C_6$ alkyl, $C_3$-$C_6$ cycloalkyl, aryl and Het, wherein said $C_1$-$C_8$ alkyl, $C_3$-$C_8$ cycloalkyl, Ar and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{12}$, —$C_0$-$C_6$alkyl-C(O)$SR^{12}$, —$C_0$-$C_6$alkyl-$CONR^{13}R^{14}$, —$C_0$-$C_6$ alkyl-$COR^{15}$, —$C_0$-$C_6$ alkyl-$NR^{13}R^{14}$, —$C_0$-$C_6$ alkyl-$SR^{12}$, —$C_0$-$C_6$alkyl-$OR^{12}$, —$C_0$-$C_6$alkyl-$SO_3H$, —$C_0$-$C_6$alkyl-$SO_2NR^{13}R^{14}$, —$C_0$-$C_6$alkyl-$SO_2R^{12}$, —$C_0$-$C_6$alkyl-$SOR^{15}$, —$C_0$-$C_6$alkyl$OCOR^{15}$, —$C_0$-$C_6$alkyl-OC(O)$NR^{13}R^{14}$, —$C_0$-$C_6$alkyl-OC(O)$OR^{15}$, —$C_0$-$C_6$ alkyl-$NR^{13}$C(O)$OR^{15}$, —$C_0$-$C_6$ alkyl-$NR^{13}$C(O)$NR^{13}R^{14}$, and —$C_0$-$C_6$ alkyl-$NR^{13}COR^{15}$, where said $C_1$-$C_6$ alkyl, is optionally unsubstituted or substituted by one or more halo substituents;

$W^2$ is selected from H, halo, $C_1$-$C_6$alkyl, $C_2$-$C_6$alkenyl, $C_2$-$C_6$ alkynyl, —$C_0$-$C_6$ alkyl-$NR^{13}R^{14}$, —$C_0$-$C_6$alkyl-$SR^{12}$, —$C_0$-$C_6$ alkyl-$OR^{12}$, —$C_0$-$C_6$alkyl$CO_2R^{12}$, —$C_0$-$C_6$alkyl-C(O)$SR^{12}$, —$C_0$-$C_6$ alkyl$CONR^{13}R^{14}$, —$C_0$-$C_6$alkyl-$COR^{15}$, —$C_0$-$C_6$ alkyl$OCOR^{15}$, —$C_0$-$C_6$alkyl-$OCONR^{13}R^{14}$, —$C_0$-$C_6$alkyl-$NR^{13}CONR^{13}R^{14}$, —$C_0$-$C_6$ alkyl-$NR^{13}COR^{15}$, —$C_0$-$C_6$alkyl-Het, —$C_0$-$C_6$alkyl-Ar and —$C_0$-$C_6$ alkyl-$C_3$-$C_7$ cycloalkyl, wherein said $C_1$-$C_6$ alkyl is optionally unsubstituted or substituted by one or more halo substituents, and wherein the $C_3$-$C_7$cycloalkyl, Ar and Het moieties of said —$C_0$-$C_6$alkyl-Het, —$C_0$-$C_6$alkyl-Ar and —$C_0$-$C_6$alkyl-$C_3$-$C_7$cycloalkyl are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$alkyl-CO2$R^{12}$, —$C_0$-$C_6$ alkyl-C(O)$SR^{12}$, —$C_0$-$C_6$alkyl-$CONR^{13}R^{14}$, —$C_0$-$C_6$alkyl-$COR^{15}$, —$C_0$-$C_6$alkyl-$NR^{13}R^{14}$, —$C_0$-$C_6$alkyl-$SR^{12}$, —$C_0$-$C_6$alkyl-$OR^{12}$, —$C_0$-$C_6$ alkyl-$SO_3H$, —$C_0$-$C_6$alkyl-$SO_2NR^{13}R^{14}$, —$C_0$-$C_6$alkyl-$SO_2R^{12}$, —$C_0$-$C_6$alkyl-$SOR^{15}$, —$C_0$-$C_6$alkyl-$OCOR^{15}$, —$C_0$-$C_6$alkylOC(O)$NR^{13}R^{14}$, —$C_0$-$C_6$alkyl-OC(O)$OR^{15}$, —$C_0$-$C_6$alkyl-$NR^{13}$C(O)$OR^{15}$, —$C_0$-$C_6$alkyl-$NR^{13}$C(O)$NR^{13}R^{14}$, and —$C_0$-$C_6$alkyl-$NR^{13}COR^{15}$, where said $C_1$-$C_6$ alkyl, is optionally unsubstituted or substituted by one or more halo substituents;

$W^3$ is selected from the group consisting of: H, halo, $C_1$-$C_6$ alkyl, —$C_0$-$C_6$ alkyl-$NR^{13}R^{14}$, —$C_0$-$C_6$alkyl$SR^{12}$, —$C_0$-$C_6$alkyl-$OR^{12}$, —$C_0$-$C_6$alkyl-$CO_2R^{12}$, —$C_0$-$C_6$alkyl-C(O)$SR^{12}$, —$C_0$-$C_6$alkyl-$CONR^{13}R^{14}$, —$C_0$-$C_6$alkyl-$COR^{15}$, —$C_0$-$C_6$alkyl-$OCOR^{15}$, —$C_0$-$C_6$ alkyl-$OCONR^{13}R^{14}$, —$C_0$-$C_6$alkyl$NR^{13}CONR^{13}R^{14}$, —$C_0$-$C_6$alkyl-$NR^{13}COR^{15}$, —$C_0$-$C_6$alkyl-Het, —$C_1$-$C_6$alkyl-Ar and —$C_1$-$C_6$alkyl-$C_3$-$C_7$cycloalkyl, wherein said $C_1$-$C_6$ alkyl is optionally unsubstituted or substituted by one or more halo substituents;

Q is selected from $C_3$-$C_8$cycloalkyl, Ar and Het; wherein said $C_3$-$C_8$cycloalkyl, Ar and Het are optionally unsubstituted or substituted with one or more groups independently selected from halo, cyano, nitro, $C_1$-$C_6$alkyl, $C_3$-$C_6$alkenyl, $C_3$-$C_6$alkynyl, —$C_0$-$C_6$alkyl$CO_2R^{12}$, —$C_0$-$C_6$ alkyl-C(O)$SR^{12}$, —$C_0$-$C_6$alkyl$CONR^{13}R^{14}$, —$C_0$-$C_6$ alkyl-$COR^{15}$, —$C_0$-$C_6$alkyl$NR^{13}R^{14}$, —$C_0$-$C_6$alkyl-$SR^{12}$, —$C_0$-$C_6$alkyl-$OR^{12}$, —$C_0$-$C_6$ alkyl-$SO_3H$, —$C_0$-$C_6$ alkyl-$SO_2NR^{13}R^{14}$, $C_0$-$C_6$alkyl-$SO_2R^{12}$, —$C_0$-$C_6$alkyl-$SOR^{15}$, —$C_0$-$C_6$alkyl-$OCOR^{15}$, —$C_0$-$C_6$alkyl-OC(O)$NR^{13}R^{14}$, —$C_0$-$C_6$alkyl-OC(O)$OR^{15}$, —$C_0$-$C_6$alkyl$NR^{13}$C(O)$OR^{15}$, —$C_0$-$C_6$ alkyl-$NR^{13}$C(O)$NR^{13}R^{14}$, and —$C_0$-$C_6$alkyl-$NR^{13}COR^{15}$, where said $C_1$-$C_6$alkyl is optionally unsubstituted or substituted by one or more halo substituents;

is 0-8;

n is 2-8;

m is 0 or 1;

q is 0 or 1;

t is 0 or 1;

each $R^1$ and $R^2$ are independently selected from H, halo, $C_1$-$C_6$alkyl, $C_3$-$C_6$alkenyl, $C_3$-$C_6$alkynyl, —$C_0$-$C_6$alkyl-$NR^{13}R^{14}$, —$C_0$-$C_6$alkyl-$OR^{12}$, —$C_0$-$C_6$ alkyl-$SR^{12}$, —$C_1$-$C_6$alkyl-Het, —$C_1$-$C_6$alkyl-Ar and —$C_1$-C6alkyl-$C_3$-$C_7$cycloalkyl, or $R^1$ and $R^2$ together with the carbon to which they are attached form a 3-5 membered carbocyclic or heterocyclic ring, wherein said heterocyclic ring contains one, or more heteroatoms selected from N, O, and S, where any of said $C_1$-$C_6$ alkyl is optionally unsubstituted or substituted by one or more halo substituents;

each $R^3$ is the same or different and is independently selected from halo, cyano, nitro, $C_1$-$C_6$ alkyl, $C_3$-$C_6$alkenyl, $C_3$-$C_6$alkynyl, —$C_0$-$C_6$alkyl-Ar, —$C_0$-$C_6$alkyl-Het, —$C_0$-$C_6$alkyl-$C_3$-$C_7$cycloalkyl, —$C_0$-$C_6$alkyl-CO2$R^{12}$, —$C_0$-$C_6$alkyl-C(O)$SR^{12}$, —$C_0$-$C_6$alkyl-$CONR^{13}R^{14}$, —$C_0$-$C_6$alkyl-$COR^{15}$, —$C_0$-$C_6$alkyl-$NR^{13}R^{14}$, —$C_0$-$C_6$alkyl-$SR^{12}$, —$C_0$-$C_6$alkyl-$OR^{12}$, —$C_0$-$C_6$alkyl-$SO_3H$, —$C_0$-$C_6$alkyl$SO_2NR^{13}R^{14}$, —$C_0$-$C_6$ alkyl-$SO_2R^{12}$, —$C_0$-$C_6$alkyl$SOR^{15}$, —$C_0$-$C_6$alkyl-$OCOR^{15}$, —$C_0$-$C_6$ alkyl-OC(O)$NR^{13}R^{14}$, —$C_0$-$C_6$alkyl-OC(O)$OR^{15}$, —$C_0$-$C_6$alkyl-$NR^{13}$C(O)$OR^{15}$, —$C_0$-$C_6$alkyl-$NR^{13}$C(O)$NR^{13}R^{14}$, and —$C_0$-$C_6$alkyl-$NR^{13}COR^{15}$, wherein said $C_1$-$C_6$alkyl is optionally unsubstituted or substituted by one or more halo substituents;

each $R^4$ and $R^5$ is independently selected from H, halo, $C_1$-$C_6$alkyl, —$C_0$-$C_6$alkyl-Het, —$C_0$-$C_6$alkyl-Ar and —$C_0$-$C_6$alkyl-$C_3$-$C_7$cycloalkyl;

$R^6$ and $R^7$ are each independently selected from H, halo, $C_1$-$C_6$ alkyl, —$C_0$-$C_6$alkyl-Het, —$C_0$-$C_6$ alkyl-Ar and —$C_0$-$C_6$alkyl-$C_3$-$C_7$cycloalkyl;

$R^8$ and $R^9$ are each independently selected from H, halo, $C_1$-$C_6$ alkyl, —$C_0$-$C_6$alkyl-Het, —$C_0$-$C_6$ alkyl-Ar and —$C_0$-$C_6$alkyl-$C_3$-$C_7$ cycloalkyl;

$R^{10}$ and $R^{11}$ are each independently selected from H, $C_1$-$C_{12}$ alkyl, $C_3$-$C_{12}$alkenyl, $C_3$-$C_{12}$alkynyl, —$C_0$-$C_8$alkyl-Ar, —$C_0$-$C_8$ alkyl-Het, —$C_0$-$C_8$ alkyl-$C_3$-$C_7$ cycloalkyl, —$C_0$-$C_8$ alkyl-O—Ar, —$C_0$-$C_8$ alkyl-O-Het, —$C_0$-$C_8$ alkyl-O—$C_3$-$C_7$cycloalkyl, —$C_0$-$C_8$alkyl-$S(O)_x$$C_0$-$C_6$alkyl, —$C_0$-$C_8$alkyl-$S(O)_x$Ar, —$C_0$-$C_8$ alkyl-$S(O)_x$-Het, —$C_0$-$C_8$ alkyl-$S(O)_x$—$C_3$-$C_7$cycloalkyl, —$C_0$-$C_8$alkyl-NH—Ar, —$C_0$-$C_8$alkyl-NH-Het, —$C_0$-$C_8$alkyl-NH—$C_3$-$C_7$cycloalkyl, —$C_0$-$C_8$alkyl-N($C_1$-$C_4$ alkyl)-Ar, —$C_0$-$C_8$ alkyl —N($C_1$-$C_4$alkyl)-Het, —$C_0$-$C_8$alkyl-N($C_1$-$C_4$alkyl-$C_3$-$C_7$cycloalkyl, —$C_0$-$C_8$alkyl-Ar, —$C_0$-$C_8$alkyl-Het and —$C_0$-$C_8$alkyl-$C_3$-$C_7$cycloalkyl, where x is 0, 1, or 2, or $R^{10}$ and $R^{11}$, together with the nitrogen to which they are attached, form a 4-7 membered heterocyclic ring which optionally contains one or more additional heteroatoms selected from N, O, and S, wherein said $C_1$-$C_{12}$alkyl, $C_3$-$C_{12}$ alkenyl, or $C_3$-$C_{12}$alkynyl is optionally substituted by one or more of the substituents independently selected from the group halo, —OH, —SH, —$NH_2$, —NH(unsubstituted $C_1$-$C_6$alkyl), —N(unsubstituted $C_1$-$C_6$ alkyl)(unsubstituted $C_1$-$C_6$alkyl), unsubstituted —$OC_1$-$C_6$ alkyl, —$CO_2H$, —$CO_2$(unsubstituted $C_1$-$C_6$ alkyl), —$CONH_2$, —CONH(unsubstituted $C_1$-$C_6$ alkyl), —CON(unsubstituted $C_1$-$C_6$ alkyl)(unsubstituted $C_1$-$C_6$ alkyl), —$SO_3H$, —$SO_2NH_2$, —$SO_2$NH(unsubstituted $C_1$-$C_6$alkyl) and —$SO_2$N(unsubstituted $C_1$-$C_6$alkyl)(unsubstituted $C_1$-$C_6$ alkyl);

$R^{12}$ is selected from H, $C_1$-$C_6$ alkyl, $C_3$-$C_6$alkenyl, $C_3$-$C_6$alkynyl, —$C_0$-$C_6$alkyl-Ar, —$C_0$-$C_6$alkyl-Het and —$C_0$-$C_6$alkyl-$C_3$-$C_7$cycloalkyl;

each $R^{13}$ and each $R^{14}$ are independently selected from H, $C_1$-$C_6$alkyl, $C_3$-$C_6$alkenyl, $C_3$-$C_6$alkynyl, —$C_0$-$C_6$alkyl-Ar, —$C_0$-$C_6$alkyl-Het and —$C_0$-$C_6$alkyl-$C_3$-$C_7$cycloalkyl, or $R^{13}$ and $R^{14}$ together with the nitrogen to which they are attached form a 4-7 membered heterocyclic ring which optionally contains one or more additional heteroatoms selected from N, O, and S;

and $R^{15}$ is selected from $C_1$-$C_6$alkyl, $C_3$-$C_6$ alkenyl, $C_3$-$C_6$alkynyl, —$C_0$-$C_6$alkyl-Ar, —$C_0$-$C_6$ alkyl-Het and —$C_0$-$C_6$ alkyl-$C_3$-$C_7$ cycloalkyl;

or a pharmaceutically acceptable salt thereof.

In some embodiments, X is hydrogen, p is 0, t is 0, Z is CH, and Y is —O—.

In further embodiments, X is hydrogen, p is 0, t is 0, Z is CH, and Y is —O—, $W^1$ and $W^2$ are phenyl, $W^3$ is hydrogen, q is 1, and $R^8$ and $R^9$ are hydrogen.

In other embodiments, X is hydrogen, p is 0, t is 0, Z is CH, and Y is —O—, $W^1$ and $W^2$ are phenyl, $W^3$ is hydrogen, q is 1, $R^8$ and $R^9$ are hydrogen, and Q is Ar.

Accordingly, the compounds of Formula III include but are not limited the compounds with structures shown below GW3965 2 and SB742881 25:

2

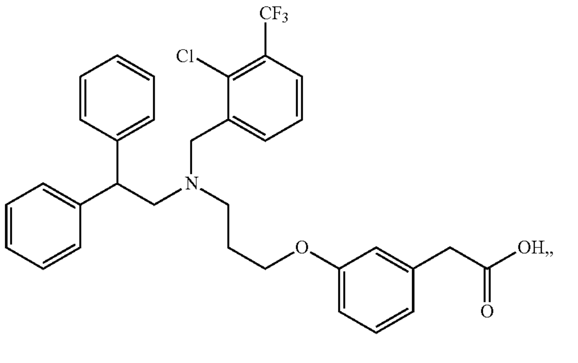

-continued

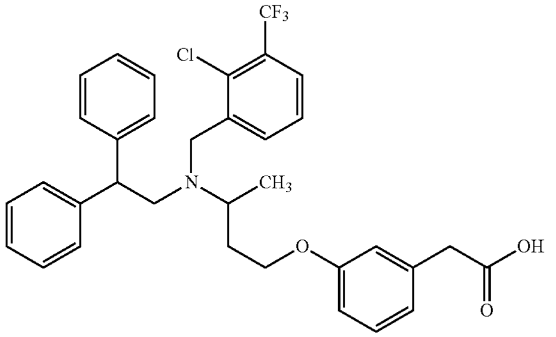

Compounds of Formula III can be synthesized as described in U.S. Pat. Nos. 7,365,085 and 7,560,586 incorpoarated herein by reference.

Formula IV is shown below:

Formula IV

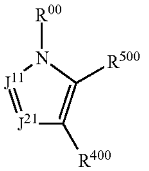

or a pharmaceutically acceptable salt thereof, wherein:

$J^{11}$ is —N═ and $J^{21}$ is —$CR^{300}$—, or $J^{11}$ is —$CR^{200}$— and J21 is ═N—;

$R^{00}$ is $G^1$, $G^{21}$, or $R^N$;

$R^{200}$ is $G^1$, $G^{21}$, or $R^C$;

$R^{300}$ and $R^{400}$ are independently $R^C$ or Q, provided one and only one of $R^{300}$, $R^{400}$, and $R^{500}$ is

Q;

Q is $C_{3-6}$ cycloalkyl, heteroaryl or heterocyclyl, each optionally substituted with 1 to 4$R^Q$, or Q is —X— Y—Z; wherein each $R^Q$ is independently aryloxy, aralkyloxy, aryloxyalkyl, aryl$C_0$-$C_6$alkylcarboxy, $C(R^{110})$═$C(R^{110})$—COOH, oxo, ═S, —Z, —Y'—Z, or —X—Y—Z, wherein each $R^Q$ is optionally substituted with 1 to 4 $R^{80}$;

$R^{500}$ is $G^1$ $G^{21}$, Q, or $R^C$; provided that only one of $R^{00}$, $R^{200}$, and $R^{500}$ is $G^1$ and only one of $R^{00}$, N═, and $R^{500}$ is $G^{21}$;

$G^{21}$ is -$J^0$-$K^o$, wherein $J^0$ and $K^0$ are independently aryl or heteroaryl, each optionally substituted with one to four $R^K$ groups; each $R^K$ is independently hydrogen, halogen, $CR^{110}$═$CR^{110}COOR^{110}$, nitro, —Z, —Y—Z, or —X—Y—Z;

$G^1$ is -$L^{10}$-R, wherein $L^{10}$ is a bond, $L^{50}$, $L^{60}$, -$L^{50}$-$L^{60}$-$L^{50}$-, or -$L^{60}$-$L^{50}$-$L^{50}$-, wherein each $L^{50}$ is independently —$[C(R^{150})_2]_m$—;

each $L^{60}$ is independently —CS—, —CO—, —$SO_2$—, —O—, —$CON(R^{110})$—, —$CONR^{110}N(R^{110})$—, $C(═NR^{llO})$—, —$C(NOR^{ll})$—, —$C(═N—N(R^{110})_2)$—, —$C_3$-$C_8$cycloalkyl-, or -heterocyclyl-, wherein the cycloalkyl or heterocyclyl is optionally substituted with one to 4 $R^{140}$ groups; or or each $L^{60}$ is independently $C_2$-$C_6$ alidiyl, wherein the alidiyl chain is optionally interrupted by —$C(R^{100})_2$—, —$C(R^{110})_2C(R^{110})_z$—, —$(R^{11})C(R^{110})$—, —$C(R^{110})_2O$—, —$C(R^{110})_zNR^{110}$—, —C C—, —O—, —S—, —N(RO)CO—, —$N(R^{100})CO_2$—, —CON$(R^{110})$—, —CO—, —$CO_2$—, —OC(═O)—, —OC(═O)$N(R^{100})$—, —$SO_2$—, —$N(R^{100})SO_2$, or —$SO_2N(R^{100})$;

R is aryl, heterocyclyl, heteroaryl or —($C_3$-$C_6$)cycloalkyl, wherein R is optionally substituted with 1 to 4 $R^A$, wherein each $R^A$ is independently halogen, nitro, heterocyclyl, $C_1$-$C_6$ alkyl, $C_2$-$C_6$ alkenyl, $C_2$-$C_6$ alkynyl, $C_3$-$C_8$ cycloalkyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_1C_6$ alkenyl-, arylalkyl, aryloxy, aryl$C_1$-$C_6$ alkoxy, $C_1$-$C_6$ haloalkyl, $SO_2R^{110}$, $OR^{110}$, $SR^{110}$, $N_3$, $SOR^{110}$, $COR^{110}$, $SO_2N(R^{110})_2$, $SO_2NR^{110}COR^{110}$, C≡N, C(O)$OR^{110}$, $CON(R^{110})_2$, —$CON(R^{110})OR^{110}$, $OCON(R^{110})_2$, —$NR^{110}COR^{110}$, $NR^{110}CON(R^{110})_2$, $NR^{110}COOR^{110}$, —C(═N—OH)$R^{110}$, —C(═S)$N(R^{110})_2$, —S(═O)$N(R^{110})_2$, —S(═O)$OR^{110}$, —$N(R^{110})S(═O)_2$ $R^{110}$, —C(═O)$N(R^{110})N(R^{110})_2$, —OC(═O)—$R^{110}$, —OC(═O)—$OR^{110}$ or $N(R^{11})_2$, wherein each $R^A$ is optionally substituted with 1 to 4 groups which independently are -halogen, —$C_1$-$C_6$ alkyl, aryloxy, $C_{0-6}$ alkyl$SO_2R^{110}$, $C_{0-6}$ alkyl$COOR^{110}$, $C_{1-6}$ alkoxyaryl, $C_1$-$C_6$ haloalkyl, —$SO_2R^{110}$, —$OR^{110}$, $SR^{110}$, —$N_3$, —$SO_2R^{110}$, —$COR^{110}$, —$SO_2N(R^{110})_2$, —$SO_2NR^{110}COR^{11}$, —C≡N, —C(O) $OR^{110}$, —$CON(R^{110})_2$, —$CON(R^{110})OR^{110}$, —$OCON(R^{110})_2$, —$NR^{110}COR^{110}$, —$NR^{110}CON(R^{110})_2$, —$NR^{110}COOR^{110}$, or —$N(R^{110})_2$;

$R^N$ is -$L^{31}$-$R^{60}$, wherein $L^{31}$ is a bond, —$X^3(CH_z)_n$—$X^3$—, —$(CH_2)_m$—X3—$(CH_2)_n$— or —$(CH_2)_{1+w}$, —$Y^3$—$(CH_2)_w$—, wherein each w is independently 0-5: and each $X^3$ is independently a bond, —$C(R^{110})_2$—, —$C(R^{110})_2C(R^{110})_2$—, —$C(R^{110})$═$C(R^{110})$—, —C≡C—, —CO—, —CS—, —$CONR^{100}$—, —C(═N)$(R^{100})$—, —C(═N—$OR^{110})$—, —C[═N—$N(R^{110})_2$], —$CO_2$—, —$SO_2$—, or —$SO_2N(R^{110})$—; and $Y^3$ is —O—, —S—, —$NR^{70}$—, —$N(R^{100})CO$—, —$N(R^{110})$CO2-, —OCO—, —OC(═O)N)$(R^{100})$—, —$NR^{100}CONR^{100}$—, —$N(R^{110})SO_2$—, or —$NR^{100}CSNR^{100}$—;

or $L^{31}$ is $C_{2-6}$ alidiyl chain wherein the alidiyl chain is optionally interrupted by —$C(R^{110})_2$—, —$C(R^{110})_2C(R^{110})_2$—, —$C(R^{110})$═$C(R^{110})$—, —$C(R^{110})_2O$—, —$C(R^{110})_2NR^{110}$—, —C≡C—, —O—, —S—, —$N(R^{100})CO$—, —$N(R^{100})CO_2$—, —$CON(R^{100})$—, —CO—, —$CO_2$—, —OC(═O)—, —OC(═O)$N(R^{110})$—, —$SO_2$—, —$N(R^{100})SO_2$—, or —$SO_2N(R^{100})$; and $R^{60}$ is $C_1$-$C_6$ alkyl, $C_1$-$C_6$ halo alkyl, aryl, $C_3$-$C_8$ cycloalkyl, heteroaryl, heterocyclyl, —CN, —C(═O)$R^{110}$, —C(═O)$OR^{110}$, —C(═O)$N(R^{110})_2$, —$N(R^{110})_2$, —$SO_2R^{110}$, —$S(═O)_2N(R^{110})_2$, —C(═O)$N(R^{110})N(R^{110})_2$, or —C(═O)$N(R^{11})(OR^{110})$, wherein the aryl, heteroaryl, cycloalkyl, or heterocyclyl is optionally substituted with 1 to 4 $R^{60a}$, wherein each $R^{60a}$ is independently —Z, —Y'—Z, or —X—Y—Z;

each $R^C$ is independently -$L^{30}$-$R^{70}$, wherein each $L^{30}$ is independently a bond or —$(CH_2)_m$—$V^{10}$—$(CH_2)_n$—, wherein $V^{10}$ is —$C(R^{110})_2$—, —$C(R^{110})_2C(R^{110})_2$, —$C(R^{110})$═$C(R^{110})$—, —$C(R^{110})_2O$—, —$C(R^{110})_2NR^{110}$—, —C≡C—, —O—, —S—, —$NR^{10}$—, —$N(R^{100})CO$—, —$N(R^{100})CO2$-, —OCO—, —CO—, —CS—, —$CONR^{100}$—, —$C(=N—R^{110})$—, —$C(=N—OR^{110}$—, —$C[=N—N(R^{110})_2]$, —$CO_2$—, —$OC(=O)$—, —$OC(=O)N(R^{100})$—, $SO_2$—, —$N(R^{100})SO_2$—, —$SO_2N(R^{100})$—, —$NR^{100}CONR^{100}$—, —$NR^{100}CSNR^{100}$—, $C_3$-$C_6$cyclo alkyl, or $C_3$-$C_6$ cyclohaloalkyl; or each $L^{30}$ is independently $C_2$-$C_6$ alidiyl, wherein the alidiyl chain is optionally interrupted by —$C(R^{110})_2$—, —$C(R^{110})_2C(R^{110})_2$—, —$C(R^{110})C(R^{110})$—, —$C(R^{110})_2O$—, —$C(R^{110})_2NR^{110}$, —C≡C—, —O—, —S—, —$N(R^{100})CO$—, —$N(R^{100})CO_2$—, —$NR^{110}$—, —$CON(R^{100})$—, —CO—, —$CO_2$—, —$O(C=O)$—, —$O(C=O)N(R^{100})$—, —$SO_2$—, —$N(R^{100})SO_2$—, or —$SO_2N(R^{100})$—;

each $R^{70}$ is independently hydrogen, halogen, nitro, aryl, heteroaryl, heterocyclyl, —Z, —Y—Z, or —X—YZ, wherein the aryl, heteroaryl, and heterocyclyl, are each optionally substituted with 1 to 4 $R^{70a}$, wherein each $R^{70a}$ is independently aryloxy, aralkyloxy, aryloxyalkyl, aryl$C_o$-$C_6$alkylcarboxy, $C(R^{110})=C(R^{110})COOH$, oxo, —Z, —Y'—Z, or —X—Y—Z, wherein each $R^{70a}$ is optionally substituted with 1 to 4 $R^{80}$, and wherein each $R^{80}$ is independently halogen, $C_1$-$C_6$alkyl, $C_1$-$C_6$ alkoxy, $C_1$-$C_8$haloalkyl, $C_1$-$C_8$ haloalkyl($OR^{110}$), $C_0$-$C_6$ alkyl$OR^{110}$, $C_0$-$C_6$alkyl$CON(R^{110})_2$, $C_0$-$C_6$ alkyl$COR^{110}$, $C_0$-$C_6$ alkyl-$COOR^{110}$, or $C_0$-$C_6$ alkyl$SO_2R^{110}$;

each $R^{100}$ is independently —$R^{110}$, —$C(=O)R^{110}$, —$CO_2R^{110}$, or —$SO_2R^{110}$;

each $R^{110}$ is independently -hydrogen, —$C_1$-$C_6$ alkyl, $C_2$-$C_6$ alkenyl, $C_1$-$C_6$ alkynyl, —$C_1$-$C_6$ haloalkyl, or —$N(R^{12})_2$, wherein any of $R^{110}$ is optionally substituted with 1 to 4 radicals of $R^{120}$;

each $R^{120}$ is independently halogen, cyano, nitro, oxo, —$B(OR^{130})$, $C_0$-$C_6$ alkyl$N(R^{13})_2$, $C_1$-$C_6$haloalkyl, $C_1$-$C_6$ alkyl, $C_1$-$C_6$ alkoxy, ($C_0$-$C_6$ alkyl)$C=O(OR^{130})$, $C_0$-$C_6$ alkyl$OR^{130}$, $C_0$-$C_6$alkyl$COR^{130}$, $C_0$-$C_6$alkyl$SO_2R^{130}$, $C_o$-$C_6$alkyl$CON(R^{13})_2$, $C_0$-$C_6$alkyl$CONR^{130}OR^{130}$, $C_0$-$C_6$alkyl$SO_2N(R^{130})_2$, $C_0$-$C_6$alkyl$SR^{130}$, $C_0$-$C_6$ haloalkyl$OR^{130}$, $C_0$-$C_6$alkylCN, —$C_0$-$C_6$alky$N(R^{13})_2$, —$NR^{13}SO_2R^{13}$, or —$OC_{O-6}$ alkyl$COOR^{130}$;

each $R^{130}$ is independently hydrogen, $C_1$-$C_6$ alkyl, $C_2$-$C_6$ alkenyl, or $C_2$-$C_6$ alkynyl;

each $R^{140}$ is independently $C_1$-$C_6$ alkyl, $C_1$-$C_6$ alkoxy, halogen, $C_1$-$C_6$ haloalkyl, $C_0$-$C_6$alkyl$CON(R^{110})_o$, $C_0$-$C_6$ alkyl$CONR^{110}R^{10}$, $C_0$-$C_6$ alkyl$OR^{110}$, or $C_0$-$C_6$ alkyl-$COOR^{110}$; and each $R^{150}$ is independently hydrogen, halogen, $OR^{130}$, ($C_1$-$C_6$)alkyl or ($C_1$-$C_6$)haloalkyl, wherein each alkyl is optionally substituted with at least one group which are each independently halogen, cyano, nitro, azido, $OR^{130}$, $C(O)R^{130}$, $C(O)OR^{13}C(O)N(R^{130})_2$, $N(R^{130})_2$, $N(R^{130})C(O)R^{130}$, $N(R^{130})S(O)_2R^{130}$, —$OC(O)OR^{130}$, $OC(O)N(R^{130})_2$, $N(R^{130})C(O)OR^{130}$, $N(R^{130})C(O)N(R^{130})$, $SR^{130}$, $S(O)R^{130}$, $S(O)_2R'$, or $S(O)_2N(R^{130})_2$; or two $R^{150}$ (bonded to same or different atoms) can be taken together to form a C3-C6 cycloalkyl;

each X is independently —O—, —S—, or —$N(R^{100})$—;

each Y is independently —$[C(R^{150})_2]_p$—, or —$C_2$-$C_6$ alkenyl, wherein p is 1, 2, 3, 4, 5, or 6;

each Y' is independently —$[C(R^{150})_2]_p$—, —$C_2$-$C_6$ alkenyl $C_3$-$C_8$ cycloalkyl, or heterocyclyl, wherein the cycloalkyl or heterocyclyl is optionally substituted with 1 to 3 Z groups;

each Z is independently —H, halogen, —$OR^{110}$, —$SR^{110}$, —$C(=O)R^{110}$, —$C(=O)OR^{110}$, —$C(=O)N(R^{110})_2$, —$N(R^{100})_2$, —$N_3$, —$NO_2$, —$C(=N—OH)R^{110}$, —$C(=S)N(R^{110})_2$, —CN, —$S(=O)R^{110}$, —$S(=O)N(R^{110})_2$, —$S(=O)OR^{110}$, —$S(=O)_2R^{110}$, $S(=O)_2N(R^{110})_2$, —$NR^{110}COR^{110}$, —$N(R^{110})C(=O)N(R^{110})_2$, —$N(R^{110})COOR^{110}$, —$N(R^{110})S(=O)_2R^{110}$, —$C(=O)N(R^{110})N(R^{110})_2$, —$C(=O)N(R^{110})(OR^{110})$, —$OC(=O)$—$R^{110}$, —$OC(=O)$—$OR^{110}$, or —$OC(=O)$—$N(R^{110})_2$; and each m and n is independently 0, 1, 2, 3, 4, 5, or 6.

In some embodiments the compound of Formula IV has a structure of Formula V or VI:

Formula V

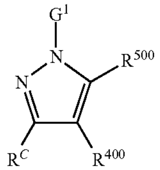

Formula VI

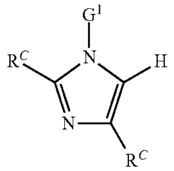

In other embodiments the compound of Formula VI has a structure of Formula VII:

Formula VII

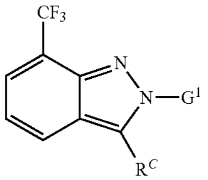

In yet other embodiments the compound of Formula VI has a structure of Formula VIII:

Formula VIII

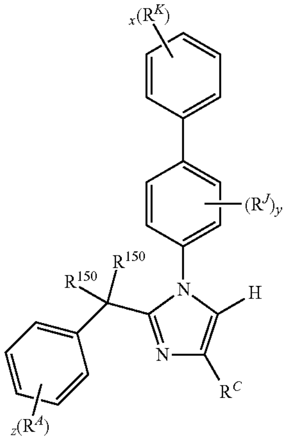

In still further embodiments the compound of Formula VI has a structure of Formula IX:

Formula IX
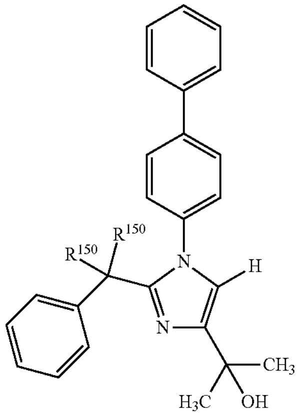
Accordingly, the compounds of Formula IV which can be useful in the methods of the invention include, but are not limited to, compounds having the structures are shown below, and pharmaceutically acceptable salts thereof:
3
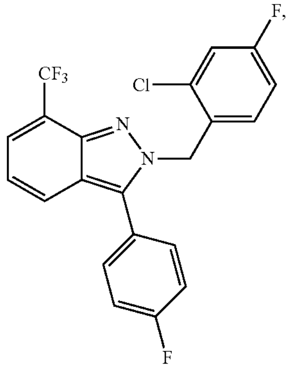
4
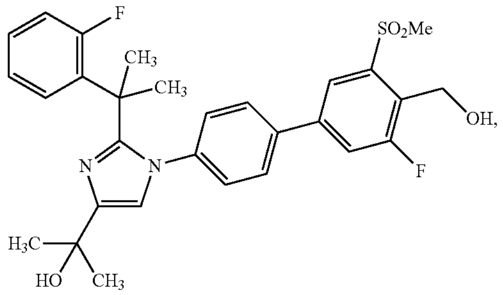
5
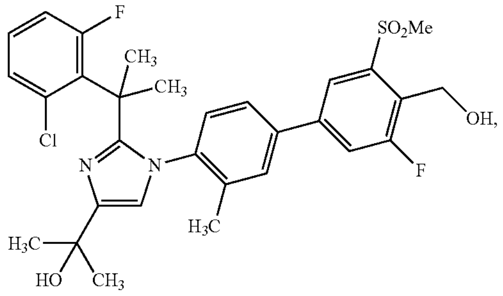
-continued
6
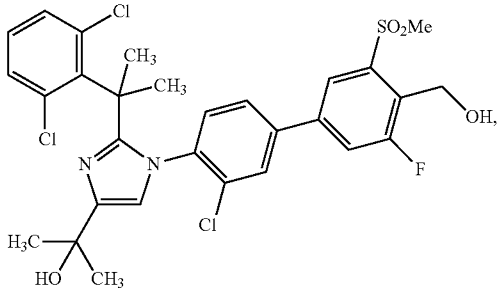
7
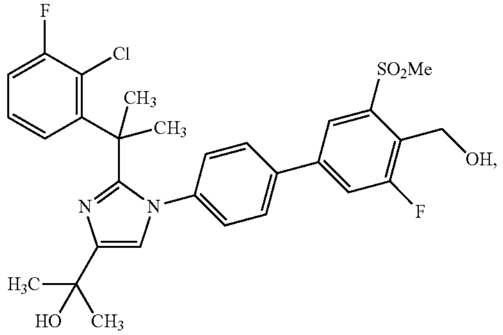
8
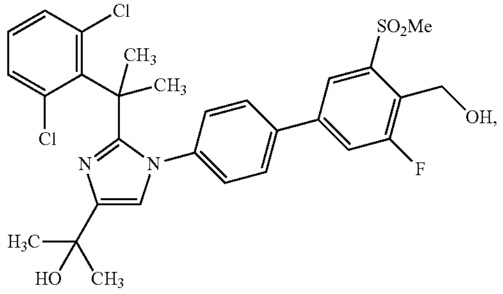
9
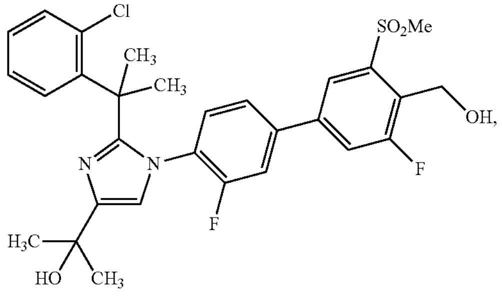
10
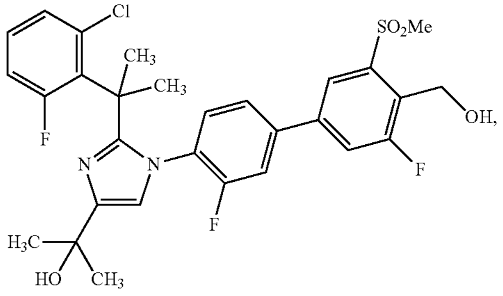

-continued
11
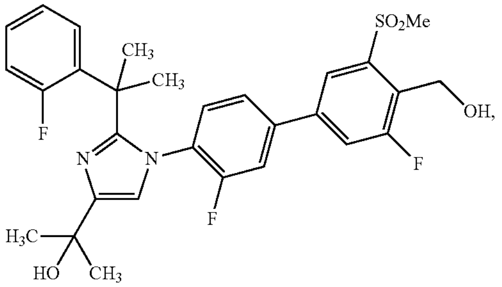
12
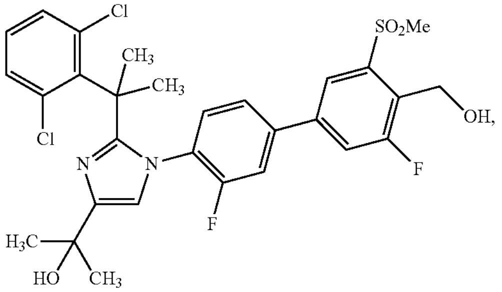
13
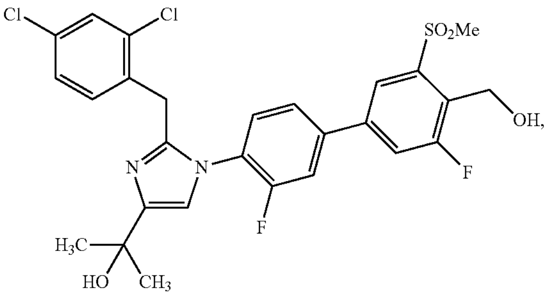
14
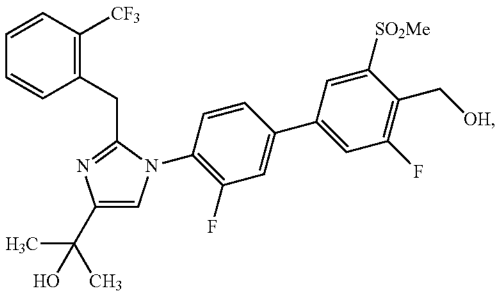
15
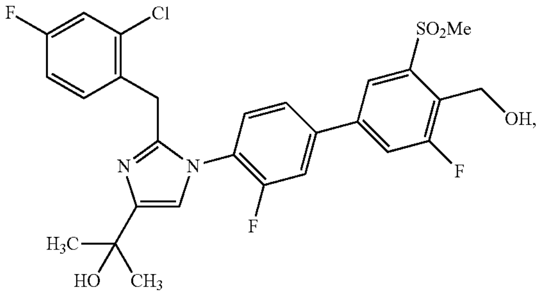
-continued
16
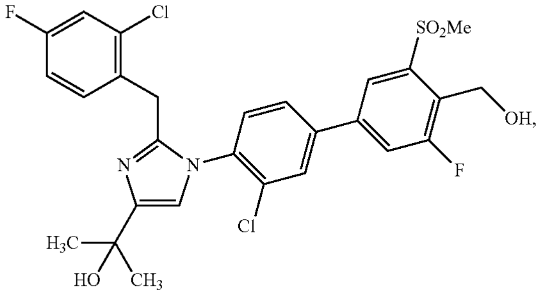
17
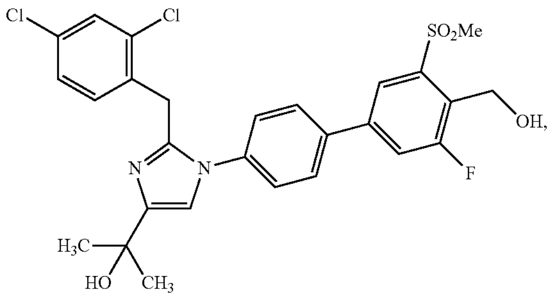
18
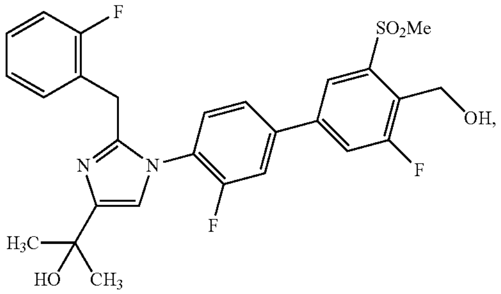
19
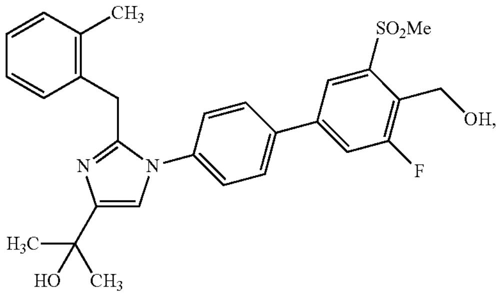
20
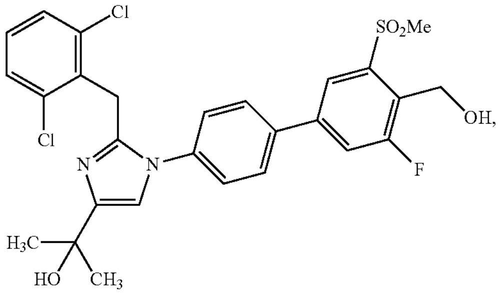

-continued

21

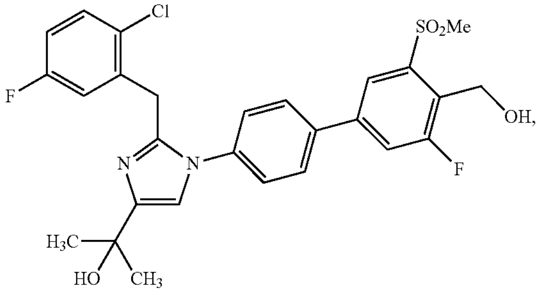

22

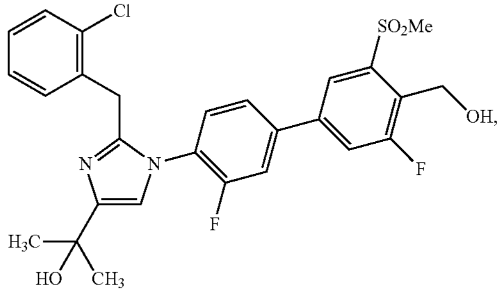

23

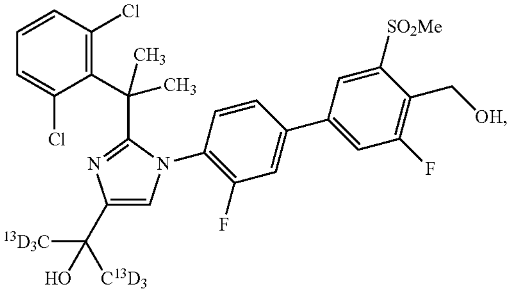

38

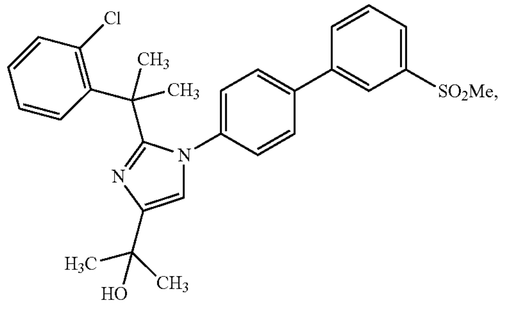

-continued

39

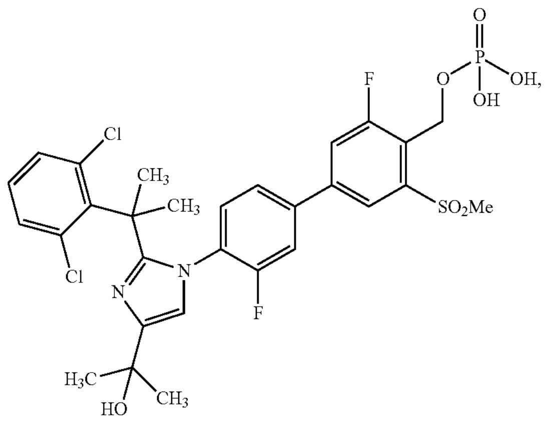

and selected from the list comprising:

33 2-(1-(3 chloro-3'-fluoro-4'-(hydroxymethyl)-5'-(methyl sulfonyl)biphenyl-4-yl)-2-(2-(2,6dichlorophenyl) propan-2-yl)-1H-imidazol-4-yl)propan-2-ol; 34 2-(2-(2(2-chloro-3-fluorophenyl)propan-2-yl)-1-(3'-fluoro-4'-(hydroxymethyl)-5' (methyl sulfonyl)biphenyl-4-yl)-1H-imidazol-4-yl)propan-2-ol; 35 2-(2-(2 (2,6-dichlorophenyl) propan-2-yl)-1-(3'-fluoro-4'-(hydroxymethyl)-5'(methyl sulfonyl)biphenyl-4-yl)-1H-imidazol-4-yl)propan-2-ol; 36 2-(2-(2(2,6-dichlorophenyl)propan-2-yl)-1-(3,3'-difluoro-4'-(hydroxymethyl)-5'(methylsulfonyl)biphenyl-4-yl)-1H-imidazol-4-yl)propan-2-ol; and 37 2-(2-[1(2,6-dichlorophenyl)ethyl]-1-[3,3'-difluoro-4'-(hydroxymethyl)-5' (methylsulfonyl)biphenyl-4-yl]-1H-imidazol-4-yl)propan-2-ol. Compound 12 is also known as WO2010 0138598 Ex. 9. Compound 38 is also known WO2007 002563 Ex. 19. Compound 39 is also known as WO2012 0135082.

Compounds of Formula IV can be synthesized as described in PCT publication No. US2010/0069367 and WO2010/138598 incorpoarated herein by reference.

The LXR agonist that can be used for the treatment and/or prevention of metastasis can be compound 24, or a pharmaceutically acceptable salt thereof.

24

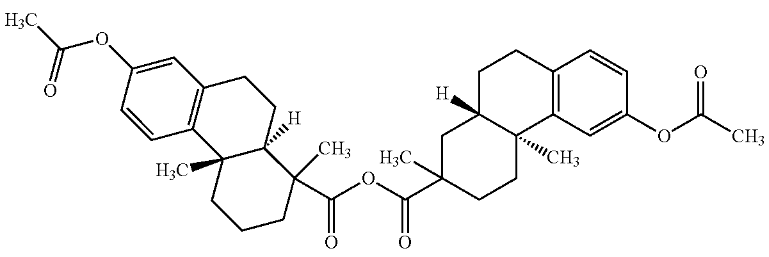

In further embodiments compounds that can be used for the treatment and/or prevention of metastasis can be found in the PCT publications in the list consisting of: WO2006/094034, WO2008/049047, WO2009/020683, WO2009/086138, WO2009/086123, WO2009/086130, WO2009/086129, WO2007/002559, WO2007/002563, WO2007/081335, WO2006/017055, WO2006/102067, WO2009/024550, US2006/0074115, US2006/0135601, WO2009/021868, WO2009/040289, WO2007/047991, WO2007/050425, WO2006/073363, WO2006/073364, WO2006/073365, WO2006/073366, WO2006/073367, US2009/0030082, WO2008/065754, JP2008/179562, WO2007/092065, US2010/0069367, U.S. Pat. Nos. 7,998,995, 7,247,748, WO2010/138598, U.S. Pat. No. 7,365,085, US75776215, US63/136,503, US2004/0072868, US2005/0107444, US2005/0113580, US2005/0131014, US2005/0282908, US2009/0286780, incorporated herein by reference.

LXRα and LXRβ, initially discovered by multiple groups at roughly the same time (Apfel et al., 1994; Willy et al., 1995; Song et al., 1994; Shinar et al., 1994; Teboul et al., 1995), belong to a family of nuclear hormone receptors that are endogenously activated by cholesterol and its oxidized derivatives to mediate transcription of genes involved in maintaining glucose, cholesterol, and fatty acid metabolism (Janowski et al., 1996; Calkin and Tontonoz, 2012). Given the intricate link between lipid metabolism and cancer cell growth (Cairns et al., 2011), the ubiquitous expression of LXRβ in melanoma is unlikely to be coincidental, allowing melanoma cells to synthesize lipids and lipoprotein particles to sustain their growth. At the same time, however, such stable basal expression levels make LXRβ an ideal therapeutic target, as exemplified by the broad-ranging responsiveness of melanoma cells to LXRβ activation therapy.

Compounds have been shown to have selectivity for LXRβ or LXRα. This selectivity may allow for increased activity and/or decreased off target effects. Examples of compounds with selectivity towards LXRβ or LXRα are shown in Table 1.

TABLE 1

$EC_{50}$ values for selected compounds against LXRα and LXRβ

| Compound | $EC_{50}$ – LXRα (nM) | $EC_{50}$ – LXRβ (nM) |
|---|---|---|
| GW3965 2 | 200 | 40 |
| SB742881 25 | 74 | 25 |
| TO9013171 | 20 | 50 |
| LXR-623 3 | 179 | 24 |
| 12 | <100 | 11 |
| 38 | 101-1000 | 630 |

As used herein, reference to the activity of an LXR agonist at LXRα and LXRβ refer to the activity as measured using the ligand sensing assay (LiSA) described in Spencer et al. Journal of Medicinal Chemistry 2001, 44, 886-897, incorporated herein by reference. In some embodiments, the LXR agonist has an EC50 of less than 1 μM in the ligand sensing assay (e.g., 0.5 nm to 500 nM, 10 nM to 100 nM). For example, the methods of the invention can be performed using an LXRβ agonist having activity for LXRβ that is at least 3-fold greater than the activity of the agonist for LXRα, or having activity for LXRβ that is at least 10-fold greater than the activity of the agonist for LXRα, or having activity for LXRβ that is at least 100-fold greater than the activity of said agonist for LXRα, or having activity for LXRβ that is at least within 3-fold of the activity of the agonist for LXRα. The term "greater activity" in the LiSA assay assay refers to a lower EC50. For example, GW3965 2 has approximately 6-fold greater activity for LXRβ (EC50=30) compared to LXRα (EC50=190).

As used herein, the term "increases the level of ApoE expression in vitro" refers to certain LXR agonists capable of increasing the level of ApoE expression 2.5-fold in the qPCR assay of Example 21 at a concentration of less than 5 μM (e.g., at a concentration of 100 nM to 2 μM, at a concentration of less than or equal to 1 μM). The LXR agonists exhibiting this in vitro effect can be highly efficacious for use in the methods of the invention.

The term "alkyl" used is the present application relates a saturated branched or unbranched aliphatic univalent substituent. The alkyl substituent has 1 to 100 carbon atoms, (e.g., 1 to 22 carbon atoms, 1 to 10 carbon atoms 1 to 6 carbon atoms, 1 to 3 carbon atoms). Accordingly, examples of the alkyl substituent include methyl, ethyl, n-propyl, isopropyl, n-butyl, isobutyl, sec-butyl, tert-butyl, n-pentyl and n-hexyl.

The term "alkoxy" represents a chemical substituent of formula —OR, where R is an optionally substituted C1-C6 alkyl group, unless otherwise specified. In some embodiments, the alkyl group can be substituted, e.g., the alkoxy group can have 1, 2, 3, 4, 5 or 6 substituent groups as defined herein.

The term "alkoxyalkyl" represents a heteroalkyl group, as defined herein, that is described as an alkyl group that is substituted with an alkoxy group. Exemplary unsubstituted alkoxyalkyl groups include between 2 to 12 carbons. In some embodiments, the alkyl and the alkoxy each can be further substituted with 1, 2, 3, or 4 substituent groups as defined herein for the respective group.

As used herein, the term "cycloalkyl" refers to a monocyclic, bicyclic, or tricyclic substituent, which may be saturated or partially saturated, i.e. possesses one or more double bonds. Monocyclic substituents are exemplified by a saturated cyclic hydrocarbon group containing from 3 to 8 carbon atoms. Examples of monocyclic cycloalkyl substituents include cyclopropyl, cyclobutyl, cyclopentyl, cyclopentenyl, cyclohexyl, cyclohexenyl, cycloheptyl and cyclooctyl. Bicyclic fused cycloalkyl substituents are exemplified by a cycloalkyl ring fused to another cycloalkyl ring. Examples of bicyclic cycloalkyl substituents include, but are not limited to decalin, 1,2,3,7,8,8a-hexahydro-naphthalene, and the like. Tricyclic cycloalkyl substituents are exemplified by a cycloalkyl bicyclic fused ring fused to an additional cycloalkyl substituent.

The term "alkylene" used is the present application relates a saturated branched or unbranched aliphatic bivalent substituent (e.g. the alkylene substituent has 1 to 6 carbon atoms, 1 to 3 carbon atoms). Accordingly, examples of the alkylene substituent include methylene, ethylene, trimethylene, propylene, tetramethylene, isopropylidene, pentamethylene and hexamethylene.

The term "alkenylene or alkenyl" as used in the present application is an unsaturated branched or unbranched aliphatic bivalent substituent having a double bond between two adjacent carbon atoms (e.g. the alkenylene substituent has 2 to 6 carbon atoms, 2 to 4 carbon atoms). Accordingly, examples of the alkenylene substituent include but are not limited to vinylene, 1-propenylene, 2-propenylene, methylvinylene, 1-butenylene, 2-butenylene, 3-butenylene, 2-methyl-1-propenylene, 2-methyl-2-propenylene, 2-pentenylene, 2-hexenylene.

The term "alkynylene or alkynyl" as used is the present application is an unsaturated branched or unbranched aliphatic bivalent substituent having a tripple bond between two adjacent carbon atoms(e.g. the alkynylene substituent has 2 to 6 carbon atoms 2 to 4 carbon atoms). Examples of the alkynylene substituent include but are not limited to ethynylene, 1-propynylene, 1-butynylene, 2-butynylene, 1-pentynylene, 2-pentynylene, 3-pentynylene and 2-hexynylene.

The term “alkadienylene” as used is the present application is an unsaturated branched or unbranched aliphatic bivalent substituent having two double bonds between two adjacent carbon atoms(e.g. the alkadienylene substituent has 4 to 10 carbon atoms). Accordingly, examples of the alkadienylene substituent include but are not limited to 2,4-pentadienylene, 2,4-hexadienylene, 4-methyl-2,4-pentadienyl ene, 2,4-heptadienylene, 2,6-heptadienylene, 3-methyl-2,4-hexadienylene, 2,6-octadienylene, 3-methyl-2,6-heptadienylene, 2-methyl-2,4-heptadienylene, 2,8-nonadienylene, 3-methyl-2,6-octadienylene, 2,6-decadienylene, 2,9-decadienylene and 3,7-dimethyl-2,6-octadienylene substituents.

The term “heteroaliphatic substituent or heteroalkyl”, as used herein, refers to a monovalent or a bivalent substituent, in which one or more carbon atoms have been substituted with a heteroatom, for instance, with an oxygen, sulfur, nitrogen, phosphorus or silicon atom, wherein the nitrogen and sulfur atoms may optionally be oxidized, and the nitrogen heteroatom may optionally be quaternized. The heteroatom(s) O, N and S may be placed at any interior position of the heteroaliphatic substituent. Examples include —CH2-CH2-O—CH3, —CH2-CH2-NH—CH3, —CH2-CH2-N(CH3)-CH3, —CH2-S—CH2-CH3, —S(O)—CH3, —CH2-CH2-S(O)2-CH3, —CH═CH—O—CH3, —CH2-CH═N—OCH3, and —CH═CH—N(CH3)-CH3. A heteroaliphatic substituent may be linear or branched, and saturated or unsaturated.

In one embodiment, the heteroaliphatic substituent has 1 to 100, (e.g 1 to 42 carbon atoms). In yet another embodiment, the heteroaliphatic substituent is a polyethylene glycol residue.

As used herein, “aromatic substituent or aryl” is intended to mean any stable monocyclic, bicyclic or polycyclic carbon ring of up to 10 atoms in each ring, wherein at least one ring is aromatic, and may be unsubstituted or substituted. Examples of such aromatic substituents include phenyl, p-toluenyl (4-methylphenyl), naphthyl, tetrahydronaphthyl, indanyl, biphenyl, phenanthryl, anthryl or acenaphthyl. In cases where the aromatic substituent is bicyclic and one ring is non-aromatic, it is understood that attachment is via the aromatic ring.

The term “alkylaryl substituents or arylalkyl” refers to alkyl substituents as described above wherein one or more bonds to hydrogen contained therein are replaced by a bond to an aryl substituent as described above. It is understood that an arylalkyl substituents is connected to the carbonyl group if the compound of the invention through a bond from the alkyl substituent. Examples of arylalkyl substituents include, but are not limited to, benzyl (phenylmethyl), p-trifluoromethylbenzyl (4-trifluoromethylphenylmethyl), 1-phenyl ethyl, 2-phenylethyl, 3-phenylpropyl, 2-phenylpropyl and the like.

The term “heteroaromatic substituent or heteroaryl” as used herein, represents a stable monocyclic, bicyclic or polycyclic ring of up to 10 atoms in each ring, wherein at least one ring is aromatic and contains from 1 to 4 heteroatoms selected from the group consisting of 0, N and S. Bicyclic heteroaromatic substituents include phenyl, pyridine, pyrimidine or pyridizine rings that are a) fused to a 6-membered aromatic (unsaturated) heterocyclic ring having one nitrogen atom;
b) fused to a 5- or 6-membered aromatic (unsaturated) heterocyclic ring having two nitrogen atoms;
c) fused to a 5-membered aromatic (unsaturated) heterocyclic ring having one nitrogen atom together with either one oxygen or one sulfur atom; or
d) fused to a 5-membered aromatic (unsaturated) heterocyclic ring having one heteroatom selected from O, N or S.

Heteroaryl groups within the scope of this definition include but are not limited to: benzoimidazolyl, benzofuranyl, b enzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The aliphatic, heteroaliphatic, aromatic and heteroaromatic substituents can be optionally substituted one or more times, the same way or differently with any one or more of the following substituents including, but not limited to: aliphatic, heteroaliphatic, aromatic and heteroaromatic substituents, aryl, heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; CI; Br; I; —OH; —NO2; —CN; —CF3; —CH2CF3; —CHC12; —CH2OH; —CH2CH2OH; —CH2NH2; —CH2SO2CH3; —C(O)Rx; —CO2(Rx); —CON(Rx)2; —OC(O)Rx; —OCO2Rx; —OCON(Rx)2; —N(RX)2; —S(O)Rx; —S(O)2Rx; —NRx (CO)Rx wherein each occurrence of Rx independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, (alkyl)aryl or (alkyl)heteroaryl substituents described above and herein may be substituted or unsubstituted. Additionally, it will be appreciated, that any two adjacent substituents taken together may represent a 4, 5, 6, or 7-membered substituted or unsubstituted alicyclic or heterocyclic substituents. Additional examples of generally applicable substituents are illustrated by the specific embodiments shown below.

The terms “halo” and “halogen” refer to a halogen atom selected from the group consisting of F, Cl, Br and I.

The term “halogenated alkyl substituent, haloalkyl” refers to an alkyl substituents as defined above which is substituted with at least one halogen atom. In an embodiment, the halogenated alkyl substituent is perhalogenated. In another embodiment, perfluoroalkyl refers to the halogenated alkyl substituent is a univalent perfluorated substituent of formula CnF2n+1. For example, the halogenated alkyl substituent may have 1 to 6 carbon atoms, (e.g. 1 to 3 carbon atoms). Accordingly, examples of the alkyl group include trifluoromethyl, 2,2,2-trifluoroethyl, n-perfluoropropyl, n-perfluorobutyl and n-perfluoropentyl.

The term “amino,” as used herein, represents —N(RN1)2, wherein each RN1 is, independently, H, OH, NO2, N(RN2)2, SO2ORN2, SO2RN2, SORN2, an N-protecting group, alkyl, alkenyl, alkynyl, alkoxy, aryl, alkaryl, cycloalkyl, alkcycloalkyl, heterocyclyl (e.g., heteroaryl), alkheterocyclyl (e.g., alkheteroaryl), or two RN1 combine to form a heterocyclyl or an N-protecting group, and wherein each RN2 is, independently, H, alkyl, or aryl. In a preferred embodiment, amino is —NH2, or —NHRN1, wherein RN1 is, independently, OH, NO2, NH2, NRN22, SO2ORN2, SO2RN2, SORN2, alkyl, or aryl, and each RN2 can be H, alkyl, or aryl. The term “aminoalkyl,” as used herein, represents a heteroalkyl group, as defined herein, that is described as an alkyl group, as defined herein, substituted by an amino group, as defined herein. The alkyl and amino each can be further substituted with 1, 2, 3, or 4 substituent groups as described herein for the respective group. For example, the alkyl moiety may comprise an oxo (═O) substituent.

As used herein, the term “aryloxy” refers to aromatic or heteroaromatic systems which are coupled to another residue through an oxygen atom. A typical example of an O-aryl is phenoxy. Similarly, “arylalkyl” refers to aromatic and heteroaromatic systems which are coupled to another residue through a carbon chain, saturated or unsaturated, typically of C1-C8, C1-C6, or more particularly C1-C4 or C1-C3 when saturated or C2-C8, C2-C6, C2-C4, or C2-C3 when unsaturated, including the heteroforms thereof. For greater certainty, arylalkyl thus includes an aryl or heteroaryl group as defined above connected to an alkyl, heteroalkyl, alkenyl, heteroalkenyl, alkynyl or heteroalkynyl moiety also as defined above. Typical arylalkyls would be an aryl(C6-C12)alkyl(C1-C8), aryl(C6-C12)alkenyl(C2-C8), or aryl(C6-C12)alkynyl(C2-C8), plus the heteroforms. A typical example is phenylmethyl, commonly referred to as benzyl.

Typical optional substituents on aromatic or heteroaromatic groups include independently halo, CN, NO2, CF3, OCF3, COOR', CONR'2, OR', SR', SOR', SO2R', NR'2, NR'(CO)R',NR'C(O)OR', NR'C(O)NR'2, NR'SO2NR'2, or NR'SO2R', wherein each R' is independently H or an optionally substituted group selected from alkyl, alkenyl, alkynyl, heteroalkyl, heteroalkenyl, heteroalkynyl, heteroaryl, and aryl (all as defined above); or the substituent may be an optionally substituted group selected from alkyl, alkenyl, alkynyl, heteroalkyl, heteroalkenyl, heteroalkynyl, aryl, heteroaryl, O-aryl, O-heteroaryl and arylalkyl.

Optional substituents on a non-aromatic group (e.g., alkyl, alkenyl, and alkynyl groups), are typically selected from the same list of substituents suitable for aromatic or heteroaromatic groups, except as noted otherwise herein. A non-aromatic group may also include a substituent selected from ═O and ═NOR' where R' is H or an optionally substituted group selected from alkyl, alkenyl, alkynyl, heteroalkyl, heteroalkenyl, heteralkynyl, heteroaryl, and aryl (all as defined above).

In general, a substituent group (e.g., alkyl, alkenyl, alkynyl, or aryl (including all heteroforms defined above) may itself optionally be substituted by additional substituents. The nature of these substituents is similar to those recited with regard to the substituents on the basic structures above. Thus, where an embodiment of a substituent is alkyl, this alkyl may optionally be substituted by the remaining substituents listed as substituents where this makes chemical sense, and where this does not undermine the size limit of alkyl per se; e.g., alkyl substituted by alkyl or by alkenyl would simply extend the upper limit of carbon atoms for these embodiments, and is not included. However, alkyl substituted by aryl, amino, halo and the like would be included. For example, where a group is substituted, the group may be substituted with 1, 2, 3, 4, 5, or 6 substituents. Optional substituents include, but are not limited to: C1-C6 alkyl or heteroaryl, C2-C6 alkenyl or heteroalkenyl, C2-C6 alkynyl or heteroalkynyl, halogen; aryl, heteroaryl, azido(—N3), nitro (—NO2), cyano (—CN), acyloxy(—OC(═O)R'), acyl (—C(═O)R'), alkoxy (—OR'), amido (—NR'C(═O)R" or —C(═O)NRR'), amino (—NRR'), carboxylic acid (—CO2H), carboxylic ester (—CO2R'), carbamoyl (—OC(═O)NR'R" or —NRC(═O)OR'), hydroxy (—OH), isocyano (—NC), sulfonate (—S(═O)2OR), sulfonamide (—S(═O)2NRR' or —NRS(═O)2R'), or sulfonyl (—S(═O)2R), where each R or R' is selected, independently, from H, C1-C6 alkyl or heteroaryl, C2-C6 alkenyl or heteroalkenyl, 2C-6C alkynyl or heteroalkynyl, aryl, or heteroaryl. A substituted group may have, for example, 1, 2, 3, 4, 5, 6, 7, 8, or 9 substituents.

The term “heterocyclyl, heterocyclic, or Het” as used herein represents cyclic heteroalkyl or heteroalkenyl that is, e.g., a 3-, 4-, 5-, 6- or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds. The term “heterocyclyl” also represents a heterocyclic compound having a bridged multicyclic structure in which one or more carbons and/or heteroatoms bridges two non-adjacent members of a monocyclic ring, e.g., a quinuclidinyl group. The term “heterocyclyl” includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, benzothienyl and the like.

Some of the compounds of the present invention can comprise one or more stereogenic centers, and thus can exist in various isomeric forms, e.g. stereoisomers and/or diastereomers. Thus, the compounds of the invention and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided. Moreover, when compounds of the invention exist in tautomeric forms, each tautomer is embraced herein.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Treatment Methods

As disclosed herein, miR-1908, miR-199a-3p, miR-199a-5p, and CTGF were identified as endogenous metastasis promoters of metastatic invasion, endothelial recruitment, and colonization in melanoma while DNAJA4, ApoE, LRP1, LRP8, LXR, and miR7 function as metastasis suppressors or inhibitors of the same process. In addition, it was found that these miRNAs convergently target ApoE and the heat-shock factor DNAJA4. Cancer-secreted ApoE suppresses invasion and endothelial recruitment by activating melanoma cell LRP1 and endothelial LRP8 receptors, respectively. DNAJA4, in turn, induces ApoE expression. These miRNAs strongly predict human metastatic outcomes. Pre-treatment with locked nucleic acids (LNAs) targeting miR-199a-3p, miR-199a-5p, and miR-1908 inhibits metastasis to multiple organs, while therapeutic delivery of these LNAs significantly suppresses human melanoma cell metastasis in a mouse model.

Accordingly, this invention provides methods for treating melanoma via increasing in the subject the expression level or activity level of one of the metastasis suppressors. This increasing can be achieved by, among others, forced expression of one or more of the metastasis suppressors DNAJA4, ApoE, LRP1, and LRP8, or decreasing the expression level or activity level of one or more miR-199a-3p, miR-199a-5p, and miR-1908. In addition, the treatment can be achieved by decreasing the expression level or activity level of one or more of the metastasis promoters.

The invention also provides methods for treating in a subject an angiogenic disorder or a disorder of angiogenesis. The terms "angiogenic disorder," "disorder of angiogenesis," and "angiogenesis disorder" are used interchangeably herein, and refer to a disorder characterized by pathological angiogenesis. A disorder characterized by pathological angiogenesis refers to a disorder where abnormal or aberrant angiogenesis, alone or in combination with others, contributes to causation, origination, or symptom of the disorder. Examples of this disorder include various cancers (e.g., vascularized tumors), eye disorders, inflammatory disorders, and others.

Typical vascularized tumors that can be treated with the method include solid tumors, particularly carcinomas, which require a vascular component for the provision of oxygen and nutrients. Exemplary solid tumors include, but are not limited to, carcinomas of the lung, breast, bone, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, glioblastomas, neuroblastomas, Kaposi's sarcoma, and sarcomas.

A number of disorders or conditions, other than cancer, also can be treated with the above-described method. Examples include arthritis, rheumatoid arthritis, psoriasis, atherosclerosis, diabetic retinopathy, age-related macular degeneration, Grave's disease, vascular restenosis (including restenosis following angioplasty), arteriovenous malformations (AVM), meningioma, hemangioma, neovascular glaucoma, chronic kidney disease, diabetic nephropathy, polycystic kidney disease, interstitial lung disease, pulmonary hypertension, chronic obstructive pulmonary disease (COPD), emphysema, autoimmune hepatitis, chronic inflammatory liver disease, hepatic cirrhosis, cutaneous T-cell lymphoma, rosacea, and basal cell carcinoma.

Other treatment targets include those described in, e.g., US Applications 2009004297, 20090175791, and 20070161553, such as angiofibroma, atherosclerotic plaques, corneal graft neovascularization, hemophilic joints, hypertrophic scars, Osler-Weber syndrome, pyogenic granuloma retrolental fibroplasia, scleroderma, trachoma, vascular adhesions, synovitis, dermatitis, various other inflammatory diseases and disorders, and endometriosis.

Forced Expression of Metastasis Suppressors

Both polypeptides of the aforementioned metastasis suppressors (e.g., DNAJA4, ApoE, LRP1, LRP8, and LXR) and nucleic acid encoding the polypeptides can be used to practice the invention. While many polypeptide preparations can be used, a highly purified or isolated polypeptide is preferred. The terms "peptide," "polypeptide," and "protein" are used herein interchangeably to describe the arrangement of amino acid residues in a polymer. A peptide, polypeptide, or protein can be composed of the standard 20 naturally occurring amino acid, in addition to rare amino acids and synthetic amino acid analogs. They can be any chain of amino acids, regardless of length or post-translational modification (e.g., glycosylation or phosphorylation).

The polypeptide "of this invention" includes recombinantly or synthetically produced fusion or chimeric versions of any of the aforementioned metastasis suppressors, having the particular domains or portions that are involved in the network. The term also encompasses polypeptides that have an added amino-terminal methionine (useful for expression in prokaryotic cells).

Within the scope of this invention are fusion proteins containing one or more of the afore-mentioned sequences and a heterologous sequence. A "chimeric" or "fusion" refers to the combination of amino acid sequences of different origin in one polypeptide chain by in-frame combination of their coding nucleotide sequences. The term explicitly encompasses internal fusions, i.e., insertion of sequences of different origin within a polypeptide chain, in addition to fusion to one of its termini. A heterologous polypeptide, nucleic acid, or gene is one that originates from a foreign species, or, if from the same species, is substantially modified from its original form. Two fused domains or sequences are heterologous to each other if they are not adjacent to each other in a naturally occurring protein or nucleic acid.

An "isolated" or "purified" polypeptide refers to a polypeptide that has been separated from other proteins, lipids, and nucleic acids with which it is naturally associated. The polypeptide can constitute at least 10% (i.e., any percentage between 10% and 100%, e.g., 20%, 30%, 40%, 50%, 60%, 70%, 80%, 85%, 90%, 95%, and 99%) by dry weight of the purified preparation. Purity can be measured by any appropriate standard method, for example, by column chromatography, polyacrylamide gel electrophoresis, or HPLC analysis. An isolated polypeptide described in the invention can be purified from a natural source, produced by recombinant DNA techniques, or by chemical methods.

A "recombinant" polypeptide refers to a polypeptide produced by recombinant DNA techniques; i.e., produced from cells transformed by an exogenous DNA construct encoding the desired polypeptide. A "synthetic" polypeptide refers to a polypeptide prepared by chemical synthesis. The term "recombinant" when used with reference, e.g., to a cell, nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified.

"Overexpression" refers to the expression of a RNA or polypeptide encoded by a nucleic acid introduced into a host cell, wherein the RNA or polypeptide or protein is either not normally present in the host cell, or wherein the RNA or polypeptide is present in said host cell at a higher level than that normally expressed from the endogenous gene encoding the RNA or polypeptide.

The amino acid composition of each of the above-mentioned polypeptides may vary without disrupting their functions—the ability to up-regulate the above-mentioned network (e.g., increase the activation level of the ApoE/LRP signaling pathway), thereby inhibiting metastasis to multiple organs. For example, it can contain one or more conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). Thus, a predicted nonessential amino acid residue in one of the above-described polypeptides (e.g., SEQ ID NOs: 2, 4, 6, 8, 10, 12, 14, 16, and 18) is preferably replaced with another amino acid residue from the same side chain family. Alternatively, mutations can be introduced randomly along all or part of the sequences, such as by saturation mutagenesis, and the resultant mutants can be screened for the ability to up-regulate the above-mentioned network or ApoE/LRP signaling pathway, and trigger the respective cellular response to identify mutants that retain the activity as descried below in the examples.

A functional equivalent of a polypeptide of this invention refers to a derivative of the polypeptide, e.g., a protein having one or more point mutations, insertions, deletions, truncations, a fusion protein, or a combination thereof. It retains substantially the activity to of the above-mentioned polypeptide. The isolated polypeptide of this invention can contain the sequence of one of SEQ ID NOs: 2, 4, 6, 8, 10, 12, 14, 16, and 18, or a functional equivalent or fragment thereof. In general, the functional equivalent is at least 75% (e.g., any number between 75% and 100%, inclusive, e.g., 70%, 80%, 85%, 90%, 95%, and 99%) identical to one of SEQ ID NOs: 2, 4, 6, 8, 10, 12, 14, 16, and 18.

A polypeptide described in this invention can be obtained as a recombinant polypeptide. To prepare a recombinant polypeptide, a nucleic acid encoding it can be linked to another nucleic acid encoding a fusion partner, e.g., glutathione-s-transferase (GST), 6×-His epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant polypeptide of this invention. Alternatively, the polypeptide of the invention can be chemically synthesized (see e.g., Creighton, "Proteins: Structures and Molecular Principles," W.H. Freeman & Co., NY, 1983). For additional guidance, skilled artisans may consult Ausubel et al. (Current Protocols in Molecular Biology and Short Protocols in Molecular Biology, 3rd Ed. 1987 & 1995), Sambrook et al. (Molecular Cloning, A Laboratory Manual, Cold Spring Harbor Press, Cold Spring Harbor, N.Y., 1989), and chemical synthesis Gait, M. J. Ed. (Oligonucleotide Synthesis, IRL Press, Oxford, 1984).

Due to their functions as cellular protein or membrane protein, DNAJA4, LRP1, LRP8, and LXR can be associated with, e.g., conjugated or fused to, one or more of an amino acid sequence comprising a cell-penetrating peptide (CPP) sequence, and the like. In this manner, a composition of the invention as discussed below can include a transport enhancer. A cell-penetrating peptide (CPP) generally consists of less than 30 amino acids and has a net positive charge. CPPs internalize in living animal cells in an endocytotic or receptor/energy-independent manner. There are several classes of CPPs with various origins, from totally protein-derived CPPs via chimeric CPPs to completely synthetic CPPs. Examples of CPPs are known in the art. See, e.g., U.S. Application Nos. 20090099066 and 20100279918. It is know that CPPs can delivery an exogenous protein into various cells.

All of naturally occurring versions, genetic engineered versions, and chemically synthesized versions of the above-mentioned polypeptides can be used to practice the invention disclosed therein. Polypeptides obtained by recombinant DNA technology may have the same amino acid sequence as a naturally occurring version (e.g., one of SEQ ID NOs: 2, 4, 6, 8, 10, 12, 14, 16, and 18) or a functionally equivalent thereof. They also include chemically modified versions. Examples of chemically modified polypeptides include polypeptides subjected to conformational change, addition or deletion of a side chain, and those to which a compound such as polyethylene glycol has been bound. Once purified and tested by standard methods or according to the method described in the examples below or other methods known in the art, the polypeptides can be included in suitable composition.

For expressing the above-mentioned factors, the invention provides a nucleic acid that encodes any of the polypeptides mentioned above. Preferably, the nucleotide sequences are isolated and/or purified. A nucleic acid refers to a DNA molecule (e.g., but not limited to, a cDNA or genomic DNA), an RNA molecule (e.g., but not limited to, an mRNA), or a DNA or RNA analog. A DNA or RNA analog can be synthesized from nucleotide analogs. The nucleic acid molecule can be single-stranded or double-stranded. An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein.

The terms "RNA," "RNA molecule," and "ribonucleic acid molecule" are used interchangeably herein, and refer to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA also can be chemically synthesized. DNA and RNA can be single-stranded (i.e., ssRNA and ssDNA, respectively) or multi-stranded (e.g., double-stranded, i.e., dsRNA and dsDNA, respectively).

The present invention also provides recombinant constructs having one or more of the nucleotide sequences described herein. Example of the constructs include a vector, such as a plasmid or viral vector, into which a nucleic acid sequence of the invention has been inserted, in a forward or reverse orientation. In a preferred embodiment, the construct further includes regulatory sequences, including a promoter, operably linked to the sequence. Large numbers of suitable vectors and promoters are known to those of skill in the art, and are commercially available. Appropriate cloning and expression vectors for use with prokaryotic and eukaryotic hosts are also described in Sambrook et al. (2001, Molecular Cloning: A Laboratory Manual, Cold Spring Harbor Press).

Examples of expression vectors include chromosomal, nonchromosomal and synthetic DNA sequences, e.g., derivatives of or Simian virus 40 (SV40), bacterial plasmids, phage DNA, baculovirus, yeast plasmids, vectors derived from combinations of plasmids and phage DNA, viral DNA such as vaccinia, adenovirus, fowl pox virus, and pseudorabies. However, any other vector may be used as long as it is replicable and viable in the host. The appropriate nucleic acid sequence may be inserted into the vector by a variety of procedures. In general, a nucleic acid sequence encoding one of the polypeptides described above can be inserted into an appropriate restriction endonuclease site(s) by procedures known in the art. Such procedures and related sub-cloning procedures are within the scope of those skilled in the art.

The nucleic acid sequence in the aforementioned expression vector is preferably operatively linked to an appropriate transcription control sequence (promoter) to direct mRNA synthesis. Examples of such promoters include: the retroviral long terminal (LTR) or SV40 promoter, the *E. coli* lac or trp promoter, the phage lambda PL promoter, and other promoters known to control expression of genes in prokaryotic or eukaryotic cells or viruses. The expression vector can also contain a ribosome binding site for translation initiation, and a transcription terminator. The vector may include appropriate sequences for amplifying expression. In addition, the expression vector preferably contains one or more selectable marker genes to provide a phenotypic trait for selection of transformed host cells such as dihydrofolate reductase or neomycin resistance for eukaryotic cell cultures, or such as tetracycline or ampicillin resistance in *E. coli.*

The vector containing the appropriate nucleic acid sequences as described above, as well as an appropriate promoter or control sequence, can be employed to transform an appropriate host to permit the host to express the polypeptides described above. Such vectors can be used in gene therapy. Examples of suitable expression hosts include bacterial cells (e.g., *E. coli, Streptomyces, Salmonella typhimurium*), fungal cells (yeast), insect cells (e.g., *Drosophila* and *Spodoptera frugiperda* (Sf9)), animal cells (e.g., CHO, COS, and HEK 293), adenoviruses, and plant cells. The selection of an appropriate host is within the scope of those skilled in the art. In some embodiments, the present invention provides methods for producing the above mentioned polypeptides by transfecting a host cell with an expression vector having a nucleotide sequence that encodes one of the polypeptides. The host cells are then cultured under a suitable condition, which allows for the expression of the polypeptide.

Decreasing Expression or Activity Level of Metastasis Promoters

As mentioned above, one can use an inhibitory agent that decreases the expression or activity level of miR-199a-3p, miR-199a-5p, miR-1908, or CTGF in treating melanoma. An inhibitory agent (i.e., inhibitor) can be a nucleic acid, a polypeptide, an antibody, or a small molecule compound. In one example, the inhibitor functions at a level of transcription, mRNA stability, translation, protein stability/degradation, protein modification, and protein binding.

A nucleic acid inhibitor can encode a small interference RNA (e.g., an RNAi agent) that targets one or more of the above-mentioned genes, e.g., CTGF, and inhibits its expression or activity. The term "RNAi agent" refers to an RNA, or analog thereof, having sufficient sequence complementarity to a target RNA to direct RNA interference. Examples also include a DNA that can be used to make the RNA. RNA interference (RNAi) refers to a sequence-specific or selective process by which a target molecule (e.g., a target gene, protein or RNA) is down-regulated. Generally, an interfering RNA ("iRNA") is a double stranded short-interfering RNA (siRNA), short hairpin RNA (shRNA), or single-stranded micro-RNA (miRNA) that results in catalytic degradation of specific mRNAs, and also can be used to lower or inhibit gene expression.

The term "short interfering RNA" or "siRNA" (also known as "small interfering RNAs") refers to an RNA agent, preferably a double-stranded agent, of about 10-50 nucleotides in length, preferably between about 15-25 nucleotides in length, more preferably about 17, 18, 19, 20, 21, 22, 23, 24, or 25 nucleotides in length, the strands optionally having overhanging ends comprising, for example 1, 2 or 3 overhanging nucleotides (or nucleotide analogs), which is capable of directing or mediating RNA interference. Naturally-occurring siRNAs are generated from longer dsRNA molecules (e.g., >25 nucleotides in length) by a cell's RNAi machinery (e.g., Dicer or a homolog thereof).

The term "miRNA" or "microRNA" refers to an RNA agent, preferably a single-stranded agent, of about 10-50 nucleotides in length, preferably between about 15-25 nucleotides in length, more preferably about 17, 18, 19, 20, 21, 22, 23, 24, or 25 nucleotides in length, which is capable of directing or mediating RNA interference. Naturally-occurring miRNAs are generated from stem-loop precursor RNAs (i.e., pre-miRNAs) by Dicer. The term "Dicer" as used herein, includes Dicer as well as any Dicer orthologue or homologue capable of processing dsRNA structures into siRNAs, miRNAs, siRNA-like or miRNA-like molecules. The term microRNA (or "miRNA") is used interchangeably with the term "small temporal RNA" (or "stRNA") based on the fact that naturally-occurring microRNAs (or "miRNAs") have been found to be expressed in a temporal fashion (e.g., during development).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region.

Within the scope of this invention is utilization of RNAi featuring degradation of RNA molecules (e.g., within a cell). Degradation is catalyzed by an enzymatic, RNA-induced silencing complex (RISC). A RNA agent having a sequence sufficiently complementary to a target RNA sequence (e.g., the above-mentioned CTGF gene) to direct RNAi means that the RNA agent has a homology of at least 50%, (e.g., 50%, 60%, 70%, 80%, 90%, 95%, 98%, 99%, or 100% homology) to the target RNA sequence so that the two are sufficiently complementary to each other to hybridize and trigger the destruction of the target RNA by the RNAi machinery (e.g., the RISC complex) or process. A RNA agent having a "sequence sufficiently complementary to a target RNA sequence to direct RNAi" also means that the RNA agent has a sequence sufficient to trigger the translational inhibition of the target RNA by the RNAi machinery or process. A RNA agent also can have a sequence sufficiently complementary to a target RNA encoded by the target DNA sequence such that the target DNA sequence is chromatically silenced. In other words, the RNA agent has a sequence sufficient to induce transcriptional gene silencing, e.g., to down-modulate gene expression at or near the target DNA sequence, e.g., by inducing chromatin structural changes at or near the target DNA sequence.

The above-mentioned polynucleotides can be delivered using polymeric, biodegradable microparticle or microcapsule delivery devices known in the art. Another way to achieve uptake of the polynucleotides is using liposomes, prepared by standard methods. The polynucleotide can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano, et al., 1995, J. Mol. Med. 73:479). Alternatively, tissue specific targeting can be achieved by the use of tissue-specific transcriptional regulatory elements that are known in the art. Delivery of naked DNA (i.e., without a delivery vehicle) to an intramuscular, intradermal, or subcutaneous site is another means to achieve in vivo expression.

siRNA, miRNA, and asRNA (antisense RNA) molecules can be designed by methods well known in the art. siRNA, miRNA, and asRNA molecules with homology sufficient to provide sequence specificity required to uniquely degrade any RNA can be designed using programs known in the art, including, but not limited to, those maintained on websites for AMBION, Inc. and DHARMACON, Inc. Systematic testing of several designed species for optimization of the siRNA, miRNA, and asRNA sequence can be routinely performed by those skilled in the art. Considerations when designing short interfering nucleic acid molecules include, but are not limited to, biophysical, thermodynamic, and structural considerations, base preferences at specific positions in the sense strand, and homology. These considerations are well known in the art and provide guidelines for designing the above-mentioned RNA molecules.

An antisense polynucleotide (preferably DNA) of the present invention can be any antisense polynucleotide so long as it possesses a base sequence complementary or substantially complementary to that of the gene encoding a component of the aforementioned network. The base sequence can be at least about 70%, 80%, 90%, or 95% homology to the complement of the gene encoding the polypeptide. These antisense DNAs can be synthesized using a DNA synthesizer.

The antisense DNA of the present invention may contain changed or modified sugars, bases or linkages. The antisense DNA, as well as the RNAi agent mentioned above, may also be provided in a specialized form such as liposomes, microspheres, or may be applied to gene therapy, or may be provided in combination with attached moieties. Such attached moieties include polycations such as polylysine that act as charge neutralizers of the phosphate backbone, or hydrophobic moieties such as lipids (e.g., phospholipids, cholesterols, etc.) that enhance the interaction with cell membranes or increase uptake of the nucleic acid. Preferred examples of the lipids to be attached are cholesterols or derivatives thereof (e.g., cholesteryl chloroformate, cholic acid, etc.). These moieties may be attached to the nucleic acid at the 3' or 5' ends thereof and may also be attached thereto through a base, sugar, or intramolecular nucleoside linkage. Other moieties may be capping groups specifically placed at the 3' or 5' ends of the nucleic acid to prevent degradation by nucleases such as exonuclease, RNase, etc. Such capping groups include, but are not limited to, hydroxyl protecting groups known in the art, including glycols such as polyethylene glycol, tetraethylene glycol and the like. The inhibitory action of the antisense DNA can be examined using a cell-line or animal based gene expression system of the present invention in vivo and in vitro.

The above-discussed nucleic acids encoding one or more of the polypeptides mentioned above or RNAi agents can be cloned in a vector for delivering to cells in vitro or in vivo. For in vivo uses, the delivery can target a specific tissue or organ (e.g., skin). Targeted delivery involves the use of vectors (e.g., organ-homing peptides) that are targeted to specific organs or tissues after systemic administration. For example, the vector can have a covalent conjugate of avidin and a monoclonal antibody to a liver specific protein.

In certain embodiments, the present invention provides methods for in vivo expression the above-mentioned metastsis suppressors. Such method would achieve its therapeutic effect by introduction of nucleic acid sequences encoding any of the factors into cells or tissues of a human or a non-human animal in need of inhibiting endothelial recruitment, cancer cell invasion, or metastatic angiogenesis. Delivery of the nucleic acid sequences can be achieved using a recombinant expression vector such as a chimeric virus or a colloidal dispersion system. Preferred for therapeutic delivery of the nucleic acid sequences is the use of targeted liposomes.

Various viral vectors which can be utilized for gene therapy disclosed herein include, adenovirus, adeno-associated virus (AAV), herpes virus, vaccinia, or, preferably, an RNA virus such as a retrovirus and a lentivirus. Preferably, the retroviral vector is a lentivirus or a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes.

All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using a target-specific antibody or hormone that has a receptor in the target. Those of skill in the art will recognize that specific polynucleotide sequences can be inserted into the retroviral genome or attached to a viral envelope to allow target specific delivery of the retroviral vector.

Another targeted system for delivery of nucleic acids is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA, and intact virions can be encapsulated within the aqueous interior and delivered to cells in a biologically active form. Methods for efficient gene transfer using a liposome vehicle are known in the art. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Exemplary phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

When used in vivo, it is desirable to use a reversible delivery-expression system. To that end, the Cre-loxP or FLP/FRT system and other similar systems can be used for reversible delivery-expression of one or more of the above-described nucleic acids. See WO2005/112620, WO2005/039643, U.S. Applications 20050130919, 20030022375, 20020022018, 20030027335, and 20040216178. In particular, the reversible delivery-expression system described in US Application NO 20100284990 can be used to provide a selective or emergency shut-off.

In another example, the above-mentioned inhibitory agent can be a polypeptide or a protein complex, such as an antibody. The term "antibody" refers to an immunoglobulin molecule or immunologically active portion thereof, i.e., an antigen-binding portion. Examples include, but are not limited to, a protein having at least one or two, heavy (H) chain variable regions (VH), and at least one or two light (L) chain variable regions (VL). The VH and VL regions can be further subdivided into regions of hypervariability, termed "complementarity determining regions" ("CDR"), interspersed with regions that are more conserved, termed "framework regions" (FR). As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, and IgG4), delta, epsilon and mu constant region genes, as well as the myriad immunoglobulin variable region genes.

The term "antigen-binding portion" of an antibody (or "antibody portion") refers to one or more fragments of an antibody that retain the ability to specifically bind to an antigen (e.g., LRP1, LRP8, and CTGF). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

Antibodies that specifically bind to one of the above-mentioned target proteins (e.g., CTGF) can be made using methods known in the art. This antibody can be a polyclonal or a monoclonal antibody. In one embodiment, the antibody can be recombinantly produced, e.g., produced by phage display or by combinatorial methods. In another embodiment, the antibody is a fully human antibody (e.g., an antibody made in a mouse which has been genetically engineered to produce an antibody from a human immunoglobulin sequence), a humanized antibody, or a non-human antibody, for example, but not limited to, a rodent (mouse or rat), goat, primate (for example, but not limited to, monkey), rabbit, or camel antibody. Examples of methods to generate humanized version of antibodies include, but are not limited to, CDR grafting (Queen et al., U.S. Pat. No. 5,585,089; Riechmann et al., Nature 332:323 (1988)), chain shuffling (U.S. Pat. No. 5,565,332); and veneering or resurfacing (EP 592,106; EP 519,596); Padlan, Molecular Immunology 28(415):489-498 (1991); Studnicka et al., Protein Engineering 7(6):805-814 (1994); Roguska. et al., PNAS 91:969-973 (1994)). Examples of methods to generate fully human antibodies include, but are not limited to, generation of antibodies from mice that can express human immunoglobulin genes and use of phage-display technology to generate and screen human immunoglobulin gene libraries.

An "isolated antibody" is intended to refer to an antibody that is substantially free of other antibodies having different antigenic specificities (e.g., an isolated antibody that specifically binds CTGF is substantially free of antibodies that specifically bind antigens other than such an antigen). Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, "isotype" refers to the antibody class (e.g., IgM or IgG1) that is encoded by the heavy chain constant region genes. The phrases "an antibody recognizing an antigen" and "an antibody specific for an antigen" are used interchangeably herein with the term "an antibody which binds specifically to an antigen." As used herein, the term "high affinity" for an IgG antibody refers to an antibody having a KD of 10-7 M or less, preferably 10-8 M or less, more preferably 10-9 M or less and even more preferably 10-10 M or less for a target antigen. However, "high affinity" binding can vary for other antibody isotypes. For example, "high affinity" binding for an IgM isotype refers to an antibody having a KD of 10-7 M or less, more preferably 10-8 M or less.

In one example, a composition contains a monoclonal antibody that neutralizes CTGF. In one embodiment, this antibody can be a fully human antibody, a humanized antibody, or a non-human antibody, for example, but not limited to, a rodent (mouse or rat), goat, primate (for example, but not limited to, monkey), rabbit, or camel antibody. In one embodiment, one or more amino-acids of this monoclonal monoclonal antibody may be substituted in order to alter its physical properties. These properties include, but are not limited to, binding specificity, binding affinity, immunogenicity, and antibody isotype. Pharmaceutical compositions containing fully human or humanized versions of the above described antibodies can be used for treating melanoma or for inhibiting endothelial recruitment, cancer cell invasion, or metastatic angiogenesi s.

As used herein, a "subject" refers to a human and a non-human animal. Examples of a non-human animal include all vertebrates, e.g., mammals, such as non-human mammals, non-human primates (particularly higher primates), dog, rodent (e.g., mouse or rat), guinea pig, cat, and rabbit, and non-mammals, such as birds, amphibians, reptiles, etc. In one embodiment, the subject is a human. In another embodiment, the subject is an experimental animal or animal suitable as a disease model. A subject to be treated for a disorder can be identified by standard diagnosing techniques for the disorder. Optionally, the subject can be examined for mutation, expression level, or activity level of one or more of the miR-199a-3p, miR-199a-5p, miR-1908, and CTGF mentioned above by methods known in the art or described above before treatment. If the subject has a particular mutation in the gene, or if the gene expression or activity level is, for example, greater in a sample from the subject than that in a sample from a normal person, the subject is a candidate for treatment of this invention.

To confirm the inhibition or treatment, one can evaluate and/or verify the inhibition of endothelial recruitment or resulting angiogenesis using technology known in the art before and/or after the administering step. Exemplary technologies include angiography or arteriography, a medical imaging technique used to visualize the inside, or lumen, of blood vessels and organs of the body, can generally be done by injecting a radio-opaque contrast agent into the blood vessel and imaging using X-ray based techniques such as fluoroscopy.

"Treating" or "treatment" as used herein refers to administration of a compound or agent to a subject who has a disorder with the purpose to cure, alleviate, relieve, remedy, delay the onset of, prevent, or ameliorate the disorder, the symptom of a disorder, the disease state secondary to the disorder, or the predisposition toward the disorder. An "effective amount" or "therapeutically effective amount" refers to an amount of the compound or agent that is capable of producing a medically desirable result in a treated subject. The treatment method can be performed in vivo or ex vivo, alone or in conjunction with other drugs or therapy. A therapeutically effective amount can be administered in one or more administrations, applications or dosages and is not intended to be limited to a particular formulation or administration route.

The expression "effective amount" as used herein, refers to a sufficient amount of the compound of the invention to exhibit the desired therapeutic effect. The exact amount required will vary from subject to subject, depending on the species, age, and general condition of the subject, the particular therapeutic agent and the like. The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the anticancer activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

A therapeutic agent can be administered in vivo or ex vivo, alone or co-administered in conjunction with other drugs or therapy, i.e., a cocktail therapy. As used herein, the term "co-administration" or "co-administered" refers to the administration of at least two agent(s) or therapies to a subject. For example, in the treatment of tumors, particularly vascularized, malignant tumors, the agents can be used alone or in combination with, e.g., chemotherapeutic, radiotherapeutic, apoptopic, anti-angiogenic agents and/or immunotoxins or coaguligands. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary.

In an in vivo approach, a compound or agent is administered to a subject. Generally, the compound is suspended in a pharmaceutically-acceptable carrier (such as, for example, but not limited to, physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily.

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-100 mg/kg. Variations in the needed dosage are to be expected in view of the variety of compounds available and the different efficiencies of various routes of administration. For example, oral administration would be expected to require higher dosages than administration by i.v. injection. Variations in these dosage levels can be adjusted using standard empirical routines for optimization as is well understood in the art. Encapsulation of the compound in a suitable delivery vehicle (e.g., polymeric microparticles or implantable devices) can increase the efficiency of delivery, particularly for oral delivery.

Compositions

Within the scope of this invention is a composition that contains a suitable carrier and one or more of the therapeutic agents described above. The composition can be a pharmaceutical composition that contains a pharmaceutically acceptable carrier, a dietary composition that contains a dietarily acceptable suitable carrier, or a cosmetic composition that contains a cosmetically acceptable carrier.

The term "pharmaceutical composition" refers to the combination of an active agent with a carrier, inert or active, making the composition especially suitable for diagnostic or therapeutic use in vivo or ex vivo. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active compound. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, sodium lauryl sulfate, and D&C Yellow #10.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in J. Pharmaceutical Sciences, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts, include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; natural and synthetic phospholipids, such as soybean and egg yolk phosphatides, lecithin, hydrogenated soy lecithin, dimyristoyl lecithin, dipalmitoyl lecithin, distearoyl lecithin, dioleoyl lecithin, hydroxylated lecithin, lysophosphatidylcholine, cardiolipin, sphingomyelin, phosphatidylcholine, phosphatidyl ethanolamine, diastearoyl phosphatidylethanolamine (DSPE) and its pegylated esters, such as DSPE-PEG750 and, DSPE-PEG2000, phosphatidic acid, phosphatidyl glycerol and phosphatidyl serine. Commercial grades of lecithin which are preferred include those which are available under the trade name Phosal® or Phospholipon® and include Phosal 53 MCT, Phosal 50 PG, Phosal 75 SA, Phospholipon 90H, Phospholipon 90G and Phospholipon 90 NG; soy-phosphatidylcholine (SoyPC) and DSPE-PEG2000 are particularly preferred; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The above-described composition, in any of the forms described above, can be used for treating melanoma, or any other disease or condition described herein. An effective amount refers to the amount of an active compound/agent that is required to confer a therapeutic effect on a treated subject. Effective doses will vary, as recognized by those skilled in the art, depending on the types of diseases treated, route of administration, excipient usage, and the possibility of co-usage with other therapeutic treatment.

A pharmaceutical composition of this invention can be administered parenterally, orally, nasally, rectally, topically, or buccally. The term "parenteral" as used herein refers to subcutaneous, intracutaneous, intravenous, intrmuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent. Such solutions include, but are not limited to, 1,3-butanediol, mannitol, water, Ringer's solution, and isotonic sodium chloride solution. In addition, fixed oils are conventionally employed as a solvent or suspending medium (e.g., synthetic mono- or diglycerides). Fatty acid, such as, but not limited to, oleic acid and its glyceride derivatives, are useful in the preparation of injectables, as are natural pharmaceutically acceptable oils, such as, but not limited to, olive oil or castor oil, polyoxyethylated versions thereof. These oil solutions or suspensions also can contain a long chain alcohol diluent or dispersant such as, but not limited to, carboxymethyl cellulose, or similar dispersing agents. Other commonly used surfactants, such as, but not limited to, Tweens or Spans or other similar emulsifying agents or bioavailability enhancers, which are commonly used in the manufacture of pharmaceutically acceptable solid, liquid, or other dosage forms also can be used for the purpose of formulation.

A composition for oral administration can be any orally acceptable dosage form including capsules, tablets, emulsions and aqueous suspensions, dispersions, and solutions. In the case of tablets, commonly used carriers include, but are not limited to, lactose and corn starch. Lubricating agents, such as, but not limited to, magnesium stearate, also are typically added. For oral administration in a capsule form, useful diluents include, but are not limited to, lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

Pharmaceutical compositions for topical administration according to the described invention can be formulated as solutions, ointments, creams, suspensions, lotions, powders, pastes, gels, sprays, aerosols, or oils. Alternatively, topical formulations can be in the form of patches or dressings impregnated with active ingredient(s), which can optionally comprise one or more excipients or diluents. In some preferred embodiments, the topical formulations include a material that would enhance absorption or penetration of the active agent(s) through the skin or other affected areas.

A topical composition contains a safe and effective amount of a dermatologically acceptable carrier suitable for application to the skin. A "cosmetically acceptable" or "dermatologically-acceptable" composition or component refers a composition or component that is suitable for use in contact with human skin without undue toxicity, incompatibility, instability, allergic response, and the like. The carrier enables an active agent and optional component to be delivered to the skin at an appropriate concentration(s). The carrier thus can act as a diluent, dispersant, solvent, or the like to ensure that the active materials are applied to and distributed evenly over the selected target at an appropriate concentration. The carrier can be solid, semi-solid, or liquid. The carrier can be in the form of a lotion, a cream, or a gel, in particular one that has a sufficient thickness or yield point to prevent the active materials from sedimenting. The carrier can be inert or possess dermatological benefits. It also should be physically and chemically compatible with the active components described herein, and should not unduly impair stability, efficacy, or other use benefits associated with the composition.

Combination Therapies

In some embodiments, the pharmaceutical composition may further comprise an additional compound having anti-proliferative activity. The additional compound having anti-proliferative activity can be selected from a group of anti-proliferative agents including those shown in Table 2.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder, or they may achieve different effects (e.g., control of any adverse effects).

By "antiproliferative agent" is meant any antiproliferative agent, including those antiproliferative agents listed in Table 2, any of which can be used in combination with a LXR agonist to treat the medical conditions recited herein. Antiproliferative agents also include organo-platine derivatives, naphtoquinone and benzoquinone derivatives, chrysophanic acid and anthroquinone derivatives thereof

TABLE 2

| | | |
|---|---|---|
| Alkylating agents | Busulfan | Chlorambucil |
| | dacarbazine | procarbazine |
| | ifosfamide | altretamine |
| | hexamethylmelamine | estramustine phosphate |
| | thiotepa | mechlorethamine |
| | dacarbazine | streptozocin |
| | lomustine | temozolomide |
| | cyclophosphamide | Semustine |
| Platinum agents | spiroplatin | lobaplatin (Aeterna) |
| | tetraplatin | satraplatin (Johnson Matthey) |
| | ormaplatin | BBR-3464 (Hoffmann-La Roche) |
| | iproplatin | |
| | ZD-0473 (AnorMED) | SM-11355 (Sumitomo) |
| | oxaliplatin | AP-5280 (Access) |
| | carboplatin | cisplatin |
| Antimetabolites | azacytidine | trimetrexate |
| | Floxuridine | deoxycoformycin |
| | 2-chlorodeoxyadenosine | pentostatin |
| | 6-mercaptopurine | hydroxyurea |
| | 6-thioguanine | decitabine (SuperGen) |
| | cytarabine | clofarabine (Bioenvision) |
| | 2-fluorodeoxy cytidine | irofulven (MGI Pharma) |
| | methotrexate | DMDC (Hoffmann-La Roche) |
| | tomudex | ethynylcytidine (Taiho) |
| | fludarabine | gemcitabine |
| | raltitrexed | capecitabine |
| Topoisomerase inhibitors | amsacrine | exatecan mesylate (Daiichi) |
| | epirubicin | quinamed (ChemGenex) |
| | etoposide | gimatecan (Sigma-Tau) |
| | teniposide or mitoxantrone | diflomotecan (Beaufour-Ipsen) |
| | 7-ethyl-10-hydroxy-camptothecin | TAS-103 (Taiho) |
| | dexrazoxanet (TopoTarget) | elsamitrucin (Spectrum) |
| | pixantrone (Novuspharma) | J-107088 (Merck & Co) |
| | rebeccamycin analogue (Exelixis) | BNP-1350 (BioNumerik) |
| | BBR-3576 (Novuspharma) | CKD-602 (Chong Kun Dang) |
| | rubitecan (SuperGen) | KW-2170 (Kyowa Hakko) |
| | irinotecan (CPT-11) | hydroxycamptothecin (SN-38) |
| | topotecan | |
| Antitumor antibiotics | valrubicin | azonafide |
| | therarubicin | anthrapyrazole |
| | idarubicin | oxantrazole |
| | rubidazone | losoxantrone |
| | plicamycin | MEN-10755 (Menarini) |
| | porfiromycin | GPX-100 (Gem Pharmaceuticals) |
| | mitoxantrone (novantrone) | |
| | amonafide | Epirubicin |
| | | mitoxantrone |
| | | doxorubicin |
| Antimitotic agents | colchicine | E7010 (Abbott) |
| | vinblastine | PG-TXL (Cell Therapeutics) |
| | vindesine | IDN 5109 (Bayer) |
| | dolastatin 10 (NCI) | A 105972 (Abbott) |
| | rhizoxin (Fujisawa) | A 204197 (Abbott) |
| | mivobulin (Warner-Lambert) | LU 223651 (BASF) |
| | cemadotin (BASF) | D 24851 (ASTAMedica) |
| | RPR 109881A (Aventis) | ER-86526 (Eisai) |
| | TXD 258 (Aventis) | combretastatin A4 (BMS) |
| | epothilone B (Novartis) | isohomohalichondrin-B (PharmaMar) |
| | T 900607 (Tularik) | |
| | T 138067 (Tularik) | ZD 6126 (AstraZeneca) |
| | cryptophycin 52 (Eli Lilly) | AZ10992 (Asahi) |
| | vinflunine (Fabre) | IDN-5109 (Indena) |
| | auristatin PE (Teikoku Hormone) | AVLB (Prescient NeuroPharma) |
| | BMS 247550 (BMS) | azaepothilone B (BMS) |
| | BMS 184476 (BMS) | BNP-7787 (BioNumerik) |
| | BMS 188797 (BMS) | CA-4 prodrug (OXiGENE) |
| | taxoprexin (Protarga) | dolastatin-10 (NIH) |
| | SB 408075 (GlaxoSmithKline) | CA-4 (OXiGENE) |
| | Vinorelbine | docetaxel |
| | Trichostatin A | vincristine |
| | | paclitaxel |

TABLE 2-continued

| | | |
|---|---|---|
| Aromatase inhibitors | aminoglutethimide<br>atamestane (BioMedicines)<br>letrozole<br>anastrazole | YM-511 (Yamanouchi)<br>formestane<br>exemestane |
| Thymidylate synthase inhibitors | pemetrexed (Eli Lilly)<br>ZD-9331 (BTG) | nolatrexed (Eximias)<br>CoFactor ™ (BioKeys) |
| DNA antagonists | trabectedin (PharmaMar)<br>glufosfamide (Baxter International)<br>albumin + 32 P (Isotope Solutions)<br>thymectacin (NewBiotics) | edotreotide (Novartis)<br>mafosfamide (Baxter International)<br>apaziquone (Spectrum Pharmaceuticals)<br>O6 benzyl guanine (Paligent) |
| Farnesyltransferase inhibitors | arglabin (NuOncology Labs)<br>lonafarnib (Schering-Plough)<br>BAY-43-9006 (Bayer) | tipifarnib (Johnson & Johnson)<br>perillyl alcohol (DOR BioPharma) |
| Pump inhibitors | CBT-1 (CBA Pharma)<br>tariquidar (Xenova)<br>MS-209 (Schering AG) | zosuquidar trihydrochloride (Eli Lilly)<br>biricodar dicitrate (Vertex) |
| Histone acetyltransferase inhibitors | tacedinaline (Pfizer)<br>SAHA (Aton Pharma)<br>MS-275 (Schering AG) | pivaloyloxymethyl butyrate (Titan)<br>depsipeptide (Fujisawa) |
| Metalloproteinase inhibitors | Neovastat (Aeterna Laboratories)<br>marimastat (British Biotech) | CMT-3 (CollaGenex)<br>BMS-275291 (Celltech) |
| Ribonucleoside reductase inhibitors | gallium maltolate (Titan)<br>triapine (Vion) | tezacitabine (Aventis)<br>didox (Molecules for Health) |
| TNF alpha agonists/antagonists | virulizin (Lorus Therapeutics)<br>CDC-394 (Celgene) | revimid (Celgene) |
| Endothelin A receptor antagonist | atrasentan (Abbott)<br>ZD-4054 (AstraZeneca) | YM-598 (Yamanouchi) |
| Retinoic acid receptor agonists | fenretinide (Johnson & Johnson)<br>LGD-1550 (Ligand) | alitretinoin (Ligand) |
| Immuno-modulators | interferon<br>oncophage (Antigenics)<br>GMK (Progenics)<br>adenocarcinoma vaccine (Biomira)<br>CTP-37 (AVI BioPharma)<br>IRX-2 (Immuno-Rx)<br>PEP-005 (Peplin Biotech)<br>synchrovax vaccines (CTL Immuno)<br>melanoma vaccine (CTL Immuno)<br>p21 RAS vaccine (GemVax)<br>MAGE-A3 (GSK)<br>nivolumab (BMS)<br>abatacept (BMS) | dexosome therapy (Anosys)<br>pentrix (Australian Cancer Technology)<br>ISF-154 (Tragen)<br>cancer vaccine (Intercell)<br>norelin (Biostar)<br>BLP-25 (Biomira)<br>MGV (Progenics)<br>β-alethine (Dovetail)<br>CLL therapy (Vasogen)<br>Ipilimumab (BMS),<br>CM-10 (cCam Biotherapeutics)<br>MPDL3280A (Genentech) |
| Hormonal and antihormonal agents | estrogens<br>conjugated estrogens<br>ethinyl estradiol<br>chlortrianisen<br>idenestrol<br>hydroxyprogesterone caproate<br>medroxyprogesterone<br>testosterone<br>testosterone propionate;<br>fluoxymesterone<br>methyltestosterone<br>diethylstilbestrol<br>megestrol<br>bicalutamide<br>flutamide<br>nilutamide | dexamethasone<br>prednisone<br>methylprednisolone<br>prednisolone<br>aminoglutethimide<br>leuprolide<br>octreotide<br>mitotane<br>P-04 (Novogen)<br>2-methoxyestradiol (EntreMed)<br>arzoxifene (Eli Lilly)<br>tamoxifen<br>toremofine<br>goserelin<br>Leuporelin<br>bicalutamide |
| Photodynamic agents | talaporfin (Light Sciences)<br>Theralux (Theratechnologies)<br>motexafin gadolinium (Pharmacyclics) | Pd-bacteriopheophorbide (Yeda)<br>lutetium texaphyrin (Pharmacyclics)<br>hypericin |
| Kinase Inhibitors | imatinib (Novartis)<br>leflunomide (Sugen/Pharmacia)<br>ZD1839 (AstraZeneca)<br>erlotinib (Oncogene Science)<br>canertinib (Pfizer)<br>squalamine (Genaera)<br>SU5416 (Pharmacia)<br>SU6668 (Pharmacia)<br>ZD4190 (AstraZeneca)<br>ZD6474 (AstraZeneca)<br>vatalanib (Novartis)<br>PKI166 (Novartis)<br>GW2016 (GlaxoSmithKline) | EKB-569 (Wyeth)<br>kahalide F (PharmaMar)<br>CEP-701 (Cephalon)<br>CEP-751 (Cephalon)<br>MLN518 (Millenium)<br>PKC412 (Novartis)<br>Phenoxodiol (Novogen)<br>C225 (ImClone)<br>rhu-Mab (Genentech)<br>MDX-H210 (Medarex)<br>2C4 (Genentech)<br>MDX-447 (Medarex)<br>ABX-EGF (Abgenix) |

TABLE 2-continued

| | |
|---|---|
| EKB-509 (Wyeth) | IMC-1C11 (ImClone) |
| trastuzumab (Genentech) | Tyrphostins |
| OSI-774 (Tarceva ™) | Gefitinib (Iressa) |
| CI-1033 (Pfizer) | PTK787 (Novartis) |
| SU11248 (Pharmacia) | EMD 72000 (Merck) |
| RH3 (York Medical) | Emodin |
| Geni stein | Radicinol |
| Radicinol | Vemurafenib (B-Raf enzyme inhibitor, Daiichi Sankyo) |
| Met-MAb (Roche) | |
| SR-27897 (CCK A inhibitor, Sanofi-Synthelabo) | ceflatonin (apoptosis promotor, ChemGenex) |
| tocladesine (cyclic AMP agonist, Ribapharm) | BCX-1777 (PNP inhibitor, BioCryst) |
| alvocidib (CDK inhibitor, Aventis) | ranpirnase (ribonuclease stimulant, Alfacell) |
| CV-247 (COX-2 inhibitor, Ivy Medical) | |
| P54 (COX-2 inhibitor, Phytopharm) | galarubicin (RNA synthesis inhibitor, Dong-A) |
| CapCell ™ (CYP450 stimulant, Bavarian Nordic) | tirapazamine (reducing agent, SRI International) |
| GCS-100 (gal3 antagonist, GlycoGenesys) | |
| G17DT immunogen (gastrin inhibitor, Aphton) | N-acetylcysteine (reducing agent, Zambon) |
| efaproxiral (oxygenator, Allos Therapeutics) | R-flurbiprofen (NF-kappaB inhibitor, Encore) |
| PI-88 (heparanase inhibitor, Progen) | |
| tesmilifene (histamine antagonist, YM BioSciences) | 3 CPA (NF-kappaB inhibitor, Active Biotech) |
| histamine (histamine H2 receptor agonist, Maxim) | seocalcitol (vitamin D receptor agonist, Leo) |
| tiazofurin (IMPDH inhibitor, Ribapharm) | 131-I-TM-601 (DNA antagonist, TransMolecular) |
| cilengitide (integrin antagonist, Merck KGaA) | |
| SR-31747 (IL-1 antagonist, Sanofi-Synthelabo) | eflornithine (ODC inhibitor, ILEX Oncology) |
| CCI-779 (mTOR kinase inhibitor, Wyeth) | minodronic acid (osteoclast inhibitor, Yamanouchi) |
| exisulind (PDE V inhibitor, Cell Pathways) | |
| CP-461 (PDE V inhibitor, Cell Pathways) | indisulam (p53 stimulant, Eisai) |
| AG-2037 (GART inhibitor, Pfizer) | aplidine (PPT inhibitor, PharmaMar) |
| WX-UK1 (plasminogen activator inhibitor, Wilex) | gemtuzumab (CD33 antibody, Wyeth Ayerst) |
| PBI-1402 (PMN stimulant, ProMetic LifeSciences) | PG2 (hematopoiesis enhancer, Pharmagenesis) |
| bortezomib (proteasome inhibitor, Millennium) | Immunol ™ (triclosan oral rinse, Endo) |
| | triacetyluridine (uridine prodrug, Wellstat) |
| SRL-172 (T cell stimulant, SR Pharma) | |
| TLK-286 (glutathione S transferase inhibitor, Telik) | SN-4071 (sarcoma agent, Signature BioScience) |
| PT-100 (growth factor agonist, Point Therapeutics) | TransMID-107 ™ (immunotoxin, KS Biomedix) |
| midostaurin (PKC inhibitor, Novartis) | PCK-3145 (apoptosis promotor, Procyon) |
| bryostatin-1 (PKC stimulant, GPC Biotech) | doranidazole (apoptosis promotor, Pola) |
| CDA-II (apoptosis promotor, Everlife) | CHS-828 (cytotoxic agent, Leo) |
| SDX-101 (apoptosis promotor, Salmedix) | trans-retinoic acid (differentiator, NIH) |
| rituximab (CD20 antibody, Genentech | MX6 (apoptosis promotor, MAXIA) |
| carmustine | apomine (apoptosis promotor, ILEX Oncology) |
| Mitoxantrone | |
| Bleomycin | urocidin (apoptosis promotor, Bioniche) |
| Absinthin | Ro-31-7453 (apoptosis promotor, La Roche) |
| Chrysophanic acid | |
| Cesium oxides | brostallicin (apoptosis promotor, Pharmacia) |
| BRAF inhibitors, | |
| PDL1 inhibitors | β-lapachone |
| MEK inhibitors | gelonin |
| bevacizumab | cafestol |
| angiogenesis inhibitors | kahweol |
| dabrafenib | caffeic acid |
| | Tyrphostin AG |
| | PD-1 inhibitors |
| | CTLA-4 inhibitors |
| | sorafenib |
| | BRAF inhibitors |

Diagnosis and Prognosis Methods

The above-describe genes can be used in determining whether a subject has, or is at risk of having, metastatic melanoma. Alternatively, they can be used for determining a prognosis of such a disorder in a subject.

Diagnosis Methods

In one aspect, the invention provides qualitative and quantitative information to determine whether a subject has or is predisposed to metastatic melanoma or other disease characterized by endothelial recruitment, cancer cell invasion, or metastatic angiogenesis. A subject having such a disorder or prone to it can be determined based on the expression levels, patterns, or profiles of the above-described genes or their products (mRNAs, microRNAs, or polypeptides) in a test sample from the subject. In other words, the products can be used as markers to indicate the presence or absence of the disorder. Diagnostic and prognostic assays of the invention include methods for assessing the expression level of the products. The methods allow one to detect the disorder. For example, a relative increase in the expression level of one or more promoters (i.e., miR-199a-3p, miR-199a-5p, miR-1908, and CTGF) is indicative of presence the disorder. Conversely, a lower expression level or a lack of the expression is indicative lack of the disorder.

The presence, level, or absence of, an mRNA, microRNA, or polypeptide product in a test sample can be evaluated by obtaining a test sample from a test subject and contacting the test sample with a compound or an agent capable of detecting the nucleic acid (e.g., RNA or DNA probe) or polypeptide. The "test sample" includes tissues, cells and biological fluids isolated from a subject, as well as tissues, cells and fluids present within a subject. The level of expression of a gene(s) of interest can be measured in a number of ways, including measuring the RNA encoded by the gene.

Expressed RNA samples can be isolated from biological samples using any of a number of well-known procedures. For example, biological samples can be lysed in a guanidinium-based lysis buffer, optionally containing additional components to stabilize the RNA. In some embodiments, the lysis buffer can contain purified RNAs as controls to monitor recovery and stability of RNA from cell cultures. Examples of such purified RNA templates include the Kanamycin Positive Control RNA from PROMEGA (Madison, Wis.), and 7.5 kb Poly(A)-Tailed RNA from LIFE TECHNOLOGIES (Rockville, Md.). Lysates may be used immediately or stored frozen at, e.g., −80° C.

Optionally, total RNA can be purified from cell lysates (or other types of samples) using silica-based isolation in an automation-compatible, 96-well format, such as the RNEASY purification platform (QIAGEN, Inc., Valencia, Calif.). Other RNA isolation methods are contemplated, such as extraction with silica-coated beads or guanidinium. Further methods for RNA isolation and preparation can be devised by one skilled in the art.

The methods of the present invention can be performed using crude samples (e.g., blood, serum, plasma, or cell lysates), eliminating the need to isolate RNA. RNAse inhibitors are optionally added to the crude samples. When using crude cellular lysates, it should be noted that genomic DNA can contribute one or more copies of a target sequence, e.g., a gene, depending on the sample. In situations in which the target sequence is derived from one or more highly expressed genes, the signal arising from genomic DNA may not be significant. But for genes expressed at low levels, the background can be eliminated by treating the samples with DNAse, or by using primers that target splice junctions for subsequent priming of cDNA or amplification products.

The level of RNA corresponding to a gene in a cell can be determined both in situ and in vitro. RNA isolated from a test sample can be used in hybridization or amplification assays that include, Southern or Northern analyses, PCR analyses, and probe arrays. A preferred diagnostic method for the detection of RNA levels involves contacting the isolated RNA with a nucleic acid probe that can hybridize to the RNA encoded by the gene. The probe can be a full-length nucleic acid or a portion thereof, such as an oligonucleotide of at least 10 nucleotides in length and sufficient to specifically hybridize under stringent conditions to the RNA.

In one format, RNA (or cDNA prepared from it) is immobilized on a surface and contacted with the probes, for example, by running the isolated RNA on an agarose gel and transferring the RNA from the gel to a membrane, such as nitrocellulose. In another format, the probes are immobilized on a surface and the RNA (or cDNA) is contacted with the probes, for example, in a gene chip array. A skilled artisan can adapt known RNA detection methods for detecting the level of RNA.

The level of RNA (or cDNA prepared from it) in a sample encoded by a gene to be examined can be evaluated with nucleic acid amplification, e.g., by standard PCR (U.S. Pat. No. 4,683,202), RT-PCR (Bustin S. J Mol Endocrinol. 25:169-93, 2000), quantitative PCR (Ong Y. et al., Hematology. 7:59-67, 2002), real time PCR (Ginzinger D. Exp Hematol. 30:503-12, 2002), and in situ PCR (Thaker V. Methods Mol Biol. 115:379-402, 1999), or any other nucleic acid amplification method, followed by the detection of the amplified molecules using techniques known in the art. In another embodiment, the methods of the invention further include contacting a control sample with a compound or agent capable of detecting the RNA of a gene and comparing the presence of the RNA in the control sample with the presence of the RNA in the test sample.

The above-described methods and markers can be used to assess the risk of a subject for developing melanoma. In particular, the invention can be applied to those in high risk cohort who already have certain risks so as to gain critical insight into early detection. A change in levels of miR gene products associated with melanoma can be detected prior to, or in the early stages of, the development of transformed or neoplastic phenotypes in cells of a subject. The invention therefore also provides a method for screening a subject who is at risk of developing melanoma, comprising evaluating the level of at least one gene product, or a combination of gene products, associated with melanoma in a biological sample obtained form the subject's skin. Accordingly, an alteration in the level of the gene product, or combination of gene products, in the biological sample as compared to the level of a corresponding gene product in a control sample, is indicative of the subject being at risk for developing melanoma. The biological sample used for such screening can include skin tissue that is either normal or suspected to be cancerous. Subjects with a change in the level of one or more gene products associated with melanoma are candidates for further monitoring and testing. Such further testing can comprise histological examination of tissue samples, or other techniques within the skill in the art.

As used herein, the term "diagnosis" means detecting a disease or disorder or determining the stage or degree of a disease or disorder. Usually, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease; i.e. there may be differential diagnoses that can be inferred from a diagnostic factor or symptom. Likewise, there may be instances where a factor or symptom that is indicative of a particular disease is present in an individual that does not have the particular disease. The diagnostic methods may be used independently, or in combination with other diagnosing and/or staging methods known in the medical art for a particular disease or disorder, e.g., melanoma.

Prognosis Methods

The diagnostic methods described above can identify subjects having, or at risk of developing, a melanoma. In addition, changes in expression levels and/or trends of the above-mentioned genes in a biological sample, e.g., peripheral blood samples, can provide an early indication of recovery or lack thereof. For example, a further increase (or decline) or persistently-altered gene expression levels of the promoter genes (or inhibitor genes) indicate a poor prognosis, i.e., lack of improvement or health decline. Accordingly, these genes allow one to assess post-treatment recovery of melanoma. The analysis of this select group of genes or a subset thereof indicates outcomes of the conditions.

The prognostic assays described herein can be used to determine whether a subject is suitable to be administered with an agent (e.g., an agonist, antagonist, peptidomimetic, protein, peptide, nucleic acid, small molecule, or other drug candidate) to treat melanoma or other disorders associated with endothelial recruitment, cancer cell invasion, or metastatic angiogenesis. For example, such assays can be used to determine whether a subject can be administered with a chemotherapeutic agent.

Thus, also provided by this invention is a method of monitoring a treatment for a cellular proliferative disorder in a subject. For this purpose, gene expression levels of the genes disclosed herein can be determined for test samples from a subject before, during, or after undergoing a treatment. The magnitudes of the changes in the levels as compared to a baseline level are then assessed. A decrease in the expression of the above-mentioned promoter genes (miR-199a-3p, miR-199a-5p, miR-1908, and CTGF) after the treatment indicates that the subject can be further treated by the same treatment. Similarly, an increase in the inhibitors (DNAJA4, ApoE, LRP1, and LRP8) also indicates that the subject can be further treated by the same treatment. Conversely, further increase or persistent high expression levels of one or more of the promoter genes is indicate lack of improvement or health decline.

Information obtained from practice of the above assays is useful in prognostication, identifying progression of, and clinical management of diseases and other deleterious conditions affecting an individual subject's health status. In preferred embodiments, the foregoing diagnostic assays provide information useful in prognostication, identifying progression of and management of melanoma and other conditions characterized by endothelial recruitment, cancer cell invasion, or metastatic angiogenesis. The information more specifically assists the clinician in designing chemotherapeutic or other treatment regimes to eradicate such conditions from the body of an afflicted subject, a human.

The term "prognosis" as used herein refers to a prediction of the probable course and outcome of a clinical condition or disease. A prognosis is usually made by evaluating factors or symptoms of a disease that are indicative of a favorable or unfavorable course or outcome of the disease. The phrase "determining the prognosis" as used herein refers to the process by which the skilled artisan can predict the course or outcome of a condition in a patient. The term "prognosis" does not refer to the ability to predict the course or outcome of a condition with 100% accuracy instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition.

The terms "favorable prognosis" and "positive prognosis," or "unfavorable prognosis" and "negative prognosis" as used herein are relative terms for the prediction of the probable course and/or likely outcome of a condition or a disease. A favorable or positive prognosis predicts a better outcome for a condition than an unfavorable or negative prognosis. In a general sense, a "favorable prognosis" is an outcome that is relatively better than many other possible prognoses that could be associated with a particular condition, whereas an unfavorable prognosis predicts an outcome that is relatively worse than many other possible prognoses that could be associated with a particular condition. Typical examples of a favorable or positive prognosis include a better than average cure rate, a lower propensity for metastasis, a longer than expected life expectancy, differentiation of a benign process from a cancerous process, and the like. For example, a positive prognosis is one where a patient has a 50% probability of being cured of a particular cancer after treatment, while the average patient with the same cancer has only a 25% probability of being cured.

The terms "determining," "measuring," "assessing," and "assaying" are used interchangeably and include both quantitative and qualitative measurement, and include determining if a characteristic, trait, or feature is present or not. Assessing may be relative or absolute. "Assessing the presence of" a target includes determining the amount of the target present, as well as determining whether it is present or absent.

Arrays

Also provided in the invention is a biochip or array. The biochip/array may contain a solid or semi-solid substrate having an attached probe or plurality of probes described herein. The probes may be capable of hybridizing to a target sequence under stringent hybridization conditions. The probes may be attached at spatially defined address on the substrate. More than one probe per target sequence may be used, with either overlapping probes or probes to different sections of a particular target sequence. The probes may be capable of hybridizing to target sequences associated with a single disorder appreciated by those in the art. The probes may either be synthesized first, with subsequent attachment to the biochip, or may be directly synthesized on the biochip.

"Attached" or "immobilized" as used herein to refer to a nucleic acid (e.g., a probe) and a solid support may mean that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

The solid substrate can be a material that may be modified to contain discrete individual sites appropriate for the attachment or association of the probes and is amenable to at least one detection method. Examples of such substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate can be planar, although other configurations of substrates may be used as well. For example, probes may be placed on the inside surface of a tube, for flow-through sample analysis to minimize sample volume. Similarly, the substrate may be flexible, such as flexible foam, including closed cell foams made of particular plastics.

The array/biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker. The probes may be attached to the solid support by either the 5' terminus, 3' terminus, or via an internal nucleotide. The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography. Detailed discussion of methods for linking nucleic acids to a support substrate can be found in, e.g., U.S. Pat. Nos. 5,837,832, 6,087,112, 5,215,882, 5,707,807, 5,807,522, 5,958,342, 5,994,076, 6,004,755, 6,048,695, 6,060,240, 6,090,556, and 6,040,138.

In some embodiments, an expressed transcript (e.g., a transcript of a microRNA gene described herein) is represented in the nucleic acid arrays. In such embodiments, a set of binding sites can include probes with different nucleic acids that are complementary to different sequence segments of the expressed transcript. Examples of such nucleic acids can be of length of 15 to 200 bases, 20 to 100 bases, 25 to 50 bases, 40 to 60 bases. Each probe sequence can also include one or more linker sequences in addition to the sequence that is complementary to its target sequence. A linker sequence is a sequence between the sequence that is complementary to its target sequence and the surface of support. For example, the nucleic acid arrays of the invention can have one probe specific to each target microRNA gene. However, if desired, the nucleic acid arrays can contain at least 2, 5, 10, 100, 200, 300, 400, 500 or more probes specific to some expressed transcript (e.g., a transcript of a microRNA gene described herein).

Kits

In another aspect, the present invention provides kits embodying the methods, compositions, and systems for analysis of the polypeptides and microRNA expression as described herein. Such a kit may contain a nucleic acid described herein together with any or all of the following: assay reagents, buffers, probes and/or primers, and sterile saline or another pharmaceutically acceptable emulsion and suspension base. In addition, the kit may include instructional materials containing directions (e.g., protocols) for the practice of the methods described herein. For example, the kit may be a kit for the amplification, detection, identification or quantification of a target mRNA or microRNA sequence. To that end, the kit may contain a suitable primer (e.g., hairpin primers), a forward primer, a reverse primer, and a probe.

In one example, a kit of the invention includes one or more microarray slides (or alternative microarray format) onto which a plurality of different nucleic acids (each corresponding to one of the above-mentioned genes) have been deposited. The kit can also include a plurality of labeled probes. Alternatively, the kit can include a plurality of polynucleotide sequences suitable as probes and a selection of labels suitable for customizing the included polynucleotide sequences, or other polynucleotide sequences at the discretion of the practitioner. Commonly, at least one included polynucleotide sequence corresponds to a control sequence, e.g., a normalization gene or the like. Exemplary labels include, but are not limited to, a fluorophore, a dye, a radiolabel, an enzyme tag, that is linked to a nucleic acid primer.

In one embodiment, kits that are suitable for amplifying nucleic acid corresponding to the expressed RNA samples are provided. Such a kit includes reagents and primers suitable for use in any of the amplification methods described above. Alternatively, or additionally, the kits are suitable for amplifying a signal corresponding to hybridization between a probe and a target nucleic acid sample (e.g., deposited on a microarray).

In addition, one or more materials and/or reagents required for preparing a biological sample for gene expression analysis are optionally included in the kit. Furthermore, optionally included in the kits are one or more enzymes suitable for amplifying nucleic acids, including various polymerases (RT, Taq, etc.), one or more deoxynucleotides, and buffers to provide the necessary reaction mixture for amplification.

Typically, the kits are employed for analyzing gene expression patterns using mRNA or microRNA as the starting template. The RNA template may be presented as either total cellular RNA or isolated RNA; both types of sample yield comparable results. In other embodiments, the methods and kits described in the present invention allow quantitation of other products of gene expression, including tRNA, rRNA, or other transcription products.

Optionally, the kits of the invention further include software to expedite the generation, analysis and/or storage of data, and to facilitate access to databases. The software includes logical instructions, instructions sets, or suitable computer programs that can be used in the collection, storage and/or analysis of the data. Comparative and relational analysis of the data is possible using the software provided.

The kits optionally contain distinct containers for each individual reagent and/or enzyme component. Each component will generally be suitable as aliquoted in its respective container. The container of the kits optionally includes at least one vial, ampule, or test tube. Flasks, bottles and other container mechanisms into which the reagents can be placed and/or aliquoted are also possible. The individual containers of the kit are preferably maintained in close confinement for commercial sale. Suitable larger containers may include injection or blow-molded plastic containers into which the desired vials are retained. Instructions, such as written directions or videotaped demonstrations detailing the use of the kits of the present invention, are optionally provided with the kit.

In a further aspect, the present invention provides for the use of any composition or kit herein, for the practice of any method or assay herein, and/or for the use of any apparatus or kit to practice any assay or method herein.

A “test sample” or a “biological sample” as used herein may mean a sample of biological tissue or fluid that comprises nucleic acids. Such samples include, but are not limited to, tissue or body fluid isolated from animals. Biological samples may also include sections of tissues such as biopsy and autopsy samples, frozen sections taken for histological purposes, blood, plasma, serum, sputum, stool, tears, mucus, urine, effusions, amniotic fluid, ascitic fluid, hair, and skin. Biological samples also include explants and primary and/or transformed cell cultures derived from patient tissues. A biological sample may be provided by removing a sample of cells from an animal, but can also be accomplished by using previously isolated cells (e.g., isolated by another person, at another time, and/or for another purpose), or by performing the methods described herein in vivo. Archival tissues, such as those having treatment or outcome history, may also be used.

The term "body fluid" or "bodily fluid" refers to any fluid from the body of an animal. Examples of body fluids include, but are not limited to, plasma, serum, blood, lymphatic fluid, cerebrospinal fluid, synovial fluid, urine, saliva, mucous, phlegm and sputum. A body fluid sample may be collected by any suitable method. The body fluid sample may be used immediately or may be stored for later use. Any suitable storage method known in the art may be used to store the body fluid sample: for example, the sample may be frozen at about −20° C. to about −70° C. Suitable body fluids are acellular fluids. "Acellular" fluids include body fluid samples in which cells are absent or are present in such low amounts that the miRNA level determined reflects its level in the liquid portion of the sample, rather than in the cellular portion. Such acellular body fluids are generally produced by processing a cell-containing body fluid by, for example, centrifugation or filtration, to remove the cells. Typically, an acellular body fluid contains no intact cells however, some may contain cell fragments or cellular debris. Examples of acellular fluids include plasma or serum, or body fluids from which cells have been removed.

The term "gene" used herein refers to a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto. The term also includes pseudogenes, which are dysfunctional relatives of known genes that have lost their protein-coding ability or are otherwise no longer expressed in a cell.

"Expression profile" as used herein refers to a genomic expression profile, e.g., an expression profile of microRNAs. Profiles may be generated by any convenient means for determining a level of a nucleic acid sequence e.g., quantitative hybridization of microRNA, cRNA, etc., quantitative PCR, ELISA for quantification, and the like, and allow the analysis of differential gene expression between two samples. A subject or patient sample, e.g., cells or a collection thereof, e.g., tissues, is assayed. Samples are collected by any convenient method, as known in the art. Nucleic acid sequences of interest are nucleic acid sequences that are found to be predictive, including the nucleic acid sequences of those described herein, where the expression profile may include expression data for 5, 10, 20, 25, 50, 100 or more of, including all of the listed nucleic acid sequences. The term "expression profile" may also mean measuring the abundance of the nucleic acid sequences in the measured samples.

"Differential expression" refers to qualitative or quantitative differences in the temporal and/or cellular gene expression patterns within and among cells and tissue. Thus, a differentially expressed gene can qualitatively have its expression altered, including an activation or inactivation, in, e.g., normal versus disease tissue. Genes may be turned on or turned off in a particular state, relative to another state thus permitting comparison of two or more states. A qualitatively regulated gene will exhibit an expression pattern within a state or cell type that may be detectable by standard techniques. Some genes will be expressed in one state or cell type, but not in both. Alternatively, the difference in expression may be quantitative, e.g., in that expression is modulated, up-regulated, resulting in an increased amount of transcript, or down-regulated, resulting in a decreased amount of transcript. The degree to which expression differs need only be large enough to quantify via standard characterization techniques such as expression arrays, quantitative reverse transcriptase PCR, Northern analysis, and RNase protection.

"Nucleic acid" or "oligonucleotide" or "polynucleotide" as used herein refers to at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

The term "primer" refers to any nucleic acid that is capable of hybridizing at its 3' end to a complementary nucleic acid molecule, and that provides a free 3' hydroxyl terminus which can be extended by a nucleic acid polymerase. As used herein, amplification primers are a pair of nucleic acid molecules that can anneal to 5' or 3' regions of a gene (plus and minus strands, respectively, or vice-versa) and contain a short region in between. Under appropriate conditions and with appropriate reagents, such primers permit the amplification of a nucleic acid molecule having the nucleotide sequence flanked by the primers. For in situ methods, a cell or tissue sample can be prepared and immobilized on a support, such as a glass slide, and then contacted with a probe that can hybridize to RNA. Alternative methods for amplifying nucleic acids corresponding to expressed RNA samples include those described in, e.g., U.S. Pat. No. 7,897,750.

The term "probe" as used herein refers to an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

"Complement" or "complementary" as used herein to refer to a nucleic acid may mean Watson-Crick (e.g., A-T/U and C-G) or Hoogsteen base pairing between nucleotides or nucleotide analogs of nucleic acid molecules. A full complement or fully complementary may mean 100% complementary base pairing between nucleotides or nucleotide analogs of nucleic acid molecules.

"Stringent hybridization conditions" as used herein refers to conditions under which a first nucleic acid sequence (e.g., probe) hybridizes to a second nucleic acid sequence (e.g., target), such as in a complex mixture of nucleic acids. Stringent conditions are sequence-dependent and be different in different circumstances, and can be suitably selected by one skilled in the art. Stringent conditions may be selected to be about 5-10° C. lower than the thermal melting point (Tm) for the specific sequence at a defined ionic strength pH. The Tm may be the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C. However, several factors other than temperature, such as salt concentration, can influence the stringency of hybridization and one skilled in the art can suitably select the factors to accomplish a similar stringency.

As used herein the term "reference value" refers to a value that statistically correlates to a particular outcome when compared to an assay result. In preferred embodiments, the reference value is determined from statistical analysis of studies that compare microRNA expression with known clinical outcomes. The reference value may be a threshold score value or a cutoff score value. Typically a reference value will be a threshold above (or below) which one outcome is more probable and below which an alternative threshold is more probable.

In one embodiment, a reference level may be one or more circulating miRNA levels expressed as an average of the level of the circulating miRNA from samples taken from a control population of healthy (disease-free) subjects. In another embodiment, the reference level may be the level in the same subject at a different time, e.g., before the present assay, such as the level determined prior to the subject developing the disease or prior to initiating therapy. In general, samples are normalized by a common factor. For example, acellular body fluid samples are normalized by volume body fluid and cell-containing samples are normalized by protein content or cell count. Nucleic acid samples may also be normalized relative to an internal control nucleic acid.

As disclosed herein, the difference of the level of one or more polypeptides or RNAs (mRNAs or microRNAs) is indicative of a disease or a stage thereof. The phrase "difference of the level" refers to differences in the quantity of a particular marker, such as a nucleic acid, in a sample as compared to a control or reference level. For example, the quantity of a particular biomarker may be present at an elevated amount or at a decreased amount in samples of patients with a neoplastic disease compared to a reference level. In one embodiment, a "difference of a level" may be a difference between the quantity of a particular biomarker present in a sample as compared to a control (e.g., reference value) of at least about 1%, 2%, 3%, 5%, 10%, 15%, 20%, 25%, 30%, 35%, 40%, 50%, 60%, 75%, 80% 100%, 150%, 200%, or more. In one embodiment, a "difference of a level" may be a statistically significant difference between the quantities of a biomarker present in a sample as compared to a control. For example, a difference may be statistically significant if the measured level of the biomarker falls outside of about 1.0 standard deviation, about 1.5 standard deviations, about 2.0 standard deviations, or about 2.5 stand deviations of the mean of any control or reference group. With respect to miRNA measurement, the level may be measured from real-time PCR as the Ct value, which may be normalized to a ΔCt value as described in the Examples below.

Drug Screening

The invention provides a method for identifying a compound that are useful for treating melanoma or for inhibiting endothelial recruitment, cell invasion, or metastatic angiogenesis.

Candidate compounds to be screened (e.g., proteins, peptides, peptidomimetics, peptoids, antibodies, small molecules, or other drugs) can be obtained using any of the numerous approaches in combinatorial library methods known in the art. Such libraries include: peptide libraries, peptoid libraries (libraries of molecules having the functionalities of peptides, but with a novel, non-peptide backbone that is resistant to enzymatic degradation); spatially addressable parallel solid phase or solution phase libraries; synthetic libraries obtained by deconvolution or affinity chromatography selection; and the "one-bead one-compound" libraries. See, e.g., Zuckermann et al. 1994, J. Med. Chem. 37:2678-2685; and Lam, 1997, Anticancer Drug Des. 12:145. Examples of methods for the synthesis of molecular libraries can be found in, e.g., DeWitt et al., 1993, PNAS USA 90:6909; Erb et al., 1994, PNAS USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994 J. Med. Chem. 37:1233. Libraries of compounds may be presented in solution (e.g., Houghten, 1992, Biotechniques 13:412-421), or on beads (Lam, 1991, Nature 354:82-84), chips (Fodor, 1993, Nature 364:555-556), bacteria (U.S. Pat. No. 5,223,409), spores (U.S. Pat. No. 5,223,409), plasmids (Cull et al., 1992, PNAS USA 89:1865-1869), or phages (Scott and Smith 1990, Science 249:386-390; Devlin, 1990, Science 249:404-406; Cwirla et al., 1990, PNAS USA 87:6378-6382; Felici 1991, J. Mol. Biol. 222:301-310; and U.S. Pat. No. 5,223,409).

To identify a useful compound, one can contact a test compound with a system containing test cells expressing a reporter gene encoded by a nucleic acid operatively liked to a promoter of a marker gene selected from the above-mentioned metastasis promoters or suppressors. The system can be an in vitro cell line model or an in vivo animal model. The cells can naturally express the gene, or can be modified to express a recombinant nucleic acid. The recombinant nucleic acid can contain a nucleic acid coding a reporter polypeptide to a heterologous promoter. One then measures the expression level of the miRNA, polypeptide, or reporter polypeptide.

For the polypeptide, the expression level can be determined at either the mRNA level or at the protein level. Methods of measuring mRNA levels in a cell, a tissue sample, or a body fluid are well known in the art. To measure mRNA levels, cells can be lysed and the levels of mRNA in the lysates or in RNA purified or semi-purified from the lysates can be determined by, e.g., hybridization assays (using detectably labeled gene-specific DNA or RNA probes) and quantitative or semi-quantitative RT-PCR (using appropriate gene-specific primers). Alternatively, quantitative or semi-quantitative in situ hybridization assays can be carried out using tissue sections or unlysed cell suspensions, and detectably (e.g., fluorescent or enzyme) labeled DNA or RNA probes. Additional mRNA-quantifying methods include RNA protection assay (RPA) and SAGE. Methods of measuring protein levels in a cell or a tissue sample are also known in the art.

To determine the effectiveness of a candidate compound to treat melanoma or inhibiting endothelial recruitment, cell invasion, or metastatic angiogenesis, one can compare the level obtained in the manner described above with a control level (e.g., one obtained in the absence of the candidate compound). The compound is identified as being effective if (i) a metastasis suppressor's level is lower than a control or reference value or (ii) a metastasis promoter's level is higher than the control or reference value. One can further verify the efficacy of a compound thus-identified using the in vitro cell culture model or an in vivo animal model as disclosed in the example below.

EXAMPLES

Example 1

Materials and Methos

This example describes materials and methods used in EXAMPLES 2-11 below.

Compounds

TABLE 3

Compound Names

| Compound # | Compound Name |
|---|---|
| 1 | TO901317 |
| 2 | GW3965 |
| 3 | LXR-623 |
| 12 | WO-2010-0138598 Ex. 9 or WO-201000138598 |
| 25 | SB742881 |
| 38 | WO-2007-002563 Ex. 19 or WO-2007-002563 |

Animal Studies

All mouse experiments were conducted in agreement with a protocol approved by the Institutional Animal Care and Use Committee (IACUC) at The Rockefeller University. 6-8-week old age-matched and sex-matched mice were used for primary tumor growth and metastasis assays as previously described (Minn et al., 2005; Tavazoie et al., 2008). See Extended Experimental Procedures.

Cell Culture

All cancer cell lines were cultured as previously described (Tavazoie et al., 2008). 293T and human umbilical vein endothelial cells (HUVEC's) were maintained in standard conditions. miRNA and gene knock-down/over-expression studies in cell lines and in vitro functional assays are detailed in Extended Experimental Procedures.

Microarray Hybridization

In order to identify miRNAs deregulated across highly metastatic derivatives, small RNAs were enriched from total RNA derived from MeWo and A375 cell lines and profiled by LC sciences. In order to identify potential gene targets of miR-199a-3p, miR-199a-5p, and miR-1908, total RNA from MeWo cell lines was labeled and hybridized onto Illumina HT-12 v3 Expression BeadChip arrays by The Rockefeller University genomics core facility. See Extended Experimental Procedures for thresholds and criteria used to arrive at miRNA and mRNA targets.

Analysis of miRNA Expression in Human Melanoma Skin Lesions

All human clinical samples used in this study were obtained, processed, and analyzed in accordance with IRB guidelines. Total RNA was extracted from paraffin-embedded cross-sections of primary melanoma skin lesions previously resected from patients at MSKCC, and specific miRNA expression levels were analyzed in a blinded fashion using TaqMan miRNA Assays (Applied Biosystems). Kaplan-Meier curves representing each patient's metastasis-free-survival data as a function of primary tumor miRNA expression values were generated using the GraphPad Prism software package.

In Vivo LNA Therapy

Following tail-vein injection of $4\times10^4$ MeWo-LM2 cells, NOD-SCID mice were treated intravenously twice a week for four weeks with in vivo-optimized LNAs (Exiqon) antisense to miR-199a-3p, miR-199a-5p, and miR-1908 at a combinatorial dose of 12.5 mg/kg delivered in 0.1 mL of PBS.

Histology

For gross macroscopic metastatic nodule visualization, 5-μm-thick lung tissue sections were H&E stained. For in vivo endothelial content analyses, lung sections were double-stained with antibodies against MECA-32 (Developmental Studies Hybridoma Bank, The University of Iowa, Iowa), which labels mouse endothelial cells, and human vimentin (Vector Laboratories), which labels human melanoma cells. See Extended Experimental Procedures.

Data Analysis

All data are represented as mean±SEM. The Kolmogorov-Smirnov test was used to determine significance of differences in metastatic blood vessel density cumulative distributions. The prognostic power of the miRNAs to predict metastatic outcomes was tested for significance using the Mantel-Cox log-rank test. The one-way Mann-Whitney t-test was used to determine significance values for non-Gaussian bioluminescence measurements. For all other comparisons, the one-sided student's t-test was used. P values<0.05 were deemed to be statistically significant.

In Vivo Selection, Experimental Metastasis, and Primary Tumor Growth Assays

All mouse experiments were conducted in agreement with a protocol approved by the Institutional Animal Care and Use Committee (IACUC) at The Rockefeller University. To generate multiple metastatic derivatives from two independent human melanoma cell lines, in vivo selection was performed as previously described (Minn et al., 2005 Nature 436, 518-524; Pollack and Fidler, 1982 J. Natl. Cancer Inst. 69, 137-141). In brief, $1\times10^6$ pigmented MeWo or non-pigmented A375 melanoma parental cells were resuspended in 0.1 mL of PBS and intravenously injected into 6-8-week old immunocompromised NOD-SCID mice. Following lung metastases formation, nodules were dissociated and cells were propagated in vitro, giving rise to first generation of lung metastatic derivatives (LM1). The LM1 cells were then subjected to another round of in vivo selection by injecting $2\times10^5$ cells via the tail-vein into NOD-SCID mice, giving rise to metastatic nodules, whose subsequent dissociation yielded second generation of lung metastatic derivatives (LM2). For the A375 cell line, a third round of in vivo selection was performed, yielding the highly metastatic A375-LM3 derivatives.

In order to monitor metastasis in vivo through bioluminescence imaging, A375 and MeWo parental cells and their metastatic derivatives were transduced with a retroviral construct expressing a luciferase reporter (Ponomarev et al., 2004 Eur J Nucl Med Mol Imaging 31, 740-751). For all metastasis experiments, lung or systemic colonization was monitored over time and quantified through non-invasive bioluminescence imaging as previously described (Minn et al., 2005). To determine whether in vivo selection had been achieved, $4\times10^4$ MeWo parental or MeWo-LM2 cells and $1\times10^5$ A375 parental or A375-LM3 cells were resuspended in 0.1 mL of PBS and injected via the lateral tail vein into 6-8-week old NOD-SCID mice. For experimental metastasis assays testing the effects of putative promoter miRNAs on lung colonization, $4\times10^4$ MeWo parental cells over-expressing miR-199a, miR-1908, miR-214, or a control hairpin, $4\times10^4$ MeWo-LM2 cells with silenced expression of miR-199a-3p, miR-199a-5p, miR-1908, or a control sequence, and $2\times10^5$ A375-LM3 cells inhibited for miR-199a-3p, miR-199a-5p, miR-1908, or a control sequence were resuspended in 0.1 mL of PBS and tail-vein injected into 6-8-week old NOD-SCID mice. For epistasis experiments, $1\times10^5$ MeWo-LM2 cells expressing an shRNA targeting ApoE, DNAJA4, or a control sequence or siRNA inhibiting LRP1 or a control sequence in the setting of miRNA inhibition were intravenously injected into 6-8-week old NOD-SCID mice. For ApoE pre-treatment experiments, MeWo-LM2 cells were incubated in the presence of ApoE or BSA at 100 μg/mL at 37° C. After 24 hours, $4\times10^4$ cells were injected via the tail-vein into 7-week old NOD-SCID mice. To determine the effect of pre-treating highly metastatic melanoma cells with LNAs targeting miR-199a-3p, miR-199a-5p, and miR-1908 on metastasis, MeWo-LM2 cells were transfected with each LNA individually, a cocktail of LNAs targeting all three miRNAs, or a control LNA. After 48 hours, $1\times10^5$ cells, resuspended in 0.1 mL of PBS, were administered intravenously into 7-week old NOD-SCID mice for lung metastatic colonization studies or through intracardiac injection into 7-week old athymic nude mice for systemic metastasis assays. To determine the effect of genetic deletion of ApoE on metastasis, 8-week old C57BL/6-WT or C57BL/6-ApoE−/− mice were intravenously injected with $5\times10^4$ B16F10 mouse melanoma cells. For primary tumor growth studies, $1\times10^6$ parental MeWo cells over-expressing miR-199a, miR-1908, or a control hairpin were mixed 1:1 with matrigel and subcutaneously injected into the lower right flank of 6-week old immunodeficient NOD-SCID mice. Animals were palpated weekly for tumor formation, after which sizeable tumors were measured twice a week. Tumor volume was calculated as (small diameter)× (large diameter)/2.

Lentiviral miRNA Inhibition and Gene Knock-Down 293T cells were seeded in a 10-cm plate and allowed to reach 60% confluency. Prior to transfection, the cell media was replaced with fresh antibiotic-free DMEM media supplemented with 10% FBS. 6 μg of vector A, 12 μg of vector K, and 12 μg of the appropriate miR-Zip (System Biosciences, Mountain View, Calif.) or shRNA plasmid construct (MSKCC HTS Core Facility, New York, N.Y.) were co-transfected using 60 μL of TransIT-293 transfection reagent (MIR 2700, Minis Bio LLC, Madison, Wis.). The cells were incubated at 37° C. for 48 hours, and the virus was harvested by spinning the cell media for 10 minutes at 2000 g followed by virus filtration through a 0.45 μm filter. $1\times10^5$ cancer cells were transduced with 2 mL of the appropriate virus in the presence of 10 μg/mL of polybrene (TR-1003-G, Millipore, Billerica, Mass.) for 6 hrs. After 48 hours, 2 μg/mL of puromycin (P8833, Sigma-Aldrich, St Louis, Mo.) was added to the cell media for lentiviral selection. The cells were kept in puromycin selection for 72 hours. The following miR-Zip sequences were used:

```
miR-Zip-199a-3p:
5'-
GATCCGACAGTAGCCTGCACATTAGTCACTTCCTGTCAGTAACCAATG
TGCAGACTACTGTTTTTTGAATT-3'

miR-Zip-199a-5p:
5'-
GATCCGCCCAGTGCTCAGACTACCCGTGCCTTCCTGTCAGGAACAGGTAG
TCTGAACACTGGGTTTTTGAATT-3'

miR-Zip-1908
5'-
GATCCGCGGCGGGAACGGCGATCGGCCCTTCCTGTCAGGACCAATCGCCG
TCCCCGCCGTTTTTGAATT-3'
```

The following shRNA sequences were used:

```
shAPOE1:
5'CCGGGAAGGAGTTGAAGGCCTACAACTCGAGTTGTAGGCCTTCAACTC
CTTCTTTTT3'

shAPOE2:
5'CCGGGCAGACACTGTCTGAGCAGGTCTCGAGACCTGCTCAGACAGTGT
CTGCTTTTT3'

shDNAJA41:
5'CCGGGCGAGAAGTTTAAACTCATATCTCGAGATATGAGTTTAAACTTC
TCGCTTTTT3'

shDNAJA42:
5'CCGGCCTCGACAGAAAGTGAGGATTCTCGAGAATCCTCACTTTCTGTC
GAGGTTTTT3'
```

Retroviral miRNA and Gene Over-Expression

6 μg of vector VSVG, 12 μg of vector Gag-Pol, and 12 μg of pBabe plasmid containing the coding sequences of human ApoE, DNAJA4, or an empty vector or miR-Vec containing the precursor sequence of miR-199a, miR-214, miR-1908, or a control hairpin were co-transfected into 60%-confluent 293T cells using 60 μL of TransIT-293 transfection reagent. The cells were incubated at 37° C. for 48 hours, after which the virus was harvested and transduced into cancer cells in the presence of 10 μg/mL of polybrene for 6 hours. After 48 hours, 2 μg/mL of puromycin or 10 μg/mL of blasticidin (15205, Sigma-Aldrich, St Louis, Mo.) were added to the cell media for retroviral selection. The cells were kept in puromycin selection for 72 hours or in blasticidin selection for 7 days. The following cloning primers were used for over-expression of the coding sequences of ApoE and DNAJA4:

```
ApoE_CDS_Fwd:
5'-TCATGAGGATCCATGAAGGTTCTGTGGGCT-3'

ApoE_CDS_Rev:
5'-TAGCAGAATTCTCAGTGATTGTCGCTGGG-3'

DNAJA4_CDS_Fwd:
5'-ATCCCTGGATCCATGTGGGAAAGCCTGACCC-3'

DNAJA4_CDS_Rev:
5'-TACCATGTCGACTCATGCCGTCTGGCACTGC-3'
```

LNA-Based miRNA Knock-Down

LNAs complimentary to mature miR-199a-3p, miR-199a-5p, miR-1908, or a control sequence (426917-00, 426918-00, 426878-00, and 1990050, respectively; Exiqon, Vedbaek, Denmark) were transfected at a final concentration of 50 nM into 50% confluent MeWo-LM2 cancer cells cultured in antibiotics-free media using Lipofectamine™ 2000 transfection reagent (11668-09, Invitrogen, Carlsbad, Calif.). After 8 hours, the transfection media was replaced with fresh media. After 48 hours, $1\times10^5$ cells were injected intravenously into NOD-SCID mice to assess lung metastatic colonization or through intracardiac injection into athymic nude mice to assess systemic metastasis. For cell invasion and endothelial recruitment in vitro assays, the cells were used 96 hours post-transfection.

siRNA-Based mRNA Knock-Down siRNAs targeting LRP1, LRP8, VLDLR, LDLR, or a control seqeuence were transfected into cancer cells or HUVEC's at a final concentration of 100 nM using Lipofectamine™ 2000 transfection reagent. After 5 hours, the transfection media was replaced with fresh media. The cells were subjected to matrigel invasion and endothelial recruitment assays 96 hours post-transfection. Cells transduced with siRNAs targeting LRP1 or a control sequence in the setting of miRNA inhibition were tail-vein injected for lung colonization assays 72 hours post-transfecton. Control non-targeting siRNAs were obtained from Dharmacon. The following LRP1 and LRP8 target sequences were used:

```
siLRP1¹:    5'-CGAGGACGAUGACUGCUUA-3';

siLRP1²:    5'-GCUAUGAGUUUAAGAAGUU-3';

siLRP8¹:    5'-CGAGGACGAUGACUGCUUA-3';

siLRP8²:    5'-GAACUAUUCACGCCUCAUC-3'.
```

Cell Proliferation Assay

To determine the effects of miR-199a or miR-1908 over-expression and combinatorial LNA-induced miRNA inhibition on cell proliferation, $2.5\times10^4$ cells were seeded in triplicate in 6-well plates, and viable cells were counted after 5 days. To assess the effects of recombinant ApoE addition on melanoma cell or endothelial cell proliferation, $3\times10^4$ melanoma MeWo-LM2 cells or endothelial cells were incubated in the presence of ApoE (100 μM) or BSA (100 μM). Viable cells were counted after 8, 24, 48, 72, and 120 hours.

Matrigel Invasion Assay

Cancer cells were serum-starved in 0.2% FBS DMEM-based media for 12 hours. Trans-well invasion chambers (354480, BD Biosciences, Bedford, Mass.) were pre-equilibrated prior to beginning the assay by adding 0.5 mL of starvation media to the top and bottom chambers. After 30 minutes, the media in the top chamber was removed, and 0.5 mL of media containing $1\times10^5$ cancer cells was added into each matrigel-coated trans-well insert and incubated at 37° C. for 24 hours. For neutralization antibody and/or recombinant protein experiments, antibody/recombinant protein was added to each well at the start of the assay at the following concentrations as indicated in the figures: 5-40 μg/mL anti-ApoE 1D7 (Heart Institute, University of Ottawa), 5-40 μg/mL anti-IgG (AB-108-C, R&D Systems, Minneapolis, Minn.), 100 μM recombinant human ApoE3 (4696, BioVision, Mountain View, Calif.), and 100 μM BSA (A2153, Sigma-Aldrich). Upon completion of the assay, matrigel-coated inserts were washed with PBS, the cells at the top side of each insert were scraped off, and the inserts were fixed in 4% paraformaldehyde for 15 minutes. The inserts were then cut out and mounted onto slides using VectaShield mounting medium containing DAPI (H-1000, Vector Laboratories, Burlingame, Calif.). The basal side of each insert was imaged using an inverted fluorescence microscope (Zeiss Axiovert 40 CFL) at 5× magnification, taking three representative images for each insert. The number of invaded cells was quantified using ImageJ (NIH).

Endothelial Recruitment Assay $5\times10^4$ cancer cells were seeded into 24-well plates approximately 24 hours prior to the start of the assay. HUVEC's were grown to 80% confluency and serum starved in EGM-2 media supplemented with 0.2% FBS for 16 hours. HUVEC's were then pulsed with Cell Tracker Red CMTPX dye (C34552, Invitrogen) for 45 minutes. Meanwhile, cancer cells were washed with PBS, 0.5 mL of 0.2% FBS EGM-2 media was added to each well, and a 3.0 μm HTS Fluoroblock insert (351151, BD Falcon, San Jose, Calif.) was placed into each well. $1\times10^5$ HUVEC's, resuspended in 0.5 mL of starvation media, were seeded into each trans-well insert, and the recruitment assay was allowed to proceed for 16-18 hours at 37° C. For neutralization antibody and/or recombinant protein experiments, antibody/protein was then added to each well at the appropriate concentration as indicated in the figures: 40 μg/mL anti-ApoE 1D7, 40 μg/mL anti-IgG, 100 μM rhApoE3, and 100 μM BSA. Upon completion of the assay, the inserts were processed and analyzed as described for the matrigel invasion assay above (See Matrigel Invasion Assay).

Endothelial Migration Assay

Serum-starved HUVEC's were pulsed with Cell Tracker Red CMTPX dye for 45 minutes and seeded into HTS Fluoroblock trans-well inserts at a concentration of $1\times10^5$ HUVEC's in 0.5 mL starvation media per each insert. The assay was allowed to proceed for 16-18 hours at 37° C., and the inserts were processed and analyzed as described above (See Matrigel Invasion Assay).

Chemotaxis Assay

HUVEC's were serum-starved in 0.2% FBS EGM-2 media for 16 hours and labeled with Cell Tracker Red CMTPX dye for 45 minutes. Meanwhile, the indicated amounts (1-5 μg) of recombinant human ApoE3 or BSA were mixed with 250 μL of matrigel (356231, BD Biosciences) and allowed to solidify at the bottom of a 24-well plate for 30 min. 250 μL of HUVEC EGM-2 media containing 0.2% FBS was then added to each matrigel-coated well, and 3.0 μM HTS Fluoroblock inserts were fitted into each well. $1\times10^5$ HUVEC's, resuspended in 0.5 mL of starvation media, were seeded into each insert and allowed to migrate along the matrigel gradient for 16-18 hours at 37° C. Upon completion of the assay, the inserts were mounted on slides and analyzed as described above (See Matrigel Invasion Assay).

Endothelial Adhesion Assay

HUVEC's were seeded in 6-well plates and allowed to form monolayers. Cancer cells were serum starved in 0.2% FBS DMEM-based media for 30 minutes and pulsed with Cell Tracker Green CMFDA dye (C7025, Invitrogen) for 45 minutes. $2\times10^5$ cancer cells, resuspended in 0.5 mL starvation media, were seeded onto each endothelial monolayer. The cancer cells were allowed to adhere to the HUVEC monolayers for 30 minutes at 37° C. The endothelial monolayers were then washed gently with PBS and fixed with 4% paraformaldehyde for 15 minutes. Each well was then coated with PBS, and 8 images were taken for each endothelial monolayer using an inverted Fluorescence microscope (Zeiss Axiovert 40 CFL) at 10× magnification. The number of cancer cells adhering to HUVEC's was quantified using ImageJ.

Anoikis Assay $1\times10^6$ MeWo cells over-expressing miR-199a, miR-1908, or a control hairpin were seeded in low adherent plates containing cell media supplemented with 0.2% methylcellulose. Following 48 hours in suspension, the numbers of dead and viable cells were counted using trypan blue.

Serum Starvation Assay

To determine the effects of miR-199a and miR-1908 on melanoma cell serum starvation capacity, $1\times10^5$ MeWo parental cells over-expressing miR-199a, miR-1908, or a control hairpin were seeded in quadruplicate into 6-well plates and incubated in 0.2% FBS starvation DMEM-based media for 48 hours, after which the number of viable cells was counted using trypan blue. To determine the effect of recombinant ApoE3 addition on the survival of melanoma cells or endothelial cells in serum starvation conditions, $3\times10^4$ MeWo-LM2 cells or endothelial cells were incubated in the presence of ApoE3 (100 μM) or BSA (100 μM) in low serum conditions (0.2% FBS). The number of viable cells was counter after 8, 16, and 24 hours.

Colony Formation Assay

Fifty MeWo parental cells over-expressing miR-199a, miR-1908, or a control hairpin were seeded in quadruplicate into 6-cm plates. After two weeks, the cells were washed with PBS, fixed with 6% glutaraldehyde, and stained with 0.5% crystal violet. The number of positive-staining colonies was counted.

miRNA Microarray Hybridization

For identification of miRNAs showing deregulated expression across highly metastatic melanoma cell line derivatives, total RNA from multiple independent metastatic derivatives and their respective parental MeWo and A375 cell populations was used to enrich for small RNAs which were then labelled and hybridized onto microfluidic custom microarray platforms by LC sciences. The arrays were designed to detect 894 mature miRNAs corresponding to the miRNA transcripts listed in Sanger miRBase Release 13.0. Out of all the probes analyzed, those corresponding to 169 miRNAs yielded signal above a background threshold across the multiple cell lines analyzed. The raw signal intensities, corresponding to probe hybridization, were median-normalized for each cell line. A threshold of 2-fold or higher up-regulation of median-normalized expression values were used in order to identify miRNAs commonly induced in multiple metastatic derivatives for two independent human melanoma cell lines.

Microarray-Based Gene Target Prediction for miR-199a and miR-1908

In order to identify potential genes targeted by miR-199a-3p, miR-199a-5p, and miR-1908, total RNA was extracted from MeWo cell lines with loss- or gain-of-function of each miRNA and submitted to the genomics core facility at The Rockefeller University for hybridization onto Illumina HT-12 v3 Expression BeadChip microarrays. The raw signal intensities, corresponding to probe hybridization, were then median-normalized for each cell line sample. Three sets of microarray profile comparisons were generated: (1) MeWo control cells relative to MeWo cells over-expressing miR-199a or miR-1908, (2) MeWo-LM2 control cells relative to MeWo-LM2 cells expressing a short hairpin (miR-Zip) targeting miR-199a-3p, miR-199a-5p, or miR-1908, and (3) MeWo parental cells relative to MeWo-LM2 cells. Based on the median-normalized expression values from these arrays, the following criteria were used to arrive at possible target genes common to miR-199a and miR-1908: (1) Genes down-regulated by more than 1.5 fold upon individual over-expression of each miR-199a and miR-1908, (2) Genes up-regulated by more than 1.5 fold upon inhibition of either both miR-199a-3p and miR-1908 or both miR-199a-5p and miR-1908, and (3) genes down-regulated by more than 1.5 fold in LM2 cells, which express physiologically higher levels of the three miRNAs, relative to MeWo parental cells.

Analysis of miRNA and mRNA Expression in Cell Lines

Total RNA was extracted from various cell lines using the miRvana kit (AM1560, Applied Biosystems, Austin, Tex.). The expression levels of mature miRNAs were quantified using the Taqman miRNA expression assay (4427975-0002228, Applied Biosystems). RNU44 was used as an endogenous control for normalization. For mRNA expression analyses, 600 ng of total RNA was reverse transcribed using the cDNA First-Strand Synthesis Kit (18080-051, Invitrogen), and roughly 200 ng of the resulting cDNA was then mixed with SYBR green PCR Master Mix (4309155, Applied Biosystems) and the appropriate primers. Each reaction was performed in quadruplicate, and mRNA expression was quantified by performing real-time PCR amplification using an ABI Prism 7900HT Real-Time PCR System (Applied Biosystems). GAPDH was used as an endogenous control for normalization. The following primers were used:

| | |
|---|---|
| ApoE_Fwd: | 5'-TGGGTCGCTTTTGGGATTAC-3' |
| ApoE_Rev: | 5'-TTCAACTCCTTCATGGTCTCG-3' |
| DNAJA4_Fwd: | 5'-CCAGCTTCTCTTCACCCATG-3' |
| DNAJA4_Rev: | 5'-GCCAATTTCTTCGTGACTCC-3' |
| GAPDH_Fwd: | 5'-AGCCACATCGCTCAGACAC-3' |
| GAPDH_Rev: | 5'-GCCCAATACGACCAAATCC-3' |
| LRP1_Fwd: | 5'-TTTAACAGCACCGAGTACCAG-3' |
| LRP1_Rev: | 5'CAGGCAGATGTCAGAGCAG-3' |
| LRP8_Fwd: | 5'-GCTACCCTGGCTACGAGATG-3' |
| LRP8_Rev: | 5'-GATTAGGGATGGGCTCTTGC-3' |

ELISA

Conditioned cancer cell media was prepared by incubating cells in 0.2% FBS serum starvation DMEM-based media for 24 hours. ApoE levels in conditioned media were determined using the APOE ELISA kit (IRAPKT031, Innovative Research, Novi, Mich.).

Luciferase Reporter Assays

Heterologous luciferase reporter assays were performed as previously described (Tavazoie et al., 2008). In brief, full-length 3'UTRs and CDS's of ApoE and DNAJA4 were cloned downstream of a renilla luciferase reporter into the psiCheck2 dual luciferase reporter vector (C8021, Promega, Madison, Wis.). $5\times10^4$ parental MeWo cells, MeWo-LM2 cells, MeWo cells over-expressing miR-199a, miR-1908, or a control hairpin, and MeWo-LM2 cells expressing a miR-Zip hairpin targeting miR-199a-3p, miR-199a-5p, miR-1908, or a control sequence were transfected with 100 ng of the respective specific reporter constructs using TransiT-293 transfection reagent. Twenty-four hours post-transfection, the cells were lysed, and the ratio of renilla to firefly luciferase expression was determined using the dual luciferase assay (E1910, Promega). Putative miRNA binding sites in each target construct were identified by alignment to the complimentary miRNA seed sequences (miR-199a-3p: 5'-CAGUAGUC-3'; miR-199a-5p: 5'-CCAGUGUU-3'; miR-1908: 5'-GGCGGGGA-3'). The miRNA complimentary sites on each target construct were mutated using the QuickChange Multi Site-Directed Mutagenesis Kit (200514, Agilent Technologies, Santa Clara, Calif.). Based on miRNA seed sequence complimentarity analysis, the CDS of ApoE was mutated at position 141 (CTG to ACT), the 3'UTR of ApoE was mutated at positions 83 (GCC to ATA) and 98 (CTG to ACA), the CDS of DNAJA4 was mutated at positions 373 (CGC to TAT) and 917 (CTG to AGA), and the 3'UTR of DNAJA4 was mutated at positions 576 (CTG to ACA), 1096 (CTG to TCT), 1396 (CGC to TGT), and 1596 (CTG to TGT). The following primers were used to clone the 3 ‘UTR’ s and CDS's of ApoE and DNAJA4:

```
ApoE_CDS_Fwd:
5'-AGTACCTCGAGGGGATCCTTGAGTCCTACTC-3'

APOE_CDS_Rev:
5'-TAATTGCGGCCGCTCAGACAGTGTCTGCACCCAG-3'

DNAJA4_CDS_Fwd:
5'-TAATATCTCGAGATGTGGGAAAGCCTGACCC-3'

DNAJA4_CDS_Rev:
5'-CAATTGCGGCCGCTCATGCCGTCTGGCACTGC-3'

APOE_3'UTR_Fwd:
5'-TTAGCCTCGAGACGCCGAAGCCTGCAGCCA-3'

APOE_3'UTR_Rev:
5'-TTACTGCGGCCGCTGCGTGAAACTTGGTGAATCTT-3'

DNAJA4_3'UTR_Fwd:
5'-TAATATCTCGAGCGTGGTGCGGGGCAGCGT-3'

DNAJA4_3'UTR_Rev:
5'-CAATTGCGGCCGCTTATCTCTCATACCAGCTCAAT-3'
```

The following primers were used to mutagenize the miRNA binding sites on each target:

```
APOE_CDS_mut:
5'-
GCCAGCGCTGGGAACTGGCAACTGGTCGCTTTTGGGATTACCT-3'
```

-continued

```
APOE_3'UTR_mut1:
5'-
CAGCGGGAGACCCTGTCCCCATACCAGCCGTCCTCCTGGGGTG-3'

APOE_3'UTR_mut2:
5'-
TCCCCGCCCCAGCCGTCCTCACAGGGTGGACCCTAGTTTAATA-3'

DNAJA4_CDS_mut1:
5'-
GGGATCGGTGGAGAAGTGCCTATTGTGCAAGGGGCGGGGGATG-3'

DNAJA4_CDS_mut2:
5'-
GTAGGGGGCGGGGAACGTGTTATCCGTGAAGAGGTGGCTAGGG-3'

DNAJA4_3'UTR_mut1:
5'-
CAGGGCCAACTTAGTTCCTAACATTCTGTGCCCTTCAGTGGAT-3'

DNAJA4_3'UTR_mut2:
5'-
ACAGTTTGTATGGACTACTATCTTAAATTATAGCTTGTTTGGA-3'

DNAJA4_3'UTR_mut3:
5'-
TAATTATTGCTAAAGAACTATGTTTTAGTTGGTAATGGTGTAA-3'

DNAJA4_3'UTR_mut4:
5'-
CAGCTGCACGGACCAGGTTCCATAAAAACATTGCCAGCTAGTGAG-3'
```

Analysis of miRNA Expression in Human Melanoma Skin Lesions

All human clinical samples used in this study were obtained, processed, and analyzed in accordance with institutional IRB guidelines. Paraffin-embedded cross-sections of primary melanoma skin lesions from 71 human patients were obtained from MSKCC. The samples were de-paraffinized by five consecutive xylene washes (5 minutes each). Following de-paraffinization, the malignancy-containing region was identified by H&E staining, dissected, and total RNA was extracted from it using the RecoverAll Total Nucleic Acid Isolation Kit (AM1975, Applied Biosystems). The expression levels of mature miR-199a-3p, miR-199a-5p, and miR-1908 in each sample were quantified in a blinded fashion using the Taqman miRNA assay. RNU44 was used as an endogenous control for normalization. The expression levels of each miRNA were compared between primary melanomas with propensity to metastasize and primary melanomas that did not metastasize. Kaplan-Meier curves were plotted using metastasis-free survival data of patients as a function of the expression levels for each miRNA in each patient's tumor. Metastatic recurrence to such sites as lung, brain, bone, and soft tissue were previously documented and allowed for a retrospective analysis of the relationship between the expression levels of identified miRNAs and metastatic recurrence.

Histology

Animals were perfused with PBS followed by fixation with 4% paraformaldehyde infused via intracardiac and subsequently intratracheal injection. The lungs were sectioned out, incubated in 4% paraformaldehyde at 4° C. overnight, embedded in paraffin, and sliced into 5-μm-thick increments. For gross macroscopic metastatic nodule visualization, lung sections were H&E stained. For endothelial content analysis in metastatic nodules formed by human melanoma MeWo cells in mice, representative lung sections were double-stained with primary antibodies against MECA-32 (Developmental Studies Hybridoma Bank, The University of Iowa, Iowa), which labels mouse endothelial cells, and human vimentin (VP-V684, Vector Laboratories), which labels human melanoma cells. Various Alexa Flour dye-conjugated secondary antibodies were used to detect primary antibodies. To determine the blood vessel density within metastatic nodules, fluorescence was measured using a Zeiss laser scanning confocal microscope (LSM 510), and the MECA-32 signal within each metastatic nodule, outlined based on co-staining with human vimentin, was quantified in a blinded fashion using ImageJ (NIH). For endothelial content analysis in metastatic nodules formed by mouse B16F10 mouse melanoma cells in wild type and ApoE genetically null mice, representative lung sections were stained for MECA-32, and the MECA-32 signal within each nodule, demarcated based on cell pigmentation, was quantified in a blinded fashion. The collective vessel area, given as the percentage area covered by blood vessels relative to the total area of each metastatic nodule, was obtained by background subtraction (rolling ball radius of 1 pixel) and use of a pre-determined threshold as a cut-off. A metastatic nodule was defined as any region of greater than 2000 $\mu m^2$ total area. For large nodules, minimum of four representative images were obtained, and their average blood vessel density was calculated.

In Vivo Matrigel Plug Assay

10 μg/mL recombinant human ApoE3 (4696, BioVision), 10 μg/mL BSA (A2153, Sigma Aldrich), or 400 ng/ml VEGF were mixed with matrigel (356231, BD Biosciences) as indicated. 400 μL of matrigel containing the indicated recombinant proteins were injected subcutaneously just above the ventral flank of immunocompromised NOD-SCID mice. Plugs were extracted on day 3 post-injection and fixed in 4% paraformaldehyde for 48 hours. Plugs were then paraffin-embedded and sectioned at 5-μm-thick increments. Plug cross-sectional sections were immunohistochemically stained using a primary antibody against the mouse endothelial antigen MECA-32 (Developmental Studies Hybridoma Bank, The University of Iowa, Iowa), detected by peroxidase-conjugated secondary antibody, and subsequently visualized by DAB oxidization. To quantify the extent of endothelial cell invasion into each matrigel plug, the number of endothelial cells was counted in 4-5 random fields for each plug, and the average number of endothelial cells per given plug area was calculated.

Tissue Culture

The SK-Mel-334 primary human melanoma line was established from a soft tissue metastasis of a Braf-mutant melanoma of a patient at the MSKCC. Following minimum expansion in vitro, the cells were in vivo selected (Pollack and Fidler, 1982) to generate the lung-metastatic derivatives SK-Mel-334.2. The SK-Mel-239 vemurafenib-resistant clone (C1) was a gift from Poulikos Poulikakos (Mount Sinai Medical School) and the B-$Raf^{V600E/+}$; $Pten^{-/-}$; $CDKN2A^{-/-}$ primary murine melanoma cell line was generously provided by Marcus Rosenberg (Yale University). All other cell lines used were purchased from ATCC.

ApoE Elisa

Extracellular ApoE levels in serum-free conditioned media from melanoma cells treated with DMSO, GW3965, or T0901317 (1 μM each) were quantified using the ApoE ELISA kit (Innovative Research) at 72 hours following treatment.

Western Blotting

Mouse lung and brain tissue samples were homogenized on ice in RIPA buffer (Sigma-Aldrich) supplemented with protease inhibitors (Roche). Mouse adipose tissue was homogenized on ice in TNET buffer (1.5 mM Tris pH 7.5, 150 mM NaCl, 2 mM EDTA 1% triton, protease inhibitors). Total protein lysate (2 μg) was separated by SDS-PAGE, transferred to PVDF membrane, and blotted with an anti-mouse ApoE (ab20874, Abcam) and anti-tubulin α/β (2148, Cell Signaling) antibodies.

ApoE Expression Analysis in Melanoma Clinical Samples

All clinical sample procurement, processing, and analyses were performed in strict agreement with IRB guidelines. Primary melanoma skin lesions were previously resected from patients at the MSKCC, formalin-fixed, paraffin-embedded, and sectioned into 5-μm-thick slides. ApoE protein expression was assessed by double-blinded immunohistochemical analysis using the D6E10 anti-ApoE antibody (ab1906, Abcam).

Histochemistry

Animals were intracardially perfused with PBS followed by 4% paraformaldehyde (PFA). Fixed lungs were embedded in paraffin and sectioned into 5-μm-thick increments. Macroscopic lung metastatic nodules were visualized by H&E staining. For analysis of tumor endothelial cell content, proliferation, and apoptosis, primary tumor paraffin-embedded sections were stained with antibodies against MECA-32 (Developmental Studies Hybridoma Bank, University of Iowa), KI-67 (ab15580, Abcam), and cleaved caspase-3 (9661, Cell Signaling), respectively.

Tail-Vein Metastasis Assays

Melanoma cells used for in vivo metastasis assays were transduced with a stably expressed retroviral construct encoding a luciferase reporter gene (Ponomarev et al., 2004), allowing us to monitor the in vivo progression of melanoma cells by bioluminescence imaging. The following numbers of melanoma cells, resuspended in 100 μL of PBS, were injected intravenously via the tail-vein: $4\times10^4$ MeWo cells, $2.5\times10^5$ HT-144 cells, $2\times10^5$ SK-Mel-334.2 cells, $5\times10^4$B16F10 cells, and $1\times10^5$YUMM cells. The MeWo, HT-144, and SK-Mel-334.2 cells were injected into 6-8 week-old sex-matched NOD scid mice, while the B16F10 and YUMM cells were injected into 6-8 week-old sex-matched C57BL/6 mice. In all experiments assessing at the effects of GW3965 on metastasis formation, mice were pre-treated on a control diet or a GW3965-supplemented diet (20 mg/kg) for 10 days. To assess the effect of GW3965 treatment on brain metastasis, $1\times10^5$ MeWo brain-metastatic derivatives were injected intracardially into athymic nude mice. Immediately following injection, mice were randomly assigned to a control diet or GW3965-supplemented diet (100 mg/kg). To determine whether oral delivery of GW3965 can inhibit the progression of incipient metastasis, NOD Scid mice were intravenously injected with $4\times10^4$MeWo cells and the cells were allowed to colonize the lungs for 42 days, after which mice were blindedly assigned to a control diet or a GW3965-supplemented diet (100 mg/kg) treatment.

Orthotopic Metastasis Assays

To determine the effect of GW3965 treatment on lung colonization by melanoma cells dissociated from an orthotopic site, $1\times10^6$ MeWo cells expressing a luciferase reporter were subcutaneously injected into both lower flanks of NOD Scid mice. Upon the formation of tumors measuring ~300 $mm^3$ in volume, the tumors were excised and the mice were randomly assigned to a control diet or a GW3965-supplemented diet (100 mg/kg) treatment. One month after tumor excision, the lungs were extracted and lung colonization was measured by ex vivo bioluminescence imaging. To histologically confirm the extent of melanoma lung colonization, lungs were then fixed in 4% PFA overnight, paraffin-embedded, section into 5 μM increments and stained for human vimentin (VP-V684, Vector Laboratories).

Generation of Dacarbazine-Resistant Melanoma Cells

Dacarbazine-resistant B16F10 mouse melanoma cells were generated by continuously culturing the cells in the presence of DTIC (D2390, Sigma-Aldrich, St. Louis, Mo.). First, the cells were treated with 500 μg/mL DTIC for one week. Following this initial DTIC treatment, the remaining (~10%) viable cells were allowed to recover for one week, after which 750 μg/mL of DTIC was added to the cell media for 5 days. Subsequent to this high-dose treatment, the cells were allowed to recover in the presence of low-dose DTIC (100 μg/mL) for one week. The cells were then continuously cultured in cell media containing 200 μg/mL DTIC for at least one month prior to grafting the cells into mice. DTIC was added to fresh cancer cell media every 3 days. For tumor growth experiments, $5\times10^4$ B16F10 parental and DTIC-resistant cells were subcutaneously injected into the lower flank of 7-week-old C57BL/6 mice. Following formation of small tumors measuring 5-10 $mm^3$ in volume, the mice were randomly assigned to the following treatment groups: (1) control diet+vehicle, i.p.; (2) control diet+DTIC i.p. (50 mg/kg); (3) GW3965-supplemented diet (100 mg/kg)+vehicle i.p. DTIC was dissolved in the presence of citric acid (1:1 by weight) in water and administered daily by intraperitoneal injection.

The DTIC-resistant MeWo human melanoma cell line clone was generated following DTIC treatment of mice bearing MeWo tumors measuring 600-800 $mm^3$ in volume. After initial tumor shrinkage in response to daily DTIC dosing (50 mg/kg, i.p.) during the first two weeks, the tumors eventually developed resistance and resumed growth, at which point tumor cells were dissociated and the DTIC-resistant MeWo cell line was established. The cells were expanded in vitro in the presence of DTIC (200 μg/mL) for one week, after which $5\times10^5$ DTIC-resistant MeWo cells were re-injected into 8-week old Nod SCID gamma mice. Following growth of tumors to 5-10 $mm^3$ in volume, mice were blindedly assigned to the following treatment groups: (1) control diet; (2) control diet+DTIC (50 mg/kg); (3) GW3965-supplemented diet (100 mg/kg). To determine the effect of DTIC on tumor growth by parental unselected MeWo cells, $5\times10^5$ MeWocells were subcutaneously injected into Nod SCID gamma mice, and the mice were treated with a control vehicle or DTIC (50 mg/kg) subsequent to formation of tumors measuring 5-10 $mm^3$ in volume. DTIC was administered daily, as described above, in cycles consisting of 5 consecutive daily treatments interspersed by 2-day off-treatment intervals. Tumor growth was measured twice a week.

Genetically-Initiated Model of Melanoma Progression

The Tyr::CreER; B-Raf$^{V600E/+}$; Pten$^{lox/+}$/Tyr::CreER; B-Raf$^{V600E/+}$; Pten$^{lox/lox}$ conditional model of melanoma progression was previously established and characterized by Dankort et al. (2009). Briefly, melanoma in these mice was induced at 6 weeks of age by intraperitoneally injecting 4-HT (H6278, 70% isomer, Sigma-Aldrich, St Louis, Mo.) at 25 mg/kg administered in peanut oil on three consecutive days. The 4-HT stock solution was prepared by dissolving it in 100% EtOH at 50 mg/mL by heating at 45° C. for 5 min and mixing. Once dissolved, the stock 4-HT solution was then diluted by 10-fold in peanut oil, yielding a 5 mg/mL 4-HT working solution that was then injected into mice. After the first 4-HT injection, mice were blindedly assigned to receive either a control diet or a diet supplemented with GW3965 (100 mg/kg). Mice were examined three times a week for the presence and progression of melanoma lesions. At day 35, dorsal skin samples were harvested from control-treated and GW3965-treated mice, fixed in 4% PFA and photographed at 10×. The percentage of pigmented melanoma lesion area out of the total skin area was quantified using ImageJ. For survival analyses, mice were monitored daily for melanoma progression and euthanized according to a standard body condition score, taking into account initial signs of moribund state and discomfort associated with the progression of melanoma burden. Post-mortem, the lungs, brains, and salivary glands were harvested and examined for the presence of macroscopic melanoma lesions.

Mouse Genotyping

All mouse genotyping was performed using standard PCR conditions, as recommended by Jackson Labs. The following genotyping primers were used for the respective PCR reactions:

Tyr::CreER; B-Raf$^{V600E/+}$; Ptenlox/+ and
Tyr::CreER; B-Raf$^{V600E/+}$; Pten$^{lox/lox}$ mice:
B-Raf Forward:
5'-TGA GTA TTT TTG TGG CAA CTG C-3'

B-Raf Reverse:
5'-CTC TGC TGG GAA AGC GGC-3'

Pten Forward:
5'-CAA GCA CTC TGC GAA CTG AG-3'

Pten Reverse:
5'-AAG TTT TTG AAG GCA AGA TGC-3'

Cre Transgene Forward:
5'-GCG GTC TGG CAG TAA AAA CTA TC-3'

Cre Transgene Reverse:
5'-GTG AAA CAG CAT TGC TGT CAC TT-3'

Internal Positive Control Forward:
5'-CTA GGC CAC AGA ATT GAA AGA TCT-3'

Internal Positive Control Reverse:
5'-GTA GGT GGA AAT TCT AGC ATC ATC C-3'

ApoE-I-mice:
Common Forward:
5'-GCC TAG CCG AGG GAG AGC CG-3'

Wild-type Reverse:
5'-TGT GAC TTG GGA GCT CTG CAG C-3'

Mutant Reverse:
5'-GCC GCC CCG ACT GCA TCT-3'

LXRα-I-mice:
Common Forward:
5'-TCA GTG GAG GGA AGG AAA TG-3'

Wild-type Reverse:
5'-TTC CTG CCC TGG ACA CTT AC-3'

Mutant Reverse:
5'-TTG TGC CCA GTC ATA GCC GAA T-3'

LXRβ-I-mice:
Common Forward:
5'-CCT TTT CTC CCT GAC ACC G-3'

Wild-type Reverse:
5'-GCA TCC ATC TGG CAG GTT C-3'

Mutant Reverse:
5'-AGG TGA GAT GAC AGG AGA TC-3'

Cell Proliferation and Viability Assay:

To determine the effects of GW3965, T0901317, and Bexarotene on in vitro cell growth, $2.5\times10^4$ melanoma cells were seeded in triplicate in 6-well plates and cultured in the presence of DMSO, GW3965, T0901317, or Bexarotene at 1 μM each. After 5 days, the number of viable and dead cells was counted using the trypan blue dye (72-57-1, Sigma-Aldrich), which selectively labels dead cells.

Cell Invasion Assay

The cell invasion assay was performed as previously described in detail (Pencheva et al., 2012) using a trans-well matrigel invasion chamber system (354480, BD Biosciences). In brief, various melanoma cells were cultured in the presence of DMSO, GW3965, T0901317, or Bexarotene at 1 μM for 56 hours, after which melanoma cells were switched to starvation media (0.2% FBS) for 16 hours in the presence of each drug. Following starvation, cells were seeded into matrigel-coated trans-well inserts, and the invasion assay was allowed to proceed for 24 hours at 37° C. For ApoE antibody neutralization experiments, 40 μg/mL 1D7 anti-ApoE blocking antibody (Heart Institute, University of Ottawa, Ottawa, Canada) or 40 μg/mL anti-IgG control antibody (AB-108-C, R&D Systems, Minneapolis, Minn.) was added to each trans-well insert at the start of the assay.

Endothelial Recruitment Assay

The endothelial recruitment assay was carried out as previously described (Pencheva et al., 2012; Png et al., 2012). Melanoma cells were treated with DMSO, GW3965, T0901317, or Bexarotene at 1 μM for 56 hours, after which $5\times10^4$ cells were seeded in a 24-well plate in the presence of each drug and allowed to attach for 16 hours prior to starting the assay. HUVEC cells were serum-starved overnight in EGM-2 media containing 0.2% FBS. The following day, $1\times10^5$ HUVEC cells were seeded into a 3.0 μM HTS Fluoroblock trans-well migration insert (351151, BD Falcon, San Jose, Calif.) fitted into each well containing cancer cells at the bottom. The HUVEC cells were allowed to migrate towards the cancer cells for 20 hours at 37° C., after which the inserts were processed as previously described (Pencheva et al., 2012). For ApoE antibody neutralization experiments, 40 μg/mL 1D7 anti-ApoE blocking antibody (Heart Institute, University of Ottawa, Ottawa, Canada) or 40 μg/mL anti-IgG control antibody (AB-108-C, R&D Systems, Minneapolis, Minn.) was added to each trans-well insert at the start of the assay.

Lentiviral shRNA-Based Gene Knockdown shRNAs were integrated into lentiviral particles that were prepared by transfection of 6 μg of vector A, 12 μg of vector K, and 12 μg of shRNA plasmid into HEK-293T packaging cells, as previously described (Pencheva et al., 2012; Png et al., 2012). Lentiviral shRNA transduction was performed in the presence of 10 μg/mL of polybrene (TR-1003-G, Millipore, Billerica, Mass.) for 6 hours, as described previously (Pencheva et al., 2012). The cells were expanded for 72 hours after transduction and lentiviral selection was performed by culturing the cells in the presence of 2 μg/mL of puromycin (P8833, Sigma-Aldrich) for 72 hours.

The following shRNA sequences were used:

Human:

```
sh1LXRα:
5'-
CCGGCCGACTGATGTTCCCACGGATCTCGAGATCCGTGGGAACATCAGTC
GGTTTTT-3'
```

-continued

```
sh2LXRα:
5'-
CCGGGCAACTCAATGATGCCGAGTTCTCGAGAACTCGGCATCATTGAGTT
GCTTTTT-3'

sh1LXRβ:
5'-
CCGGAGAGTGTATCACCTTCTTGAACTCGAGTTCAAGAAGGTGATACACT
CTTTTTT-3'

sh2LXRβ:
5'-
CCGGGAAGGCATCCACTATCGAGATCTCGAGATCTCGATAGTGGATGCCT
TCTTTTT-3'

shApoE:
5'-
CCGGGCAGACACTGTCTGAGCAGGTCTCGAGACCTGCTCAGACAGTGTCT
GCTTTTT-3'
```

Mouse:

```
sh_mLXRα:
5'-
CCGGGCAACTCAATGATGCTGAGTTCTCGAGAACTCAGCATCATTGAGTT
GCTTTTT-3'

sh_mLXRβ:
5'-
CCGGTGAGATCATGTTGCTAGAAACCTCGAGGTTTCTAGCAACATGATCT
CATTTTTG-3'

sh_mApoE:
5'-
CCGGGAGGACACTATGACGGAAGTACTCGAGTACTTCCGTCATAGTGTCC
TCTTTTT-3'
```

Gene Expression Analysis by qRT-PCR:

RNA was extracted from whole cell lysates using the Total RNA Purification Kit (17200, Norgen, Thorold, Canada). 600 ng of total RNA was then reverse transcribed into cDNA using the cDNA First-Strand Synthesis Kit (18080-051, Invitrogen), and quantitative real-time PCR amplification was performed as previously described (Pencheva et al., 2012) using an ABI Prism 7900HT Real-Time PCR System (Applied Biosystems, Austin, Tex.). Each PCR reaction was carried out in quadruplicates. Gene expression was normalized to GAPDH, which was used as an endogenous control.

The following primers were used:

Human:

| | |
|---|---|
| ApoE Forward: | 5'-TGGGTCGCTTTTGGGATTAC-3' |
| ApoE Reverse: | 5'-TTCAACTCCTTCATGGTCTCG-3' |
| GAPDH Forward: | 5'-AGCCACATCGCTCAGACAC-3' |
| GAPDH Reverse: | 5'-GCCCAATACGACCAAATCC-3' |

-continued

| | |
|---|---|
| LXRα_Fwd: | 5'-GTTATAACCGGGAAGACTTTGC-3' |
| LXRα_Rev: | 5'-AAACTCGGCATCATTGAGTTG-3' |
| LXRβ_Fwd: | 5'-TTTGAGGGTATTTGAGTAGCGG-3' |
| LXRβ_Rev: | 5'-CTCTCGCGGAGTGAACTAC-3' |

Mouse:

| | |
|---|---|
| ApoE Forward: | 5'-GACCCTGGAGGCTAAGGACT-3' |
| ApoE Reverse: | 5'-AGAGCCTTCATCTTCGCAAT-3' |
| GAPDH Forward: | 5'-GCACAGTCAAGGCCGAGAAT-3' |
| GAPDH Reverse: | 5'-GCCTTCTCCATGGTGGTGAA-3' |
| LXRα Forward: | 5'-GCGCTCAGCTCTTGTCACT-3' |
| LXRα Reverse: | 5'-CTCCAGCCACAAGGACATCT-3' |
| LXRβ Forward: | 5'-GCTCTGCCTACATCGTGGTC-3' |
| LXRβ Reverse: | 5'-CTCATGGCCCAGCATCTT-3' |
| ABCA1 Forward: | 5'-ATGGAGCAGGGAAGACCAC-3' |
| ABCA1 Reverse: | 5'-GTAGGCCGTGCCAGAAGTT-3' |

ApoE Promoter Activity Assay

The ApoE promoter, consisting of a sequence spanning 980 base pairs upstream and 93 base pairs downstream of the ApoE gene, was cloned into a pGL3-Basic vector (E1751, Promega Corporation, Madison, Wis.) upstream of the firefly luciferase gene using NheI and SacI restriction enzymes. Then, multi-enhancer elements 1 (ME.1) and 2 (ME.2) were cloned directly upstream of the ApoE promoter using MluI and SacI restriction enzymes. To assess ApoE promoter- and ME.1/ME.2-driven transcriptional activation by LXR agonists, $5\times10^4$ MeWo cells were seeded into a 24-well plate. The following day, 100 ng of pGL3-ME.1/ME.2-ApoE promoter construct and 2 ng of pRL-CMV renilla luciferase construct (E2261, Promega) were co-transfected into cells in the presence of DMSO, GW3965, or T0901317 at 1 μM, each condition in quadruplicate. To assess transcriptional activation by LXRα or LXRβ, $5\times10^4$ MeWo cells expressing a control shRNA or shRNA targeting LXRα or LXRβ were seeded into a 24-well plate. The following day, 200 ng of pGL3-ME.1/ME.2-ApoE promoter construct and 2 ng of pRL-CMV renilla luciferase were co-transfected into cells in the presence of DMSO, GW3965, or T0901317 at 1 μM, each condition in quadruplicate. After 24 hours, cells were lysed, and cell lysate was analyzed for firefly and renilla luciferase activity using the Dual Luciferase Assay System (E1960, Promega) and a Bio-Tek Synergy NEO Microplate Reader. Firefly luciferase signal was normalized to renilla luciferase signal and all data are expressed relative to the luciferase activity ratio measured in the DMSO-treated control cells.

The following cloning primers were used:

ApoE-promoter Forward:
5'-
TCA TAG CTA GCG CAG AGC CAG GAT TCA CGC CCT G-3'

ApoE-promoter Reverse:
5'-
TGG TCC TCG AGG AAC CTT CAT CTT CCT GCC TGT GA-3'

ME.1 Forward:
5'-TAG TTA CGC GTA GTA GCC CCC ATC TTT GCC-3'

ME.1 Reverse:
5'-AAT CAG CTA GCC CCT CAG CTG CAA AGC TC-3'

ME.2 Forward:
5'-TAG TTA CGC GTA GTA GCC CCC TCT TTG CC-3'

ME.2 Reverse:
5'-AAT CAG CTA GCC CTT CAG CTG CAA AGC TCT G-3'

Tumor Histochemistry

Tumors were excised from mice and fixed in 4% paraformaldehyde at 4° C. for 48 hours. Then, tumors were paraffin-embedded and sectioned into 5-μm-thick increments. For endothelial cell content analysis in tumors, tumor sections were stained with a primary antibody against the mouse endothelial cell marker MECA-32 (Developmental Studies Hybridoma Bank, The University of Iowa, Iowa) and counterstained with DAPI nuclear stain. To determine tumor cell proliferation and apoptosis, tumor sections were stained with antibodies against the proliferative marker Ki-67 (Abcam, ab15580, Cambridge, Mass.) and the apoptotic marker cleaved caspase-3 (9661, Cell Signaling, Danvers, Mass.), respectively. Various Alexa Flour dye-conjugated secondary antibodies were used to detect primary antibodies. Fluorescence was measured using inverted fluorescence microscope (Zeiss Axiovert 40 CFL) at 5× magnification for MECA-32 and Ki-67 staining and 10× magnification for cleaved caspase-3 staining. Endothelial cell content density and tumor proliferation rate were quantified by calculating the average percentage of MECA-32 or Ki-67 positively-staining area out of the total tumor area. Tumor apoptosis was measured by counting the number of cleaved caspase-3 expressing cells per given tumor area.

Analysis of ApoE Expression in Primary Melanoma Lesions

Human primary melanoma skin samples were resected from melanoma patients at MSKCC, formalin-fixed, embedded in paraffin, and sectioned into 5-μm-thick increments. To determine ApoE protein expression, the samples were first de-paraffinized by two consecutive xylene washes (5 minutes each), and rehydrated in a series of ethanol washes (100%, 95%, 80%, and 70% EtOH). ApoE antigen was retrieved by incubating the samples in the presence of proteinase K (5 μg/mL) for 20 minutes at room temperature. To quench endogenous peroxidase activity, the slides were incubated in 3% $H_2O_2$ solution. The slides were then blocked in three consecutive Avidin, Biotin, and horse serum block solutions for 15 min each at room temperature (SP-2001, Vector Laboratories, Burlingame, Calif.). ApoE was detected by staining with D6E10 anti-ApoE antibody (ab1908, Abcam), which was used at a 1:100 dilution in PBS at 4° C. overnight. The primary antibody was then recognized by incubating the slides in a peroxidase-conjugated secondary antibody (PK-4002, Vector Laboratories) and exposed by DAB (SK-4105, Vector Laboratories) oxidation reaction. The slides were imaged at 10× magnification and analysed in a double-blinded manner. ApoE expression was quantified by counting the number of DAB-positive cells and measuring the area of extracellular ApoE staining. Total ApoE staining signal was expressed as the percentage staining area per given tumor area, determined based on matched H&E-stained slides for each sample. Kaplan-Meier curves depicting patients' metastasis-free survival times were generated by plotting each patient's relapse-free survival data as a function of ApoE expression in that patient's primary melanoma lesion. Patients whose tumors had ApoE levels lower than the median ApoE expression of the population were classified as ApoE-negative, whereas patients whose melanomas expressed ApoE above the median were classified as ApoE-positive. Previously documented patients' history of metastatic recurrence to sites such as lung, brain, bone, soft and subcutaneous tissues, and skin enabled us to retrospectively determine the relationship between ApoE expression at a primary melanoma site and metastatic relapse.

Example 2

Figures 1C, 1D:
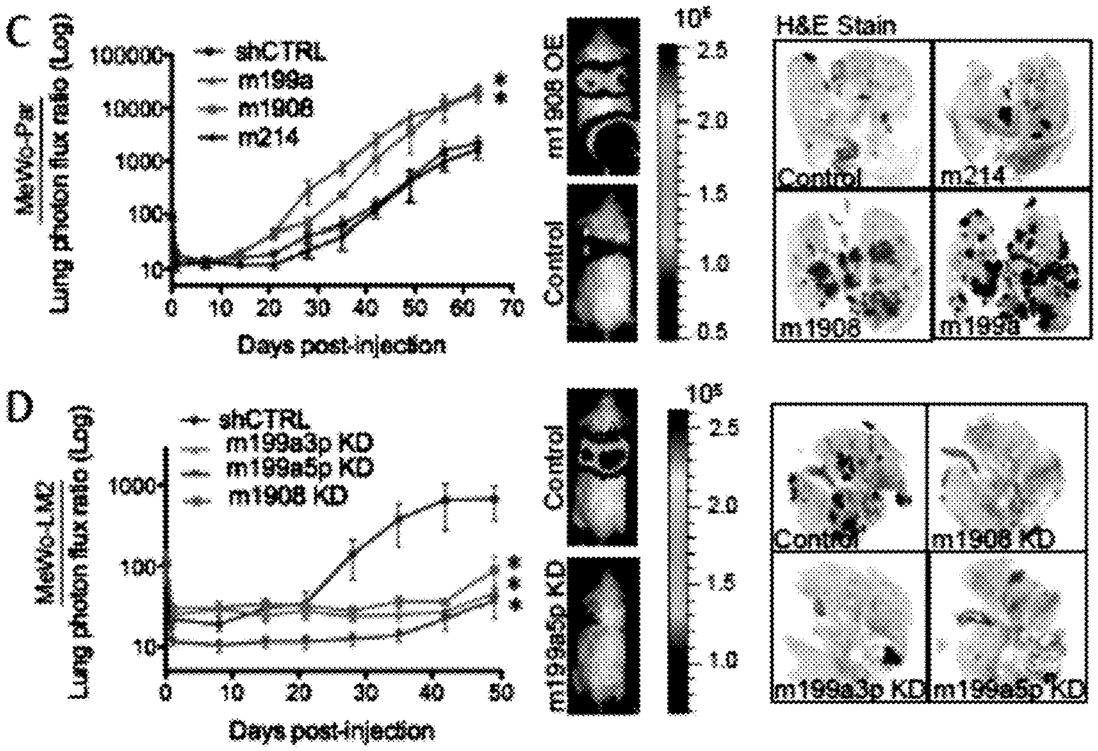
Figures 12A, 12B, 12C, 12D:
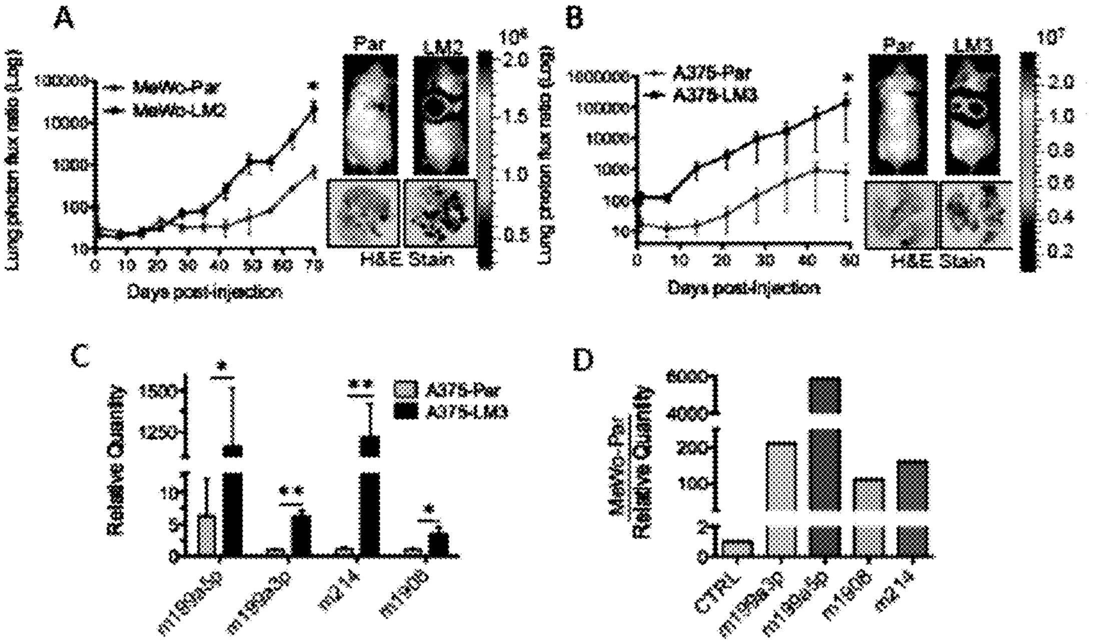

Endogenous Mir-1908, Mir-199a-3p, and Mir-199a-5p Promote Human Melanoma Metastasis In order to identify miRNA regulators of melanoma metastasis, in vivo selection (Pollack and Fidler, 1982) was utilized with the pigmented MeWo and non-pigmented A375 human melanoma cell lines to generate multiple second (LM2) and third generation (LM3) lung metastatic derivatives. Comparison of the metastatic potential of the MeWo-LM2 and A375-LM3 lines showed these derivatives to metastasize significantly more efficiently than their respective parental populations in lung colonization assays (FIGS. 12A-B). Hybridization-based small RNA profiling of 894 mature miRNAs followed by quantitative stem-loop PCR (qRT-PCR) revealed four miRNAs (miR-1908, miR-199a-3p, miR-199a-5p, and miR-214) to be upregulated greater than two-fold in multiple A375 and MeWo metastatic derivatives relative to their respective parental cells (FIGS. 1A-B, 12C). The significant induction of miR-199a-3p, miR-199a-5p, miR-214, and miR-1908 across multiple metastatic derivatives suggested a metastasis-promoting role for these miRNAs. Retrovirally mediated transduction and over-expression of the precursors for miR-199a-3p and miR-199a-5p (over-expressed concomitantly as the miR-199a hairpin) and miR-1908 lead to a robust increase in lung metastatic colonization based on both bioluminescence signal quantification and gross lung histology (FIGS. 1C, 12D; 9.64-fold increase, P=0.016 for miR-1908; 8.62-fold increase, P=0.028 for miR-199a), while miR-214 over-expression did not significantly affect metastasis. Importantly, over-expression of each miR-199a and miR-1908 increased the number of metastatic nodules formed (FIG. 12E), consistent with a role for these miRNAs in metastatic initiation. These findings also revealed miR-199a and miR-1908 to be sufficient for enhanced metastatic colonization.

Figures 12E, 12F:
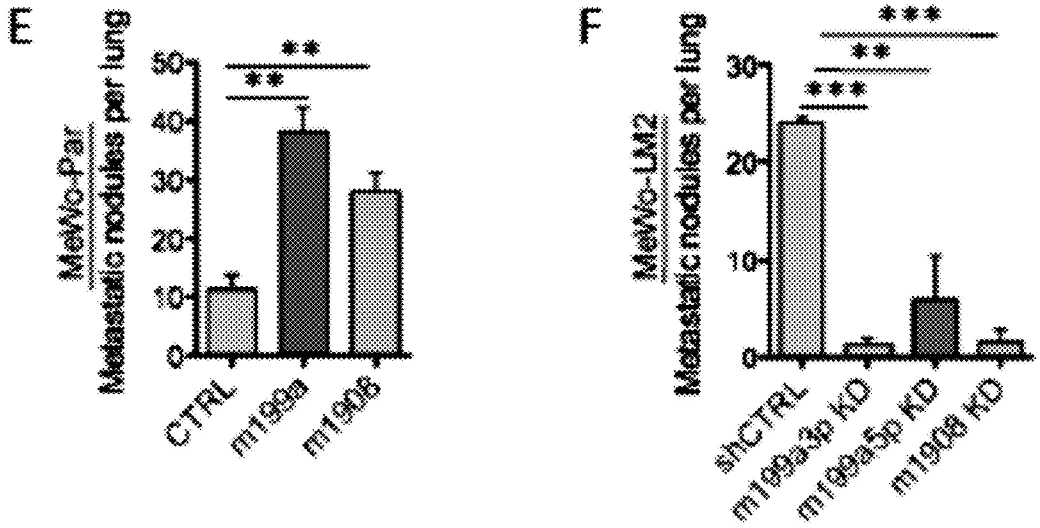

Next, assays were carried out to examine if endogenous levels of these miRNAs promote metastasis. To this end, miR-1908 and each of the two miRNAs arising from the miR-199a hairpin (miR-199a-3p and miR-199a-5p) were inhibited in the highly metastatic cells through miR-Zip technology. Individual inhibition of each of these miRNAs suppressed metastatic colonization by more than 7-fold (FIG. 1D; P=0.047 for miR-1908 inhibition; P=0.010 for miR-199a-3p inhibition; P=0.015 for miR-199a-5p inhibition) and dramatically decreased the number of metastatic nodules formed (FIG. 12F).

Figures 1E, 1F:
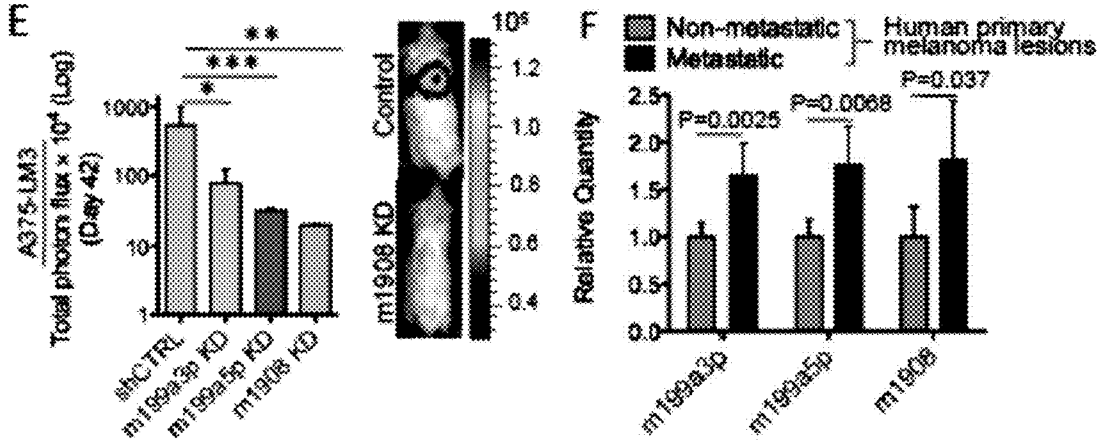

To determine whether these miRNAs also promote metastasis in an independent cell line, their expression was silenced in the A375 metastatic derivative cell line. Indeed, inhibition of miR-1908, miR-199a-3p, or miR-199a-5p significantly reduced the lung colonization capacity of metastatic A375-LM3 cells (FIG. 1E), establishing these three miRNAs as endogenous promoters of metastasis by human melanoma cells.

Given the robust functional roles of miR-1908, miR-199a-3p, and miR-199a-5p in promoting melanoma metastasis in a mouse model of human cell metastasis, further assays were carried out to examine whether expression of these miRNAs correlates with the capacity of human primary melanoma lesions to metastasize. To this end, 71 primary melanoma skin lesions obtained from Memorial Sloan-Kettering Cancer Center (MSKCC) patients were analyzed in a blinded fashion for the expression levels of miR-1908, miR-199a-3p, and miR-199a-5p through qRT-PCR. Consistent with the above functional studies, all three miRNAs were significantly induced in primary melanomas that had metastasized relative to those that had not (FIG. 1F; P=0.037 for miR-1908; P=0.0025 for miR-199a-3p; P=0.0068 for miR-199a-5p), suggesting that upregulated expression of these miRNAs in primary lesions is an early event predictive of melanoma cancer progression.

Example 3

Mir-1908, Mir-199a-3p, and Mir-199a-5p Promote Cell Invasion and Endothelial Recruitment In this Examiner, assays were carried out to determine the cellular mechanisms by which miR-1908, miR-199a-3p, and miR-199a-5p regulate metastasis.

Figures 13A, 13B, 13C, 13D, 13E, 13F, 13G:
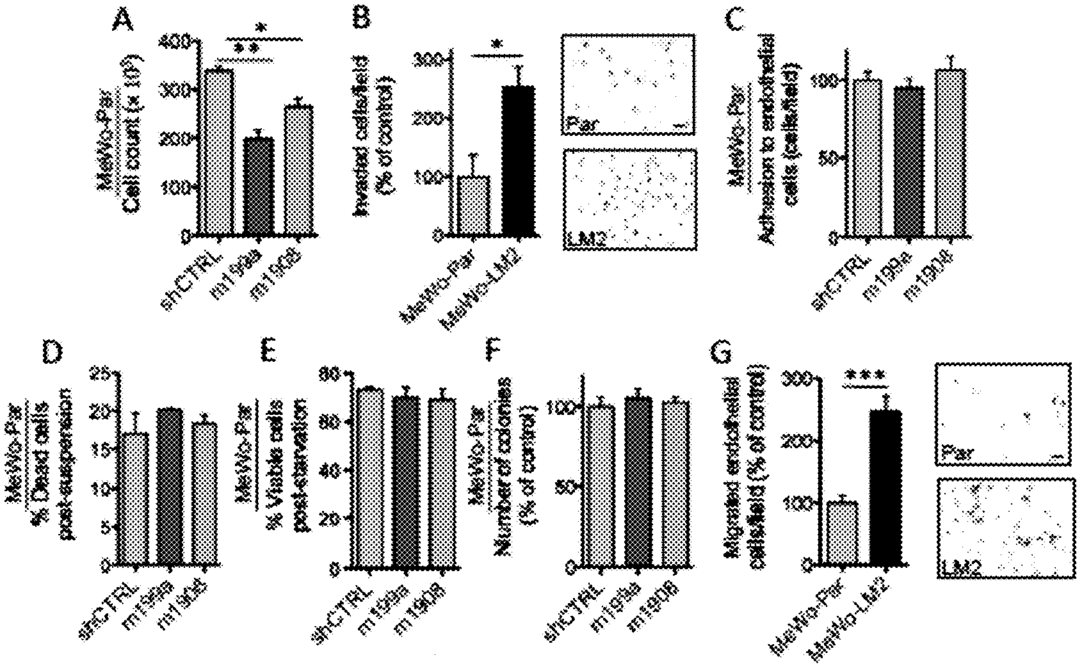

First, it was examined if these miRNAs promote metastasis by enhancing proliferation or tumor growth. Contrary to this, over-expression of each miRNA reduced cell proliferation (FIG. 13A). More importantly, miR-1908 over-expression did not increase primary tumor growth, while miR-199a over-expression actually lead to a significant decrease (35%; P<0.001) in tumor volume (FIG. 2A), indicating that the pro-metastatic effects of miR-1908 and miR-199a are not secondary to tumor growth promotion or enhanced cell proliferation.

Next, it was examined whether these miRNAs regulate cell invasion, a key metastatic phenotype. Metastatic LM2 cells, which express higher levels of these miRNAs, displayed significantly increased matrigel invasion capacity relative to their less metastatic parental population (FIG. 13B). Accordingly, over-expression of miR-199a and miR-1908 individually enhanced the ability of parental MeWo cells to invade through matrigel (FIG. 2B; three-fold increase for miR-199; two-fold increase for miR-1908). Conversely, individual inhibition of miR-199a-3p, miR-199a-5p, and miR-1908 significantly decreased the invasive capacity of MeWo-LM2 (FIG. 2C) as well as A375-LM3 (FIG. 2D) metastatic melanoma cell derivatives.

Figures 2A, 2B, 2C, 2D, 2E:
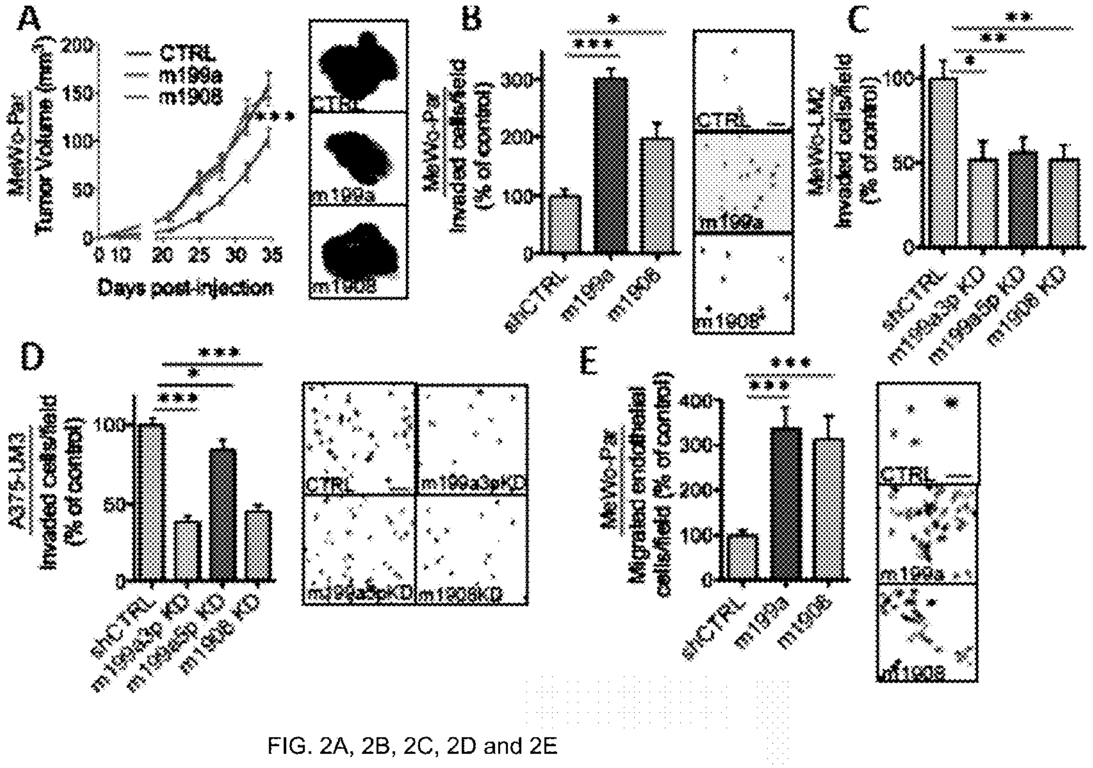
FIGS. 2A, 2B, 2C, 2D, 2E, 2F, 2G and 2H. MiR-1908, miR-199a-3p, and miR-199a-5p Display Dual Cell-Autonomous/Non-Cell-Autonomous Roles in Regulating Melanoma Metastatic Progression (2A) 1×106 parental MeWo cells over-expressing miR-199a, miR-1908, or a control hairpin were injected subcutaneously into immuno-deficient mice, and primary tumor volume was monitored over time. n=4-6. (2B) 1×105 parental MeWo cells over-expressing miR-199a, miR-1908, or a control hairpin were allowed to invade through a trans-well matrigel-coated insert for 24 hours, and the number of cells invaded into the basal side of each insert was quantified. n=7. (2C-2D) 1×105 highly metastatic MeWo-LM2 (2C) and A375-LM3 (2D) cells with miR-Zip-induced inhibition of miR-199a-3p, miR-199a-5p, miR-1908, or a control sequence were subjected to the cell invasion assay. n=6-8. (2E) 5×104 MeWo cells over-expressing miR-199a, miR-1908, or a control hairpin were seeded on the bottom of a well, and 1×105 human umbilical vein endothelial cells (HUVEC's) were allowed to migrate towards the cancer cells for 16 hours through a trans-well insert. Endothelial recruitment capacity was measured by quantifying the number of HUVEC's migrated to the basal side of each insert. n=7. (2F-2G) Endothelial recruitment by 5×104 MeWo-LM2 (2F) and A375-LM3 (2G) cells inhibited for miR-199a-3p, miR-199a-5p, miR-1908, or a control sequence. n=6-10. (2H) Cumulative fraction plot of the percentage blood vessel density distribution for metastatic nodules formed following intravenous injection of 2×105 highly metastatic MeWo-LM2 cells depleted for miR-199-3p, miR-199a-5p, miR-1908, or a control sequence. Lung sections were immunohistochemically double-stained for human vimentin (blue) and MECA-32 (red), and the percentage MECA-32 positive area within each metastatic nodule, demarcated based on vimentin staining, was quantified. n=211 nodules (control KD); n=60 nodules (m199a3p KD); n=138 nodules (m199a5p KD); n=39 nodules (m1908 KD). All data are represented as mean±SEM. Scale bar, 100 μm. See also FIG. 13.
Figures 2F, 2G, 2H:
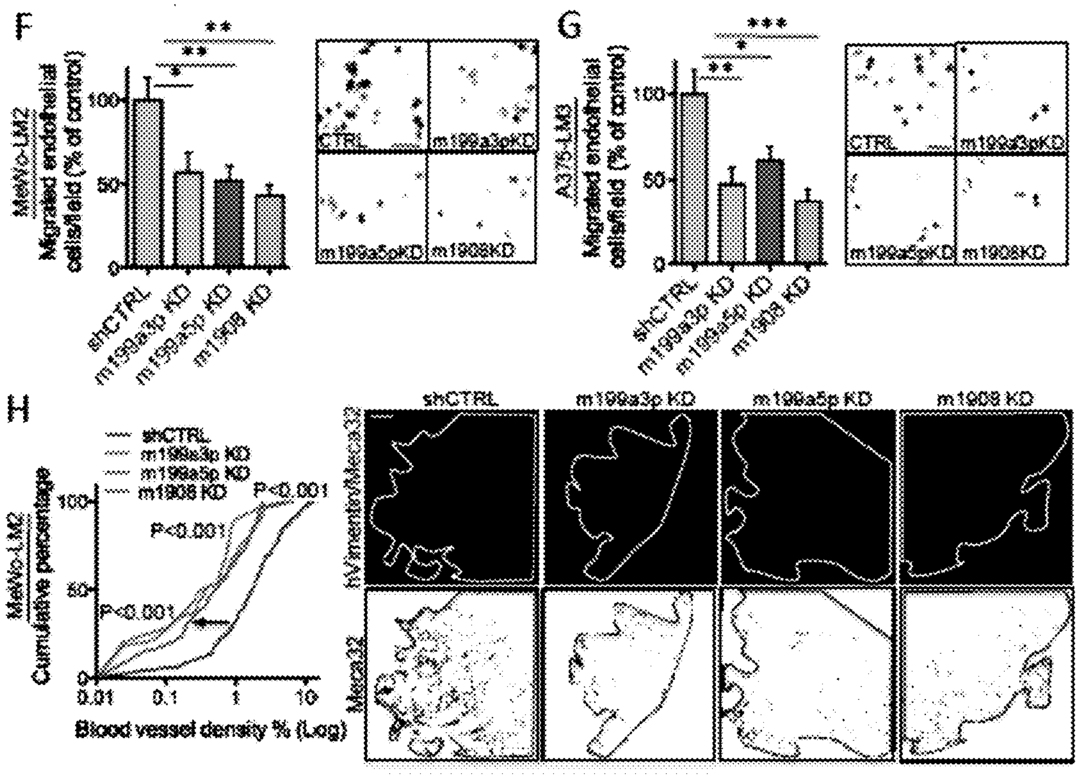

Given the robust effects of these miRNAs on metastatic progression, further analyses were conducted to examiner whether they may regulate any additional pro-metastatic phenotypes. While over-expression of miR-199a or miR-1908 did not modulate melanoma cell adhesion to endothelial cells (FIG. 13C), resistance to anoikis (FIG. 13D), survival in the setting of serum starvation (FIG. 13E), or colony formation (FIG. 13F), each miRNA dramatically enhanced (more than three-fold increase) the ability of parental MeWo cells to recruit endothelial cells in trans-well endothelial recruitment assays (FIG. 2E). Consistent with this, metastatic Mewo-LM2 cells, which physiologically over-express miR-199a and miR-1908, were more efficient at recruiting endothelial cells relative to their parental cells (FIG. 13G). Conversely, inhibition of miR-199a-3p, miR- 199a-5p, or miR-1908 in the metastatic MeWo-LM2 (FIG. 2F) as well as A375-LM3 cells (FIG. 2G) suppressed endothelial recruitment, consistent with the requirement and sufficiency of these miRNAs for enhanced endothelial recruitment capacity of metastatic melanoma cells.

Figure 13H:
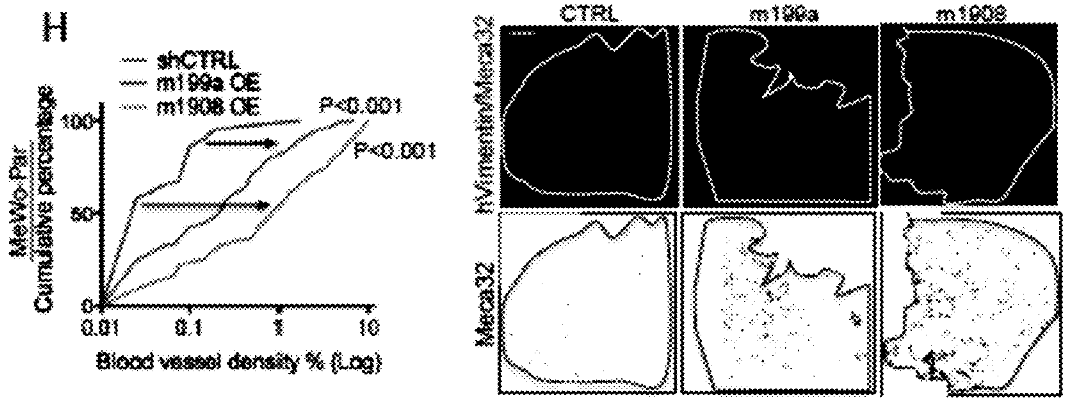

To determine whether endogenous miR-199a-3p, miR-199a-5p, and miR-1908 regulate endothelial recruitment by metastatic cells in vivo, assays were carried out to examine metastatic blood vessel density by performing co-immunostaining for human vimentin, which labels human MeWo melanoma cells, and mouse endothelial cell antigen (MECA-32), which labels mouse endothelial cells. Strikingly, inhibition of miR-199a-3p, miR-199a-5p, or miR-1908 individually led to pronounced decreases (an average of 3-fold for miR-199a-3p and miR-199a-5p and 4.7-fold for miR-1908) in blood vessel density within metastatic nodules (FIG. 2H; P<0.001 for miR-199a-3p; P<0.001 for miR-199a-5p; and P<0.001 for miR-1908), revealing a role for these miRNAs in promoting metastatic endothelial content and metastatic angiogenesis. Conversely, over-expression of each miRNA in poorly metastatic melanoma cells dramatically increased metastatic blood vessel density (FIG. 13H). These findings reveal miR-199a-3p, miR-199a-5p, and miR-1908 as necessary and sufficient for enhanced invasion and endothelial recruitment during melanoma progression.

Example 4

Mir-1908, Mir-199a-3p, and Mir-199a-5p Convergently and Cooperatively Target Apoe and DNAJA4

In this example, a systematic and unbiased approach was employed to identify the direct molecular targets of these miRNAs.

Figures 14A, 14B, 14C, 14D:
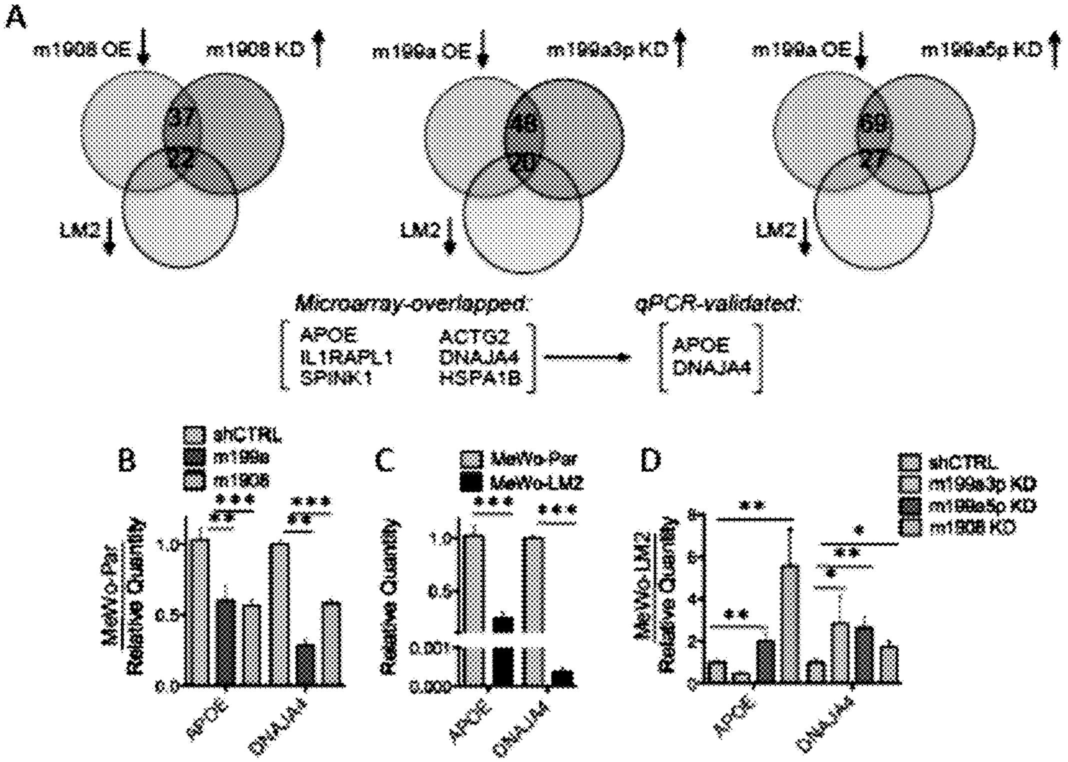

Since miR-1908, miR-199a-3p, and miR-199a-5p mediate the same sets of in vitro and in vivo phenotypes and miR-199a-5p and miR-199a-3p arise from the same precursor hairpin, it was hypothesized that the pro-metastatic phenotypes of these miRNAs may arise through silencing of common target genes. Given that mammalian miRNAs act predominantly by destabilizing target mRNA transcripts (Guo et al., 2010 Nature 466, 835-840), transcriptomic profiling of melanoma cells was performed in the context of both loss- and gain-of-function for each miRNA. This revealed a small set of genes that were repressed by both miR-199a and miR-1908 and that also displayed lower levels in the metastatic LM2 derivatives, which express higher endogenous levels of these miRNAs (FIG. 14A). Quantitative RT-PCR validated two genes, the metabolic gene Apolipoprotein E (ApoE) and the heat-shock protein DNAJA4, as significantly modulated by miR-199a and miR-1908 and dramatically silenced in the highly metastatic LM2 cells (FIGS. 3A and 14B-D).

Figures 3, 3A, 3B, 3C, 3D:
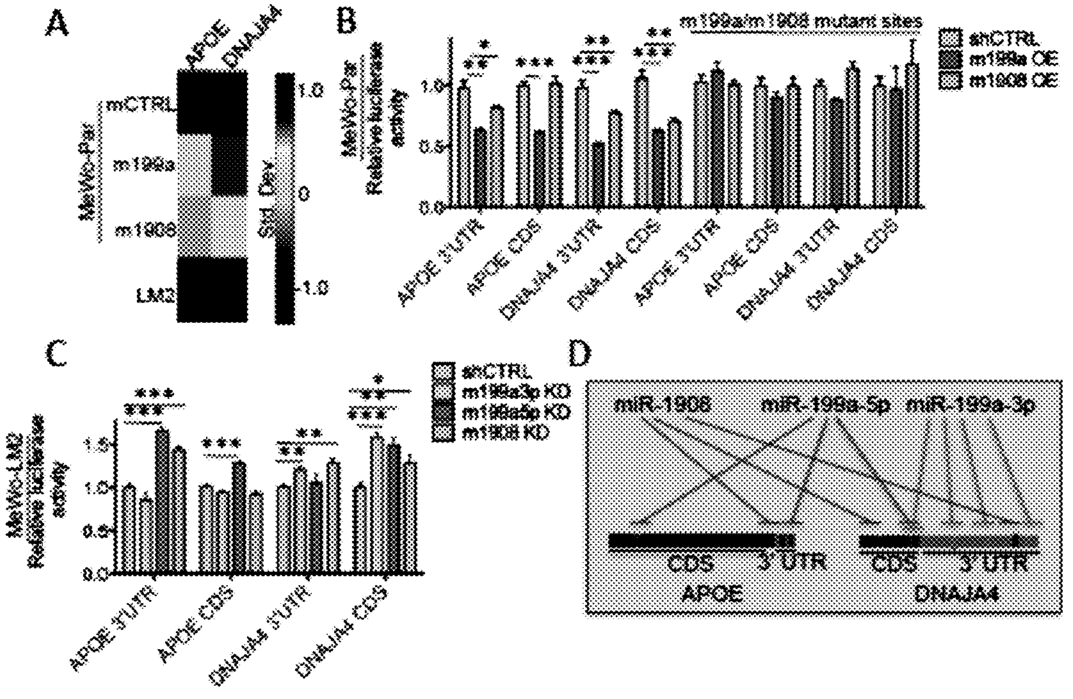
FIGS. 3A, 3B, 3C, 3D, 3E, 3F, 3G, 3H and 3I. Identification of ApoE and DNAJA4 as Common Target Genes of miR-199a and miR-1908 (3A) Heat map depicting mRNA levels of ApoE and DNAJA4, measured by qRT-PCR, in poorly metastatic MeWo cells over-expressing miR-199a, miR-1908, or a control hairpin and in highly metastatic MeWo-LM2 cells. Color map illustrates standard deviation changes from the mean of each heat map column. (3B) Heterologous luciferase reporter assays measuring the stability of wild-type ApoE and DNAJA4 3'UTR/CDS luciferase fusions or miRNA target-site mutant ApoE and DNAJA4 3'UTR/CDS fusions in parental MeWo cells over-expressing miR-199a, miR-1908, or a control hairpin. n=3-4. (3C) Stability of wild-type ApoE and DNAJA4 3'UTR/CDS luciferase fusions in MeWo-LM2 cells with silenced expression of miR-199a-3p, miR-199a-5p, miR-1908, or a control sequence. n=4. (3D) Schematic of experimentally derived model of ApoE and DNAJA4 3'UTR/CDS targeting by miR-199a-3p, miR-199a-5p, and miR-1908. (3E) Luciferase activity of wild-type and miRNA target-site mutant ApoE and DNAJA4 3'UTR/CDS luciferase fusions in highly metastatic MeWo-LM2 derivatives and their poorly metastatic parental cell line. n=4. (3F) Matrigel invasion capacity by 1×105 MeWo-LM2 cells expressing a control vector or over-expressing ApoE or DNAJA4. n=4. (3G) Endothelial recruitment ability by 5×104 MeWo-LM2 cells transduced with a control vector or an over-expression vector for ApoE or DNAJA4. n=6. (3H-3I) Poorly metastatic parental MeWo cells transduced with lentiviral short hairpins targeting ApoE, DNAJA4, or a control sequence were assessed for their matrigel invasion capacity (3H) and ability to recruit endothelial cells (3I). n=6-8. All data are represented as mean±SEM. Scale bar, 100 See also FIG. 14.
Figures 3E, 3F, 3G, 3H, 3I:
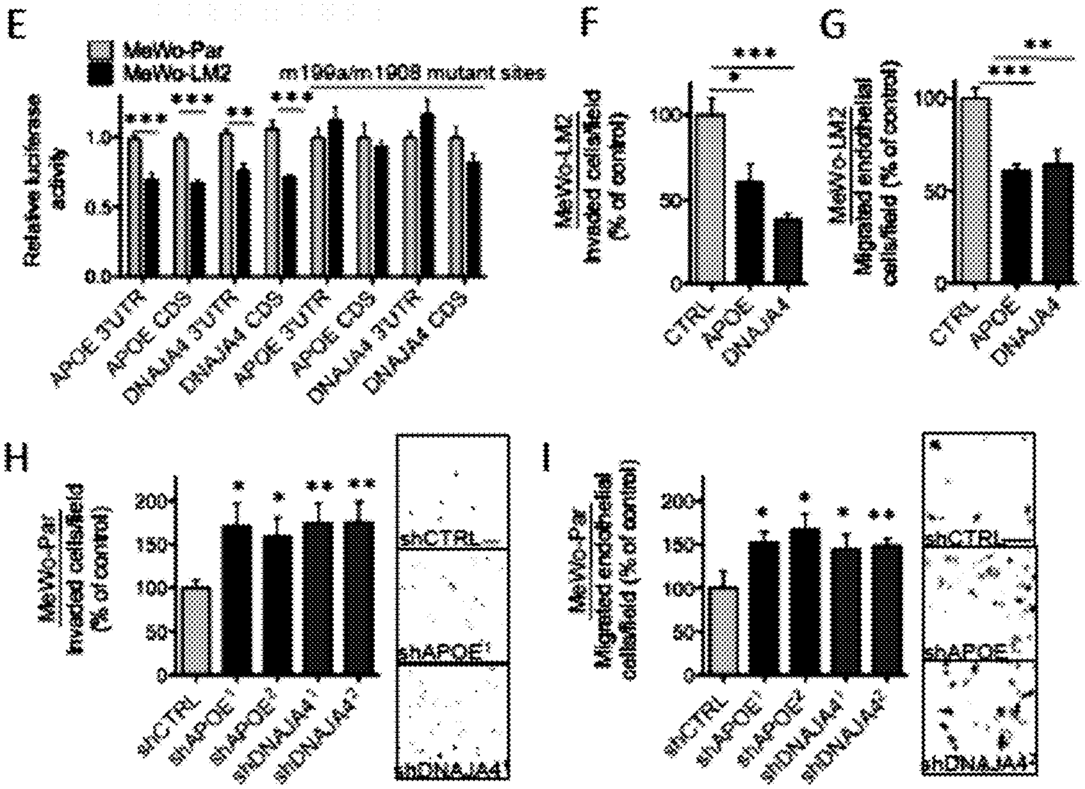

To determine whether ApoE and DNAJA4 are directly targeted by miR-1908, miR-199a-3p, and miR-199a-5p, the effects of each miRNA on the stability of its putative targets were examined through heterologous luciferase reporter assays. Interestingly, over-expression of miR-199a repressed the stability of the 3' untranslated region (UTR) and coding sequence (CDS) of both ApoE and DNAJA4, while over-expression of miR-1908 destabilized the 3'UTR of ApoE and the 3'UTR and CDS of DNAJA4. Consistent with direct targeting, mutating the miRNA complementary sequences on each target abrogated miRNA-mediated regulation (FIG. 3B). In a direct test of endogenous targeting, individual miRNA inhibition in metastatic LM2 cells resulted in increased target stability (FIG. 3C) that was abrogated upon mutating the miRNA target sites (FIG. 14E), revealing ApoE to be directly targeted by miR-1908 and miR-199a-5p and DNAJA4 to be directly targeted by all three miRNAs (FIG. 3D). Importantly, the CDS's and 3'UTR's of both of these genes were less stable in the highly metastatic LM2 cells, which express physiologically higher levels of the three regulatory miRNAs, indicating that endogenous targeting of ApoE and DNAJA4 by these miRNAs is relevant to melanoma metastasis (FIG. 3E).

Figures 14E, 14F, 14G:
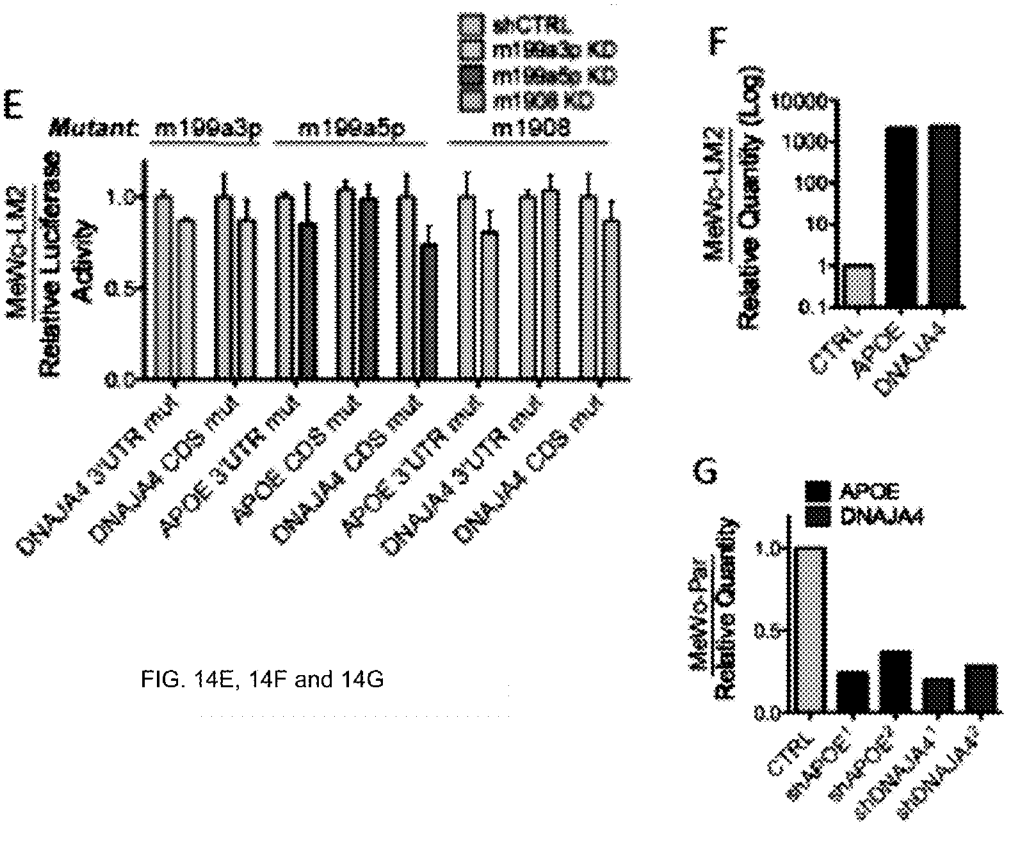

Given the molecular convergence of miR-199a-3p, miR-199a-5p, and miR-1908 onto common target genes, it was next examined whether these targets, ApoE and DNAJA4, could mediate the metastatic phenotypes conferred by these miRNAs. Over-expression of each gene in the metastatic LM2 cells led to pronounced reductions in cell invasion and endothelial recruitment phenotypes (FIGS. 3F-G, 14F). Conversely, knock-down of ApoE or DNAJA4 in the poorly metastatic cells using independent hairpins significantly enhanced cell invasion and endothelial recruitment (FIGS. 3H-I, 14G), revealing ApoE and DNAJA4 to act as endogenous suppressors of these pro-metastatic phenotypes—consistent with their targeting by the above mentioned metastasis-promoting miRNAs.

Example 5

Figures 4A, 4B, 4C, 4D, 4E, 4F:
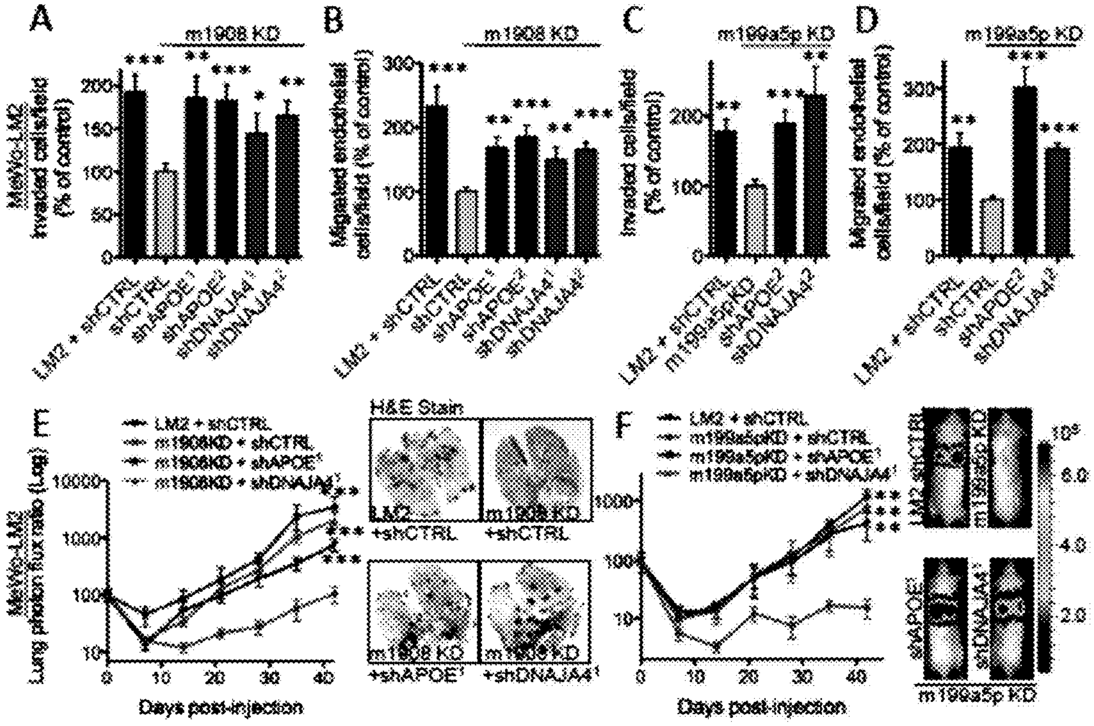
FIGS. 4A, 4B, 4C, 4D, 4E, 4F, 4G, 4H, 4I, 4J and 4K. Direct Targeting of ApoE and DNAJA4 by miR-199a and miR-1908 Promotes Metastatic Invasion, Endothelial Recruitment, and Colonization (4A-4D) Highly metastatic LM2 cells expressing a control shRNA or shRNAs targeting ApoE or DNAJA4 in the context of miR-1908 inhibition (m1908 KD; 4A, 4B) or miR-199a-5p inhibition (m199a5p KD; 4C, 4D) were subjected to the cell invasion (4A, 4C) and endothelial recruitment assays (4B, 4D). n=6-8. (4E-4F) Bioluminescence imaging plot and H&E-stained lungs representative of lung metastasis after intravenous injection of 1×105 LM2 cells expressing a control hairpin or hairpins targeting ApoE, DNAJA4, or a control sequence in the setting of miR-1908 silencing (4E) or miR-199a-5p silencing (4F). n=5. (4G-4H) Parental MeWo cells over-expressing ApoE or DNAJA4 or expressing a control vector in the context of miR-1908 over-expression were analyzed for the matrigel invasion (4G) and endothelial recruitment (4H) phenotypes. (4I-4J) A375-LM3 derivatives expressing a control shRNA or shRNAs targeting ApoE and DNAJA4 were transduced with a cocktail of LNAs targeting miR-199a-3p, miR-199a-5p, and miR-1908 or a control LNA and analyzed in the matrigel invasion (4I) and endothelial recruitment (4J) assays. n=4. (4K) Blood vessel density distribution, represented in a cumulative fraction plot, for metastatic nodules formed by MeWo-LM2 cells inhibited for miR-1908 and transduced with shRNAs targeting ApoE, DNAJA4, or a control sequence. Lung sections from FIG. 4E were immunocytochemically double-stained for human vimentin (blue) and the endothelial marker MECA-32 (red). The percentage MECA-32 positive area within each vimentin-positive nodule was quantified. n=39 nodules (shCTRL); n=97 (shAPOE1); n=38 (shAPOE2); n=200 (shDNAJA41); n=19 (shDNAJA42). All data are represented as mean±SEM. Scale bar, 100 See also FIG. 15.
Figures 4G, 4H, 4I, 4J, 4K:
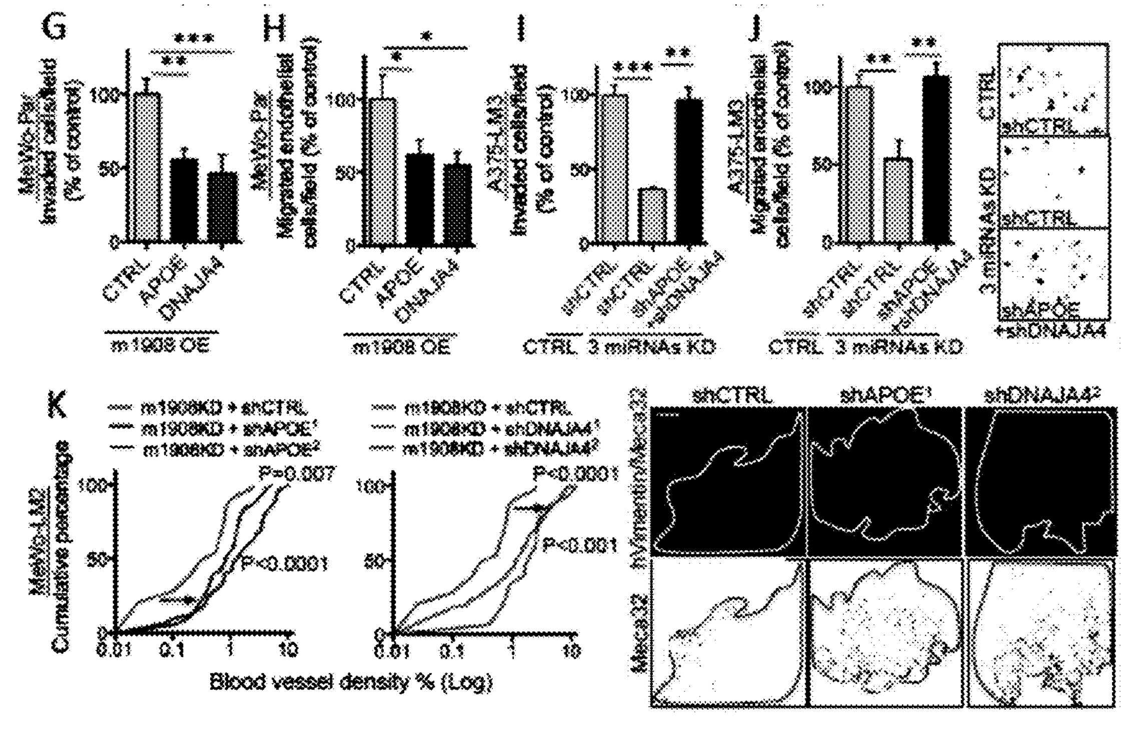
Figures 15A, 15B, 15C, 15D, 15E, 15F, 15G:
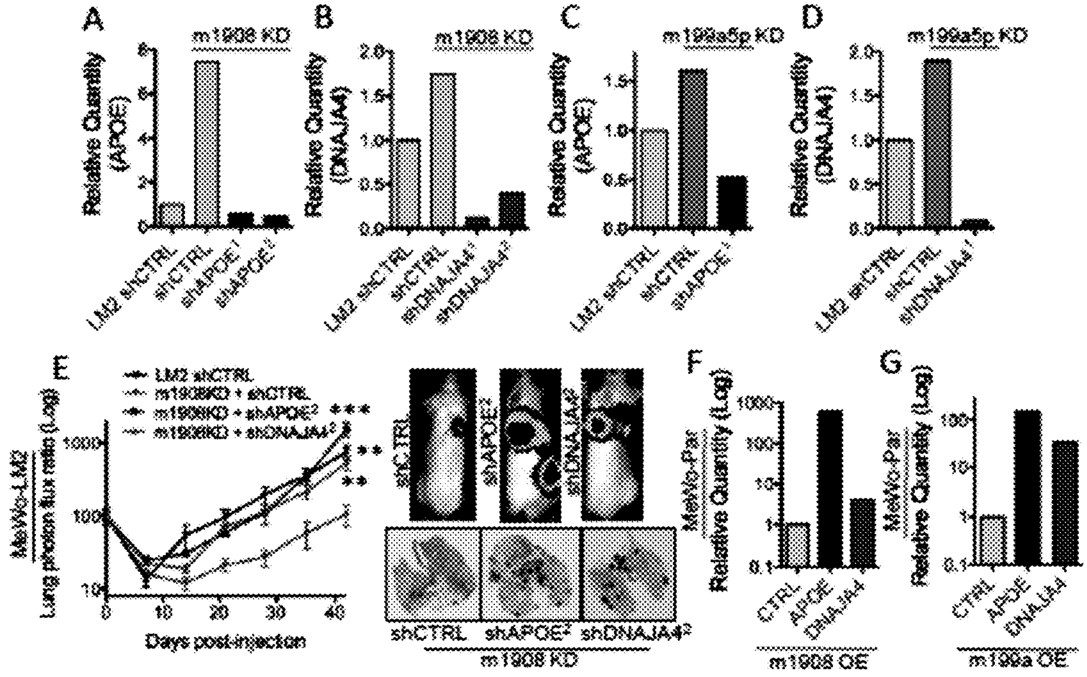
Figures 15H, 15I, 15J, 15K:
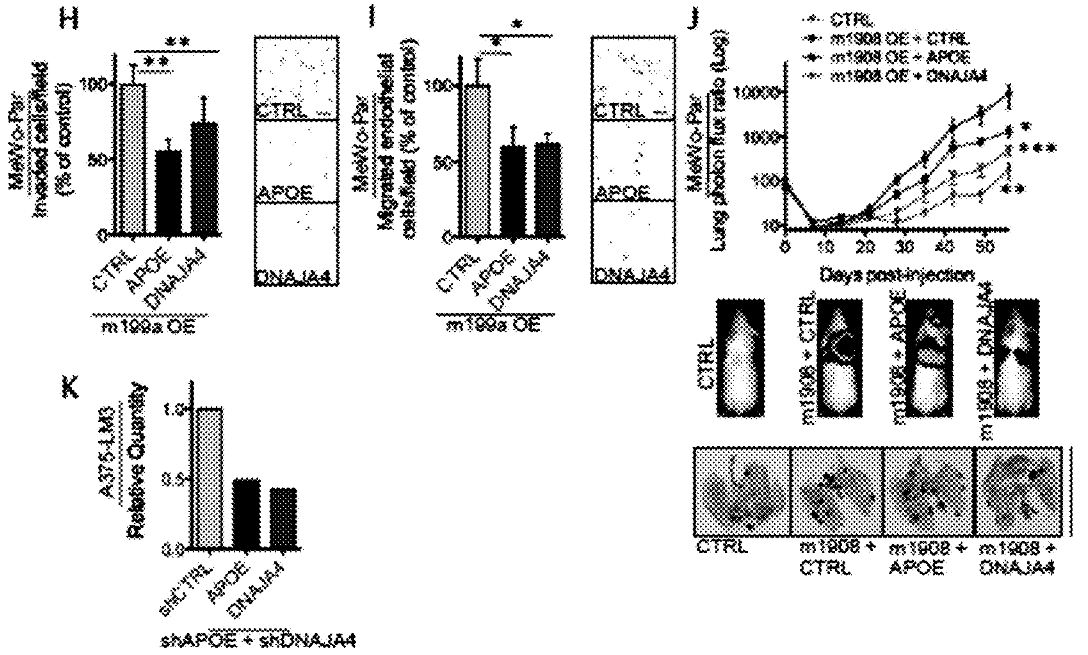

ApoE and DNAJA4 Mediate miR-199a- and miR-1908-Dependent Metastatic Invasion, Endothelial Recruitment, and Colonization To determine whether ApoE and DNAJA4 are the direct biological effectors downstream of miR-199a and miR-1908, assays were carried out to examine whether these two target genes epistatically interact with each miRNA. As expected, miRNA silencing reduced the invasion and endothelial recruitment capacity of highly metastatic melanoma cells. Importantly, knock-down of ApoE or DNAJA4 in the setting of miRNA inhibition significantly occluded the suppression of invasion (FIGS. 4A and 4C) and endothelial recruitment (FIGS. 4B and 4D) upon silencing of each miRNA. Strikingly, knock-down of either of these genes in cells depleted for miR-1908 or miR-199a-5p fully rescued the dramatic suppression of metastatic colonization resulting from miRNA inhibition (FIG. 4E-F, 15E). Conversely, over-expression of ApoE or DNAJA4 in cells over-expressing miR-1908 (FIG. 4G-H, 15F) or miR-199a (FIG. 15G-I) was sufficient to suppress cell invasion and endothelial recruitment. Additionally, ApoE or DNAJA4 over-expression was sufficient to inhibit miRNA-mediated metastatic colonization (FIG. 15J). Importantly, ApoE and DNAJA4 were also required for miRNA-dependent enhanced cell invasion and endothelial recruitment by the highly metastatic A375-LM3 cells (FIGS. 4 I-J, 15K).

To determine whether ApoE and DNAJA4 also regulate miRNA-dependent metastatic endothelial recruitment in vivo, co-immunostaining of melanoma metastases (human vimentin) and endothelial cells (MECA-32) was performed in lung metastatic nodules formed by cells knocked-down for each of these genes in the context of miRNA inhibition. Notably, knock-down of ApoE or DNAJA4 resulted in a significant (>3.5-fold) increase in metastatic blood vessel density in metastases arising from cells with miRNA silencing (FIG. 4K, P<0.01 for both ApoE and DNAJA4 knock-down cells). These findings reveal ApoE and DNAJA4 as direct downstream effectors of miRNA-dependent metastatic invasion, colonization, and endothelial recruitment phenotypes induced by these pro-metastatic miRNAs in melanoma.

Example 6

Figures 5A, 5B, 5C, 5D, 5E, 5F, 5G:
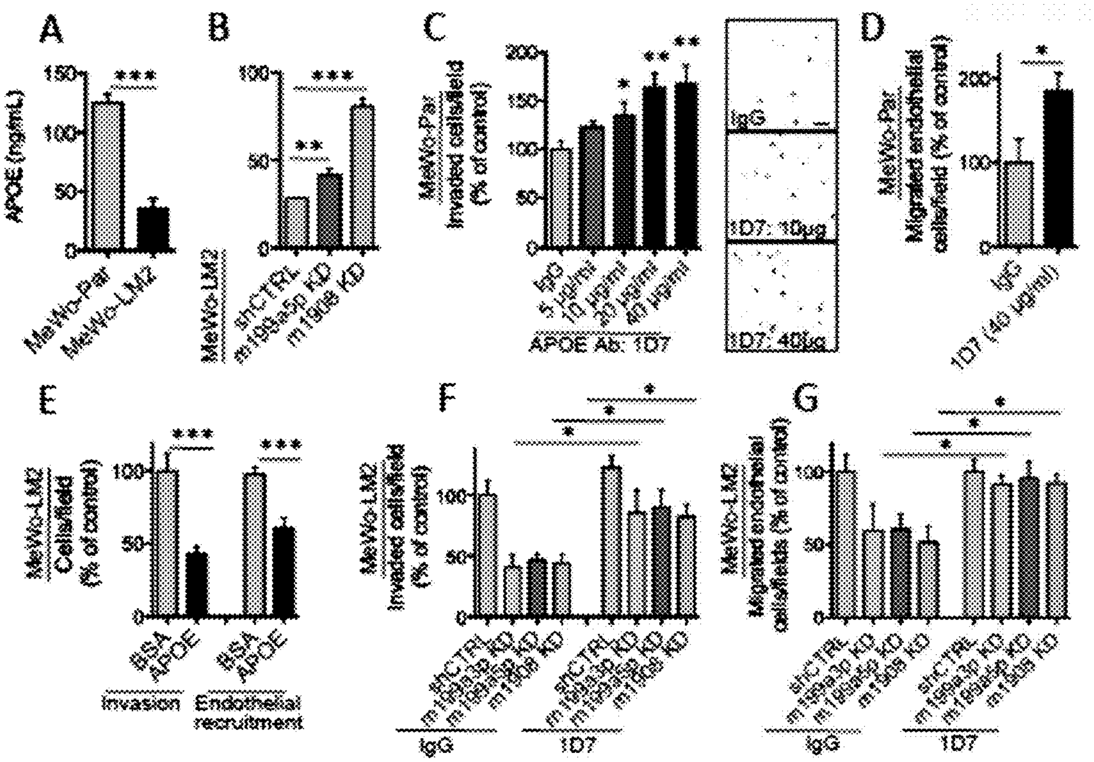
FIGS. 5A, 5B, 5C, 5D, 5E, 5F, 5G, 5H, 5I, 5J, 5K, 5L and 5M. Melanoma-Cell Secreted ApoE Inhibits Melanoma Invasion and Endothelial Recruitment, while Genetic Deletion of ApoE Accelerates Metastasis (5A-5B) Extracellular ApoE levels quantified by ELISA in conditioned media from MeWo-LM2 metastatic derivatives and their parental cells (5A) and LM2 cells silenced for miR-199a-5p, miR-1908, or a control sequence (5B). n=3. (5C) ApoE-neutralizing antibody 1D7 (10-40 μg/mL) or IgG (40 μg/mL) was added to the cell media, and matrigel invasion by parental MeWo cells was assessed. n=4-6. (5D) Endothelial recruitment by parental MeWo cells in the presence of 1D7 (40 μg/mL) or a control IgG antibody (40 μg/mL). n=4. (5E) The matrigel invasion and endothelial recruitment phenotypes were assessed in LM2 cells in the presence of bovine serum albumin (BSA) (100 μM) or recombinant ApoE3 (100 μM) added to the cell media. n=7-10. (5F-5G) LM2 cells with silenced expression of miR-199a-3p, miR-199a-5p, miR-1908, or a control sequence were examined for matrigel invasion capacity (5F) and endothelial recruitment ability (5G) in the presence of IgG or ApoE-neutralizing 1D7 antibodies (40 μg/mL). n=5-6. (5H) ApoE levels quantified by ELISA in conditioned media from parental MeWo cells transduced with shRNAs targeting DNAJA4 or a control sequence. n=3. (5I-5J) Parental MeWo cells with shRNA-induced silencing of DNAJA4 were analyzed for the matrigel invasion (5I) and endothelial recruitment (5J) phenotypes in the presence of either BSA (100 μM) or recombinant ApoE3 (100 μM). n=4. (5K) Array-based ApoE expression levels in nevi (n=9), primary melanomas (n=6), and distant melanoma metastases samples (n=19). (5L) Highly metastatic MeWo-LM2 cells were incubated in the presence of recombinant ApoE3 or BSA at 100 μg/mL. After 24 hours, 4×104 cells were intravenously injected into NOD-SCID mice, and lung colonization was monitored by bioluminescence imaging. n=6. (5M) Lung metastasis by 5×104 B16F10 mouse melanoma cells intravenously injected into ApoE genetically null C57BL/6 mice or their wild-type control littermates. Lung bioluminescence quantification and representative H&E-stained lungs correspond to 19 days post-injection. n=8-18. All data are represented as mean±SEM. Scale bar, 100 μm.
Figures 16A, 16B, 16C, 16D, 16E, 16F:
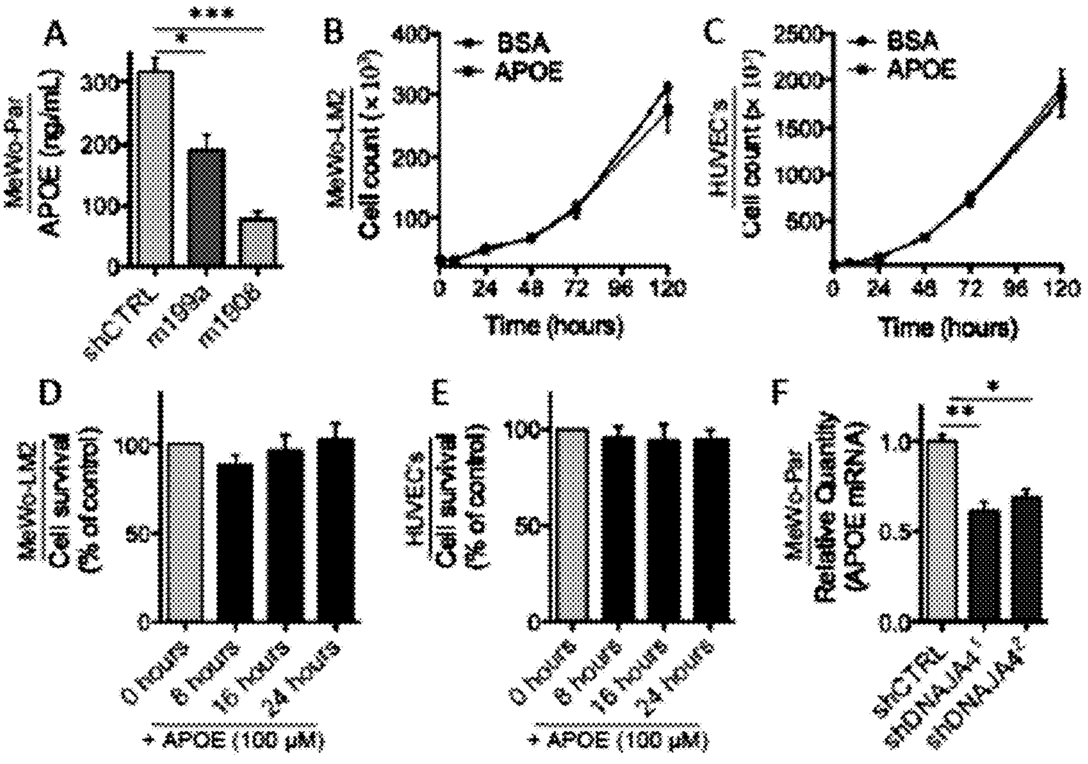

Melanoma Cell-Secreted Apoe is Both a Necessary and Sufficient Mediator of Invasion and Endothelial Recruitment, While Genetic Deletion of Apoe Promotes Metastasis ApoE is a secreted factor. As such, it was examined whether melanoma-cell secreted ApoE could suppress invasion and endothelial recruitment. Accordingly, extracellular ApoE levels, detected by ELISA, were 3.5-fold lower in metastatic LM2 cells—which express higher levels of miR-199a and miR-1908—than their less metastatic parental cells (FIG. 5A). Secreted ApoE levels were also significantly suppressed by endogenous miR-199a and miR-1908 (FIGS. 5B and 16A).

Next, inhibiting ApoE through use of a neutralizing antibody (1D7) that recognizes the receptor-binding domain of ApoE enhanced both cell invasion (FIG. 5C; 1.68-fold increase) and endothelial recruitment (FIG. 5D; 1.84-fold increase) by parental MeWo cells, which express high endogenous levels of ApoE (FIG. 14C). Conversely, addition of recombinant human ApoE significantly suppressed invasion and endothelial recruitment by metastatic LM2 cells (FIG. 5E), which exhibit low endogenous ApoE levels (FIG. 14C). Importantly, recombinant ApoE addition did not affect melanoma cell or endothelial cell in vitro proliferation (FIG. 16B-C) or survival in serum starvation conditions (FIG. 16D-E), indicating that suppression of these phenotypes by recombinant ApoE is not secondary to a decrease in proliferation or impaired survival. Consistent with ApoE being epistatically downstream of miR-199a and miR-1908, neutralization of ApoE with the ApoE neutralizing antibody 1D7 significantly abrogated the suppressed invasion and endothelial recruitment phenotypes seen with inhibition of each miRNA (FIGS. 5F-G). The above findings reveal melanoma cell-secreted ApoE as a necessary and sufficient suppressor of miRNA-dependent invasion and endothelial recruitment phenotypes in melanoma.

Figures 5H, 5I, 5J, 5K, 5L, 5M:
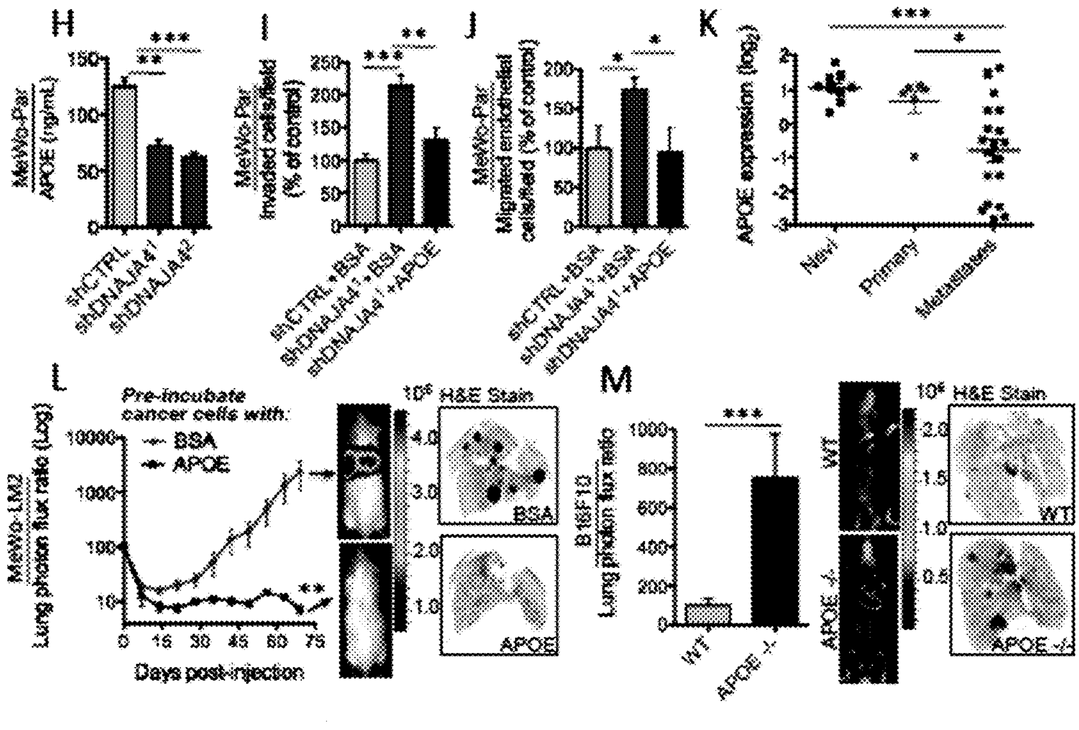
Figures 16G, 16H, 16I:
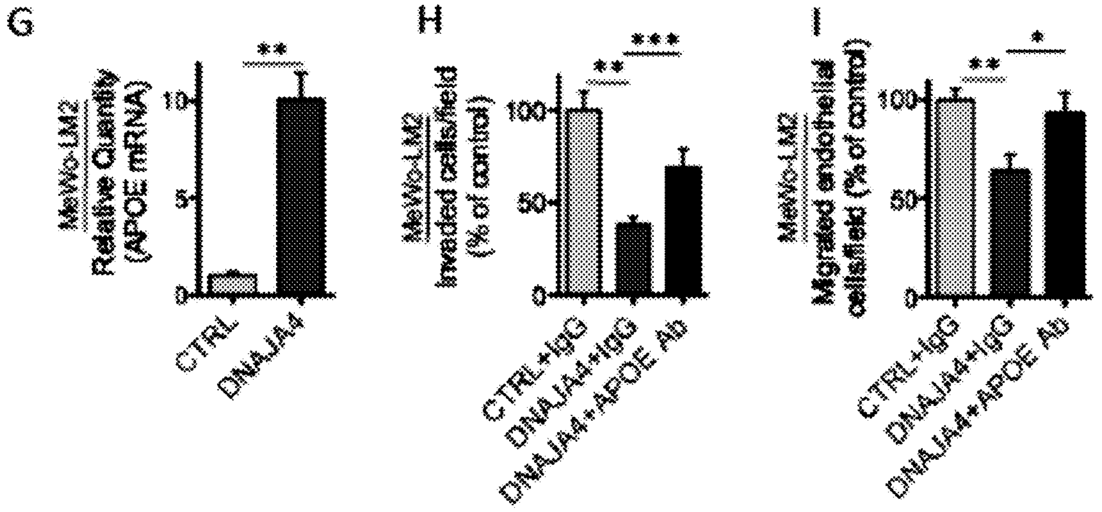

Further assays were carried out to investigate the mechanism by which DNAJA4, a poorly characterized heat-shock protein, mediates endothelial recruitment and invasion. Given the phenotypic commonalities displayed by ApoE and DNAJA4, it was hypothesized that DNAJA4 may play a regulatory role and enhance ApoE levels. Indeed, knock-down of DNAJA4 reduced both ApoE transcript levels (FIG. 16F) as well as secreted ApoE levels (FIG. 5H), while DNAJA4 over-expression substantially elevated ApoE expression (FIG. 16G). Consistent with DNAJA4 acting upstream of ApoE, addition of recombinant ApoE abrogated the enhanced cell invasion and endothelial recruitment phenotypes seen with DNAJA4 knock-down (FIG. 5I-J). Conversely, the suppression of invasion and endothelial recruitment seen with DNAJA4 over-expression phenotypes were significantly occluded by antibody neutralization of ApoE (FIGS. 16H-I). These findings reveal DNAJA4 to suppress melanoma invasion and endothelial recruitment through positive regulation of ApoE expression and resulting secretion.

In view of the regulatory convergence of three metastasis-promoting miRNAs and the DNAJA4 gene on ApoE, assays were carried out to determine whether ApoE expression correlates with human melanoma progression. To this end, published array-based expression data for ApoE (Haqq et al., 2005 Proc. Natl. Acad. Sci. USA 102, 6092-6097) was analyzed in nevi, primary, and metastatic lesions. Consistent with a metastasis-suppressive role, ApoE levels were significantly lower in distal organ metastases relative to primary ($P<0.025$) and nevi lesions ($P<0.0003$) (FIG. 5K).

Given its significant correlation with human melanoma progression, it was next examined whether increasing ApoE signaling in melanoma cells could have therapeutic efficacy in suppressing melanoma metastasis. More specifically, metastatic MeWo-LM2 cells were pre-incubated with recombinant ApoE or BSA for 24 hours prior to injection into mice. Strikingly, pre-treatment of cancer cells with ApoE robustly suppressed metastatic colonization by over 300-fold (FIG. 5L). This dramatic suppression of metastasis by ApoE pre-incubation of melanoma cells reflects that the effects of ApoE on melanoma cells are pivotal for metastatic initiation, as cells pre-treated with ApoE exhibit reduced invasive ability, which is needed to initiate metastatic events leading to lung colonization.

Given the robust influence exerted by ApoE on metastasis and metastatic phenotypes, as well as its strong association with human melanoma progression, further assays were carried out to investigate the impact of genetic deletion of systemic ApoE on melanoma progression in an immunocompetent mouse model of melanoma metastasis. Consistent with a major suppressive role for extracellular ApoE in metastasis, B16F10 mouse melanoma cells injected into the circulation exhibited a greater than 7-fold increase in metastatic colonization in ApoE genetically null mice compared to their wild-type littermates (FIG. 5M). These findings establish systemic and cancer-secreted ApoE as a robust suppressor of human and mouse melanoma metastasis.

Example 7

Extracellular ApoE Divergently Targets Melanoma Cell LRPJ and Endothelial Cell LRP8 Receptors In this example, assays were carried out to investigate the molecular mechanisms by which ApoE suppresses metastasis.

Figures 6A, 6B, 6C, 6D, 6E, 6F:
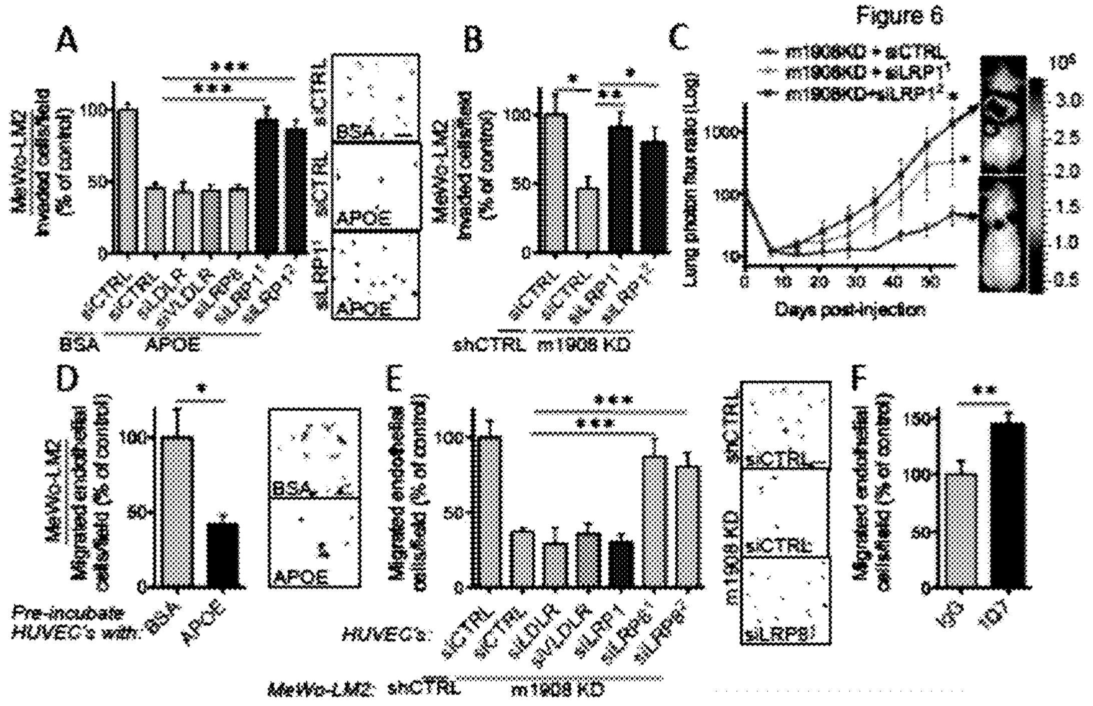
FIGS. 6A, 6B, 6C, 6D, 6E, 6F, 6G, 6H, 6I and 6J. Identification of Distinct Melanoma and Endothelial Cell Receptors that Mediate the Effects of ApoE on Melanoma Invasion and Endothelial Recruitment (6A) Matrigel invasion capacity was examined in 1×105 LM2 cells transduced with siRNAs targeting LDLR, VLDLR, LRP8, LRP1, or a control sequence in the presence of either BSA (100 μM) or recombinant ApoE3 (100 μM). n=4-7. (6B) 1×105 MeWo-LM2 cells transduced with short hairpins targeting miR-1908 or a control sequence were transfected with siRNAs targeting LRP1 or a control siRNA and subjected to the matrigel invasion assay. n=4. (6C) Bioluminescence imaging of lung colonization by 1×105 LM2 cells transduced with siRNAs targeting LRP1 or a control sequence in the setting of miR-1908 inhibition. n=5. (6D) 1×105 endothelial cells pre-incubated with BSA (100 μM) or recombinant ApoE3 (100 μM) for 24 hours were analyzed for the endothelial recruitment phenotype by 5×105 LM2 cells. n=3-4. (6E) 1×105 endothelial cells were transduced with siRNAs targeting LDLR, VLDLR, LRP1, LRP8, or a control sequence and allowed to migrate in a trans-well system towards LM2 cells inhibited for miR-1908 or a control sequence. n=4-12. (6F) Trans-well migration by 1×105 endothelial cells in the presence of IgG (40 μg/mL) or 1D7 antibodies (40 μg/mL) added to the cell media. n=6-8. (6G) Trans-well migration by 1×105 endothelial cells transduced with siRNAs targeting LRP8 or a control sequence in the presence of BSA (100 μM) or recombinant ApoE3 (100 μM).

In order to identify the ApoE receptor(s) that mediate(s) invasion, down all four known ApoE receptors, VLDLR, LRP1, LRP8, and LDLR (Hatters et al., 2006 Trends Biochem. Sci. 31, 445-454; Hauser et al., 2011 Prog. Lipid Res. 50, 62-74) were knocked in melanoma cells. Interestingly, knock-down of LRP1, but not the other ApoE receptors, abolished the cell invasion suppression effect induced by recombinant ApoE (FIG. 6A). Importantly, knock-down of LRP1 in metastatic LM2 cells, which display low levels of ApoE, only modestly increased cell invasion (FIG. 17A), suggesting the effects of LRP1 to be mediated by endogenous ApoE.

Figures 17A, 17B, 17C, 17D, 17E:
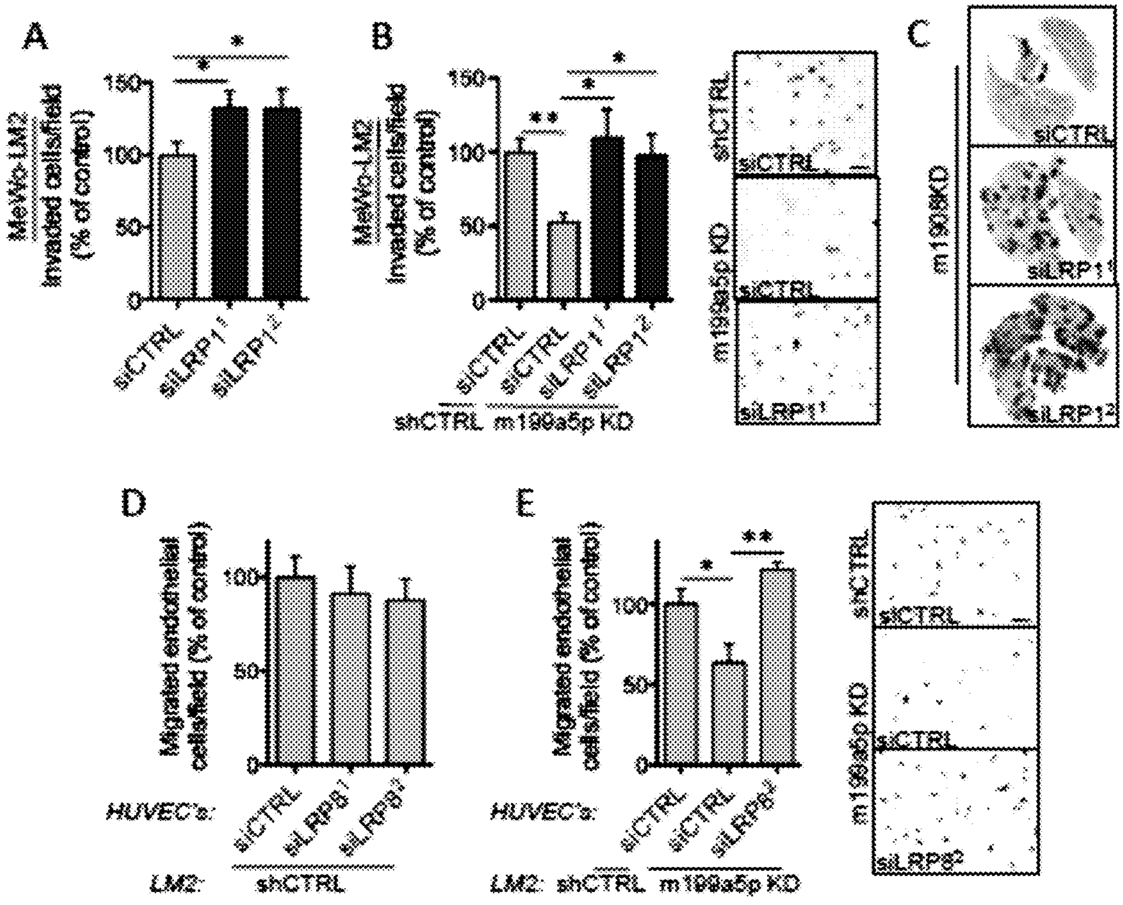

To determine if LRP1 also mediates the miRNA-dependent effects on invasion and metastatic colonization, LRP1 was knocked down in the context of miRNA inhibition. LRP1 knock-down in the setting of miRNA silencing rescued the suppressed invasion phenotype arising from miRNA inhibition (FIGS. 6B, 17B). Consistent with these in vitro results, LRP1 knock-down significantly enhanced in vivo metastatic colonization by LM2 cells silenced for miR-1908 (FIG. 6C, 17C). These findings reveal LRP1 to be epistatically downstream of miRNA/ApoE-dependent melanoma invasion and metastatic colonization.

While the invasion phenotype reflects the cell-autonomous effects of ApoE on melanoma cells, the endothelial recruitment phenotype suggests a non-cell-autonomous role of cancer-expressed ApoE directly on endothelial cells. Consistent with this, pre-treatment of endothelial cells with ApoE significantly reduced their ability to migrate towards highly metastatic cancer cells (FIG. 6D). In order to identify the ApoE receptor(s) on endothelial cells that mediate(s) the endothelial recruitment phenotype, all four known ApoE receptors were knocked down on endothelial cells. Interestingly, unlike for cancer cell invasion, knock-down of endothelial LRP8, but not any of the other receptors, selectively and significantly abrogated the inhibition of endothelial recruitment caused by miRNA silencing (FIGS. 6E, 17D-E). These findings are consistent with the LRP8 receptor being the downstream endothelial mediator of miRNA/ApoE-dependent effects on endothelial recruitment.

Figures 6G, 6H, 6I, 6J:
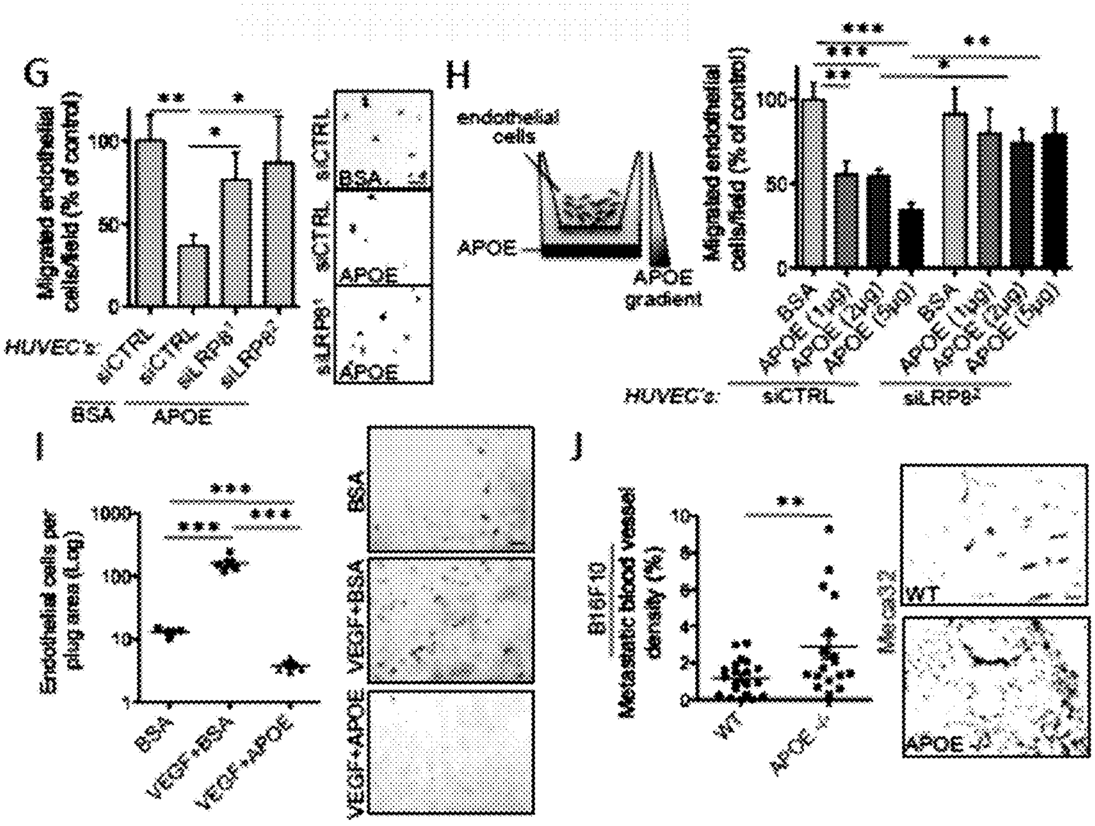

Next, assays were carried out to examine whether ApoE/LRP8 signaling might also regulate general endothelial migration in a cancer cell-free system. Accordingly, antibody neutralization of ApoE, which is present in endothelial cell media, significantly enhanced endothelial migration (FIG. 6F), while recombinant ApoE was sufficient to inhibit endothelial migration in a trans-well assay (FIG. 6G) and a gradient-based chemotactic assay (FIG. 6H) in an endothelial cell LRP8 receptor-dependent manner. Importantly, addition of ApoE lead to a dramatic (greater than 40-fold) suppression of VEGF-induced endothelial recruitment in vivo into subcutaneous matrigel plugs (FIG. 6I).

Given the requirement and sufficiency of ApoE in mediating endothelial recruitment, further assays were carried out to examine whether systemic ApoE might regulate metastatic angiogenesis. Consistent with the robust suppression of metastatic endothelial content by melanoma cell-secreted ApoE (FIG. 4K), genetically null ApoE mice displayed higher blood vessel densities within their lung metastatic nodules formed by B16F10 mouse melanoma cells compared to their wild-type littermates (FIG. 6J; 2.41-fold increase, P=0.0055). Taken together, the above findings reveal dual cell-autonomous/non-cell-autonomous roles for ApoE in metastasis suppression through divergent signaling mediated by melanoma cell LRP1 and endothelial cell LRP8 receptors.

Example 8

MiR-199a-3p, miR-199a-5p, and miR-1908 as Robust Prognostic and Therapeutic Targets in Melanoma Metastasis To examine whether the metastasis promoter miRNAs described herein could serve as clinical predictors of metastatic outcomes, the expression levels of miR-199a-3p, miR-199a-5p, and miR-1908 were quantified in a blinded fashion by qRT-PCR in a cohort of human melanoma samples obtained from patients at MSKCC. The relationships between the levels of these miRNAs in primary melanoma lesions and metastatic relapse outcomes were then determined.

Figures 7A, 7B, 7C, 7D, 7E:
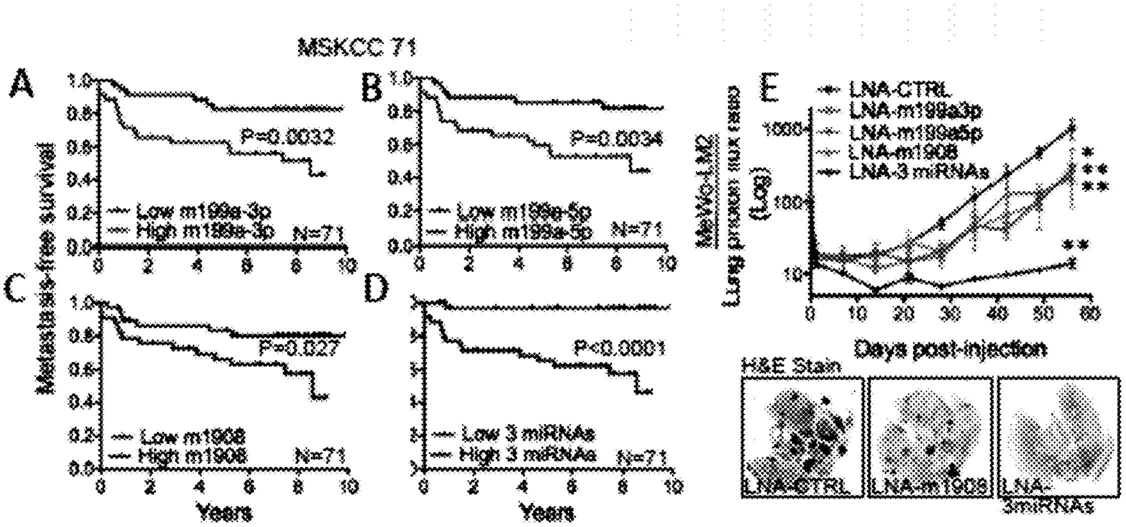

Importantly, patients whose primary melanoma lesions expressed higher (greater than the median for the population) levels of miR-199a-3p, miR-199a-5p, or miR-1908 were more likely to develop distal metastases and exhibited significantly shorter metastasis-free survival times than patients whose primary melanomas expressed lower levels of each of these miRNAs (FIGS. 7A-C, P=0.0032 for miR-199a-3p, P=0.0034 for miR-199a-5p, and P=0.027 for miR-1908). Strikingly, the aggregate expression levels of the three miRNAs displayed the strongest prognostic capacity in stratifying patients at high risk from those with very low risk for metastatic relapse (FIG. 7D, P<0.0001). These clinical findings are consistent with functional cooperativity between these miRNAs in the regulation of cancer progression and suggest utility for these molecules as clinical prognostic biomarkers of melanoma metastasis.

In light of the current lack of effective treatment options for the prevention of melanoma metastasis and the strong prognostic value of the three regulatory miRNAs in melanoma metastasis, these miRNAs therapeutically targeted using antisense LNA therapy (Elmer et al., 2008(a); Elmer et al., 2008(b)). Highly metastatic MeWo-LM2 cells pre-treated with LNA oligonucleotides antisense to mature miR-199a-3p, miR-199a-5p, or miR-1908 exhibited roughly a four-fold decrease in metastatic activity. Given clinical evidence for cooperativity among these miRNAs, the impact of silencing all three miRNAs on metastatic progression was examined. Remarkably, co-transfection of LNAs against all three miRNAs suppressed metastatic colonization by over seventy-fold, revealing dramatic synergy and cooperativity between endogenous miR-199a-3p, miR-199a-5p, and miR-1908 (FIG. 7E, P=0.004). Importantly, inhibition of these miRNAs with triple LNA pre-treatment did not result in decreased in vitro proliferation (FIG. 18A), indicating that the dramatic metastasis suppression phenotype is not secondary to impaired proliferation. Combinatorial LNA-mediated miRNA targeting in the independent A375 metastatic derivative line also significantly inhibited lung colonization (FIG. 18B).

Figures 7F, 7G, 7H, 7I, 7J:
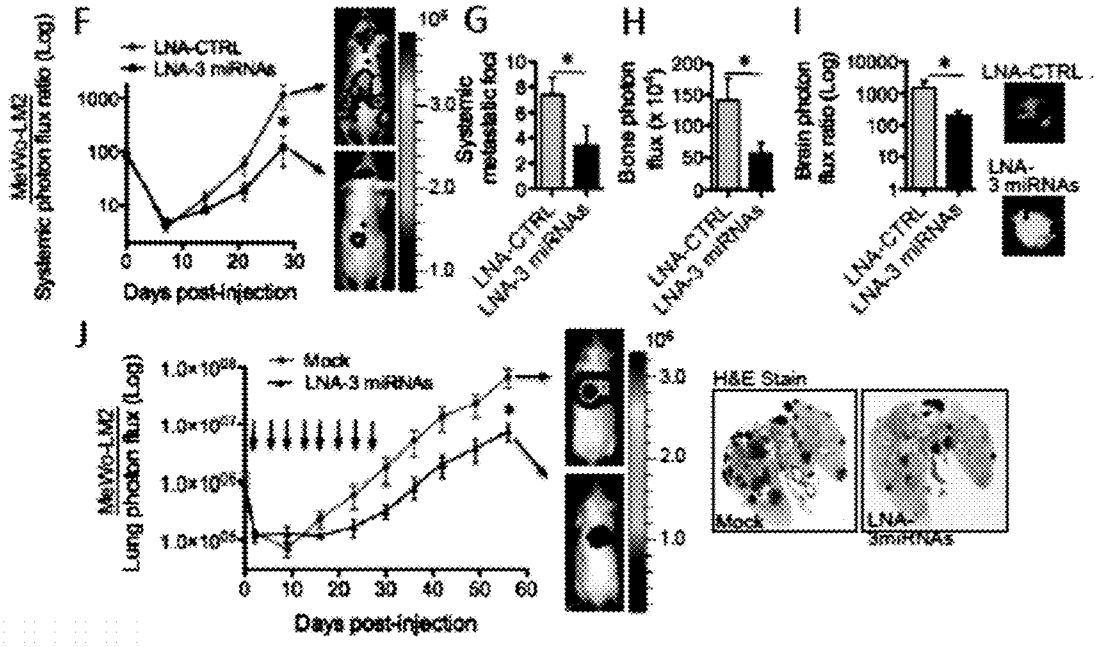

Next, it was examined whether combinatorial LNA-induced miRNA inhibition could suppress systemic melanoma metastasis to multiple distant organs. Indeed, intracardiac injection of highly metastatic melanoma cells pre-treated with a cocktail of LNAs targeting the three regulatory miRNAs revealed endogenous miR-199a-3p, miR-199a-5p, and miR-1908 to promote systemic melanoma metastasis (FIG. 7F). Combinatorial LNA-mediated inhibition of the three miRNAs lead to a reduction in the number of systemic metastatic foci (FIG. 7G) in distal sites such as the brain and bone (FIGS. 7H-I).

Figure 7K:
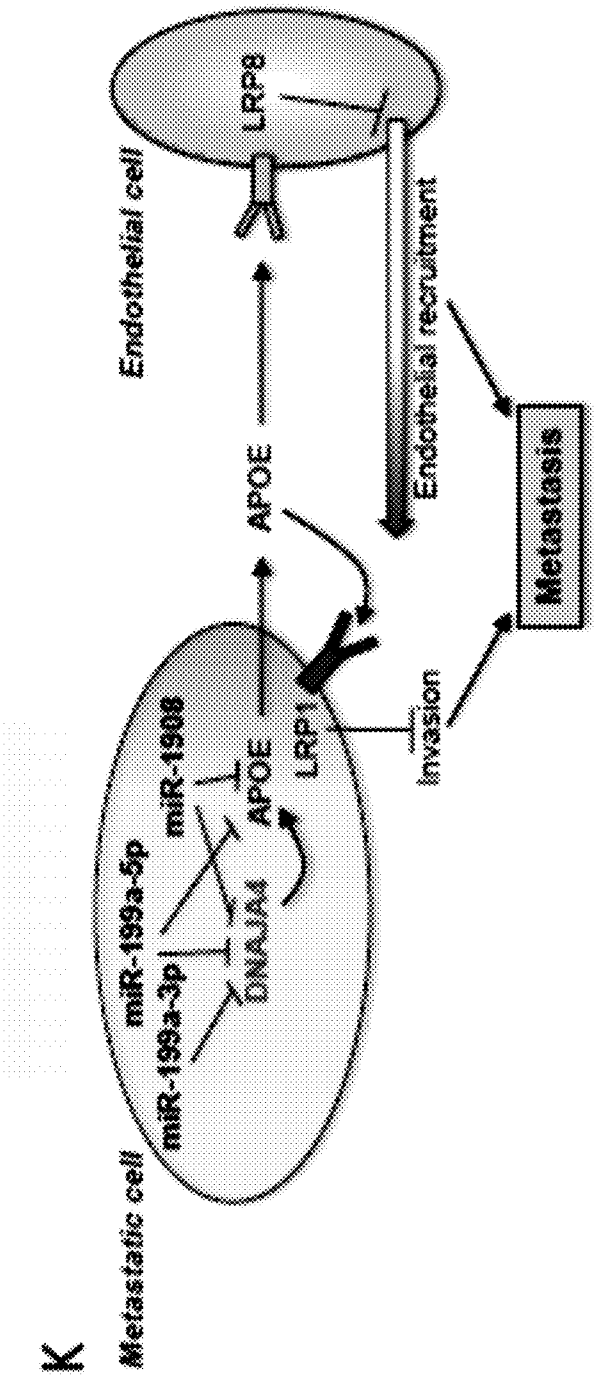

Further assays were carried out to examine the therapeutic efficacy of systemically administered in vivo-optimized LNAs in melanoma metastasis prevention. To this end, highly metastatic MeWo-LM2 cells were injected into mice. The following day, mice were intravenously treated with LNAs targeting miR-199a-3p, miR-199a-5p, and miR-1908 at a low total dose (12.5 mg/kg) on a bi-weekly basis for four weeks. Notably, combinatorial LNA treatment reduced lung colonization by 9-fold (FIG. 7J, P=0.031) without any apparent signs of toxicity (FIG. 18C). Taken together, the above findings reveal a novel miRNA-dependent regulatory network that converges on ApoE signaling to control cell-autonomous and non-cell-autonomous features of melanoma metastatic progression (FIG. 7K). The above basic studies have identified a set of miRNAs with powerful prognostic and therapeutic potential in the clinical management of melanoma.

Figures 8A, 8B, 8C, 8D, 8E:
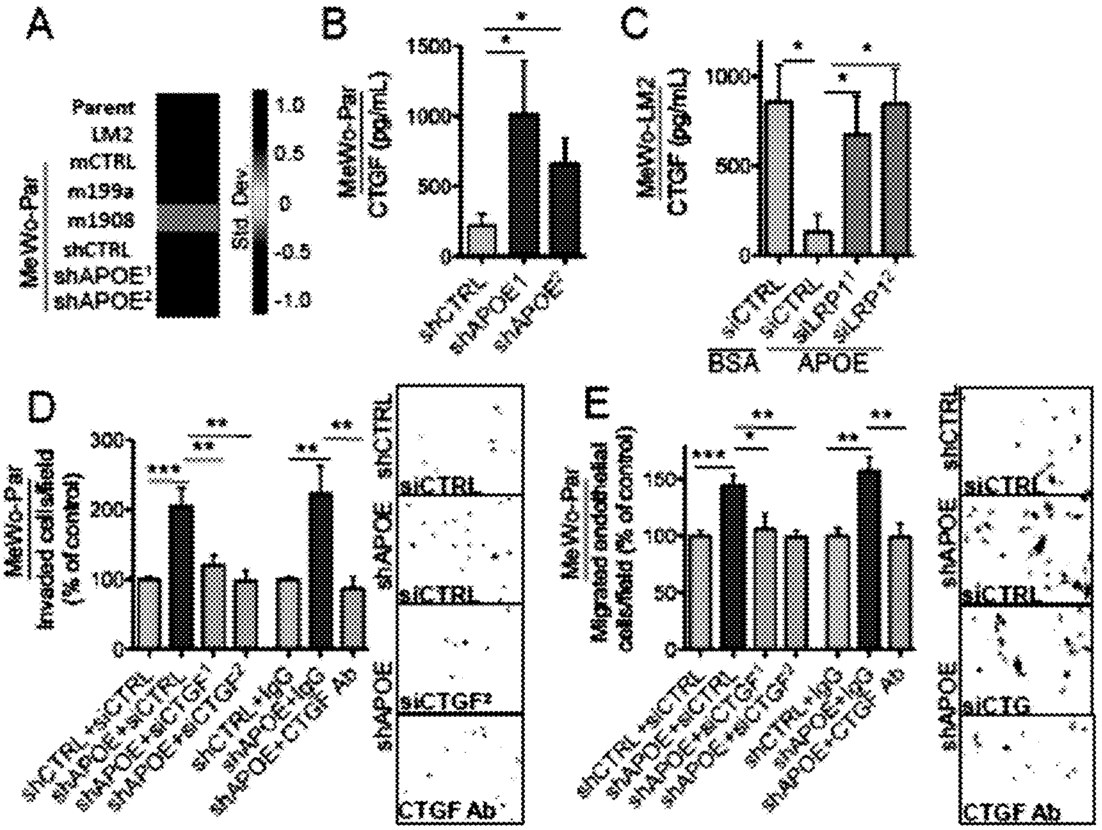

Example 9 miRNA-Dependent Targeting Of Apoe/LRP1 Signaling Promotes Cancer Cell Invasion and Endothelial Recruitment through CTGF Induction In this example, Connective Tissue Growth Factor (CTGF) was identified as a downstream mediator of ApoE/LRP1 signaling in cancer cell invasion and endothelial recruitment. CTGF expression level, as determined by qRT-PCR analysis and ELISA, is mediated by ApoE/LRP1 signaling (FIGS. 8A, 8B, and 8C). Additionally, ApoE/LRP1 regulated cancer cell invasion and endothelial recruitment are mediated by CTGF (FIG. 8D, 8E).

Example 10

CTGF Mediates miRNA-Dependent Metastatic Invasion, Endothelial Recruitment, and Colonization In this Examiner, assays were carried out to investigate whether CTGF mediates miRNA-dependent invasion and endothelial recruitment. Briefly, trans-well cell invasion and endothelial recruitment assays were performed on parental MeWo cells over-expressing miR-199a or miR-1908 in the presence of a blocking antibody targeting CTGF. Indeed, it was found that mir-199a and mir-1908 dependent metastatic invasion and endothelial recruitment are mediated by CTGF (FIGS. 9A and 9B). In order to investigate whether in vivo melanoma metastasis (metastatic colonization) is mediated by CTGF, bioluminescence imaging was performed on lung metastasis by 5×104 parental MeWo cells knocked down for CTGF in the setting of miR-199a or miR-1908 over-expression. Knock-down of CTGF in this setting resulted in significant reduction of in vivo melanoma metastasis (FIG. 9C).

Example 11

Figures 10A, 10B, 10C, 10D, 10E:
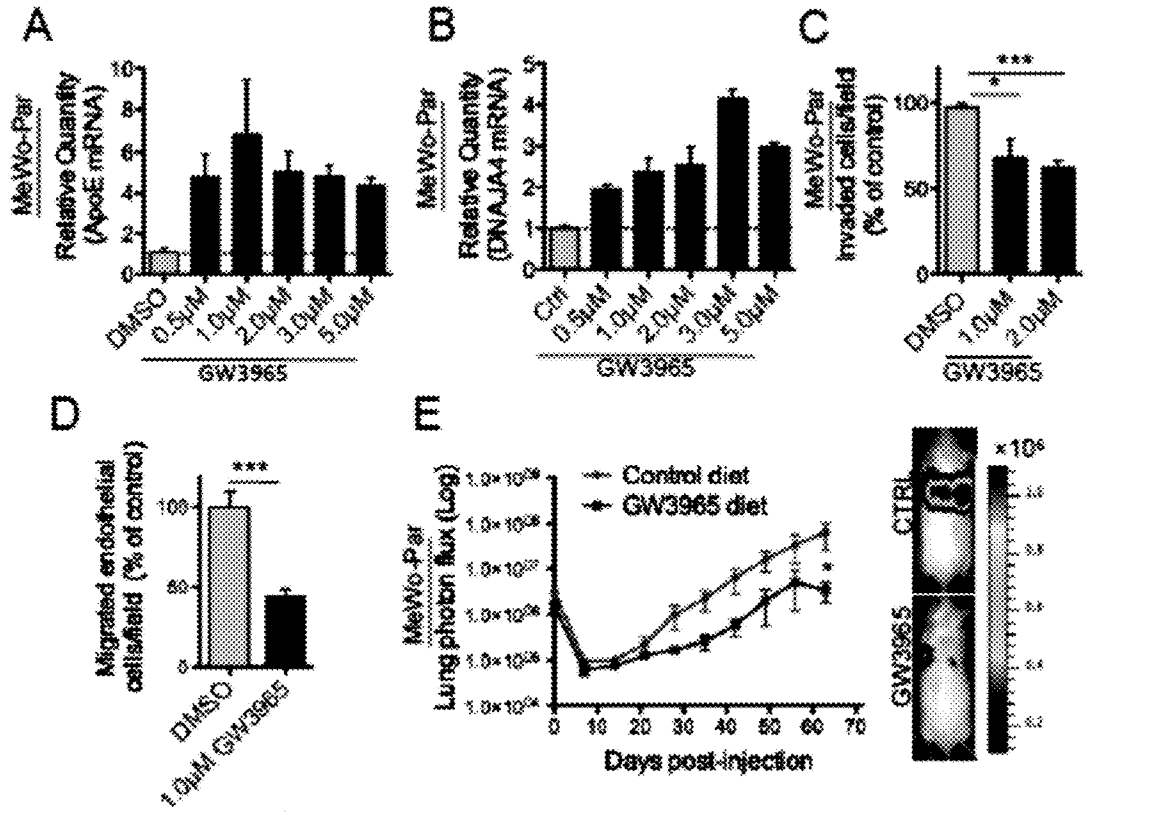

Treatment with LXR Agonist GW3965 Elevates Melanoma Cell ApoE and DNAJA4 Levels and Suppresses Cancer Cell Invasion, Endothelial Recruitment, and Metastatic Colonization Small molecule agonists of the Liver X Receptor (LXR) have previously been shown to increase Apo E levels. To investigate whether increasing Apo-E levels via LXR activation resulted in therapeutic benefit, assays were carried out to assess the effect of the LXR agonist GW3965 [chemical name: 3-[3-[N-(2-Chloro-3-trifluoromethylbenzyl)-(2,2-diphenylethyl)amino]propyloxy] phenylacetic acid hydrochloride) on Apo-E levels, tumor cell invasion, endothelial recruitment, and in vivo melanoma metastasis (FIG. 10). Incubation of parental MeWo cells in the presence of therapeutic concentrations of GW3965 increased expression of ApoE and DNAJA4 (FIGS. 10A and 10B). Pre-treatment of MeWO cells with GW3965 decreased tumor cell invasion (FIG. 10C) and endothelial recruitment (FIG. 10D). To test whether GW3965 could inhibit metastasis in vivo, mice were administered a grain-based chow diet containing GW3965 (20 mg/kg) or a control diet, and lung metastasis was assayed using bioluminescence after tail-vein injection of $4\times10^4$ parental MeWo cells into the mice (FIG. 10E). Oral administration of GW3965 to the mice in this fashion resulted in a significant reduction in in vivo melanoma metastasis (FIG. 10E).

Example 12

Identification of Mir-7 as an Endogenous Suppressor of Melanoma Metastasis

In this example, miR-7 was identified as an endogenous suppressor of melanoma metastasis (FIG. 11). To test whether miR-7 suppresses melanoma metastasis in vivo, its expression was knocked down in parental MeWo cells using miR-Zip technology (FIG. 11A). Bioluminescence imaging plot of lung metastatic colonization following intravenous injection of 4×104 parental MeWo cells expressing a short hairpin (miR-Zip) inhibitor of miR-7 (miR-7 KD) significantly increased lung metastasis in vivo (FIG. 11A). Conversely, overexpression of miR-7 in LM2 cells significantly reduced lung metastasis in vivo (FIG. 11B).

The complexity of cancer requires the application of systematic analyses (Pe'er and Hacohen, 2011). Via a systematic global approach, a cooperative network of miRNAs was uncovered. The miRNAs are i) upregulated in highly metastatic human melanoma cells, ii) required and sufficient for metastatic colonization and angiogenesis in melanoma, and iii) robust pathologic predictors of human melanoma metastatic relapse. Through a transcriptomic-based and biologically guided target identification approach, miR-1908, miR-199a-3p, and miR-199a-5p were found to convergently target the heat shock factor DNAJA4 and the metabolic gene ApoE. The requirement of each individual miRNA for metastasis indicates that these three convergent miRNAs are non-redundant in promoting melanoma metastasis, while the robust synergistic metastasis suppression achieved by combinatorial miRNA inhibition reveals functional cooperativity between these miRNAs, presumably achieved through maximal silencing of ApoE and DNAJA4. The identification of ApoE as a gene negatively regulated by three metastasis promoter miRNAs, positively regulated by a metastasis suppressor gene (DNAJA4), and silenced in clinical metastasis samples highlights the significance of this gene as a suppressor of melanoma progression.

Example 13

Identification of LXRβ Signaling as a Novel Therapeutic Target in Melanoma

Figures 19A, 19B, 19C:
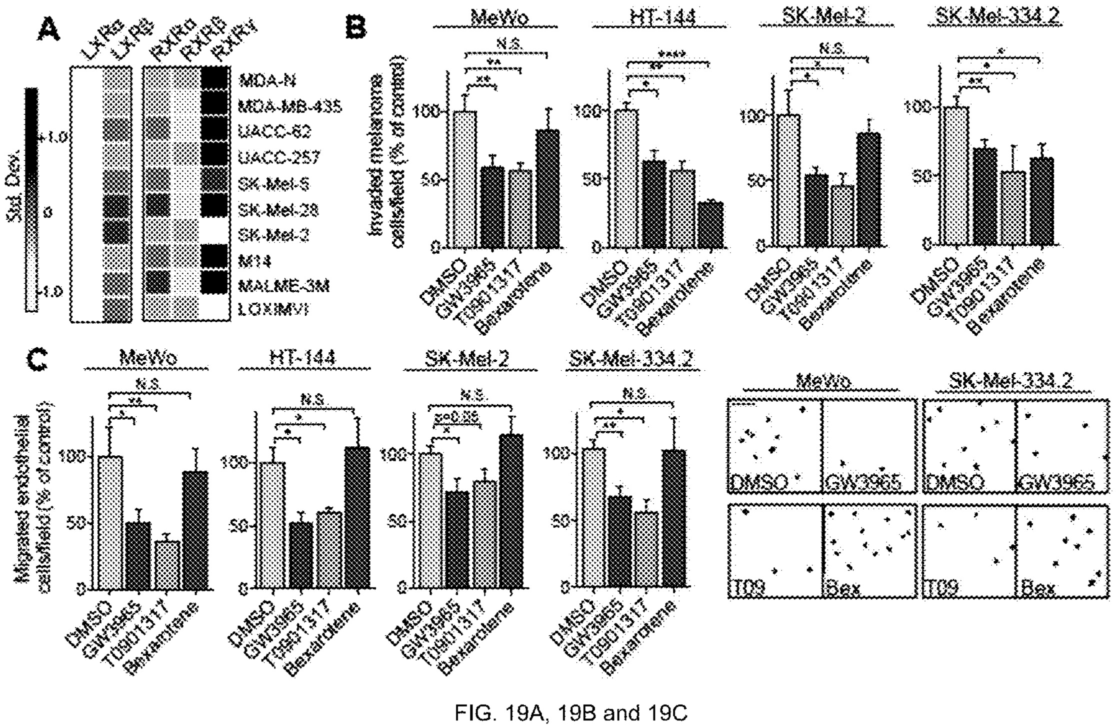
Figures 19D, 19E, 19F, 19G:
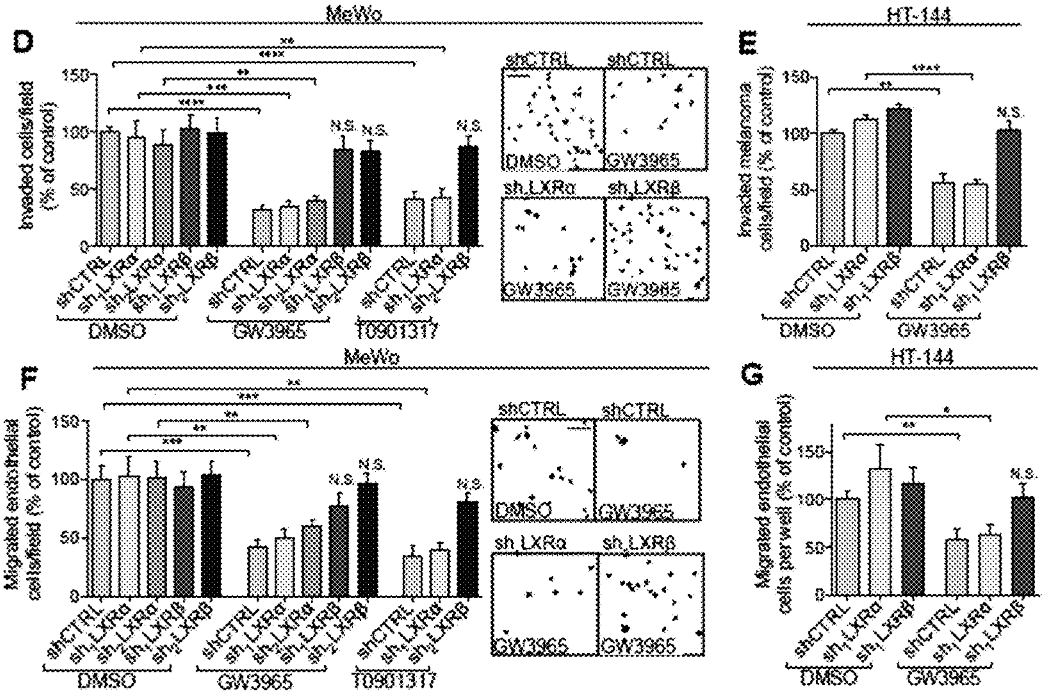
Figure 20A:
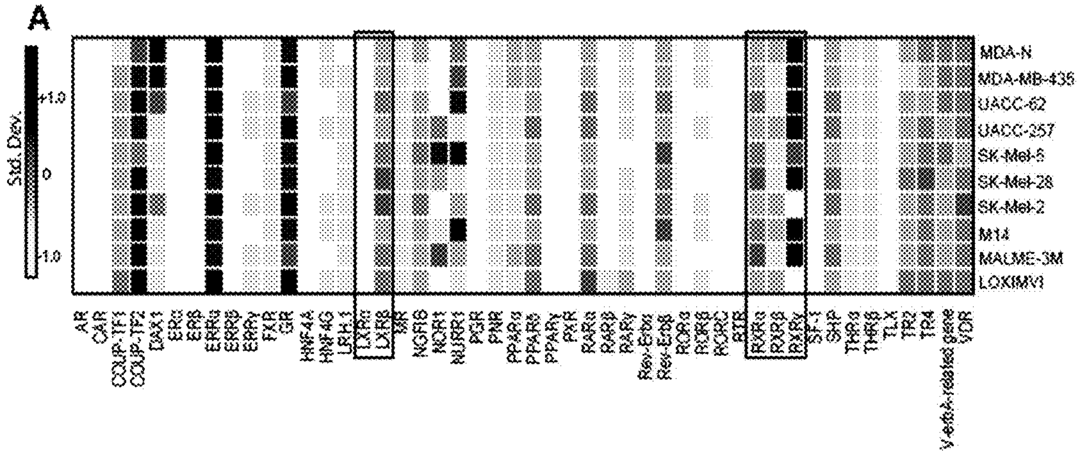
Figures 20B, 20C, 20D, 20E, 20F, 20G:
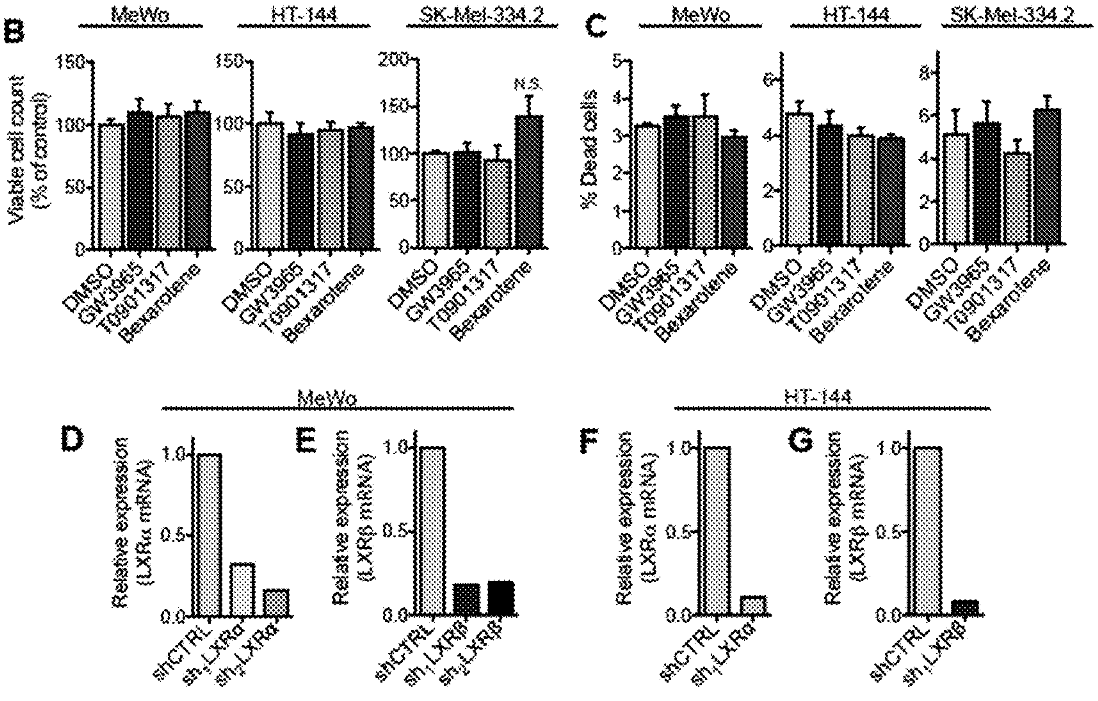

To identify nuclear hormone receptors that show broad expression in melanoma, we examined the expression levels of all nuclear hormone receptor family members across the NCI-60 collection of human melanoma cell lines. Several receptors exhibited stable expression across multiple melanoma lines, suggesting that they could represent novel potential targets in melanoma (FIGS. 19A and 20A). Notably, out of these, liver-X receptors (LXRs) were previously shown to enhance ApoE transcription in adipocytes and macrophages (Laffitte et al., 2001), while pharmacologic activation of RXRs was found to drive ApoE expression in pre-clinical Alzheimer's models (Cramer et al., 2012).

Given the recently uncovered metastasis-suppressive role of ApoE in melanoma (Pencheva et al., 2012), the ubiquitous basal expression of LXRβ and RXRα in melanoma, and the availability of pharmacologic agents to therapeutically activate LXRs and RXRs, we investigated whether activation of LXRs or RXRs in melanoma cells might inhibit melanoma progression phenotypes. In light of the established roles of nuclear hormone receptors such as ER and AR in regulating breast and prostate cancer cell proliferation, we first examined whether pharmacologic agonism of LXRs or RXRs in melanoma cells affects in vitro cell growth.

Treatment of melanoma cells with two structurally-distinct LXR agonists, GW3965 2 or T0901317 1, or the RXR agonist bexarotene did not affect cell proliferation or cell viability rates (FIG. 20 B-C). We next assessed the effects of LXR or RXR activation on cell invasion and endothelial recruitment—phenotypes displayed by metastatic melanoma and metastatic breast cancer populations (Pencheva et al., 2012; Png et al., 2012). Treatment of the mutationally diverse MeWo (B-Raf/N-Ras wild-type), HT-144 (B-Raf mutant), and SK-Mel-2 (N-Ras mutant) human melanoma lines as well as the SK-Mel-334.2 (B-Raf mutant) primary human melanoma line with GW3965 2 or T0901317 1 consistently suppressed the ability of melanoma cells to invade through matrigel and to recruit endothelial cells in trans-well assays (FIG. 19B-C). In comparison, treatment with bexarotene suppressed invasion only in half of the melanoma lines tested and it did not significantly affect the endothelial recruitment phenotype (FIGS. 19B-C).

Given the superiority of LXR over RXR agonism in broadly inhibiting both cell invasion and endothelial recruitment across multiple melanoma lines, we investigated the requirement for LXR signaling in mediating the suppressive effects of LXR agonists. Knockdown of melanoma LXRβ, but not LXRα, abrogated the ability of GW3965 2 and T0901317 1 to suppress invasion and endothelial recruitment (FIGS. 19D-G and FIGS. 20D-G), revealing melanoma-cell LXRβ to be the functional target of LXR agonists in eliciting the suppression of these in vitro phenotypes. Our molecular findings are consistent with LXRβ being the predominant LXR isoform expressed by melanoma cells (FIG. 19A, $P<0.0001$).

The ubiquitous basal expression of LXRβ in melanoma is likely reflective of the general role that LXRs play in controlling lipid transport, synthesis, and catabolism (Calkin and Tontonoz, 2013). While such stable LXRβ expression would be key to maintaining melanoma cell metabolism and growth, it also makes LXR signaling an attractive candidate for broad-spectrum therapeutic targeting in melanoma.

Example 14

Therapeutic Delivery of LXR Agonists Suppresses Melanoma Tumor Growth

LXR agonists were originally developed as oral drug candidates for the purpose of cholesterol lowering in patients with dyslipidemia and atherosclerosis (Collins et al., 2002; Joseph and Tontonoz, 2003). These compounds were abandoned clinically secondary to their inability to reduce lipid levels in large-animal pre-clinical models (Groot et al., 2005).

Given the robust ability of GW3965 2 and T0901317 1 to suppress in vitro melanoma progression phenotypes (FIG. 19B-C), we investigated whether therapeutic LXR activation could be utilized for the treatment of melanoma. Indeed, oral administration of GW3965 2 or T0901317 1 at low doses (20 mg/kg), subsequent to formation of subcutaneous tumors measuring 5-10 mm3 in volume, suppressed tumor growth by the aggressive B16F10 mouse melanoma cells in an immunocompetent model by 67% and 61%, respectively (FIG. 21A-B). Administration of a higher LXR agonist dose (100 mg/kg) led to an 80% reduction in tumor growth (FIG. 21A), consistent with dose-dependent suppressive effects.

Oral administration of GW3965 2 also robustly suppressed tumor growth by the MeWo (70% inhibition) and SK-Mel-2 (49% inhibition) human melanoma cell lines, as well as the SK-Mel-334.2 primary human melanoma line (73% inhibition) (FIGS. 21C-E and FIG. 22A).

Encouraged by the robust tumor-suppressive impact of LXR agonists on small tumors (5-10 mm3) (FIG. 21A-E), we next investigated whether LXR activation therapy could inhibit the growth of large (~150 mm3) tumors.

We found that treatment with GW3965 2 led to a roughly 50% reduction in the growth of established large B16F10 tumors (FIG. 21F). Importantly, therapeutic delivery of GW3965 2 subsequent to tumor establishment substantially prolonged the overall survival time of immunocompetent mice injected with mouse B16F10 cells, immunocompromised mice bearing tumor xeongrafts derived from the human MeWo established melanoma line, as well as the SK-Mel.334-2 primary human melanoma line (FIG. 21G-I). These findings are consistent with broad-spectrum responsiveness to LXR activation therapy across melanotic and amelanotic established melanoma tumors of diverse mutational subtypes: B-Raf and N-Ras wild-type (B16F10 and MeWo; FIG. 21A-C), B-Raf mutant (SK-Mel-334.2; FIG. 21D), and N-Ras mutant (SK-Mel-2; FIG. 21E).

We next sought to determine the cell biological phenotypes regulated by LXR agonists in suppressing tumor growth. Consistent with the inhibitory effects of GW3965 2 on endothelial recruitment by melanoma cells in vitro, GW3965 2 administration led to a roughly 2-fold reduction in the endothelial cell content of tumors (FIG. 21J). This effect was accompanied by a modest decrease (23%) in the number of actively proliferating tumor cells in vivo (FIG. 21K) without a change in the number of apoptotic cells (FIG. 21L). These results suggest that, in addition to reducing local tumor invasion, LXR activation suppresses melanoma tumor growth primarily through inhibition of tumor angiogenesis with a resulting reduction in in vivo proliferation.

Example 15

Figures 23A, 23B, 23C, 23D, 23E, 23F:
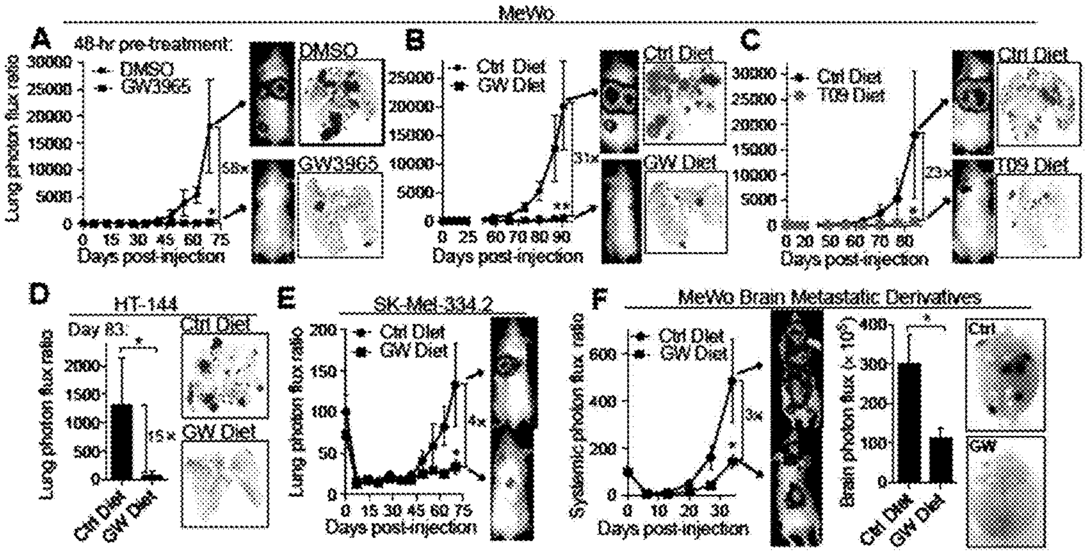

LXR Agonism Suppresses Melanoma Metastasis to the Lung and Brain and Inhibits the Progression of Incipient Metastases The strong suppressive effects of LXR agonists on melanoma tumor growth motivated us to examine whether LXR activation could also suppress metastatic colonization by melanoma cells. To this end, pre-treatment of human MeWo melanoma cells with GW3965 2 led to a more than 50-fold reduction in their metastatic colonization capacity (FIG. 23A). In light of this dramatic inhibitory effect, we next assessed the ability of orally administered LXR agonists to suppress metastasis. Immunocompromised mice that were orally administered GW3965 2 or T0901317 1 experienced 31-fold and 23-fold respective reductions in lung metastatic colonization by human MeWo cells (FIG. 23B-C). Treatment with GW3965 2 also suppressed metastatic colonization by the HT-144 melanoma line (FIG. 23D) as well as the SK-Mel-334.2 primary melanoma line (FIG. 23E).

GW3965 2 is a lipophilic molecule that can efficiently cross the blood brain barrier and potently activate LXR signaling in the brain. Consistent with this, oral delivery of GW3965 2 was previously shown to improve amyloid plaque pathology and memory deficits in pre-clinical models of Alzheimer's disease (Jiang et al., 2008). We thus wondered whether LXR agonism could exhibit therapeutic activity in the suppression of melanoma brain metastasis—a dreaded melanoma outcome in dire need of effective therapies (Fonkem et al., 2012). Notably, oral administration of GW3965 2 inhibited both systemic dissemination and brain colonization following intracardiac injection of brain-metastatic melanoma cells derived from the MeWo parental line (FIG. 23F). These results reveal robust metastasis suppression by LXR activation therapy across multiple melanoma lines and in multiple distal organ metastatic sites.

Figures 23G, 23H, 23I, 23J, 23K:
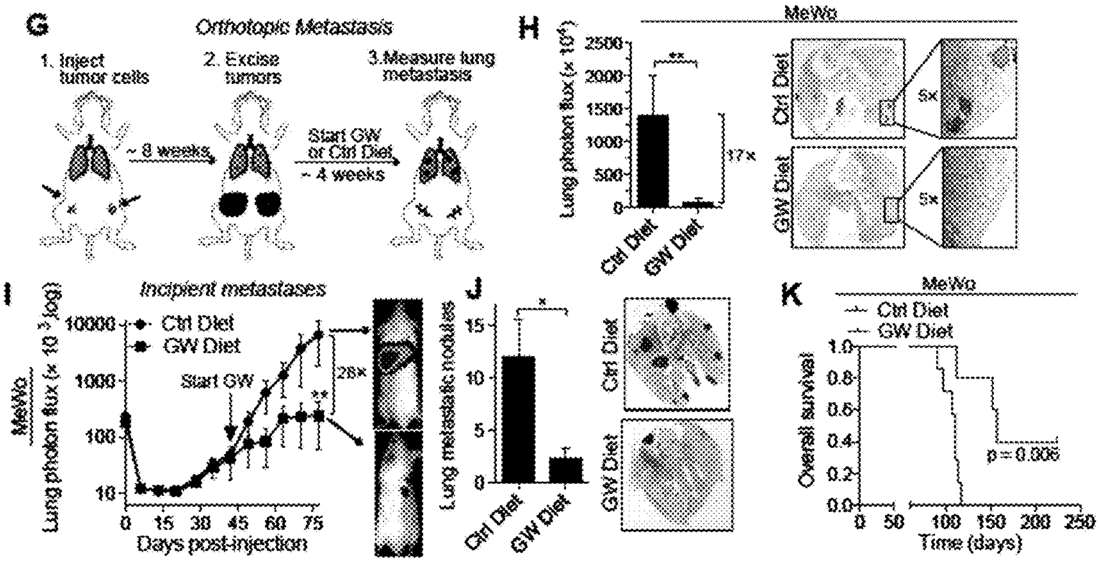

Encouraged by the robust effects observed in suppressing metastasis formation (FIG. 23A-F), we next sought to determine whether LXR activation therapy could halt the progression of melanoma cells that had already metastatically disseminated. We first tested the ability of GW3965 2 to reduce lung colonization by melanoma cells disseminating from an orthotopic site following removal of the primary tumor (FIG. 23G). Importantly, oral administration of GW3965 2 post-tumor excision inhibited lung colonization by disseminated melanoma cells by 17-fold (FIG. 23H). Remarkably, treatment of mice with GW3965 2 also dramatically suppressed (28-fold) colonization by incipient lung metastases that had progressed 8-fold from the baseline at seeding (FIG. 23I). Consistent with LXR activation inhibiting metastatic initiation, GW3965 2 treatment decreased the number of macroscopic metastatic nodules formed (FIG. 23J). Finally, treatment of mice with GW3965 2 in this 'adjuvant' pre-clinical context significantly prolonged their survival times following metastatic colonization (FIG. 23K).

Example 16

LXR Activation Reduces Melanoma Progression and Metastasis in a Genetically-Driven Mouse Model of Melanoma Roughly 60% of human melanoma tumors are marked by activating mutations in the Braf oncogene, with one single amino acid variant, B-RafV600E, being the predominant mutation found (Davies et al., 2002). Nearly 20% of melanomas exhibit activating mutations in B-Raf with concurrent silencing of the Pten tumor-suppressor, which drives progression to a malignant melanoma state (Tsao et al., 2004; Chin et al., 2006). Recently, Tyrosinase (Tyr)-driven conditional B-Raf activation and Pten loss were shown to genetically cooperate in driving mouse melanoma progression (Dankort et al., 2009).

To determine whether LXR activation could suppress melanoma progression in this genetically-initiated model, we induced melanomas in Tyr::CreER; B-RafV600E/+; Ptenlox/+ and Tyr: :CreER; B-RafV600E/+; Ptenlox/lox mice by intraperitoneal administration of 4-hydroxytamoxifen (4-HT). Notably, oral administration of GW3965 2 following melanoma initiation attenuated tumor progression and significantly extended the overall survival times of both PTEN heterozygous Tyr::CreER; B-RafV600E/+; Ptenlox/+ and PTEN homozygous Tyr::CreER; B-RafV600E/+; Ptenlox/lox mice (FIGS. 24A-B and FIGS. 25A-B). Next, we examined the ability of GW3965 2 to suppress melanoma metastasis in this genetic context. While we did not detect macroscopic metastases in the lungs or brains of 4-HT-treated Tyr::CreER; B-Raf$^{V600E/+}$; Pten$^{lox/lox}$ control mice, we consistently observed melanoma metastases to the salivary gland lymph nodes. Importantly, Tyr::CreER; B-Raf$^{V600E/+}$; Pten$^{lox/lox}$ mice treated with GW3965 2 exhibited a decrease in the number of lymphatic metastases detected post-mortem (FIG. 24C). These findings indicate that LXR activation inhibits orthotopic metastasis in a genetically-driven melanoma model, in addition to its suppressive effects on primary melanoma tumor progression.

The cooperativity between B-Raf activation and Pten loss in driving melanoma progression can be further enhanced by inactivation of CDKN2A, a cell cycle regulator frequently mutated in familial melanomas (Hussussian et al., 1994; Kamb et al., 1994). We thus examined the effect of LXR activation on B-Raf$^{V600E/+}$; Pten$^{-/-}$; CDKN2A$^{-/-}$ melanomas, allowing us to test the therapeutic efficacy of LXR agonism in a more aggressive genetically-driven melanoma progression model. Importantly, therapeutic delivery of GW3965 2 robustly inhibited tumor growth and lung metastasis by B-Raf$^{V600E/+}$; Pten$^{-/-}$; CDKN2A$^{-/-}$ primary mouse melanoma cells injected into syngeneic immunocompetent mice and extended the overall survival of mice bearing B-Raf$^{V600E/+}$; Pten$^{-/-}$; CDKN2A$^{-/-}$ melanoma burden (FIG. 24D-F). Taken together, the robust suppression of melanoma progression across independent xenograft and genetically-induced immunocompetent melanoma mouse models that exhibit the diverse mutational profiles of human melanomas motivates the clinical testing of LXR activation therapy.

Example 17

Pharmacologic Activation of LXRβ Suppresses Melanoma Phenotypes by Transcriptionally Inducing Melanoma-Cell ApoE Expression We next sought to determine the downstream molecular target of LXRβ that mediates suppression of melanoma progression. To this end, we transcriptomically profiled human MeWo melanoma cells treated with the LXR agonist GW3965 2.

Figures 27A, 27B, 27C, 27D, 27E, 27F:
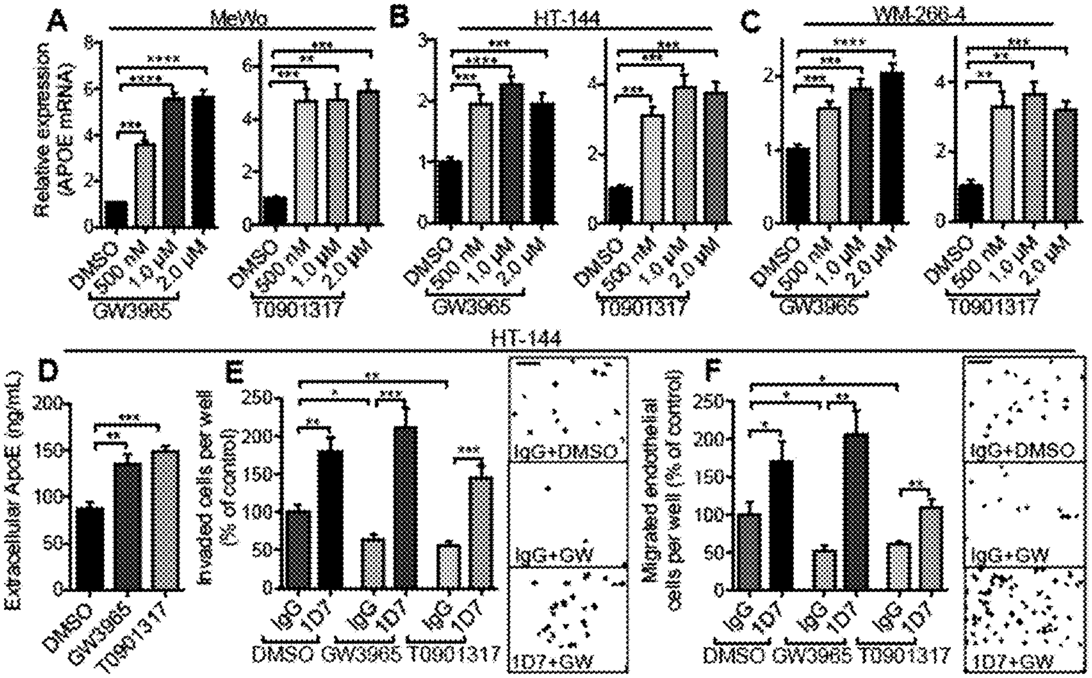

Out of the 365 genes that were significantly induced in response to LXR activation, we identified ApoE, a previously validated transcriptional target of LXRs in macrophages and adipocytes (Laffitte et al., 2001), as the top upregulated secreted factor in melanoma cells (FIG. 26). Quantitative real-time PCR (qRT-PCR) validation revealed robust upregulation of ApoE transcript expression following treatment with independent LXR agonists across multiple human melanoma lines (FIG. 27A-C).

Figures 28A, 28B, 28C, 28D, 28E, 28F, 28G:
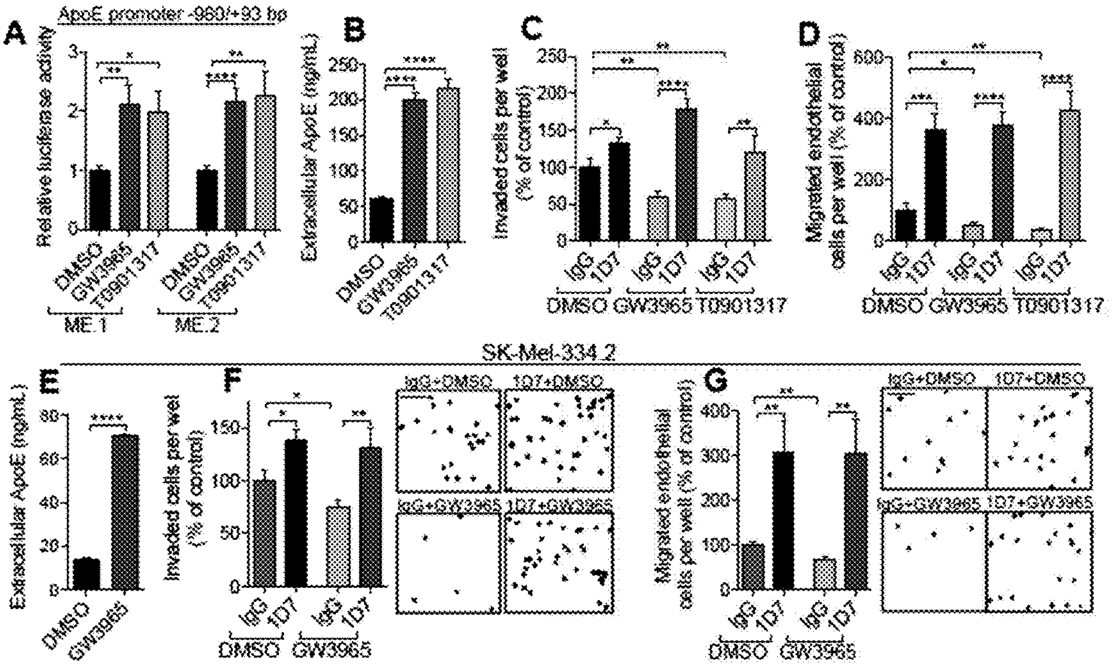
Figures 28H, 28I:
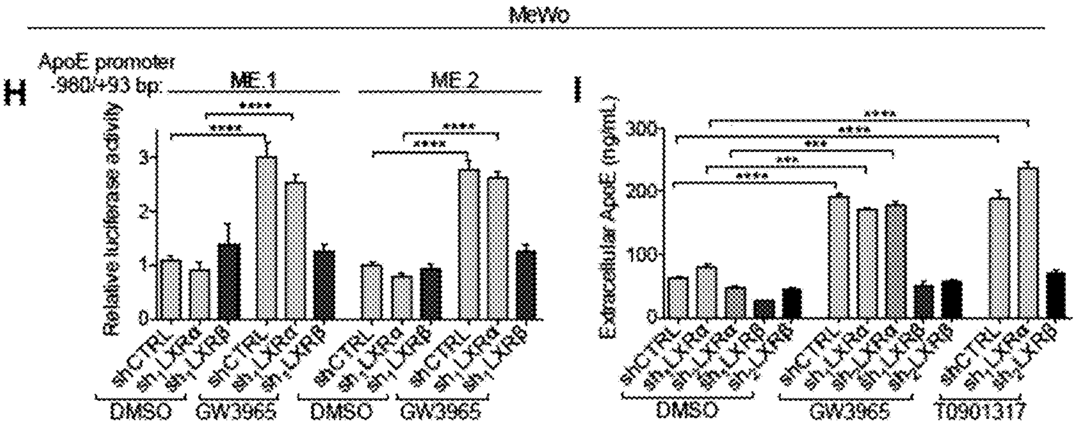

In light of the previously reported metastasis-suppressive function of ApoE in melanoma (Pencheva et al., 2012), we investigated whether LXRβ activation suppresses melanoma progression through transcriptional induction of ApoE. Indeed, GW3965 2 and T0901317 1 were found to enhance the melanoma cell-driven activity of a luciferase reporter construct containing the ApoE promoter fused to either of two previously characterized LXR-binding multi-enhancer elements (ME.1 or ME.2) (Laffitte et al., 2001) (FIG. 28A). Importantly, this transcriptional induction resulted in elevated levels of secreted ApoE protein (FIG. 28B). Consistent with direct LXRβ targeting of ApoE in melanoma cells, neutralization of extracellular ApoE with an antibody fully blocked the LXRβ-mediated suppression of cell invasion and endothelial recruitment and further enhanced these phenotypes relative to the control IgG treatment (FIGS. 28C-G and FIGS. 27D-F), revealing the effects of LXR agonism to be modulated by extracellular ApoE.

Figures 27G, 27H, 27I, 27J, 27K:
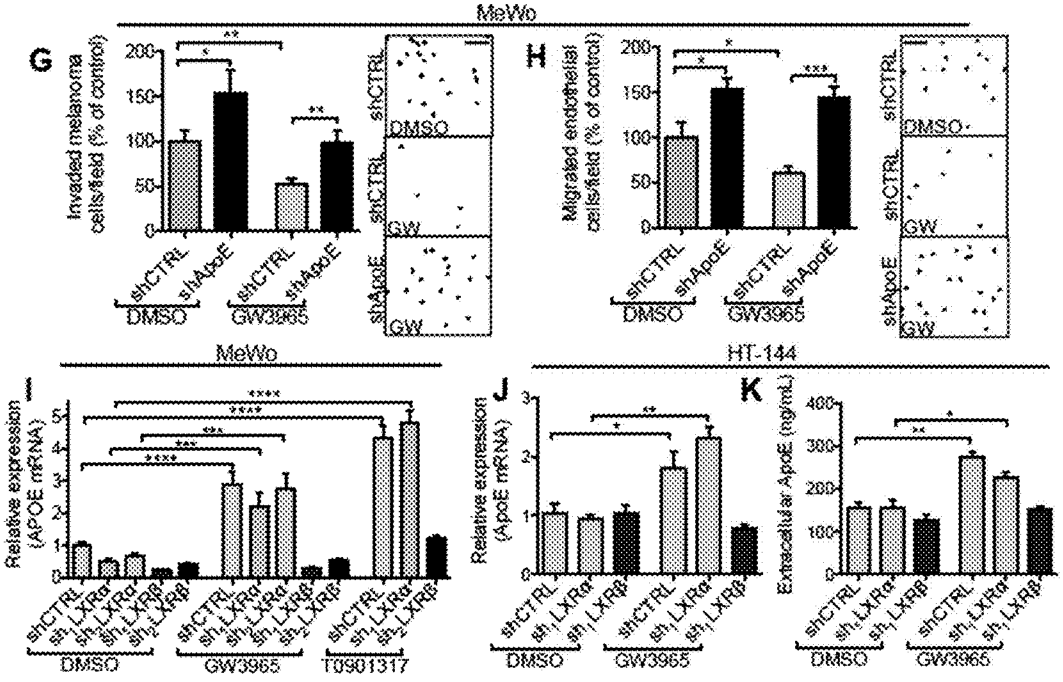

Additionally, molecular knockdown of ApoE in melanoma cells also blocked the GW3965 2-mediated suppression of cell invasion and endothelial recruitment phenotypes (FIG. 27G-H). In agreement with this, melanoma cell depletion of LXRβ, but not LXRα, abrogated the ability of GW3965 2 and T0901317 1 to upregulate ApoE transcription and ultimately protein expression (FIGS. 28H-I and FIGS. 27I-K). Collectively, these findings indicate that pharmacologic activation of LXRβ, the predominant LXR isoform expressed by melanoma cells, suppresses cell-intrinsic invasion and endothelial recruitment by melanoma cells through transcriptionally activating ApoE expression in melanoma cells.

Example 18

Engagement of Melanoma-Derived and Systemic ApoE by LXRβ Activation Therapy

The LXRβ-induced suppression of key melanoma phenotypes by extracellular ApoE in vitro suggested that the suppressive effects of LXR agonists in vivo might be further augmented by the activation of LXRs in peripheral tissues, which could serve as robust sources of extracellular ApoE.

Importantly, such non-transformed tissues would be less vulnerable to developing resistance to LXR activation therapy, allowing for chronic ApoE induction in patients. We thus investigated whether therapeutic LXR agonism suppresses melanoma progression by inducing ApoE derived from melanoma cells or systemic tissues. Consistent with LXRβ agonism increasing ApoE expression in melanoma cells in vivo, ApoE transcript levels were upregulated in melanoma primary tumors as well as in melanoma lung and brain metastases dissociated from mice that were fed an LXR agonist-supplemented diet (FIG. 29A-E). Importantly, treatment of mice with either GW3965 2 or T0901317 1 significantly elevated ApoE protein expression in systemic adipose, lung, and brain tissues of mice (FIGS. 30A-B) and also upregulated ApoE transcript levels in circulating white blood cells (FIG. 30C). These results indicate that LXR activation therapy induces both melanoma-cell and systemic tissue ApoE expression in vivo.

To determine the in vivo requirement of melanoma-derived and systemic LXR activation for the tumor-suppressive effects of orally administered LXR agonists, we first tested the ability of GW3965 2 to suppress tumor growth by B16F10 mouse melanoma cells depleted of LXRβ.

Figures 29A, 29B, 29C, 29D, 29E, 29F, 29G, 29H:
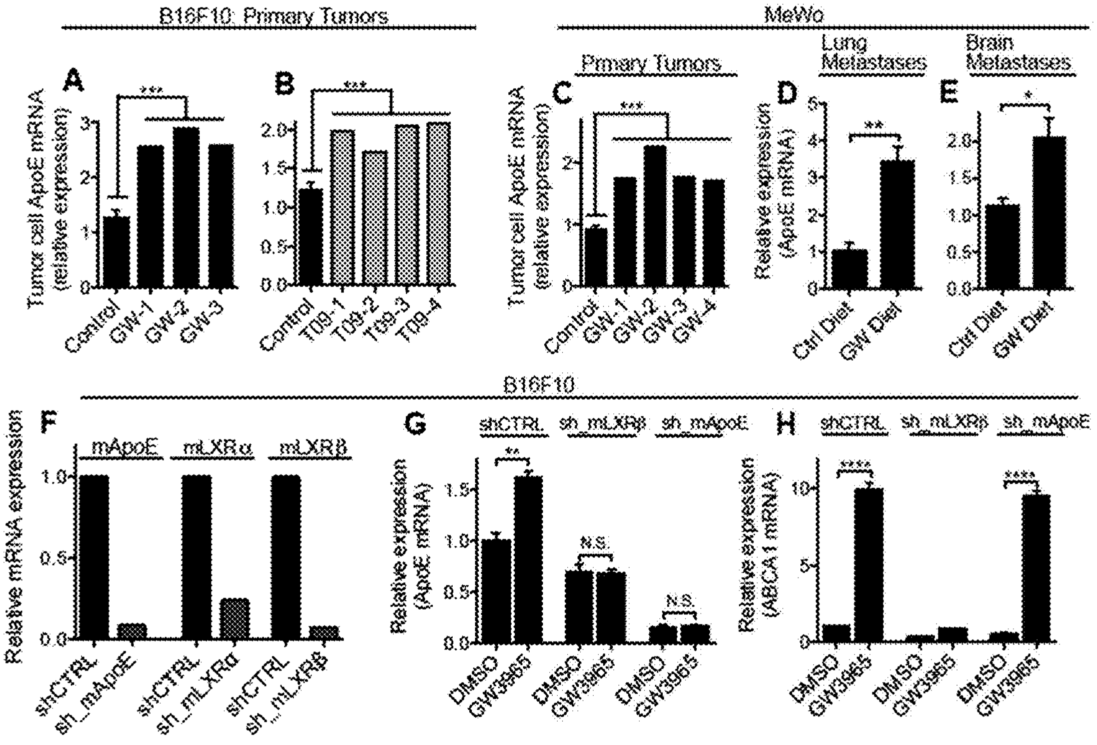
Figures 29I, 29J, 29K:
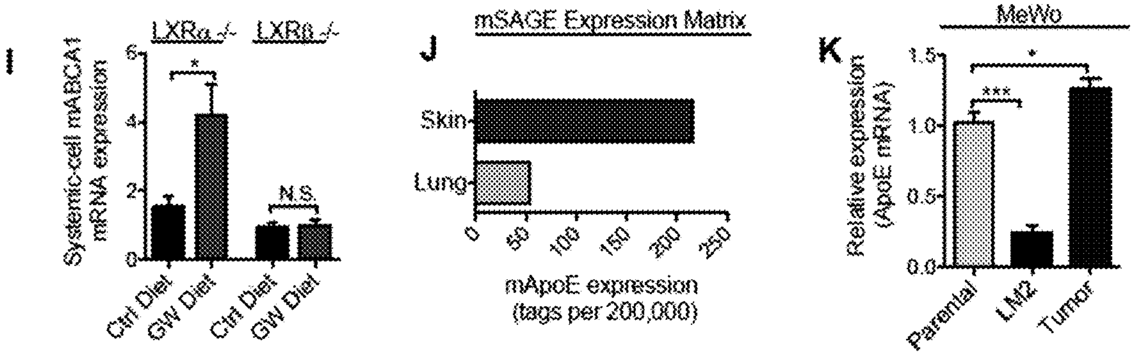
Figures 30A, 30B, 30C, 30D, 30E, 30F:
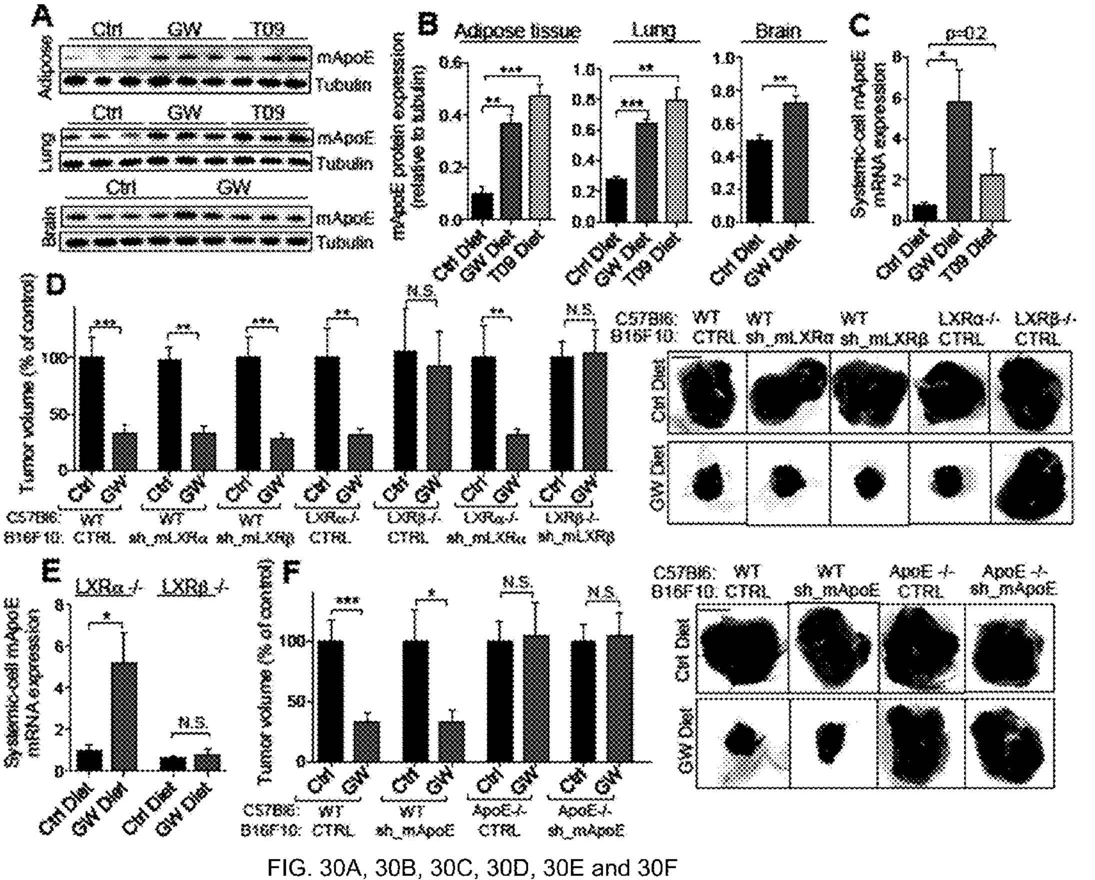

Consistent with our findings in human melanoma cells, knockdown of mouse melanoma-cell LXRβ abrogated the GW3965-mediated induction of ApoE expression (FIG. 29F-H). Despite this, melanoma-cell LXRβ knockdown was unable to prevent the suppression of tumor growth by GW3965 2 (FIG. 29D), implicating a role for systemic LXR activation in tumor growth inhibition by GW3965 2. To identify the LXR isoform that mediates this non-tumor autonomous suppression of melanoma growth by LXR agonists, we examined the effects of GW3965 2 on tumors implanted onto LXRα or LXRβ genetically null mice. Interestingly, genetic ablation of systemic LXRβ blocked the ability of GW3965 to suppress melanoma tumor growth, while LXRα inactivation had no effect on tumor growth inhibition by GW3965 (FIG. 6D). Importantly, the upregulation of systemic ApoE expression by GW3965 2, an agonist with 6-fold greater activity towards LXRβ than LXRα, was abrogated in LXRβ −/−, but not in LXRα −/− mice (FIG. 30E and FIG. 29I). These results indicate that ApoE induction by GW3965 2 in peripheral tissues is predominantly driven by systemic LXRβ activation. In agreement with this, we find systemic LXRβ to be the primary molecular target and effector of GW3965 2 in mediating melanoma tumor growth suppression.

We next examined whether ApoE is required for the in vivo melanoma-suppressive effects of LXR agonists. Consistent with the lack of an impact for melanoma-cell LXRβ knockdown on the tumor-suppressive activity of GW3965 2, depletion of melanoma-cell ApoE did not prevent tumor growth inhibition by GW3965 2 neither (FIGS. 29F-H and FIG. 30F). These findings suggest that the tumor suppressive effects of GW3965 2 might be primarily mediated through ApoE induction in systemic tissues.

Figures 30G, 30H, 30I:
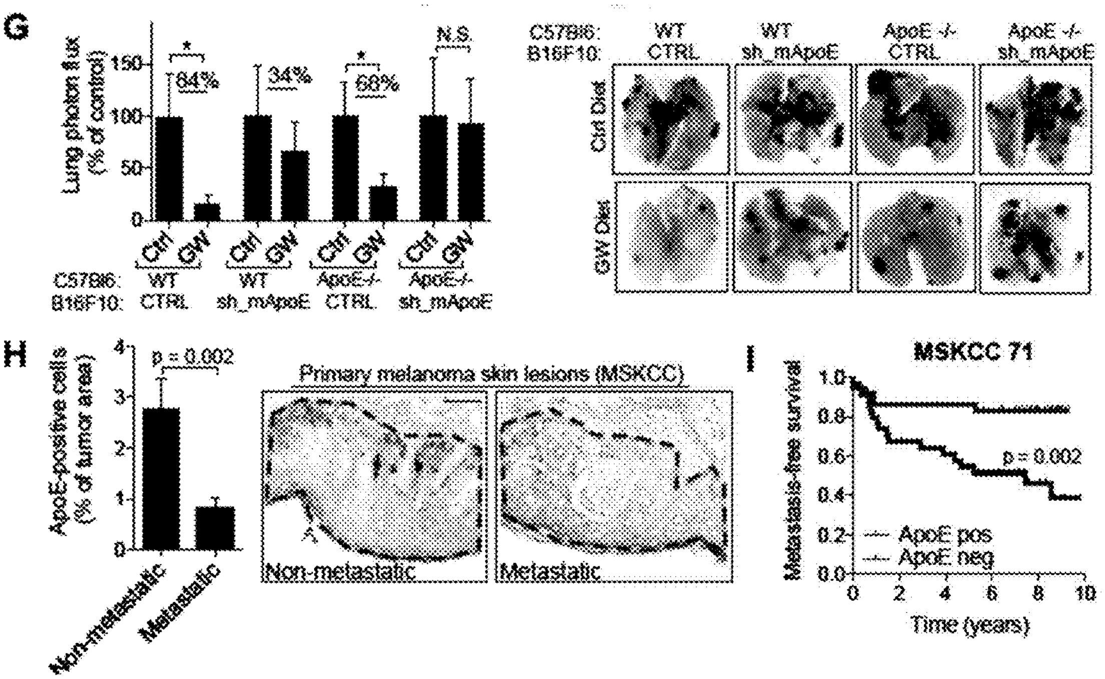

Indeed, GW3965 2 was completely ineffective in suppressing tumor growth in mice genetically inactivated for ApoE (FIG. 30F), revealing systemic ApoE as the downstream effector of systemic LXRβ in driving melanoma tumor growth suppression. Interestingly, in contrast to primary tumor growth regulation, knockdown of melanoma-cell ApoE partially prevented the metastasis-suppressive effect of GW3965 2 (FIG. 30G). Similarly, genetic inactivation of ApoE only partially prevented the metastasis suppression elicited by GW3965 2 as well (FIG. 30G). The GW3965-driven inhibition of metastasis was completely blocked only in the context of both melanoma-cell ApoE knockdown and genetic inactivation of systemic ApoE (FIG. 30G), indicative of a requirement for both melanoma-derived and systemic ApoE engagement by LXRβ in suppressing metastasis. We thus conclude that the effects of LXRβ activation on primary tumor growth are elicited primarily through systemic ApoE induction, while the effects of LXRβ agonism on metastasis are mediated through ApoE transcriptional induction in both melanoma cells and systemic tissues.

The identification of ApoE as the sole downstream mediator of the LXRβ-induced suppression of melanoma phenotypes further highlights the importance of this gene as a suppressor of melanoma progression. To determine whether ApoE expression is clinically prognostic of melanoma metastatic outcomes, we assessed ApoE protein levels by performing blinded immunohistochemical analysis on 71 surgically resected human primary melanoma lesions.

We found that patients whose melanomas had metastasized exhibited roughly 3-fold lower ApoE expression in their primary tumors relative to patients whose melanomas did not metastasize (FIG. 30H, P=0.002). Remarkably, ApoE expression levels in patients' primary melanoma lesions robustly stratified patients at high risk from those at low risk for metastatic relapse (FIG. 30I, P=0.002). These observations are consistent with previous findings that revealed significantly lower levels of ApoE in distant melanoma metastases relative to primary lesions (Pencheva et al., 2012). Collectively, this work indicates that ApoE, as a single gene, could likely act as a prognostic and predictive biomarker in primary melanomas to identify patients that i.) are at risk for melanoma metastatic relapse and as such ii.) could obtain clinical benefit from LXRβ agonist-mediated ApoE induction.

Example 19

LXRβ Activation Therapy Suppresses the Growth of Melanomas Resistant to Dacarbazine and Vemurafenib Encouraged by the robust ability of LXRβ activation therapy to suppress melanoma tumor growth and metastasis across a wide range of melanoma lines of diverse mutational backgrounds, we next sought to determine whether melanomas that are resistant to two of the mainstay clinical agents used in the management of metastatic melanoma—dacarbazine and vemurafenib—could respond to LXRβ-activation therapy.

Figures 31A, 31B, 31C, 31D, 31E, 31F:
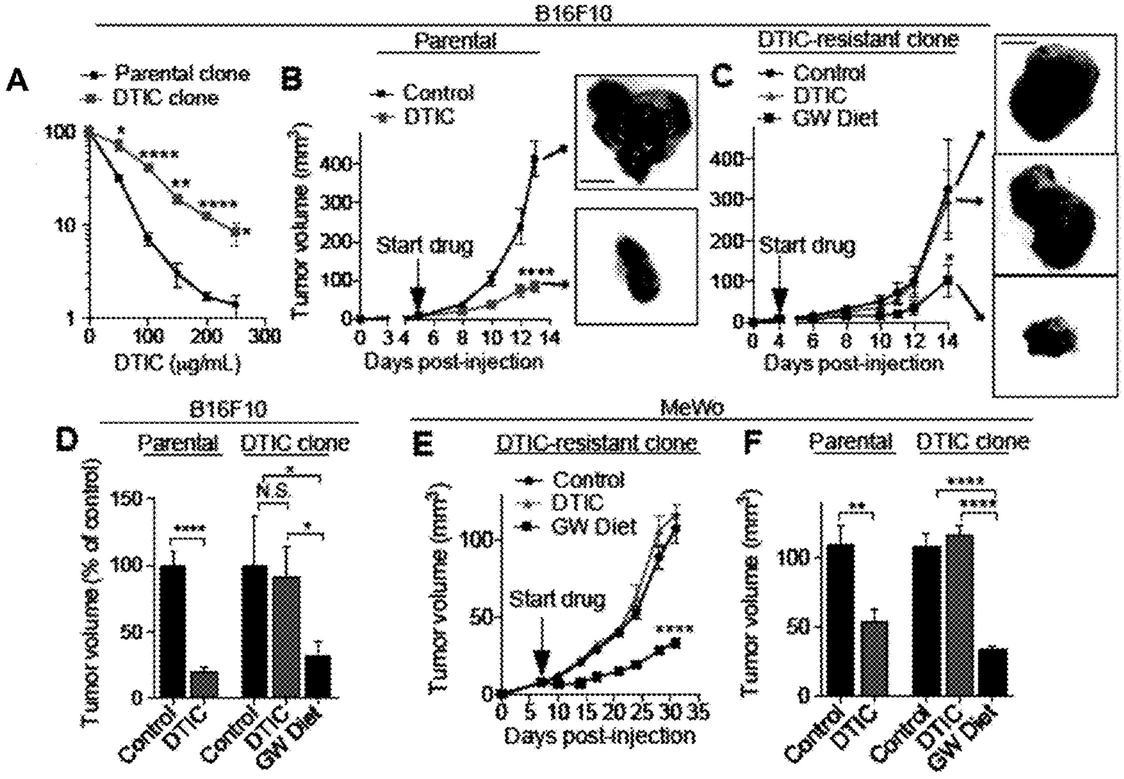

To this end, we generated B16F10 clones resistant to dacarbazine (DTIC) by continuously culturing melanoma cells in the presence of DTIC for two months. This yielded a population of cells that exhibited a 7-fold increase in viability in response to high-dose DTIC treatment compared to the parental B16F10 cell line (FIG. 31A). To confirm that this in vitro-derived DTIC clone was also resistant to DTIC in vivo, we assessed the effects of dacarbazine treatment on tumor growth.

While dacarbazine significantly suppressed the growth of the DTIC-sensitive parental line (FIG. 31B), it did not affect tumor growth by B16F10 DTIC-resistant cells (FIG. 31C). GW3965 2 robustly suppressed tumor growth by the DTIC-resistant B16F10 melanoma clone by more than 70% (FIGS. 31C-D). Importantly, oral delivery of GW3965 2 also strongly inhibited the growth of in vivo-derived DTIC-resistant human melanoma tumors formed by the independent MeWo cell line (FIGS. 31E-F and FIG. 32A).

These results reveal that LXRβ agonism is effective in suppressing multiple melanoma cell populations that are resistant to dacarbazine—the only FDA-approved cytotoxic chemotherapeutic in metastatic melanoma. Our findings have important clinical implications for melanoma treatment since all stage IV patients who are treated with dacarbazine ultimately progress by developing tumors that are resistant to this agent.

Figures 31G, 31H, 31I:
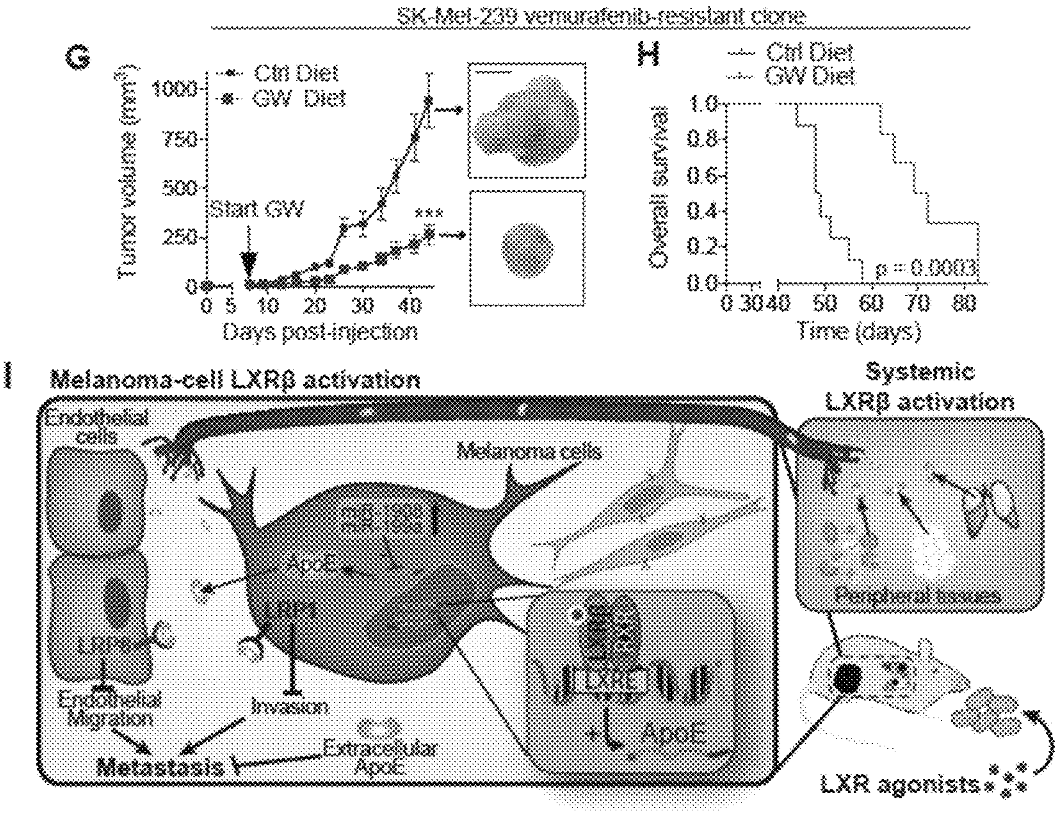

We tested the impact of LXRβ activation therapy on melanoma cells resistant to the recently approved B-Raf kinase inhibitor, vemurafenib—a regimen that shows activity against B-Raf-mutant melanomas (Bollag et al., 2010; Sosman et al., 2012). Numerous investigators have derived melanoma lines resistant to vemurafenib (Poulikakos et al., 2011; Shi et al., 2012, Das Thakur et al., 2013). GW3965 2 treatment suppressed the growth of the previously derived SK-Me1-239 vemurafenib-resistant line by 72% (FIG. 31G) and significantly prolonged the survival of mice bearing vemurafenib-resistant melanoma burden (FIG. 31H). Our findings from combined pharmacologic, molecular and genetic studies in diverse pre-clinical models of melanoma establish LXRβ targeting as a novel therapeutic approach that robustly suppresses melanoma tumor growth and metastasis through the transcriptional induction of ApoE—a key suppressor of melanoma invasion and metastatic angiogenesis (Pencheva et al., 2012; FIG. 31I).

Example 20

Treatment with ApoE Inhibits Tumor Cell Invasion and Endothelial Recruitment Across Multiple Cancer Types, Including Breast Cancer, Renal Cell Cancer and Pancreatic Cancer In order to determine if ApoE treatment could be effective for treating cancer types in addition to melanoma, in vitro assays were performed to assess the effect of ApoE treatment on several different cancer cell lines, including breast cancer, renal cell cancer, and pancreatic cancer cell lines (FIG. 33).

The ability of cancer cells to invade through matrigel in vitro was tested by using a trans-well matrigel invasion chamber system (354480, BD Biosciences). Various cancer cell lines were serum-starved overnight in media containing 0.2% FBS. The following day, invasion chambers were pre-equilibrated prior to the assay by adding 0.5 mL of starvation media to the top and bottom wells. Meanwhile, cancer cells were trypsinized and viable cells were counted using the trypan blue dead cell exclusion dye. Cancer cells were then resuspended at a concentration of 1×105 cells/1 mL starvation media, and 0.5 mL of cell suspension, containing 5×104 cells, was seeded into each trans-well. To determine the effect of recombinant ApoE on cancer cell invasion, human recombinant ApoE3 (4696, Biovision) or BSA were added to each trans-well at 100 μg/mL at the start of the assay. The invasion assay was allowed to proceed for 24 hours at 37° C. Upon completion of the assay, the inserts were washed in PBS, the cells that did not invade were gently scraped off from the top side of each insert using q-tips, and the cells that invaded into the basal insert side were fixed in 4% PFA for 15 minutes at room temperature. Following fixation, the inserts were washed in PBS and then cut out and mounted onto slides using VectaShield mounting medium containing DAPI nuclear stain (H-1000, Vector Laboratories). The basal side of each insert was imaged using an inverted fluorescence microscope (Zeiss Axiovert 40 CFL) at 5× magnification, and the number of DAPI-positive cells was quantified using ImageJ.

Indeed, treatment with ApoE inhibited both tumor cell invasion and endothelial recruitment across all three of these cancer types (FIG. 33A-I).

Example 21

LXR agonists LXR-623, WO-2007-002563 Ex. 19, WO-2010-0138598 Ex. 9, and SB742881, Induce ApoE Expression in Human Melanoma Cells Given that ApoE activation by treatment with LXR agonists GW3965 2 and T0901317 1 resulted in therapeutic benefit for inhibiting tumor growth and metastasis, we next examined the ability of other LXR agonists to induce ApoE expression in human melanoma cell lines (FIG. 34).

To determine the effect of the various LXR agonists (LXR-623, WO-2007-002563 Ex. 19, WO-2010-0138598 Ex. 9, and SB742881 on ApoE expression in melanoma cells, 1×105 human MeWo melanoma cells were seeded in a 6-well plate. The following day, DMSO or the respective LXR agonist was added to the cell media at a concentration of 500 nM, 1 μM, or 2 μM, as indicated, and the cells were incubated in the presence of DMSO or the drug for 48 hours at 37° C. The total amount of DMSO added to the cell media was kept below 0.2%. RNA was extracted from whole cell lysates using the Total RNA Purification Kit (17200, Norgen). For every sample, 600 ng of RNA was reverse transcribed into cDNA using the cDNA First-Strand Synthesis kit (Invitrogen). Approximately 200 ng of cDNA was mixed with SYBR® green PCR Master Mix and the corresponding forward and reverse primers specific for detection of human ApoE. Each reaction was carried out in quadruplicates, and ApoE mRNA expression levels were measured by quantitative real-time PCR amplification using an ABI Prism 7900HT Real-Time PCR System (Applied Biosystems). The relative ApoE expression was determined using the ΔΔCt method. GAPDH was used as an endogenous control for normalization purposes.

Figures 34A, 34B, 34C, 34D:
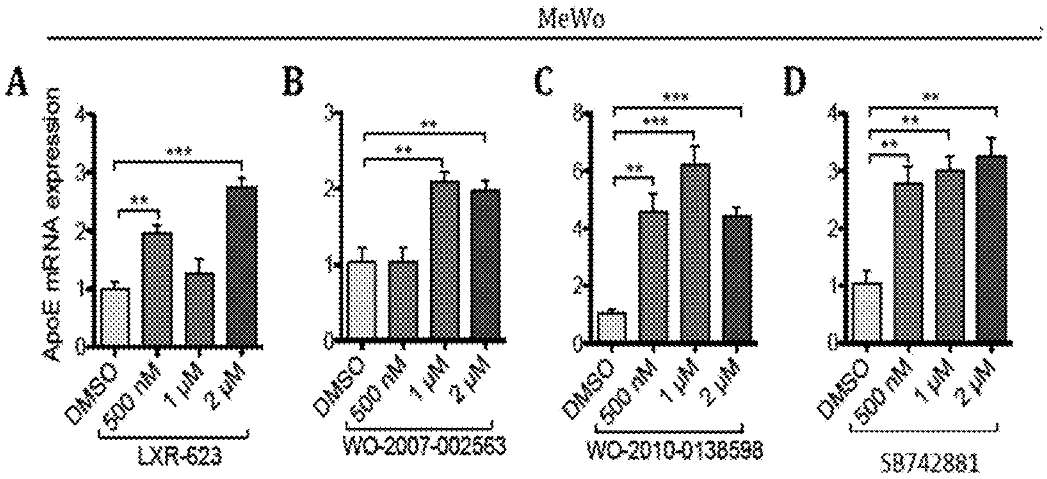

Indeed, treatment with the LXR agonists LXR-623, WO-2007-002563 Ex. 19, WO-2010-0138598 Ex. 9, and SB742881 all led to varied degrees of ApoE expression induction. (FIG. 34A-C).

Example 22

Treatment with the LXR Agonist GW3965 Inhibits In Vitro Tumor Cell Invasion of Renal Cancer, Pancreatic Cancer, and Lung Cancer We have demonstrated that treatment with LXR agonists resulted in inhibition of melanoma tumor cell invasion. Given that this effect is mediated by activation of ApoE expression, we hypothesized that treatment with LXR agonists would result in inhibition of in vitro tumor cell invasion in breast cancer, pancreatic cancer, and renal cancer, since these cancer types were responsive to ApoE treatment. In order to test this hypothesis, we performed in vitro tumor cell invasion assays by treating breast cancer, pancreatic cancer, and renal cell cancer cell lines with the LXR agonist GW3965 2 (FIG. 35).

Various cell lines ($5\times10^4$ RCC human renal cancer cells, $5\times10^4$ PANC1 human pancreatic cancer cells, and $5\times10^4$H460 human lung cancer cells) were treated with DMSO or GW3965 at 1 μM for 56 hours. The cells were serum starved for 16 hours in 0.2% FBS media in the presence of DMSO or GW3965. Following serum starvation, the cells were subjected to the trans-well invasion assay using a matrigel invasion chamber system (354480, BD Biosciences). Invasion chambers were pre-equilibrated prior to the assay by adding 0.5 mL of starvation media to the top and bottom wells. Meanwhile, cancer cells were trypsinized and viable cells were counted using trypan blue. Cancer cells were then resuspended at a concentration of $1\times10^5$ cells/1 mL starvation media, and 0.5 mL of cell suspension, containing $5\times10^4$ cells, was seeded into each trans-well. The invasion assay was allowed to proceed for 24 hours at 37° C. Upon completion of the assay, the inserts were washed in PBS, the cells that did not invade were gently scraped off from the top side of each insert using q-tips, and the cells that invaded into the basal insert side were fixed in 4% PFA for 15 minutes at room temperature. Following fixation, the inserts were washed in PBS and then cut out and mounted onto slides using VectaShield mounting medium containing DAPI nuclear stain (H-1000, Vector Laboratories). The basal side of each insert was imaged using an inverted fluorescence microscope (Zeiss Axiovert 40 CFL) at 5× magnification, and the number of DAPI-positive cells was quantified using ImageJ.

Indeed, treatment with GW3965 2 resulted in inhibition of tumor cell invasion in all three cancer types tested (FIG. 35A-C). This further demonstrated the broad therapeutic potential of LXR agonists for treating various cancer types.

Example 23

Treatment with the LXR Agonist GW3965 Inhibits Breast Cancer Tumor Growth In Vivo We have demonstrated that LXR agonists inhibit in vitro cancer progression phenotypes in breast cancer, pancreatic cancer, and renal cancer. To investigate if LXR agonist treatment inhibits breast cancer primary tumor growth in vivo, mice injected with MDA-468 human breast cancer cells were treated with either a control diet or a diet supplemented with LXR agonist GW3965 2 (FIG. 36).

To determine the effect of orally delivered GW3965 2 on breast cancer tumor growth, $2\times10^6$ MDA-468 human breast cancer cells were resuspended in 50 μL PBS and 50 μL matrigel and the cell suspension was injected into both lower memory fat pads of 7-week-old Nod Scid gamma female mice. The mice were assigned to a control diet treatment or a GW3965-supplemented diet treatment (75 mg/kg/day) two days prior to injection of the cancer cells. The GW3965 2 drug compound was formulated in the mouse chow by Research Diets, Inc. Tumor dimensions were measured using digital calipers, and tumor volume was calculated as (small diameter)$^2$×(large diameter)/2.

Treatment with GW3965 resulted in significant reduction in breast cancer tumor size in vivo (FIG. 36).

Example 24

Effects of Treatment with LXR Agonists LXR-623, WO-2007-002563 Ex. 19, WO-2010-0138598 Ex. 9, and SB742881 on In Vitro Melanoma Progression Phenotypes We have demonstrated the ability of various LXR agonists to induce ApoE expression with varying potency in melanoma cells (FIG. 34). Since the therapeutic effect of LXR agonists on cancer is via activation of ApoE expression, we hypothesized that the therapeutic potency of any given LXR agonist is directly correlated with its ability to induce ApoE expression. To confirm this, we quantified the effect of treatment with various LXR agonists on in vitro endothelial recruitment and tumor cell invasion of melanoma cells. As shown in FIG. 37, the degree to which LXR agonists inhibit in vitro cancer progression phenotypes is related to the LXR agonist's ApoE induction potency.

Cell Invasion: MeWo human melanoma cells were treated with DMSO, LXR-623, WO-2007-002563 Ex. 19, WO-2010-0138598 Ex. 9, or SB742881 at 1 μM each for 56 hours. The cells were then serum starved for 16 hours in 0.2% FBS media in the presence of each corresponding drug or DMSO. Following serum starvation, the cells were subjected to the trans-well invasion assay using a matrigel invasion chamber system (354480, BD Biosciences). Invasion chambers were pre-equilibrated prior to the assay by adding 0.5 mL of starvation media to the top and bottom wells. Meanwhile, cancer cells were trypsinized and viable cells were counted using trypan blue. Cancer cells were then resuspended at a concentration of $2\times10^5$ cells/1 mL starvation media, and 0.5 mL of cell suspension, containing $1\times10^5$ cells, was seeded into each trans-well. The invasion assay was allowed to proceed for 24 hours at 37° C. Upon completion of the assay, the inserts were washed in PBS, the cells that did not invade were gently scraped off from the top side of each insert using q-tips, and the cells that invaded into the basal insert side were fixed in 4% PFA for 15 minutes at room temperature. Following fixation, the inserts were washed in PBS, cut out, and mounted onto slides using VectaShield mounting medium containing DAPI nuclear stain (H-1000, Vector Laboratories). The basal side of each insert was imaged using an inverted fluorescence microscope (Zeiss Axiovert 40 CFL) at 5× magnification, and the number of DAPI-positive cells was quantified using ImageJ.

Endothelial Recruitment:

MeWo human melanoma cells were treated with DMSO, LXR-623, WO-2007-002563 Ex. 19, WO-2010-0138598 Ex. 9, or SB742881 at 1 μM each for 56 hours. Subsequently, $5\times10^4$ cancer cells were seeded into 24-well plates in the presence of each drug or DMSO and allowed to attach for 16 hours prior to starting the assay. Human umbilical vein endothelial cells (HUVEC cells) were serum-starved in 0.2% FBS-containing media overnight. The following day, $1\times10^5$ HUVEC cells were seeded into a 3.0 μm HTS Fluoroblock insert (351151, BD Falcon) fitted into each well containing the cancer cells at the bottom. The HUVEC cells were allowed to migrate towards the cancer cells for 20 hours, after which the inserts were washed in PBS, fixed in 4% PFA, labeled with DAPI, and mounted on slides. The basal side of each insert was imaged using an inverted fluorescence microscope (Zeiss Axiovert 40 CFL) at 5× magnification, and the number of DAPI-positive cells was quantified using ImageJ.

LXR agonists that potently induce ApoE expression (e.g. WO-2010-0138598 Ex. 9 and SB742881) are more effective at inhibiting cancer progression phenotypes (FIG. 37) than lower potency LXR agonists. This further demonstrates that the therapeutic benefit of LXR agonist treatment for cancer is a result of ApoE induction.

Example 25

Treatment with LXR Agonists Inhibit Melanoma Tumor Growth In Vivo

We have demonstrated that LXR agonists that induce ApoE expression inhibit in vitro tumor activity. To confirm if these agonists inhibit melanoma tumor growth in vivo, mice that were injected with B16F10 melanoma cells were treated with either LXR-623, WO-2007-002563 Ex. 19, WO-2010-0138598 Ex. 9, or SB742881.

To assess the effect of orally administered LXR-623, WO-2007-002563 Ex. 19, WO-2010-0138598 Ex. 9, or SB742881 on melanoma tumor growth, $5\times10^4$ B16F10 mouse melanoma cells were resuspended in 50 μL PBS and 50 μL matrigel and the cell suspension was subcutaneously injected into both lower dorsal flanks of 7-week-old C57BL/6 mice. The mice were palpated daily for tumor formation and after detection of tumors measuring 5-10 $m^3$ in volume, the mice were assigned to a control chow or a chow containing each respective LXR agonist: LXR-623 (20 mg/kg/day), WO-2007-002563 Ex. 19 (100 mg/kg/day), WO-2010-0138598 Ex. 9 (10 mg/kg/day or 100 mg/kg/day), or SB742881 (100 mg/kg/day). The LXR drug compounds were formulated in the mouse chow by Research Diets, Inc. Tumor dimensions were measured using digital calipers, and tumor volume was calculated as (small diameter)×(large diameter)/2.

Consistent with our in vitro data, LXR agonists that potently induce ApoE expression in vitro (WO-2010-0138598 Ex. 9, and SB742881) significantly inhibited melanoma primary tumor growth in vivo (FIG. 38). This is also consistent with our results demonstrating that other LXR agonists which potently induce ApoE expression (GW3965 2, T0901317 1) also inhibit primary tumor growth in vivo (FIG. 21).

Accordingly, the above examples focused on characterizing the molecular and cellular mechanisms by which it exerts its effects. To this end, it was found that ApoE targets two distinct, yet homologous, receptors on two diverse cell types. ApoE acting on melanoma cell LRP1 receptors inhibits melanoma invasion, while its action on endothelial cell LRP8 receptors suppresses endothelial migration. The results from loss-of-function, gain-of-function, epistasis, clinical correlation, and in vivo selection derivative expression analyses give rise to a model wherein three miRNAs convergently target a metastasis suppressor network to limit ApoE secretion, thus suppressing ApoE/LRP1 signaling on melanoma cells and ApoE/LRP8 signaling on endothelial cells (FIG. 7K). Although the above systematic analysis has identified ApoE and DNAJA4 as key targets and direct mediators of the metastatic phenotypes regulated by these miRNAs, it cannot be excluded that the three miRNAs may individually retain additional target genes whose silencing may contribute to metastatic progression. The ability of ApoE or DNAJA4 knock-down to fully rescue the metastasis suppression phenotypes seen with individual miRNA silencing, however, strongly suggests that these genes are the key mediators of the miRNA-dependent effects on metastasis.

The above results reveal combined molecular, genetic, and in vivo evidence for a required and sufficient role for ApoE in the suppression of melanoma metastatic progression. ApoE can distribute in the circulatory system both in a lipoprotein-bound and a lipid-free state (Hatters et al., 2006). While it has been shown that lipid-free recombinant ApoE is sufficient to suppress melanoma invasion and endothelial migration, it is possible that ApoE contained in lipoprotein particles could also suppress melanoma invasion and endothelial recruitment. The ability of recombinant ApoE to inhibit these pro-metastatic phenotypes, as well as the increased melanoma invasion and endothelial recruitment phenotypes seen with antibody-mediated ApoE neutralization suggests that the ApoE molecule itself is the key mediator of these phenotypes. Consistent with the findings disclosed herein, a synthetic peptide fragment of ApoE was previously found to inhibit endothelial migration through unknown mechanisms (Bhattacharjee et al., 2011). The findings disclosed herein are consistent with a role for melanoma cell-secreted and systemic endogenous ApoE in inhibiting endothelial recruitment, which is not secondary to impaired endothelial cell growth.

The above-described molecular, genetic, and in vivo studies reveal a role for endogenous cancer-derived ApoE in the modulation of endothelial migration and cancer angiogenesis through endothelial LRP8 receptor signaling. This robust non-cell-autonomous endothelial recruitment phenotype mediated by ApoE/LRP8 signaling suggests that ApoE may also modulate metastatic angiogenesis in other cancer types, and such a general role for ApoE in cancer angiogenesis biology remains to be explored. ApoE is a polymorphic molecule with well-established roles in lipid, cardiovascular, and neurodegenerative disorders. Its three major variants, ApoE2, ApoE3, and ApoE4, display varying representations in the human population, with ApoE3 being the most common variant (Hatters et al., 2006). The three isoforms differ at residues 112 and 158 in the N-terminal domain, which contains the ApoE receptor-binding domain. These structural variations are thought to give rise to distinct functional attributes among the variants. Consistent with this, the three ApoE isoforms differ in their binding affinity for members of the LDL receptor family, lipoprotein-binding preferences, and N-terminus stability. Namely, ApoE2 has 50- to 100-fold attenuated LDL receptor binding ability compared to ApoE3 and ApoE4 (Weisgraber et al., 1982), while ApoE4, unlike the other two variants, preferentially binds to large lower-density lipoproteins (Weisgraber et al., 1990) and exhibits the lowest N-terminus stability (Morrow et al., 2000). These functional differences confer pathophysiological properties to select ApoE isoforms. While ApoE3, found in 78% of the population, is considered a neutral allele, ApoE2 is associated with type III hyperlipoproteinemia (Hatters et al., 2006) and ApoE4 represents the major known genetic risk factor for Alzheimer's disease (Corder et al., 1993) and also correlates with a modest increase in the risk of developing cardiovascular disease (Luc et al., 1994). Given that the multiple human melanoma cell lines analyzed in the above study are homozygous for the ApoE3 allele, as well as the ability of recombinant ApoE3 to inhibit melanoma invasion and endothelial recruitment, the above findings are consistent with ApoE3 being sufficient and required for the suppression of melanoma metastatic progression. However, it will be of interest in the future to determine whether ApoE2 and ApoE4 can modulate these pro-metastatic phenotypes to a similar extent as ApoE3 and whether specific ApoE genotypes confer enhanced risk of melanoma metastatic progression.

Besides surgical resection of primary melanoma lesions, there are currently no effective therapies for the prevention of melanoma metastasis with interferon therapy increasing overall survival rates at 5 years by a meager 3% based on meta-analyses, while phase III trial data demonstration of significant survival benefits is still outstanding (Garbe et al., 2011). The dramatic enhancement of melanoma metastatic progression in the context of genetic ablation of systemic ApoE suggests that modulating ApoE levels may have significant therapeutic implications for melanoma—a disease that claims approximately 48,000 lives a year globally (Lucas et al., 2006). Given the robust ability of ApoE to suppress melanoma invasion, endothelial migration, metastatic angiogenesis, and metastatic colonization, therapeutic approaches aimed at pharmacological induction of endogenous ApoE levels may significantly reduce melanoma mortality rates by decreasing metastatic incidence.

The above-described unbiased in vivo selection based approach led to discovery of deregulated miRNAs that synergistically and dramatically promote metastasis by cancer cells from independent patients' melanoma cell lines representing both melanotic and amelanotic melanomas. While miR-1908 has not been previously characterized, miR-199a has been implicated in hepatocellular carcinoma (Hou et al., 2011; Shen et al., 2010) and osteosarcoma (Duan et al., 2011) that, contrary to melanoma, display down-regulation of miR-199a expression levels. These differences are consistent with the established tissue-specific expression profiles of miRNAs in various cancer types. The identification of miR-199a as a promoter of melanoma metastasis is supported by a previous clinical association study revealing that increased miR-199a levels correlate with uveal melanoma progression (Worley et al., 2008), suggesting that induced miR-199a expression may be a defining feature of metastatic melanoma regardless of site of origin. Previous studies have implicated additional miRNAs in promoting melanoma metastatic progression such as miR-182 (Segura et al., 2009), miR-214 (which was upregulated in metastatic melanoma cells, but it did not functionally perform in the above studies; Penna et al., 2011), and miR-30b/miR-30d (Gaziel-Sovran et al., 2011). Each of these miRNAs have been reported to only modestly modulate melanoma metastasis, leading to 1.5- to 2-fold increased or decreased metastasis modulation upon miRNA over-expression or knock-down, respectively. In contrast, over-expression of either miR-199a or miR-1908 enhanced metastasis by 9-fold (FIG. 1C), while combinatorial miRNA knock-down synergistically suppressed melanoma metastasis by over 70-fold (FIG. 7E). Therefore, the study disclosed herein represents the first systematic discovery of multiple miRNAs that convergently and robustly promote human melanoma metastasis, as well as the first to assign dual cell-autonomous/non-cell-autonomous roles to endogenous metastasis-regulatory miRNAs in cancer.

Previous systematic analysis of miRNAs in breast cancer revealed primarily a decrease in the expression levels of multiple microRNAs in in vivo selected metastatic breast cancer cells (Tavazoie et al., 2008). Those findings were consistent with the subsequent discovery of many additional metastasis suppressor miRNAs in breast cancer (Shi et al., 2010; Wang and Wang, 2011), the identification of a number of miRNAs as direct transcriptional targets of the p53 tumour suppressor (He et al., 2007), the downregulation of miRNAs in breast cancer relative to normal tissues (Calin and Groce, 2006; Iorio et al., 2005), the downregulation of drosha and dicer in breast cancer (Yan et al., 2011) and metastatic breast cancer (Grelier et al., 2011), as well as the pro-tumorigenic and pro-metastatic effects of global miRNA silencing through dicer knock-down (Kumar et al., 2007; Kumar et al., 2009; Martello et al., 2010; Noh et al., 2011). In contrast to breast cancer, the above findings in melanoma reveal a set of miRNAs upregulated in metastatic human melanoma, raising the intriguing possibility that miRNA processing may actually act in a pro-tumorigenic or pro-metastatic manner in melanoma. Consistent with this, dicer is required for melanocytic development (Levy et al., 2010), and dicer expression was recently found to positively correlate with human melanoma progression in a clinico-pathological study (Ma et al., 2011). These findings, when integrated with the findings disclosed here, motivate future studies to investigate the functional requirement for dicer (Bernstein et al., 2001) in melanoma metastasis.

The establishment of in vivo selection models of melanotic and amelanotic melanoma metastasis has allowed one to identify the cellular phenotypes displayed by highly metastatic melanoma cells. The work reveals that, in addition to enhanced invasiveness, the capacity of melanoma cells to recruit endothelial cells is significantly enhanced in highly metastatic melanoma cells relative to poorly metastatic melanoma cells. Additionally, it was found that three major post-transcriptional regulators of metastasis strongly mediate endothelial recruitment. It was further found that the downstream signaling pathway modulated by these miRNAs also regulates endothelial recruitment. These findings reveal endothelial recruitment to be a defining feature of metastatic melanoma cells. Enhanced endothelial recruitment capacity was also recently found to be a defining feature of metastatic breast cancer, wherein suppression of metastasis by miR-126 was mediated through miRNA targeting of two distinct signaling pathways that promote endothelial recruitment (Png et al., 2012). In breast cancer, endothelial recruitment increased the likelihood of metastatic initiation rather than tumor growth. Similarly, the melanoma metastasis promoter miRNAs studied here dramatically enhanced metastatic colonization, without enhancing primary tumor growth, and increased the number of metastatic nodules—consistent with a role for these miRNAs and their regulatory network in metastatic initiation rather than tumor growth promotion. Taken together, these findings are consistent with endothelial recruitment into the metastatic niche acting as a promoter of metastatic initiation and colonization in these distinct epithelial cancer types. Such a non-canonical role for endothelial cells in cancer progression would contrast with the established role of endothelial cells in angiogenic enhancement of blood flow spurring enhanced tumor growth. Endothelial cells are known to play such non-canonical roles in development by supplying cues to neighboring cells during organogenesis (Lammert et al., 2001). Such cues have also been recently shown to promote organ regeneration (Ding et al., 2011; Ding et al., 2010; Kobayashi et al., 2010). Future work is needed to determine the metastasis stimulatory factors provided by endothelial cells that catalyze metastatic initiation.

The ability of miR-199a-3p, miR-199a-5p, and miR-1908 to individually predict metastasis-free survival in a cohort of melanoma patients indicates the significance of each miRNA as a clinical predictor of melanoma cancer progression. Importantly, the dramatic and highly significant capacity of the three miRNA aggregate signature (FIG. 7D) to stratify patients at high risk from those at essentially no risk for metastatic relapse reveals both the cooperativity of these miRNAs, as well as their clinical potential as melanoma biomarkers (Sawyers, 2008) for identifying the subset of patients that might benefit from miRNA inhibition therapy. Therapeutic miRNA targeting has gained momentum through the use of in vivo LNAs that have been shown to antagonize miRNAs in mice (Elmer et al., 2008(b); Krutzfeldt et al., 2005; Obad et al., 2011) and primates (Elmer et al., 2008(a)) and are currently being tested in human clinical trials. The powerful prognostic capacity of the three miRNAs, proof-of-principle demonstration of robust synergistic metastasis prevention achieved by treating highly metastatic melanoma cells with a cocktail of LNAs targeting miR-199a-3p, miR-199a-5p, and miR-1908 (FIG. 7E), as well as the metastasis suppression effect of therapeutically delivered in vivo-optimized LNAs targeting these miRNAs (FIG. 7J) motivate future clinical studies aimed at determining the therapeutic potential of combinatorially targeting these pro-metastatic and pro-angiogenic miRNAs in patients at high risk for melanoma metastasis—an outcome currently lacking effective chemotherapeutic options.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated in their entireties.

The invention claimed is:

1. A method of treating cancer in a subject in need thereof, wherein the cancer is resistant to a PD-1 inhibitor, a PD-L1 inhibitor, and/or a CTLA-4 inhibitor, the method comprising administering to the subject an effective amount of an LXRβ agonist, or a pharmaceutically acceptable salt thereof, and a PD-1 inhibitor, a PD-L1 inhibitor, or a CTLA-4 inhibitor, wherein the LXRβ agonist is:

compound 1

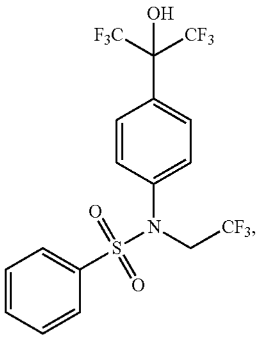

compound 2

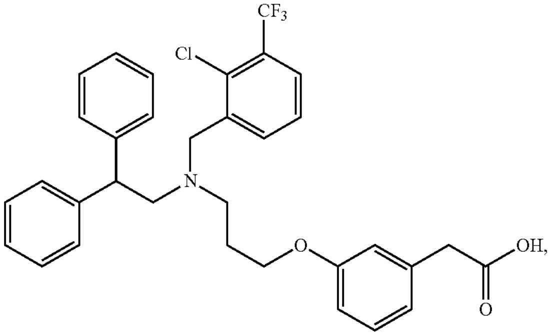

compound 12

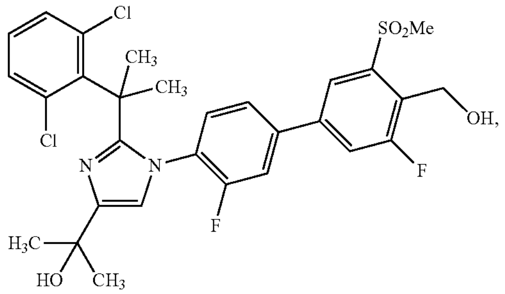

or

-continued compound 25

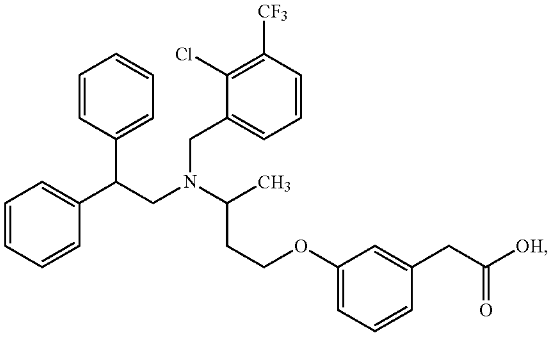

or a pharmaceutically acceptable salt thereof, wherein the cancer is ovarian cancer, breast cancer, lung cancer, glioblastoma, melanoma, bladder cancer, head and neck cancer, renal cell cancer, colorectal cancer, lymphoma, leukemia, multiple myeloma, or hepatocellular carcinoma.

2. The method of claim 1, wherein the cancer is breast cancer, ovarian cancer, lung cancer, glioblastoma, or melanoma.

3. The method of claim 1, wherein the cancer is ovarian cancer.

4. The method of claim 3, wherein the ovarian cancer is also resistant to platinum agents.

5. The method of claim 1, wherein the cancer is breast cancer.

6. The method of claim 5, wherein the breast cancer is triple negative breast cancer.

7. The method of claim 1, wherein the cancer is lung cancer.

8. The method of claim 7, wherein the lung cancer is non-small cell lung cancer.

9. The method of claim 1, wherein the cancer is glioblastoma.

10. The method of claim 1, wherein the cancer is melanoma.

11. The method of claim 10, wherein the melanoma is also resistant to dacarbazine, a BRAF inhibitor, and/or a MEK inhibitor.

12. The method of claim 1, wherein the cancer is bladder cancer.

13. The method of claim 1, wherein the cancer is head and neck cancer.

14. The method of claim 1, wherein the cancer is renal cell cancer.

15. The method of claim 1, wherein the cancer is colorectal cancer.

16. The method of claim 1, wherein the cancer is lymphona.

17. The method of claim 1, wherein the cancer is leukemia.

18. The method of claim 1, wherein the cancer is multiple myeloma.

19. The method of claim 1, wherein the cancer is hepatocellular carcinoma.

20. The method of claim 1, wherein the LXRβ agonist is compound 1, or a pharmaceutically acceptable salt thereof.

21. The method of claim 1, wherein the LXRβ agonist is compound 2, or a pharmaceutically acceptable salt thereof.

22. The method of claim 1, wherein the LXRβ agonist is compound 12, or a pharmaceutically acceptable salt thereof.

23. The method of claim 1, wherein the LXRβ agonist is compound 25, or a pharmaceutically acceptable salt thereof.

24. The method of claim 1, wherein the cancer is metastatic.

25. The method of claim 24, wherein the LXRβ agonist is administered in an amount sufficient to increase the expression level or activity level of ApoE to a level sufficient to suppress metastatic progression of the cancer.

26. The method of claim 1, wherein the LXRβ agonist, or a pharmaceutically acceptable salt thereof, and the PD-1 inhibitor or PD-L1 inhibitor are administered within 28 days of each other.

27. The method of claim 1, wherein the cancer progressed on or after treatment with a PD-1 inhibitor, a PD-L1 inhibitor, and/or a CTLA-4 inhibitor.

28. The method of claim 1, wherein the cancer has been determined to be, or is predicted to be resistant to a PD-1 inhibitor, a PD-L1 inhibitor, and/or a CTLA-4 inhibitor.

* * * * *